(12) United States Patent  (10) Patent No.: US 8,658,641 B2
Barvian et al.  (45) Date of Patent: Feb. 25, 2014

(54) FUSED, SPIROCYCLIC HETEROAROMATIC COMPOUNDS FOR THE TREATMENT OF BACTERIAL INFECTIONS

(75) Inventors: Kevin Barvian, Waltham, MA (US); Gregory Steven Basarab, Waltham, MA (US); Madhusudhan Reddy Gowravaram, Waltham, MA (US); Sheila Irene Hauck, Waltham, MA (US); Fei Zhou, Waltham, MA (US)

(73) Assignee: AstraZeneca AB, Sodertalje (SE)

( * ) Notice: Subject to any disclaimer, the term of this patent is extended or adjusted under 35 U.S.C. 154(b) by 250 days.

(21) Appl. No.: 13/124,889

(22) PCT Filed: Oct. 13, 2009

(86) PCT No.: PCT/GB2009/051363
§ 371 (c)(1),
(2), (4) Date: Jun. 8, 2011

(87) PCT Pub. No.: WO2010/043893
PCT Pub. Date: Apr. 22, 2010

(65) Prior Publication Data
US 2011/0245224 A1  Oct. 6, 2011

Related U.S. Application Data

(60) Provisional application No. 61/105,189, filed on Oct. 14, 2008.

(51) Int. Cl.
*A61K 31/5383* (2006.01)
*C07D 413/14* (2006.01)

(52) U.S. Cl.
USPC ........ 514/233.2; 544/106; 544/111; 544/114; 544/123; 514/231.2; 514/232.8

(58) Field of Classification Search
USPC ......... 544/99, 106, 111, 114, 123; 514/231.2, 514/232.8, 233.2
See application file for complete search history.

(56) References Cited

U.S. PATENT DOCUMENTS 7,371,757 B2 * 5/2008 Morningstar et al. ........ 514/267

FOREIGN PATENT DOCUMENTS

| WO | 2004/031195 A1 | 4/2004 |
| WO | 2006/120563 A2 | 11/2006 |
| WO | 2007/072151 A1 | 6/2007 |
| WO | 2010/043893 A1 | 4/2010 |

OTHER PUBLICATIONS

International Search Report for PCT/GB2009/051363; mailed Feb. 26, 2010.

* cited by examiner

*Primary Examiner* — Golam M M Shameem

(57) ABSTRACT

The present invention relates to compounds of Formula (I); to pharmaceutically acceptable salts thereof, to methods of using them to treat bacterial infections, and to methods for their preparation.

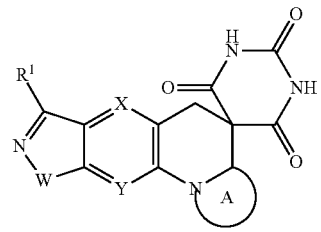

8 Claims, No Drawings

FUSED, SPIROCYCLIC HETEROAROMATIC COMPOUNDS FOR THE TREATMENT OF BACTERIAL INFECTIONS

RELATED APPLICATIONS

This application is a US National Stage under 35 U.S.C §371 of International Application No. PCT/GB2009/051363 (Oct. 13, 2009) which claims priority under 35 U.S.C. §119 (e) to Application No. 61/105,189 filed on Oct. 14, 2008.

FIELD OF THE INVENTION

The present invention relates to novel substituted heterocycles, their pharmaceutical compositions and methods of use. In addition, the present invention relates to therapeutic methods for the treatment of bacterial infections.

BACKGROUND OF THE INVENTION

The international microbiological and infectious disease community continues to express serious concern that the continuing evolution of antibacterial resistance could result in bacterial strains against which currently available antibacterial agents will be ineffective. The outcome of such an occurrence could have considerable morbidity and mortality. In general, bacterial pathogens may be classified as either Gram-positive or Gram-negative pathogens. Antibiotic compounds with effective activity against both Gram-positive and Gram-negative pathogens are generally regarded as having a broad spectrum of activity.

Gram-positive pathogens are of particular concern because of the development of resistant strains that are both difficult to treat and difficult to eradicate from the hospital environment once established. Examples of such strains are methicillin resistant *Staphylococcus aureus* (MRSA), methicillin resistant coagulase-negative *staphylococci* (MRCNS), penicillin resistant *Streptococcus pneumoniae* and multiple resistant *Enterococcus faecium*. Resistance is increasing at a steady rate rendering many agents less effective in the treatment of Gram-positive pathogens. In addition, there is increasing resistance to agents such as β-lactams, quinolones and macrolides used for the treatment of upper respiratory tract infections caused by Gram-negative strains including *H. influenzae* and *M. catarrhalis*. In addition, nosocomial Gram-negative pathogens, such as *Pseudomonas aeruginosa*, are difficult to treat due to resistance development. Consequently, in order to overcome the threat of widespread multi-drug resistant organisms, there is an on-going need to develop new antibacterials.

Deoxyribonucleic acid (DNA) gyrase is a member of the type II family of topoisomerases that control the topological state of DNA in cells (Champoux, J. J.; 2001. Ann. Rev. Biochem. 70: 369-413). Type II topoisomerases use the free energy from adenosine triphosphate (ATP) hydrolysis to alter the topology of DNA by introducing transient double-stranded breaks in the DNA, catalyzing strand passage through the break and resealing the DNA. DNA gyrase is an essential and conserved enzyme in bacteria and is unique among topoisomerases in its ability to introduce negative supercoils into DNA. The enzyme consists of two subunits, encoded by gyrA and gyrB, forming an $A_2B_2$ tetrameric complex. The A subunit of gyrase (GyrA) is involved in DNA breakage and resealing and contains a conserved tyrosine residue that forms the transient covalent link to DNA during strand passage. The B subunit (GyrB) catalyzes the hydrolysis of ATP and interacts with the A subunit to translate the free energy from hydrolysis to the conformational change in the enzyme that enables strand-passage and DNA resealing.

Another conserved and essential type II topoisomerase in bacteria, called topoisomerase IV, is primarily responsible for separating the linked closed circular bacterial chromosomes produced in replication. This enzyme is closely related to DNA gyrase and has a similar tetrameric structure formed from subunits homologous to Gyr A and to Gyr B. The overall sequence identity between gyrase and topoisomerase IV in different bacterial species is high. Therefore, compounds that target bacterial type II topoisomerases have the potential to inhibit two targets in cells, DNA gyrase and topoisomerase IV; as is the case for existing quinolone antibacterials (Maxwell, A. 1997, Trends Microbiol. 5: 102-109).

Antibacterials targeting DNA gyrase are well established in the art, including examples such as the quinolones and the coumarins. The quinolones (e.g. ciprofloxacin) are broad-spectrum antibacterials that inhibit the DNA breakage and reunion activity of the enzyme and trap the GyrA subunit covalently complexed with DNA (Drlica, K., and X. Zhao, 1997, Microbiol. Molec. Biol. Rev. 61: 377-392). Members of this class of antibacterials also inhibit topoisomerase IV and as a result, the primary target of these compounds varies among species. Although the quinolones are successful antibacterials, resistance generated primarily by mutations in the target (DNA gyrase and topoisomerase IV) is becoming an increasing problem in several organisms, including *S. aureus* and *Streptococcus pneumoniae* (Hooper, D. C., 2002, The Lancet Infectious Diseases 2: 530-538). In addition, quinolones, as a chemical class, suffer from toxic side effects, including arthropathy that prevents their use in children (Lipsky, B. A. and Baker, C. A., 1999, Clin. Infect. Dis. 28: 352-364). Furthermore, the potential for cardiotoxicity, as predicted by prolongation of the $QT_c$ interval, has been cited as a toxicity concern for quinolones.

There are several known natural product inhibitors of DNA gyrase that compete with ATP for binding the GyrB subunit (Maxwell, A. and Lawson, D. M. 2003, Curr. Topics in Med. Chem. 3: 283-303). The coumarins are natural products isolated from *Streptomyces* spp., examples of which are novobiocin, chlorobiocin and coumermycin A1. Although these compounds are potent inhibitors of DNA gyrase, their therapeutic utility is limited due to toxicity in eukaryotes and poor penetration in Gram-negative bacteria (Maxwell, A. 1997, Trends Microbiol. 5: 102-109). Another natural product class of compounds that targets the GyrB subunit is the cyclothialidines, which are isolated from *Streptomyces filipensis* (Watanabe, J. et al 1994, J. Antibiot. 47: 32-36). Despite potent activity against DNA gyrase, cyclothialidine is a poor antibacterial agent showing activity only against some eubacterial species (Nakada, N, 1993, Antimicrob. Agents Chemother. 37: 2656-2661).

SUMMARY OF THE INVENTION

The present invention relates to compounds of Formula (I):

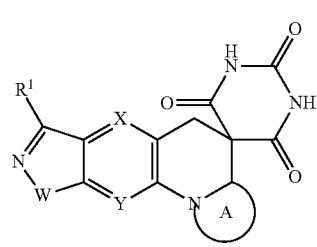

Formula (I)

and to pharmaceutically acceptable salts thereof.

Typical compounds of Formula (I) are believed to inhibit bacterial DNA gyrase and are therefore of interest for their antibacterial effects. The inventive compounds are believed to be active against a variety of bacterial organisms, including both Gram positive and Gram negative aerobic and anaerobic bacteria.

DETAILED DESCRIPTION OF THE INVENTION

The present invention relates to compounds of Formula (I):

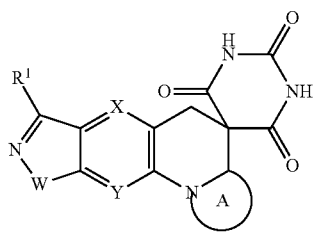

Formula (I)

and to pharmaceutically acceptable salts thereof, wherein:

Ring A is fused 5- to 7-membered non-aromatic heterocyclic ring, wherein said fused 5- to 7-membered non-aromatic heterocyclic ring is optionally substituted on carbon with one or more $R^4$, and wherein any —NH— moiety of said 5- to 7-membered heterocyclic ring is optionally substituted with $R^{4*}$;

W is selected from —O—, —NH—, —S—, and —S(O)$_2$—;

X is selected from N and C—$R^2$;

Y is selected from N and C—$R^3$;

$R^1$ is selected from H, halo, —CN, $C_{1-6}$alkyl, $C_{2-6}$alkenyl, $C_{2-6}$alkynyl, carbocyclyl, heterocyclyl, —OR$^{1a}$, —SR$^{1a}$, —N(R$^{1a}$)$_2$, —N(R$^{1a}$)C(O)R$^{1b}$, —N(R$^{1a}$)C(O)R$^{1b}$, —N(R$^{1a}$)N(R$^{1a}$)$_2$, —NO$_2$, —N(R$^{1}$)OR$^{2a}$, —ON(R$^{1a}$)$_2$, —C(O)H, —C(O)R$^{1b}$, —C(O)$_2$R$^{1a}$, —C(O)N(R$^{1a}$)$_2$, —C(O)N(R$^{1a}$)(OR$^{1a}$), —OC(O)N(R$^{1a}$)$_2$, —N(R$^{1a}$)C(O)$_2$R$^{1a}$, —N(R$^{1a}$)C(O)N(R$^{1a}$)$_2$, —OC(O)R$^{1b}$, —S(O)R$^{1b}$, —S(O)$_2$R$^{1b}$, —S(O)$_2$N(R$^{1a}$)$_2$, —N(R$^{1a}$)S(O)$_2$R$^{1b}$, —C(R$^{1a}$)=N(R$^{1a}$), and —C(R$^{1a}$)=N(OR$^{1a}$), wherein said $C_{1-6}$alkyl, $C_{2-6}$alkenyl, $C_{2-6}$alkynyl, carbocyclyl, and heterocyclyl are optionally substituted on carbon with one or more $R^{10}$, and wherein any —NH— moiety of said heterocyclyl is optionally substituted with $R^{10*}$;

$R^{1a}$ in each occurrence is independently selected from H, $C_{1-6}$alkyl, carbocyclyl, and heterocyclyl, wherein said $C_{1-6}$alkyl, carbocyclyl, and heterocyclyl in each occurrence are optionally and independently substituted on carbon with one or more $R^{10}$, and wherein any —NH— moiety of said heterocyclyl is optionally substituted with $R^{10*}$;

$R^{1b}$ in each occurrence is independently selected from $C_{1-6}$alkyl, $C_{2-6}$alkenyl, $C_{2-6}$alkynyl, carbocyclyl, and heterocyclyl, wherein said $C_{1-6}$alkyl, $C_{2-6}$alkenyl, $C_{2-6}$alkynyl, carbocyclyl, and heterocyclyl in each occurrence are optionally and independently substituted on carbon with one or more $R^{10}$, and wherein any —NH— moiety of said heterocyclyl is optionally substituted with $R^{10*}$;

$R^2$ is selected from H, halo, and —CN;

$R^3$ is selected from H, halo, —CN, $C_{1-6}$alkyl, $C_{2-6}$alkenyl, $C_{2-6}$alkynyl, —OR$^{3a}$, —SR$^{3a}$, and —N(R$^{3a}$)$_2$, wherein said $C_{1-6}$alkyl, $C_{2-6}$alkenyl, and $C_{2-6}$alkynyl are optionally substituted on carbon with one or more $R^{30}$;

$R^{3a}$ in each occurrence is independently selected from H and $C_{1-6}$alkyl, wherein said $C_{1-6}$alkyl in each occurrence is optionally and independently substituted on carbon with one or more $R^{30}$;

$R^4$ in each occurrence is independently selected from halo, —CN, $C_{1-6}$alkyl, $C_{2-6}$alkenyl, $C_{2-6}$alkynyl, carbocyclyl, heterocyclyl, —OR$^{4a}$, —SR$^{4a}$, —N(R$^{4a}$)$_2$, —N(R$^{4a}$)C(O)R$^{4b}$, —N(R$^{4a}$)N(R$^{4a}$)$_2$, —NO$_2$, —N(R$^{4a}$)—OR$^{4a}$, —O—N(R$^{4a}$)$_2$, —C(O)H, —C(O)R$^{4b}$, —C(O)$_2$R$^{4a}$, —C(O)N(R$^{4a}$)$_2$, —C(O)N(R$^{4a}$)(OR$^{4a}$)—OC(O)N(R$^{4a}$)$_2$, —N(R$^{4a}$)C(O)$_2$R$^{4a}$, —N(R$^{4a}$)C(O)N(R$^{4a}$)$_2$, —OC(O)R$^{4b}$, —S(O)R$^{4b}$, —S(O)$_2$R$^{4b}$, —S(O)$_2$N(R$^{4a}$)$_2$, —N(R$^{4a}$)S(O)$_2$R$^{4b}$, —C(R$^{4a}$)=N(R$^{4a}$), and —C(R$^{4a}$)=N(OR$^{4a}$), wherein said $C_{1-6}$alkyl, $C_{2-6}$alkenyl, $C_{2-6}$alkynyl, carbocyclyl, and heterocyclyl are optionally substituted on carbon with one or more $R^{40}$, and wherein any —NH— moiety of said heterocyclyl is optionally substituted with $R^{40*}$;

$R^{4*}$ in each occurrence is independently selected from $C_{1-6}$alkyl, carbocyclyl, heterocyclyl, —C(O)H, —C(O)R$^{4b}$, —C(O)$_2$R$^{4a}$, —C(O)N(R$^{4a}$)$_2$, —S(O)R$^{4b}$, —S(O)$_2$R$^{4b}$, —S(O)$_2$N(R$^{4a}$)$_2$, —C(R$^{4a}$)=N(R$^{4a}$), and —C(R$^{4a}$)=N(OR$^{4a}$), wherein said $C_{1-6}$alkyl, carbocyclyl, and heterocyclyl in each occurrence are optionally and independently substituted on carbon with one or more $R^{40}$, and wherein any —NH— moiety of said heterocyclyl is optionally substituted with $R^{40*}$;

$R^{4a}$ in each occurrence is independently selected from H, $C_{1-6}$alkyl, carbocyclyl, and heterocyclyl, wherein said $C_{1-6}$alkyl, carbocyclyl, and heterocyclyl in each occurrence are optionally and independently substituted on carbon with one or more $R^{40}$, and wherein any —NH— moiety of said heterocyclyl is optionally substituted with $R^{40*}$;

$R^{4b}$ in each occurrence is independently selected from $C_{1-6}$alkyl, $C_{2-6}$alkenyl, $C_{2-6}$alkynyl, carbocyclyl, and heterocyclyl, wherein said $C_{1-6}$alkyl, $C_{2-6}$alkenyl, $C_{2-6}$alkynyl, carbocyclyl, and heterocyclyl in each occurrence are optionally and independently substituted on carbon with one or more $R^{40}$, and wherein any —NH— moiety of said heterocyclyl is optionally substituted with $R^{40*}$;

$R^{10}$ in each occurrence is independently selected from halo, —CN, $C_{1-6}$alkyl, $C_{2-6}$alkenyl, $C_{2-6}$alkynyl, carbocyclyl, heterocyclyl, —OR$^{10a}$, —SR$^{10a}$, —N(R$^{10a}$)$_2$, —N(R$^{10a}$)C(O)R$^{10b}$, —N(R$^{10a}$)N(R$^{10a}$)$_2$, —NO$_2$, —C(O)R$^{10b}$, —N(R$^{10a}$)—OR$^{10a}$, —O—N(R$^{10a}$)$_2$, —C(O)H, —C(O)R$^{10b}$, —C(O)$_2$R$^{10a}$, —C(O)N(R$^{10a}$)$_2$, —C(O)N(R$^{10a}$)(OR$^{10a}$), —OC(O)N(R$^{10a}$)$_2$, —N(R$^{10a}$)C(O)$_2$R$^{10a}$, —N(R$^{10a}$)C(O)N(R$^{10a}$)$_2$, —OC(O)R$^{10b}$, —S(O)R$^{10b}$, —S(O)$_2$R$^{10b}$, —S(O)$_2$N(R$^{10a}$)$_2$, —N(R$^{10a}$)S(O)$_2$R$^{10b}$, —C(R$^{10a}$)=N(R$^{10a}$), and N(OR$^{10a}$), wherein said $C_{1-6}$alkyl, $C_{2-6}$alkenyl, $C_{2-6}$alkynyl, carbocyclyl, and heterocyclyl in each occurrence are optionally and independently substituted on carbon with one or more $R^a$, and wherein any —NH— moiety of said heterocyclyl is optionally substituted with $R^{a*}$;

$R^{10*}$ in each occurrence is independently selected from $C_{1-6}$alkyl, carbocyclyl, heterocyclyl, —C(O)H, —C(O)R$^{10b}$, —C(O)$_2$R$^{10a}$, —C(O)N(R$^{10a}$)$_2$, —S(O)R$^{mb}$, —S(O)$_2$R$^{10b}$, —S(O)$_2$N(R$^{10a}$)$_2$, —C(R$^{10a}$)=N(R$^{10a}$), and —C(R$^{10a}$)=N(OR$^{10a}$), wherein said $C_{1-6}$alkyl, carbocyclyl, and heterocyclyl in each occurrence are optionally and independently substituted on carbon with one or more $R^a$, and wherein any —NH— moiety of said heterocyclyl is optionally substituted with $R^{a*}$;

$R^{10a}$ in each occurrence is independently selected from H, $C_{1-6}$alkyl, carbocyclyl, and heterocyclyl, wherein said $C_{1-6}$alkyl, carbocyclyl, and heterocyclyl in each occurrence are optionally and independently substituted on carbon with one or more $R^a$, and wherein any —NH— moiety of said heterocyclyl is optionally substituted with $R^{a*}$;

$R^{10b}$ in each occurrence is independently selected from $C_{1-6}$alkyl, $C_{2-6}$alkenyl, $C_{2-6}$alkynyl, carbocyclyl, and heterocyclyl, wherein said $C_{1-6}$alkyl, $C_{2-6}$alkenyl, $C_{2-6}$alkynyl, carbocyclyl, and heterocyclyl in each occurrence are optionally and independently substituted on carbon with one or more $R^a$, and wherein any —NH— moiety of said heterocyclyl is optionally substituted with $R^{a*}$;

$R^{30}$ in each occurrence is independently selected from halo, —CN, $C_{1-6}$alkyl, $C_{2-6}$alkenyl, $C_{2-6}$alkynyl, —OR$^{30a}$, —SR$^{30a}$, and —N(R$^{30a}$)$_2$;

$R^{30a}$ in each occurrence is independently selected from H and $C_{1-6}$alkyl;

$R^{40}$ in each occurrence is independently selected from halo, —CN, $C_{1-6}$alkyl, $C_{2-6}$alkenyl, $C_{2-6}$alkynyl, carbocyclyl, heterocyclyl, —OR$^{40a}$, —SR$^{40a}$, —N(R$^{40a}$)$_2$, —N(R$^{40a}$)C(O)R$^{40b}$, —N(R$^{40a}$)N(R$^{40a}$)$_2$, —NO$_2$, —N(R$^{40a}$)—OR$^{40a}$, —O—N(R$^{40a}$)$_2$, —C(O)H, —C(O)R$^{40b}$, —C(O)$_2$R$^{40a}$, —C(O)N(R$^{40a}$)$_2$, —C(O)N(R$^{40a}$)(OR$^{40a}$), —OC(O)N(R$^{40a}$)$_2$, —N(R$^{40a}$)C(O)$_2$R$^{40a}$, —N(R$^{40a}$)C(O)N(R$^{40a}$)$_2$, —OC(O)R$^{40b}$, —S(O)R$^{40b}$, —S(O)$_2$R$^{40b}$, —S(O)$_2$N(R$^{40a}$)$_2$, —N(R$^{40a}$)S(O)$_2$R$^{40b}$, —C(R$^{40a}$)=N(R$^{40a}$), and —C(R$^{40a}$)=N(OR$^{40a}$);

$R^{40*}$ in each occurrence is independently selected from $C_{1-6}$alkyl, carbocyclyl, heterocyclyl, —C(O)H, —C(O)R$^{40b}$, —C(O)$_2$R$^{40a}$, —C(O)N(R$^{40a}$)$_2$, —S(O)R$^{40b}$, —S(O)$_2$R$^{40b}$, —S(O)$_2$N(R$^{40a}$)$_2$, —C(R$^{40a}$)=N(R$^{40a}$), and —C(R$^{40a}$)=N(OR$^{40a}$);

$R^{40a}$ in each occurrence is independently selected from H, $C_{1-6}$alkyl, carbocyclyl, and heterocyclyl;

$R^{40b}$ in each occurrence is independently selected from $C_{1-6}$alkyl, $C_{2-6}$alkenyl, $C_{2-6}$alkynyl, carbocyclyl, and heterocyclyl;

$R^a$ in each occurrence is independently selected from halo, —CN, $C_{1-6}$alkyl, $C_{2-6}$alkenyl, $C_{2-6}$alkynyl, carbocyclyl, heterocyclyl, —OR$^m$, —SR$^m$, —N(R$^m$)$_2$, —N(R$^m$)C(O)R$^n$, —N(R$^m$)N(R$^m$)$_2$, —NO$_2$, —N(R$^m$)—OR$^m$, —O—N(R$^m$)$_2$, —C(O)H, —C(O)R$^n$, —C(O)$_2$R$^m$, —C(O)N(R$^m$)$_2$, —C(O)N(R$^m$)(OR$^m$), —OC(O)N(R$^m$)$_2$, —N(R$^m$)C(O)$_2$R$^m$, —N(R$^m$)C(O)N(R$^m$)$_2$, —OC(O)R$^n$, —S(O)R$^n$, —S(O)$_2$R$^n$, —S(O)$_2$N(R$^m$)$_2$, —N(R$^m$)S(O)$_2$R$^n$, —C(R$^m$)=N(R$^m$), and —C(R$^m$)=N(OR$^m$);

$R^{a*}$ in each occurrence is independently selected from $C_{1-6}$alkyl, carbocyclyl, heterocyclyl, —C(O)H, —C(O)R$^n$, —C(O)$_2$R$^m$, —C(O)N(R$^m$)$_2$, —S(O)R$^n$, —S(O)$_2$R$^n$, —S(O)$_2$N(R$^m$)$_2$, —C(R$^m$)=N(R$^m$), and —C(R$^m$)=N(OR$^m$);

$R^m$ in each occurrence is independently selected from H, $C_{1-6}$alkyl, carbocyclyl, and heterocyclyl; and $R^n$ in each occurrence is independently selected from $C_{1-6}$alkyl, $C_{2-6}$alkenyl, $C_{2-6}$alkynyl, carbocyclyl, and heterocyclyl.

Alkyl—As used herein the term "alkyl" refers to both straight and branched chain saturated hydrocarbon radicals having the specified number of carbon atoms. References to individual alkyl groups such as "propyl" are specific for the straight chain version only and references to individual branched chain alkyl groups such as 'isopropyl' are specific for the branched chain version only. In one aspect, "alkyl" is methyl.

Alkylene—As used herein the term "alkylene" refers to both straight and branched chain saturated hydrocarbon diradicals having the specified number of carbon atoms. For example, "$C_{1-6}$alkylene" includes groups such as $C_{1-3}$alkylene, methylene, ethylene, propylene, isopropylene, butylene, pentylene, and hexylene.

Alkenyl—As used herein, the term "alkenyl" refers to both straight and branched chain hydrocarbon radicals having the specified number of carbon atoms and containing at least one carbon-carbon double bond. For example, "$C_{2-6}$alkenyl" includes groups such as $C_{2-5}$alkenyl, $C_{2-4}$alkenyl, ethenyl, 2-propenyl, 2-methyl-2-propenyl, 3-butenyl, 4-pentenyl, 5-hexenyl, 2-heptenyl, and 2-methyl-1-heptenyl.

Alkenylene—As used herein, the term "alkenylene" refers to both straight and branched chain hydrocarbon radicals having the specified number of carbon atoms and containing at least one carbon-carbon double bond. In one aspect, "alkenylene" may be ethene-1,2-diyl.

Alkynyl—As used herein, the term "alkynyl" refers to both straight and branched chain hydrocarbon radicals having the specified number of carbon atoms and containing at least one carbon-carbon triple bond. For example, "$C_{2-8}$alkynyl" includes groups such as $C_{2-6}$alkynyl, $C_{2-4}$alkynyl, ethynyl, 2-propynyl, 2-methyl-2-propynyl, 3-butynyl, 4-pentynyl, 5-hexynyl, 2-heptynyl, and 4-methyl-5-heptynyl.

Alkynylene—As used herein, the term "alkynylene" refers to both straight and branched chain hydrocarbon radicals having the specified number of carbon atoms and containing at least one carbon-carbon triple bond. In one aspect, "alkynylene" may be ethyne-1,2-diyl.

Halo—As used herein, the term "halo" is intended to include fluoro, chloro, bromo and iodo. In one aspect, the "halo" may refer fluoro, chloro, and bromo. In another aspect, "halo" may refer to fluoro and chloro. In still another aspect, "halo" may refer to fluoro. In yet another aspect, "halo" may refer to chloro.

Carbocyclyl—As used herein, the term "carbocyclyl" refers to a saturated, partially saturated, or unsaturated, mono or bicyclic carbon ring that contains 3-12 atoms, wherein one or more —CH$_2$— groups may optionally be replaced by a corresponding number of —C(O)— groups. In one aspect, the term "carbocyclyl" may refer to a monocyclic ring containing 5 or 6 atoms or a bicyclic ring containing 9 or 10 atoms. Illustrative examples of "carbocyclyl" include adamantyl, cyclopropyl, cyclobutyl, cyclopentyl, cyclopentenyl, cyclohexyl, cyclohexenyl, 1-oxocyclopentyl, phenyl, naphthyl, tetralinyl, indanyl or 1-oxoindanyl. In one aspect, "carbocyclyl" may be phenyl. In another aspect, "carbocyclyl" may be selected from cyclopropyl, cyclobutyl, cyclopentyl, cyclopentenyl, and cyclohexyl. In still another aspect, carbocyclyl may be phenyl.

3- to 6-Membered Carbocyclyl—In one aspect, "carbocyclyl" may be "3- to 6-membered carbocyclyl." The term "3- to 6-membered carbocyclyl" refers to a saturated or partially saturated monocyclic carbon ring containing 3 to 6 ring atoms, of which one or more —CH$_2$— groups may be optionally replaced with a corresponding number of —C(O)— groups. Illustrative examples of "3- to 6-membered carbocyclyl" include cyclopropyl, cyclobutyl, cyclopentyl, oxocyclopentyl, cyclopentenyl, cyclohexyl, and phenyl. In another aspect, "3- to 6-membered carbocyclyl" may be cyclopropyl and phenyl. In still another aspect, "3- to 6-membered carbocyclyl" may be phenyl.

3- to 5-Membered Carbocyclyl—In one aspect, "carbocyclyl" and "3- to 6-membered carbocyclyl" may be "3- to 5-membered carbocyclyl." The term "3- to 5-membered carbocyclyl" refers to a saturated or partially saturated monocyclic carbon ring containing 3 to 5 ring atoms, of which one or more —CH$_2$— groups may be optionally replaced with a corresponding number of —C(O)— groups. Illustrative examples of "3- to 5-membered carbocyclyl" include cyclopropyl, cyclobutyl, cyclopentyl, and cyclopentenyl. In one aspect, "3- to 5-membered carbocyclyl" may be cyclopropyl.

Heterocyclyl—As used herein, the term "heterocyclyl" refers to a saturated, partially saturated or unsaturated, mono or bicyclic ring containing 4 to 12 atoms of which at least one atom is selected from nitrogen, sulfur or oxygen, which may, unless otherwise specified, be carbon or nitrogen linked, wherein one or more —CH$_2$— groups can optionally be replaced with a corresponding number of —C(O)— groups. Ring sulfur atoms may be optionally oxidized to form S-oxides. Ring nitrogen atoms may be optionally oxidized to form N-oxides. Illustrative examples of the term "heterocyclyl" include benzimidazolyl, 1,3-benzodioxolyl, benzofuranyl, 1-benzothiophenyl, 1,3-benzothiazolyl, 1,3-benzoxazolyl, dioxidotetrahydrothiophenyl, 3,5-dioxopiperidinyl, imidazolyl, indolyl, isoquinolone, isothiazolyl, isoxazolyl, morpholinyl, 1,2,4-oxadiazolyl, oxoimidazolidinyl, 2-oxopyrrolidinyl, 2-oxotetrahydrofuranyl, 2-oxo-1,3-thiazolidinyl, piperazinyl, piperidylpiperidinyl, pyranyl, pyrazolyl, pyridinyl, pyrrolyl, pyrrolidinyl, pyrrolinyl, pyrimidyl, pyrazinyl, pyrazolyl, pyridazinyl, 4-pyridone, quinolyl, tetrazolyl, tetrahydrofuranyl, tetrahydropyranyl, thiazolyl, 1,3,4-thiadiazolyl, thiazolidinyl, thienyl, thiomorpholino, 4H-1,2,4-triazolyl, pyridine-N-oxide and quinoline-N-oxide. In one aspect of the invention the term "heterocyclyl" may refer to a saturated, partially saturated, or unsaturated, monocyclic ring containing 5 or 6 atoms of which at least one atom is chosen from nitrogen, sulfur or oxygen, and may, unless otherwise specified, be carbon or nitrogen linked, and a ring nitrogen atom may be optionally oxidized to form an N-oxide.

4- to 6-Membered Heterocyclyl—In one aspect, "heterocycl" may be "4- to 6-membered heterocyclyl." The term "4- to 6-membered heterocyclyl" refers to a saturated, partially saturated, or unsaturated, monocyclic ring containing 4 to 6 ring atoms, of which at least one ring atom is selected from nitrogen, sulfur, and oxygen, and of which a —CH$_2$— group may be optionally replaced by a —C(O)— group. Unless otherwise specified, "4- to 6-membered heterocyclyl" groups may be carbon or nitrogen linked. Ring nitrogen atoms may be optionally oxidized to form an N-oxide. Ring sulfur atoms may be optionally oxidized to form S-oxides. Illustrative examples of "4- to 6-membered heterocyclyl" include, but are not limited to, azetidin-1-yl, dioxidotetrahydrothiophenyl, 2,4-dioxoimidazolidinyl, 3,5-dioxopiperidinyl, furanyl, imidazolyl, isothiazolyl, isoxazolyl, morpholinyl, oxazolyl, oxetanyl, oxoimidazolidinyl, 3-oxo-1-piperazinyl, 2-oxopyrrolidinyl, 2-oxotetrahydrofuranyl, oxo-1,3-thiazolidinyl, piperazinyl, piperidyl, 2H-pyranyl, pyrazolyl, pyridinyl, pyrrolyl, pyrrolidinyl, pyrimidinyl, pyrazinyl, pyrazolyl, pyridazinyl, 4-pyridonyl, tetrahydrofuranyl, tetrahydropyranyl, thiazolyl, 1,3,4-thiadiazolyl, thiazolidinyl, thiomorpholinyl, thiophenyl, 4H-1,2,4-triazolyl, and pyridine-N-oxidyl.

5- or 6-Membered Heterocyclyl—In one aspect, "heterocyclyl" and "4- to 6-membered heterocyclyl" may be "5- or 6-membered heterocyclyl," which refers to a saturated, partially saturated, or unsaturated, monocyclic ring containing 5 or 6 ring atoms, of which at least one ring atom is selected from nitrogen, sulfur, and oxygen, and of which one or more —CH$_2$— groups may be optionally replaced with a corresponding number of —C(O)— groups. Unless otherwise specified, "5- or 6-membered heterocyclyl" groups may be carbon or nitrogen linked. Ring nitrogen atoms may be optionally oxidized to form an N-oxide. Ring sulfur atoms may be optionally oxidized to form S-oxides. Illustrative examples of "5- or 6-membered heterocyclyl" include dioxidotetrahydrothiophenyl, 2,4-dioxoimidazolidinyl, 3,5-dioxopiperidinyl, furanyl, imidazolyl, isothiazolyl, isoxazolyl, morpholinyl, oxazolyl, oxoimidazolidinyl, 2-oxopyrrolidinyl, 2-oxotetrahydrofuranyl, oxo-1,3-thiazolidinyl, piperazinyl, piperidinyl, 2H-pyranyl, pyrazolyl, pyridinyl, pyrrolyl, pyrrolidinyl, pyrimidinyl, pyrazinyl, pyrazolyl, pyridazinyl, 4-pyridonyl, tetrazolyl, tetrahydrofuranyl, tetrahydropyranyl, thiazolyl, 1,3,4-thiadiazolyl, 1,34-thiazolidinyl, thiomorpholinyl, thiophenyl, 4H-1,2,4-triazolyl, and pyridine-N-oxidyl.

6-Membered Heterocyclyl—In one aspect, "heterocyclyl," "4- to 6-membered heterocyclyl," and "5- or 6-membered heterocyclyl" may be "6-membered heterocyclyl," which refers to a saturated, partially saturated, or unsaturated, monocyclic ring containing 6 ring atoms, of which at least one ring atom is selected from nitrogen, sulfur, and oxygen, and of which one or more —CH$_2$— groups may be optionally replaced with a corresponding number of —C(O)— groups. Unless otherwise specified, "6-membered heterocyclyl" groups may be carbon or nitrogen linked. Ring nitrogen atoms may be optionally oxidized to form an N-oxide. Ring sulfur atoms may be optionally oxidized to form S-oxides. Illustrative examples of "6-membered heterocyclyl" include 3,5-dioxopiperidinyl, morpholinyl, 3-oxo-1-piperazinyl, piperazinyl, piperidinyl, 2H-pyranyl, pyrazinyl, pyridazinyl, pyridinyl, and pyrimidinyl.

5 or 6-Membered Non-Aromatic Heterocyclyl—In one aspect, "heterocyclyl" and "5- or 6-membered heterocyclyl" may be "5 or 6-membered non-aromatic heterocyclyl." The term "5- or 6-membered non-aromatic heterocyclyl" is intended to refer to a saturated or partially saturated, monocyclic, non-aromatic heterocyclyl ring containing 5 or 6 ring atoms, of which at least one ring atom is selected from nitrogen, sulfur, and oxygen, and which may, unless otherwise specified, be carbon or nitrogen linked, and of which one or more —CH$_2$— group can optionally be replaced with a corresponding number of —C(O)— groups. Ring sulfur atoms may be optionally oxidized to form S-oxides. Ring nitrogen atoms may be optionally oxidized to form N-oxides. Illustrative examples of "5 or 6-membered non-aromatic heterocyclyl" include dioxidotetrahydrothiophenyl, 2,4-dioxoimidazolidinyl, 3,5-dioxopiperidinyl, morpholinyl, oxoimidazolidinyl, 2-oxopyrrolidinyl, 2-oxotetrahydrofuranyl, oxo-1,3-thiazolidinyl, piperazinyl, piperidinyl, 2H-pyranyl, pyrrolidinyl, tetrahydrofuranyl, tetrahydropyranyl, thiomorpholinyl, and thiazolidinyl.

5- or 6-Membered Heteroaryl—In one aspect, "heterocyclyl" and "5- or 6-membered heterocyclyl" may be "5- or 6-membered heteroaryl." The term "5- or 6-membered heteroaryl" is intended to refer to a monocyclic, aromatic heterocyclyl ring containing 5 or 6 ring atoms, of which at least one ring atom is selected from nitrogen, sulfur, and oxygen. Unless otherwise specified, "5- or 6-membered heteroaryl" groups may be carbon or nitrogen linked. Ring nitrogen atoms may be optionally oxidized to form an N-oxide. Ring sulfur atoms may be optionally oxidized to form S-oxides. Illustrative examples of "5- or 6-membered heteroaryl" include furanyl, imidazolyl, isothiazolyl, isoxazole, oxazolyl, pyrazinyl, pyrazolyl, pyridazinyl, pyrimidinyl, pyridinyl, pyrrolyl, tetrazolyl, 1,3,4-thiadiazolyl, thiazolyl, thiophenyl, 4H-1,2,4-triazolyl.

6-Membered Heteroaryl—In one aspect, "heterocyclyl," 5- or 6-membered heterocyclyl," "6-membered heterocyclyl," and "5- or 6-membered heteroaryl" may be "6-membered heteroaryl." The term "6-membered heteroaryl" is intended to refer to a monocyclic, aromatic heterocyclyl ring containing 6 ring atoms. Ring nitrogen atoms may be optionally oxidized to form an N-oxide. Illustrative examples of "6-membered heteroaryl" include pyrazinyl, pyridazinyl, pyrimidinyl, and pyridinyl.

Fused 5- to 7-Membered Heterocycle—For the purposes of Ring A, the term "fused 5- to 7-membered heterocycle" is intended to refer to a non-aromatic monocyclic ring containing 5 or 7 ring atoms, which shares two atoms, a carbon and nitrogen, with the piperidine ring of Formula (I) to which it is fused, forming a bicyclic ring system. The "fused 5- to 7-membered heterocycle" may contain, in addition to the bridgehead nitrogen shown in Formula (I), one or more ring heteroatom moieties selected from —O—, —NH—, and —S—. Ring sulfur atoms may be optionally oxidized to form S-oxides, ring nitrogen atoms may be optionally oxidized to form N-oxides, and one or more —CH$_2$— groups can optionally be replaced by a corresponding number of —C(O)— or —C=N(OR$^{4a}$)— groups. Illustrative examples of the term "fused 5- to 7-membered heterocycle" include fused azepane, fused 3,5-dioxopiperidine, fused morpholine, fused oxopiperidine, fused 2-oxopyrrolidine, fused oxo-1,3-thiazolidine, fused piperazine, fused piperidine, fused pyrrolidine, fused thiazolidine, and fused thiomorpholine. In one aspect, "fused 5- to 7-membered heterocycle" is fused morpholine.

Fused 6-Membered Heterocycle—In one aspect "fused 5 to 7-membered heterocycle" may be "fused 6-membered heterocycle." The term "fused 6-membered heterocycle" is intended to refer to a non-aromatic monocyclic ring containing 6 ring atoms, which shares two atoms, a carbon and nitrogen, with the piperidine ring to which it is fused, forming a bicyclic ring system. The "fused 6-membered heterocycle" may contain, in addition to the bridgehead nitrogen shown in Formula (I), one or more ring heteroatom moieties selected from —O—, —NH—, and —S—. Ring sulfur atoms may be optionally oxidized to form S-oxides, ring nitrogen atoms may be optionally oxidized to form N-oxides, and one or more —CH$_2$— groups can optionally be replaced by a corresponding number of —C(O)— or —C=N(OR$^{4a}$)— groups. Illustrative examples of the term "fused 6-membered heterocycle" include, fused 3,5-dioxopiperidine, fused morpholine, fused oxopiperidine, fused piperazine, fused piperidine, and fused thiomorpholine. In one aspect, "fused 6-membered heterocycle" is fused morpholine.

To resolve any potential ambiguity in the discussion of "fused 5- to 7-membered heterocycle" and "fused 6-membered heterocycle" above the term "piperidine ring" is intended to denote the nitrogen-containing, six-membered ring enclosed by the dotted lines in the following structure:

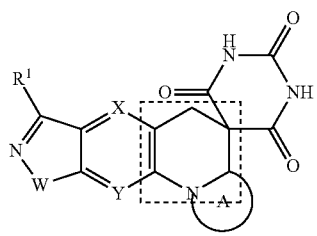

To resolve any potential ambiguity in the discussion of "fused 5- to 7-membered heterocycle" and "fused 6-membered heterocycle" above, the term "fused morpholine" is intended to denote the 6-membered oxygen- and nitrogen-containing ring enclosed by the dotted lines in the following structure:

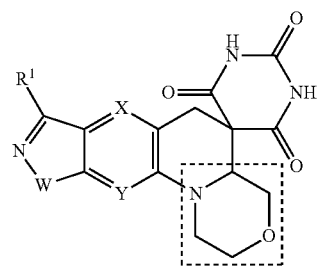

The morpholine ring may be optionally substituted as indicated hereinabove and hereinbelow.

Optionally substituted—As used herein, the phrase "optionally substituted" indicates that substitution is optional and therefore it is possible for the designated group to be either substituted or unsubstituted. In the event a substitution is desired, the appropriate number of hydrogens on the designated group may be replaced with a selection from the indicated substituents, provided that the normal valency of the atoms on a particular substituent is not exceeded, and that the substitution results in a stable compound.

In one aspect, when a particular group is designated as being optionally substituted with one or more substituents, the particular group may be unsubstituted. In another aspect, the particular group may bear one substituent. In another aspect, the particular substituent may bear two substituents. In still another aspect, the particular group may bear three substituents. In yet another aspect, the particular group may bear four substituents. In a further aspect, the particular group may bear one or two substituents. In still a further aspect, the particular group may be unsubstituted, or may bear one or two substituents.

Pharmaceutically Acceptable—As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Effective Amount—As used herein, the phrase "effective amount" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician.

Leaving Group—As used herein, the phrase "leaving group" is intended to refer to groups readily displaceable by a nucleophile such as an amine nucleophile, and alcohol nucleophile, or a thiol nucleophile. Examples of suitable leaving groups include halo, such as fluoro, chloro, bromo, and sulfonyloxy group, such as methanesulfonyloxy and toluene-4-sulfonyloxy.

Protecting Group—As used herein, the term "protecting group" is intended to refer to those groups used to prevent selected reactive groups (such as carboxy, amino, hydroxy, and mercapto groups) from undergoing undesired reactions.

Illustrative examples of suitable protecting groups for a hydroxy group include acyl groups; alkanoyl groups such as acetyl; aroyl groups, such as benzoyl; silyl groups, such as trimethylsilyl; and arylmethyl groups, such as benzyl. The deprotection conditions for the above hydroxy protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively a silyl group such as trimethylsilyl may be removed, for example, by fluoride or by aqueous acid; or an arylmethyl group such as a benzyl group may be removed, for example, by hydrogenation in the presence of a catalyst such as palladium-on-carbon.

Illustrative examples of suitable protecting groups for an amino group include acyl groups; alkanoyl groups such as acetyl; alkoxycarbonyl groups, such as methoxycarbonyl, ethoxycarbonyl, and t-butoxycarbonyl; arylmethoxycarbonyl groups, such as benzyloxycarbonyl; and aroyl groups, such benzoyl. The deprotection conditions for the above amino protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulfuric, phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid, for example boron trichloride). A suitable alternative protecting group for a primary amino group is, for example, a phthaloyl group, which may be removed by treatment with an alkylamine, for example dimethylaminopropylamine or 2-hydroxyethylamine, or with hydrazine. Another suitable protecting group for an amine is, for example, a cyclic ether such as tetrahydrofuran, which may be removed by treatment with a suitable acid such as trifluoroacetic acid.

The protecting groups may be removed at any convenient stage in the synthesis using conventional techniques well known in the chemical art, or they may be removed during a later reaction step or during work-up.

Compounds of Formula (I) may form stable pharmaceutically acceptable acid or base salts, and in such cases administration of a compound as a salt may be appropriate. Examples of acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethyl-sulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate. Examples of base salts include ammonium salts; alkali metal salts such as sodium, lithium and potassium salts; alkaline earth metal salts such as aluminum, calcium and magnesium salts; salts with organic bases such as dicyclohexylamine salts and N-methyl-D-glucamine; and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates such as dimethyl, diethyl, dibutyl; diamyl sulfates; long chain halides such as decyl, lauryl, myristyl and stearyl halides; arylalkyl halides such as benzyl bromide and others. Non-toxic physiologically-acceptable salts are preferred, although other salts may be useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

Some compounds of Formula (I) may have chiral centres and/or geometric isomeric centres (E- and Z-isomers), and it is to be understood that the invention encompasses all such optical, diastereoisomers and geometric isomers. The invention further relates to any and all tautomeric forms of the compounds of Formula (I).

It is also to be understood that certain compounds of Formula (I) can exist in solvated as well as unsolvated forms such as, for example, hydrated forms. It is to be understood that the invention encompasses all such solvated forms.

Additional embodiments of the invention are as follows. These additional embodiments relate to compounds of Formula (I) and pharmaceutically acceptable salts thereof. Such specific substituents may be used, where appropriate, with any of the definitions, claims or embodiments defined hereinbefore or hereinafter. All the embodiments disclosed hereinabove and hereinbelow are illustrative, and are not to be read as limiting the scope of the invention as defined by the claims.

Ring A

In one aspect, Ring A is fused 6-membered heterocycle, wherein said fused 6-membered heterocycle is optionally substituted on carbon with one or more $R^4$; and $R^4$ is $C_{1-6}$alkyl.

In another aspect, Ring A is fused morpholine, wherein said fused morpholine is optionally substituted with one or more $R^4$; and $R^4$ is $C_{1-6}$alkyl.

In still another aspect, Ring A is fused morpholine, wherein said fused morpholine is optionally substituted with one or more $R^4$; and $R^4$ is methyl.

In yet another aspect, Ring A, together with the piperidine ring to which it is fused, forms octahydropyrido[2,1-c][1,4]oxazine, wherein said octahydropyrido[2,1-c][1,4]oxazine is optionally substituted with one or more $R^4$; and $R^4$ is methyl.

In a further aspect, Ring A, together with the piperidine ring to which it is fused, forms 1,3-dimethyloctahydropyrido[2,1-c][1,4]oxazine.

In still a further aspect, Ring A, together with the piperidine ring to which it is fused, forms (1R,3S)-1,3-dimethyloctahydropyrido[2,1-c][1,4]oxazine.

W

In one aspect, W is —O—.

X

In one aspect, X is C—H.

Y

In one aspect, Y is C—$R^3$; and $R^3$ is halo.

In another aspect, Y is C—$R^3$; and $R^3$ is selected from fluoro and chloro.

In still another aspect, Y is C—$R^3$; and $R^3$ is fluoro.

$R^1$

In one aspect, $R^1$ is selected from $C_{1-6}$alkyl, 3- to 5-membered carbocyclyl, 5- or 6-membered heterocyclyl, —$OR^{1a}$, —$SR^{1a}$, —$N(R^{1a})_2$, —$N(R^{1a})C(O)R^{1b}$, —$C(O)N(R^{1a})_2$, —$C(O)R^{1b}$, —$C(O)_2R^{1a}$, —$C(O)N(R^{1a})_2$, —$C(O)N(R^{1a})(OR^{1a})$, and —$S(O)_2R^{1b}$, wherein said $C_{1-6}$alkyl, 3 to 5-membered carbocyclyl, and 5- or 6-membered heterocyclyl are optionally substituted on carbon with one or more $R^{10}$, and wherein any —NH— moiety of said 5- or 6-membered heterocyclyl is optionally substituted with $R^{10*}$;

$R^{1a}$ in each occurrence is independently selected from H, $C_{1-6}$alkyl, 3- to 5-membered carbocyclyl, and 5- or 6-membered heterocyclyl, wherein said $C_{1-6}$alkyl, 3- to 5-membered carbocyclyl, and 5- or 6-membered heterocyclyl in each occurrence are optionally and independently substituted with one or more $R^{10}$, wherein any —NH— moiety of said 5- or 6-membered heterocyclyl is optionally substituted with $R^{10*}$;

$R^{1b}$ in each occurrence is independently selected from $C_{1-6}$alkyl and 4- to 6-membered heterocyclyl, wherein said $C_{1-6}$alkyl and 4- to 6-membered heterocyclyl are optionally and independently substituted on carbon with one or more $R^{10}$, and wherein any —NH— moiety of said 4- to 6-membered heterocyclyl is optionally substituted with $R^{10*}$;

$R^{10}$ in each occurrence is independently selected from halo, —CN, $C_{1-6}$alkyl, 3- to 6-membered carbocyclyl, 5- or 6-membered heterocyclyl, —$OR^{10a}$, —$SR^{10a}$, —$N(R^{10a})_2$, —$N(R^{10a})C(O)R^{10b}$, —$C(O)_2R^{10a}$, —$C(O)N(R^{10a})_2$, wherein said $C_{1-6}$alkyl, 3- to 6-membered carbocyclyl, and 5- or 6-membered heterocyclyl in each occurrence are optionally substituted with one or more $R^a$, and wherein any —NH— moiety of said 5- or 6-membered heterocyclyl is optionally substituted with $R^{a*}$;

$R^{10*}$ in each occurrence is independently selected from $C_{1-6}$alkyl and —$C(O)R^{10b}$;

$R^{10a}$ in each occurrence is independently selected from H and $C_{1-6}$alkyl, wherein said $C_{1-6}$alkyl in each occurrence is optionally and independently substituted with one or more $R^a$;

$R^{10b}$ is $C_{1-6}$alkyl;

$R^a$ in each occurrence is independently selected from halo, —CN, and —$OR^m$;

$R^{a*}$ is $C_{1-6}$alkyl; and $R^m$ in each occurrence is independently selected from H and $C_{1-6}$alkyl.

In another aspect, $R^1$ is selected from $C_{1-6}$alkyl, 3- to 5-membered carbocyclyl, 5- or 6-membered heterocyclyl, and —$C(O)N(R^{1a})_2$, wherein said $C_{1-6}$alkyl, 3 to 5-membered carbocyclyl, and 5- or 6-membered heterocyclyl are optionally substituted on carbon with one or more $R^{10}$, and wherein any —NH— moiety of said 5- or 6-membered heterocyclyl is optionally substituted with $R^{10*}$;

$R^{1a}$ in each occurrence is independently selected from H and $C_{1-6}$alkyl, wherein said $C_{1-6}$alkyl in each occurrence is optionally and independently substituted with one or more $R^{10}$;

$R^{10}$ in each occurrence is independently selected from halo, —CN, $C_{1-6}$alkyl, 5- or 6-membered heterocyclyl, —$OR^{10a}$, —$SR^{10a}$, —$N(R^{10a})_2$, —$N(R^{10a})C(O)R^{10b}$, —$C(O)_2R^{10a}$, —$C(O)N(R^{10a})_2$; wherein said $C_{1-6}$alkyl in each occurrence is optionally and independently substituted with one or more $R^a$;

$R^{10*}$ in each occurrence is independently selected from $C_{1-6}$alkyl and —$C(O)R^{10b}$;

$R^{10a}$ in each occurrence is independently selected from H and $C_{1-6}$alkyl, wherein said $C_{1-6}$alkyl in each occurrence is optionally and independently substituted with one or more $R^a$;

$R^{10b}$ is $C_{1-6}$alkyl;

$R^a$ in each occurrence is independently selected from —$OR^m$ and halo; and $R^m$ in each occurrence is independently selected from H and $C_{1-6}$alkyl.

In still another aspect, $R^1$ is selected from $C_{1-6}$alkyl, 5- or 6-membered heterocyclyl, and —$C(O)N(R^{1a})_2$, wherein said $C_{1-6}$alkyl and 5- or 6-membered heterocyclyl are optionally substituted with one or more $R^{10}$, and wherein any —NH— moiety of said 5- or 6-membered heterocyclyl is optionally substituted with $R^{10*}$;

$R^{1a}$ in each occurrence is independently selected from H and $C_{1-6}$alkyl, wherein said $C_{1-6}$alkyl in each occurrence is optionally and independently substituted with one or more $R^{10}$;

$R^{10}$ in each occurrence is independently selected from halo, —CN, —$SR^{10a}$, and —$N(R^{10a})_2$;

$R^{10*}$ is $C_{1-6}$alkyl; and $R^{10a}$ in each occurrence is independently selected from H and $C_{1-6}$alkyl.

In one aspect, $R^1$ is selected from 3- to 5-membered carbocyclyl and 5- or 6-membered heterocyclyl, wherein said 3 to 5-membered carbocycyl and 5- or 6-membered heterocyclyl are optionally substituted on carbon with one or more $R^{10}$, and wherein any —NH— moiety of said 5- or 6-membered heterocyclyl is optionally substituted with $R^{10*}$;

$R^{10}$ in each occurrence is independently selected from halo, —CN, $C_{1-6}$alkyl, 5- or 6-membered heterocyclyl, —$OR^{10a}$, —$SR^{10a}$, —$N(R^{10a})_2$, —$N(R^{10a})C(O)R^{10b}$, —$C(O)_2R^{10a}$, —$C(O)N(R^{10a})_2$; wherein said $C_{1-6}$alkyl is optionally substituted with one or more $R^a$;

$R^{10*}$ in each occurrence is independently selected from $C_{1-6}$alkyl and —$C(O)R^{10b}$;

$R^{10a}$ in each occurrence is independently selected from H and $C_{1-6}$alkyl, wherein said $C_{1-6}$alkyl in each occurrence is optionally and independently substituted with one or more $R^a$;

$R^{10b}$ is $C_{1-6}$ alkyl;

$R^a$ in each occurrence is independently selected from —$OR^m$ and halo; and $R^m$ in each occurrence is independently selected from H and $C_{1-6}$alkyl.

In yet another aspect, $R^1$ is selected from 5- or 6-membered heterocyclyl, wherein said 5- or 6-membered heterocyclyl is optionally substituted on carbon with one or more $R^{10}$, and wherein any —NH— moiety of said 5- or 6-membered heterocyclyl is optionally substituted with $R^{10*}$;

$R^{10}$ in each occurrence is independently selected from halo, —CN, $C_{1-6}$alkyl, 5- or 6-membered heterocyclyl, —$OR^{10a}$, —$SR^{10a}$, —$N(R^{10a})_2$, —$N(R^{10a})C(O)R^{10b}$, —$C(O)_2R^{10a}$, —$C(O)N(R^{10a})_2$; wherein said $C_{1-6}$alkyl is optionally substituted with one or more $R^a$;

$R^{10*}$ in each occurrence is independently selected from $C_{1-6}$alkyl and —$C(O)R^{10b}$;

$R^{10a}$ in each occurrence is independently selected from H and $C_{1-6}$alkyl, wherein said $C_{1-6}$alkyl in each occurrence is optionally and independently substituted with one or more $R^a$;

$R^{10b}$ is $C_{1-6}$ alkyl;

$R^a$ in each occurrence is independently selected from —$OR^m$ and halo; and $R^m$ in each occurrence is independently selected from H and $C_{1-6}$alkyl.

In a further aspect, R¹ is selected from —C(O)R¹ᵇ, —C(O)₂R¹ᵃ, —C(O)N(R¹ᵃ)₂, and —C(O)N(R¹ᵃ)(OR¹ᵃ);

R¹ᵃ in each occurrence is independently selected from H, C₁₋₆alkyl, 3- to 5-membered carbocyclyl, and 5- or 6-membered heterocyclyl, wherein said C₁₋₆alkyl is optionally substituted with one or more R¹⁰, and wherein any —NH— moiety of said 5- or 6-membered heterocyclyl is optionally substituted with R¹⁰*;

R" in each occurrence is independently selected from C₁₋₆alkyl and 4- to 6-membered heterocyclyl, wherein said 4- to 6-membered heterocyclyl is optionally substituted on carbon with one or more R¹⁰, and wherein any —NH— moiety of said 4- to 6-membered heterocyclyl is optionally substituted with R¹⁰*;

R¹⁰ in each occurrence is independently selected from halo, —CN, 3- to 6-membered carbocyclyl, 5- or 6-membered heterocyclyl, —OR¹⁰ᵃ, and —N(R¹⁰ᵃ)C(O)R¹⁰ᵇ, wherein said 3- to 6-membered carbocyclyl is optionally substituted on carbon with one or more Rᵃ, and wherein any —NH— moiety of said 5- or 6-membered heterocyclyl is optionally substituted with Rᵃ*;

R¹⁰* is C₁₋₆alkyl;
R¹⁰ᵃ is C₁₋₆alkyl;
R¹⁰ᵇ is C₁₋₆alkyl;
Rᵃ is —CN; and
Rᵃ* is C₁₋₆alkyl.

In still a further aspect, R¹ is selected from —C(O)N(R¹ᵃ)₂;

R¹ᵃ in each occurrence is independently selected from H, C₁₋₆alkyl, and 3 to 5-membered carbocyclyl, wherein said C₁₋₆alkyl is optionally substituted with one or more R¹⁰;

R¹⁰ in each occurrence is independently selected from halo, 3- to 6-membered carbocyclyl, 5- or 6-membered heterocyclyl, and —OR¹⁰ᵃ, wherein said 3- to 6-membered carbocyclyl is optionally substituted on carbon with one or more Ra, and wherein any —NH— moiety of said 5- or 6-membered heterocyclyl is optionally substituted with Rᵃ*;

R¹⁰ᵃ is C₁₋₆alkyl;
Rᵃ is —CN; and
Rᵃ* is C₁₋₆alkyl.

In yet a further aspect, R¹ is selected from —C(O)N(R¹ᵃ)₂;
R¹ᵃ in each occurrence is independently selected from H and C₁₋₆alkyl.

In one aspect, R¹ is selected from C₁₋₆alkyl, 3- to 6-membered carbocyclyl, 5- or 6-membered heterocyclyl, —NH₂, and —N(H)C(O)R¹ᵇ; and
R¹ᵇ is C₁₋₆alkyl.

In another aspect, R¹ is selected from C₁₋₆alkyl and —C(O)N(R¹ᵃ)₂;
R¹ᵃ in each occurrence is independently selected from H and C₁₋₆alkyl, wherein said C₁₋₆alkyl in each occurrence is optionally substituted with one or more R¹⁰; and
R¹⁰ is halo.

In still another aspect, R¹ is selected from C₁₋₆alkyl, 3- to 6-membered carbocyclyl, 6-membered heterocyclyl, —NH₂, and —N(H)C(O)R¹ᵇ; and
R¹ᵇ is C₁₋₆alkyl.

In a further aspect, R¹ is C₁₋₆alkyl, wherein said C₁₋₆alkyl is optionally substituted with one or more R¹⁰; and
R¹⁰ in each occurrence is independently selected from halo and —OR¹⁰ᵃ;
R¹⁰ᵃ in each occurrence is independently selected from H and C₁₋₆alkyl.

In yet a further aspect, R¹ is C₁₋₆alkyl, wherein said C₁₋₆alkyl is optionally substituted with one or more halo.

In still a further aspect, R¹ is selected from aminocarbonyl, 2-aminopyrimidin-4-yl, 2-cyanopyrimidin-4-yl, 3,3-difluoroazetidin-1-yl, [(2,2-difluoroethyl)amino]carbonyl, difluoromethyl, (isopropylamino)carbonyl, methyl, (methylamino)carbonyl, 2-(methylsulfanyl)pyrimidin-4-yl, 1-methyl-1H-1,2,4-triazol-5-yl, pyrazin-2-yl, pyridazin-3-yl, pyrimidin-4-yl, pyrimidin-2-yl, 1,3-thiazol-2-yl, 1H-1,2,4-triazol-1-yl, 2H-1,2,3-triazol-2-yl, and trifluoromethyl.

In one aspect, R¹ is selected from methyl, phenyl, cyclopropyl, pyridinyl, —NH₂, and —N(H)C(O)R¹ᵇ; and
R¹ᵇ is methyl.

In another aspect, R¹ is selected from methyl, phenyl, cyclopropyl, pyridin-2-yl, —NH₂, and —N(H)C(O)R¹ᵇ; and
R¹ᵇ is methyl.

In still another aspect, R¹ is selected from methyl, (methylamino)carbonyl, and [(2,2-difluoroethyl)amino]carbonyl.

Ring A, W, X, Y, and R¹

In one aspect, Ring A is fused 6-membered heterocycle, wherein said fused 6-membered heterocycle is optionally substituted on carbon with one or more R⁴;
W is —O—;
X is C—H
Y is C—R³;
R¹ is selected from C₁₋₆alkyl, 3- to 6-membered carbocyclyl, 5- or 6-membered heterocyclyl, —NH₂, and —N(H)C(O)R¹ᵇ;
R¹ᵇ is C₁₋₆alkyl;
R³ is halo; and
R⁴ is C₁₋₆alkyl.

In another aspect, Ring A is fused morpholine, wherein said fused morpholine is optionally substituted with one or more R⁴;
W is —O—;
X is C—H
Y is C—R³;
R¹ is selected from C₁₋₆alkyl, 3- to 6-membered carbocyclyl, 6-membered heterocyclyl, —NH₂, and —N(H)C(O)R¹ᵇ;
R¹ᵇ is C₁₋₆alkyl;
R³ is halo; and
R⁴ is C₁₋₆alkyl.

In still another aspect, Ring A, together with the piperidine ring to which it is fused, forms 1,3-dimethyloctahydropyrido[2,1-c][1,4]oxazine;
W is —O—;
X is C—H;
Y is C—R³;
R¹ is selected from methyl, phenyl, cyclopropyl, pyridin-2-yl, —NH₂, and —N(H)C(O)R¹ᵇ;
R¹ᵇ is methyl; and
R³ is fluoro.

In yet another aspect, the compound of Formula (I) is a compound of Formula (Ia):

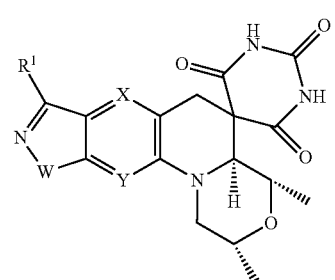

Formula (Ia)

or a pharmaceutically acceptable salt thereof, wherein W, X, Y, and R¹ are as described hereinabove.

In yet another aspect, the compound of Formula (I) is a compound of Formula (Ia):

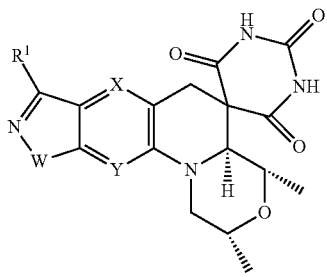

Formula (Ia)

or a pharmaceutically acceptable salt thereof, wherein $R^1$ is as described hereinabove, and wherein:
W is —O—;
X is C—H;
Y is C—$R^3$; and
$R^3$ is halo.

In a further aspect, the compound of Formula (I) is a compound of Formula (Ib):

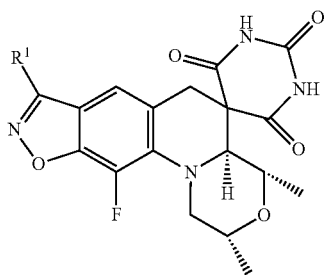

Formula (Ib)

or a pharmaceutically acceptable salt thereof, wherein $R^1$ is as described hereinabove.

In still a further aspect, present invention provides a compound of Formula (I) selected from the Examples, free bases thereof, and pharmaceutically acceptable salts thereof.

In yet a further aspect, the present invention provides a compound selected from:
(2R,4S,4aS)-8-Amino-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;
(2R,4S,4aS)-11-Fluoro-2,4,8-trimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;
(2R,4S,4aS)-11-Fluoro-2,4-dimethyl-8-phenyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;
(2R,4S,4aS)-8-Cyclopropyl-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;
(2R,4S,4aS)-11-Fluoro-2,4-dimethyl-8-pyridin-2-yl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;
N-[(2R,4S,4aS)-11-Fluoro-2,4-dimethyl-2',4',6'-trioxo-1,1',2,3',4,4',4a,6'-octahydro-2'H,6H-spiro[isoxazolo[4,5-g][1,4]oxazino[4,3-a]quinoline-5,5'-pyrimidin-8-yl]acetamide;
(2R,4S,4aS)-11-chloro-2,4,8-trimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;
(2R,4S,4aS)-8-(4-acetylpiperazin-1-yl)-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;
(2R,4S,4aS)-8-(benzylamino)-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;
(2R,4S,4aS)-11-fluoro-2,4-dimethyl-8-[(1,3-thiazol-2-ylmethyl)amino]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;
(2R,4S,4aS)-11-fluoro-8-[(1H-imidazol-4-ylmethyl)amino]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;
(2R,4S,4aS)-11-fluoro-2,4-dimethyl-8-{[(1-methyl-1H-pyrazol-4-yl)methyl]amino}-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;
(2R,4S,4aS)-11-fluoro-2,4-dimethyl-8-{[(5-methyl-1,2-oxazol-3-yl)methyl]amino}-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;
(2R,4S,4aS)-11-fluoro-2,4-dimethyl-8-[(pyridin-2-ylmethyl)amino]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;
(2R,4S,4aS)-11-fluoro-2,4-dimethyl-8-[(pyridin-3-ylmethyl)amino]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;
(2R,4S,4aS)-11-fluoro-2,4-dimethyl-8-[(pyridin-4-ylmethyl)amino]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;
(2R,4S,4aS)-8-[(cyclopropylmethyl)amino]-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;
(2R,4S,4aS)-8-[(cyclohexylmethyl)amino]-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;
(2R,4S,4aS)-11-fluoro-2,4-dimethyl-8-[(tetrahydro-2H-pyran-4-ylmethyl)amino]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;
tert-butyl 4-[(2R,4S,4aS)-11-fluoro-2,4-dimethyl-2',4',6'-trioxo-1,1',2,3',4,4',4a,6'-octahydro-2'H,6H-spiro[isoxazolo[4,5-g][1,4]oxazino[4,3-a]quinoline-5,5'-pyrimidin]-8-yl]piperazine-1-carboxylate;
(2R,4S,4aS)-11-fluoro-2,4-dimethyl-8-(piperazin-1-yl)-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;
(2R,4S,4aS)-11-fluoro-2,4-dimethyl-8-(morpholin-4-yl)-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;
(2R,4S,4aS)-8-(diethylamino)-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2R,4S,4aS)-8-(dimethylamino)-11-fluoro-2,4-dimethyl-1, 2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2R,4S,4aS)-11-fluoro-2,4-dimethyl-8-(pyrrolidin-1-yl)-1, 2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2R,4S,4aS)-8-(azepan-1-yl)-11-fluoro-2,4-dimethyl-1,2,4, 4a-tetrahydro-2'H,6H-spiro[isoxazolo[4,5-g][1,4]oxazino[4,3-a]quinoline-5,5'-pyrimidine]-2',4',6'(1'H,3'H)-trione;

(2R,4S,4aS)-11-fluoro-2,4-dimethyl-8-[5-methyl-3-(trifluoromethyl)-1H-pyrazol-1-yl]-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

N-{1-[(2R,4S,4aS)-11-fluoro-2,4-dimethyl-2',4',6'-trioxo-1, 1',2,3',4,4',4a,6'-octahydro-2'H,6H-spiro[1,4-oxazino[4, 3-a][1,2]oxazolo[4,5-g]quinoline-5,5'-pyrimidin]-8-yl]-1H-pyrazol-3-yl}acetamide;

(2R,4S,4aS)-11-fluoro-2,4-dimethyl-8-[3-(trifluoromethyl)-1H-pyrazol-1-yl]-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2R,4S,4aS)-8-[3-(difluoromethyl)-5-methyl-1H-pyrazol-1-yl]-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2R,4S,4aS)-11-fluoro-2,4-dimethyl-8-(propylamino)-1,2,4, 4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-8-[benzyl(methyl)amino]-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

3-amino-1-[(2R,4S,4aS)-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-1H-pyrazole-4-carbonitrile;

(2R,4S,4aS)-11-fluoro-2,4-dimethyl-8-[4-(pyrimidin-4-yl)-1H-pyrazol-1-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-[4-(pyrazin-2-yl)-1H-pyrazol-1-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-8-(4-iodo-1H-pyrazol-1-yl)-2,4-dimethyl-1,2,4,4a-tetrahydro-2'H,6H-spiro[1,4-oxazino[4,3-a][1,2]oxazolo[4,5-g]quinoline-5,5'-pyrimidine]-2', 4',6'(1'H,3'H)-trione;

ethyl 1-[(2R,4S,4aS)-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-1H-pyrazole-4-carboxylate;

(2R,4S,4aS)-11-chloro-2,4-dimethyl-8-(pyridin-2-yl)-1,2,4, 4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-chloro-8-cyclopropyl-2,4-dimethyl-1,2,4, 4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-chloro-2,4-dimethyl-8-(6-methylpyridin-3-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-chloro-2,4-dimethyl-8-(1,3-thiazol-5-yl)-1, 2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-chloro-2,4-dimethyl-8-(pyrimidin-2-yl)-1, 2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-chloro-2,4-dimethyl-8-(pyrimidin-4-yl)-1, 2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-chloro-2,4-dimethyl-8-(pyrimidin-5-yl)-1, 2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-chloro-2,4-dimethyl-8-(pyridazin-4-yl)-1,2, 4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-chloro-2,4-dimethyl-8-(pyridin-4-yl)-1,2,4, 4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-chloro-2,4-dimethyl-8-(pyridin-3-yl)-1,2,4, 4a-tetrahydro-2'H,6H-spiro[1,4-oxazino[4,3-a][1,2]oxazolo[4,5-g]quinoline-5,5'-pyrimidine]-2',4',6'(1'H,3'H)-trione (2R,4S,4aS)-11-chloro-2,4-dimethyl-8-(1,3-thiazol-2-yl)-1, 2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-chloro-8-(methoxymethyl)-2,4-dimethyl-1, 2,4,4a-tetrahydro-2'H,6H-spiro[1,4-oxazino[4,3-a][1,2]oxazolo[4,5-g]quinoline-5,5'-pyrimidine]-2',4',6'(1'H, 3'H)-trione;

(2R,4S,4aS)-11-fluoro-2,4-dimethyl-8-[methyl(propyl)amino]-1,2,4,4a-tetrahydro-2'H,6H-spiro[1,4-oxazino[4, 3-a][1,2]oxazolo[4,5-g]quinoline-5,5'-pyrimidine]-2',4',6' (1'H,3'H)trione;

(2R,4S,4aS)-11-fluoro-8-methoxy-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-8-(benzyloxy)-11-fluoro-2,4-dimethyl-1,2,4, 4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-(1H-1,2,4-triazol-1-yl)-1,2,4,4a-tetrahydro-2'H,6H-spiro[1,4-oxazino[4,3-a][1,2]oxazolo[4,5-g]quinoline-5,5'-pyrimidine]-2',4',6' (1'H,3'H)-trione;

(2R,4S,4aS)-11-fluoro-2,4-dimethyl-8-(3-methyl-1H-1,2,4-triazol-1-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

1-[(2R,4S,4aS)-11-fluoro-2,4-dimethyl-2',4',6'-trioxo-1,1',2, 3',4,4',4a,6'-octahydro-2'H,6H-spiro[1,4-oxazino[4,3-a][1,2]oxazolo[4,5-g]quinoline-5,5'-pyrimidin]-8-yl]-1H-1, 2,4-triazole-3-carbonitrile;

(2R,4S,4aS)-11-fluoro-2,4-dimethyl-8-(2H-1,2,3-triazol-2-yl)-1,2,4,4a-tetrahydro-2'H,6H-spiro[1,4-oxazino[4,3-a][1,2]oxazolo[4,5-g]quinoline-5,5'-pyrimidine]-2',4',6' (1'H,3'H)-trione;

(2R,4S,4aS)-11-fluoro-2,4-dimethyl-8-(1H-1,2,3-triazol-1-yl)-1,2,4,4a-tetrahydro-2'H,6H-spiro[1,4-oxazino[4,3-a][1,2]oxazolo[4,5-g]quinoline-5,5'-pyrimidine]-2',4',6' (1'H,3'H)-trione;

(2R,4S,4aS)-11-fluoro-8-(1H-imidazol-1-yl)-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-[4-(trifluoromethyl)-1H-imidazol-1-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-(4-methyl-1H-pyrazol-1-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-8-(4-chloro-1H-pyrazol-1-yl)-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-(methylsulfanyl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-8-(3,5-dimethyl-1H-pyrazol-1-yl)-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-(1H-pyrazol-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-(2-methyl-1,3-oxazol-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-(5-methyl-1,2-oxazol-3-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-8-(3,5-dimethyl-1,2-oxazol-4-yl)-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aR)-11-fluoro-2,4-dimethyl-8-(1-methyl-1H-imidazol-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-(1-methyl-1H-imidazol-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-(1-methyl-1H-imidazol-5-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-(4-methyl-1,3-thiazol-5-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-(4-methyl-1,2,3-thiadiazol-5-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-(pyridazin-3-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-(pyrimidin-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4,8-trimethyl-1,2,4,4a-tetrahydro-2'H,6H-spiro[1,4-oxazino[4,3-a][1,2]thiazolo[4,5-g]quinoline-5,5'-pyrimidine]-2',4',6'(1'H,3'H)-trione;

(2R,4S,4aS)-11-fluoro-2,4-dimethyl-8-(pyridin-2-yl)-1,2,4,4a-tetrahydro-2'H,6H-spiro[1,4-oxazino[4,3-a][1,2]thiazolo[4,5-g]quinoline-5,5'-pyrimidine]-2',4',6'(1'H,3'H)-trione;

(2S,4R,4aR)-11-fluoro-2,4,8-trimethyl-1,2,3,4,4a,6-hexahydro-1'H-spiro[isoxazolo[4,5-g]pyrido[1,2-a]quinoline-5,5'-pyrimidine]-2',4',6'(3'H)-trione;

(2R,4S,4aS)-8-(3-chloropyrazin-2-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-8-(6-chloropyrazin-2-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-2,4-dimethyl-8-(5-(methylthio)pyrazin-2-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-8-((1H-1,2,4-triazol-1-yl)methyl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-2,4-dimethyl-8-(pyridin-4-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-8-(5-hydroxy-1,3,4-oxadiazol-2-yl)-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2R,4S,4aS)-11-fluoro-2,4-dimethyl-8-[4-(morpholin-4-ylcarbonyl)-1,3-thiazol-2-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-[4-(morpholin-4-ylcarbonyl)-1,3-thiazol-5-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

2-[(2R,4S,4aS)-11-fluoro-2,4-dimethyl-2',4',6'-trioxo-1,1',2,3',4,4',4a,6-octahydro-2'H,6H-spiro[1,4-oxazino[4,3-a][1,2]oxazolo[4,5-g]quinoline-5,5'-pyrimidin-8-yl]-N,N-dimethyl-1,3-thiazole-4-carboxamide;

2-[(2R,4S,4aS)-11-fluoro-2,4-dimethyl-2',4',6'-trioxo-1,1',2,3',4,4',4a,6-octahydro-2'H,6H-spiro[1,4-oxazino[4,3-a][1,2]oxazolo[4,5-g]quinoline-5,5'-pyrimidin-8-yl]-N,N-dimethyl-1,3-thiazole-5-carboxamide;

5-[(2R,4S,4aS)-11-fluoro-2,4-dimethyl-2',4',6'-trioxo-1,1',2,3',4,4',4a,6-octahydro-2'H,6H-spiro[1,4-oxazino[4,3-a][1,2]oxazolo[4,5-g]quinoline-5,5'-pyrimidin-8-yl]-1,3-thiazole-4-carbonitrile;

(2R,4S,4aS)-11-chloro-2,4-dimethyl-8-(1-methyl-1H-imidazol-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-2,4,11-trimethyl-8-(1,3-thiazol-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-rel-11-fluoro-2,4-dimethyl-8-(6-methylpyridin-3-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-2,4-dimethyl-8-(trifluoromethyl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-8-(difluoromethyl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)—N-(2,2-difluoroethyl)-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)-8-(3,3-difluoroazetidine-1-carbonyl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-2,4-dimethyl-8-(thiazol-2-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-8-(furan-2-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-2,4-dimethyl-8-(thiazol-5-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-8-(2-fluorophenyl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-2,4-dimethyl-8-(tetrahydro-2H-pyran-4-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-2,4,11-trimethyl-8-(pyrazin-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

tert-butyl(2R,4S,4aS)-11-fluoro-2',4',6'-trioxo-1,1',2,3',4,4',4a,6'-octahydro-2'H,6H-spiro[isoxazolo[4,5-g][1,4]oxazino[4,3-a]quinoline-5,5'-pyrimidin]-8-yl carbonate;

(2R,4S,4aS)-8-acetyl-9,10-difluoro-2,4-dimethyl-1,2,4,4a-tetrahydro-2'H,6H-spiro[1,4-oxazino[4,3-a]quinoline-5,5'-pyrimidine]-2',4',6'(1'H,3'H)-trione;

(2R,4S,4aS)-2-ethyl-11-fluoro-4,8-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2R,4R,4aS)-11-fluoro-4-(methoxymethyl)-2,8-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4S,4aS)-11-fluoro-2-(methoxymethyl)-4,8-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-chloro-2,4-dimethyl-8-(pyridyin-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2R,4S,4aS)-11-chloro-2,4-dimethyl-8-(pyridyin-4-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2R,4S,4aS)-11-chloro-2,4-dimethyl-8-(pyridyin-3-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2R,4S,4aS)-11-chloro-2,4-dimethyl-8-(pyrazin-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2R,4S,4aS)-11-chloro-2,4-dimethyl-8-(thiazol-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2R,4S,4aS)-11-fluoro-2,4-dimethyl-8-(1-methyl-1H-imidazol-2-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-Chloro-2,4-dimethyl-8-(4-methylthiazol-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2R,4S,4aS)-11-Chloro-2,4-dimethyl-8-(1-methyl-1H-imidazol-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2R,4S,4aS)-11-chloro-2,4-dimethyl-8-(thiazol-5-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2R,4S,4aS)-11-chloro-2,4-dimethyl-8-(2,4-dichlorothiazol-5-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2R,4S,4aS)-11-Chloro-2,4-dimethyl-8-(2-methylthiazol-5-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2R,4S,4aS)-11-chloro-2,4-dimethyl-8-(1-methyl-1H-1,2,4-triazol-5-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2R,4S,4aS)-11-chloro-2,4-dimethyl-8-(2-bromothiazol-5-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2R,4S,4aS)-11-chloro-2,4-dimethyl-8-(pyrazin-2-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

4-((2R,4S,4aS)-11-chloro-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-yl)-2-fluorobenzonitrile;

(2R,4S,4aS)-11-Chloro-2,4-dimethyl-8-(5-methylthiazol-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

5-((2R,4S,4aS)-11-chloro-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-yl)picolinamide;

(2R,4S,4aS)-11-Chloro-2,4,8-trimethyl-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2R,4S,4aS)-11-Chloro-N,2,4-trimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2R,4S,4aS)-11-chloro-N-ethyl-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2R,4S,4aS)-Chloro-N-isopropyl-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2R,4S,4aS)—N-tert-butyl-11-chloro-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2R,4S,4aS)-11-Chloro-2,4-dimethyl-N-neopentyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2R,4S,4aS)-11-Chloro-8-(3,3-difluoroazetidine-1-carbonyl)-2,4-dimethyl-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2R,4S,4aS)—N-benzyl-11-chloro-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2R,4S,4aS)-11-chloro-N-(4-cyanobenzyl)-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2R,4S,4aS)-11-chloro-N-(3-cyanobenzyl)-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2R,4S,4aS)-ethyl 11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxylate;

(2R,4S,4aS)-11-fluoro-2,4-dimethyl-8-(morpholine-4-carbonyl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-N,N,2,4-tetramethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)-11-fluoro-N-methoxy-N,2,4-trimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)—N-ethyl-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)—N-ethyl-11-fluoro-N,2,4-trimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)-11-fluoro-N,2,4-trimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)-11-fluoro-2,4-dimethyl-8-(4-methyl-3-oxopiperazine-1-carbonyl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-2,4-dimethyl-2',4',6'-trioxo-2,2',3',4,4a,4',6,6'-octahydro-¹H,1'H-spiro[isoxazolo[4,5-g][1,4]oxazino[4,3-a]quinoline-5,5'-pyrimidine]-8-carboxamide;

(2R,4S,4aS)-11-fluoro-2,4-diethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)-11-fluoro-N-(2-methoxyethyl)-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)—N-tert-butyl-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)-8-[(1,1-dioxidothiomorpholin-4-yl)carbonyl]-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2R,4S,4aS)-11-fluoro-2,4-dimethyl-2',4',6'-trioxo-N-(tetrahydro-2H-pyran-4-yl)-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)-11-fluoro-N-isopropyl-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)-11-fluoro-2,4-dimethyl-8-(pyrimidin-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4S,4aS)-11-fluoro-4,8-dimethyl-2-(trifluoromethyl)-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2R,4S,4aS)—N-cyclopropyl-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)-11-fluoro-8-(4-methoxypiperidine-1-carbonyl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)—N-(cyclopropylmethyl)-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)-11-fluoro-2,4-dimethyl-8-(1,2-oxazinan-2-ylcarbonyl)-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2R,4S,4aS)-11-fluoro-2,4-dimethyl-2',4',6'-trioxo-N-(thiophen-2-ylmethyl)-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)-11-fluoro-2,4-dimethyl-2',4',6'-trioxo-N-(pyridin-4-ylmethyl)-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)—N-(cyclohexylmethyl)-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)-8-(4,4-difluoropiperidine-1-carbonyl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-8-(3,3-difluoropyrrolidine-1-carbonyl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-2,4-dimethyl-N-(1-methylazetidin-3-yl)-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

N-(1-((2R,4S,4aS)-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-ylcarbonyl)azetidin-3-yl)acetamide;

(2R,4S,4aS)-11-fluoro-2,4-dimethyl-N-((1-methyl-1H-pyrazol-3-yl)methyl)-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)-11-fluoro-2,4-dimethyl-N-((1-methyl-1H-pyrazol-5-yl)methyl)-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)—N-(1,3-dimethoxy-2-(methoxymethyl)propan-2-yl)-11-fluoro-2,4-dimethyl-2',4',6'-trioxo-2,2',3',4,4a,4',6,6'-octahydro-1H,1'H-spiro[isoxazolo[4,5g][1,4]oxazino[4,3-a]quinoline-5,5'-pyrimidine]-8-carboxamide;

1-((2R,4S,4aS)-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-ylcarbonyl)azetidine-3-carbonitrile;

(2R,4S,4aS)-11-fluoro-2,4-dimethyl-8-(pyrazin-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-(5-morpholinopyrazin-2-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-8-(6-methoxypyrazin-2-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-2,4-dimethyl-8-(2-(methylthio)pyrimidin-4-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-2,4-dimethyl-8-(2-(methylsulfonyl)pyrimidin-4-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-8-(2-(2-methoxyethylamino)pyrimidin-4-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-8-(2-(2-hydroxyethylamino)pyrimidin-4-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-8-(2-methoxypyrimidin-4-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

4-((2R,4S,4aS)-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-yl)pyrimidine-2-carbonitrile;

(2R,4S,4aS)-8-(2-aminopyrimidin-4-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-8-(2-hydroxypyrimidin-4-yl)-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2R,4S,4aS)-11-Fluoro-2,4-dimethyl-8-(2-morpholinopyrimidin-4-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-8-(6-(Dimethylamino)pyrazin-2-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-Fluoro-2,4-dimethyl-8-(1-methyl-1H-1,2,4-triazol-5-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-Fluoro-2,4-dimethyl-8-(piperazin-1-yl)-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2R,4S,4aS)-8-Chloro-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-Fluoro-2,4-dimethyl-8-(methylsulfinyl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-Fluoro-2,4-dimethyl-8-(methylsulfonyl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-Fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidine]-8-carbonitrile;

ethyl 2-[(2R,4S,4aS)-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin-8-yl]-1,3-thiazole-4-carboxylate;

(2R,4S,4aS)-11-fluoro-8-(hydroxymethyl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

1-[(2R,4S,4aS)-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin-8-yl]-1H-pyrazole-4-carboxylic acid;

1-[(2R,4S,4aS)-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin-8-yl]-N,N-dimethyl-1H-pyrazole-4-carboxamide;

1-[(2R,4S,4aS)-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin-8-yl]-N-methyl-1H-pyrazole-4-carboxamide;

1-[(2R,4S,4aS)-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin-8-yl]-1H-pyrazole-4-carboxamide;

(2R,4S,4aS)-11-fluoro-8-[4-(hydroxymethyl)-1H-pyrazol-1-yl]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione, or a pharmaceutically acceptable salt thereof.

In yet a further aspect, the present invention provides a compound selected from:

(2S,4R,4aR)-8-Amino-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-11-Fluoro-2,4,8-trimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-11-Fluoro-2,4-dimethyl-8-phenyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-8-Cyclopropyl-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-11-Fluoro-2,4-dimethyl-8-pyridin-2-yl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-11-Fluoro-2,4-dimethyl-2',4',6'-trioxo-1,1',2,3',4,4',4a,6'-octahydro-2'H,6H-spiro[isoxazolo[4,5-g][1,4]oxazino[4,3-a]quinoline-5,5'-pyrimidin-8-yl]acetamide;

(2S,4R,4aR)-11-chloro-2,4,8-trimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-8-(4-acetylpiperazin-1-yl)-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-8-(benzylamino)-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-[(1,3-thiazol-2-ylmethyl)amino]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-8-[(1H-imidazol-4-ylmethyl)amino]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-{[(1-methyl-1H-pyrazol-4-yl)methyl]amino}-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-{[(5-methyl-1,2-oxazol-3-yl)methyl]amino}-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-[(pyridin-2-ylmethyl)amino]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-[(pyridin-3-ylmethyl)amino]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-[(pyridin-4-ylmethyl)amino]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-8-[(cyclopropylmethyl)amino]-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-8-[(cyclohexylmethyl)amino]-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-[(tetrahydro-2H-pyran-4-ylmethyl)amino]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

tert-butyl 4-[(2S,4R,4aR)-11-fluoro-2,4-dimethyl-2',4',6'-trioxo-1,1',2,3',4,4',4a,6'-octahydro-2'H,6H-spiro[isoxazolo[4,5-g][1,4]oxazino[4,3-a]quinoline-5,5'-pyrimidin]-8-yl]piperazine-1-carboxylate;

(2S,4R,4aR)-11-fluoro-2,4-dimethyl-8-(piperazin-1-yl)-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-11-fluoro-2,4-dimethyl-8-(morpholin-4-yl)-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-8-(diethylamino)-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-8-(dimethylamino)-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-11-fluoro-2,4-dimethyl-8-(pyrrolidin-1-yl)-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-8-(azepan-1-yl)-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-11-fluoro-2,4-dimethyl-8-[5-methyl-3-(trifluoromethyl)-1H-pyrazol-1-yl]-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

N-{1-[(2S,4R,4aR)-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidine]-8-yl]-1H-pyrazol-3-yl}acetamide;

(2S,4R,4aR)-11-fluoro-2,4-dimethyl-8-[3-(trifluoromethyl)-1H-pyrazol-1-yl]-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-8-[3-(difluoromethyl)-5-methyl-1H-pyrazol-1-yl]-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-11-fluoro-2,4-dimethyl-8-(propylamino)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-8-[benzyl(methyl)amino]-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

3-amino-1-[(2S,4R,4aR)-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-1H-pyrazole-4-carbonitrile;

(2S,4R,4aR)-11-fluoro-2,4-dimethyl-8-[4-(pyrimidin-4-yl)-1H-pyrazol-1-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-[4-(pyrazin-2-yl)-1H-pyrazol-1-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-8-(4-iodo-1H-pyrazol-1-yl)-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

ethyl 1-[(2S,4R,4aR)-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-1H-pyrazole-4-carboxylate;

(2S,4R,4aR)-11-chloro-2,4-dimethyl-8-(pyridin-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-chloro-8-cyclopropyl-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-chloro-2,4-dimethyl-8-(6-methylpyridin-3-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-chloro-2,4-dimethyl-8-(1,3-thiazol-5-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-chloro-2,4-dimethyl-8-(pyrimidin-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-chloro-2,4-dimethyl-8-(pyrimidin-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-chloro-2,4-dimethyl-8-(pyrimidin-5-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-chloro-2,4-dimethyl-8-(pyridazin-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-chloro-2,4-dimethyl-8-(pyridin-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-chloro-2,4-dimethyl-8-(pyridin-3-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-chloro-2,4-dimethyl-8-(1,3-thiazol-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-chloro-8-(methoxymethyl)-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-[methyl(propyl)amino]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)trione;

(2S,4R,4aR)-11-fluoro-8-methoxy-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-8-(benzyloxy)-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-(1H-1,2,4-triazol-1-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-(3-methyl-1H-1,2,4-triazol-1-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-1H-1,2,4-triazole-3-carbonitrile;

(2S,4R,4aR)-11-fluoro-2,4-dimethyl-8-(2H-1,2,3-triazol-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-(1H-1,2,3-triazol-1-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-8-(1H-imidazol-1-yl)-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-[4-(trifluoromethyl)-1H-imidazol-1-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-(4-methyl-1H-pyrazol-1-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-8-(4-chloro-1H-pyrazol-1-yl)-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-(methylsulfanyl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-8-(3,5-dimethyl-1H-pyrazol-1-yl)-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-(1H-pyrazol-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-(2-methyl-1,3-oxazol-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-(5-methyl-1,2-oxazol-3-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-8-(3,5-dimethyl-1,2-oxazol-4-yl)-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-(1-methyl-1H-imidazol-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,371)-trione;

(2S,4R,4aR)-11-fluoro-2,4-dimethyl-8-(1-methyl-1H-imidazol-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,371)-trione;

(2S,4R,4aR)-11-fluoro-2,4-dimethyl-8-(1-methyl-1H-imidazol-5-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,371)-trione;

(2S,4R,4aR)-11-fluoro-2,4-dimethyl-8-(4-methyl-1,3-thiazol-5-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,371)-trione;

(2S,4R,4aR)-11-fluoro-2,4-dimethyl-8-(4-methyl-1,2,3-thiadiazol-5-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-(pyridazin-3-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-(pyrimidin-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4,8-trimethyl-1,2,4,4a-tetrahydro-2'H,6H-spiro[1,4-oxazino[4,3-a][1,2]thiazolo[4,5-g]quinoline-5,5'-pyrimidine]-2',4',6'(1'H,3'H)-trione;

(2S,4R,4aR)-11-fluoro-2,4-dimethyl-8-(pyridin-2-yl)-1,2,4,4a-tetrahydro-2'H,6H-spiro[1,4-oxazino[4,3-a][1,2]thiazolo[4,5-g]quinoline-5,5'-pyrimidine]-2',4',6'(1'H,3'H)-trione;

(2S,4R,4aR)-11-fluoro-2,4,8-trimethyl-1,2,3,4,4a,6-hexahydro-1'H-spiro[isoxazolo[4,5-g]pyrido[1,2-a]quinoline-5,5'-pyrimidine]-2',4',6'(3'H)-trione;

(2S,4R,4aR)-8-(3-chloropyrazin-2-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-8-(6-chloropyrazin-2-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-11-fluoro-2,4-dimethyl-8-(5-(methylthio)pyrazin-2-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-8-((1H-1,2,4-triazol-1-yl)methyl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-11-fluoro-2,4-dimethyl-8-(pyridin-4-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-11-fluoro-8-(5-hydroxy-1,3,4-oxadiazol-2-yl)-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-11-fluoro-2,4-dimethyl-8-[4-(morpholin-4-ylcarbonyl)-1,3-thiazol-2-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-[4-(morpholin-4-ylcarbonyl)-1,3-thiazol-5-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-2',4',6'-trioxo-1,1',2',3',4,4',4a,6'-octahydro-2'H,6H-spiro[1,4-oxazino[4,3-a][1,2]oxazolo[4,5-g]quinoline-5,5'-pyrimidin]-8-yl]-N,N-dimethyl-1,3-thiazole-4-carboxamide;

(2S,4R,4aR)-11-fluoro-2,4-dimethyl-2',4',6'-trioxo-1,1',2',3',4,4',4a,6'-octahydro-2'H,6H-spiro[1,4-oxazino[4,3-a][1,2]oxazolo[4,5-g]quinoline-5,5'-pyrimidin]-8-yl]-N,N-dimethyl-1,3-thiazole-5-carboxamide;

(2S,4R,4aR)-11-fluoro-2,4-dimethyl-2',4',6'-trioxo-1,1',2',3',4,4',4a,6'-octahydro-2'H,6H-spiro[1,4-oxazino[4,3-a][1,2]oxazolo[4,5-g]quinoline-5,5'-pyrimidin]-8-yl]-1,3-thiazole-4-carbonitrile;

(2S,4R,4aR)-11-chloro-2,4-dimethyl-8-(1-methyl-1H-imidazol-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-2,4,11-trimethyl-8-(1,3-thiazol-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-(6-methylpyridin-3-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-rel-11-fluoro-2,4-dimethyl-8-(trifluoromethyl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-8-(difluoromethyl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)—N-(2,2-difluoro ethyl)-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)-8-(3,3-difluoro azetidine-1-carbonyl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-11-fluoro-8-(furan-2-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-11-fluoro-2,4-dimethyl-8-(thiazol-5-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-11-fluoro-8-(2-fluorophenyl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-11-fluoro-2,4-dimethyl-8-(tetrahydro-2H-pyran-4-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-2,4,11-trimethyl-8-(pyrazin-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

tert-butyl(2S,4R,4aR)-11-fluoro-2,4-dimethyl-2',4',6'-trioxo-1,1',2,3',4,4',4a,6'-octahydro-2'H,6H-spiro[isoxazolo[4,5-g][1,4]oxazino[4,3-a]quinoline-5,5'-pyrimidin]-8-yl carbonate;

(2S,4R,4aR)-8-acetyl-9,10-difluoro-2,4-dimethyl-1,2,4,4a-tetrahydro-2'H,6H-spiro[1,4-oxazino[4,3-a]quinoline-5,5'-pyrimidine]-2',4',6'(1'H,3'H)-trione;

(2S,4R,4aR)-2-ethyl-11-fluoro-4,8-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4S,4aR)-11-fluoro-4-(methoxymethyl)-2,8-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4R,4aR)-11-fluoro-2-(methoxymethyl)-4,8-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-chloro-2,4-dimethyl-8-(pyridyin-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2S,4R,4aR)-11-chloro-2,4-dimethyl-8-(pyridyin-4-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2S,4R,4aR)-11-chloro-2,4-dimethyl-8-(pyridyin-3-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2S,4R,4aR)-11-chloro-2,4-dimethyl-8-(pyrazin-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2S,4R,4aR)-11-chloro-2,4-dimethyl-8-(thiazol-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2S,4R,4aR)-11-fluoro-2,4-dimethyl-8-(1-methyl-1H-imidazol-2-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-11-Chloro-2,4-dimethyl-8-(4-methylthiazol-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2S,4R,4aR)-11-Chloro-2,4-dimethyl-8-(1-methyl-1H-imidazol-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2S,4R,4aR)-11-chloro-2,4-dimethyl-8-(thiazol-5-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2S,4R,4aR)-11-chloro-2,4-dimethyl-8-(2,4-dichlorothiazol-5-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2S,4R,4aR)-11-Chloro-2,4-dimethyl-8-(2-methylthiazol-5-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2S,4R,4aR)-11-chloro-2,4-dimethyl-8-(1-methyl-1H-1,2,4-triazol-5-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2S,4R,4aR)-11-chloro-2,4-dimethyl-8-(2-bromothiazol-5-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2S,4R,4aR)-11-chloro-2,4-dimethyl-8-(pyrazin-2-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

4-((2S,4R,4aR)-11-chloro-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-yl)-2-fluorobenzonitrile;

(2S,4R,4aR)-11-Chloro-2,4-dimethyl-8-(5-methylthiazol-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

5-((2S,4R,4aR)-11-chloro-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-yl)picolinamide;

(2S,4R,4aR)-11-Chloro-2,4,8-trimethyl-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2S,4R,4aR)-11-Chloro-N,2,4-trimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2S,4R,4aR)-11-chloro-N-ethyl-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2S,4R,4aR)-Chloro-N-isopropyl-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2S,4R,4aR)—N-tert-butyl-11-chloro-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2S,4R,4aR)-11-Chloro-2,4-dimethyl-N-neopentyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2S,4R,4aR)-11-Chloro-8-(3,3-difluoroazetidine-1-carbonyl)-2,4-dimethyl-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2S,4R,4aR)—N-benzyl-11-chloro-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2S,4R,4aR)-11-chloro-N-(4-cyanobenzyl)-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2S,4R,4aR)-11-chloro-N-(3-cyanobenzyl)-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2S,4R,4aR)-ethyl 11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxylate;

(2S,4R,4aR)-11-fluoro-2,4-dimethyl-8-(morpholine-4-carbonyl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-11-fluoro-N,N,2,4-tetramethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)-11-fluoro-N-methoxy-N,2,4-trimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)—N-ethyl-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)—N-ethyl-11-fluoro-N,2,4-trimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)-11-fluoro-N,2,4-trimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)-11-fluoro-2,4-dimethyl-8-(4-methyl-3-oxopiperazine-1-carbonyl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)-11-fluoro-N-(2-methoxyethyl)-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)—N-tert-butyl-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)-8-[(1,1-dioxidothiomorpholin-4-yl)carbonyl]-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-11-fluoro-2,4-dimethyl-2',4',6'-trioxo-N-(tetrahydro-2H-pyran-4-yl)-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)-11-fluoro-N-isopropyl-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)-11-fluoro-2,4-dimethyl-8-(pyrimidin-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-4,8-dimethyl-2-(trifluoromethyl)-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)—N-cyclopropyl-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)-11-fluoro-8-(4-methoxypiperidine-1-carbonyl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)—N-(cyclopropylmethyl)-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)-11-fluoro-2,4-dimethyl-8-(1,2-oxazinan-2-ylcarbonyl)-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-11-fluoro-2,4-dimethyl-2',4',6'-trioxo-N-(thiophen-2-ylmethyl)-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)-11-fluoro-2,4-dimethyl-2',4',6'-trioxo-N-(pyridin-4-ylmethyl)-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)—N-(cyclohexylmethyl)-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)-8-(4,4-difluoropiperidine-1-carbonyl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-8-(3,3-difluoropyrrolidine-1-carbonyl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-11-fluoro-2,4-dimethyl-N-(1-methylazetidin-3-yl)-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

N-(1-((2S,4R,4aR)-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-ylcarbonyl)azetidin-3-yl)acetamide;

(2S,4R,4aR)-11-fluoro-2,4-dimethyl-N-((1-methyl-1H-pyrazol-3-yl)methyl)-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)-11-fluoro-2,4-dimethyl-N-((1-methyl-1H-pyrazol-5-yl)methyl)-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)—N-(1,3-dimethoxy-2-(methoxymethyl)propan-2-yl)-11-fluoro-2,4-dimethyl-2',4',6'-trioxo-2,2',3',4,4a,4',6,6'-octahydro-1H,1'H-spiro[isoxazolo[4,5g][1,4]oxazino[4,3-a]quinoline-5,5'-pyrimidine]-8-carboxamide;

(2S,4R,4aR)-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-ylcarbonyl)azetidine-3-carbonitrile;

(2S,4R,4aR)-11-fluoro-2,4-dimethyl-8-(pyrazin-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-8-(6-(Dimethylamino)pyrazin-2-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-11-Fluoro-2,4-dimethyl-8-(piperazin-1-yl)-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-11-Fluoro-2,4-dimethyl-8-(methylsulfinyl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-Fluoro-2,4-dimethyl-8-(methylsulfonyl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione (2S,4R,4aR)-11-Fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidine]-8-carbonitrile;

ethyl 2-[(2S,4R,4aR)11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-1,3-thiazole-4-carboxylate;

(2S,4R,4aR)-11-fluoro-8-(hydroxymethyl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-1H-pyrazole-4-carboxylic acid;

(2S,4R,4aR)-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-N,N-dimethyl-1H-pyrazole-4-carboxamide;

(2S,4R,4aR)-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-N-methyl-1H-pyrazole-4-carboxamide;

(2S,4R,4aR)-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-1H-pyrazole-4-carboxamide;

(2S,4R,4aR)-11-fluoro-8-[4-(hydroxymethyl)-1H-pyrazol-1-yl]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione, or a pharmaceutically acceptable salt thereof.

Biological Activity

Typical compounds of Formula (I) are believed to inhibit bacterial DNA gyrase and are therefore of interest for their antibacterial effects. The inventive compounds are believed to be active against a variety of bacterial organisms, including both Gram positive and Gram negative aerobic and anaerobic bacteria.

These properties may be assessed using, for example, the assay shown below.

DNA Gyrase Supercoiling Activity Fluorescence Polarisation Assay

In a black, 384-well polystyrene assay plate, 30 microliters/well of 5 nM *Escherichia coli* DNA gyrase A/B tetramer and 130 micrograms/ml of topologically relaxed plasmid containing the triplex-forming sequence TTCTTCTTCT-TCTTCTTCTTCTTC in an assay buffer consisting of 35 mM Tris-HCl (pH 7.5), 24 mM KCl, 4 mM $MgCl_2$, 2 mM dithiothreitol, 1.8 mM spermidine, 5% (v/v) glycerol, 200 nM bovine serum albumin, 0.8% dimethylsulfoxide, and 0.3 mM ATP may be incubated at ambient temperature for (typically 30 minutes) in the absence or presence of 5-10 different concentrations of test compound. The supercoiling reactions may be quenched by the addition of 10 microliters/well of 40 nM oligodeoxynucleotide probe in 3× triplex-forming buffer consisting of 150 mM NaCl, and 150 mM sodium acetate at pH 3.5. The oligodeoxynucleotide probe may be 5'-BODIPY-FL-labeled TTCTTCTTC. After 60 minutes, the fluorescence anisotropy of the BODIPY-FL may be measured in a Tecan Ultra plate reader, using 485 nm excitation and 535 nm emission filters equipped with polarizers. The $IC_{50}$ may be determined by nonlinear regression using two control reactions. The first contains no test compound but 0.8% DMSO (100% activity) while the second control reaction contains 5 µM Ciprofloxacin and 0.8% DMSO (0% activity).

When tested in an in-vitro assay based on the DNA gyrase supercoiling activity fluorescence polarisation assay described above, the *E. coli* DNA gyrase supercoiling $IC_{50}$ assay inhibitory activity of the following Examples was measured at the indicated $IC_{50}$. A hyphen indicates that an $IC_{50}$ measurement is not provided for that particular compound, and is not meant to imply that the particular compound does not possess $IC_{50}$ activity.

| Example | $IC_{50}$ (µM) |
|---|---|
| 1 | 0.5 |
| 2 | 0.4 |
| 2(a) | 83 |
| 2(b) | 0.3 |
| 3 | 0.4 |
| 4 | 0.3 |
| 5 | 0.2 |
| 6 | 0.8 |
| 7 | 0.4 |
| 8 | 8.3 |
| 9 | 1.7 |
| 10 | 1.9 |
| 11 | 0.8 |
| 12 | 1.2 |
| 13 | 1.7 |
| 14 | 2.0 |
| 15 | 1.0 |
| 16 | 2.4 |
| 17 | 1.4 |
| 18 | 2.9 |
| 19 | 2.9 |
| 20 | 20 |
| 21 | 2.4 |
| 22 | 2.6 |
| 23 | 4.3 |
| 24 | 0.3 |
| 25 | 1.5 |
| 26 | 3.7 |
| 27 | 7.1 |
| 28 | 3.1 |
| 29 | — |
| 30 | 5.4 |
| 31 | 2.2 |
| 32 | 0.6 |
| 33 | 1.0 |
| 34 | 16.3 |
| 35 | 30 |
| 36 | 2.1 |
| 37 | 8.5 |
| 38 | 0.8 |
| 39 | 0.6 |
| 40 | 1.6 |
| 41 | 0.8 |
| 42 | 1.2 |
| 43 | 0.5 |
| 44 | 1.0 |
| 45 | 1.6 |
| 46 | 1.0 |
| 47 | 0.3 |
| 48 | 1.0 |

-continued

| Example | IC$_{50}$ (μM) |
|---|---|
| 49 | 1.7 |
| 50 | 0.5 |
| 51 | 1.0 |
| 52 | 2.4 |
| 53 | 2.8 |
| 53(a) | 0.2 |
| 53(b) | 20 |
| 54 | 2.0 |
| 55 | 2.6 |
| 56 | 0.7 |
| 57 | 1.5 |
| 58 | 0.5 |
| 59 | 6.6 |
| 60 | 1.2 |
| 61 | 9.3 |
| 62 | 0.9 |
| 63 | 2.7 |
| 64 | 0.8 |
| 65 | 1.1 |
| 66 | 0.4 |
| 67 | 3.2 |
| 68 | 0.7 |
| 69 | 17 |
| 70 | 0.5 |
| 71 | 0.9 |
| 72 | 0.9 |
| 73 | 0.5 |
| 74 | — |
| 74(a) | 27 |
| 74(b) | 0.3 |
| 75 | 0.2 |
| 76 | — |
| 77 | 0.3 |
| 78 | 0.8 |
| 79 | 0.8 |
| 80 | 1.7 |
| 81 | 3.0 |
| 82 | 0.2 |
| 83 | — |
| 84 | — |
| 85 | 17 |
| 86 | 5.0 |
| 87 | 6.7 |
| 88 | 1.2 |
| 89 | 1.3 |
| 90 | — |
| 91 | 1.9 |
| 92 | 1.4 |
| 92(a) | 65 |
| 92(b) | 0.6 |
| 93 | 0.7 |
| 93(a) | 56 |
| 93(b) | 0.4 |
| 94 | 1.6 |
| 94(a) | 51 |
| 94(b) | 0.8 |
| 95 | 0.3 |
| 95(a) | 1.0 |
| 95(b) | — |
| 96 | 0.7 |
| 97 | 0.7 |
| 98 | 0.4 |
| 99 | 0.4 |
| 100 | 4.1 |
| 101 | 1.4 |
| 102 | 2.7 |
| 103 + 104 | 0.2 |
| 105 | 0.7 |
| 106 | 1.1 |
| 107 | 1.4 |
| 108 | 0.8 |
| 109 | 0.5 |
| 110 | 3.0 |
| 111 | 0.7 |
| 111(a) | 83 |
| 111(b) | 1.1 |
| 112 | — |
| 113 | 2.5 |

-continued

| Example | IC$_{50}$ (μM) |
|---|---|
| 114 | 5.2 |
| 115 | 1.1 |
| 116 | 2.0 |
| 117 | 2.0 |
| 118 | — |
| 119 | 3.1 |
| 120 | 0.2 |
| 121 | 0.6 |
| 122 | 0.5 |
| 123 | 5.8 |
| 124 | 1.8 |
| 125 | 0.7 |
| 126 | 0.5 |
| 127 | 19 |
| 128 | 19 |
| 129 | 31 |
| 130 | 30 |
| 131 | 4.4 |
| 132 | 7.7 |
| 133 | 13 |
| 134 | 1.0 |
| 135 | 3.3 |
| 136 | 2.8 |
| 137 | 2.3 |
| 138 | 1.7 |
| 139 | 7.6 |
| 140 | 1.1 |
| 140(a) | 0.9 |
| 141 | 4.9 |
| 142 | 0.3 |
| 142(a) | 1.7 |
| 143 | 1.0 |
| 144 | 2.9 |
| 145 | 5.2 |
| 146 | 4.9 |
| 147 | 3.9 |
| 147(a) | 0.9 |
| 147(b) | — |
| 148 | 0.9 |
| 148(a) | 83 |
| 148(b) | 0.4 |
| 149 | 4.4 |
| 150 | 1.3 |
| 151 | 5.5 |
| 152 | 2.1 |
| 153 | 3.7 |
| 154 | 1.5 |
| 155 | 1.2 |
| 156 | 1.5 |
| 157 | 6.4 |
| 158 | 1.4 |
| 159 | 1.4 |
| 160 | 1.0 |
| 161 | 1.3 |
| 162 | 2.1 |
| 163 | 17 |
| 164 | 1.2 |
| 165 | 0.4 |
| 165(a) | 7.8 |
| 165(b) | 0.2 |
| 166(a) | 83 |
| 166(b) | 6.9 |
| 167 | 1.1 |
| 168 | 0.6 |
| 169 | — |
| 170 | 0.7 |
| 171 | 0.3 |
| 172 | 0.9 |
| 173 | 0.1 |
| 174 | 0.5 |
| 175 | 0.9 |
| 176 | 3.2 |
| 177 | 5.0 |
| 178 | 1.3 |
| 179 | 2.0 |
| 180 | 0.2 |
| 181 | 3.3 |
| 182 | 2.4 |

-continued

| Example | IC$_{50}$ (μM) |
|---------|----------------|
| 183 | 12 |
| 184 | — |
| 185 | 1.4 |
| 186 | 7.6 |
| 187 | 3.3 |
| 188 | 2.7 |
| 189 | 2.2 |
| 190 | 2.1 |

In one aspect there is provided a compound of Formula (I), or a pharmaceutically acceptable salt thereof, for use as a medicament.

In one aspect, the terms "infection" and "bacterial infection" may refer to a bacterial infection caused by *Acinetobacter baumanii*. In another aspect, the terms "infection" and "bacterial infection" may refer to a bacterial infection caused by *Aeromis hydrophile*. In still another aspect, the terms "infection" and "bacterial infection" may refer to a bacterial infection caused by *Bacillus anthracis*. In yet another aspect, the terms "infection" and "bacterial infection" may refer to a bacterial infection caused by *Bacteroides fragilis*. In a further aspect, the terms "infection" and "bacterial infection" may refer to a bacterial infection caused by *Bordatella pertussis*. In still a further aspect, the terms "infection" and "bacterial infection" may refer to a bacterial infection caused by *Burkholderia cepacia*. In yet a further aspect, the terms "infection" and "bacterial infection" may refer to a bacterial infection caused by *Chlamyida pneumoniae*. In one aspect, the terms "infection" and "bacterial infection" may refer to a bacterial infection caused by *Citrobacter freundii*. In another aspect, the terms "infection" and "bacterial infection" may refer to a bacterial infection caused by *Clostridium difficile*. In still another aspect, the terms "infection" and "bacterial infection" may refer to a bacterial infection caused by *Enterobacter cloacae*. In yet another aspect, the terms "infection" and "bacterial infection" may refer to a bacterial infection caused by *Enterococcus faecalis*. In a further aspect, the terms "infection" and "bacterial infection" may refer to a bacterial infection caused by *Enterococcus faecium*. In still a further aspect, the terms "infection" and "bacterial infection" may refer to a bacterial infection caused by *Enterobacter aerogenes*. In yet a further aspect, the terms "infection" and "bacterial infection" may refer to a bacterial infection caused by *Escherichia coli*. In one aspect, the terms "infection" and "bacterial infection" may refer to a bacterial infection caused by *Fusobacterium necrophorum*. In another aspect, the terms "infection" and "bacterial infection" may refer to a bacterial infection caused by *Haemophilus influenzae*. In still another aspect, the terms "infection" and "bacterial infection" may refer to a bacterial infection caused by *Haemophilus parainfluenzae*. In yet another aspect, the terms "infection" and "bacterial infection" may refer to a bacterial infection caused by *Haemophilus somnus*. In a further aspect, the terms "infection" and "bacterial infection" may refer to a bacterial infection caused by *Klebsiella oxytoca*. In still a further aspect, the terms "infection" and "bacterial infection" may refer to a bacterial infection caused by *Klebsiella pneumoniae*. In yet a further aspect, the terms "infection" and "bacterial infection" may refer to a bacterial infection caused by *Legionella pneumophila*. In one aspect, the terms "infection" and "bacterial infection" may refer to a bacterial infection caused by *Listeria monocytogenes*. In another aspect, the terms "infection" and "bacterial infection" may refer to a bacterial infection caused by *Moraxella catarrhalis*. In still another aspect, the terms "infection" and "bacterial infection" may refer to a bacterial infection caused by *Morganella morganii*. In yet another aspect, the terms "infection" and "bacterial infection" may refer to a bacterial infection caused by *Mycoplasma pneumoniae*. In a further aspect, the terms "infection" and "bacterial infection" may refer to a bacterial infection caused by *Neisseria gonorrhoeae*. In still a further aspect, the terms "infection" and "bacterial infection" may refer to a bacterial infection caused by *Neisseria meningitidis*. In yet a further aspect, the terms "infection" and "bacterial infection" may refer to a bacterial infection caused by *Pasteurella multocida*. In one aspect, the terms "infection" and "bacterial infection" may refer to a bacterial infection caused by *Proteus mirabilis*. In another aspect, the terms "infection" and "bacterial infection" may refer to a bacterial infection caused by *Proteus vulgaris*. In still another aspect, the terms "infection" and "bacterial infection" may refer to a bacterial infection caused by *Pseudomonas aeruginosa*. In yet another aspect, the terms "infection" and "bacterial infection" may refer to a bacterial infection caused by *Salmonella typhi*. In a further aspect, the terms "infection" and "bacterial infection" may refer to a bacterial infection caused by *Salmonella typhimurium*. In still a further aspect, the terms "infection" and "bacterial infection" may refer to a bacterial infection caused by *Serratia marcesens*. In yet a further aspect, the terms "infection" and "bacterial infection" may refer to a bacterial infection caused by *Shigella flexneria*. In one aspect, the terms "infection" and "bacterial infection" may refer to a bacterial infection caused by *Shigella dysenteriae*. In another aspect, the terms "infection" and "bacterial infection" may refer to a bacterial infection caused by *Staphylococcus aureus*. In still another aspect, the terms "infection" and "bacterial infection" may refer to a bacterial infection caused by *Staphylococcus epidermidis*. In yet another aspect, the terms "infection" and "bacterial infection" may refer to a bacterial infection caused by *Staphylococcus haemolyticus*. In a further aspect, the terms "infection" and "bacterial infection" may refer to a bacterial infection caused by *Staphylococcus intermedius*. In still a further aspect, the terms "infection" and "bacterial infection" may refer to a bacterial infection caused by *Staphylococcus saprophyticus*. In yet a further aspect, the terms "infection" and "bacterial infection" may refer to a bacterial infection caused by *Stenotrophomonas maltophila*. In one aspect, the terms "infection" and "bacterial infection" may refer to a bacterial infection caused by *Streptococcus agalactiae*. In another aspect, the terms "infection" and "bacterial infection" may refer to a bacterial infection caused by *Streptococcus mutans*. In a still another aspect, the terms "infection" and "bacterial infection" may refer to a bacterial infection caused by *Streptococcus pneumoniae*. In yet another aspect, the terms "infection" and "bacterial infection" may refer to a bacterial infection caused by *Streptococcus pyrogenes*.

In one aspect, the terms "infection and "bacterial infection" may refer to a bacterial infection caused by a bacteria of the genus Aeromonas. In another aspect, the terms "infection and "bacterial infection" may refer to a bacterial infection caused by a bacteria of the genus *Acinetobacter*. In still another aspect, the terms "infection and "bacterial infection" may refer to a bacterial infection caused by a bacteria of the genus *Bacillus*. In yet another aspect, the terms "infection and "bacterial infection" may refer to a bacterial infection caused by a bacteria of the genus *Bacteroides*. In a further aspect, the terms "infection and "bacterial infection" may refer to a bacterial infection caused by a bacteria of the genus *Bordetella*. In still a further aspect, the terms "infection and "bacterial infection" may refer to a bacterial infection caused by a bacteria of the genus *Burkholderia*. In yet a further aspect, the terms "infection and "bacterial infection" may refer to a bacterial infection caused by a bacteria of the genus *Chlamydophila*. In one aspect, the terms "infection and "bacterial infection" may refer to a bacterial infection caused by a bacteria of the genus *Citrobacter*. In another aspect, the terms "infection and "bacterial infection" may refer to a bacterial infection caused by a bacteria of the genus *Clostridium*. In still another aspect, the terms "infection and "bacterial infection" may refer to a bacterial infection caused by a bacteria of the genus *Enterobacter*. In yet another aspect, the terms "infection and "bacterial infection" may refer to a bacterial infection caused by a bacteria of the genus *Enterococcus*. In a further aspect, the terms "infection and "bacterial infection" may refer to a bacterial infection caused by a bacteria of the genus *Escherichia*. In still a further aspect, the terms "infection and "bacterial infection" may refer to a bacterial infection caused by a bacteria of the genus *Flavobacterium*. In yet a further aspect, the terms "infection and "bacterial infection" may refer to a bacterial infection caused by a bacteria of the genus *Fusobacterium*. In one aspect, the terms "infection and "bacterial infection" may refer to a bacterial infection caused by a bacteria of the genus *Haemophilus*. In one aspect, the terms "infection and "bacterial infection" may refer to a bacterial infection caused by a bacteria of the genus *Klebsiella*. In another aspect, the terms "infection and "bacterial infection" may refer to a bacterial infection caused by a bacteria of the genus *Legionella*. In still another aspect, the terms "infection and "bacterial infection" may refer to a bacterial infection caused by a bacteria of the genus *Listeria*. In yet another aspect, the terms "infection and "bacterial infection" may refer to a bacterial infection caused by a bacteria of the genus *Morganella*. In a further aspect, the terms "infection and "bacterial infection" may refer to a bacterial infection caused by a bacteria of the genus *Moraxella*. In still a further aspect, the terms "infection and "bacterial infection" may refer to a bacterial infection caused by a bacteria of the genus *Mycoplasma*. In yet a further aspect, the terms "infection and "bacterial infection" may refer to a bacterial infection caused by a bacteria of the genus *Neisseria*. In one aspect, the terms "infection and "bacterial infection" may refer to a bacterial infection caused by a bacteria of the genus *Pasteurella*. In another aspect, the terms "infection and "bacterial infection" may refer to a bacterial infection caused by a bacteria of the genus *Peptococci*. In still another aspect, the terms "infection and "bacterial infection" may refer to a bacterial infection caused by a bacteria of the genus *Peptostreptococci*. In yet another aspect, the terms "infection and "bacterial infection" may refer to a bacterial infection caused by a bacteria of the genus *Prevotella*. In a further aspect, the terms "infection and "bacterial infection" may refer to a bacterial infection caused by a bacteria of the genus *Proteus*. In still a further aspect, the terms "infection and "bacterial infection" may refer to a bacterial infection caused by a bacteria of the genus *Pseudomonas*. In still another aspect, the terms "infection and "bacterial infection" may refer to a bacterial infection caused by a bacteria of the genus *Salmonella*. In yet a further aspect, the terms "infection and "bacterial infection" may refer to a bacterial infection caused by a bacteria of the genus *Serratia*. In one aspect, the terms "infection and "bacterial infection" may refer to a bacterial infection caused by a bacteria of the genus *Shigella*. In yet another aspect, the terms "infection and "bacterial infection" may refer to a bacterial infection caused by a bacteria of the genus *Staphylococcus*. In another aspect, the terms "infection and "bacterial infection" may refer to a bacterial infection caused by a bacteria of the genus *Stenotrophomonas*. In still another aspect, the terms "infection and "bacterial infection" may refer to a bacterial infection caused by a bacteria of the genus *Streptococcus*.

In one aspect, the terms "infection" and "bacterial infection" may refer to a gynecological infection. In another aspect the terms "infection" and "bacterial infection" may refer to a respiratory tract infection (RTI). In still another, the terms "infection" and "bacterial infection" may refer to a sexually transmitted disease. In yet another aspect, the terms "infection" and "bacterial infection" may refer to a urinary tract infection. In a further aspect, the terms "infection" and "bacterial infection" may refer to acute exacerbation of chronic bronchitis (ACEB). In yet a further aspect, the terms "infection" and "bacterial infection" may refer to acute otitis media. In one aspect, the terms "infection" and "bacterial infection" may refer to acute sinusitis. In another aspect, the terms "infection" and "bacterial infection" may refer to an infection caused by drug resistant bacteria. In still another aspect, the terms "infection" and "bacterial infection" may refer to catheter-related sepsis. In yet another aspect, the terms "infection" and "bacterial infection" may refer to chancroid. In a further aspect, the terms "infection" and "bacterial infection" may refer to chlamydia. In still a further aspect, the terms "infection" and "bacterial infection" may refer to community-acquired pneumonia (CAP). In yet a further aspect, the terms "infection" and "bacterial infection" may refer to complicated skin and skin structure infection. In one aspect, the terms "infection" and "bacterial infection" may refer to uncomplicated skin and skin structure infection. In another aspect, the terms "infection" and "bacterial infection" may refer to endocarditis. In still another aspect, the terms "infection" and "bacterial infection" may refer to febrile neutropenia. In yet another aspect, the terms "infection" and "bacterial infection" may refer to gonococcal cervicitis. In a further aspect, the terms "infection" and "bacterial infection" may refer to gonococcal urethritis. In still a further aspect, the terms "infection" and "bacterial infection" may refer to hospital-acquired pneumonia (HAP). In yet another aspect, the terms "infection" and "bacterial infection" may refer to osteomyelitis. In a further aspect, the terms "infection" and "bacterial infection" may refer to sepsis. In still a further aspect, the terms "infection" and "bacterial infection" may refer to syphilis.

In one aspect, there is provided the use of a compound of Formula (I), or a pharmaceutically acceptable salt thereof, in the manufacture of a medicament for the production of a bacterial DNA gyrase inhibitory effect, in a warm-blooded animal such as man.

In another aspect, there is provided the use a compound of Formula (I), or a pharmaceutically acceptable salt thereof, in the manufacture of a medicament for the treatment of a bacterial infection in a warm-blooded animal such as man.

In still another aspect, there is provided the use of a compound of Formula (I), or a pharmaceutically acceptable salt thereof, in the manufacture of a medicament for the treatment of urinary tract infections, pneumonia, prostatitis, skin and soft tissue infections, and intra-abdominal infections, in a warm-blooded animal such as man.

In yet another aspect, there is provided a method for producing a bacterial DNA gyrase inhibitory effect in a warm-blooded animal such as man, said method comprising administering to said animal an effective amount of a compound of Formula (I), or a pharmaceutically acceptable salt thereof.

In a further aspect, there is provided a method for treating a bacterial infection in a warm-blooded animal such as man, said method comprising administering to said animal an effective amount of a compound of formula (I), or a pharmaceutically acceptable salt thereof.

In still a further aspect, there is provided a method for treating urinary tract infections, pneumonia, prostatitis, skin and soft tissue infections, and intra-abdominal infections, in a warm-blooded animal such as man, said method comprising administering to said animal an effective amount of a compound of Formula (I), or a pharmaceutically acceptable salt thereof In yet a further aspect, there is provided a compound of Formula (I), or a pharmaceutically acceptable salt thereof, for use in producing a bacterial DNA gyrase inhibitory effect in a warm-blooded animal such as man.

In one aspect, there is provided a compound of Formula (I), or a pharmaceutically acceptable salt thereof, for use in treating a bacterial infection in a warm-blooded animal, such as man.

In another aspect, there is provided a compound of Formula (I), or a pharmaceutically acceptable salt thereof, for use in treating urinary tract infections, pneumonia, prostatitis, skin and soft tissue infections, and intra-abdominal infections, in a warm-blooded animal such as man.

In still another aspect, there is provided a pharmaceutical composition comprising a compound of Formula (I), or a pharmaceutically acceptable salt thereof, and at least one pharmaceutically acceptable carrier, diluent, or excipient.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients well known in the art. Thus, compositions intended for oral use may contain, for example, one or more coloring, sweetening, flavoring and/or preservative agents.

Suitable pharmaceutically acceptable excipients for a tablet formulation include, for example, inert diluents such as lactose, sodium carbonate, calcium phosphate or calcium carbonate; granulating and disintegrating agents such as corn starch or algenic acid; binding agents such as starch; lubricating agents such as magnesium stearate, stearic acid or talc; preservative agents such as ethyl or propylp-hydroxybenzoate; and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form or in the form of nano or micronized particles together with one or more suspending agents, such as sodium carboxymethylcellulose, methylcellulose, hydroxypropylmethylcellulose, sodium alginate, polyvinylpyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives such as ethyl or propyl p-hydroxybenzoate; anti-oxidants such as ascorbic acid); coloring agents; flavoring agents; and/or sweetening agents such as sucrose, saccharine or aspartame.

Oily suspensions may be formulated by suspending the active ingredient in a vegetable oil such as arachis oil, olive oil, sesame oil or coconut oil or in a mineral oil such as liquid paraffin. The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 4 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

In addition to the compounds of the present invention, the pharmaceutical composition of this invention may also contain or be co-administered (simultaneously, sequentially or separately) with one or more known drugs selected from other clinically useful classes of antibacterial agents (for example, macrolides, quinolones, β-lactams or aminoglycosides) and/or other anti-infective agents (for example, an antifungal triazole or amphotericin). These may include carbapenems, for example meropenem or imipenem, to broaden the therapeutic effectiveness. Compounds of this invention may also contain or be co-administered with bactericidal/permeability-increasing protein (BPI) products or efflux pump inhibitors to improve activity against gram negative bacteria and bacteria resistant to antimicrobial agents.

As stated above the size of the dose required for the therapeutic or prophylactic treatment of a particular disease state will necessarily be varied depending on the host treated, the route of administration and the severity of the illness being treated. Preferably a daily dose in the range of 1-50 mg/kg is employed. Accordingly, the optimum dosage may be determined by the practitioner who is treating any particular patient.

In addition to its use in therapeutic medicine, the compound of Formulas (I) and its pharmaceutically acceptable salts are also useful as pharmacological tools in the development and standardization of in vitro and in vivo test systems for the evaluation of the effects of inhibitors of DNA gyrase in laboratory animals such as cats, dogs, rabbits, monkeys, rats and mice, as part of the search for new therapeutic agents.

If not commercially available, the necessary starting materials for the procedures such as those described herein may be made by procedures which are selected from standard organic chemical techniques, techniques which are analogous to the synthesis of known, structurally similar compounds, or techniques which are analogous to the described procedure or the procedures described in the Examples.

It is noted that many of the starting materials for synthetic methods as described herein are commercially available and/or widely reported in the scientific literature, or could be made from commercially available compounds using adaptations of processes reported in the scientific literature. The reader is further referred to *Advanced Organic Chemistry*, 5th Edition, by Jerry March and Michael Smith, published by John Wiley & Sons 2001, for general guidance on reaction conditions and reagents.

Compounds of Formula (I) may be prepared in a variety of ways. The processes shown below illustrates a method for synthesizing compounds of Formula (I) (wherein Ring A, W, X, Y, and $R^1$, unless otherwise defined, are as defined hereinabove). The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents, which are compatible with the reaction conditions, will be readily apparent to one skilled in the art and alternate methods must then be used. The Schemes and Processes are not intended to present an exhaustive list of methods for preparing the compounds of Formula (I); rather, additional techniques of which the skilled chemist is aware may be also be used for the compounds' synthesis. The claims are not intended to be limited to the structures shown in the Schemes and Processes.

It will also be appreciated that in some of the reactions shown in the the Schemes and Processes mentioned herein, it may be necessary/desirable to protect any sensitive groups in compounds. The instances where protection is necessary or desirable are known to those skilled in the art, as are suitable methods for such protection. Conventional protecting groups may be used in accordance with standard practice (for illustration see T. W. Greene, *Protective Groups in Organic Synthesis*, published by John Wiley and Sons, 1991) and as described hereinabove.

The skilled chemist will be able to use and adapt the information contained and referenced within the above references, and accompanying Examples therein and also the Examples and Scheme herein, to obtain necessary starting materials and products.

In one aspect, compounds of Formula (I), or pharmaceutically acceptable salts thereof, may be prepared by:

Process A—reacting a compound of Formula (A1):

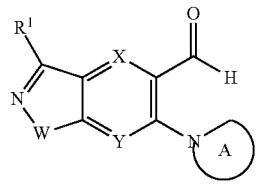

Formula (A1)

with barbituric acid:

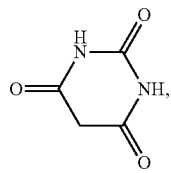

and thereafter if necessary:
i) converting a compound of Formula (I) into another compound of Formula (I);
ii) removing any protecting groups; and/or
iii) forming a pharmaceutically acceptable salt.

In another aspect compounds of Formula (Ib), which are compounds of Formula (I) in which W is —O— or —NH—, or pharmaceutically acceptable salts thereof, may be prepared by:

Process B—reacting a compound of Formula (A3):

Formula (A3)

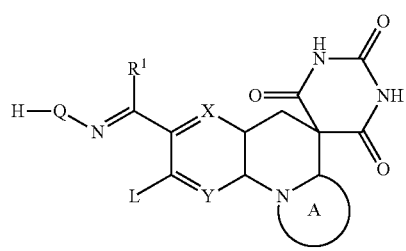

with a suitable ring-forming agent,
and thereafter if necessary:
i) converting a compound of Formula (I) into another compound of Formula (I);
ii) removing any protecting groups; and/or
iii) forming a pharmaceutically acceptable salt,
wherein
L is a leaving group, as discussed hereinabove; and
Q is selected from —O— and —NH—.

Process A

The reaction of Process A may be carried out in one or two separate reaction steps by reaction of a compound of Formula (A1) with a compound of Formula (A2) under standard Knoevenagel reaction conditions to form an intermediate olefin. Solvents suitable for such a reaction include alcohols such as methanol, isopropanol, and butanol, hydrocarbon solvents such as toluene and benzene and ethereal solvents such as dioxane and dimethoxyethane. Typical temperatures can range from about 60° C. to about 120° C. The Knoevenagel reaction may be catalyzed by a base such as triethylamine or pyrrolidine or an organic salt such as piperidinium acetate. Oftentimes under the reaction conditions, the intermediate olefin (Knoevenagel adduct) rearranges to a compound of Formula (A1), the rearrangement being due to what is sometimes referred to as the "tertiary amine effect." If the rearrangement does not occur, the temperature of the reaction may be increased and/or solvents can be exchanged to more polar solvents such as dimethylformamide and dimethylsulfoxide. Increased reaction temperature may then range from about 70° C. to about 180° C.

Process B

The reaction shown for Process B can be run in protic solvents such as MeOH, EtOH or IPA or ethereal solvents such as THF and dioxane or aprotic solvents such as DMF or acetonitrile depending on the nature of the base. Reaction temperatures can vary from room temperature to 130° C. Illustrtative examples of the "ring-forming agent" include carbonate bases such as $CsCO_3$ and $Na_2CO_3$, alkoxides such as NaOMe and NaOEt, amines such as triethylamine and DBU and hydride bases such as NaH.

Scheme 1 depicts a procedure by which compounds of Formula (A3) may be prepared.

Scheme 1

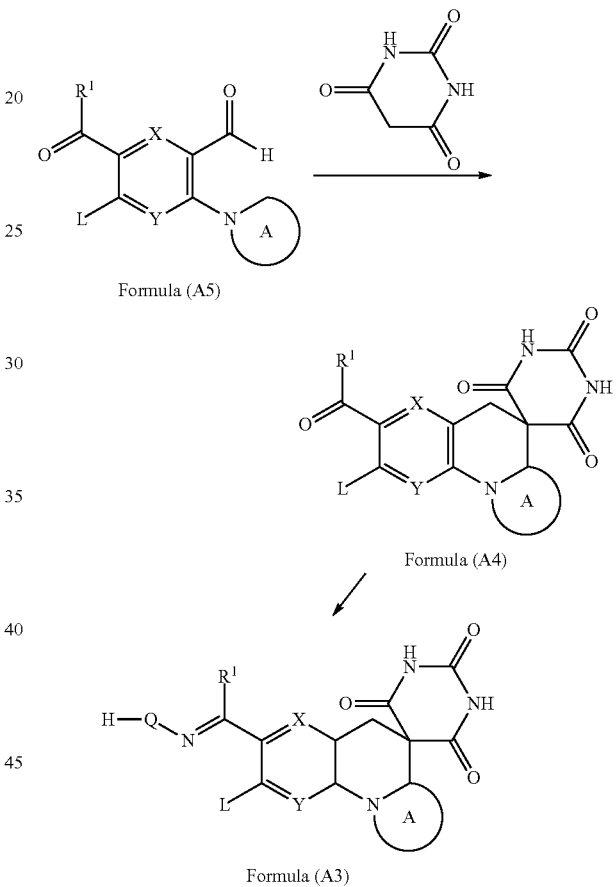

Compounds of Formula (A5) may be reacted with barbituric acid under the conditions described for the reaction of Process A, providing a compound of Formula (A4). The compound of Formula (A3) may be obtained by reaction of the compound of Formula (A4) with hydroxylamine hydrochloride or hydrazine optionally in the presence of a catalyst or reagent such as sodium acetate, sodium bicarbonate, or pyridine at temperatures ranging from room temperature to 130° C. in suitable solvents including protic solvents such as methanol or ethanol, polar solvents such as DMF or DMSO, ethereal solvents such as THF or dioxane and aromatic solvents such as toluene or pyridine. Oftentimes under the reaction conditions, the intermediate compounds A3 cyclize to compounds of Formula A (W is O or NH).

Scheme 2 depicts a process by which compounds of Formula (A5) are prepared. Leaving group $L^1$ typically include halogens such as fluorine, chlorine or bromine or sulfonic esters such as trifluomethanesulfonyloxy.

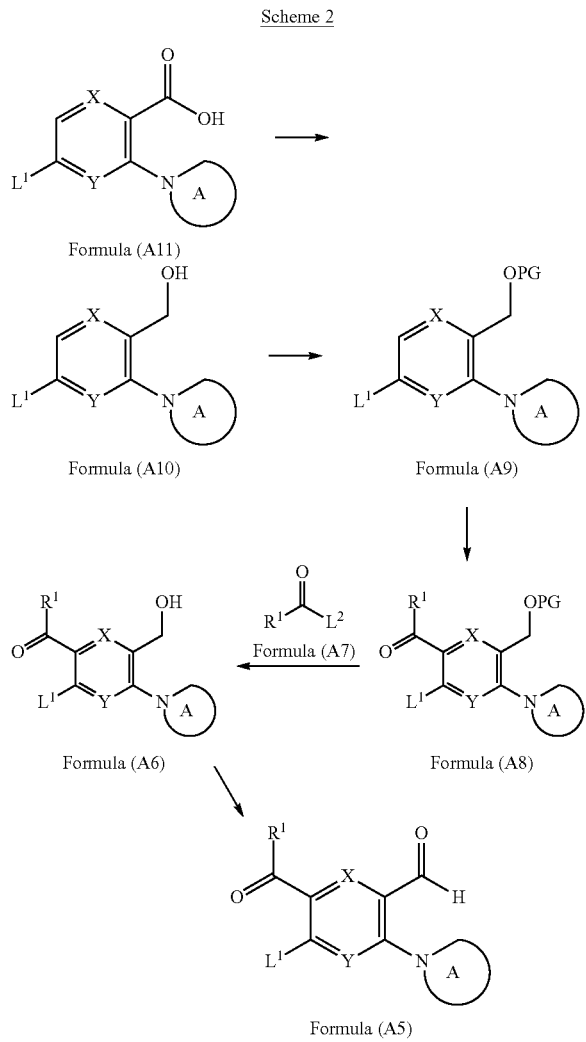

Scheme 2

Formula (A11)
Formula (A10)
Formula (A9)
Formula (A7)
Formula (A6)
Formula (A8)
Formula (A5)

Compounds of Formula (A5) may be prepared from compounds of Formula (A11) using the synthesis showed in Scheme 2. Reduction of the acid group of the compound of Formula (A11) to an alcohol may be accomplished using typical reducing agents such as borane, sodium borohydride and iodine, and ethyl chloroformate and lithium borohydride under standard reducing conditions, providing the compound of Formula (A10). Protection of the compound of Formula (A10) under typical conditions with standard alcohol protecting groups, including silyl protecting groups such as TBMS, provides the compound of Formula (A9). The $R^1$—(CO)— moiety may be added by reaction of the compound of Formula (A9) with a compound of Formula (A7) under basic conditions, providing the compound of Formula (A6). Typical leaving groups (designated by $L^2$) suitable for such a reaction include amines such as dimethylamine and (N-methoxy)-methylamine, alcohols such as methanol or ethanol or halides such as chloride or bromide. Bases suitable for such a reaction include alkyllithiums such s-butyllithium and n-butyllithium and amines such a lithium diisopropylamine, lithium hexamethyldisilazine and lithium tetramethylpiperidine. Oxidation of the alcohol of the compound of Formula (A6) using an oxidizing agent such as $MnO_2$, pyrdinium chlorochromate, the Dess-Martin periodinane and DMF/oxalyl chloride.DMSO provides the compound of Formula (A5).

In any of the above-mentioned pharmaceutical compositions, processes, methods, uses, medicaments, and manufacturing features of the instant invention, any of the alternate embodiments of the compounds of the invention described herein also apply.

EXAMPLES

The invention will now be further described with reference to the following illustrative examples in which, unless stated otherwise:

(i) temperatures are given in degrees Celsius (° C.); operations are carried out at room temperature or ambient temperature, that is, in a range of 18-25° C.;

(ii) organic solutions were dried over anhydrous magnesium sulfate; evaporation of organic solvent was carried out using a rotary evaporator under reduced pressure (4.5-30 mmHg) with a bath temperature of up to 60° C.;

(iii) chromatography means flash chromatography on silica gel; thin layer chromatography (TLC) was carried out on silica gel plates;

(iv) in general, the course of reactions was followed by TLC or liquid chromatography/mass spectroscopy (LC/MS) and reaction times are given for illustration only;

(v) final products have satisfactory proton nuclear magnetic resonance (NMR) spectra and/or mass spectra data;

(vi) yields are given for illustration only and are not necessarily those which can be obtained by diligent process development; preparations were repeated if more material was required;

(vii) when given, NMR data is in the form of delta values for major diagnostic protons, given in part per million (ppm) relative to tetramethylsilane (TMS) as an internal standard, determined at 300 MHz in DMSO-$d_6$ unless otherwise stated;

(viii) chemical symbols have their usual meanings;

(ix) solvent ratio was given in volume:volume (v/v) terms;

(x) an ISCO Combiflash refers to flash chromatography on silica gel using Isco Combiflash® separation system: RediSep normal phase flash column, flow rate, 30-40 ml/min;

(xi) the following abbreviations may have been used:
BINAP 2,2'-bis(diphenylphosphino)-1,1'-binapthyl
$Boc_2O$ tert-butyloxycarbonyl anhydride
DAST Diethylaminosulfur trifluoride
DCM dichloromethane
DIPEA N,N-diisopropylethylamine
DMAc N,N-dimethylacetamide
DMF N,N-dimethylformamide
dppf 1,1'-bis(diphenylphosphino)ferrocene
DMAP 4-dimethylaminopyridine
DMSO dimethylsulfoxide
ee enantiomeric excess
EtOAc ethyl acetate
$Et_2O$ diethyl ether
GC gas chromatography
HATU O-(7-Azabenzotriazol-1-yl)-N,N,N',N'-tetramethyluronium hexafluorophosphate
HPLC high-performance liquid chromatography
hr hours
LDA Lithium diisopropylamide
mins minutes NMO 4-methylmorpholine-N-oxide
NMP N-methylpyrrolidone
o/n overnight
Pd$_2$(dba)$_3$ Tris(dibenzylideneacetone)dipalladium(0)
iPrOH i-propanol
rac. rracemic
SEM 1-((2-(trimethylsilyl)ethoxy)methyl
TBME tert-butylmethyl ether
TEA triethylamine
TFA trifluoroacetic acid
TFAA trifluoroacetic anhydride
THF tetrahydrofuran
TMS trimethyl silyl
Tosyl, Ts para-toluenesulfonyl
TPAP tetrapropylammonium perruthenate
Xantphos 9,9-dimethyl-4,5-bis(diphenylphosphino) xanthene In those instances in which a compound name includes "rel," as in, for example, "(2R,4S,4aS)-rel-8-amino-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione," it is to be understood that such a designation implies that the indicated compound is in the form of a racemic mixture. In the indicated example, the name indicates that the compound is in the form of a racemic mixture of two enantiomers: the (2R,4S,4aS) enantiomer and the (2S,4R,4aR) enantiomer.

Additionally, the structural depiction of a (2R,4S,4aS) enantiomer preceded by a "(±)" sign indicates that the compound is present in the form a racemic mixture containing the (2R,4S,4aS) enantiomer and the (2S,4R,4aR) enantiomer of the compound. For example, the structure shown for Example 1:

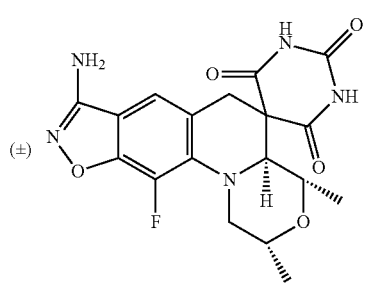

indicates that the title compound is present as a racemic mixture of the following two enantiomers:

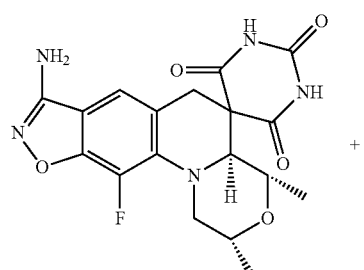

+

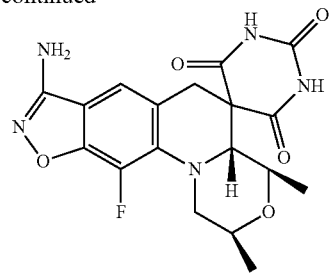

The examples are illustrative and are not to be read as limiting the scope of the invention as defined by the claims.

Intermediate 1

2-((2R,6S)-2,6-dimethyl-morpholin-4-yl)-3,4-difluoro-benzoic acid

To a stirred solution of 2,3,4-trifluorobenzoic acid (25.0 g, 142 mmol) in THF (250 mL), was added lithium bis(trimethylsilyl)amide (1M in THF, 156 mL, 156 mmol) at −78° C. under nitrogen atmosphere and the solution stirred for 45 min. To this was added a premixed solution of cis-2,6-dimethylmorpholine (17.4 mL, 142 mmol) and lithium bis(trimethylsilyl)amide (1M in THF, 156 mL, 156 mmol) (which was stirred for 45 minutes at −78° C., before the addition was made) and stirring continued for 1 h at −78° C. It was brought to room temperature and stirring continued for additional 12 hours. Solvents were evaporated and the residue dissolved in ethyl acetate, which was washed with 1N HCl, water and brine. The organic layer was dried and concentrated to give the title compound as semi-solid. Yield: 27.5 g, (72%).

MS (ES) M+H$^-$: 271.2 for C$_{13}$H$_{15}$F$_2$NO$_3$ $^1$H NMR (400 MHz—CDCl$_3$) δ: 1.2 (s, 6H), 2.9 (d, 2H), 3.1 (d, 2H), 3.9 (m, 2H), 7.2 (s, 1H), 7.3 (t, 1H), 8.1 (m, 1H).

Intermediate 2

[2-((2R,6S)-2,6-dimethyl-morpholin-4-yl)-3,4-difluoro-phenyl]-methanol

To a stirred and ice-bath cooled solution of 2-((2R,6S)-2,6-dimethyl-morpholin-4-yl)-3,4-difluoro-benzoic acid (Intermediate 1, 27.0 g, 99.6 mmol) in THF (250 mL) was added sodium borohydride (12.56 g, 358.6 mmol) in small portions, followed by iodine (32.5 g, 139.4 mmol) in THF (250 mL). The addition was carried out such that the temperature maintained below 10° C. The mixture brought to room temperature and refluxed for 12 hours. It was cooled and then quenched with methanol (250 mL). Solvents were evaporated and the residue treated with 2M NaOH (500 mL) for 2 hours. The aqueous layer extracted with ethyl acetate (3×150 mL), and the combined organic phases were washed with water and brine before being dried (Na$_2$SO$_4$) and concentrated to give the title compound as a gummy solid. MS (ES) MH$^+$: 257.2 for C$_{13}$H$_{17}$F$_2$NO$_2$ $^1$H NMR (400 MHz, CDCl$_3$) δ: 1.24 (s, 6H), 3.0 (d, 3H), 3.1 (d, 2H), 3.9 (m, 2H), 4.78 (s, 2H), 6.9 (d, 1H), 7.0 (t, 1H).

Intermediate 3

(2R,6S)-4-[6-({[tert-butyl(diphenyl)silyl]oxy}methyl)-2,3-difluorophenyl]-2,6-dimethylmorpholine To an ice cooled and stirred solution of [2-((2R,6S)-2,6-dimethyl-morpholin-4-yl)-3,4-difluoro-phenyl]-methanol (Intermediate 2, 27.0 g, 105 mmol) in CH$_2$Cl$_2$ was added imidazole (8.5 g, 126 mmol) followed by t-butyl chlorodiphenylsilane (30 mL, 115 mmol) over a period of 15 min. The mixture was brought to room temperature and stirred for 12 h during which tlc showed the disappearance of starting material. The reaction mixture diluted with CH$_2$Cl$_2$ and washed successively with 1 N HCl (1×250 mL), water and brine. The organic layer dried (Na$_2$SO$_4$), filtered and concentrated. The residue was purified over a silica gel flash column using a gradient of ethyl acetate in pet. ether to give the title compound as a white solid. Yield: 45 g (94%).

MS (ES) MH$^+$: 495.6 for C$_{29}$H$_{35}$F$_2$NO$_2$Si $^1$H NMR (400 MHz, CDCl$_3$) δ: 1.1 (s, 15H), 2.6 (d, 2H), 2.8 (m, 2H), 3.5 (t, 2H), 4.7 (s, 2H), 7.0 (q, 1H); 7.3 (t, 1H), 7.4 (m, 10H).

Intermediate 4

5-(tert-butyl-diphenyl-silanyloxymethyl)-4-((2R,6S)-2,6-dimethyl-morpholin-4-yl)-2,3-difluoro-benzaldehyde To a stirred solution of (2R,6S)-4-[6-({[tert-Butyl(diphenyl)silyl]oxy}methyl)-2,3-difluorophenyl]-2,6-dimethylmorpholine (Intermediate 3, 15.0 g, 30.0 mmol) in THF (150 mL) was added sec-butyllithium (1.4 M in cyclohexane, 66.4 mL, 93 mmol) at −78° C. under a nitrogen atmosphere. After stirring for 1 h at this temperature, DMF (3.4 mL, 45 mmol) was added dropwise such that the temperature was maintained below −60° C. After stirring for ½ h, reaction mixture treated with saturated aqueous NH$_4$Cl solution and the aqueous layer extracted with EtOAc (2×100 mL). The combined organic phases were dried (Na$_2$SO$_4$), filtered and concentrated. The residue was purified over a silica gel flash column using a gradient of ethyl acetate in pet. ether to give the title compound as a yellow solid.

MS (ES) MH$^+$: 523.6 for C$_{30}$H$_{35}$F$_2$NO$_3$Si $^1$H NMR (400 MHz—CDCl$_3$) δ: 1.1 (s, 15H), 2.8 (m, 4H), 3.4 (m, 2H), 4.6 (s, 2H), 7.3 (t, 4H), 7.4 (t, 2H), 7.6 (d, 4H), 7.8 (s, 1H), 10.2 (s, 1H).

Intermediate 5

1-{5-({[tert-butyl(diphenyl)silyl]oxy}methyl)-4-[(2R,6S)-2,6-dimethylmorpholin-4-yl]-2,3-difluorophenyl}-N-hydroxymethanimine To an ice-bath cooled and stirred solution of 5-(tert-Butyl-diphenyl-silanyloxymethyl)-4-((2R,6S)-2,6-dimethyl-morpholin-4-yl)-2,3-difluoro-benzaldehyde (Intermediate 4, 9.1 g, 17 mmol) in THF was added DIPEA (4.5 mL, 26 mmol) followed by hydroxylamine hydrochloride (1.3 g, 19 mmol) over a period of 15 min. The mixture was brought to room temperature and stirred for 12 hours. The reaction mixture was diluted with CH$_2$Cl$_2$ and washed successively with 1 N HCl (1×250 mL), water and brine. The organic layer dried (Na$_2$SO$_4$), filtered and concentrated. The residue was purified over a silica gel flash column using a gradient of ethyl acetate in pet. ether to give the title compound as white solid. Yield: 8.9 g, (86%).

MS (ES) MH$^+$: 539.6 for C$_{30}$H$_{36}$F$_2$N$_2$O$_3$Si.

Intermediate 6

5-({[tert-butyl(diphenyl)silyl]oxy}methyl)-4-[(2R,6S)-2,6-dimethylmorpholin-4-yl]-2,3-difluorobenzonitrile A mixture of (E)-1-{5-({[tert-butyl(diphenyl)silyl]oxy}methyl)-4-[(2R,6S)-2,6-dimethylmorpholin-4-yl]-2,3-difluorophenyl}-N-hydroxymethanimine (Intermediate 5, 8.0 g, 14.8 mmol) and acetic anhydride (10 mL) was stirred at 130° C. for 12 hours. the reaction mixture cooled to room temperature and concentrated, and the residue was purified over a silica gel flash column using a gradient of ethyl acetate in pet. ether to give the title compound as yellow solid. Yield: 6.5 g, (85%).

MS (ES) MH$^+$: 521.2 for C$_{30}$H$_{34}$F$_2$N$_2$O$_2$Si $^1$H NMR (300 MHz, CDCl$_3$) δ: 1.1 (s, 6H), 1.3 (s, 9H), 2.8 (d, 2H), 2.9 (m, 2H), 3.5 (d, 2H), 4.7 (s, 2H), 7.3 (s, 1H), 7.4 (s, 1H), 7.6 (d, 1H).

Intermediate 7

{3-amino-6-[(2R,6S)-2,6-dimethylmorpholin-4-yl]-7-fluoro-1,2-benzisoxazol-5-yl}methanol To an ice-bath cooled and stirred solution of 5-({[tert-butyl(diphenyl)silyl]oxy}methyl)-4-[(2R,6S)-2,6-dimethylmorpholin-4-yl]-2,3-difluorobenzonitrile (Intermediate 6, 500 mg, 0.96 mmol) in DMF was added t-BuOK (161 mg, 1.4 mmol) followed by acetohydroxamic acid (108 mg, 1.4 mmol). The mixture was brought to room temperature and stirred for 12 hours. The reaction mixture was diluted with EtOAc and washed successively with 1 N HCl (1×250 mL), water and brine. The organic layer was dried (Na$_2$SO$_4$), filtered and concentrated. The residue was purified over silica gel flash column using a gradient of ethyl acetate in pet. ether to give the title compound as a white solid. Yield: 200 mg, (70%).

MS (ES) MH$^+$: 296.6 for C$_{14}$H$_{18}$FN$_3$O$_3$ $^1$H NMR (400 MHz, CDCl$_3$) δ: 1.1 (s, 6H), 2.8 (d, 2H), 2.9 (m, 2H), 3.6 (t, 2H), 4.7 (s, 2H), 5.3 (t, 1H), 6.5 (s, 2H), 7.8 (d, 1H).

Intermediate 8

3-amino-6-[(2R,6S)-2,6-dimethylmorpholin-4-yl]-7-fluoro-1,2-benzisoxazole-5-carbaldehyde To an ice-cooled solution of {3-amino-6-[(2R,6S)-2,6-dimethylmorpholin-4-yl]-7-fluoro-1,2-benzisoxazol-5-yl}methanol (Intermediate 7, 200 mg, 0.67 mmol) in CH$_2$Cl$_2$/CH$_3$CN mixture (4 mL, 1:1 v/v) was added NMO (119 mg, 1.0 mmol) followed TPAP (23 mg, 0.06 mmol) and mixture stirred for 2 h at room temperature. The reaction mixture filtered thorough a silica gel bed and washed with EtOAc. The organic phase concentrated under reduced pressure to give the title compound as a yellow solid. Yield: 100 mg, (50%).

MS (ES) MH$^+$: 294.6 for C$_{14}$H$_{16}$FN$_3$O$_3$.

Intermediate 9

1-{5-({[tert-butyl(diphenyl)silyl]oxy}methyl)-4-[(2R,6S)-2,6-dimethylmorpholin-4-yl]-2,3-difluorophenyl}ethanone To a stirred solution of (2R,6S)-4-[6-({[tert-Butyl(diphenyl)silyl]oxy}methyl)-2,3-difluorophenyl]-2,6-dimethylmorpholine (Intermediate 3, 15.0 g, 30.0 mmol) in THF (150 mL) was added sec-butyllithium (1.4 M in cyclohexane, 66.4 mL, 93 mmol) at −78° C. under a nitrogen atmosphere. After stirring for 1 h, N-methoxy-N-methyl-acetamide (3.4 mL, 45 mmol) was added and, after stirring for ½ h at −78° C., the solution was allowed reach room temperature with stirring continuing for 12 hours. The reaction mixture treated with saturated aqueous NH$_4$Cl solution and the aqueous layer extracted by EtOAc (2×100 mL). The organic phases were combined, dried (Na$_2$SO$_4$) and concentrated. The residue was purified over a silica gel flash column using a gradient of ethyl acetate in pet. ether to give the title compound as yellow solid.
Yield: 13.2 g (82%)
MS (ES) MH$^+$: 538.6 for $C_{31}H_{37}F_2NO_3Si$
$^1$H NMR (400 MHz, CDCl$_3$) δ: 1.1 (s, 15H), 2.8 (m, 4H), 3.4 (m, 2H), 4.6 (s, 2H), 7.3 (t, 4H), 7.4 (t, 2H), 7.6 (d, 4H), 7.8 (s, 1H), 10.2 (s, 1H).

Intermediate 10

1-[4-((2R,6S)-2,6-dimethyl-morpholin-4-yl)-2,3-difluoro-5-hydroxymethyl-phenyl]-ethanone A mixture of 1-[5-(tert-butyl-diphenyl-silanyloxymethyl)-4-((2R,6S)-2,6-dimethyl-morpholin-4-yl)-2,3-difluoro-phenyl]-ethanone (Intermediate 9, 7.2 g, 28 mmol) and 4N HCl in dry dioxane (75 mL) was stirred at room temperature for 12 hours. The reaction mixture was treated with cold water (20 mL) and extracted with ethyl acetate (3×50 mL). The combined organic phases combined were dried (Na$_2$SO$_4$) and concentrated. The residue was purified over a silica gel flash column using a gradient of ethyl acetate in pet. ether to give the title compound as yellow solid.
Yield: 3.4 g (42%).
MS (ES) MH$^+$: 300 for $C_{15}H_{19}F_2NO_3$
$^1$H NMR (400 MHz, CDCl$_3$) δ: 1.1 (s, 15H), 2.5 (d, 2H), 2.7 (t, 2H), 2.8 (s, 2H), 4.7 (s, 2H), 5.2 (t, 1H), 7.3 (t, 1H), 7.4 (s, 10H).

Intermediate 11

5-acetyl-2-((2R,6S)-2,6-dimethyl-morpholin-4-yl)-3,4-difluoro-benzaldehyde

To an ice-cooled solution of 1-[4-((2R,6S)-2,6-dimethyl-morpholin-4-yl)-2,3-difluoro-5-hydroxymethyl-phenyl]-ethanone (Intermediate 10, 3.2 g, 9.72 mmol) in CH$_2$Cl$_2$/CH$_3$CN mixture (20 mL, 1:1 v/v) was added NMO (2.2 g, 19.44 mmol) followed by TPAP (340 mg, 0.97 mmol) and mixture stirred for 2 hours at room temperature. The reaction mixture filtered thorough silica gel bed and washed with EtOAc. The organic phase concentrated under reduced pressure to give the title compound as a yellow crystalline solid.
Yield: 3.0 g (94%).
MS (ES) MH$^+$: 298.2 for $C_{15}H_{17}F_2NO_3$
$^1$H NMR (400 MHz, CDCl$_3$): δ 1.2 (d, 6H); 2.1 (s, 3H), 3.0 (d, 2H), 3.1 (t, 2H), 3.8 (s, 2H), 5.1 (s, 2H), 7.6 (t 1H), 10.2 (s, 1H).

Intermediate 12

(2R,4S,4aS)-rel-8-acetyl-9,10-difluoro-2,4-dimethyl-1,2,4,4a-tetrahydro-2'H,6H-spiro[1,4-oxazino[4,3-a]quinoline-5,5'-pyrimidine]-2',4',6'(1'H,3'H)-trione To a solution of 5-acetyl-2-((2R,6S)-2,6-dimethyl-morpholin-4-yl)-3,4-difluoro-benzaldehyde (Intermediate 11, 3.0 g, 9.17 mmol) in IPA was added barbituric acid (1.4 g, 11.00 mmol), and the mixture was heated at 85° C. for 12 hours. Solvents were evaporated and the residue was purified over neutral alumina using a gradient of methanol in CH$_2$Cl$_2$ to give the title compound as a racemic mixture in the form of an off-white solid. Yield: 3.0 g (75%).
MS (ES) MH$^+$: 408.2 for $C_{19}H_{19}F_2N_3O_5$
$^1$H NMR (400 MHz-DMSO-d$_6$) δ: 0.8 (d, 3H), 1.1 (d, 3H), 2.1 (s, 3H), 2.8 (d, 1H), 3.0 (t, 1H), 3.5 (d, 1H), 3.6 (m, 1H), 3.7 (d, 1H), 3.9 (d, 1H), 4.1 (d, 1H), 7.2 (d, 1H), 11.5 (s, 1H), 11.8 (s, 1H).

Intermediates 13 to 15 were prepared from the indicated starting materials using a method similar to the one described for the syntheses of Intermediate 12. Each was obtained as a racemic mixture.

Intermediate 13

(2R,4S,4aS)-rel-9,10-difluoro-2,4-dimethyl-8-(phenylcarbonyl)-1,2,4,4a-tetrahydro-2'H,6H-spiro[1,4-oxazino[4,3-a]quinoline-5,5'-pyrimidine]-2',4',6'(1'H,3'H)-trione Starting material: 2-[(2R,6S)-2,6-dimethylmorpholin-4-yl]-3,4-difluoro-5-(phenylcarbonyl)benzaldehyde (Intermediate 26).
MS (ES) MH$^+$: 470.2 for $C_{24}H_{21}F_2N_3O_5$
$^1$H NMR (400 MHz, DMSO-d$_6$) δ: 0.8 (d, 3H), 1.1 (d, 3H), 2.9 (d, 1H), 3.1 (t, 1H), 3.6 (m, 2H), 3.8 (m, 1H), 3.9 (d, 1H), 4.1 (d, 1H), 7.1 (d, 1H), 7.5 (m, 2H), 7.6 (m, 3H), 11.5 (s, 1H), 11.8 (s, 1H):

Intermediate 14

(2R,4S,4aS)-rel-9,10-difluoro-2,4-dimethyl-8-(pyridin-2-ylcarbonyl)-1,2,4,4a-tetrahydro-2'H,6H-spiro[1,4-oxazino[4,3-a]quinoline-5,5'-pyrimidine]-2',4',6'(1'H,3'H)-trione Starting material: 2-[(2R,6S)-2,6-dimethylmorpholin-4-yl]-3,4-difluoro-5-(pyridin-2-ylcarbonyl)benzaldehyde (Intermediate 27).
MS (ES) MH$^+$: 471.2 for $C_{23}H_{20}F_2N_4O_5$ Intermediate 15

(2R,4S,4aS)-rel-8-(cyclopropylcarbonyl)-9,10-difluoro-2,4-dimethyl-1,2,4,4a-tetrahydro-2'H,6H-spiro[1,4-oxazino[4,3-a]quinoline-5,5'-pyrimidine]-2',4',6'(1'H,3'H)-trione Starting material: 5-(Cyclopropylcarbonyl)-2-[(2R,6S)-2,6-dimethylmorpholin-4-yl]-3,4-difluorobenzaldehyde (Intermediate 28).
MS (ES) MH$^+$: 434.1 for $C2_1H_{21}F_2N_3O_5$ Intermediate 16

(2R,4S,4aS)-rel-9,10-difluoro-8-[(1E)-N-hydroxyethanimidoyl]-2,4-dimethyl-1,2,4,4a-tetrahydro-2'H,6H-spiro[1,4-oxazino[4,3-a]quinoline-5,5'-pyrimidine]-2',4',6'(1'H,3'H)-trione To a solution of (2R,4S,4aS)-rel-8-acetyl-9,10-difluoro-2,4-dimethyl-1,2,4,4a-tetrahydro-2'H,6H-spiro[1,4-oxazino[4,3-a]quinoline-5,5'-pyrimidine]-2',4',6'(1'H,3'H)-trione (Intermediate 12, 250 mg, 0.63 mmol) in MeOH, was added hydroxylamine hydrochloride (88 mg, 1.3 mmol) and the mixture heated to 85° C. for 12 hours. After cooling to room temperature, solvent was removed, and the residue was purified via normal phase HPLC (95:5: Hexane:IPA) to give the title compound as a racemic mixture in the form of a pale yellow solid. Yield: 50 mg (20%).
MS (ES) MH$^+$: 423.2 for $C_{19}H_{20}F_2N4O_5$
$^1$H NMR (400 MHz, DMSO-d$_6$) δ: 0.9 (d, 3H), 1.1 (d, 3H), 2.0 (d, 3H), 2.8 (d, 1H), 3.0 (t, 1H), 3.3 (d, 1H), 3.6 (d, 1H), 3.7 (t, 1H), 3.8 (t, 1H), 4.0 (d, 1H), 4.1 (d, 2H), 6.8 (d, 1H), 11.1 (s, 1H), 11.4 (s, 1H), 11.8 (s, 1H).

Intermediate 17

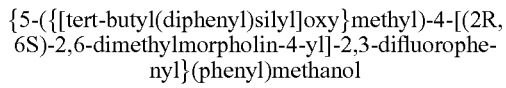
{5-({[tert-butyl(diphenyl)silyl]oxy}methyl)-4-[(2R,6S)-2,6-dimethylmorpholin-4-yl]-2,3-difluorophenyl}(phenyl)methanol To a stirred solution of (2R,6S)-4-[6-({[tert-butyl(diphenyl)silyl]oxy}methyl)-2,3-difluorophenyl]-2,6-dimethylmorpholine (Intermediate 3, 1 g, 2.0 mmol) in anhydrous THF (10 mL), s-butyllithium (4.5 ml, 1.4M in cyclohexane, 6.3 mmol) was added and stirred for 2 h at −78° C. Benzaldehyde (685 mg, 0.0064 mmol) in THF (5 mL) was added dropwise and the solution was stirred for additional 1 h. The reaction mixture was quenched with saturated ammonium chloride solution and extracted with ethyl acetate. The organic layer was washed with brine and dried ($Na_2SO_4$), and solvent was removed. The residue was purified over a silica gel chromatography column using ethyl acetate-pet. ether gradient, providing the title compound.

Yield: 1.1 g, (92%)
MS (ES) $MH^+$: 602.2 for $C_{36}H_{41}F_2NO_3Si$

Intermediates 18 to 19 were prepared from the indicated starting materials using a method similar to the one described for the syntheses of Intermediate 17. Each was obtained as a racemic mixture.

Intermediate 18

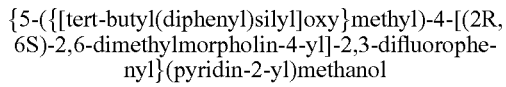
{5-({[tert-butyl(diphenyl)silyl]oxy}methyl)-4-[(2R,6S)-2,6-dimethylmorpholin-4-yl]-2,3-difluorophenyl}(pyridin-2-yl)methanol Starting material: (2R,6S)-4-[6-({[tert-butyl(diphenyl)silyl]oxy}methyl)-2,3-difluorophenyl]-2,6-dimethylmorpholine (Intermediate 3) and pyridine-2-carboxaldehyde.
MS (ES) $MH^+$: 603.2 for $C_{35}H_{40}F_2N_2O_3Si$ Intermediate 19

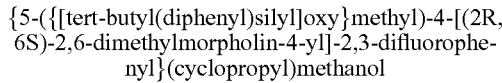
{5-({[tert-butyl(diphenyl)silyl]oxy}methyl)-4-[(2R,6S)-2,6-dimethylmorpholin-4-yl]-2,3-difluorophenyl}(cyclopropyl)methanol Starting material: (2R,6S)-4-[6-({[tert-butyl(diphenyl)silyl]oxy}methyl)-2,3-difluorophenyl]-2,6-dimethylmorpholine (Intermediate 3) and cylopropyl carboxaldehyde.
MS (ES) $MH^+$: 566.2 for $C_{33}H_{41}F_2NO_3Si$ Intermediate 20

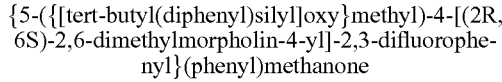
{5-({[tert-butyl(diphenyl)silyl]oxy}methyl)-4-[(2R,6S)-2,6-dimethylmorpholin-4-yl]-2,3-difluorophenyl}(phenyl)methanone NMO (428 mg, 0.0037 mmol) and TPAP (65 mg, 0.0002 mmol) were added to a stirred solution of {5-({[tert-butyl(diphenyl)silyl]oxy}methyl)-4-[(2R,6S)-2,6-dimethylmorpholin-4-yl]-2,3-difluorophenyl}(phenyl)methanol (Intermediate 17, 1.1 g, 0.002 mmol) in $CH_2Cl_2$:$CH_3CN$ (1:1, 10 mL) 0° C. The mixture was allowed to warm to room temperature with stirring for 12 hours. The solvents were removed, and the residue was purified over a silica gel chromatography column using an ethyl acetate-pet. ether gradient, providing the title compound. Yield: 1 g, (92%)
MS (ES) $MH^+$: 600.2 for $C_{36}H_{39}F_2NO_3Si$ Intermediate 21

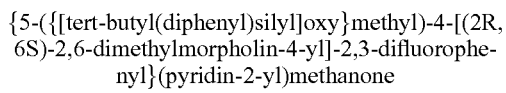
{5-({[tert-butyl(diphenyl)silyl]oxy}methyl)-4-[(2R,6S)-2,6-dimethylmorpholin-4-yl]-2,3-difluorophenyl}(pyridin-2-yl)methanone PCC (1.07 g, 0.005 mmol) was added to a solution of {5-({[tert-butyl(diphenyl)silyl]oxy}methyl)-4-[(2R,6S)-2,6-dimethylmorpholin-4-yl]-2,3-difluorophenyl}(pyridin-2-yl)methanol (Intermediate 18, 1.8 g, 0.002 mmol) in anhydrous DMC (15 mL) at 0° C. and the mixture was allowed to stir for 1 h at room temperature. The reaction mixture was filtered and the solvents were removed under vacuum and the residue was purified over silica gel chromatography column using an ethyl acetate-pet. ether gradient, providing the title compound. Yield: 1.5 g (83%). MS (ES) $MH^+$: 603.2 for $C_{35}H_{40}F_2N_2O_3Si$ Intermediate 22 was prepared from the indicated starting materials using a method similar to the one described for the syntheses of Intermediate 21:

Intermediate 22

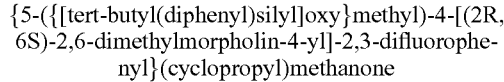
{5-({[tert-butyl(diphenyl)silyl]oxy}methyl)-4-[(2R,6S)-2,6-dimethylmorpholin-4-yl]-2,3-difluorophenyl}(cyclopropyl)methanone Starting material: {5-({[tert-butyl(diphenyl)silyl]oxy}methyl)-4-[(2R,6S)-2,6-dimethylmorpholin-4-yl]-2,3-difluorophenyl}(cyclopropyl)methanol (Intermediate 19).
MS (ES) $MH^+$: 564.2 for $C_{33}H_{39}F_2NO_3Si$ Intermediate 23

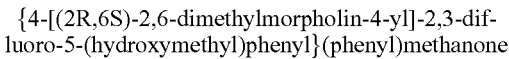
{4-[(2R,6S)-2,6-dimethylmorpholin-4-yl]-2,3-difluoro-5-(hydroxymethyl)phenyl}(phenyl)methanone tert-Butyl ammonium fluoride (435 mg, 0.002 mmol) was added in small portions to a stirred solution of {5-({[tert-butyl(diphenyl)silyl]oxy}methyl)-4-[(2R,6S)-2,6-dimethylmorpholin-4-yl]-2,3-difluorophenyl}(phenyl)methanone (Intermediate 20, 1 g, 0.002 mmol) in anhydrous THF (10 mL) at 0° C. and stirring was continued for 1 h with warming to room temperature. The solvent was removed and the residue was purified over a silica gel chromatography column using ethyl acetate-pet. ether gradient, providing the title compound. Yield: 450 mg, (75%)
MS (ES) $MH^+$: 362.2 for $C_{20}H_{21}F_2NO_3$ Intermediates 24 and 25 were prepared from the indicated starting materials using a method similar to the one described for the syntheses of Intermediate 23:

Intermediate 24

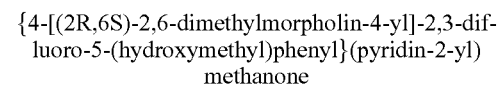
{4-[(2R,6S)-2,6-dimethylmorpholin-4-yl]-2,3-difluoro-5-(hydroxymethyl)phenyl}(pyridin-2-yl)methanone Starting material: {5-({[tert-butyl(diphenyl)silyl]oxy}methyl)-4-[(2R,6S)-2,6-dimethylmorpholin-4-yl]-2,3-difluorophenyl}(pyridin-2-yl)methanol (Intermediate 18).
MS (ES) $MH^+$: 363.2 for $C_{19}H_{20}F_2N_2O_3$ Intermediate 25

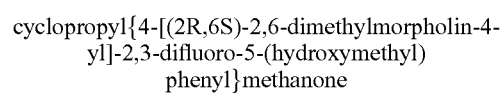
cyclopropyl{4-[(2R,6S)-2,6-dimethylmorpholin-4-yl]-2,3-difluoro-5-(hydroxymethyl)phenyl}methanone Starting material: {5-({[tert-butyl(diphenyl)silyl]oxy}methyl)-4-[(2R,6S)-2,6-dimethylmorpholin-4-yl]-2,3-difluorophenyl}(cyclopropyl)methanone (Intermediate 22).
MS (ES) $MH^+$: 326.2 for $C_{17}H_{21}F_2NO_3$ Intermediate 26

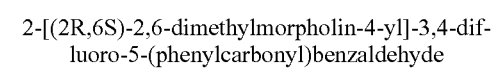
2-[(2R,6S)-2,6-dimethylmorpholin-4-yl]-3,4-difluoro-5-(phenylcarbonyl)benzaldehyde NMO (295 mg, 0.0025 mmol) and TPAP (44 mg, 0.0001 mmol) were added to a stirred solution of {4-[(2R,6S)-2,6- dimethylmorpholin-4-yl]-2,3-difluoro-5-(hydroxymethyl)phenyl}(phenyl)methanone (Intermediate 23, 450 mg, 0.001 mmol) in anhydrous CH$_2$Cl$_2$:CH$_3$CN (1:1, 10 mL) at 0° C., and the mixture was stirred for 12 hours with warming to room temperature. The solvents were removed and the residue was purified over a silica gel chromatography column using ethyl acetate-pet. ether gradient, providing the title compound. Yield: 340 mg, (76%)

MS (ES) MH$^+$: 360.2 for C$_{20}$H$_{19}$F$_2$NO$_3$

Intermediate 27

2-[(2R,6S)-2,6-cimethylmorpholin-4-yl]-3,4-difluoro-5-(pyridin-2-ylcarbonyl)benzaldehyde PCC (297 mg, 0.002 mmol) was added to a solution of {4-[(2R,6S)-2,6-dimethylmorpholin-4-yl]-2,3-difluoro-5-(hydroxymethyl)phenyl}(pyridin-2-yl)methanone (Intermediate 24, 500 mg, 0.001 mmol) in anhydrous CH$_2$Cl$_2$ (5 mL), at 0° C. and the mixture was stired with warming to room temperature for 1 h. The reaction mixture was filtered, the solvents were removed, and the residue was purified over silica gel chromatography column using ethyl acetate-pet. ether gradient, providing the title compound. Yield: 350 mg, (70%).

MS (ES) MH$^+$: 361.2 for C$_{19}$H$_{18}$F$_2$N$_2$O$_3$

Intermediate 28 was prepared from the indicated starting materials using a method similar to the one described for the syntheses of Intermediate 27:

Intermediate 28

5-(cyclopropylcarbonyl)-2-[(2R,6S)-2,6-dimethylmorpholin-4-yl]-3,4-difluorobenzaldehyde Starting material: cyclopropyl{4-[(2R,6S)-2,6-dimethylmorpholin-4-yl]-2,3-difluoro-5-(hydroxymethyl)phenyl}methanone (Intermediate 25).

MS (ES) MH$^+$: 324.2 for C$_{17}$H$_{19}$F$_2$NO$_3$

Intermediate 29

(2R,4S,4aS)-rel-9,10-difluoro-8-[(E)-(hydroxyimino)(phenyl)methyl]-2,4-dimethyl-1,2,4,4a-tetrahydro-2'H,6H-spiro[1,4-oxazino[4,3-a]quinoline-5,5'-pyrimidine]-2',4',6'(1'H,3'H)-trione Hydroxylamine hydrochloride (77 mg, 0.001 mmol) was added to a solution of (2R,4S,4aS)-rel-9,10-difluoro-2,4-dimethyl-8-(phenylcarbonyl)-1,2,4,4a-tetrahydro-2'H,6H-spiro[1,4-oxazino[4,3-a]quinoline-5,5'-pyrimidine]-2',4',6'(1'H,3'H)-trione (Intermediate 13, 280 mg, 0.6 mmol) in methanol:pyridine (1:1, 3 mL) and the solution was heated to 90° C. for 12 hours. Solvents were removed and the residue was subjected to silica gel column chromatography using a gradient of ethyl acetate in pet. ether to give the title compound as a racemic mixture. Yield: 120 mg (42%).

MS (ES) MH$^+$: 485.2 for C$_{24}$H$_{22}$F$_2$N$_4$O$_5$ $^1$H NMR (400 MHz-DMSO-d$_6$) δ: 0.8 (d, 3H), 1.2 (d, 3H), 2.8 (d, 1H), 3.0 (m, 1H), 3.4 (d, 1H), 3.6 (m, 1H), 3.7 (m, 1H), 3.8 (d, 1H), 4.0 (d, 1H), 6.6 (d, 1H), 7.4 (s, 5H), 11.5 (s, 2H).

Intermediates 30 and 31 were prepared from the indicated starting materials using a method similar to the one described for the syntheses of Intermediate 29. Each was obtained as a racemic mixture.

Intermediate 30

(2R,4S,4aS)-rel-9,10-difluoro-8-[(Z)-(hydroxyimino)(pyridin-2-yl)methyl]-2,4-dimethyl-1,2,4,4a-tetrahydro-2'H,6H-spiro[1,4-oxazino[4,3-a]quinoline-5,5'-pyrimidine]-2',4',6'(1'H,3'H)-trione Starting material: (2R,4S,4aS)-rel-9,10-Difluoro-2,4-dimethyl-8-(pyridin-2-ylcarbonyl)-1,2,4,4a-tetrahydro-2'H,6H-spiro[1,4-oxazino[4,3-a]quinoline-5,5'-pyrimidine]-2',4',6'(1'H,3'H)-trione (Intermediate 14).

MS (ES) MH$^+$: 486.3 for C$_{23}$H$_{21}$F$_2$N$_5$O$_5$ $^1$H NMR (400 MHz, DMSO-d$_6$) δ: 0.8 (d, 3H), 1.1 (d, 3H), 2.9 (d, 1H), 3.0 (m, 1H), 3.4 (d, 1H), 3.6 (m, 1H), 3.7 (m, 1H), 3.8 (d, 1H), 4.0 (d, 1H), 6.65 (d, 1H), 7.3 (m, 1H), 7.8 (m, 2H), 8.4 (d, 1H), 11.5 (s, 1H), 11.8 (s, 1H), 11.8 (d, 1H).

Intermediate 31

(2R,4S,4aS)-rel-8-[(E)-cyclopropyl(hydroxyimino)methyl]-9,10-difluoro-2,4-dimethyl-1,2,4,4a-tetrahydro-2'H,6H-spiro[1,4-oxazino[4,3-a]quinoline-5,5'-pyrimidine]-2',4',6'(1'H,3'H)-trione Starting material: (2R,4S,4aS)-rel-8-(Cyclopropylcarbonyl)-9,10-difluoro-2,4-dimethyl-1,2,4,4a-tetrahydro-2'H,6H-spiro[1,4-oxazino[4,3-a]quinoline-5,5'-pyrimidine]-2',4',6'(1'H,3'H)-trione (Intermediate 15).

MS (ES) MH$^+$: 449.1 for C$_{21}$H$_{22}$F$_2$N$_4$O$_5$ $^1$H NMR (400 MHz, DMSO-d$_6$) δ: 0.3 (m, 1H), 0.8 (d, 2H), 0.85 (d, 3H), 1.1 (d, 3H), 2.3 (m, 1H), 2.9 (d, 1H), 3.0 (m, 1H), 3.3 (m, 1H), 3.6 (m, 1H), 3.7 (m, 1H), 3.8 (d, 1H), 4.0 (d, 1H), 6.55 (d, 1H), 11.1 (s, 3H).

Intermediate 32

1-(5-((tert-butyldiphenylsilyloxy)methyl)-4-((2R,6S)-2,6-dimethylmorpholino)-3-fluoro-2-(propan-2-ylideneaminooxy)phenyl)ethanone To a stirred solution of propan-2-one oxime (913 mg, 12.50 mmol) in THF (15 ml) was added KOtBu (935 mg, 8.33 mmol) at room temperature. After stirring for 45 minutes, 1-{5-({[tert-butyl(diphenyl)silyl]oxy}methyl)-4-[(2R,6S)-2,6-dimethylmorpholin-4-yl]-2,3-difluorophenyl}ethanone (Intermediate 9, 2240 mg, 4.17 mmol) dissolved in 10 ml of THF was added. After stirring for 3 hours reaction quenched with saturated aqueous ammonium chloride solution and extracted with EtOAc. The organic layer was dried (Na$_2$SO$_4$), filtered, and concentrated to give the crude title compound (2.5 g). LCMS and NMR indicates >90% purity. Used in the next step without any further purification.

MS (ES): 591 (M+H) for C$_{34}$H$_{43}$FN$_2$O$_4$Si $^1$H NMR (300 MHz, CDCl$_3$) δ ppm 1.0-1.1 (s and d, 15H), 2.0 (s, 3H), 2.1 (s, 3H), 2.5-2.95 (m, 7H), 3.3-3.6 (m, 2H), 4.7 (s, 2H), 7.3-7.5 (m, 6H), 7.55-7.8 (m, 5H).

Intermediate 33

(6-((2R,6S)-2,6-dimethylmorpholino)-7-fluoro-3-methylbenzo[d]isoxazol-5-yl)methanol To a stirred solution of 1-(5-((tert-butyldiphenylsilyloxy)methyl)-4-((2R,6S)-2,6-dimethylmorpholino)-3-fluoro-2-(propan-2-ylideneaminooxy)phenyl)ethanone (Intermediate 32, 77 mg, 0.13 mmol, crude reaction product from above reaction) dissolved in ethanol (5 ml) was treated with 5 ml of 5% aqueous HCl at 75° C. for 2 hours. Reaction quenched with 10% aqueous sodium bicarbonate solution and extracted with EtOAc. The organic layer washed with water, dried, and concentrated. The residue purified over a silica gel flash coulmn (elution with 50-70% EtOAc in hexanes) to give the title compound (15 mg, 39%).

MS (ES): 295 (M+H) for $C_{15}H_{19}FN_2O_3$ $^1$H NMR (300 MHz, CDCl$_3$) δ ppm 1.2 (d, 6H), 2.5 (s, 3H), 2.8-3.2 (m, 5H), 3.7-3.95 (m, 2H), 4.8 (s, 2H), 7.3 (s, 1H).

Intermediate 34

6-((2R,6S)-2,6-dimethylmorpholino)-7-fluoro-3-methylbenzo[d]isoxazole-5-carbaldehyde To a stirred solution of (6-((2R,6S)-2,6-dimethylmorpholino)-7-fluoro-3-methylbenzo[d]isoxazol-5-yl)methanol (Intermediate 33, 0.65 g, 2.21 mmol) in CH$_2$Cl$_2$ (30 ml) was added MnO$_2$ (3.84 g, 44.17 mmol). After stirring for 3 days at room temperature MnO$_2$ was filtered and washed with CH$_2$Cl$_2$. The filtrate was concentrated and dried to give the title compound (0.547 g, 85%).

MS (ES): 293 (M+H) for $C_{15}H_{17}FN_2O_3$ $^1$H NMR (300 MHz, CDCl$_3$) δ ppm 1.2 (d, 6H) 2.6 (s, 3H) 2.9-3.2 (m, 4H) 3.7-4.0 (m, 2H), 7.9 (s, 1H), 10.4 (s, 1H).

Intermediates 35 and 36 were prepared from the indicated starting materials using a method similar to the one described for the synthesis of Intermediate 1:

Intermediate 35

3-chloro-2-[(2R,6S)-2,6-dimethylmorpholin-4-yl]-4-fluorobenzoic acid

Starting materials: 3-chloro-2,4-difluorobenzoic acid and cis-2,6-dimethylmorpholine.

MS (ES) MH$^+$: 288 for $C_{13}H_{15}ClFNO_3$ $^1$H NMR (400 MHz, CDCl$_3$) δ: 1.1 (d, 6H), 2.5 (d, 2H), 3.1 (t, 2H), 3.4 (m, 2H), 6.9 (d, 1H), 7.0 (t, 1H), 13.2 (br, 1H).

Intermediate 36

2-((2R,6R)-2,6-dimethylmorpholino)-3,4-difluorobenzoic acid

Starting materials: 2,3,4-trifluorobenzoic acid and (2R, 6R)-2,6-dimethylmorpholine (BASF).

MS (ES) MH$^+$: 272 for $C_{13}H_{15}F_2NO_3$ $^1$H NMR (300 MHz, CDCl$_3$) δ: 1.17 (d, 6H), 2.84 (dd, 2H), 3.20 (d, 2H), 3.86-4.19 (m, 2H), 7.14-7.40 (m, 1H), 7.44-7.61 (m, 1H), 14.14 (s, 1H).

Intermediates 37 and 38 were prepared from the indicated starting material, I$_2$ and NaBH$_4$ using a method similar to the one described for the synthesis of Intermediate 2:

Intermediate 37

{3-chloro-2-[(2R,6S)-2,6-dimethylmorpholin-4-yl]-4-fluorophenyl}methanol

Starting material: 3-chloro-2-[(2R,6S)-2,6-dimethylmorpholin-4-yl]-4-fluorobenzoic acid (Intermediate 35).

MS (ES) MH$^+$: 274 for $C_{13}H_{17}ClFNO_2$ $^1$H NMR (400 MHz, CDCl$_3$) δ: 1.1 (d, 6H), 2.5 (d, 2H), 3.1 (t, 2H), 3.4 (m, 2H), 4.78 (s, 2H), 6.9 (d, 1H), 7.0 (t, 1H).

Intermediate 38

(2-((2R,6R)-2,6-dimethylmorpholino)-3,4-difluorophenyl)methanol

Starting material: 2-((2R,6R)-2,6-dimethylmorpholino)-3,4-difluorobenzoic acid (Intermediate 36).

MS (ES) MH$^+$: 258 for $C_{13}H_{17}F_2NO_2$ $^1$H NMR (300 MHz, CDCl$_3$) δ: ppm 1.32 (d, 6H), 2.73-3.41 (m, 4H), 4.00-4.29 (m, 2H), 4.60-4.89 (m, 2H), 6.78-7.19 (m, 2H).

Intermediate 39

1-(dimethoxymethyl)-2,3,4-trifluorobenzene

A solution of 2,3,4-trifluorobenzaldehyde (25 g, 156.16 mmol), 2,2-dimethoxypropane (58.1 ml, 468.48 mmol), and 4-methylbenzenesulfonic acid (0.269 g, 1.56 mmol) was stirred at room temperature overnight. The reaction mixture diluted with ether and washed successively with aq. sodium bicarbonate solution, water, and brine. The organic layer dried over sodium sulfate and concentrated. The residue was-distilled under high vacuum to give the title compound (23.07 g, 71.7%).

$^1$H NMR (300 MHz, CDCl$_3$) δ: 3.36 (s, 6H), 5.54 (s, 1H), 6.8-7.1 (m, 1H), 7.1-7.4 (m, 1H).

Intermediate 40

3-((2R,6S)-2,6-dimethylmorpholino)-5-fluoropicolinic acid

A solution of 3,5-difluoropicolinic acid (20.5 g, 128.86 mmol), cis-2,6-dimethylmorpholine (63.5 ml, 515.43 mmol) and DIEA (45.0 ml, 257.72 mmol) in THF (200 ml) was stirred at room temperature for 3 days. The mixture was diluted with EtOAc and extracted 3 times with aqueous Na$_2$CO$_3$. The aqueous layer was acidified with 1N HCl to bring pH to about 3 and was then saturated with NaCl before being extracted 10 times with EtOAc. The EtOAc layers were dried (MgSO$_4$) and solvent was removed to give 33.5 g of product as a solid.

MS (ES) (M−H)$^−$: 253 for $C_{12}H_{15}FN_2O_3$.

$^1$H NMR (DMSO-d$^6$): 1.1 (d, 6H), 2.5 (m, 2H), 3.2 (d, 2H), 3.7 (m 2H), 7.5 (d, 1H), 8.1 (s, 1H), 13.3 (s, broad, 1H).

Intermediate 41

(3-((2R,6S)-2,6-dimethylmorpholino)-5-fluoropyridin-2-yl)methanol

Ethyl chloroformate (4.04 ml, 42.05 mmol) was added to a solution of 3-((2R,6S)-2,6-dimethylmorpholino)-5-fluoropicolinic acid (Intermediate 40, 8.91 g, 35.04 mmol) and TEA (5.86 ml, 42.05 mmol) cooled in an ice water bath. After completion of the addtion, the reaction mixture was allowed to warm to room temperature with stirring for 1 hour. Lithium borohydride (1.985 g, 91.11 mmol) was added portionwise and the mixture was stirred for 1 hour. The mixture was quenched first with water and then with 1N HCl. It was then taken up in EtOAc and aqueous Na$_2$CO$_3$. The organic layer was separated and washed with brine. The combined aqueous layers were extracted with EtOAc 3 times, each extract being washed with brine. The combined EtOAc layers were dried (MgSO$_4$) and concentrated to give an oil that slowly solidified. The residue was recrystallized from cyclohexane to give product as a white solid. The mother liquor was concentrated and the residue was chromatographed on silica gel (100% CH$_2$Cl$_2$ followed by gradient elution to 50% EtOAc in CH$_2$Cl$_2$) to give additional product as a white solid. Total yield of 5.6 g.

MS (ES) MH$^+$: 241 for $C_{12}H_{17}FN_2O_2$.

$^1$H NMR (DMSO-d$^6$): 1.1 (d, 6H), 2.4 (t, 2H), 3.1 (d, 2H), 3.7-3.8 (m, 2H), 4.5 (d, 2H), 5.1 (t, 1H), 7.4 (d, 1H), 8.2 (s, 1H).

Intermediates 42 to 44 were prepared from the indicated starting material and t-butyl chloro diphenylsilane using a method similar to the one described for the synthesis of Intermediate 3:

Intermediate 42

(2R,6S)-4-[6-({[tert-butyl(diphenyl)silyl]oxy}methyl)-2-chloro-3-fluorophenyl]-2,6-dimethylmorpholine Starting material: {3-chloro-2-[(2R,6S)-2,6-dimethylmorpholin-4-yl]-4-fluorophenyl}methanol (Intermediate 37).

MS (ES) MH+: 496 for $C_{29}H_{35}F_2NO_2Si$ $^1$H NMR (400 MHz, CDCl$_3$) δ: 1.0 (s, 15H), 1.1 (s, 9H), 2.5 (d, 2H), 3.1 (t, 2H), 3.4 (m, 2H); 4.7 (s, 2H), 7.0 (t, 1H), 7.3 (t, 1H), 7.4 (m, 10H).

Intermediate 43

(2R,6R)-4-(6-((tert-butyldiphenylsilyloxy)methyl)-2,3-difluorophenyl)-2,6-dimethylmorpholine Starting material: (2-((2R,6R)-2,6-dimethylmorpholino)-3,4-difluorophenyl)methanol (Intermediate 38).

MS (ES) MH+: 496 for $C_{29}H_{35}F_2NO_2Si$ $^1$H NMR (300 MHz, CDCl$_3$) δ: 1.04 (d, 6H) 1.09 (s, 9H), 2.44-2.77 (m, 2H), 2.82-3.15 (m, 2H), 3.72-4.03 (m, 2H), 4.62-4.93 (m, 2H), 6.91-7.12 (m, 1H), 7.29-7.52 (m, 7H), 7.57-7.76 (m, 4H).

Intermediate 44

(2R,6S)-4-(2-((tert-Butyldiphenylsilyloxy)methyl)-5-fluoropyridin-3-yl)-2,6-dimethylmorpholine Starting material: (3-((2R,6S)-2,6-dimethylmorpholino)-5-fluoropyridin-2-yl)methanol (Intermediate 41).

MS (ES) MH+: 479 for $C_{28}H_{35}FNO_2Si$.

$^1$H NMR (CDCl$_3$): δ 1.0 (s, 9H), 1.15 (d, 6H, 2.4 (t, 2H), 3.0 (d, 2H), 3.6-3.7 (m, 2H), 4.8 (s, 2H), 7.0 (d, 1H), 7.4 (m, 6H), 7.7 (m, 4H), 8.2 (s, 1H).

Intermediate 45

(2R,6S)-4-(2-((tert-butyldiphenylsilyloxy)methyl)-4-chloro-5-fluoropyridin-3-yl)-2,6-dimethylmorpholine A solution of diisopropylamine (3.51 ml, 24.65 mmol) in THF (30 ml) was cooled in a dry ice-acetone bath. A solution of n-butyllithium (2.5 M in hexanes, 9.28 ml, 23.20 mmol) was added and the mixture was warmed to 0° C. and recooled in a dry ice-acetone bath. The solution was added to a second solution of (2R,6S)-4-(2-((tert-butyldiphenylsilyloxy)methyl)-5-fluoropyridin-3-yl)-2,6-dimethylmorpholine (Intermediate 44, 6.94 g, 14.50 mmol) in THF (30 ml) cooled in a dry ice-acetone bath. The mixture was stirred for 45 minutes before the solution was transferred via cannula to a solution of hexachloroethane (2.79 ml, 24.65 mmol) in 60 ml THF also cooled in a dry ice-acetone bath. The mixture was allowed to warm to room temperature before being diluted with EtOAc and washed with water and brine. The combined aqueous layers were extracted again with EtOAc, which was washed with brine. Drying (MgSO$_4$) of the combined EtOAc extracts and removal of solvent gave a gummy solid that was chromatographed on silica gel (50% hexanes in CH$_2$Cl$_2$ followed by gradient elution to 100% CH$_2$Cl$_2$) to afford product as an oil that slowly solidified (5.26 g yield). MS (ES) MH+: 513 for $C_{28}H_{34}ClFN_2O_2Si$.

$^1$H NMR (CDCl$_3$): δ 1.0 (s, 9H), 1.15 (d, 6H, 2.4 (t, 2H), 3.0 (d, 2H), 3.6-3.7 (m, 2H), 4.8 (s, 2H), 7.0 (d, 1H), 7.4 (m, 6H), 7.7 (m, 4H), 8.2 (s, 1H).

Intermediate 46

2,4-difluoro-3-methylbenzoic acid

To a stirred solution of diisopropylamine (1.7 g, 16.4 mmol) in THF 2.6 M solution of n-BuLi (1.1 g, 16.4 mmol) was added at −30° C. and the mixture was stirred for an hour at the same temperature. To this mixture a solution of 2,4-difluorobenzoic acid (1.0 g, 6.3 mmol) in THF was added slowly at −78° C., followed by methyl iodide (2.2 g, 15.7 mmol) and it was stirred for another 2 h at the same temperature and allowed to attain the room temperature. The reaction mixture was treated with saturated aqueous NH$_4$Cl solution and the aqueous layer extracted with ethylacetate (3×25 mL). The organic phases were combined and dried over anhydrous sodium sulfate. After removal of solvent, the residue was purified over a silica gel flash column using a gradient of ethyl acetate in pet. ether to give product as a white solid. Yield: 0.77 g (70%)

MS (ES) MH+: 172 for $C_8H_6F_2O_2$ $^1$H NMR (400 MHz, CDCl$_3$) δ: 2.2 (s, 3H), 7.0 (m, 1H), 7.9 (m, 1H).

Intermediate 47 methyl 3-chloro-2-[(2R,6S)-2,6-dimethylmorpholin-4-yl]-4-fluorobenzoate

To a stirred solution of 3-chloro-2-[(2R,6S)-2,6-dimethylmorpholin-4-yl]-4-fluorobenzoic acid (Intermediate 35, 10.0 g, 34.8 mmol) in methanol (50 mL) was added concentrated H$_2$SO$_4$ (1 mL) and the solution was refluxed for 12 hours. The reaction mixture was concentrated and diluted with EtOAc (100 mL). The organic layer washed with H$_2$O (2×20 mL), dried over anhydrous sodium sulfate and concentrated. The residue was purified by column chromatography with ethyl acetate-pet. ether to give product as a solid. Yield: 9.0 g (86%)

MS (ES) MH+: 303 for $C_{14}H_{17}ClFNO_3$.

Intermediate 48 tert-butyldiphenyl(2,3,4-trifluorobenzyloxy)silane tert-Butylchlorodiphenylsilane (8.86 ml, 34 mmol) was added slowly via syringe to a solution of (2,3,4-trifluorophenyl)methanol (5.0 g, 31 mmol) and imidazole (2.53 g, 37.2 mmol) in CH$_2$Cl$_2$ (30 ml) cooled in an ice water bath. The mixture warmed to room temperature and stir overnight. Solvent was removed and the residue was partitioned between Et$_2$O and water. The Et$_2$O was separated and washed with brine, and the combined aqueous layers were twice more extracted with Et$_2$O, which was washed with brine. Drying (MgSO$_4$) and removal of solvent gave an oil that was chromatographed on silica gel (50% CH$_2$Cl$_2$ in hexanes followed by gradient elution to 100% CH$_2$Cl$_2$) to isolate an oil that slowly solidified to afford 11.9 g (96%) of a white solid.

$^1$H NMR: δ 7.7 (m, 4H), 7.4 (m, 6H), 7.3 (m, 1H), 7.0 (m, 1H), 4.8 (s, 1H), 1.1 (s, 9H).

Intermediate 49

N-methoxy-N,1-dimethyl-1H-1,2,4-triazole-5-carboxamide

A mixture of 1-methyl-1H-1,2,4-triazole (3.15 mL, 55.56 mmol) and methoxy(methyl)carbamic chloride (7.55 g, 61.11 mmol) in acetonitrile (60 mL) was cooled in an ice water bath before addition of TEA (8.52 mL, 61.11 mmol). The mixture was allowed to slowly warm to room temperature and was then stirred overnight. The material was diluted with ether and solids were filtered and rinsed well with ether. The filtrate was concentrated and the residue was taken up in ether. Insoluble solids were filtered off and rinsed well with additional ether. The filtrate was concentrated to give and oil that was chromatographed on silica gel (100% $CH_2Cl_2$ followed by gradient elution to 40% EtOAc in $CH_2Cl_2$) to afford product as an oil that slowly solidified. 6.13 g (65% yield).

MS ES$^+$ (MH): 171

$^1$H NMR (300 MHz, CHLOROFORM-d) δ ppm 3.4 (br. s., 3H) 3.9 (s, 3H) 4.1 (br. s., 3H) 7.9 (s, 1H).

Intermediate 50

N-methoxy-N-methylpyrazine-2-carboxamide

To a 500 ml round bottom flask, pyrazine-2-carboxylic acid (58 g, 467.37 mmol) was suspended in dry $CH_2Cl_2$ (250 ml); oxalyl chloride (50.1 ml, 560.85 mmol) was added along with a few drops of DMF, and the mixture was stirred at room temperature for 12 hours. N,O-Dimethylhydroxylamine hydrochloride (54.7 g, 560.85 mmol) was added, and the resultant mixture was cooled down to 5° C. Triethylamine (195 ml, 1402.12 mmol) was added via a dropping funnel, and the reaction mixture was stirred at room temperature for 30 minutes before being filtered. The filter cake was washed with EtOAc, and the combined filtrate was washed with saturated sodium bicarbonate and brine, concentrated to an oil and dried under high vacuum to give the desired product (72 g).

MS (ES) MH$^+$: 168 for $C_7H_9N_3O_2$

Intermediate 51

6-chloro-N-methoxy-N-methylpyrazine-2-carboxamide

To a 100 ml round bottom flask, 6-chloropyrazine-2-carboxylic acid (1 g, 6.31 mmol) was suspended in dry $CH_2Cl_2$ (30 ml). Oxalyl chloride (3.78 ml, 7.57 mmol) was added along with a few drop of DMF, the mixture was stirred at room temperature for 12 hrs, N,O-Dimethylhydroxylamine hydrochloride (0.800 g, 8.20 mmol) was added, the resulting mixture was cooled down to 5° C., TEA (2.64 ml, 18.92 mmol) was added via a dropping funnel, the reaction mixture was stirred at room temperature for 30 minutes, filtered and the filter cake was washed with EtOAc, the combined filtrate was washed with saturated sodium bicarbonate and brine, concentrated to an oil, purified on silica gel with Hexanes/EtOAc solvents to give product (1.06 g).

MS (ES) MH$^+$: 202 for $C_7H_8ClN_3O_2$

Intermediates 52 to 55 were prepared from the indicated starting materials using a method similar to the one described for the synthesis of Intermediate 50:

Intermediate 52

N-methoxy-N-methyl-5-morpholinopyrazine-2-carboxamide

Starting material: 5-morpholinopyrazine-2-carboxylic acid

MS (ES) MH$^+$: 253 for $C_{11}H_{16}N_4O_3$

Intermediate 53

3-chloro-N-methoxy-N-methylpyrazine-2-carboxamide

Starting material: 3-chloropyrazine-2-carboxylic acid

MS (ES) MH$^+$: 202 for $C_7H_8ClN_3O_2$

Intermediate 54

5-chloro-N-methoxy-N-methylpyrazine-2-carboxamide

Starting material: 5-chloropyrazine-2-carboxylic acid

Intermediate 55

N,6-Dimethoxy-N-methylpyrazine-2-carboxamide

Starting material: 6-methoxypyrazine-2-carboxylic acid

MS (ES) MH$^+$: 198 for $C_8H_{11}N_3O_3$

Intermediate 56

Ethyl 2-(methoxy(methyl)amino)-2-oxoacetate

To a solution of N,O-dimethylhydroxylamine hydrochloride (10 g, 102.52 mmol) and ethyl chlorooxoacetate (13.77 ml, 123.02 mmol) in dichloromethane (163 ml) at 0° C. was added triethylamine (28.6 ml, 205.04 mmol) drop wise. The reaction was stirred at room temperature for 1.5 hrs. The reaction was quenched with 20 ml of methanol, and then concentrated. The resulting solid was triturated with THF and filtered away. The filtrate was concentrated. The residue was vacuum distilled bulb to bulb. At approximately 85° C. impurities were collected and then discarded. The title compound was collected at approximately 120° C. as a neat oil (11.6 g, 72.0 mmol, 70.2%).

MS (ES) MH$^+$: 162 for $C_6H_{11}NO_4$ $^1$H NMR (300 MHz, DMSO-d$_6$) δ ppm 1.27 (t, 3H) 3.17 (s, 3H) 3.70 (s, 3H) 4.29 (q, 2H)

Intermediate 57

2,4-difluoro-5-[hydroxy(1,3-thiazol-2-yl)methyl]-3-methylbenzoic acid

A solution of 1.9 M n-BuLi (3.8 ml, 7.2 mmol) in hexanes was added at −30° C. to a stirred solution of 2,2,6,6-tetramethylpiperidine (1.2 g, 9.0 mmol) in THF and the mixture was stirred for an hour at the same temperature. After cooling to −78° C., a solution of 2,4-difluoro-3-methylbenzoic acid (Intermediate 46, 0.5 g, 3.0 mmol) in THF was added slowly at and the mixture was stirred for another 2 h at the same temperature. To this mixture, a solution of thiazole-2-carboxaldehyde (0.8 g, 7.2 mmol) in THF was added dropwise over a period of 10 mins and the mixture was brought to the room temperature. The reaction mixture was quenched with 1.5N hydrochloric acid and the organic layer was separated, the aqueous layer was extracted with ethyl acetate (3×10 mL) and the combined organic layer was dried over sodium sulfate. Removal of solvent afforded the title compound as colorless product. Yield: 0.42 g (51%).

MS (ES) MH$^+$: 285 for $C_{12}H_9F_2NO_3S$

Intermediate 58 was prepared from the indicated starting materials using a method similar to the one described for the synthesis of 2,4-difluoro-5-[hydroxy(1,3-thiazol-2-yl)methyl]-3-methylbenzoic acid (Intermediate 57):

Intermediate 58

2,4-difluoro-3-methyl-5-(pyrazin-2-ylcarbonyl)benzoic acid

Starting materials: 2,4-difluoro-3-methylbenzoic acid (Intermediate 46) and N-methoxy-N-methylpyrazine-2-carboxamide.

MS (ES) MH$^+$: 278 for $C_{13}H_8F_2N_2O_3$ $^1$H NMR (400 MHz, CDCl$_3$) δ: 2.1 (s, 3H), 7.8 (t, 1H), 8.8 (s, 1H), 8.9 (t, 1H), 9.3 (d, 1H), 13.6 (s, 1H).

Intermediate 59

2,4-difluoro-3-methyl-5-(1,3-thiazol-2-ylcarbonyl) benzoic acid

A stirred mixture of 2,4-difluoro-5-[hydroxy(pyrazin-2-yl)methyl]-3-methylbenzoic acid (Intermediate 57, 0.43 g, 1.5 mmol) in 1,4-dioxane (10 mL), $MnO_2$ (0.65 g, 7.4 mmol) was refluxed for 5 hours. The reaction mixture was cooled to room temperature and filtered through celite and the solvent was removed by vacuum to afford product. Yield: 0.4 g (95%).

MS (ES) MH$^+$: 283 for $C_{12}H_7F_2NO_3S$

Intermediate 60

2-[(2R,6S)-2,6-dimethylmorpholin-4-yl]-4-fluoro-3-methyl-5-(1,3-thiazol-2-ylcarbonyl)benzoic acid

In a sealed tube, a mixture of 2,4-difluoro-3-methyl-5-(1,3-thiazol-2-ylcarbonyl)benzoic acid (Intermediate 59, 0.4 g, 1.4 mmol), cis-2,6-dimethylmorpholine (0.25 g, 2.1 mmol) and diisopropylethylamine (0.55 g, 4.2 mmol) in acetonitrile (1 mL) were heated at 90° C. overnight. The solvents were removed under vacuum and the residue was taken up in ethyl acetate, which was washed with 1.5N hydrochloric acid and dried over sodium sulfate. Removal of ethyl acetate afforded crude product that was purified by silica gel column chromatography (eluent: 3% methanol in chloroform) to afford product. Yield: 0.31 g (58%).

MS (ES) MH$^+$: 378.2 for $C_{18}H_{19}FN_2O_4S$

Intermediate 61 was prepared from the indicated starting materials using a method similar to the one described for the synthesis of 2-[(2R,6S)-2,6-dimethylmorpholin-4-yl]-4-fluoro-3-methyl-5-(1,3-thiazol-2-ylcarbonyl)benzoic acid (Intermediate 60):

Intermediate 61

2-[(2R,6S)-2,6-dimethylmorpholin-4-yl]-4-fluoro-3-methyl-5-(pyrazin-2-ylcarbonyl)benzoic acid

Starting material: 2,4-difluoro-3-methyl-5-(pyrazin-2-ylcarbonyl)benzoic acid Intermediate 58).

MS (ES) MH$^+$: 383 for $C_{19}H_{20}FN_3O_4$ $^1$H NMR (400 MHz, DMSO-d6) δ: 1.2 (d, 6H), 2.5 (s, 3H), 3.0 (d, 2H), 3.2 (t, 2H), 3.9 (m, 2H), 8.5 (d, 1H), 8.6 (t, 1H), 8.8 (d, 1H), 9.3 (s, 1H).

Intermediate 62

{5-({[tert-butyl(diphenyl)silyl]oxy}methyl)-3-chloro-4-[(2R,6S)-2,6-dimethylmorpholin-4-yl]-2-fluorophenyl}(pyridin-2-yl)methanol

To a stirred solution of (2R,6S)-[6-({[tert-butyl(diphenyl)silyl]oxy}methyl)-2-chloro-3-fluorophenyl]-2,6-dimethylmorpholine (Intermediate 42, 2.0 g, 3.9 mmol) in anhydrous THF (10 mL), sec-Butyl lithium (1.4 M in cyclohexane, 2.1 eq) was added and the solution was stirred for ½ h at −78° C. Pyridine-2-carbaldehyde (0.74 mL, 7.8 mmol) in THF (5 mL) was added dropwise and the solution was stirred for additional 1 h. The reaction mixture was quenched with saturated ammonium chloride solution and extracted with ethyl acetate. The organic layer was washed with brine and dried over anhydrous sodium sulphate. The solvent was removed under vacuum and the residue was purified over silica gel chromatography column using ethyl acetate-pet. ether gradient to obtain product. Yield: 900 mg, (37%)

MS (ES) MH$^+$: 619 for $C_{35}H_{40}ClFN_2O_3Si$;

Intermediates 63 to 70 were prepared from the indicated starting materials using a method similar to the one described for the synthesis of Intermediate 62:

Intermediate 63

{5-({[tert-butyl(diphenyl)silyl]oxy}methyl)-3-chloro-4-[(2R,6S)-2,6-dimethylmorpholin-4-yl]-2-fluorophenyl}(1,3-thiazol-5-yl)methanol

Starting materials: (2R,6S)-4-[6-({[tert-butyl(diphenyl)silyl]oxy}methyl)-2-chloro-3-fluorophenyl]-2,6-dimethylmorpholine (Intermediate 42), 1,3-thiazole-5-carbaldehyde and lithium 2,2,6,6-tetramethylpiperidide.

MS (ES) MH$^+$: 625 for $C_{33}H_{38}ClFN_2O_3Si$;

Intermediate 64

{5-({[tert-butyl(diphenyl)silyl]oxy}methyl)-3-chloro-4-[(2R,6S)-2,6-dimethylmorpholin-4-yl]-2-fluorophenyl}(pyridin-4-yl)methanol

Starting materials: (2R,6S)-4-[6-({[tert-butyl(diphenyl)silyl]oxy}methyl)-2-chloro-3-fluorophenyl]-2,6-dimethylmorpholine (Intermediate 42), 4-pyridine carboaldehyde and lithium 2,2,6,6-tetramethylpiperidide.

MS (ES) MH$^+$: 619 for $C_{35}H_{40}ClFN_2O_3Si$;

Intermediate 65

{5-({[tert-butyl(diphenyl)silyl]oxy}methyl)-3-chloro-4-[(2R,6S)-2,6-dimethylmorpholin-4-yl]-2-fluorophenyl}(pyridin-3-yl)methanol

Starting material: (2R,6S)-4-[6-({[tert-butyl(diphenyl)silyl]oxy}methyl)-2-chloro-3-fluorophenyl]-2,6-dimethylmorpholine (Intermediate 42), pyridine-3-carboaldehyde and LDA MS (ES) MH$^+$: 619 for $C_{35}H_{40}ClFN_2O_3Si$;

Intermediate 66

{5-({[tert-butyl(diphenyl)silyl]oxy}methyl-3-chloro-4-[(2R,6S)-2,6-dimethylmorpholin-4-yl]-2-fluorophenyl}(1,3-thiazol-2-yl)methanol

Starting material: (2R,6S)-4-[6-({[tert-butyl(diphenyl)silyl]oxy}methyl)-2-chloro-3-fluorophenyl]-2,6-dimethylmorpholine (Intermediate 42), 1,3-thiazole-2-carbaldehyde and lithium 2,2,6,6-tetramethylpiperidide.

MS (ES) MH$^+$: 626 for $C_{33}H_{38}ClFN_2O_3SSi$;

Intermediate 67

{5-({[tert-butyl(diphenyl)silyl]oxy}methyl-3-chloro-4-[(2R,6S)-2,6-dimethylmorpholin-4-yl]-2-fluorophenyl}(1-methyl-1H-imidazol-2-yl)methanol

Starting material: (2R,6S)-4-[6-({[tert-butyl(diphenyl)silyl]oxy}methyl)-2-chloro-3-fluorophenyl]-2,6-dimethylmorpholine (Intermediate 42), 1-methyl-imidazole-2-carbaldehyde and n-BuLi MS (ES) MH$^+$: 622 for $C_{34}H_{41}ClFN_3O_3Si$;

Intermediate 68 methyl 3-chloro-5-[cyclopropyl(hydroxy)methyl]-2-[(2R,6S)-2,6-dimethylmorpholin-4-yl]-4-fluorobenzoate

Starting materials: methyl 3-chloro-2-[(2R,6S)-2,6-dimethylmorpholin-4-yl]-4-fluorobenzoate (Intermediate 47), cyclopropyl carbaldehyde and LDA.

MS (ES) MH$^+$: 372 for $C_{18}H_{23}ClFNO_4$

Intermediate 69

{5-({[tert-butyl(diphenyl)silyl]oxy}methyl)-4-[(2R,
6S)-2,6-dimethylmorpholin-4-yl]-2,3-difluorophe-
nyl}(1-methyl-1H-imidazol-5-yl)methanol Starting materials: (2R,6S)-4-[6-({[tert-butyl(diphenyl) silyl]oxy}methyl)-2,3-difluorophenyl]-2,6-dimethylmorpholine (Intermediate 3), 1-methyl-imidazole-5-carbaldehyde (116 mg, 1.06 mmol) and sec-butyllithium.
MS (ES) MH$^+$: 605 for $C_{34}H_{41}F_2N_3O_3Si$;

Intermediate 70

{5-({[tert-butyl(diphenyl)silyl]oxy}methyl)-4-[(2R,
6S)-2,6-dimethylmorpholin-4-yl]-2,3-difluorophe-
nyl}(4-methyl-1,3-thiazol-5-yl)methanol Starting materials: (2R,6S)-4-[6-({[tert-butyl(diphenyl)silyl]oxy}methyl)-2,3-difluorophenyl]-2,6-dimethylmorpholine (Intermediate 3, 1.0 g, 2.02 mmol), 4-methyl-1,3-thiazole-5-carbaldehyde and sec-butyllithium
MS (ES) MH$^+$: 623 for $C_{34}H_{40}F_2N_2O_3SSi$ Intermediate 71

(5-((tert-butyldiphenylsilyloxy)methyl)-4-((2R,6R)-
2,6-dimethylmorpholino)-2,3-difluorophenyl)(2-
(methylthio)pyrimidin-4-yl)methanol Starting materials: (2R,6R)-4-(6-((tert-butyldiphenylsilyloxy)methyl)-2,3-difluorophenyl)-2,6-dimethylmorpholine (Intermediate 43, 7.36 g, 14.84 mmol) in t-BuOMe (20 mL) was added s-BuLi (12.45 mL, 16.19 mmol) at −75° C. under nitrogen atmosphere. After stirring for 20 minutes at this temperature, it was then transferred via cannula to a solution of 2-(methylthio)pyrimidine-4-carbaldehyde (2.08 g, 13.49 mmol) in t-BuOMe (20 mL) (precooled down to −70° C.), the mixture was then stirred for 0.5 hour at −70° C., quenched with saturated aqueouse ammonium chloride solution and extracted with ethylacetate, dried and concentrated, purified by flash column chromatography on silica gel with Hex/ EtOAc to give the desired product (3.024 g).
MS (ES) MH$^+$: 650 for $C_{35}H_{41}F_2N_3O_3SSi$ Intermediate 72

(5-((tert-Butyldiphenylsilyloxy)methyl)-3-chloro-4-
((2R,6S)-2,6-dimethylmorpholino)-2-fluorophenyl)
(pyrazin-2-yl)methanone A solution of butyllithium, 2.5M in hexanes (1.718 mL, 4.30 mmol) was added dropwise to a solution of 2,2,6,6-tetramethylpiperidine (0.802 mL, 4.73 mmol) in 15 ml THF at −78° C. The flask was removed from the −78° C. bath, and stirred at ca 0° C. for 10 minutes, then recooled to −78° C. to give a pale yellow solution of LiTMP. A solution of (2R,6S)-4-[6-({[tert-butyl(diphenyl)silyl]oxy}methyl)-2-chloro-3-fluorophenyl]-2,6-dimethylmorpholine (Intermediate 42, 1.1 g, 2.15 mmol) 20 ml THF was cannulated into the LiTMP solution to give a yellow solution which was stirred at −78 for about 1 hour; then N-methoxy-N-methylpyrazine-2-carboxamide (1.077 g, 6.44 mmol) was added. The mixture was stirred at −78° C. After 5 hours the reaction was worked up by adding saturated NH$_4$Cl to the −78° C. solution and extracting with EtOAc (3×). After drying over MgSO$_4$, concentration of the mixture gave material that was purified on SiO$_2$ using 0-10% acetone/hexanes to recover 891 mg (67%) of the title compound as a yellow oil.
MS (ES) MH$^+$: 618 for $C_{34}H_{37}ClFN_3O_3Si$ $^1$H NMR (CD$_2$Cl$_2$) δ: 1.0-1.1 (overlapping m, 15H), 2.5-2.7 (m, 2H), 3.0-3.2 (m, 2H), 3.3-3.4 (m, 2H), 4.8 (s, 2H), 7.3-7.5 (m, 6H), 7.6-7.7 (m, 4H), 7.9 (br s, 1H), 8.6 (m, 1H), 8.7 (d, 1H), 9.2 (br s, 1H).

Intermediate 73

(6-((tert-butyldiphenylsilyloxy)methyl)-4-chloro-5-
((2R,6S)-2,6-dimethylmorpholino)-3-fluoropyridin-
2-yl)(1-methyl-1H-imidazol-2-yl)methanol Diisopropylamine (0.868 mL, 6.14 mmol) was added dropwise to a stirring solution of 2.5M butyllithium in hexanes (2.339 mL, 5.85 mmol) in THF (20 mL) at −78° C. The solution was warmed to 0° C. for 10 minutes and then cooled again to −78° C. Cannulation of the LDA at −78° C. into (2R,6S)-4-(2-((tert-butyldiphenylsilyloxy)methyl)-4-chloro-5-fluoropyridin-3-yl)-2,6-dimethylmorpholine (Intermediate 45, 1.5 g, 2.92 mmol) in THF (10 mL) at −78° C. Allowed dark solution to stir for 20 minutes then cannulated into a stirring solution of 1-methyl-1H-imidazole-2-carbaldehyde (0.644 g, 5.85 mmol) in THF (10 mL) at −78° C. The solution was allowed to warm to −50° C. then quenched with saturated ammonium chloride solution. The mixture was extracted with ethyl acetate and washed resulting organics with brine. After drying the organics over sodium sulfate, filtering, and evacuating the filtrate under vacuum, a crude yellow oil was obtained. The crude oil was purified on silica using 40% ethyl acetate in n-hexane to give 1.2 g (66%) of the title compound as oil.
MS (ES) MH$^+$: 623 for $C_{33}H_{40}ClFN_4O_3Si$
$^1$H NMR (300 MHz, CDCl$_3$) δ: 1.0 (s, 9H), 1.1 (d, 6H), 2.8 (br.s., 2H), 3.1 (br.s., 2H), 3.6 (br.s., 2H), 3.7 (s, 3H), 5.0 (br.s., 2H), 6.0 (br.s., 1H), 6.8 (br.s., 1H), 6.9 (d, 1H) 7.3-7.4 (m, 6H), 7.6-7.7 (m, 4H), 9.1 (s, 1H).

Intermediates 74 to 79 were prepared from the indicated starting materials using a method similar to the one described for the synthesis of Intermediate 73:

Intermediate 74

(6-((tert-butyldiphenylsilyloxy)methyl)-4-chloro-5-
((2R,6S)-2,6-dimethylmorpholino)-3-fluoropyridin-
2-yl)(thiazol-5-yl)methanol Starting materials: (2R,6S)-4-(2-((tert-butyldiphenylsilyloxy)methyl)-4-chloro-5-fluoropyridin-3-yl)-2,6-dimethylmorpholine (Intermediate 45) and thiazole-5-carbaldehyde.
MS (ES) MH$^+$: 626 for $C_{32}H_{37}ClFN_3O_3SiS$
$^1$H NMR (300 MHz, CDCl$_3$) δ: 1.0 (s, 9H), 1.1-1.2 (m, 6H), 2.7-2.8 (m, 2H), 3.1 (br.s., 2H), 3.7 (br.s., 2H), 4.8 (br.s., 2H), 6.2 (s, 1H), 7.2 (br.s., 1H), 7.3-7.4 (m, 6H), 7.6-7.7 (m, 4H), 8.5 (s, 1H), 9.1 (s, 1H).

Intermediate 75

(6-((tert-butyldiphenylsilyloxy)methyl)-4-chloro-5-
((2R,6S)-2,6-dimethylmorpholino)-3-fluoropyridin-
2-yl)(2-methylthiazol-5-yl)methanol Starting materials: (2R,6S)-4-(2-((tert-butyldiphenylsilyloxy)methyl)-4-chloro-5-fluoropyridin-3-yl)-2,6-dimethylmorpholine (Intermediate 45) and 2-methylthiazole-5-carbaldehyde.
MS (ES) MH$^+$: 640 for $C_{33}H_{39}ClFN_3O_3SiS$
$^1$H NMR (300 MHz, CDCl$_3$) δ: 1.0 (s, 9H), 1.1-1.2 (m, 6H), 2.6 (s, 3H), 2.7-2.8 (m, 2H), 3.1 (br.s., 2H), 3.7 (br.s., 2H), 4.8 (br.s., 2H), 6.1 (s, 1H), 7.2 (br.s., 1H), 7.3-7.5 (m, 6H), 7.6-7.7 (m, 4H), 8.2 (s, 1H).

Intermediate 76

4-((6-((tert-butyldiphenylsilyloxy)methyl)-4-chloro-5-((2R,6S)-2,6-dimethylmorpholino)-3-fluoropyridin-2-yl)(hydroxy)methyl-2-fluorobenzonitrile Starting materials: (2R,6S)-4-(2-((tert-butyldiphenylsilyloxy)methyl)-4-chloro-5-fluoropyridin-3-yl)-2,6-dimethylmorpholine (Intermediate 45) and 2-fluoro-4-formylbenzonitrile.

MS (ES) MH$^+$: 662 for $C_{36}H_{38}ClF_2N_3O_3Si$ $^1$H NMR (300 MHz, CDCl$_3$) δ: 1.0 (s, 9H), 1.1-1.2 (m, 6H), 2.7 (br.s., 2H), 3.1 (br.s., 2H), 3.6 (br.s., 2H), 4.8 (br.s., 2H), 5.9 (s, 1H), 6.1 (s, 1H), 7.2-7.5 (m, 6H), 7.5 (dd, 1H), 7.6 (br.s., 2H), 7.6-7.7 (m, 4H).

Intermediate 77

(6-((tert-butyldiphenylsilyloxy)methyl)-4-chloro-5-((2R,6S)-2,6-dimethylmorpholino)-3-fluoropyridin-2-yl)methanol Starting materials: (2R,6S)-4-(2-((tert-butyldiphenylsilyloxy)methyl)-4-chloro-5-fluoropyridin-3-yl)-2,6-dimethylmorpholine (Intermediate 45) and 5-methylthiazole-2-carbaldehyde.

MS (ES) MH$^+$: 640 for $C_{33}H_{39}ClFN_3O_3SiS$ $^1$H NMR (300 MHz, CDCl$_3$) δ: 1.0 (s, 9H), 1.1-1.2 (m, 6H), 2.4 (d, 3H), 2.7 (br.s., 2H), 3.1 (br.s., 2H), 3.6 (br.s., 2H), 4.8 (br.s., 2H), 5.0 (s, 1H), 6.1 (s, 1H), 7.2 (s, 1H), 7.3-7.5 (m, 6H), 7.6-7.7 (m, 4H).

Intermediate 78

(2-bromothiazol-5-yl)(6-((tert-butyldiphenylsilyloxy)methyl)-4-chloro-5-((2R,6S)-2,6-dimethylmorpholino)-3-fluoropyridin-2-yl)methanol Starting materials: 2R,6S)-4-(2-((tert-butyldiphenylsilyloxy)methyl)-4-chloro-5-fluoropyridin-3-yl)-2,6-dimethylmorpholine (Intermediate 45) and 2-bromothiazole-5-carbaldehyde.

MS (ES) MH$^+$: 705 for $C_{32}H_{36}ClFBrN_3O_3SiS$ $^1$H NMR (300 MHz, CDCl$_3$) δ: 1.0 (s, 9H), 1.1-1.2 (m, 6H), 2.7 (br.s., 2H), 3.1 (br.s., 2H), 3.7 (br.s., 2H), 4.8 (br.s., 2H), 6.1 (d, 1H,) 7.3-7.5 (m, 6H), 7.6-7.7 (m, 4H), 8.1 (s, 1H), 9.9 (m, 1H).

Intermediate 79

(6-((tert-butyldiphenylsilyloxy)methyl)-4-chloro-5-((2R,6S)-2,6-dimethylmorpholino)-3-fluoropyridin-2-yl)(2,4-dichlorothiazol-5-yl)methanol Starting materials: (2R,6S)-4-(2-((tert-butyldiphenylsilyloxy)methyl)-4-chloro-5-fluoropyridin-3-yl)-2,6-dimethylmorpholine (Intermediate 45) and 2,4-dichlorothiazole-5-carbaldehyde.

MS (ES) MH$^+$: 694 for $C_{32}H_{35}Cl_3FN_3O_3SiS$ $^1$H NMR (300 MHz, CDCl$_3$) δ: 1.0 (s, 9H), 1.1-1.2 (m, 6H), 2.8 (br.s., 2H), 3.1 (br.s., 2H), 3.7 (br.s., 2H), 4.8 (br.s., 2H), 6.2 (d, 1H), 7.3-7.5 (m, 6H), 7.6-7.7 (m, 4H).

Intermediate 80 and Intermediate 81

{5-({[tert-butyl(diphenyl)silyl]oxy}methyl)-4-[(2R,6S)-2,6-dimethylmorpholin-4-yl]-2,3-difluorophenyl}[4-(morpholin-4-ylcarbonyl)-1,3-thiazol-2-yl]methanol (Intermediate 80) and {5-{5-({[tert-butyl(diphenyl)silyl]oxy}methyl)-4-[(2R,6S)-2,6-dimethylmorpholin-4-yl]-2,3-difluorophenyl}[4-(morpholin-4-ylcarbonyl)-1,3-thiazol-5-yl]methanol (Intermediate 81)

Morpholin-4-yl(1,3-thiazol-4-yl)methanone (1.0 g, 5.05 mmol) in anhydrous THF (10 mL) was added to a stirred solution of LiTMP (3.2 eq, generated from n-butyllithium and 2,2,6,6-tetramethylpiperidine in 10 ml THF) at −78° C., and the mixture was stirred for 2 hours at −78° C. A solution of 5-(tert-butyl-diphenyl-silanyloxymethyl)-4-((2R,6S)-2,6-dimethyl-morpholin-4-yl)-2,3-difluoro-benzaldehyde (Intermediate 4, 2.6 g, 5.05 mmol) in THF (10 mL) was added dropwise and the mixture was stirred for an additional 1 hour at −78° C. The reaction mixture was quenched with saturated ammonium chloride solution and extracted with ethyl acetate. The organic layer were washed with brine and dried over anhydrous sodium sulphate. The solvent was removed under vacuum and the residue was purified on a silica gel column using ethyl acetate-pet. ether gradient to give two products: Intermediate 80 and Intermediate 81. Yield: 600 mg (17%).

Intermediate 80 MS (ES) MH$^+$: 722 for $C_{38}H_{45}F_2N_3O_5SSi$.

Intermediate 81 MS (ES) MH$^+$: 722 for $C_{38}H_{45}F_2N_3O_5SSi$;

Intermediates 82 to 84 were prepared from the indicated starting materials using a method similar to the one described for the synthesis of Intermediate 80 and Intermediate 81:

Intermediate 82

2-[{5-({[tert-butyl(diphenyl)silyl]oxy}methyl)-4-[(2R,6S)-2,6-dimethylmorpholin-4-yl]-2,3-difluorophenyl}(hydroxy)methyl]-N,N-dimethyl-1,3-thiazole-4-carboxamide Starting material: 5-(tert-Butyl-diphenyl-silanyloxymethyl)-4-((2R,6S)-2,6-dimethyl-morpholin-4-yl)-2,3-difluoro-benzaldehyde (Intermediate 4) and N,N-dimethyl-1,3-thiazole-4-carboxamide.

MS (ES) MH$^+$: 680 for $C_{36}H_{43}F_2N_3O_4SSi$

Intermediate 83

2-[{5-({[tert-butyl(diphenyl)silyl]oxy}methyl)-4-[(2R,6S)-2,6-dimethylmorpholin-4-yl]-2,3-difluorophenyl}(hydroxy)methyl]-N,N-dimethyl-1,3-thiazole-5-carboxamide Starting material: 5-(tert-Butyl-diphenyl-silanyloxymethyl)-4-((2R,6S)-2,6-dimethyl-morpholin-4-yl)-2,3-difluoro-benzaldehyde (Intermediate 4) and N,N-dimethyl-1,3-thiazole-5-carboxamide MS (ES) MH$^+$: 680 for $C_{36}H_{43}F_2N_3O_4SSi$ Intermediate 84

5-[{5-({[tert-butyl(diphenyl)silyl]oxy}methyl)-4-[(2R,6S)-2,6-dimethylmorpholin-4-yl]-2,3-difluorophenyl}(hydroxy)methyl]-1,3-thiazole-4-carbonitrile Starting material: 5-(tert-Butyl-diphenyl-silanyloxymethyl)-4-((2R,6S)-2,6-dimethyl-morpholin-4-yl)-2,3-difluoro-benzaldehyde (Intermediate 4) and 4-cyano-1,3-thiazole.

MS (ES) MH$^+$: 634 for $C_{34}H_{37}F_2N_23O_3SSi$.

Intermediate 85

{5-({[tert-butyl(diphenyl)silyl]oxy}methyl)-3-chloro-4-[(2R,6S)-2,6-dimethylmorpholin-4-yl]-2-fluorophenyl}(pyridin-2-yl)methanone To the solution of {5-({[tert-butyl(diphenyl)silyl]oxy}methyl)-3-chloro-4-[(2R,6S)-2,6-dimethylmorpholin-4-yl]-2-fluorophenyl}(pyridin-2-yl)methanol (Intermediate 62, 100 mg, 0.165 mmol) in anhydrous DCM (5 mL) was added NMO (37 mg, 0.323 mmol) and TPAP (0.1 eq) at 0° C. and the mixture was allowed to stir for 1 hour at room temperature. The reaction mixture was filtered and the solvents were removed under vacuum and the residue was purified over silica gel chromatography column using ethyl acetate-pet. ether gradient to give product as a solid. Yield: 90 mg, (90%).

MS (ES) MH$^+$: 617 for $C_{35}H_{38}ClFN_2O_3Si$

Intermediates 86 to 96 were prepared from the indicated starting materials using a method similar to the one described for the synthesis of Intermediate 85:

Intermediate 86

{5-({[tert-butyl(diphenyl)silyl]oxy}methyl)-3-chloro-4-[(2R,6S)-2,6-dimethylmorpholin-4-yl]-2-fluorophenyl}(1,3-thiazol-5-yl)methanone Starting material: {5-({[tert-butyl(diphenyl)silyl]oxy}methyl)-3-chloro-4-[(2R,6S)-2,6-dimethylmorpholin-4-yl]-2-fluorophenyl}(1,3-thiazol-5-yl)methanol (Intermediate 63).

MS (ES) MH$^+$: 623 for $C_{33}H_{36}ClFN_2O_3Si$

Intermediate 87

{5-({[tert-butyl(diphenyl)silyl]oxy}methyl)-3-chloro-4-[(2R,6S)-2,6-dimethylmorpholin-4-yl]-2-fluorophenyl}(pyridin-4-yl)methanone Starting material: {5-({[tert-butyl(diphenyl)silyl]oxy}methyl)-3-chloro-4-[(2R,6S)-2,6-dimethylmorpholin-4-yl]-2-fluorophenyl}(pyridin-4-yl)methanol (Intermediate 64).

MS (ES) MH$^+$: 617 for $C_{35}H_{38}ClFN_2O_3Si$

Intermediate 88

{5-({[tert-butyl(diphenyl)silyl]oxy}methyl)-3-chloro-4-[(2R,6S)-2,6-dimethylmorpholin-4-yl]-2-fluorophenyl}(pyridin-3-yl)methanone Starting material: {5-({[tert-butyl(diphenyl)silyl]oxy}methyl)-3-chloro-4-[(2R,6S)-2,6-dimethylmorpholin-4-yl]-2-fluorophenyl}(pyridin-3-yl)methanol (Intermediate 65).

MS (ES) MH$^+$: 617 for $C_{35}H_{38}ClFN_2O_3Si$

Intermediate 89

{5-({[tert-butyl(diphenyl)silyl]oxy}methyl)-3-chloro-4-[(2R,6S)-2,6-dimethylmorpholin-4-yl]-2-fluorophenyl}(1,3-thiazol-2-yl)methanone Starting material: {5-({[tert-butyl(diphenyl)silyl]oxy}methyl)-3-chloro-4-[(2R,6S)-2,6-dimethylmorpholin-4-yl]-2-fluorophenyl}(1,3-thiazol-2-yl)methanol (Intermediate 66).

MS (ES) MH$^+$: 623 for $C_{33}H_{36}ClFN_2O_3Si$

Intermediate 90

{5-({[tert-butyl(diphenyl)silyl]oxy}methyl)-3-chloro-4-[(2R,6S)-2,6-dimethylmorpholin-4-yl]-2-fluorophenyl}(1-methyl-1H-imidazol-2-yl)methanone Starting material: {5-({[tert-butyl(diphenyl)silyl]oxy}methyl)-3-chloro-4-[(2R,6S)-2,6-dimethylmorpholin-4-yl]-2-fluorophenyl}(1-methyl-1H-imidazol-2-yl)methanol (Intermediate 67)

MS (ES) MH$^+$: 620 for $C_{34}H_{39}ClFN_3O_3Si$

Intermediate 91 methyl 3-chloro-5-(cyclopropylcarbonyl)-2-[(2R,6S)-2,6-dimethylmorpholin-4-yl]-4-fluorobenzoate Starting material: methyl 3-chloro-5-[cyclopropyl(hydroxy)methyl]-2-[(2R,6S)-2,6-dimethylmorpholin-4-yl]-4-fluorobenzoate (Intermediate 68).

MS (ES) MH$^+$: 370 for $C_{18}H_{21}ClFNO_4$

Intermediate 92

{2-[{5-({[tert-butyl(diphenyl)silyl]oxy}methyl)-4-[(2R,6S)-2,6-dimethylmorpholin-4-yl]-2,3-difluorophenyl}(hydroxy)methyl]-1,3-thiazol-4-yl}(morpholin-4-yl)methanone Starting material: {5-({[tert-butyl(diphenyl)silyl]oxy}methyl)-4-[(2R,6S)-2,6-dimethylmorpholin-4-yl]-2,3-difluorophenyl}[4-(morpholin-4-ylcarbonyl)-1,3-thiazol-2-yl]methanol (Intermediate 80)

MS (ES) MH$^+$: 720 for $C_{38}H_{43}F_2N_3O_5SSi$

Intermediate 93

{5-({[tert-butyl(diphenyl)silyl]oxy}methyl)-4-[(2R,6S)-2,6-dimethylmorpholin-4-yl]-2,3-difluorophenyl}{4-[hydroxy(morpholin-4-yl)methyl]-1,3-thiazol-5-yl}methanone Starting material: {5-{5-({[tert-butyl(diphenyl)silyl]oxy}methyl)-4-[(2R,6S)-2,6-dimethylmorpholin-4-yl]-2,3-difluorophenyl}[4-(morpholin-4-ylcarbonyl)-1,3-thiazol-5-yl]methanol (Intermediate 81)

MS (ES) MH$^+$: 720 for $C_{38}H_{43}F_2N_3O_5SSi$

Intermediate 94

2-({5-({[tert-butyl(diphenyl)silyl]oxy}methyl)-4-[(2R,6S)-2,6-dimethylmorpholin-4-yl]-2,3-difluorophenyl}carbonyl)-N,N-dimethyl-1,3-thiazole-4-carboxamide Starting material: 2-[{5-({[tert-butyl(diphenyl)silyl]oxy}methyl)-4-[(2R,6S)-2,6-dimethylmorpholin-4-yl]-2,3-difluorophenyl}(hydroxy)methyl]-N,N-dimethyl-1,3-thiazole-4-carboxamide (Intermediate 82)

MS (ES) MH$^+$: 678 for $C_{36}H_{41}F_2N_3O_4SSi$

Intermediate 95

2-({5-({[tert-butyl(diphenyl)silyl]oxy}methyl)-4-[(2R,6S)-2,6-dimethylmorpholin-4-yl]-2,3-difluorophenyl}carbonyl)-N,N-dimethyl-1,3-thiazole-5-carboxamide Starting material: 2-[{5-({[tert-butyl(diphenyl)silyl]oxy}methyl)-4-[(2R,6S)-2,6-dimethylmorpholin-4-yl]-2,3- difluorophenyl}(hydroxy)methyl]-N,N-dimethyl-1,3-thiazole-5-carboxamide (Intermediate 83)
MS (ES) MH+: 678 for $C_{36}H_{41}F_2N_3O_4SSi$
Intermediate 96

5-({5-({[tert-butyl(diphenyl)silyl]oxy}methyl)-4-[(2R,6S)-2,6-dimethylmorpholin-4-yl]-2,3-difluorophenyl}carbonyl)-1,3-thiazole-4-carbonitrile Starting material: 5-[{5-({[tert-butyl(diphenyl)silyl]oxy}methyl)-4-[(2R,6S)-2,6-dimethylmorpholin-4-yl]-2,3-difluorophenyl}(hydroxy)methyl]-1,3-thiazole-4-carbonitrile (Intermediate 84).
MS (ES) MH+: 632 for $C_{34}H_{35}F_2N_3O_3SSi$.
Intermediate 97

{5-({[tert-butyl(diphenyl)silyl]oxy}methyl)-4-[(2R,6S)-2,6-dimethylmorpholin-4-yl]-2,3-difluorophenyl}(1-methyl-1H-imidazol-5-yl)methanone To the solution of {5-({[tert-butyl(diphenyl)silyl]oxy}methyl)-4-[(2R,6S)-2,6-dimethylmorpholin-4-yl]-2,3-difluorophenyl}(1-methyl-1H-imidazol-5-yl)methanol (Intermediate 69, 50 mg, 0.08 mmol) in anhydrous DCM (5 mL), $MnO_2$ (143 mg, 1.65 mmol) was added at 0° C. and allowed to stir for 1 hour at room temperature. The reaction mixture was filtered and the solvents were removed under vacuum and the residue was purified over silica gel chromatography column using ethyl acetate-pet. ether gradient to give solid. Yield: 37 mg, (75%).
MS (ES) MH+: 604 for $C_{34}H_{39}F_2N_3O_3Si$.

Intermediate 98 was prepared from the indicated starting materials using a method similar to the one described for the synthesis of Intermediate 97:
Intermediate 98

{5-({[tert-butyl(diphenyl)silyl]oxy}methyl)-4-[(2R,6S)-2,6-dimethylmorpholin-4-yl]-2,3-difluorophenyl}(4-methyl-1,3-thiazol-5-yl)methanone Starting material: {5-({[tert-butyl(diphenyl)silyl]oxy}methyl)-4-[(2R,6S)-2,6-dimethylmorpholin-4-yl]-2,3-difluorophenyl}(4-methyl-1,3-thiazol-5-yl)methanole (Intermediate 70)
MS (ES) MH+: 621 for $C_{34}H_{38}F_2N_2O_3SSi$
Intermediate 99

(6-((tert-butyldiphenylsilyloxy)methyl)-4-chloro-5-((2R,6S)-2,6-dimethylmorpholino)-3-fluoropyridin-2-1 methanone To a stirring solution of (6-((tert-butyldiphenylsilyloxy)methyl)-4-chloro-5-((2R,6S)-2,6-dimethylmorpholino)-3-fluoropyridin-2-yl)(1-methyl-1H-imidazol-2-yl)methanol (1.2 g, 1.93 mmol, Intermediate 73) in dichloromethane (20 mL) was added Manganese(IV)oxide (0.670 g, 7.70 mmol). The mixture was allowed to stir overnight at room temperature. The reaction was filtered through Celite®, and the filtrate concentrated under vacuum to give clear oil. The oil was purified on short bed of silica using 20-30% ethyl acetate in n-hexane to give 1.0 g (84%) the title compound as oil.
MS (ES) M+: 621 for $C_{33}H_{38}ClFN_4O_3Si$
$^1$H NMR (300 MHz, CDCl$_3$) δ: 1.1 (s, 9H), 1.2 (d, 6H), 2.9 (br.s, 2H), 3.2 (m, 2H), 3.8 (br.s., 2H), 4.2 (s, 2H), 4.9 (s, 2H), 7.3-7.4 (m, 4H), 7.4-7.5 (m, 5H), 7.8 (d, 4H).

Intermediates 100 to 106 were prepared from the indicated starting materials using a method similar to the one described for the synthesis of Intermediate 99:
Intermediate 100

(6-((tert-butyldiphenylsilyloxy)methyl)-4-chloro-5-((2R,6S)-2,6-dimethylmorpholino)-3-fluoropyridin-2-yl)(thiazol-5-yl)methanone Starting material: (6-((tert-butyldiphenylsilyloxy)methyl)-4-chloro-5-((2R,6S)-2,6-dimethylmorpholino)-3-fluoropyridin-2-yl)(thiazol-5-yl)methanol (Intermediate 74).
MS (ES) MH+: 624 for $C_{32}H_{35}ClFN_3O_3SiS$
$^1$H NMR (300 MHz, CDCl$_3$) δ: 0.9-1.0 (s, 9H), 1.1 (d, 6H), 3.0-3.1 (m, 4H), 3.7 (br.s, 2H), 4.9 (s, 2H), 7.3-7.4 (m, 6H), 7.5-7.7 (m, 4H), 8.8-8.9 (m, 2H).
Intermediate 101

(6-((tert-butyldiphenylsilyloxy)methyl)-4-chloro-5-((2R,6S)-2,6-dimethylmorpholino)-3-fluoropyridin-2-yl)(2-methylthiazol-5-yl)methanone Starting material: (6-((tert-butyldiphenylsilyloxy)methyl)-4-chloro-5-((2R,6S)-2,6-dimethylmorpholino)-3-fluoropyridin-2-yl)(2-methylthiazol-5-yl)methanol (Intermediate 75).
MS (ES) MH+: 638 for $C_{33}H_{37}ClFN_3O_3SiS$
$^1$H NMR (300 MHz, CDCl$_3$) δ: 0.9-1.0 (m, 9H), 1.1 (d, 6H), 2.7 (s, 3H), 3.0 (br.s, 2H), 3.0-3.1 (m, 2H), 3.7 (br.s, 2H), 4.9 (s, 2H), 7.3-7.4 (m, 6H), 7.5-7.7 (m, 4H), 8.6 (s, 1H).
Intermediate 102

4-(6-((tert-butyldiphenylsilyloxy)methyl)-4-chloro-5-((2R,6S)-2,6-dimethylmorpholino)-3-fluoropicolinoyl)-2-fluorobenzonitrile Starting material: 4-((6-((tert-butyldiphenylsilyloxy)methyl)-4-chloro-5-((2R,6S)-2,6-dimethylmorpholino)-3-fluoropyridin-2-yl)(hydroxy)methyl)-2-fluorobenzonitrile (Intermediate 76).
MS (ES) MH+: 660 for $C_{36}H_{36}ClF_2N_3O_3Si$
$^1$H NMR (300 MHz, CDCl$_3$) δ: 0.9-1.1 (m, 9H), 1.2 (d, 6H), 1.8 (td, 3H), 3.1 (d, 2H), 3.6-3.7 (m, 4H), 4.8 (s, 2H), 7.2-7.3 (m, 2H), 7.3-7.5 (m, 2H), 7.5-7.6 (m, 5H), 7.7 (d, 2H).
Intermediate 103

(6-((tert-butyldiphenylsilyloxy)methyl)-4-chloro-5-((2R,6S)-2,6-dimethylmorpholino)-3-fluoropyridin-2-yl)(5-methylthiazol-2-yl)methanone Starting material: (6-((tert-butyldiphenylsilyloxy)methyl)-4-chloro-5-((2R,6S)-2,6-dimethylmorpholino)-3-fluoropyridin-2-yl)(5-methylthiazol-2-yl)methanol (Intermediate 77)
MS (ES) MH+: 638 for $C_{33}H_{37}ClFN_3O_3SiS$
$^1$H NMR (300 MHz, CDCl$_3$) δ: 1.0 (s, 9H), 1.1-1.2 (m, 6H), 2.5 (s, 3H), 2.9-3.0 (m, 2H), 3.0-3.1 (m, 2H), 3.7 (d, 2H), 4.9 (s, 2H), 7.3-7.5 (m, 6H), 7.6-7.7 (m, 4H), 7.8 (d, 1H).
Intermediate 104

(2-bromothiazol-5-yl)(6-((tert-butyldiphenylsilyloxy)methyl)-4-chloro-5-((2R,6S)-2,6-dimethylmorpholino)-3-fluoropyridin-2-yl)methanone Starting material: (2-bromothiazol-5-yl)(6-((tert-butyldiphenylsilyloxy)methyl)-4-chloro-5-((2R,6S)-2,6-dimethylmorpholino)-3-fluoropyridin-2-yl)methanol (Intermediate 78).

MS (ES) MH$^+$: 703 for $C_{32}H_{34}ClFBrN_3O_3SiS$ $^1$H NMR (300 MHz, CDCl$_3$) δ: 1.0 (s, 9H), 1.1-1.2 (m, 6H), 2.9-3.0 (m, 2H), 3.0-3.1 (m, 2H), 3.7 (d, 2H), 4.9 (s, 2H), 7.3-7.5 (m, 6H), 7.6-7.7 (m, 4H), 8.4 (s, 1H).

Intermediate 105

(6-((tert-butyldiphenylsilyloxy)methyl)-4-chloro-5-((2R,6S)-2,6-dimethylmorpholino)-3-fluoropyridin-2-yl)(2,4-dichlorothiazol-5-yl)methanone Starting material: (6-((tert-butyldiphenylsilyloxy)methyl)-4-chloro-5-((2R,6S)-2,6-dimethylmorpholino)-3-fluoropyridin-2-yl)(2,4-dichlorothiazol-5-yl)methanol (Intermediate 79).

MS (ES) MH$^+$: 692 for $C_{32}H_{33}Cl_3FN_3O_3SiS$ $^1$H NMR (300 MHz, CDCl$_3$) δ: 1.0 (s, 9H), 1.1-1.2 (m, 6H), 2.8 (br.s., 2H), 3.1 (br.s., 2H), 3.7 (br.s., 2H), 4.8 (s, 2H), 7.3-7.5 (m, 6H), 7.6-7.7 (m, 4H).

Intermediate 106

(5-((tert-butyldiphenylsilyloxy)methyl)-4-((2R,6R)-2,6-dimethylmorpholino)-2,3-difluorophenyl)(2-(methylthio)pyrimidin-4-yl)methanone Starting material: (5-((tert-butyldiphenylsilyloxy)methyl)-4-((2R,6R)-2,6-dimethylmorpholino)-2,3-difluorophenyl)(2-(methylthio)pyrimidin-4-yl)methanol (Intermediate 71).

MS (ES) MH$^+$: 648 (M+H) for $C_{35}H_{39}F_2N_3O_3SSi$ Intermediate 107 methyl 5-acetyl-3-chloro-2-[(2R,6S)-2,6-dimethyl-morpholin-4-yl]-4-fluorobenzoate To a stirred solution of LDA (3.1 eq) at −50° C. in THF was added methyl 3-chloro-2-[(2R,6S)-2,6-dimethylmorpholin-4-yl]-4-fluorobenzoate (Intermediate 47, 1.5 g, 4.96 mmol) in anhydrous THF (10 mL) dropwise and the solution was stirred for 1 h at −50° C. N-methoxy-N-methylacetamide (1.66 g, 14.9 mmol) in THF (5 mL) was added dropwise and stirring was continued for additional 1 h. The reaction mixture was quenched with saturated aqueous ammonium chloride and extracted with ethyl acetate. The organic layer was washed with brine and dried over anhydrous sodium sulphate. The solvent was removed under vacuum and the residue was purified over silica gel chromatography column using ethyl acetate-pet. ether gradient to obtain the title compound. Yield: 800 mg, (47%)

MS (ES) MH$^+$: 344 for $C_{16}H_{19}ClFNO_4$

Intermediates 108 to 113 were prepared from the indicated starting materials using a method similar to the one described for the synthesis of Intermediate 107:

Intermediate 108

{5-({[tert-butyl(diphenyl)silyl]oxy}methyl-3-chloro-4-[(2R,6S)-2,6-dimethylmorpholin-4-yl]-2-fluorophenyl}(6-methylpyridin-3-yl)methanone Starting materials: (2R,6S)-4-[6-({[tert-butyl(diphenyl)silyl]oxy}methyl)-2-chloro-3-fluorophenyl]-2,6-dimethylmorpholine (Intermediate 42) and N-methoxy-6,N-dimethylnicotinamide.

MS (ES) MH$^+$: 631 for $C_{36}H_{40}ClFN_2O_3Si$.

Intermediate 109

{5-({[tert-butyl(diphenyl)silyl]oxy}methyl-3-chloro-4-[(2R,6S)-2,6-dimethylmorpholin-4-yl]-2-fluorophenyl}(pyrimidin-2-yl)methanone Starting materials: (2R,6S)-4-[6-({[tert-butyl(diphenyl)silyl]oxy}methyl)-2-chloro-3-fluorophenyl]-2,6-dimethylmorpholine (Intermediate 42) and N-methoxy-N-methylpyrimidine-2-carboxamide.

MS (ES) MH$^+$: 618 for $C_{34}H_{37}ClFN_3O_3Si$.

Intermediate 110

{5-({[tert-butyl(diphenyl)silyl]oxy}methyl-3-chloro-4-[(2R,6S)-2,6-dimethylmorpholin-4-yl]-2-fluorophenyl}(pyrimidin-4-yl)methanone Starting materials: (2R,6S)-4-[6-({[tert-butyl(diphenyl)silyl]oxy}methyl)-2-chloro-3-fluorophenyl]-2,6-dimethylmorpholine (Intermediate 42) and N-methoxy-N-methylpyrimidine-4-carboxamide MS (ES) MH$^+$: 618 for $C_{34}H_{37}ClFN_3O_3Si$.

Intermediate 111

{5-({[tert-butyl(diphenyl)silyl]oxy}methyl)-3-chloro-4-[(2R,6S)-2,6-dimethylmorpholin-4-yl]-2-fluorophenyl}(pyrimidin-5-yl)methanone Starting material: (2R,6S)-4-[6-({[tert-butyl(diphenyl)silyl]oxy}methyl)-2-chloro-3-fluorophenyl]-2,6-dimethylmorpholine (Intermediate 42) and N-methoxy-N-methylpyrimidine-5-carboxamide.

MS (ES) MH$^+$: 618 for $C_{34}H_{37}ClFN_3O_3Si$.

Intermediate 112

{5-({[tert-butyl(diphenyl)silyl]oxy}methyl)-3-chloro-4-[(2R,6S)-2,6-dimethylmorpholin-4-yl]-2-fluorophenyl}(pyridazin-4-yl)methanone Starting materials: (2R,6S)-4-[6-({[tert-butyl(diphenyl)silyl]oxy}methyl)-2-chloro-3-fluorophenyl]-2,6-dimethylmorpholine (Intermediate 42) and N-methoxy-N-methylpyridazine-4-carboxamide MS (ES) MH$^+$: 618 for $C_{34}H_{37}ClFN_3O_3Si$ Intermediate 113

1-{5-({[tert-butyl(diphenyl)silyl]oxy}methyl)-3-chloro-4-[(2R,6S)-2,6-dimethylmorpholin-4-yl]-2-fluorophenyl}-2-methoxyethanone Starting material: (2R,6S)-4-[6-({[tert-butyl(diphenyl)silyl]oxy}methyl)-2-chloro-3-fluorophenyl]-2,6-dimethylmorpholine (Intermediate 42) and N,2-dimethoxy-N-methylacetamide.

MS (ES) MH$^+$: 583 for $C_{32}H_{39}ClFNO_4Si$.

Intermediate 114 and Intermediate 115

Ethyl 2-(5-((tert-butyldiphenylsilyloxy)methyl)-4-((2R,6S)-2,6-dimethylmorpholino)-2,3-difluorophenyl)-2-oxoacetate (Intermediate 114) and 2-(5-((tert-butyldiphenylsilyloxy)methyl)-4-((2R,6S)-2,6-dimethylmorpholino)-2,3-difluorophenyl)-N-methoxy-N-methyl-2-oxoacetamide (Intermediate 115)

(2R,6S)-4-(6-((tert-butyldiphenylsilyloxy)methyl)-2,3-difluorophenyl)-2,6-dimethylmorpholine (Intermediate 3, 0.5 g, 1.01 mmol) was dissolved in THF (10 ml) and cooled to −78° C. Sec-butyl lithium (1.552 ml, 2.02 mmol) was added drop wise over ~20 minutes and stirred at −78° C. for 1 hr. A solution of ethyl 2-(methoxy(methyl)amino)-2-oxoacetate (Intermediate 56) (0.406 g, 2.52 mmol) in 10 ml of THF was added drop wise over 15 minutes. The reaction was stirred at −78° C. for 30 minutes and then quenched cold with 3 ml sat NH$_4$Cl. The reaction was allowed to warm to room temperature, was diluted with water and extracted three times with ethyl acetate. The organic layers were combined, washed with brine, dried over MgSO$_4$ and concentrated. The residue was purified by silica gel column chromatography using a gradient of hexanes to ethyl acetate to give the first eluting compound, Intermediate 114 (2.38 g, 3.99 mmol, 39.6%):

MS (ES) MH$^+$: 596 for $C_{33}H_{39}F_2NO_5Si$
$^1$H NMR (300 MHz, DMSO-d$_6$) δ ppm 1.0 (d, 6H), 1.04 (s, 9H), 1.3 (t, 3H), 2.6-2.75 (m, 2H), 2.9 (d, 2H), 3.3 (m, 2H), 4.4 (q, 2H), 4.7 (s, 2H), 7.4-7.6 (m, 10H) 7.85 (d, 1H).

and the second eluting compound, Intermediate 115 (1.8 g, 2.95 mmol, 29.2%):

(1.8 g, 2.95 mmol, 29.2%):
MS (ES) MH$^+$: 611 for $C_{33}H_{40}F_2N_2O_5Si$
$^1$H NMR (300 MHz, DMSO-d$_6$) δ ppm 1.0 (d, 6H), 1.04 (s, 9H), 2.7 (t, 2H), 2.9 (d, 2H), 3.25 (s, 3H), 3.3 (m, 2H), 3.33 (s, 3H), 3.6 (s, 2H), 7.4-7.5 (m, 6H), 7.6 (d, 4H), 7.87 (d, 1H).

Intermediate 114 was also be prepared according to the following method:

Intermediate 114 (Alternate Synthesis)

Ethyl 2-(5-((tert-butyldiphenylsilyloxy)methyl)-4-((2R,6S)-2,6-dimethylmorpholino)-2,3-difluorophenyl)-2-oxoacetate (2R,6S)-4-[6-({[tert-Butyl(diphenyl)silyl]oxy}methyl)-2,3-difluorophenyl]-2,6-dimethylmorpholine (Intermediate 3, 0.5 g, 1.01 mmol) was dissolved in 10 ml of THF and cooled to −78° C. Sec-butyl lithium (1.358 ml, 1.77 mmol) was added drop wise over 5 minutes. The reaction stirred at −78° C. for 1.5 hours. The reaction mixture was cannulated into a −78° C. cooled flask containing diethyl oxalate (1.370 ml, 10.09 mmol) in 10 ml of THF. The reaction was allowed to stir at −78° C. for 30 minutes; quenched cold with 1 ml sat NH$_4$Cl and allowed to warm to room temp. The reaction was diluted with water and extracted twice with ethyl acetate. The organic layers were combined and washed twice with brine, dried over MgSO$_4$ and concentrated. The residue was purified by silica gel column chromatography using a gradient of hexanes to ethyl acetate to give the title compound (486 mg, 81% yield) contaminated with diethyl oxalate. This material was taken to the next step without further purification.

MS (ES) MH$^+$: 596 for $C_{33}H_{39}F_2NO_5Si$

Intermediates 116 and 117 were prepared from the indicated starting materials using a method similar to the one described for the synthesis of Intermediate 114 (Alternative Synthesis):

Intermediate 116

Ethyl 2-(5-((tert-butyldiphenylsilyloxy)methyl)-4-((2R,6R)-2,6-dimethylmorpholino)-2,3-difluorophenyl)-2-oxoacetate Starting materials: (2R,6R)-4-(6-((tert-butyldiphenylsilyloxy)methyl)-2,3-difluorophenyl)-2,6-dimethylmorpholine (11.96 g, 24.13 mmol) (Intermediate 43) and diethyl oxalate.
MS (ES) MH$^+$: 596 for $C_{33}H_{39}F_2NO_5Si$ Intermediate 117

Ethyl 2-(5-(dimethoxymethyl)-2,3,4-trifluorophenyl)-2-oxoacetate

Starting materials: 1-(dimethoxymethyl)-2,3,4-trifluorobenzene (Intermediate 39) and diethyl oxalate.
$^1$H NMR (300 MHz, CHLOROFORM-d) δ ppm 1.4-1.5 (m, 3H), 3.35-3.4 (m, 6H), 4.5 (q, 2H), 7.3 (s, 1H), 7.9-8.0 (m, 1H).

Intermediate 118

2-(5-((tert-butyldiphenylsilyloxy)methyl)-4-((2R,6S)-2,6-dimethylmorpholino)-2,3-difluorophenyl)-2-oxoacetic acid Ethyl 2-(5-((tert-butyldiphenylsilyloxy)methyl)-4-((2R,6S)-2,6-dimethylmorpholino)-2,3-difluorophenyl)-2-oxoacetate (Intermediate 114, 0.785 g, 3.00 mmol) was dissolved in ethanol (60 ml) and stirred at room temperature with 1 ml of 10% KOH. After 3 hours the reaction appears to have gone approximately 40-50% by LCMS. An additional 1 ml of 10% KOH was added and the reaction was stirred at room temperature for 30 minutes. The reaction has 70-80% by LCMS. An additional 1 ml of 10% KOH was added and the reaction was stirred at room temperature for 60 minutes. The reaction was made acidic with acetic acid, diluted with water and extracted three times with ethyl acetate. The organic layers were washed twice with brine, dried over MgSO$_4$ and concentrated. The resulting sticky oil was dissolved in ethyl acetate, washed with sat. NaHCO$_3$, dried over MgSO$_4$ and concentrated. The resulting oil was dried under vacuum for 2 hours to give the title compound as a yellow solid.

MS (ES) MH$^+$: 568 for $C_{31}H_{35}F_2NO_5Si$
$^1$H NMR (300 MHz, DMSO-d$_6$) δ ppm 0.96 (d, 6H), 1.02 (s, 9H), 2.6-2.7 (m, 2H), 2.7-2.8 (m, 2H), 3.2-3.3 (m, 2H), 4.7 (s, 2H), 7.4-7.5 (m, 6H), 7.6 (d, 4H), 7.87 (d, 1H).

Intermediate 119

1-(5-((tert-butyldiphenylsilyloxy)methyl)-4-((2R,6S)-2,6-dimethylmorpholino)-2,3-difluorophenyl)-2-morpholinoethane-1,2-dione 2-(5-((tert-butyldiphenylsilyloxy)methyl)-4-((2R,6S)-2,6-dimethylmorpholino)-2,3-difluorophenyl)-2-oxoacetic acid (Intermediate 118, 150 mg, 0.26 mmol), HATU (121 mg, 0.32 mmol), morpholine (0.025 ml, 0.29 mmol) and triethylamine (0.055 ml, 0.40 mmol) in DMF (5 ml) were stirred at room temperature for 1 hour. The reaction was diluted with water and extracted twice with ethyl acetate. The organic layers were washed three times with brine, dried over MgSO$_4$ and concentrated to give an oil. The oil was purified by silica gel column chromatography using a gradient of hexanes to ethyl acetate to give the title compound (130 mg, 0.204 mmol, 77%)

MS (ES) MH$^+$: 637 for $C_{35}H_{42}F_2N_2O_5Si$
$^1$H NMR (300 MHz, CHLOROFORM-d) δ ppm 1.0-1.2 (m, 15H), 2.7-2.9 (m, 4H), 3.5 (m, 4H), 3.7-3.9 (m, 6H), 4.7 (s, 2H), 7.4-7.5 (m, 6H), 7.7 (d, 4H), 7.95 (d, 1H).

Intermediate 120

2-(5-((tert-butyldiphenylsilyloxy)methyl)-4-((2R,6S)-2,6-dimethylmorpholino)-2,3-difluorophenyl)-N,N-dimethyl-2-oxoacetamide 2-(5-((tert-butyldiphenylsilyloxy)methyl)-4-((2R,6S)-2,6-dimethylmorpholino)-2,3-difluorophenyl)-2-oxoacetic acid (Intermediate 118, 250 mg, 0.44 mmol), HATU (335 mg, 0.88 mmol), triethylamine (0.184 ml, 1.32 mmol) and 2.0M dimethylamine (0.440 ml, 0.88 mmol) in THF were stirred in DMF (5 ml) in a closed vial for 16 hours. The reaction was diluted with water and extracted 3× with ethyl acetate. The organic layers were washed 3× with brine, dried over $MgSO_4$ and concentrated to give an oil. The oil was purified by silica gel column chromatography using a gradient of hexanes to ethyl acetate. Fractions were combined and concentrated to give the title compound (195 mg, 0.328 mmol, 74.5%)

MS (ES) MH$^+$: 595 for $C_{33}H_{40}F_2N_2O_4Si$ $^1$H NMR (300 MHz, CHLOROFORM-d) δ ppm 1.0-1.1 (m, 15H), 2.7-2.9 (m, 4H), 3.0 (s, 3H), 3.1 (s, 3H), 3.45 (m, 2H), 4.65 (s, 2H), 7.3-7.5 (m, 6H), 7.7 (d, 4H), 7.9 (d, 1H).

Intermediate 121

Ethyl 2-(6-((tert-butyldiphenylsilyloxy)methyl)-4-chloro-5-((2R,6S)-2,6-dimethylmorpholino)-3-fluoropyridin-2-yl)-2-oxoacetate A solution of n-butyllithium, 2.5M in hexanes (3.43 mL, 8.58 mmol) was added.dropwise to a solution of diisopropylamine (1.333 mL, 9.35 mmol) in 15 ml THF at −78° C. The flask was removed from the −78 degree bath, and placed in an ice bath. Stirred at ca 0° C. for 10 minutes, then recooled to −78° C. to give a pale yellow solution of LDA. The LDA was added by cannulation (over less than 5 min) to a pre-cooled −78° C. solution of (2R,6S)-4-(2-((tert-butyldiphenylsilyloxy)methyl)-4-chloro-5-fluoropyridin-3-yl)-2,6-dimethylmorpholine (Intermediate 45, 2 g, 3.90 mmol) in THF, 20 ml, to give a brown solution. The solution was stirred at −78 for about 1 hour, then cannulated over about 5 minutes to a −78° C. solution of diethyl oxalate (1.588 mL, 11.69 mmol) in 20 ml THF to give a yellow solution. The solution was stirred at −78° C. After about 2.5 h hours, the yellow solution was worked up by addition of saturated NH4Cl to the −78° C. solution, and extracted with EtOAc (3×). The organic phase was dried over $MgSO_4$, and concentrated to a yellow oil. The crude was purified by chromatography on $SiO_2$ using 0-25% EtOAc/hexanes to give 2.3 g (96%) yellow solid, A portion was recrystallized from EtOAc/hexanes.

MS (ES) MH$^+$: 613 for $C_{32}H_{38}ClFN_2O_5Si$ $^1$H NMR (300 MHz, DMSO-d$_6$) δ: 0.9-1.1 (overlapping multiplet, 15H), 1.2 (t, 3H), 2.9-3.0 (m, 2H), 3.1-3.2 (m, 2H). 3.5-3.7 (m, 2H), 4.2 (q, 2H), 4.8 (s, 2H), 7.4-7.6 (m, 10H).

Intermediate 122

(5-((tert-butyldiphenylsilyloxy)methyl)-4-((2R,6S)-2,6-dimethylmorpholino)-2,3-difluorophenyl)(furan-2-yl)methanone To a stirred solution of (2R,6S)-4-(6-((tert-butyldiphenylsilyloxy)methyl)-2,3-difluorophenyl)-2,6-dimethylmorpholine (Intermediate 3, 1 g, 2.02 mmol) in THF (8 mL) was added sBuLi (1.3 M in cyclohexane/hexanes, 3.1 ml, 4.03 mmol) at −70° C. under nitrogen atmosphere. After stirring for 1 h at this temperature, N-methoxy-N-methylfuran-2-carboxamide (0.939 g, 6.05 mmol) was added in 3 ml of THF. After stirring for 1½ h at −70° C., the reaction quenched with sat. ammonium chloride solution and the aqueous layer extracted by ethyl acetate (2×100 mL). The organic phases were combined, dried ($Na_2SO_4$), and concentrated. The residue purified over a silica gel flash column using a gradient of ethyl acetate in hexanes to give the title compound (0.90 g, 76%).

MS (ES) MH$^+$: 590 for $C_{34}H_{37}F_2NO_4Si$ $^1$H NMR (300 MHz, CDCl$_3$) δ: 1.05 (s, 9H), 1.08 (d, 6H), 2.59-2.93 (m, 4H), 3.35-3.58 (m, 2H), 4.71 (s, 2H), 6.58 (dd, 1H), 7.18 (d, 1H), 7.32-7.48 (m, 6H), 7.57-7.74 (m, 6H).

Intermediates 123 to 138 were prepared from the indicated starting materials using a method similar to the one described for the synthesis of Intermediate 122:

Intermediate 123

(5-((tert-butyldiphenylsilyloxy)methyl)-4-((2R,6S)-2,6-dimethylmorpholino)-2,3-difluorophenyl)(thiazol-5-yl)methanone Starting materials: (2R,6S)-4-(6-((tert-butyldiphenylsilyloxy)methyl)-2,3-difluorophenyl)-2,6-dimethylmorpholine (Intermediate 3) and N-methoxy-N-methylthiazole-5-carboxamide.

MS (ES) MH$^+$: 607 for $C_{33}H_{36}F_2N_2O_3SSi$ $^1$H NMR (300 MHz, CDCl$_3$) δ: 0.99-1.14 (overlapping doublet and singlet, 15H), 2.67-2.94 (m, 4H), 3.38-3.57 (m, 2H), 4.70 (s, 2H), 7.28-7.51 (m, 6H), 7.54-7.74 (m, 5H), 8.26 (d, 1H), 9.08 (s, 1H).

Intermediate 124

(5-((tert-butyldiphenylsilyloxy)methyl)-4-((2R,6S)-2,6-dimethylmorpholino)-2,3-difluorophenyl)(6-methylpyridin-3-yl)methanone Starting materials (2R,6S)-4-(6-((tert-butyldiphenylsilyloxy)methyl)-2,3-difluorophenyl)-2,6-dimethylmorpholine (Intermediate 3 and N-methoxy-N, 6-dimethylnicotinamide.

MS (ES) MH$^+$: 615 for $C_{36}H_{40}F_2N_2O_3Si$ $^1$H NMR (300 MHz, CDCl$_3$) δ: 1.00-1.12 (overlapping doublet and singlet, 15H), 2.67 (s, 3H), 2.69-2.93 (m, 4H), 3.32-3.61 (m, 2H), 4.70 (s, 2H), 7.25-7.71 (m, 12H), 8.02 (d, 1H), 8.88 (s, 1H).

Intermediate 125

(5-((tert-butyldiphenylsilyloxy)methyl)-4-((2R,6S)-2,6-dimethylmorpholino)-2,3-difluorophenyl)(2-fluorophenyl)methanone Starting materials: (2R,6S)-4-(6-((tert-butyldiphenylsilyloxy)methyl)-2,3-difluorophenyl)-2,6-dimethylmorpholine (Intermediate 3) and 2-fluoro-N-methoxy-N-methylbenzamide.

MS (ES) MH$^+$: 618 for $C_{36}H_{38}F_3NO_3Si$ $^1$H NMR (300 MHz, CDCl$_3$) δ: 1.01 (s, 9H), 1.07 (d, 6H), 2.59-2.93 (m, 4H), 3.30-3.59 (m, 2H), 4.67 (s, 2H), 6.99-7.81 (m, 15H).

Intermediate 126

(5-((tert-butyldiphenylsilyloxy)methyl)-4-((2R,6S)-2,6-dimethylmorpholino)-2,3-difluorophenyl)(tetrahydro-2H-pyran-4-yl)methanone Starting materials: (2R,6S)-4-(6-((tert-butyldiphenylsilyloxy)methyl)-2,3-difluorophenyl)-2,6-dimethylmorpholine (Intermediate 3) and N-methoxy-N-methyltetrahydro-2H-pyran-4-carboxamide.

MS (ES) MH$^+$: 608 for $C_{35}H_{43}F_2NO_4Si$ $^1$H NMR (300 MHz, CDCl$_3$) δ: 1.04-1.11 (overlapping singlet and doublet, 15H), 1.73-1.90 (m, 4H), 2.62-2.93 (m, 4H), 3.19-3.36 (m, 1H), 3.39-3.59 (m, 4H), 3.95-4.08 (m, 2H), 4.67 (s, 2H), 7.30-7.52 (m, 6H), 7.58-7.72 (m, 4H), 7.78 (d, 1H).

Intermediate 127

1-(5-((tert-butyldiphenylsilyloxy)methyl)-4-((2R,6S)-2,6-dimethylmorpholino)-2,3-difluorophenyl)-2-chloroethanone Starting materials (2R,6S)-4-(6-((tert-butyldiphenylsilyloxy)methyl)-2,3-difluorophenyl)-2,6-dimethylmorpholine (Intermediate 3) and 2-chloro-N-methoxy-N-methylacetamide.

MS (ES) MH$^+$: 572 for $C_{31}H_{36}ClF_2NO_3Si$ $^1$H NMR (300 MHz, CDCl$_3$) δ: 1.05-1.16 (overlapping doublet and singlet, 15H), 2.70-2.92 (m, 4H), 3.34-3.61 (m, 2H), 4.67 (s, 2H) 4.71 (d, 2H), 7.35-7.53 (m, 6H), 7.60-7.74 (m, 4H) 7.97 (dd, 1.98 Hz, 1H).

Intermediate 128

(5-((tert-butyldiphenylsilyloxy)methyl)-4-((2R,6S)-2,6-dimethylmorpholino)-2,3-difluorophenyl)(pyridin-4-yl)methanone Starting materials: (2R,6S)-4-(6-((tert-butyldiphenylsilyloxy)methyl)-2,3-difluorophenyl)-2,6-dimethylmorpholine (Intermediate 3) and N-methoxy-N-methylisonicotinamide.

MS (ES) MH$^+$: 601 for $C_{35}H_{38}F_2N_2O_3Si$ $^1$H NMR (300 MHz, CDCl$_3$) δ: 1.03 (s, 9H), 1.09 (d, 6H), 2.65-2.95 (m, 4H), 3.38-3.59 (m, 2H), 4.68 (s, 2H), 7.28-7.47 (m, 6H), 7.52-7.68 (m, 7H), 8.80 (d, 2H).

Intermediate 129

1-(5-((tert-butyldiphenylsilyloxy)methyl)-4-((2R,6S)-2,6-dimethylmorpholino)-2,3-difluorophenyl)-2,2-difluoroethanone Starting materials: (2R,6S)-4-(6-((tert-butyldiphenylsilyloxy)methyl)-2,3-difluorophenyl)-2,6-dimethylmorpholine (Intermediate 3) and 2,2-difluoro-N-methoxy-N-methylacetamide.

MS (ES) MH$^+$: 574 for $C_{31}H_{35}F_4NO_3Si$ $^1$H NMR (300 MHz, CDCl$_3$) δ: 1.05-1.10 (overlapping doublet and singlet, 15H), 2.71-2.92 (m, 4H), 3.37-3.55 (m, 2H), 4.63 (s, 2H), 6.12-6.57 (m, 1H), 7.31-7.49 (m, 6H), 7.58-7.70 (m, 4H), 7.93 (dd, 1.79 Hz, 1H).

Intermediate 130

1-(5-((tert-butyldiphenylsilyloxy)methyl)-4-((2R,6S)-2,6-dimethylmorpholino)-2,3-difluorophenyl)-2,2,2-trifluoroethanone Starting materials (2R,6S)-4-(6-((tert-butyldiphenylsilyloxy)methyl)-2,3-difluorophenyl)-2,6-dimethylmorpholine (Intermediate 3) and 2,2,2-trifluoro-N-methoxy-N-methylacetamide. Compound exists in the hydrated form.

MS (ES) MH$^+$: 610 for $C_{31}H_{34}F_5NO_3Si \cdot H_2O$

Intermediate 131

(5-((tert-butyldiphenylsilyloxy)methyl)-4-((2R,6R)-2,6-dimethylmorpholino)-2,3-difluorophenyl)(thiazol-2-yl)methanone Starting materials (2R,6R)-4-(6-((tert-butyldiphenylsilyloxy)methyl)-2,3-difluorophenyl)-2,6-dimethylmorpholine (Intermediate 43) and N-methoxy-N-methylthiazole-2-carboxamide (MTBE was used as solvent instead of THF).

MS (ES) MH$^+$: 607 for $C_{33}H_{36}F_2N_2O_3SSi$ $^1$H NMR (300 MHz, CDCl$_3$) δ: 1.05 (d, 6H) 1.07 (s, 9H), 2.58-2.80 (m, 2H), 2.91-3.21 (m, 2H), 3.78-3.96 (m, 2H), 4.64-4.94 (m, 2H, 7.30-8.20 (m, 13H).

Intermediate 132

1-(5-((tert-butyldiphenylsilyloxy)methyl)-4-((2R,6R)-2,6-dimethylmorpholino)-2,3-difluorophenyl)-2,2-difluoroethanone Starting materials (2R,6R)-4-(6-((tert-butyldiphenylsilyloxy)methyl)-2,3-difluorophenyl)-2,6-dimethylmorpholine (Intermediate 43) and 2,2-difluoro-N-methoxy-N-methylacetamide (MTBE was used as solvent instead of THF).

MS (ES) MH$^+$: 574 for $C_{31}H_{35}F_4NO_3Si$ $^1$H NMR (300 MHz, CDCl$_3$) δ: 0.99-1.17 (overlapping doublet and singlet, 15H), 2.58-2.85 (m, 2H), 2.97-3.20 (m, 2H), 3.76-3.99 (m, 2H), 4.57-4.82 (m, 2H), 6.36 (t, 1H), 7.30-8.10 (m, 11H).

Intermediate 133

(5-((tert-butyldiphenylsilyloxy)methyl)-4-((2R,6R)-2,6-dimethylmorpholino)-2,3-difluorophenyl)(pyrazin-2-yl)methanone Starting material: N-methoxy-N-methylpyrazine-2-carboxamide (Intermediate 50)

MS (ES) MH$^+$: 602 for $C_{34}H_{37}F_2N_3O_3Si$

Intermediate 134

(5-((tert-butyldiphenylsilyloxy)methyl)-4-((2R,6R)-2,6-dimethylmorpholino)-2,3-difluorophenyl)(5-morpholinopyrazin-2-yl)methanone Starting material: N-methoxy-N-methyl-5-morpholinopyrazine-2-carboxamide (Intermediate 52)

MS (ES) MH$^+$: 740 for $C_{41}H_{50}FN_5O_5Si$

Intermediate 135

(5-((tert-butyldiphenylsilyloxy)methyl)-4-((2R,6S)-2,6-dimethylmorpholino)-2,3-difluorophenyl)(3-chloropyrazin-2-yl)methanone Starting material: 3-chloro-N-methoxy-N-methylpyrazine-2-carboxamide (Intermediate 53)

MS (ES) MH$^+$: 637 for $C_{34}H_{36}ClF_2N_3O_3Si$

Intermediate 136

(5-((tert-butyldiphenylsilyloxy)methyl)-4-((2R,6S)-2,6-dimethylmorpholino)-2,3-difluorophenyl)(6-chloropyrazin-2-yl)methanone Starting material: 6-chloro-N-methoxy-N-methylpyrazine-2-carboxamide (Intermediate 51)

MS (ES) MH$^+$: 637 for $C_{34}H_{36}ClF_2N_3O_3Si$

Intermediate 137

(5-((tert-butyldiphenylsilyloxy)methyl)-4-((2R,6S)-2,6-dimethylmorpholino)-2,3-difluorophenyl)(5-chloropyrazin-2-yl)methanone Starting material: 5-chloro-N-methoxy-N-methylpyrazine-2-carboxamide (Intermediate 54).

MS (ES) MH$^+$: 637 for $C_{34}H_{36}ClF_2N_3O_3Si$

Intermediate 138

(5-((tert-butyldiphenylsilyloxy)methyl)-4-((2R,6R)-
2,6-dimethylmorpholino)-2,3-difluorophenyl)(6-
methoxypyrazin-2-yl)methanone

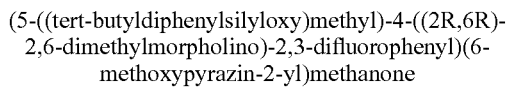

Starting material: N,6-dimethoxy-N-methylpyrazine-2-carboxamide (Intermediate 55)

MS (ES) MH$^+$: 632 for $C_{35}H_{39}F_2N_3O_4Si$

Intermediate 139

1-(5-((tert-butyldiphenylsilyloxy)methyl)-4-((2R,
6S)-2,6-dimethylmorpholino)-2,3-difluorophenyl)-2-
(1H-1,2,4-triazol-1-yl)ethanone

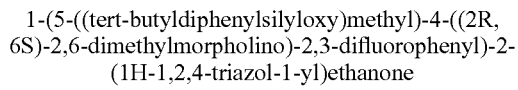

Potassium carbonate (1208 mg, 8.74 mmol) was added to a mixture of 1-(5-((tert-butyldiphenylsilyloxy)methyl)-4-((2R, 6S)-2,6-dimethylmorpholino)-2,3-difluorophenyl)-2-chloroethanone (Intermediate 127, 500 mg, 0.87 mmol) and 1H-1, 2,4-triazole (66.4 mg, 0.96 mmol) dissolved in 15 ml of Acetonitrile. The mixture was stirred at room temperature for 3 hours. Potassium carbonate was filtered from the mixture, and the filtrate was diluted with water and extracted with ethyl acetate (2×100 mL). The organic phases were combined, dried (Na$_2$SO$_4$), and concentrated. The crude residue (482 mg, 91%) contained mainly desired title compound and was used in the next step without further purification.

MS (ES) MH$^+$: 605 for $C_{33}H_{38}F_2N_4O_3Si$ $^1$H NMR (300 MHz, CDCl$_3$) δ: 1.02-1.12 (overlapping singlet and doublet, 15H), 2.67-2.91 (m, 4H), 3.35-3.54 (m, 2H), 4.63 (s, 2H), 5.56 (d, 2H), 7.29-8.32 (m, 13H).

Intermediate 140

(6-((tert-butyldiphenylsilyloxy)methyl)-4-chloro-5-
((2R,6S)-2,6-dimethylmorpholino)-3-fluoropyridin-
2-yl)(pyridin-2-yl)methanone

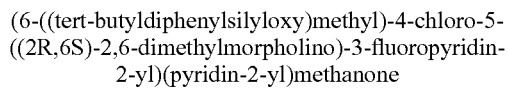

Diisopropylamine (0.925 mL, 6.55 mmol) was added dropwise to a stirring solution of 2.5M n-butyllithium in hexane (2.495 mL, 6.24 mmol) in THF (10 mL) at −78° C. Allowed solution to warm to 0° C. for 10 minutes then cooled again to −78° C. Cannulated the prepared LDA at −78° C. into (2R, 6S)-4-(2-((tert-butyldiphenylsilyloxy)methyl)-4-chloro-5-fluoropyridin-3-yl)-2,6-dimethylmorpholine (Intermediate 45, 1.6 g, 3.12 mmol) in THF (10 mL) at −78° C. Allowed the dark solution to stir for 20 minutes and then cannulated into a stirring solution of N-methoxy-N-methylpicolinamide (1.05 g, 6.24 mmol) in THF (10 mL) at −78° C. Allowed the solution to warm to −50° C. and then quenched with saturated ammonium chloride solution. Extracted mixture with ethyl acetate and washed resulting organics with brine. Dried organics over sodium sulfate, filtered, and evacuated filtrate under vacuum to give crude yellow oil. The crude oil was purified on silica using 10-30% acetone in n-hexane as eluant to give 1.3 g (67%) of the title compound as oil.

MS (ES) MH$^+$: 618 for $C_{34}H_{37}ClFN_3O_3Si$ $^1$H NMR (300 MHz, CDCl$_3$) δ: 0.9 (s, 9H), 1.0 (d, 6H), 2.7-2.9 (m, 2H), 2.9-3.1 (m, 2H), 3.6 (br.s., 2H), 4.8 (s, 2H), 7.1-7.3 (m, 4H), 7.3-7.4 (m, 2H), 7.5-7.6 (m, 5H), 7.9-8.1 (m, 2H), 8.5-8.6 (m, 1H).

Intermediates 141 to 148 were prepared from the indicated starting materials using a method similar to the one described for the synthesis of Intermediate 140:

Intermediate 141

(6-((tert-butyldiphenylsilyloxy)methyl)-4-chloro-5-
((2R,6S)-2,6-dimethylmorpholino)-3-fluoropyridin-
2-yl)(pyridin-4-yl)methanone

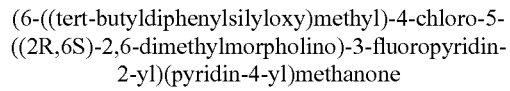

Starting material: (2R,6S)-4-(2-((tert-butyldiphenylsilyloxy)methyl)-4-chloro-5-fluoropyridin-3-yl)-2,6-dimethylmorpholine (1.5 g, 2.92 mmol) (Intermediate 45) and N-methoxy-N-methylisonicotinamide.

MS (ES) MH$^+$: 621 for $C_{34}H_{37}ClFN_3O_3Si$

Intermediate 142

(6-((tert-butyldiphenylsilyloxy)methyl)-4-chloro-5-
((2R,6S)-2,6-dimethylmorpholino)-3-fluoropyridin-
2-yl)(pyridin-3-yl)methanone

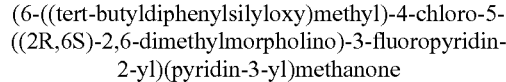

Starting material: (2R,6S)-4-(2-((tert-butyldiphenylsilyloxy)methyl)-4-chloro-5-fluoropyridin-3-yl)-2,6-dimethylmorpholine (Intermediate 45) and N-methoxy-N-methylnicotinamide.

MS (ES) MH$^+$: 618 for $C_{34}H_{37}ClFN_3O_3Si$:

$^1$H NMR (300 MHz, CDCl$_3$) δ: 0.9-1.0 (m, 9H), 1.2 (dd, 6H), 3.0-3.1 (m, 4H), 3.7 (d, 2H), 4.8 (m, 2H), 7.2-7.3 (m, 4H), 7.4 (td, 3H), 7.6 (m, 3H), 7.7 (dd, 2H), 8.6-8.7 (m, 2H).

Intermediate 143

(6-((tert-butyldiphenylsilyloxy)methyl)-4-chloro-5-
((2R,6S)-2,6-dimethylmorpholino)-3-fluoropyridin-
2-yl)(pyrazin-2-yl)methanone

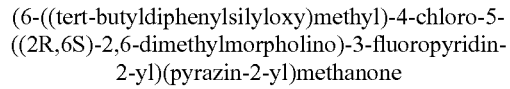

Starting material: (2-((tert-butyldiphenylsilyloxy)methyl)-4-chloro-5-fluoropyridin-3-yl)-2,6-dimethylmorpholine (Intermediate 45) and N-methoxy-N-methylpyrazine-2-carboxamide.

MS (ES) MH$^+$: 619 for $C_{33}H_{36}ClFN_4O_3Si$ $^1$H NMR (300 MHz, CDCl$_3$) δ: 0.9-1.0 (m, 9H), 1.1-1.2 (m, 6H,) 2.9-3.1 (m, 2H), 3.2 (t, 2H), 3.7 (br.s., 2H), 4.8 (s, 2H), 7.2-7.3 (m, 4H), 7.3-7.4 (m, 2H), 7.6-7.7 (m, 4H), 8.2 (m, 1H), 8.8 (m, 1H), 9.1 (d, 1H).

Intermediate 144

(6-((tert-butyldiphenylsilyloxy)methyl)-4-chloro-5-
((2R,6S)-2,6-dimethylmorpholino)-3-fluoropyridin-
2-yl)(thiazol-2-yl)methanone

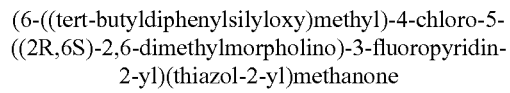

Starting material: (2-((tert-butyldiphenylsilyloxy)methyl)-4-chloro-5-fluoropyridin-3-yl)-2,6-dimethylmorpholine (Intermediate 45) and N-methoxy-N-methylthiazole-2-carboxamide.

MS (ES) MH$^+$: 624 for $C_{32}H_{35}ClFN_3O_3SiS$ $^1$H NMR (300 MHz, CDCl$_3$) δ: 1.0 (s, 9H), 1.1 (d, 6H), 3.0 (br.s, 2H), 3.1-3.2 (m, 2H), 3.7 (br.s., 2H), 4.9 (s, 2H), 7.2-7.5 (m, 6H), 7.5-7.6 (m, 4H), 8.1 (s, 1H).

Intermediate 145

(6-((tert-butyldiphenylsilyloxy)methyl)-4-chloro-5-
((2R,6S)-2,6-dimethylmorpholino)-3-fluoropyridin-
2-yl)(4-methylthiazol-2-yl)methanone

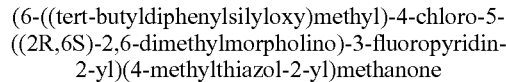

Starting material: (2-((tert-butyldiphenylsilyloxy)methyl)-4-chloro-5-fluoropyridin-3-yl)-2,6-dimethylmorpholine (Intermediate 45) and N-methoxy-N,4-dimethylthiazole-2-carboxamide.

MS (ES) MH$^+$: 638 for $C_{33}H_{37}ClFN_3O_3SiS$ $^1$H NMR (300 MHz, CDCl$_3$) δ: 1.0 (s, 9H), 1.1 (d, 6H), 2.5 (s, 3H), 3.0 (br.s, 2H), 3.1-3.2 (m, 2H), 3.7 (dd, 2H), 4.9 (s, 2H), 7.2-7.5 (m, 6H), 7.5-7.6 (m, 4H), 7.6 (s, 1H).

Intermediate 146

(6-((tert-butyldiphenylsilyloxy)methyl)-4-chloro-5-((2R,6S)-2,6-dimethylmorpholino)-3-fluoropyridin-2-yl)(1-methyl-1H-1,2,4-triazol-5-yl)methanone Starting material: (2R,6S)-4-(2-((tert-butyldiphenylsilyloxy)methyl)-4-chloro-5-fluoropyridin-3-yl)-2,6-dimethylmorpholine (Intermediate 45) and N-methoxy-N, 1-dimethyl-1H-1,2,4-triazole-5-carboxamide (Intermediate 49).

MS (ES) MH$^+$: 622 for C$_{32}$H$_{37}$ClFN$_5$O$_3$Si $^1$H NMR (300 MHz, CDCl$_3$) δ: 0.9-1.0 (m, 9H) 1.2 (d, 6H) 2.8-3.0 (m, 2H) 3.0 (d, 2H) 3.7 (d, 2H) 4.3 (s, 2H) 4.8 (s, 2H) 7.2-7.3 (m, 4H) 7.3-7.6 (m, 3H) 7.7 (d, 4H) 7.9 (s, 1H).

Intermediate 147

5-(6-((tert-butyldiphenylsilyloxy)methyl)-4-chloro-5-((2R,6S)-2,6-dimethylmorpholino)-3-fluoropicolinoyl)picolinonitrile Starting material: (2R,6S)-4-(2-((tert-butyldiphenylsilyloxy)methyl)-4-chloro-5-fluoropyridin-3-yl)-2,6-dimethylmorpholine (Intermediate 45) and 6-cyano-N-methoxy-N-methylnicotinamide.

MS (ES) MH$^+$: 643 for C$_{35}$H$_{36}$ClFN$_4$O$_3$Si $^1$H NMR (300 MHz, CDCl$_3$) δ: 0.9-1.1 (m, 9H), 1.2 (d, 6H), 3.0-3.1 (m, 2H), 3.6-3.7 (m, 2H), 3.6-3.7 (m, 2H), 4.7-4.8 m, 2H), 7.2-7.3 (m, 4H), 7.5-7.6 (m, 5H), 7.6-7.7 (m, 2H), 8.3 (dd, 1H), 9.1 (d, 1H).

Intermediate 148

1-(6-((tert-Butyldiphenylsilyloxy)methyl)-4-chloro-5-((2R,6S)-2,6-dimethylmorpholino)-3-fluoropyridin-2-yl)ethanone Starting materials: (2R,6S)-4-(2-((tert-butyldiphenylsilyloxy)methyl)-4-chloro-5-fluoropyridin-3-yl)-2,6-dimethylmorpholine (Intermediate 45) and N-methoxy-N-methylacetamide.

MS (ES) MH$^+$: 555 for C$_{30}$H$_{36}$ClFN$_2$O$_3$Si $^1$H NMR (300 MHz, CD$_2$Cl$_2$) δ: 1.05 (s, 9H), 1.1 (d, 6H), 2.6 (s, 3H), 3.0-3.2 (m, 4H), 3.7-3.8 (m, 2H), 4.9 (s, 2H), 7.4-7.5 (m 6H), 7.7-7.8 (m, 4H).

Intermediate 149

{5-({[tert-butyl(diphenyl)silyl]oxy}methyl)-4-[(2R,6S)-2,6-dimethylmorpholin-4-yl]-2,3-difluorophenyl}(2-methyl-1,3-oxazol-4-yl)methanone sec-Butyl lithium (1.4 M in cyclohexane, 3.2 eq) was added to a stirred solution of (2R,6S)-4-[6-({[tert-butyl(diphenyl)silyl]oxy}methyl)-2,3-difluorophenyl]-2,6-dimethylmorpholine (Intermediate 3, 1.0 g, 2.02 mmol) in anhydrous THF (10 mL) at −78° C., and the mixture was stirred for 2 h. N-methoxy-N,2-dimethyl-1,3-oxazole-4-carboxamide (1.0 g, 6.46 mmol) in THF (5 mL) was added dropwise and stirring was continued for an additional 1 h. The reaction mixture was quenched with saturated ammonium chloride solution and extracted with ethyl acetate. The organic layer was washed with brine and dried over anhydrous sodium sulphate. The solvent was removed under vacuum and the residue was purified by silica gel chromatography using ethyl lacetate-pet. ether gradient to obtain product. Yield: 600 mg, (50%)

MS (ES) MH$^+$: 605 for C$_{34}$H$_{38}$F$_2$N$_2$O$_4$Si $^1$H NMR (400 MHz, DMSO-d$_6$) δ: 1.0 (m, 15H), 2.5 (s, 3H), 2.7 (m, 2H), 2.8 (d, 2H), 4.8 (s, 2H), 7.4 (m, 6H), 7.6 (t, 4H), 7.7 (d, 1H), 8.8 (s, 1H).

Intermediates 150 to 156 were prepared from the indicated starting materials using a method similar to the one described for the synthesis of Intermediate 149:

Intermediate 150

{5-({[tert-butyl(diphenyl)silyl]oxy}methyl)-4-[(2R,6S)-2,6-dimethylmorpholin-4-yl]-2,3-difluorophenyl}(5-methyl-1,2-oxazol-3-yl)methanone Starting materials: (2R,6S)-4-[6-({[tert-butyl(diphenyl)silyl]oxy}methyl)-2,3-difluorophenyl]-2,6-dimethylmorpholine (Intermediate 3) and N-methoxy-N,5-dimethyl-1,2-oxazole-3-carboxamide MS (ES) MH$^+$: 605 for C$_{34}$H$_{38}$F$_2$N$_2$O$_4$Si Intermediate 151

{5-({[tert-butyl(diphenyl)silyl]oxy}methyl)-4-[(2R,6S)-2,6-dimethylmorpholin-4-yl]-2,3-difluorophenyl}(3,5-dimethyl-1,2-oxazol-4-yl)methanone Starting materials: (2R,6S)-4-[6-({[tert-butyl(diphenyl)silyl]oxy}methyl)-2,3-difluorophenyl]-2,6-dimethylmorpholine (Intermediate 3) and N-methoxy-N,3,5-trimethyl-1,2-oxazole-4-carboxamide MS (ES) MH$^+$: 619.5 for C$_{35}$H$_{40}$F$_2$N$_2$O$_4$Si Intermediate 152

{5-({[tert-butyl(diphenyl)silyl]oxy}methyl)-4-[(2R,6S)-2,6-dimethylmorpholin-4-yl]-2,3-difluorophenyl}(1-methyl-1H-imidazol-2-yl)methanone Starting materials: (2R,6S)-4-[6-({[tert-butyl(diphenyl)silyl]oxy}methyl)-2,3-difluorophenyl]-2,6-dimethylmorpholine (Intermediate 3) and N-methoxy-N,1-dimethyl-1H-imidazole-2-carboxamide MS (ES) MH$^+$: 604 for C$_{34}$H$_{39}$F$_2$N$_3$O$_3$Si;

Intermediate 153

{5-({[tert-butyl(diphenyl)silyl]oxy}methyl)-4-[(2R,6S)-2,6-dimethylmorpholin-4-yl]-2,3-difluorophenyl}(1-methyl-1H-imidazol-4-yl)methanone Starting materials: (2R,6S)-4-[6-({[tert-butyl(diphenyl)silyl]oxy}methyl)-2,3-difluorophenyl]-2,6-dimethylmorpholine (Intermediate 3) and N-methoxy-N,1-dimethyl-1H-imidazole-4-carboxamide MS (ES) MH$^+$: 604.2 for C$_{34}$H$_{39}$F$_2$N$_3$O$_3$Si;

Intermediate 154

{5-({[tert-butyl(diphenyl)silyl]oxy}methyl)-4-[(2R,6S)-2,6-dimethylmorpholin-4-yl]-2,3-difluorophenyl}(4-methyl-1,2,3-thiadiazol-5-yl)methanone Starting materials: (2R,6S)-4-[6-({[tert-butyl(diphenyl)silyl]oxy}methyl)-2,3-difluorophenyl]-2,6-dimethylmorpholine (Intermediate 3) and N-methoxy-N,4-dimethyl-1,2,3-thiadiazole-5-carboxamide MS (ES) MH$^+$: 622 for C$_{33}$H$_{37}$F$_2$N$_3$O$_3$SSi Intermediate 155

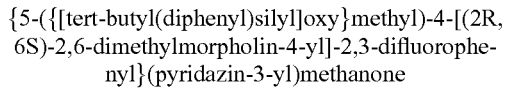
{5-({[tert-butyl(diphenyl)silyl]oxy}methyl)-4-[(2R,6S)-2,6-dimethylmorpholin-4-yl]-2,3-difluorophenyl}(pyridazin-3-yl)methanone Starting material: (2R,6S)-4-[6-({[tert-butyl(diphenyl)silyl]oxy}methyl)-2,3-difluorophenyl]-2,6-dimethylmorpholine (Intermediate 3) and N-methoxy-N-methylpyridazine-3-carboxamide MS (ES) MH$^+$: 602 for $C_{34}H_{37}F_2N_3O_3Si$;

Intermediate 156

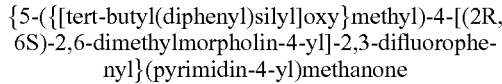
{5-({[tert-butyl(diphenyl)silyl]oxy}methyl)-4-[(2R,6S)-2,6-dimethylmorpholin-4-yl]-2,3-difluorophenyl}(pyrimidin-4-yl)methanone Starting material: (2R,6S)-4-[6-({[tert-butyl(diphenyl)silyl]oxy}methyl)-2,3-difluorophenyl]-2,6-dimethylmorpholine (Intermediate 3) and N-methoxy-N-methylpyrimidine-4-carboxamide MS (ES) MH$^+$: 602 for $C_{34}H_{37}F_2N_3O_3Si$;

Intermediate 157

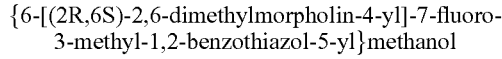
{6-[(2R,6S)-2,6-dimethylmorpholin-4-yl]-7-fluoro-3-methyl-1,2-benzothiazol-5-yl}methanol A mixture of 1-[5-(tert-Butyldiphenylsilanyloxymethyl)-4-[(2R,6S)-2,6-dimethyl-morpholin-4-yl]-2,3-difluorophenyl]ethanone (Intermediate 9, 0.5 g, 0.92 mmol), sulfur powder (0.06 g, 1.8 mmol), potassium iodide (0.08 g, 0.4 mmol) and 25% aqueous ammonia solution (10 mL) in DMSO (10 mL) was heated in a sealed tube at 100° C. for 4 hours. The reaction mixture was cooled and water was added. The mixture was extracted with ethyl acetate, which was dried (Na$_2$SO$_4$) and concentrated. The residue was purified by column chromatography (1:9 ethyl acetate:hexanes) to afford product as a yellow solid. Yield: 0.18 g (63%).

MS (ES) MH$^+$: 311 for $C_{15}H_{19}FN_2O_2S$ $^1$H NMR (400 MHz, Methanol-d$_4$): δ 1.2 (d, 6H), 2.5 (s, 3H), 3.0 (m, 4H), 3.8 (m, 2H), 4.8 (s, 2H), 8.0 (s, 1H).

Intermediate 158 was prepared from the indicated starting material using a method similar to the one described for the synthesis of Intermediate 157:

Intermediate 158

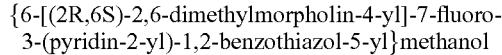
{6-[(2R,6S)-2,6-dimethylmorpholin-4-yl]-7-fluoro-3-(pyridin-2-yl)-1,2-benzothiazol-5-yl}methanol Starting material: {5-({[tert-butyl(diphenyl)silyl]oxy}methyl)-4-[(2R,6S)-2,6-dimethylmorpholin-4-yl]-2,3-difluorophenyl}(pyridin-2-yl)methanone (Intermediate 21)

MS (ES) MH$^+$: 374 for $C_{19}H_{20}FN_3O_2S$ $^1$H NMR (400 MHz, CDCl$_3$) δ: 1.25 (d, 6H), 2.7 (m, 2H), 3.0 (d, 2H), 3.1 (t, 2H), 3.8 (m, 2H), 4.9 (s, 2H), 7.5 (m, 1H), 7.9 (t, 1H), 8.3 (d, 1H), 8.8 (d, 1H), 8.9 (s, 1H).

Intermediate 159

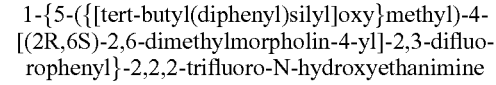
1-{5-({[tert-butyl(diphenyl)silyl]oxy}methyl)-4-[(2R,6S)-2,6-dimethylmorpholin-4-yl]-2,3-difluorophenyl}-2,2,2-trifluoro-N-hydroxyethanimine Pyridine (2597 μl, 32.11 mmol) was added to a mixture of 1-(5-((tert-butyldiphenylsilyloxy)methyl)-4-((2R,6S)-2,6-dimethylmorpholino)-2,3-difluorophenyl)-2,2,2-trifluoroethanone (Intermediate 130, 1900 mg, 3.21 mmol) and hydroxylamine hydrochloride (223 mg, 3.21 mmol) in 50 ml of ethanol and the solution was heated at 80° C. for 40 hours. The reaction mixture was concentrated, diluted with water, and extracted with ethyl acetate. The organic phases were combined, dried (Na$_2$SO$_4$), and concentrated to give the crude title compound (1.95 g, 98%), which was used in the next step without further purification.

MS (ES) MH$^+$: 607 for $C_{31}H_{35}F_5N_2O_3Si$ $^1$H NMR (300 MHz, CDCl$_3$) δ: 1.03-1.15 (m, 15H), 2.56-2.91 (m, 4H), 3.33-3.59 (m, 2H), 4.58-4.80 (m, 2H), 7.27-7.51 (m, 7H), 7.57-7.74 (m, 4H).

Intermediates 160 to 164 were prepared from the indicated starting material using a method similar to the one described for the synthesis of Intermediate 159:

Intermediate 160

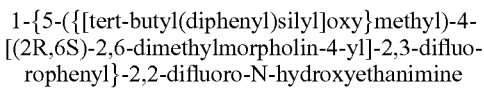
1-{5-({[tert-butyl(diphenyl)silyl]oxy}methyl)-4-[(2R,6S)-2,6-dimethylmorpholin-4-yl]-2,3-difluorophenyl}-2,2-difluoro-N-hydroxyethanimine Starting material: 1-(5-((tert-butyldiphenylsilyloxy)methyl)-4-((2R,6S)-2,6-dimethylmorpholino)-2,3-difluorophenyl)-2,2-difluoroethanone (Intermediate 129).

MS (ES) MH$^+$: 589 for $C_{31}H_{36}F_4N_2O_3Si$

Intermediate 161

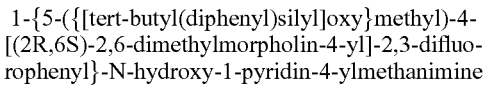
1-{5-({[tert-butyl(diphenyl)silyl]oxy}methyl)-4-[(2R,6S)-2,6-dimethylmorpholin-4-yl]-2,3-difluorophenyl}-N-hydroxy-1-pyridin-4-ylmethanimine Starting material: (5-((tert-butyldiphenylsilyloxy)methyl)-4-((2R,6S)-2,6-dimethylmorpholino)-2,3-difluorophenyl)(pyridin-4-yl)methanone (Intermediate 128).

MS (ES) MH$^+$: 616 for $C_{35}H_{39}F_2N_3O_3Si$

Intermediate 162

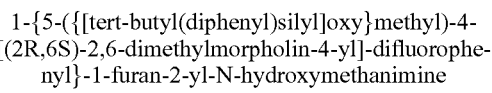
1-{5-({[tert-butyl(diphenyl)silyl]oxy}methyl)-4-[(2R,6S)-2,6-dimethylmorpholin-4-yl]-difluorophenyl}-1-furan-2-yl-N-hydroxymethanimine Starting material: (5-((tert-butyldiphenylsilyloxy)methyl)-4-((2R,6S)-2,6-dimethylmorpholino)-2,3-difluorophenyl)(furan-2-yl)methanone (Intermediate 122).

MS (ES) MH$^+$: 605 for $C_{34}H_{38}F_2N_2O_4Si$

Intermediate 163

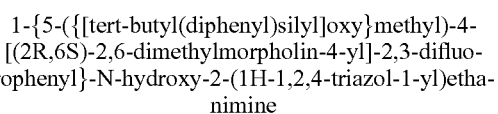
1-{5-({[tert-butyl(diphenyl)silyl]oxy}methyl)-4-[(2R,6S)-2,6-dimethylmorpholin-4-yl]-2,3-difluorophenyl}-N-hydroxy-2-(1H-1,2,4-triazol-1-yl)ethanimine Starting material: 1-(5-((tert-butyldiphenylsilyloxy)methyl)-4-((2R,6S)-2,6-dimethylmorpholino)-2,3-difluorophenyl)-2-(1H-1,2,4-triazol-1-yl)ethanone (Intermediate 139).

MS (ES) MH$^+$: 620 for $C_{33}H_{39}F_2N_5O_3Si$

Intermediate 164

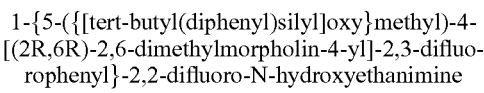
1-{5-({[tert-butyl(diphenyl)silyl]oxy}methyl)-4-[(2R,6R)-2,6-dimethylmorpholin-4-yl]-2,3-difluorophenyl}-2,2-difluoro-N-hydroxyethanimine Starting material: 1-(5-((tert-butyldiphenylsilyloxy)methyl)-4-((2R,6R)-2,6-dimethylmorpholino)-2,3-difluorophenyl)-2,2-difluoroethanone (Intermediate 132).

MS (ES) MH$^+$: 589 for $C_{31}H_{36}F_4N_2O_3Si$

Intermediate 165

Ethyl 2-(5-((tert-butyldiphenylsilyloxy)methyl)-4-((2R,6S)-2,6-dimethylmorpholino)-2,3-difluorophenyl)-2-(hydroxyimino)acetate Ethyl 2-(5-((tert-butyldiphenylsilyloxy)methyl)-4-((2R,6S)-2,6-dimethylmorpholino)-2,3-difluorophenyl)-2-oxoacetate (Intermediate 114, 2.808 g, 4.71 mmol) and hydroxylamine hydrochloride (0.360 g, 5.18 mmol) were dissolved in pyridine (40 ml) and stirred at 115° C. for 16 hours. The reaction was concentrated to remove excess pyridine. The residue was dissolved in ethyl acetate and washed with water and brine 3×. The organic layer was dried over $MgSO_4$ and concentrated. The residue was purified by silica gel column chromatography using a gradient of hexanes to ethyl acetate to give the title compound as a mixture of oxime isomers (1.924 g, 3.15 mmol, 66.8%).

MS (ES) $MH^+$: 611 for $C_{33}H_{40}F_2N_2O_5Si$ (2 peaks by LCMS).

$^1H$ NMR (300 MHz, DMSO-$d_6$) δ ppm 0.9-1.1 (m, 15H), 1.15-1.3 (m, 3H), 2.6-2.8 (m, 4H), 4.2-4.35 (m, 2H), 4.7-4.8 (m, 2H), 7.3-7.65 (m, 11H).

Intermediates 166 and 167 were prepared from the indicated starting material using a method similar to the one described for the synthesis of Intermediate 165:

Intermediate 166

Ethyl 2-(5-((tert-butyldiphenylsilyloxy)methyl)-4-((2R,6R)-2,6-dimethylmorpholino)-2,3-difluorophenyl)-2-(hydroxyimino)acetate Starting material: ethyl 2-(5-((tert-butyldiphenylsilyloxy)methyl)-4-((2R,6R)-2,6-dimethylmorpholino)-2,3-difluorophenyl)-2-oxoacetate (Intermediate 116)

MS (ES) $MH^+$: 611 for $C_{33}H_{40}F_2N_2O_5Si$

Intermediate 167

Ethyl 2-(5-(dimethoxymethyl)-2,3,4-trifluorophenyl)-2-(hydroxyimino)acetate

Starting material: ethyl 2-(5-(dimethoxymethyl)-2,3,4-trifluorophenyl)-2-oxoacetate (Intermediate 117).

MS (ES) $MH^{+\,(-CH_3O)}$: 290

Intermediate 168

2-(5-((tert-butyldiphenylsilyloxy)methyl)-4-((2R,6S)-2,6-dimethylmorpholino)-2,3-difluorophenyl)-2-(hydroxyimino)-1-morpholinoethanone 1-(5-((tert-butyldiphenylsilyloxy)methyl)-4-((2R,6S)-2,6-dimethylmorpholino)-2,3-difluorophenyl)-2-morpholinoethane-1,2-dione (Intermediate 119, 130 mg, 0.20 mmol) in pyridine was stirred at 115° C. for 16 hours. The reaction was allowed to cool to room temperature and then concentrated. The residue was dissolved in ethyl acetate, diluted with water and made acidic with 1N HCl. The mixture was extracted twice with ethyl acetate. The organic layers were washed twice with brine, dried over $MgSO_4$ and concentrated to give the title compound as an oil which was dried under vacuum. The residue was carried forward without further purification.

MS (ES) $MH^+$: 652 for $C_{35}H_{43}F_2N_3O_5Si$

Intermediates 169 and 170 were prepared from the indicated starting material using a method similar to the one described for the synthesis of Intermediate 168:

Intermediate 169

2-(5-((tert-butyldiphenylsilyloxy)methyl)-4-((2R,6S)-2,6-dimethylmorpholino)-2,3-difluorophenyl)-2-(hydroxyimino)-N,N-dimethylacetamide Starting material: 2-(5-((tert-butyldiphenylsilyloxy)methyl)-4-((2R,6S)-2,6-dimethylmorpholino)-2,3-difluorophenyl)-N,N-dimethyl-2-oxoacetamide (Intermediate 120).

MS (ES) $MH^+$: 610 for $C_{33}H_{41}F_2N_3O_4Si$

Intermediate 170

2-(5-((tert-butyldiphenylsilyloxy)methyl)-4-((2R,6S)-2,6-dimethylmorpholino)-2,3-difluorophenyl)-2-(hydroxyimino)-N-methoxy-N-methylacetamide Starting material: 2-(5-((tert-butyldiphenylsilyloxy)methyl)-4-((2R,6S)-2,6-dimethylmorpholino)-2,3-difluorophenyl)-N-methoxy-N-methyl-2-oxoacetamide (Intermediate 115).

MS (ES) $MH^+$: 626 for $C_{33}H_{41}F_2N_3O_5Si$

Intermediate 171 methyl 3-chloro-2-[(2R,6S)-2,6-dimethylmorpholin-4-yl]-4-fluoro-5-[N-hydroxyethanimidoyl]benzoate To a solution of methyl 5-acetyl-3-chloro-2-[(2R,6S)-2,6-dimethylmorpholin-4-yl]-4-fluorobenzoate (Intermediate 107, 800 mg, 2.32 mmol) in methanol:Pyridine (1:1, 6 mL) was added hydroxylamine hydrochloride (223 mg, 3.48 mmol) and the mixture was stirred at room temperature for 12 hours. Solvents were removed under vacuum and the residue was subjected to silica gel column chromatography using a gradient of ethyl acetate in pet. ether to give title compound. Yield: 700 mg (87%).

MS (ES) $MH^+$: MS (ES) $MH^+$: 359 for $C_{16}H_{20}ClFN_2O_4$

Intermediates 172 to 196 were prepared from the indicated starting material and hydroxylamine hydrochloride using a method similar to the one described for the synthesis of Intermediate 171:

Intermediate 172

1-{5-({[tert-butyl(diphenyl)silyl]oxy}methyl-3-chloro-4-[(2R,6S)-2,6-dimethylmorpholin-4-yl]-2-fluorophenyl}-N-hydroxy-1-(pyridin-2-yl)methanimine Starting material: {5-({[tert-butyl(diphenyl)silyl]oxy}methyl)-3-chloro-4-[(2R,6S)-2,6-dimethylmorpholin-4-yl]-2-fluorophenyl}(pyridin-2-yl)methanone (Intermediate 85).

MS (ES) $MH^+$: 632 for $C_{35}H_{39}ClFN_3O_3Si$

Intermediate 173

1-{5-({[tert-butyl(diphenyl)silyl]oxy}methyl)-3-chloro-4-[(2R,6S)-2,6-dimethylmorpholin-4-yl]-2-fluorophenyl}-N-hydroxy-1-(6-methylpyridin-3-yl)methanimine Starting material: {5-({[tert-butyl(diphenyl)silyl]oxy}methyl)-3-chloro-4-[(2R,6S)-2,6-dimethylmorpholin-4-yl]-2-fluorophenyl}(6-methylpyridin-3-yl)methanone (Intermediate 108).

MS (ES) $MH^+$: 646 for $C_{36}H_{41}ClFN_3O_3Si$.

Intermediate 174

1-{5-({[tert-butyl(diphenyl)silyl]oxy}methyl-3-chloro-4-[(2R,6S)-2,6-dimethylmorpholin-4-yl]-2-fluorophenyl}-N-hydroxy-1-(1,3-thiazol-5-yl)methanimine Starting material: {5-({[tert-butyl(diphenyl)silyl]oxy}methyl)-3-chloro-4-[(2R,6S)-2,6-dimethylmorpholin-4-yl]-2-fluorophenyl}(1,3-thiazol-5-yl)methanone (Intermediate 86).
MS (ES) MH$^+$: 638 for $C_{33}H_{37}ClFN_3O_3SSi$
Intermediate 175

1-{5-({[tert-butyl(diphenyl)silyl]oxy}methyl)-3-chloro-4-[(2R,6S)-2,6-dimethylmorpholin-4-yl]-2-fluorophenyl}-N-hydroxy-1-(pyridin-4-yl)methanimine Starting material: {5-({[tert-butyl(diphenyl)silyl]oxy}methyl)-3-chloro-4-[(2R,6S)-2,6-dimethylmorpholin-4-yl]-2-fluorophenyl}(pyridin-4-yl)methanone (Intermediate 87).
MS (ES) MH$^+$: 632 for $C_{35}H_{39}ClFN_3O_3Si$
Intermediate 176

1-{5-({[tert-butyl(diphenyl)silyl]oxy}methyl-3-chloro-4-[(2R,6S)-2,6-dimethylmorpholin-4-yl]-2-fluorophenyl}-N-hydroxy-1-(pyridin-3-yl)methanimine Starting material: {5-({[tert-butyl(diphenyl)silyl]oxy}methyl)-3-chloro-4-[(2R,6S)-2,6-dimethylmorpholin-4-yl]-2-fluorophenyl}(pyridin-3-yl)methanone (Intermediate 88).
MS (ES) MH$^+$: 632 for $C_{35}H_{39}ClFN_3O_3Si$
Intermediate 177

1-{5-({[tert-butyl(diphenyl)silyl]oxy}methyl-3-chloro-4-[(2R,6S)-2,6-dimethylmorpholin-4-yl]-2-fluorophenyl}-N-hydroxy-1-(1,3-thiazol-2-yl)methanimine Starting material: {5-({[tert-butyl(diphenyl)silyl]oxy}methyl)-3-chloro-4-[(2R,6S)-2,6-dimethylmorpholin-4-yl]-2-fluorophenyl}(1,3-thiazol-2-yl)methanone (Intermediate 89).
MS (ES) MH$^+$: 638 for $C_{33}H_{37}ClFN_3O_3SSi$
Intermediate 178

1-{5-({[tert-butyl(diphenyl)silyl]oxy}methyl)-3-chloro-4-[(2R,6S)-2,6-dimethylmorpholin-4-yl]-2-fluorophenyl}-N-hydroxy-1-(1-methyl-1H-imidazol-2-yl)methanimine Starting material: {5-({[tert-butyl(diphenyl)silyl]oxy}methyl)-3-chloro-4-[(2R,6S)-2,6-dimethylmorpholin-4-yl]-2-fluorophenyl}(1-methyl-1H-imidazol-2-yl)methanone (Intermediate 90).
MS (ES) MH$^+$: 635 for $C_{34}H_{40}ClFN_4O_3Si$
Intermediate 179

1-[5-({[tert-butyl(diphenyl)silyl]oxy}methyl-3-chloro-4-[(2R,6S)-2,6-dimethylmorpholin-4-yl]-2-fluorophenyl}-N-hydroxy-2-methoxyethanimine Starting material: 1-{5-({[tert-butyl(diphenyl)silyl]oxy}methyl)-3-chloro-4-[(2R,6S)-2,6-dimethylmorpholin-4-yl]-2-fluorophenyl}-2-methoxyethanone (Intermediate 113).
MS (ES) MH$^+$: 599 for $C_{32}H_{40}ClFN_2O_4Si$.

Intermediate 180

{2-[{5-({[tert-butyl(diphenyl)silyl]oxy}methyl)-4-[(2R,6S)-2,6-dimethylmorpholin-4-yl]-2,3-difluorophenyl}(hydroxyimino)methyl]-1,3-thiazol-4-yl}(morpholin-4-yl)methanone Starting material: {2-[{5-({[tert-butyl(diphenyl)silyl]oxy}methyl)-4-[(2R,6S)-2,6-dimethylmorpholin-4-yl]-2,3-difluorophenyl}(hydroxy)methyl]-1,3-thiazol-4-yl}(morpholin-4-yl)methanone (Intermediate 92).
MS (ES) MH$^+$: MS (ES) MH$^+$: 620 for $C_{34}H_{39}F_2N_3O_4Si$;
Intermediate 181

{5-[{5-({[tert-butyl(diphenyl)silyl]oxy}methyl)-4-[(2R,6S)-2,6-dimethylmorpholin-4-yl]-2,3-difluorophenyl}(hydroxyimino)methyl]-1,3-thiazol-4-yl}(morpholin-4-yl)methanone Starting material: {5-({[tert-butyl(diphenyl)silyl]oxy}methyl)-4-[(2R,6S)-2,6-dimethylmorpholin-4-yl]-2,3-difluorophenyl}{4-[hydroxy(morpholin-4-yl)methyl]-1,3-thiazol-5-yl}methanone (Intermediate 93)
MS (ES) MH$^+$: 735. for $C_{38}H_{44}F_2N_4O_5SSi$
Intermediate 182

2-[{5-({[tert-butyl(diphenyl)silyl]oxy}methyl)-4-[(2R,6S)-2,6-dimethylmorpholin-4-yl]-2,3-difluorophenyl}(hydroxyimino)methyl]-N,N-dimethyl-1,3-thiazole-4-carboxamide Starting material: 2-({5-({[tert-butyl(diphenyl)silyl]oxy}methyl)-4-[(2R,6S)-2,6-dimethylmorpholin-4-yl]-2,3-difluorophenyl}carbonyl)-N,N-dimethyl-1,3-thiazole-4-carboxamide (Intermediate 94).
MS (ES) MH$^+$: 693 for $C_{36}H_{42}F_2N_4O_4SSi$
Intermediate 183

2-[{5-({[tert-butyl(diphenyl)silyl]oxy}methyl)-4-[(2R,6S)-2,6-dimethylmorpholin-4-yl]-2,3-difluorophenyl}(hydroxyimino)methyl]-N,N-dimethyl-1,3-thiazole-5-carboxamide Starting material: 2-({5-({[tert-butyl(diphenyl)silyl]oxy}methyl)-4-[(2R,6S)-2,6-dimethylmorpholin-4-yl]-2,3-difluorophenyl}carbonyl)-N,N-dimethyl-1,3-thiazole-5-carboxamide (Intermediate 95)
MS (ES) MH$^+$: 693 for $C_{36}H_{42}F_2N_4O_4SSi$
Intermediate 184

5-[{5-({[tert-butyl(diphenyl)silyl]oxy}methyl)-4-[(2R,6S)-2,6-dimethylmorpholin-4-yl]-2,3-difluorophenyl}(hydroxyimino)methyl]-1,3-thiazole-4-carbonitrile Starting material: 5-({5-({[tert-butyl(diphenyl)silyl]oxy}methyl)-4-[(2R,6S)-2,6-dimethylmorpholin-4-yl]-2,3-difluorophenyl}carbonyl)-1,3-thiazole-4-carbonitrile (Intermediate 96)
MS (ES) MH$^+$: 647 for $C_{34}H_{36}F_2N_4O_3SSi$.

Intermediate 185

1-{5-({[tert-butyl(diphenyl)silyl]oxy}methyl)-4-[(2R,6S)-2,6-dimethylmorpholin-4-yl]-2,3-difluorophenyl}-N-hydroxy-1-(2-methyl-1,3-oxazol-4-yl)methanimine Starting material: {5-({[tert-butyl(diphenyl)silyl]oxy}methyl)-4-[(2R,6S)-2,6-dimethylmorpholin-4-yl]-2,3-difluorophenyl}(2-methyl-1,3-oxazol-4-yl)methanone (Intermediate 149).

MS (ES) MH$^+$: MS (ES) MH$^+$: 620 for $C_{34}H_{39}F_2N_3O_4Si$;

Intermediate 186

1-{5-({[tert-butyl(diphenyl)silyl]oxy}methyl)-4-[(2R,6S)-2,6-dimethylmorpholin-4-yl]-2,3-difluorophenyl}-N-hydroxy-1-(5-methyl-1,2-oxazol-3-yl)methanimine Starting material: {5-({[tert-butyl(diphenyl)silyl]oxy}methyl)-4-[(2R,6S)-2,6-dimethylmorpholin-4-yl]-2,3-difluorophenyl}(5-methyl-1,2-oxazol-3-yl)methanone (Intermediate 150)

MS (ES) MH$^+$: 620 for $C_{34}H_{39}F_2N_3O_4Si$;

Intermediate 187

1-{5-({[tert-butyl(diphenyl)silyl]oxy}methyl)-4-[(2R,6S)-2,6-dimethylmorpholin-4-yl]-2,3-difluorophenyl}-1-(3,5-dimethyl-1,2-oxazol-4-yl)-N-hydroxymethanimine Starting material: {5-({[tert-butyl(diphenyl)silyl]oxy}methyl)-4-[(2R,6S)-2,6-dimethylmorpholin-4-yl]-2,3-difluorophenyl}(3,5-dimethyl-1,2-oxazol-4-yl)methanone (Intermediate 151)

MS (ES) MH$^+$: 634 for $C_{35}H_{41}F_2N_3O_4Si$;

Intermediate 188

1-{5-({[tert-butyl(diphenyl)silyl]oxy}methyl)-4-[(2R,6S)-2,6-dimethylmorpholin-4-yl]-2,3-difluorophenyl}-N-hydroxy-1-(1-methyl-1H-imidazol-2-yl)methanimine Starting material: {5-({[tert-butyl(diphenyl)silyl]oxy}methyl)-4-[(2R,6S)-2,6-dimethylmorpholin-4-yl]-2,3-difluorophenyl}(1-methyl-1H-imidazol-2-yl)methanone (Intermediate 152)

MS (ES) MH$^+$: 618 for $C_{34}H_{40}F_2N_4O_3Si$;

Intermediate 189

1-{5-({[tert-butyl(diphenyl)silyl]oxy}methyl)-4-[(2R,6S)-2,6-dimethylmorpholin-4-yl]-2,3-difluorophenyl}-N-hydroxy-1-(1-methyl-1H-imidazol-4-yl)methanimine Starting material: {5-({[tert-butyl(diphenyl)silyl]oxy}methyl)-4-[(2R,6S)-2,6-dimethylmorpholin-4-yl]-2,3-difluorophenyl}(1-methyl-1H-imidazol-4-yl)methanone (Intermediate 153)

MS (ES) MH$^+$: 618 for $C_{34}H_{40}F_2N_4O_3Si$;

Intermediate 190

1-{5-({[tert-butyl(diphenyl)silyl]oxy}methyl)-4-[(2R,6S)-2,6-dimethylmorpholin-4-yl]-2,3-difluorophenyl}-N-hydroxy-1-(1-methyl-1H-imidazol-5-yl)methanimine Starting material: {5-({[tert-butyl(diphenyl)silyl]oxy}methyl)-4-[(2R,6S)-2,6-dimethylmorpholin-4-yl]-2,3-difluorophenyl}(1-methyl-1H-imidazol-5-yl)methanone (Intermediate 97)

MS (ES) MH$^+$: 618 for $C_{34}H_{40}F_2N_4O_3Si$;

Intermediate 191

1-{5-({[tert-butyl(diphenyl)silyl]oxy}methyl)-4-[(2R,6S)-2,6-dimethylmorpholin-4-yl]-2,3-difluorophenyl}-N-hydroxy-1-(4-methyl-1,3-thiazol-5-yl)methanimine Starting material: {5-({[tert-butyl(diphenyl)silyl]oxy}methyl)-4-[(2R,6S)-2,6-dimethylmorpholin-4-yl]-2,3-difluorophenyl}(4-methyl-1,3-thiazol-5-yl)methanone (Intermediate 98)

MS (ES) MH$^+$: 636 for $C_{34}H_{39}F_2N_3O_3SSi$

Intermediate 192

1-{5-({[tert-butyl(diphenyl)silyl]oxy}methyl)-4-[(2R,6S)-2,6-dimethylmorpholin-4-yl]-2,3-difluorophenyl}-N-hydroxy-1-(4-methyl-1,2,3-thiadiazol-5-yl)methanimine Starting material: {5-({[tert-butyl(diphenyl)silyl]oxy}methyl)-4-[(2R,6S)-2,6-dimethylmorpholin-4-yl]-2,3-difluorophenyl}(4-methyl-1,2,3-thiadiazol-5-yl)methanone (Intermediate 154)

MS (ES) MH$^+$: 637 for $C_{33}H_{38}F_2N_4O_3SSi$;

Intermediate 193

1-{5-({[tert-butyl(diphenyl)silyl]oxy}methyl)-4-[(2R,6S)-2,6-dimethylmorpholin-4-yl]-2,3-difluorophenyl}-N-hydroxy-1-(pyridazin-3-yl)methanimine Starting material: {5-({[tert-butyl(diphenyl)silyl]oxy}methyl)-4-[(2R,6S)-2,6-dimethylmorpholin-4-yl]-2,3-difluorophenyl}(pyridazin-3-yl)methanone (Intermediate 155)

MS (ES) MH$^+$: 617.2 for $C_{34}H_{38}F_2N_4O_3Si$;

Intermediate 194

1-{5-({[tert-butyl(diphenyl)silyl]oxy}methyl)-4-[(2R,6S)-2,6-dimethylmorpholin-4-yl]-2,3-difluorophenyl}-N-hydroxy-1-(pyrimidin-4-yl)methanimine Starting material: {5-({[tert-butyl(diphenyl)silyl]oxy}methyl)-4-[(2R,6S)-2,6-dimethylmorpholin-4-yl]-2,3-difluorophenyl}(pyrimidin-4-yl)methanone (Intermediate 156)

MS (ES) MH$^+$: 617 for $C_{34}H_{38}F_2N_4O_3Si$;

Intermediate 195

2-[(2R,6S)-2,6-dimethylmorpholin-4-yl]-4-fluoro-5-hydroxyimino)(1,3-thiazol-2-methyl-3-methylbenzoic acid Starting material: 2-[(2R,6S)-2,6-dimethylmorpholin-4-yl]-4-fluoro-3-methyl-5-(1,3-thiazol-2-ylcarbonyl)benzoic acid (Intermediate 60).

MS (ES) MH$^+$: 393 for $C_{18}H_{20}FN_3O_4S$

Intermediate 196

2-[(2R,6S)-2,6-dimethylmorpholin-4-yl]-4-fluoro-5-[(hydroxyimino)(pyrazin-2-yl)methyl]-3-methylbenzoic acid Starting material: 2-[(2R,6S)-2,6-dimethylmorpholin-4-yl]-4-fluoro-3-methyl-5-(pyrazin-2-ylcarbonyl)benzoic acid (Intermediate 61).

MS (ES) MH$^+$: 388 for $C_{19}H_{21}FN_4O_4$

Intermediate 197 ethyl 2-(6-((tert-butyldiphenylsilyloxy)methyl)-4-chloro-5-[(2R,6S)-2,6-dimethylmorpholino)-3-fluoropyridin-2-yl)-2-(hydroxyimino)acetate Ethyl 2-(6-((tert-butyldiphenylsilyloxy)methyl)-4-chloro-5-((2R,6S)-2,6-dimethylmorpholino)-3-fluoropyridin-2-yl)-2-oxoacetate (Intermediate 121, 13.4 g, 21.85 mmol) was slurried in isopropanol (150 ml), and pyridine (124 ml, 1529.70 mmol) was added to give a yellow solution. Hydroxylamine hydrochloride (1.670 g, 24.04 mmol) was added, and the suspension was stirred at room temperature for approximately 16 hours. The resulting solution was concentrated to an oil. The residue was purified by chromatography on $SiO_2$ using 5-40% EtOAc/hexane. A total of 11.93 g (87%) of the title product as a mixture of oxime isomers was obtained as a yellow oil.

MS (ES) MH$^+$: 628 for $C_{32}H_{39}CFN_3O_5Si$

Intermediate 198

{5-[(3-chloropyrazin-2-yl)(hydroxyimino)methyl]-2-[(2R,6S)-2,6-dimethylmorpholin-4-yl]-3,4-difluorophenyl}methanol A mixture of (5-((tert-butyldiphenylsilyloxy)methyl)-4-((2R,6S)-2,6-dimethylmorpholino)-2,3-difluorophenyl)(3-chloropyrazin-2-yl)methanone (Intermediate 135, ~150 mg) and $NH_2OH \cdot HCl$ in 10 ml of MeOH was stirred for 72 hours at room temperature. The reaction mixture was diluted with EtOAc, washed with water and brine. After drying over anhydrous sodium sulfate, filtering and concentrating, the resultant residue was purified by silica gel column chromatography (Hexanes/EtOAc) to give product. (106 mg).

MS (ES) MH$^+$: 413 for $C_{18}H_{19}ClF_2N_4O_3$

Intermediates 199 and 200 were prepared from the indicated starting material and hydroxylamine hydrochloride using a method similar to the one described for the synthesis of Intermediate 198:

Intermediate 199

1-{5-({[tert-butyl(diphenyl)silyl]oxy}methyl)-4-[(2R,6S)-2,6-dimethylmorpholin-4-yl]-2,3-difluorophenyl}-1-(6-chloropyrazin-2-yl)-N-hydroxymethanimine Starting material: (5-((tert-butyldiphenylsilyloxy)methyl)-4-((2R,6S)-2,6-dimethylmorpholino)-2,3-difluorophenyl)(6-chloropyrazin-2-yl)methanone (Intermediate 136)

MS (ES) MH$^+$: 652 for $C_{34}H_{37}ClF_2N_4O_3Si$

Intermediate 200

1-{5-({[tert-butyl(diphenyl)silyl]oxy}methyl)-4-[(2R,6S)-2,6-dimethylmorpholin-4-yl]-2,3-difluorophenyl}-1-(5-chloropyrazin-2-yl)-N-hydroxymethanimine Starting material: (5-((tert-butyldiphenylsilyloxy)methyl)-4-((2R,6S)-2,6-dimethylmorpholino)-2,3-difluorophenyl)(5-chloropyrazin-2-yl)methanone (Intermediate 137)

MS (ES) MH$^+$: 652 for $C_{34}H_{37}ClF_2N_4O_3Si$

Intermediate 201

(7-chloro-6-((2R,6S)-2,6-dimethylmorpholino)-3-(pyridin-2-yl)isoxazolo[4,5-b]pyridin-5-yl)methanol A solution of (6-((tert-butyldiphenylsilyloxy)methyl)-4-chloro-5-((2R,6S)-2,6-dimethylmorpholino)-3-fluoropyridin-2-yl)(pyridin-2-yl)methanone (Intermediate 140, 1.3 g, 2.10 mmol) and hydroxylamine hydrochloride (0.146 g, 2.10 mmol) in pyridine (10 mL)/methanol (20 mL) mixture was heated for 2 hours at 40° C. then cooled and concentrated under vacuum to give a crude yellow oil weighing 1.3 g.

To the above oil was added DMF (30 mL) and cesium carbonate (0.801 g, 2.46 mmol). The slurry was heated at 40° C. for 4 hours then cooled. The reaction mixture was quenched with water and extracted with ethyl acetate. The organics were washed with brine then dried organics over sodium sulfate, filtered, and filtrate evacuated under vacuum to give a crude yellow oil. The crude oil was purified on silica using 20-40% acetone in n-hexane to give 0.39 g (51%) of the title compound as oil.

MS (ES) MH$^+$: 375 for $C_{18}H_{19}ClN_4O_3$ $^1$H NMR (300 MHz, DMSO-d$_6$) δ: 1.0-1.1 (m, 6H), 3.0 (d, 4H), 3.7-3.9 (m, 2H), 4.8 (td, 2H), 5.2 (br.s., 1H), 7.6 (td, 1H), 8.1 (td, 1H), 8.6 (d, 1H), 8.8 (dd, 1H).

Intermediates 202 and 203 were prepared from the indicated starting materials using a method similar to the one described for the synthesis of Intermediate 201:

Intermediate 202

(7-chloro-6-((2R,6S)-2,6-dimethylmorpholino)-3-(pyridin-4-yl)isoxazolo[4,5-b]pyridin-5-yl)methanol Starting material: (6-((tert-butyldiphenylsilyloxy)methyl)-4-chloro-5-((2R,6S)-2,6-dimethylmorpholino)-3-fluoropyridin-2-yl)(pyridin-4-yl)methanone (Intermediate 141).

MS (ES) MH$^+$: 375 for $C_{18}H_{19}ClN_4O_3$ $^1$H NMR (300 MHz, DMSO-d$_6$) δ: 1.0-1.1 (m, 6H), 3.0 (d, 4H), 3.7-3.8 (m, 2H), 4.8 (td, 2H), 5.3 (br.s., 1H), 8.4 (dd, 2H), 8.8 (dd, 2H).

Intermediate 203

(7-chloro-6-((2R,6S)-2,6-dimethylmorpholino)-3-(pyridin-3-yl)isoxazolo[4,5-b]pyridin-5-yl)methanol Starting material: (6-((tert-butyldiphenylsilyloxy)methyl)-4-chloro-5-((2R,6S)-2,6-dimethylmorpholino)-3-fluoropyridin-2-yl)(pyridin-3-yl)methanone (Intermediate 142).

MS (ES) MH$^+$: 375 for $C_{18}H_{19}ClN_4O_3$ $^1$H NMR (300 MHz, DMSO-d$_6$) δ: 1.0-1.1 (m, 6H), 3.0 (d, 4H), 3.7-3.9 (m, 2H), 4.8 (td, 2H), 5.2 (br.s., 1H), 7.9 (dd, 1H), 8.7-8.8 (m, 2H).

Intermediate 204 ethyl 5-((tert-butyldiphenylsilyloxy)methyl)-6-((2R,6S)-2,6-dimethylmorpholino)-7-fluorobenzo[d]isoxazole-3-carboxylate Sodium hydride (0.159 g, 3.97 mmol) was suspended in 20 ml of DMF and cooled in an ice bath. Ethyl 2-(5-((tert-butyldiphenylsilyloxy)methyl)-4-((2R,6S)-2,6-dimethylmorpholino)-2,3-difluorophenyl)-2-(hydroxyimino)acetate (Intermediate 165, 1.94 g, 3.18 mmol) was dissolved in 20 ml of DMF and added to the reaction flask. The ice bath was removed and the reaction stirred at room temperature for 2 hours. The reaction was quenched with sat NH$_4$Cl (5 ml), diluted with water and extracted three times with ethyl acetate. The organic layers were combined, washed with water and brine 5×, dried over MgSO$_4$ and concentrated. The residue was purified by silica gel column chromatography using a gradient of hexanes to ethyl acetate to give the title compound (1.250 g, 66.6%).
MS (ES) MH$^+$: 591 for C$_{33}$H$_{39}$FN$_2$O$_5$Si
$^1$H NMR (300 MHz, DMSO-d$_6$) δ ppm 1.0 (d, 6H), 1.1 (s, 9H), 1.4 (t, 3H), 2.6-2.8 (m, 4H), 4.5 (q, 2H), 4.9 (s, 2H), 7.4-7.5 (m, 6H), 7.6 (d, 4H), 8.1 (s, 1H).

Intermediates 205 and 206 were prepared from the indicated starting materials using a method similar to the one described for the synthesis of Intermediate 204:

Intermediate 205

5-((tert-butyldiphenylsilyloxy)methyl)-6-((2R,6S)-2,6-dimethylmorpholino)-7-fluoro-N-methoxy-N-methylbenzo[d]isoxazole-3-carboxamide Starting material: 2-(5-((tert-butyldiphenylsilyloxy)methyl)-4-((2R,6S)-2,6-dimethylmorpholino)-2,3-difluorophenyl)-2-(hydroxyimino)-N-methoxy-N-methylacetamide (Intermediate 170).
MS (ES) MH$^+$: 606 for C$_{33}$H$_{40}$FN$_3$O$_5$Si
$^1$H NMR (300 MHz, CHLOROFORM-d) δ ppm 1.0-1.2 (m, 15H), 2.7 (d, 2H), 2.8-3.0 (m, 2H), 3.4-3.6 (m, 5H), 3.8 (s, 3H), 4.8 (s, 2H), 7.3-7.5 (m, 6H), 7.7 (d, 4H), 7.9 (br. s., 1H).

Intermediate 206

Ethyl 5-(dimethoxymethyl)-6,7-difluorobenzo[d]isoxazole-3-carboxylate

Starting material: ethyl 2-(5-(dimethoxymethyl)-2,3,4-trifluorophenyl)-2-(hydroxyimino)acetate (Intermediate 167).
MS (ES) M$^+$ (—CH$_3$O): 270
$^1$H NMR (300 MHz, CHLOROFORM-d) δ ppm 1.5 (t, 3H), 3.4 (s, 6H), 4.6 (q, 2H), 5.7 (s, 1H), 8.1 (d, 1H).

Intermediate 207

5-((tert-butyldiphenylsilyloxy)methyl)-6-((2R,6S)-2,6-dimethylmorpholino)-7-fluorobenzo[d]isoxazole-3-carbohydrazide Ethyl 5-((tert-butyldiphenylsilyloxy)methyl)-6-((2R,6S)-2,6-dimethylmorpholino)-7-fluorobenzo[d]isoxazole-3-carboxylate (Intermediate 204, 0.5 g, 0.85 mmol) in 4.5 ml ethanol was treated with anhydrous hydrazine (0.490 ml, 15.60 mmol) at room temperature for 2 hour. Reaction was diluted with dichloromethane and brine. Organic layer washed with water, dried over sodium sulfate, and concentrated. The residue purified on silica-gel column (elution 40% etoac in hexanes) to give 5-((tert-butyldiphenylsilyloxy)methyl)-6-((2R,6S)-2,6-dimethylmorpholino)-7-fluorobenzo[d]isoxazole-3-carbohydrazide (0.354 g, 72.5%).
MS (ES) MH$^+$: 577 for C$_{31}$H$_{37}$FN$_4$O$_4$Si Intermediate 208

5-(5-((tert-butyldiphenylsilyloxy)methyl)-6-((2R,6S)-2,6-dimethylmorpholino)-7-fluorobenzo[d]isoxazol-3-yl)-1,3,4-oxadiazol-2(3H)-one 5-((tert-Butyldiphenylsilyloxy)methyl)-6-((2R,6S)-2,6-dimethylmorpholino)-7-fluorobenzo[d]isoxazole-3-carbohydrazide (Intermediate 207, 490 mg, 0.85 mmol) and di(1H-imidazol-1-yl)methanone (207 mg, 1.27 mmol) were dissolved in 8 ml of THF and was treated with DIEA (297 μl, 1.70 mmol) at room temperature for 16 hours. Reaction diluted with ethyl acetate and quenched with aq. Ammonium chloride solution. Organic layer was separated and washed with water, dried over sodium sulfate and concentrated to give 5-(5-((tert-butyldiphenylsilyloxy)methyl)-6-((2R,6S)-2,6-dimethylmorpholino)-7-fluorobenzo[d]isoxazol-3-yl)-1,3,4-oxadiazol-2(3H)-one (495 mg, 97%)
MS (ES) MH$^+$: 603 for C$_{32}$H$_{35}$FN$_4$O$_5$Si
$^1$H NMR (300 MHz, DMSO-d$_6$) δ: 1.1 (d, 6H) 1.1 (s, 9H) 2.5-3.0 (m, 4H) 3.3-3.6 (m, 2H) 4.8 (s, 2H) 7.3-7.7 (m, 10H) 8.1 (s, 1H) 9.0 (s, 1H)

Intermediate 209

5-(6-((2R,6S)-2,6-dimethylmorpholino)-7-fluoro-5-(hydroxymethyl)benzo[d]isoxazol-3-yl)-1,3,4-oxadiazol-2(3H)-one 5-(5-((tert-butyldiphenylsilyloxy)methyl)-6-((2R,6S)-2,6-dimethylmorpholino)-7-fluorobenzo[d]isoxazol-3-yl)-1,3,4-oxadiazol-2(3H)-one (Intermediate 208, 490 mg, 0.81 mmol) in 10 ml of THF was treated with TBAF (1M in THF; 1626 μl, 1.63 mmol) at room temperature for 16 hours. Reaction quenched with aq ammonium chloride solution and Extracted with ethyl acetate. Crude product purified on column (50-80% etoac in hexanaes) to give 5-(6-((2R,6S)-2,6-dimethylmorpholino)-7-fluoro-5-(hydroxymethyl)benzo[d]isoxazol-3-yl)-1,3,4-oxadiazol-2(3H)-one (235 mg, 79%)
MS (ES) MH$^+$: 365 for C$_{16}$H$_{17}$FN$_4$O$_5$
$^1$H NMR (300 MHz, DMSO-d$_6$) δ: 1.1 (d, 6H) 2.9-3.3 (m, 4H) 3.7-3.9 (m, 2H) 8.2 (s, 1H) 10.3 (s, 1H) 13.4 (s, 1H)

Intermediate 210 ethyl 5-((tert-butyldiphenylsilyloxy)methyl)-6-((2R,6R)-2,6-dimethylmorpholino)-7-fluorobenzo[d]isoxazole-3-carboxylate Sodium hydride (0.723 g, 18.07 mmol) was suspended in 60 ml of DMF and cooled in an ice bath. Ethyl 2-(5-((tert-butyldiphenylsilyloxy)methyl)-4-((2R,6R)-2,6-dimethylmorpholino)-2,3-difluorophenyl)-2-(hydroxyimino)acetate (Intermediate 166, 8.827 g, 14.45 mmol) was dissolved in 30 ml of DMF and added to the reaction flask. The ice bath was removed and the reaction stirred at room temperature for 2 hours. LCMS analysis indicated that the reaction was incomplete, so an additional 100 mg of NaH was added and the reaction stirred for 30 minutes. LCMS analysis indicated that the reaction was incomplete, so an additional 100 mg of NaH was added and the reaction stirred for 30 minutes. The reaction was cooled in an ice bath and quenched drop wise with 5 ml of saturated NH$_4$Cl. The reaction was diluted with water and extracted three times with ethyl acetate. The organic layers were combined, washed 5× with brine, dried over MgSO$_4$ and concentrated to give an oil. The oil was purified by silica gel column chromatography using a gradient of hexanes to ethyl acetate. Fractions were combined and concentrated to give the title compound (5.156 g, 8.73 mmol, 60.4%).
MS (ES) MH$^+$: 591 for C$_{33}$H$_{39}$FN$_2$O$_5$Si
$^1$H NMR (300 MHz, DMSO-d$_6$) δ ppm 0.94 (d, 6H) 1.10 (s, 9H) 1.38 (t, 3H) 2.59-2.73 (m, 2H) 2.91-3.10 (m, 2H) 3.77 (br. s., 2H) 4.49 (q, J=7.03 Hz, 2H) 4.84-5.03 (m, 2H) 7.36-7.54 (m, 6H) 7.63 (d, 4H) 8.14 (s, 1H)

Also isolated during the purification was ethyl (2Z)-(5-((tert-butyldiphenylsilyloxy)methyl)-4-((2R,6R)-2,6-dimethylmorpholino)-2,3-difluorophenyl)-2-(hydroxyimino)acetate as a single oxime isomer (1.22 g, 14%).
MS (ES) MH$^+$: 611 for $C_{33}H_{40}F_2N_2O_5Si$
Intermediate 211

Ethyl 5-((tert-butyldiphenylsilyloxy)methyl)-7-chloro-6-((2R,6S)-2,6-dimethylmorpholino)isoxazolo[4,5-b]pyridine-3-carboxylate Sodium hydride, 60% dispersion in mineral oil (0.063 g, 1.56 mmol) was added to a flask and DMF, 5 ml, was added to give a white slurry. The mixture was cooled in an ice bath. Ethyl 2-(6-((tert-butyldiphenylsilyloxy)methyl)-4-chloro-5-((2R,6S)-2,6-dimethylmorpholino)-3-fluoropyridin-2-yl)-2-(hydroxyimino)acetate (Intermediate 197, 0.786 g, 1.25 mmol) in 5 ml DMF was added to the sodium hydride suspension. There was some gas evolution, and the mixture became an orange solution. The reaction was worked up after 1 hour. Then saturated NH4Cl solution was added; the mixture was extracted with EtOAc, and washed with water (3×). The combined organic phase was dried over MgSO$_4$ and concentrated. The residue was purified by chromatography on SiO$_2$ using 0-40% EtOAc/hexanes to recover 544 mg (71%) of the title compound as a yellow foam.
MS (ES) MH$^+$: 608 for $C_{32}H_{38}ClN_3O_5Si$
$^1$H NMR (300 MHz, CD$_2$Cl$_2$) δ: 1.0-1.2 (overlapping multiplet, 15H), 1.5 (t, 3H), 2.8-2.9 (m, 2H), 3.1 (t, 2H), 3.7 (br s, 2H), 4.6 (q, 2H), 5.0 (s, 2H), 7.3-7.8 (m, 10H).
Intermediate 212

5-((tert-butyldiphenylsilyloxy)methyl)-6-((2R,6S)-2,6-dimethylmorpholino)-N-ethyl-7-fluorobenzo[d]isoxazole-3-carboxamide Under a nitrogen atmosphere, trimethylaluminum (2M in toluene, 1206 μl, 2.41 mmol) was slowly added (gas evolution) to an ice cooled solution of ethylamine (2M in THF) (1206 μl, 2.41 mmol) in 7 ml of toluene. The reaction was allowed to warm to room temperature and stirred for 2 hours. Ethyl 5-((tert-butyldiphenylsilyloxy)methyl)-6-((2R,6S)-2,6-dimethylmorpholino)-7-fluorobenzo[d]isoxazole-3-carboxylate, (Intermediate 204, 190 mg, 0.32 mmol) was added as a solution in toluene (3 ml). The reaction was stirred at 45° C. for 18 hours. The reaction was quenched drop wise (vigorous gas evolution) with 2 ml of 1N HCl. The crude reaction was filtered to remove solids, diluted with water and extracted twice with ethyl acetate. The organic layers were combined, washed twice with brine, dried over MgSO$_4$ and concentrated to give an oil. The oil was purified by silica gel column chromatography using a gradient of hexanes to ethyl acetate. Fractions were combined and concentrated to give the title compound. (170 mg, 0.288 mmol, 90%).
MS (ES) MH$^+$: 590 for $C_{33}H_{40}FN_3O_4Si$
$^1$H NMR (300 MHz, CHLOROFORM-d) δ ppm 1.0-1.2 (m, 15H), 1.3 (t, 3H), 2.7 (d, 2H), 2.88 (t, 2H), 3.45 (m, 2H), 3.5-3.7 (m, 2H), 4.8 (s, 2H), 6.9 (m, 1H), 7.35-7.5 (m, 6H), 7.0 (d, 4H), 8.3 (s, 1H).
Intermediates 213 to 240 were prepared from the indicated starting materials using a method similar to the one described for the synthesis of Intermediate 212:
Intermediate 213

5-((tert-butyldiphenylsilyloxy)methyl)-6-((2R,6S)-2,6-dimethylmorpholino)-N-ethyl-7-fluoro-N-methylbenzo[d]isoxazole-3-carboxamide Starting materials: Ethyl 5-((tert-butyldiphenylsilyloxy)methyl)-6-((2R,6S)-2,6-dimethylmorpholino)-7-fluorobenzo[d]isoxazole-3-carboxylate (Intermediate 204) and N-methylethanamine hydrochloride
MS (ES) MH$^+$: 604 for $C_{34}H_{42}FN_3O_4Si$
$^1$H NMR (300 MHz, CHLOROFORM-d) δ ppm 1.0-1.2 (m, 15H), 1.2-1.4 (m, 3H), 2.7 (d, 2H), 2.9 (t, 2H), 3.2 (d, 3H), 3.4-3.6 (m, 2H), 3.6-3.8 (m, 2H), 4.8 (s, 2H), 7.3-7.5 (m, 6H), 7.7 (d, 4H), 7.9 (br. s., 1H).
Intermediate 214

5-((tert-butyldiphenylsilyloxy)methyl)-6-((2R,6S)-2,6-dimethylmorpholino)-7-fluoro-N-methylbenzo[d]isoxazole-3-carboxamide Starting materials: Ethyl 5-((tert-butyldiphenylsilyloxy)methyl)-6-((2R,6S)-2,6-dimethylmorpholino)-7-fluorobenzo[d]isoxazole-3-carboxylate (Intermediate 204) and methylamine (2M in THF)
MS (ES) MH$^+$: 576 for $C_{32}H_{38}FN_3O_4Si$
$^1$H NMR (300 MHz, CHLOROFORM-d) δ ppm 1.0-1.2 (m, 15H), 2.7 (d, 2H), 2.8-3.0 (m, 2H), 3.12 (d, 3H), 3.5 (m, 2H), 4.8 (s, 2H), 6.9-7.1 (m, 1H), 7.3-7.5 (m, 6H), 7.7 (d, 4H), 8.3 (s, 1H).
Intermediate 215

4-(5-((tert-butyldiphenylsilyloxy)methyl)-6-((2R,6S)-2,6-dimethylmorpholino)-7-fluorobenzo[d]isoxazole-3-carbonyl)-1-methylpiperazin-2-one Starting materials: Ethyl 5-((tert-butyldiphenylsilyloxy)methyl)-6-((2R,6S)-2,6-dimethylmorpholino)-7-fluorobenzo[d]isoxazole-3-carboxylate (Intermediate 204) and 1-methylpiperazin-2-one hydrochloride.
MS (ES) MH$^+$: 659 for $C_{36}H_{43}FN_4O_5Si$
Intermediate 216

(5-((tert-butyldiphenylsilyloxy)methyl)-6-((2R,6S)-2,6-dimethylmorpholino)-7-fluorobenzo[d]isoxazol-3-yl)(3,3-difluoroazetidin-1-yl)methanone Starting materials: ethyl 5-((tert-butyldiphenylsilyloxy)methyl)-6-((2R,6S)-2,6-dimethylmorpholino)-7-fluorobenzo[d]isoxazole-3-carboxylate (Intermediate 204) and 3,3-difluoroazetidine hydrochloride.
MS (ES) MH$^+$: 638 for $C_{34}H_{38}F_3N_3O_4Si$
$^1$H NMR (300 MHz, CHLOROFORM-d) d ppm 1.0-1.2 (m, 15H), 2.67 (d, 2H), 2.8-3.0 (m, 2H), 3.4 (d, 2H), 4.6 (t, 2H), 5.0 (t, 2H), 7.3-7.5 (m, 6H), 7.7 (d, 4H), 8.2 (s, 1H).
Intermediate 217

5-((tert-butyldiphenylsilyloxy)methyl)-6-((2R,6S)-2,6-dimethylmorpholino)-7-fluorobenzo[d]isoxazole-3-carboxamide Starting materials: Ethyl 5-((tert-butyldiphenylsilyloxy)methyl)-6-((2R,6S)-2,6-dimethylmorpholino)-7-fluorobenzo[d]isoxazole-3-carboxylate (Intermediate 204) and ammonium chloride.
MS (ES) MH$^+$: 562 for $C_{31}H_{36}FN_3O_4Si$
Intermediate 218

5-((tert-butyldiphenylsilyloxy)methyl)-6-((2R,6S)-2,6-dimethylmorpholino)-7-fluoro-N-(2-methoxyethyl)benzo[d]isoxazole-3-carboxamide Starting materials: Ethyl 5-((tert-butyldiphenylsilyloxy)methyl)-6-((2R,6S)-2,6-dimethylmorpholino)-7-fluorobenzo[d]isoxazole-3-carboxylate (Intermediate 204) and 2-methoxyethanamine MS (ES) MH+: 620 for $C_{34}H_{42}FN_3O_5Si$
$^1$H NMR (300 MHz, CHLOROFORM-d) δ ppm 1.0-1.2 (m, 15H), 2.7 (d, 2H), 2.8-2.95 (m, 2H), 3.4-3.5 (m, 5H), 3.6 (t, 2H), 3.7 (t, 2H), 4.8 (s, 2H), 7.35-7.5 (m, 6H), 7.7-7.8 (m, 4H), 8.26 (s, 1H).

Intermediate 219

N-tert-butyl-5-((tert-butyldiphenylsilyloxy)methyl)-6-((2R,6S)-2,6-dimethylmorpholino)-7-fluorobenzo[d]isoxazole-3-carboxamide Starting materials: Ethyl 5-((tert-butyldiphenylsilyloxy)methyl)-6-((2R,6S)-2,6-dimethylmorpholino)-7-fluorobenzo[d]isoxazole-3-carboxylate (Intermediate 204) and 2-methylpropan-2-amine MS (ES) MH+: 618 for $C_{35}H_{44}FN_3O_4Si$
$^1$H NMR (300 MHz, CHLOROFORM-d) d ppm 1.0-1.2 (m, 15H), 1.55 (s, 9H), 2.7 (d, 2H), 2.8-3.0 (m, 2H), 3.4-3.55 (m, 2H), 4.8 (s, 2H), 6.75 (br. s., 1H), 7.3-7. (m, 6H), 7.7 (d, 4H), 8.2 (s, 1H).

Intermediate 220

5-({[tert-butyl(diphenyl)silyl]oxy}methyl)-6-((2R,6S)-2,6-dimethylmorpholin-4-yl]-3-[(1,1-dioxidothiomorpholin-4-yl)carbonyl]-7-fluoro-1,2-benzisoxazole Starting materials: Ethyl 5-((tert-butyldiphenylsilyloxy)methyl)-6-((2R,6S)-2,6-dimethylmorpholino)-7-fluorobenzo[d]isoxazole-3-carboxylate (Intermediate 204) and thiomorpholine 1,1-dioxide MS (ES) MH+: 680 for $C_{35}H_{42}FN_3O_6SSi$ Intermediate 221

5-((tert-butyldiphenylsilyloxy)methyl)-6-((2R,6S)-2,6-dimethylmorpholino)-7-fluoro-N-(tetrahydro-2H-pyran-4-yl)benzo[d]isoxazole-3-carboxamide Starting materials: Ethyl 5-((tert-butyldiphenylsilyloxy)methyl)-6-((2R,6S)-2,6-dimethylmorpholino)-7-fluorobenzo[d]isoxazole-3-carboxylate (Intermediate 204) and tetrahydro-2H-pyran-4-amine MS (ES) MH+: 646 for $C_{36}H_{44}FN_3O_5Si$
$^1$H NMR (300 MHz, CHLOROFORM-d) δ ppm 1.0-1.2 (m, 1H), 1.6-1.8 (m, 2H), 2.0-2.1 (m, 2H), 2.7 (d, 2H), 2.8-3.0 (m, 2H), 3.4-3.5 (m, 2H), 3.6 (t, 2H), 4.1 (d, 2H), 4.2-4.4 (m, 1H), 4.8 (s, 2H), 6.85 (d, 1H), 7.3-7.5 (m, 6H), 7.7 (d, 4H), 8.3 (s, 1H).

Intermediate 222

5-((tert-butyldiphenylsilyloxy)methyl)-6-((2R,6S)-2,6-dimethylmorpholino)-7-fluoro-N-isopropylbenzo[d]isoxazole-3-carboxamide Starting materials: Ethyl 5-((tert-butyldiphenylsilyloxy)methyl)-6-((2R,6S)-2,6-dimethylmorpholino)-7-fluorobenzo[d]isoxazole-3-carboxylate (Intermediate 204) and propan-2-amine MS (ES) MH+: 604.2 for $C_{34}H_{42}FN_3O_4Si$
$^1$H NMR (300 MHz, CHLOROFORM-d) δ ppm 1.0-1.2 (m, 15H), 1.35 (d, 6H), 2.7 (d, 2H), 2.8-3.0 (m, 2H), 3.45 (m, 2H), 4.3-4.5 (m, 1H), 4.8 (s, 2H), 6.8 (d, 1H), 7.3-7.5 (m, 6H), 7.7 (d, 4H), 8.3 (s, 1H).

Intermediate 223

5-((tert-butyldiphenylsilyloxy)methyl)-N-cyclopropyl-6-((2R,6S)-2,6-dimethylmorpholino)-7-fluorobenzo[d]isoxazole-3-carboxamide Starting materials: Ethyl 5-((tert-butyldiphenylsilyloxy)methyl)-6-((2R,6S)-2,6-dimethylmorpholino)-7-fluorobenzo[d]isoxazole-3-carboxylate (Intermediate 204) and cyclopropanamine MS (ES) MH+: 602 for $C_{34}H_{40}FN_3O_4Si$
$^1$H NMR (300 MHz, CHLOROFORM-d) δ ppm 0.7-0.8 (m, 2H), 0.9-1.0 (m, 2H), 1.1 (d, 6H), 1.1 (s, 9H), 2.7 (d, 2H), 2.8-2.95 (m, 2H), 2.95-3.1 (m, 1H), 3.4-3.55 (m, 2H), 4.8 (s, 2H), 7.0 (br. s., 1H), 7.3-7.5 (m, 6H), 7.7 (d, 4H), 8.3 (s, 1H).

Intermediate 224

(5-((tert-butyldiphenylsilyloxy)methyl)-6-((2R,6S)-2,6-dimethylmorpholino)-7-fluorobenzo[d]isoxazol-3-yl)(4-methoxypiperidin-1-yl)methanone Starting materials: Ethyl 5-((tert-butyldiphenylsilyloxy)methyl)-6-((2R,6S)-2,6-dimethylmorpholino)-7-fluorobenzo[d]isoxazole-3-carboxylate (Intermediate 204) and 4-methoxypiperidine MS (ES) MH+: 660 for $C_{37}H_{46}FN_3O_5Si$
$^1$H NMR (300 MHz, CHLOROFORM-d) d ppm 1.02-1.17 (m, 15H) 1.64-2.05 (m, 4H) 2.69 (d, J=11.30 Hz, 2H) 2.81-3.00 (m, 2H) 3.41 (s, 3H) 3.43-3.66 (m, 4H) 3.72-3.86 (m, 1H) 3.86-4.08 (m, 2H) 4.82 (s, 2H) 7.33-7.52 (m, 6H) 7.69 (d, J=6.78 Hz, 4H) 7.83 (s, 1H)

Intermediate 225

5-((tert-butyldiphenylsilyloxy)methyl)-N-(cyclopropylmethyl)-6-((2R,6S)-2,6-dimethylmorpholino)-7-fluorobenzo[d]isoxazole-3-carboxamide Starting materials: Ethyl 5-((tert-butyldiphenylsilyloxy)methyl)-6-((2R,6S)-2,6-dimethylmorpholino)-7-fluorobenzo[d]isoxazole-3-carboxylate (Intermediate 204) and cyclopropylmethanamine MS (ES) MH+: 616 for $C_{35}H_{42}FN_3O_4Si$ Intermediate 226

5-({[tert-butyl(diphenyl)silyl]oxy}methyl)-6-[(2R,6S)-2,6-dimethylmorpholin-4-yl]-7-fluoro-3-(1,2-oxazinan-2-ylcarbonyl)-1,2-benzisoxazole Starting materials: Ethyl 5-((tert-butyldiphenylsilyloxy)methyl)-6-((2R,6S)-2,6-dimethylmorpholino)-7-fluorobenzo[d]isoxazole-3-carboxylate (Intermediate 204) and [1,2]oxazinane MS (ES) MH+: 632 for $C_{35}H_{42}FN_3O_5Si$
$^1$H NMR (300 MHz, CHLOROFORM-d) δ ppm 1.06-1.19 (m, 15H) 1.92 (br. s., 4H) 2.69 (d, J=10.55 Hz, 2H) 2.90 (t, J=9.42 Hz, 2H) 3.41-3.56 (m, 2H) 4.06 (br. s., 4H) 4.83 (s, 2H) 7.34-7.51 (m, 6H) 7.69 (d, J=6.78 Hz, 4H) 7.84 (br. s., 1H)

Intermediate 227

5-((tert-butyldiphenylsilyloxy)methyl)-6-((2R,6S)-2,6-dimethylmorpholino)-7-fluoro-N-(thiophen-2-ylmethyl)benzo[d]isoxazole-3-carboxamide Starting materials: Ethyl 5-((tert-butyldiphenylsilyloxy)methyl)-6-((2R,6S)-2,6-dimethylmorpholino)-7-fluorobenzo[d]isoxazole-3-carboxylate (Intermediate 204) and thiophen-2-ylmethanamine MS (ES) MH⁺: 658 for $C_{36}H_{40}FN_3O_4SSi$
¹H NMR (300 MHz, CHLOROFORM-d) δ ppm 1.11 (d, J=6.03 Hz, 6H) 1.16 (s, 9H) 2.71 (d, J=10.55 Hz, 2H) 2.83-3.00 (m, 2H) 3.39-3.56 (m, 2H) 4.85 (s, 2H) 4.92 (d, J=5.27 Hz, 2H) 6.98-7.06 (m, 1H) 7.08-7.16 (m, 1H) 7.25-7.36 (m, 2H) 7.36-7.52 (m, 6H) 7.73 (d, J=6.03 Hz, 4H) 8.29 (s, 1H)
Intermediate 228

(3,3-difluoroazetidin-1-yl)(5-(dimethoxymethyl)-6,7-difluorobenzo[d]isoxazol-3-yl)methanone Starting materials: ethyl 5-(dimethoxymethyl)-6,7-difluorobenzo[d]isoxazole-3-carboxylate (Intermediate 206) and 3,3-difluoroazetidine hydrochloride.
¹H NMR (300 MHz, CHLOROFORM-d) δ ppm 3.4 (s, 6H) 4.6 (t, 2H) 5.0 (t, 2H) 5.7 (s, 1H) 8.2 (d, 1H).
Intermediate 229

5-(dimethoxymethyl)-6,7-difluoro-N-isopropylbenzo[d]isoxazole-3-carboxamide

Starting materials: ethyl 5-(dimethoxymethyl)-6,7-difluorobenzo[d]isoxazole-3-carboxylate (Intermediate 206) and isopropyl amine.
¹H NMR (300 MHz, DMSO-d₆) δ ppm 1.2 (d, 6H), 3.3 (s, 6H), 4.2 (dq, 1H), 5.7 (s, 1H), 8.0 (d, 1H), 9.1 (d, 1H)
Intermediate 230

5-((tert-Butyldiphenylsilyloxy)methyl)-7-chloro-6-((2R,6S)-2,6-dimethylmorpholino)-N-methylisoxazolo[4,5-b]pyridine-3-carboxamide Starting materials: ethyl 5-((tert-butyldiphenylsilyloxy)methyl)-7-chloro-6-((2R,6S)-2,6-dimethylmorpholino)isoxazolo[4,5-b]pyridine-3-carboxylate (Intermediate 211) and methylamine, 2M in THF.
MS (ES) MH⁺: 593 for $C_{31}H_{37}ClN_4O_4Si$
¹H NMR (300 MHz, CD₂Cl₂) δ: 1.0-1.2 (overlapping multiplet, 15H), 2.7-2.9 (m, 2H), 3.0 (d, 3H), 3.1-3.2 (m, 2H), 3.6-3.7 (m, 2H), 5.0 (s, 2H). 7.3-7.5 (m, 6H), 7.6-7.7 (m, 4H), 8.3 (br s, 1H).
Intermediate 231

5-((tert-Butyldiphenylsilyloxy)methyl)-7-chloro-6-((2R,6S)-2,6-dimethylmorpholino)-N-ethylisoxazolo[4,5-b]pyridine-3-carboxamide Starting material: ethyl 5-((tert-butyldiphenylsilyloxy)methyl)-7-chloro-6-((2R,6S)-2,6-dimethylmorpholino)isoxazolo[4,5-b]pyridine-3-carboxylate (Intermediate 211) and ethylamine.
MS (ES) MH⁺: 607 for $C_{32}H_{39}ClN_4O_4Si$
¹H NMR (300 MHz, CD₂Cl₂) δ: 1.0-1.1 (overlapping multiplet, 15H), 1.2 (t, 3H), 2.7-2.9 (m, 2H), 3.1-3.2 (m, 2H), 3.4-3.5 (m, 2H), 3.6-3.7 (m, 2H), 5.0 (s, 2H), 7.3-7.5 (m, 6H), 7.6-7.7 (m, 4H), 8.4 (br s, 1H).
Intermediate 232

5-((tert-butyldiphenylsilyloxy)methyl)-7-chloro-6-((2R,6S)-2,6-dimethylmorpholino)-N-isopropylisoxazolo[4,5-b]pyridine-3-carboxamide Starting material: ethyl 5-((tert-butyldiphenylsilyloxy)methyl)-7-chloro-6-((2R,6S)-2,6-dimethylmorpholino)isoxazolo[4,5-b]pyridine-3-carboxylate (Intermediate 211) and isopropylamine.
MS (ES) MH⁺: 621 for $C_{33}H_{41}ClN_4O_4Si$
¹H NMR (300 MHz, CD₂Cl₂) δ: 1.0-1.1 (overlapping multiplet, 15H), 1.2 (d, 6H), 2.7-2.8 (m, 2H), 3.1-3.2 (m, 2H), 3.5-3.7 (m, 2H), 4.3 (m, 1H), 5.0 (s, 2H), 7.3-7.5 (m, 6H), 7.6-7.7 (m, 4H), 8.15 (br s, 1H).
Intermediate 233

N-tert-Butyl-5-((tert-butyldiphenylsilyloxy)methyl)-7-chloro-6-((2R,6S)-2,6-dimethylmorpholino)isoxazolo[4,5-b]pyridine-3-carboxamide Starting material: ethyl 5-((tert-butyldiphenylsilyloxy)methyl)-7-chloro-6-((2R,6S)-2,6-dimethylmorpholino)isoxazolo[4,5-b]pyridine-3-carboxylate (Intermediate 211) and t-butylamine.
MS (ES) MH⁺: 635 for $C_{34}H_{43}ClN_4O_4Si$
¹H NMR (300 MHz, CD₂Cl₂) δ: 1.0 (s, 9H), 1.1 (d, 6H), 1.4 (s, 9H), 2.7-2.8 (m, 2H), 3.1-3.2 (m, 2H), 3.5-3.7 (m, 2H), 5.0 (s, 2H), 7.3-7.5 (m, 6H), 7.6-7.9 (m, 4H), 8.1 (br s, 1H).
Intermediate 234

5-((tert-Butyldiphenylsilyloxy)methyl)-7-chloro-6-((2R,6S)-2,6-dimethylmorpholino)-N-neopentylisoxazolo[4,5-b]pyridine-3-carboxamide Starting material: ethyl 5-((tert-butyldiphenylsilyloxy)methyl)-7-chloro-6-((2R,6S)-2,6-dimethylmorpholino)isoxazolo[4,5-b]pyridine-3-carboxylate (Intermediate 211) and 2,2-dimethylpropan-1-amine.
MS (ES) MH⁺: 649 for $C_{35}H_{45}ClN_4O_4Si$
Intermediate 235

(5-((tert-Butyldiphenylsilyloxy)methyl)-7-chloro-6-((2R,6S)-2,6-dimethylmorpholino)isoxazolo[4,5-b]pyridin-3-yl)(3,3-difluoroazetidin-1-yl)methanone Starting material: ethyl 5-((tert-butyldiphenylsilyloxy)methyl)-7-chloro-6-((2R,6S)-2,6-dimethylmorpholino)isoxazolo[4,5-b]pyridine-3-carboxylate (Intermediate 211) and 3,3-difluoroazetidine-HCl.
MS (ES) MH⁺: 655 for $C_{33}H_{37}ClF_2N_4O_4Si$
¹H NMR (300 MHz, CD₂Cl₂) δ: 1.0 (s, 9H), 1.1 (d, 6H), 2.8-2.9 (m, 2H), 3.2 (t, 2H), 3.6-3.7 (m, 2H), 4.6 (t, 2H), 4.8 (t, 2H), 5.0 (s, 2H), 7.3-7.5 (m, 6H), 7.7-7.8 (m, 4H).
Intermediate 236

N-Benzyl-5-((tert-butyldiphenylsilyloxy)methyl)-7-chloro-6-((2R,6S)-2,6-dimethylmorpholino)isoxazolo[4,5-b]pyridine-3-carboxamide Starting material: ethyl 5-((tert-butyldiphenylsilyloxy)methyl)-7-chloro-6-((2R,6S)-2,6-dimethylmorpholino)isoxazolo[4,5-b]pyridine-3-carboxylate (Intermediate 211) and benzylamine.
MS (ES) MH⁺: 669 for $C_{37}H_{41}ClN_4O_4Si$
¹H NMR (300 MHz, CD₂Cl₂) δ: 1.0 (s, 9H), 1.1 (d, 6H), 2.7-2.8 (m, 2H), 3.1-3.2 (m, 2H), 3.5-3.7 (m, 2H), 4.6 (d, 2H), 5.0 (s, 2H), 7.2-7.5 (m, 11H), 7.6-7.7 (m, 4H), 8.7 (br s, 1H).
Intermediate 237

5-tert-Butyldiphenylsilyloxy)methyl-7-chloro-N-(4-cyanobenzyl-6-((2R,6S)-2,6-dimethylmorpholino)isoxazolo[4,5-b]pyridine-3-carboxamide Starting material: ethyl 5-((tert-butyldiphenylsilyloxy)methyl)-7-chloro-6-((2R,6S)-2,6-dimethylmorpholino)isoxazolo[4,5-b]pyridine-3-carboxylate (Intermediate 211) and 4-(aminomethyl)benzonitrile.

MS (ES) MH$^+$: 694 for $C_{38}H_{40}ClN_5O_4Si$
$^1$H NMR (300 MHz, CD$_2$Cl$_2$) δ: 1.0 (s, 9H), 1.1 (d, 6H), 2.7-2.8 (m, 2H), 3.1-3.2 (m, 2H), 3.5-3.7 (m, 2H), 4.7 (d, 2H), 5.0 (br s, 2H), 7.2-7.4 (m, 8H), 7.5-7.6 (m, 6H), 8. 9 (br s).

Intermediate 238

5-tert-Butyldiphenylsilyloxy)methyl-7-chloro-N-(3-cyanobenzyl-6-((2R,6S)-2,6-dimethylmorpholino)isoxazolo[4,5-b]pyridine-3-carboxamide Starting materials: ethyl 5-((tert-butyldiphenylsilyloxy)methyl)-7-chloro-6-((2R,6S)-2,6-dimethylmorpholino)isoxazolo[4,5-b]pyridine-3-carboxylate (Intermediate 211) and 3-(aminomethyl)benzonitrile-HCl.

MS (ES) MH$^+$: 694 for $C_{38}H_{40}ClN_5O_4Si$
$^1$H NMR (300 MHz, CD$_2$Cl$_2$) δ: 1.0 (s, 9H), 1.1 (d, 6H), 2.7-2.8 (m, 2H), 3.1-3.2 (m, 2H), 3.5-3.7 (m, 2H), 4.6 (d, 2H), 5.0 (br s, 2H), 7.2-7.7 (m, 14H), 8.9 (br s).

Intermediate 239

N-(2,2-difluoroethyl)-5-(dimethoxymethyl)-6,7-difluorobenzo[d]isoxazole-3-carboxamide Starting Material: ethyl 5-(dimethoxymethyl)-6,7-difluorobenzo[d]isoxazole-3-carboxylate (Intermediate 206)

MS (ES) M$^+$ (—CH$_3$O): 305
$^1$H NMR (300 MHz, DMSO-d$_6$) δ ppm 3.3 (s, 6H), 3.6-3.9 (m, 2H), 5.7 (s, 1H), 6.0-6.5 (m, 1H), 8.0 (d, 1H), 9.6 (t, 1H)

Intermediate 240

5-(dimethoxymethyl)-6,7-difluoro-N-methylbenzo[d]isoxazole-3-carboxamide

Starting Material: ethyl 5-(dimethoxymethyl)-6,7-difluorobenzo[d]isoxazole-3-carboxylate (Intermediate 206)

MS (ES) M$^+$ (—CH$_3$O): 255
$^1$H NMR (300 MHz, DMSO-d$_6$) δ ppm 2.9 (d, 3H) 3.3 (s, 6H) 5.7 (s, 1H) 8.0 (d, 1H) 9.1 (d, 1H)

Intermediate 241

3-(3,3-difluoroazetidine-1-carbonyl)-6,7-difluorobenzo[d]isoxazole-5-carbaldehyde (3,3-Difluoroazetidin-1-yl)(5-(dimethoxymethyl)-6,7-difluorobenzo[d]isoxazol-3-yl)methanone (Intermediate 228, 3.336 g, 9.58 mmol) was dissolved in a 4:1 THF:water mixture (62.5 ml) and heated at 75° C. with tosic acid monohydrate (0.911 g, 4.79 mmol) for three hours. The reaction was allowed to cool to room temperature, diluted with ethyl acetate, washed 3× with saturated NaHCO$_3$, dried over MgSO$_4$ and concentrated. The residue was purified by silica gel column chromatography using a gradient of hexanes to ethyl acetate. Fractions were combined and concentrated to give the title compound (2.66 g, 8.83 mmol).

MS (ES) MH$^+$ 303 for $C_{12}H_6F_4N_2O_3$
$^1$H NMR (300 MHz, CHLOROFORM-d) δ ppm 4.64 (t, 2H) 5.0 (t, 2H) 8.61 (d, 1H) 10.36 (s, 1H)

Intermediates 242 to 244 were prepared from the indicated starting materials using a method similar to the one described for the synthesis of Intermediate 241:

Intermediate 242

6,7-difluoro-5-formyl-N-isopropylbenzo[d]isoxazole-3-carboxamide

Starting material: 5-(dimethoxymethyl)-6,7-difluoro-N-isopropylbenzo[d]isoxazole-3-carboxamide (Intermediate 229).

MS (ES) MH$^+$ 269 for $C_{12}H_{10}F_2N_2O_3$
$^1$H NMR (300 MHz, DMSO-d$_6$) δ ppm 1.23 (d, 6H) 4.09-4.28 (m, 1H) 8.41 (d, 1H) 9.16 (d, 1H) 10.23 (s, 1H).

Intermediate 243

N-(2,2-difluoroethyl)-6,7-difluoro-5-formylbenzo[d]isoxazole-3-carboxamide

Starting Material: N-(2,2-difluoroethyl)-5-(dimethoxymethyl)-6,7-difluorobenzo[d]isoxazole-3-carboxamide (Intermediate 239).

MS (ES) MH$^-$: 289 for $C_{11}H_6F_4N_2O_3$
$^1$H NMR (300 MHz, DMSO-d$_6$) δ ppm 3.7-3.9 (m, 2H), 5.9-6.5 (m, 1H), 8.4 (d, 1H), 9.6-9.7 (m, 1H), 10.2 (s, 1H)

Intermediate 244

6,7-difluoro-5-formyl-N-methylbenzo[d]isoxazole-3-carboxamide

Starting Material: 5-(dimethoxymethyl)-6,7-difluoro-N-methylbenzo[d]isoxazole-3-carboxamide (Intermediate 240)

MS (ES) MH$^+$: 241 for $C_{10}H_6F_2N_2O_3$
$^1$H NMR (300 MHz, DMSO-d$_6$) δ ppm 2.9 (d, 3H), 8.4 (d, 1H), 9.2 (d, 1H), 10.2 (s, 1H)

Intermediate 245

3-(3,3-difluoroazetidine-1-carbonyl)-6-((2R,6R)-2,6-dimethylmorpholino)-7-fluorobenzo[d]isoxazole-5-carbaldehyde Diisopropylethylamine (1.432 ml, 8.20 mmol) and (2R, 6R)-2,6-dimethylmorpholine (1.027 ml, 8.20 mmol) were added to a solution of 3-(3,3-difluoroazetidine-1-carbonyl)-6,7-difluorobenzo[d]isoxazole-5-carbaldehyde (Intermediate 241, 1.906 g, 6.31 mmol) in acetonitrile (50 ml). The reaction was stirred at reflux for 20 hours. The reaction was cooled to room temp, diluted with water and brine and extracted twice with ethyl acetate. The organic layers were combined, dried over MgSO$_4$ and concentrated. The residue was purified by silica gel column chromatography using a gradient of DCM to ethyl acetate. Fractions were combined and concentrated to give the title compound.

MS (ES) MH$^+$ 398.1 for $C_{18}H_{18}F_3N_3O_4$
$^1$H NMR (300 MHz, CHLOROFORM-d) δ ppm 1.35 (d, 6H) 3.07 (dd, 5.65 Hz, 2H) 3.45 (d, 2H) 4.26 (m, 2H) 4.62 (t, 2H) 4.99 (t, 2H) 8.50 (s, 1H) 10.44 (s, 1H).

Intermediates 246 and 247 were prepared from the indicated starting materials using a method similar to the one described for the synthesis of Intermediate 245:

Intermediate 246

6-((2R,6R)-2,6-dimethylmorpholino)-7-fluoro-5-formyl-N-isopropylbenzo[d]isoxazole-3-carboxamide The title compound was prepared from 6,7-difluoro-5-formyl-N-isopropylbenzo[d]isoxazole-3-carboxamide (Intermediate 242) and (2R,6R)-2,6-dimethylmorpholine.

MS (ES) MH$^+$ 364 for $C_{18}H_{22}FN_3O_4$
$^1$H NMR (300 MHz, DMSO-d$_6$) δ ppm 1.14-1.29 (m, 12H) 3.02 (dd, J=10.93, 2H) 3.40 (d, 2H) 4.05-4.26 (m, 3H) 8.22 (s, 1H) 9.05 (d, 1H) 10.35 (s, 1H).

Intermediate 247

6-((2R,6R)-2,6-dimethylmorpholino)-7-fluoro-5-formyl-N-methylbenzo[d]isoxazole-3-carboxamide Starting Material: 6,7-difluoro-5-formyl-N-methylbenzo[d]isoxazole-3-carboxamide (Intermediate 244).

MS (ES) MH$^+$: 336 for $C_{16}H_{18}FN_3O_4$
$^1$H NMR (300 MHz, DMSO-d$_6$) δ ppm 1.2 (d, 6H), 2.9 (d, 3H), 2.9-3.1 (m, 2H), 3.4 (d, 2H), 4.1-4.2 (m, 2H), 8.2 (s, 1H), 9.1 (d, 1H), 10.4 (s, 1H).

Intermediate 247 was also be prepared according to the following procedure:

Intermediate 247 (Alternate Synthesis)

6-((2R,6R)-2,6-dimethylmorpholino)-7-fluoro-5-formyl-N-methylbenzo[d]isoxazole-3-carboxamide Starting material: 6-((2R,6R)-2,6-dimethylmorpholino)-7-fluoro-5-(hydroxymethyl)-N-methylbenzo[d]isoxazole-3-carboxamide (Intermediate 280)

MS (ES) MH$^+$: 336 for $C_{16}H_{18}FN_3O_4$
$^1$H NMR (300 MHz, CHLOROFORM-d) δ ppm 1.35 (d, J=6.78 Hz, 6H) 2.99-3.16 (m, 5H) 3.45 (d, J=12.06 Hz, 2H) 4.20-4.35 (m, 2H) 6.83-6.96 (m, 1H) 8.54 (s, 1H) 10.44 (s, 1H).

Intermediate 248

N-(2,2-difluoroethyl)-6-((2R,6R)-2,6-dimethylmorpholino)-7-fluoro-5-formylbenzo[d]isoxazole-3-carboxamide N-(2,2-Difluoroethyl)-6,7-difluoro-5-formylbenzo[d]isoxazole-3-carboxamide (Intermediate 243, 2.86 g, 9.86 mmol) was dissolved in butyronitrile (50 mL) and water (2.5 mL). Potassium carbonate (1.362 g, 9.86 mmol) and (2R,6R)-2,6-dimethylmorpholine (1.481 mL, 11.83 mmol) were added and the reaction was stirred at 90° C. for 4 hours. The crude reaction mixture was diluted with water, brine and ethyl acetate. The mixture was washed 2× with brine. The aqueous layer was back-extracted with ethyl acetate. The organic layers combined, dried over MgSO$_4$ and concentrated. The residue was dissolved in DCM and purified by silica gel column chromatography using a gradient of DCM to ethyl acetate. Fractions were combined and concentrated to give the title compound.

MS (ES) MH$^+$: 286 for $C_{17}H_{18}F_3N_3O_4$
$^1$H NMR (300 MHz, DMSO-d$_6$) δ ppm 1.2 (d, 6H), 3.0 (m, 2H), 3.4 (d, 2H), 3.8 (m, 2H), 4.1-4.2 (m, 2H), 6.0-6.4 (m, 1H), 8.2 (s, 1H), 9.5 (t, J=5.7 Hz, 1H), 10.3 (s, 1H).

Intermediate 249

6-((2R,6S)-2,6-dimethylmorpholino)-7-fluoro-5-(hydroxymethyl)-N-(pyridin-4-ylmethyl)benzo[d]isoxazole-3-carboxamide Trimethylaluminum (2M in Toluene, 2116 μl, 4.23 mmol) was slowly added (gas evolution) to a solution of pyridin-4-ylmethanamine (458 mg, 4.23 mmol) in toluene (10 ml) at room temperature and under a nitrogen atmosphere. The reaction was stirred for 2 hours at room temperature. Ethyl 5-((tert-butyldiphenylsilyloxy)methyl)-6-((2R,6S)-2,6-dimethylmorpholino)-7-fluorobenzo[d]isoxazole-3-carboxylate (Intermediate 204, 500 mg, 0.85 mmol) was added as a solution in 5 ml of toluene. The reaction was stirred at 45° C. for three days. The reaction was cooled to room temperature and then quenched drop wise with 3 ml of 1N HCl (vigorous gas evolution). The crude reaction was poured into a Biotage Isolute® HM-N tube (10 ml capacity) packed with a small amount of glass wool to prevent clogging. A Biotage sodium sulfate column (2.5 g) was attached to the bottom of the Isolute® tube. The reaction mixture was allowed to gravity elute through the tube and washed through with 2-3 column volumes of ethyl acetate. The eluent was concentrated. The residue was dissolved in THF (10 ml) and stirred at room temperature with acetic acid (0.097 ml, 1.70 mmol) and TBAF (1N in THF, 0.935 ml, 0.94 mmol) for 16 hours. The reactions were diluted with 1 ml of water and shaken vigorously. The sample was added to a Varian Chem Elute® CE 1003 tube with a Biotage sodium sulfate column (2.5 g) on the bottom of it. The sample was gravity eluted with 2-3 column volumes of ethyl acetate and concentrated. The residue purified by silica gel column chromatography. Fractions were combined and concentrated to give the title compound (241 mg, 0.552 mmol, 65%).

MS (ES) MH$^+$: 415 for $C_{21}H_{23}FN_4O_4$
$^1$H NMR (300 MHz, CHLOROFORM-d) δ ppm 1.26 (d, J=6.03 Hz, 6H) 2.91-3.17 (m, 4H) 3.72-3.95 (m, 2H) 4.70-4.91 (m, 4H) 7.46 (d, J=5.27 Hz, 2H) 7.51 (br. s., 1H) 7.97 (s, 1H) 8.55-8.77 (m, 2H)

Intermediates 250 to 261 were prepared from the indicated starting materials using a method similar to the one described for the synthesis of Intermediate 249:

Intermediate 250

N-(cyclohexylmethyl)-6-((2R,6S)-2,6-dimethylmorpholino)-7-fluoro-5-(hydroxymethyl)benzo[d]isoxazole-3-carboxamide Starting materials: ethyl 5-((tert-butyldiphenylsilyloxy)methyl)-6-((2R,6S)-2,6-dimethylmorpholino)-7-fluorobenzo[d]isoxazole-3-carboxylate (Intermediate 204) and cyclohexylmethanamine MS (ES) MH$^+$: 420.3 for $C_{22}H_{30}FN_3O_4$ Intermediate 251

(4,4-difluoropiperidin-1-yl)(6-((2R,6S)-2,6-dimethylmorpholino)-7-fluoro-5-(hydroxymethyl)benzo[d]isoxazol-3-yl)methanone Starting materials: ethyl 5-((tert-butyldiphenylsilyloxy)methyl)-6-((2R,6S)-2,6-dimethylmorpholino)-7-fluorobenzo[d]isoxazole-3-carboxylate (Intermediate 204) and 4,4-difluoropiperidine MS (ES) MH$^+$: 428 for $C_{20}H_{24}F_3N_3O_4$ Intermediate 252

(3,3-difluoropyrrolidin-1-yl)(6-((2R,6S)-2,6-dimethylmorpholino)-7-fluoro-5-(hydroxymethyl)benzo[d]isoxazol-3-yl)methanone Starting material: 3,3-difluoropyrrolidine
MS (ES) MH$^+$: 414 for $C_{19}H_{22}F_3N_3O_4$ Intermediate 253

6-((2R,6S)-2,6-dimethylmorpholino)-7-fluoro-5-(hydroxymethyl)-N-(1-methylazetidin-3-yl)benzo[d]isoxazole-3-carboxamide Starting materials: ethyl 5-((tert-butyldiphenylsilyloxy)methyl)-6-((2R,6S)-2,6-dimethylmorpholino)-7-fluorobenzo[d]isoxazole-3-carboxylate (Intermediate 204) and 1-methylazetidin-3-amine MS (ES) MH$^+$: 393 for $C_{19}H_{25}FN_4O_4$ Intermediate 254

N-(1-(6-((2R,6S)-2,6-dimethylmorpholino)-7-fluoro-5-(hydroxymethyl)benzo[d]isoxazole-3-carbonyl)azetidin-3-yl)acetamide Starting materials: ethyl 5-((tert-butyldiphenylsilyloxy)methyl)-6-((2R,6S)-2,6-dimethylmorpholino)-7-fluorobenzo[d]isoxazole-3-carboxylate (Intermediate 204) and N-(azetidin-3-yl)acetamide MS (ES) MH$^+$: 421 for $C_{20}H_{25}FN_4O_5$ Intermediate 255

6-((2R,6S)-2,6-dimethylmorpholino)-7-fluoro-5-(hydroxymethyl)-N-((1-methyl-1H-pyrazol-3-yl)methyl)benzo[d]isoxazole-3-carboxamide Starting materials: ethyl 5-((tert-butyldiphenylsilyloxy)methyl)-6-((2R,6S)-2,6-dimethylmorpholino)-7-fluorobenzo[d]isoxazole-3-carboxylate (Intermediate 204) and (1-methyl-1H-pyrazol-3-yl)methanamine
MS (ES) MH$^+$: 318 for $C_{20}H_{24}FN_5O_4$ Intermediate 256

6-((2R,6S)-2,6-dimethylmorpholino)-7-fluoro-5-(hydroxymethyl)-N-((1-methyl-1H-pyrazol-5-yl)methyl)benzo[d]isoxazole-3-carboxamide Starting materials: ethyl 5-((tert-butyldiphenylsilyloxy)methyl)-6-((2R,6S)-2,6-dimethylmorpholino)-7-fluorobenzo[d]isoxazole-3-carboxylate (Intermediate 204) and (1-methyl-1H-pyrazol-5-yl)methanamine
MS (ES) MH$^+$: 418. for $C_{20}H_{24}FN_5O_4$ Intermediate 257

N-(1,3-dimethoxy-2-(methoxymethyl)propan-2-yl)-6-((2R,6S)-2,6-dimethylmorpholino)-7-fluoro-5-(hydroxymethyl)benzo[d]isoxazole-3-carboxamide Starting materials: ethyl 5-((tert-butyldiphenylsilyloxy)methyl)-6-((2R,6S)-2,6-dimethylmorpholino)-7-fluorobenzo[d]isoxazole-3-carboxylate (Intermediate 204) and 1,3-dimethoxy-2-(methoxymethyl)propan-2-amine
MS (ES) MH$^+$: 470 for $C_{22}H_{32}FN_3O_7$ Intermediate 258

N-(2,2-difluoroethyl)-6-((2R,6S)-2,6-dimethylmorpholino)-7-fluoro-5-(hydroxymethyl)benzo[d]isoxazole-3-carboxamide Starting materials: ethyl 5-((tert-butyldiphenylsilyloxy)methyl)-6-((2R,6S)-2,6-dimethylmorpholino)-7-fluorobenzo[d]isoxazole-3-carboxylate (Intermediate 204) and 2,2-difluoroethanamine
MS (ES) MH$^+$: 388 for $C_{17}H_{20}F_3N_3O_4$ Intermediate 259

1-(6-((2R,6S)-2,6-dimethylmorpholino)-7-fluoro-5-(hydroxymethyl)benzo[d]isoxazole-3-carbonyl)azetidine-3-carbonitrile Starting materials: ethyl 5-((tert-butyldiphenylsilyloxy)methyl)-6-((2R,6S)-2,6-dimethylmorpholino)-7-fluorobenzo[d]isoxazole-3-carboxylate (Intermediate 204) and azetidine-3-carbonitrile
MS (ES) MH$^+$: 389 for $C_{19}H_{21}FN_4O_4$ Intermediate 260

5-((tert-butyldiphenylsilyloxy)methyl)-6-((2R,6R)-2,6-dimethylmorpholino)-7-fluoro-N-methylbenzo[d]isoxazole-3-carboxamide Starting materials: ethyl 5-((tert-butyldiphenylsilyloxy)methyl)-6-((2R,6R)-2,6-dimethylmorpholino)-7-fluorobenzo[d]isoxazole-3-carboxylate (Intermediate 210, 5.16 g, 8.73 mmol) and methylamine (2M in THF).
MS (ES) MH$^+$: 576 for $C_{32}H_{38}FN_3O_4Si$
$^1$H NMR (300 MHz, CHLOROFORM-d) δ ppm 1.06 (d, 6H) 1.17 (s, 9H) 2.64-2.80 (m, 2H) 3.04-3.15 (m, 5H) 3.82-3.96 (m, 2H) 4.80-4.98 (m, 2H) 6.93 (br. s., 1H) 7.33-7.50 (m, 6H) 7.66-7.76 (m, 4H) 8.35 (s, 1H)

Intermediate 261

5-((tert-butyldiphenylsilyloxy)methyl)-6-((2R,6R)-2,6-dimethylmorpholino)-7-fluorobenzo[d]isoxazole-3-carboxamide Starting materials: ethyl 5-((tert-butyldiphenylsilyloxy)methyl)-6-((2R,6R)-2,6-dimethylmorpholino)-7-fluorobenzo[d]isoxazole-3-carboxylate (Intermediate 210) and ammonia (0.5 M in dioxane).
MS (ES) MH$^+$: 362.2 for $C_{31}H_{36}FN_3O_4Si$ Intermediate 262 ethyl 6-((2R,6S)-2,6-dimethylmorpholino)-7-fluoro-5-(hydroxymethyl)benzo[d]isoxazole-3-carboxylate Ethyl 5-((tert-butyldiphenylsilyloxy)methyl)-6-((2R,6S)-2,6-dimethylmorpholino)-7-fluorobenzo[d]isoxazole-3-carboxylate (Intermediate 204, 693 mg, 1.17 mmol) was dissolved in THF (3 ml) along with acetic acid (0.134 ml, 2.35 mmol). TBAF (1N in THF, 1.290 ml, 1.29 mmol) was added and the reaction was stirred at room temperature for 30 minutes. The reaction was diluted with water and extracted 2× with ethyl acetate. The organic layers were combined, washed with brine, dried over MgSO$_4$ and concentrated. The residue was purified by silica gel column chromatography to give the title compound.
MS (ES) MH$^+$: 353 for $C_{17}H_{21}FN_2O_5$
$^1$H NMR (300 MHz, DMSO-d$_6$) δ ppm 1.1 (d, 6H) 1.4 (t, 3H) 2.8 (t, 2H) 3.0 (d, 2H) 3.6-3.8 (m, 2H) 4.5 (q, 2H) 4.7 (d, 2H) 5.45 (t, 1H) 7.95 (s, 1H)

Intermediates 263 to 281 were prepared from the indicated starting materials using a method similar to the one described for the syntheses of Intermediate 262:

Intermediate 263

6-((2R,6S)-2,6-dimethylmorpholino)-7-fluoro-5-(hydroxymethyl)-N-methoxy-N-methylbenzo[d]isoxazole-3-carboxamide Starting material: 5-((tert-butyldiphenylsilyloxy)methyl)-6-((2R,6S)-2,6-dimethylmorpholino)-7-fluoro-N-methoxy-N-methylbenzo[d]isoxazole-3-carboxamide (Intermediate 205)
MS (ES) MH$^+$: 368 for $C_{17}H_{22}FN_3O_5$
$^1$H NMR (300 MHz, CHLOROFORM-d) δ ppm 1.26 (d, J=6.78 Hz, 6H) 2.93-3.04 (m, 2H) 3.04-3.16 (m, 2H) 3.49 (br. s., 3H) 3.87 (br. s., 5H) 4.83 (s, 2H) 7.70 (br. s., 1H)

Intermediate 264

6-((2R,6S)-2,6-dimethylmorpholino)-N-ethyl-7-fluoro-5-(hydroxymethyl)benzo[d]isoxazole-3-carboxamide Starting material: 5-((tert-butyldiphenylsilyloxy)methyl)-6-((2R,6S)-2,6-dimethylmorpholino)-N-ethyl-7-fluorobenzo[d]isoxazole-3-carboxamide (Intermediate 212).
MS (ES) MH$^+$: 352 for $C_{17}H_{22}FN_3O_4$
$^1$H NMR (300 MHz, CHLOROFORM-d) δ ppm 1.15-1.37 (m, 9H) 2.91-3.17 (m, 4H) 3.48-3.65 (m, 2H) 3.75-3.94 (m, 2H) 4.82 (s, 2H) 6.92 (br. s., 1H) 7.95 (s, 1H)

Intermediate 265

6-((2R,6S)-2,6-dimethylmorpholino)-N-ethyl-7-fluoro-5-(hydroxymethyl)-N-methylbenzo[d]isoxazole-3-carboxamide Starting material: 5-((tert-butyldiphenylsilyloxy)methyl)-6-((2R,6S)-2,6-dimethylmorpholino)-N-ethyl-7-fluoro-N-methylbenzo[d]isoxazole-3-carboxamide (Intermediate 213).

MS (ES) MH$^+$: 366 for $C_{18}H_{24}FN_3O_4$ $^1$H NMR (300 MHz, CHLOROFORM-d) δ ppm 1.24 (d, J=6.40 Hz, 6H) 1.26-1.34 (m, 3H) 2.89-3.01 (m, 2H) 3.01-3.14 (m, 2H) 3.15-3.34 (m, 3H) 3.68 (q, J=7.16 Hz, 2H) 3.76-3.91 (m, 2H) 4.79 (s, 2H) 7.68 (d, J=7.16 Hz, 1H)

Intermediate 266

6-((2R,6S)-2,6-dimethylmorpholino)-7-fluoro-5-(hydroxymethyl)-N-methylbenzo[d]isoxazole-3-carboxamide Starting material: 5-((tert-butyldiphenylsilyloxy)methyl)-6-((2R,6S)-2,6-dimethylmorpholino)-7-fluoro-N-methylbenzo[d]isoxazole-3-carboxamide (Intermediate 214)

MS (ES) MH$^+$: 338 for $C_{16}H_{20}FN_3O_4$ $^1$H NMR (300 MHz, CHLOROFORM-d) δ ppm 1.23 (d, J=6.78 Hz, 6H) 2.93-3.13 (m, 7H) 3.76-3.93 (m, 2H) 4.81 (s, 2H) 6.99 (br. s., 1H) 7.94 (s, 1H)

Intermediate 267

4-(6-((2R,6S)-2,6-dimethylmorpholino)-7-fluoro-5-(hydroxymethyl)benzo[d]isoxazole-3-carbonyl)-1-methylpiperazin-2-one Starting material: 4-(5-((tert-butyldiphenylsilyloxy)methyl)-6-((2R,6S)-2,6-dimethylmorpholino)-7-fluorobenzo[d]isoxazole-3-carbonyl)-1-methylpiperazin-2-one (Intermediate 215)

MS (ES) MH$^+$: 421 for $C_{20}H_{25}FN_4O_5$

Intermediate 268

(3,3-difluoroazetidin-1-yl)(6-((2R,6S)-2,6-dimethylmorpholino)-7-fluoro-5-(hydroxymethyl)benzo[d]isoxazol-3-yl)methanone Starting material: (5-((tert-butyldiphenylsilyloxy)methyl)-6-((2R,6S)-2,6-dimethylmorpholino)-7-fluorobenzo[d]isoxazol-3-yl)(3,3-difluoroazetidin-1-yl)methanone (Intermediate 216).

MS (ES) MH$^+$: 400 for $C_{18}H_{20}F_3N_3O_4$ $^1$H NMR (300 MHz, CHLOROFORM-d) δ ppm 1.17 (d, J=6.03 Hz, 6H) 2.81-3.09 (m, 4H) 3.76 (br. s., 2H) 4.52 (t, J=12.06 Hz, 2H) 4.74 (s, 2H) 4.90 (t, J=11.68 Hz, 2H) 7.85 (s, 1H)

Intermediate 269

6-((2R,6S)-2,6-dimethylmorpholino)-7-fluoro-5-(hydroxymethyl)benzo[d]isoxazole-3-carboxamide Starting material: 5-((tert-butyldiphenylsilyloxy)methyl)-6-((2R,6S)-2,6-dimethylmorpholino)-7-fluorobenzo[d]isoxazole-3-carboxamide (Intermediate 217)

MS (ES) MH$^+$: 324 for $C_{15}H_{18}FN_3O_4$ $^1$H NMR (300 MHz, CHLOROFORM-d) δ ppm 1.25 (d, J=6.03 Hz, 6H) 2.93-3.19 (m, 4H) 3.78-3.94 (m, 2H) 4.84 (s, 2H) 5.72 (br. s., 1H) 6.83 (br. s., 1H) 7.96 (s, 1H)

Intermediate 270

6-((2R,6S)-2,6-dimethylmorpholino)-7-fluoro-5-(hydroxymethyl)-N-(2-methoxyethyl)benzo[d]isoxazole-3-carboxamide Starting material: 5-((tert-butyldiphenylsilyloxy)methyl)-6-((2R,6S)-2,6-dimethylmorpholino)-7-fluoro-N-(2-methoxyethyl)benzo[d]isoxazole-3-carboxamide (Intermediate 218)

MS (ES) MH$^+$: 382 for $C_{18}H_{24}FN_3O_5$ $^1$H NMR (300 MHz, CHLOROFORM-d) δ ppm 1.23 (d, J=6.03 Hz, 6H) 2.89-3.15 (m, 4H) 3.41 (s, 3H) 3.60 (t, J=4.90 Hz, 2H) 3.70 (q, J=5.27 Hz, 2H) 3.83 (m, 2H) 4.81 (s, 2H) 7.93 (s, 1H)

Intermediate 271

N-tert-butyl-6-((2R,6S)-2,6-dimethylmorpholino)-7-fluoro-5-(hydroxymethyl)benzo[d]isoxazole-3-carboxamide Starting material: N-tert-butyl-5-((tert-butyldiphenylsilyloxy)methyl)-6-((2R,6S)-2,6-dimethylmorpholino)-7-fluorobenzo[d]isoxazole-3-carboxamide (Intermediate 219)

MS (ES) MH$^+$: 380 for $C_{19}H_{26}FN_3O_4$ $^1$H NMR (300 MHz, CHLOROFORM-d) d ppm 1.23 (d, J=6.03 Hz, 6H) 1.51 (s, 9H) 2.90-3.15 (m, 4H) 3.83 (br. s., 2H) 4.80 (s, 2H) 6.78 (br. s., 1H) 7.95 (s, 1H)

Intermediate 272

{6-[(2R,6S)-2,6-dimethylmorpholin-4-yl]-[1,1-dioxidothiomorpholin-4-yl)carbonyl]-7-fluoro-1,2-benzisoxazol-5-yl}methanol Starting material: 5-({[tert-butyl(diphenyl)silyl]oxy}methyl)-6-[(2R,6S)-2,6-dimethylmorpholin-4-yl]-3-[(1,1-dioxidothiomorpholin-4-yl)carbonyl]-7-fluoro-1,2-benzisoxazole (Intermediate 220)

MS (ES) MH$^+$: 442.0 for $C_{19}H_{24}FN_3O_6S$ $^1$H NMR (300 MHz, CHLOROFORM-d) δ ppm 1.26 (d, J=6.03 Hz, 6H) 2.91-3.03 (m, 2H) 3.03-3.16 (m, 2H) 3.19-3.33 (m, 4H) 3.79-3.91 (m, 2H) 4.32-4.42 (m, 2H) 4.42-4.52 (m, 2H) 4.84 (s, 4H) 7.74 (s, 1H)

Intermediate 273

6-((2R,6S)-2,6-dimethylmorpholino)-7-fluoro-5-(hydroxymethyl)-N-(tetrahydro-2H-pyran-4-yl)benzo[d]isoxazole-3-carboxamide Starting material: 5-((tert-butyldiphenylsilyloxy)methyl)-6-((2R,6S)-2,6-dimethylmorpholino)-7-fluoro-N-(tetrahydro-2H-pyran-4-yl)benzo[d]isoxazole-3-carboxamide (Intermediate 221)

MS (ES) MH$^+$: 408 for $C_{20}H_{26}FN_3O_5$ $^1$H NMR (300 MHz, CHLOROFORM-d) δ ppm 1.26 (d, J=6.78 Hz, 6H) 1.57-1.77 (m, J=11.77, 11.77, 11.49, 4.14 Hz, 2H) 2.05 (d, J=10.55 Hz, 2H) 2.98-3.18 (m, 4H) 3.57 (t, J=11.68 Hz, 2H) 3.90 (br. s., 2H) 4.05 (d, J=10.55 Hz, 2H) 4.19-4.34 (m, 1H) 4.87 (s, 2H) 6.84 (d, J=7.54 Hz, 1H) 7.96 (s, 1H)

Intermediate 274

6-((2R,6S)-2,6-dimethylmorpholino)-7-fluoro-5-(hydroxymethyl)-N-isopropylbenzo[d]isoxazole-3-carboxamide Starting material: 5-((tert-butyldiphenylsilyloxy)methyl)-6-((2R,6S)-2,6-dimethylmorpholino)-7-fluoro-N-isopropylbenzo[d]isoxazole-3-carboxamide (Intermediate 222)

MS (ES) MH$^+$: 366 for $C_{18}H_{24}FN_3O_4$ $^1$H NMR (300 MHz, CHLOROFORM-d) δ ppm 1.26 (d, J=6.78 Hz, 6H) 1.29-1.38 (m, 6H) 2.93-3.17 (m, 4H) 3.86 (m 2H) 4.26-4.41 (m, 1H) 4.84 (s, 2H) 6.76 (d, J=6.78 Hz, 1H) 7.97 (s, 1H)

Intermediate 275

N-cyclopropyl-6-((2R,6S)-2,6-dimethylmorpholino)-7-fluoro-5-(hydroxymethyl)benzo[d]isoxazole-3-carboxamide Starting material: 5-((tert-butyldiphenylsilyloxy)methyl)-N-cyclopropyl-6-((2R,6S)-2,6-dimethylmorpholino)-7-fluorobenzo[d]isoxazole-3-carboxamide (Intermediate 223)

MS (ES) MH$^+$: 364 for $C_{18}H_{22}FN_3O_4$ $^1$H NMR (300 MHz, CHLOROFORM-d) δ ppm 0.64-0.79 (m, 2H) 0.85-1.02 (m, 2H) 1.25 (d, J=6.78 Hz, 6H) 2.88-3.18 (m, 5H) 3.85 (m, 2H) 4.84 (s, 2H) 7.02 (br. s., 1H) 7.97 (s, 1H)

Intermediate 276

(6-((2R,6S)-2,6-dimethylmorpholino)-7-fluoro-5-(hydroxymethyl)benzo[d]isoxazol-3-yl)(4-methoxypiperidin-1-yl)methanone Starting material: (5-((tert-butyldiphenylsilyloxy)methyl)-6-((2R,6S)-2,6-dimethylmorpholino)-7-fluorobenzo[d]isoxazol-3-yl)(4-methoxypiperidin-1-yl)methanone (Intermediate 224)

MS (ES) MH$^+$: 422 for $C_{21}H_{28}FN_3O_5$ $^1$H NMR (300 MHz, CHLOROFORM-d) δ ppm 1.23 (d, J=6.03 Hz, 6H) 1.62-2.04 (m, 4H) 2.84-2.97 (m, 2H) 3.04 (t, J=9.80 Hz, 2H) 3.49-3.88 (m, 6H) 3.88-4.06 (m, 2H) 4.75 (d, J=6.03 Hz, 2H) 7.62 (s, 1H)

Intermediate 277

N-(cyclopropylmethyl)-6-((2R,6S)-2,6-dimethylmorpholino)-7-fluoro-5-(hydroxymethyl)benzo[d]isoxazole-3-carboxamide Starting material: 5-((tert-butyldiphenylsilyloxy)methyl)-N-(cyclopropylmethyl)-6-((2R,6S)-2,6-dimethylmorpholino)-7-fluorobenzo[d]isoxazole-3-carboxamide (Intermediate 225)

MS (ES) MH$^+$: 378 for $C_{19}H_{24}FN_3O_4$ $^1$H NMR (300 MHz, CHLOROFORM-d) δ ppm 0.25 (d, J=5.27 Hz, 2H) 0.45-0.60 (m, 2H) 0.94-1.09 (m, 1H) 1.17 (d, J=6.03 Hz, 6H) 2.84-2.96 (m, 2H) 2.96-3.10 (m, 2H) 3.20-3.39 (m, 2H) 3.65-3.88 (m, 2H) 4.75 (s, 2H) 6.95 (br. s., 1H) 7.88 (s, 1H)

Intermediate 278

6-[(2R,6S)-2,6-dimethylmorpholin-4-yl]-7-fluoro-3-(1,2-oxazinan-2-ylcarbonyl)-1,2-benzisoxazol-5-yl}methanol Starting material: 5-({[tert-butyl(diphenyl)silyl]oxy}methyl)-6-[(2R,6S)-2,6-dimethylmorpholin-4-yl]-7-fluoro-3-(1,2-oxazinan-2-ylcarbonyl)-1,2-benzisoxazole (Intermediate 226)

MS (ES) MH$^+$: 394 for $C_{19}H_{24}FN_3O_5$ $^1$H NMR (300 MHz, CHLOROFORM-d) δppm 1.25 (d, J=6.03 Hz, 6H) 1.92 (br. s., 4H) 2.83-3.18 (m, 4H) 3.83 (br. s., 2H) 3.96-4.38 (m, 4H) 4.80 (s, 2H) 7.61 (br. s., 1H)

Intermediate 279

6-((2R,6S)-2,6-dimethylmorpholino)-7-fluoro-5-(hydroxymethyl)-N-(thiophen-2-ylmethyl)benzo[d]isoxazole-3-carboxamide Starting materials: 5-((tert-butyldiphenylsilyloxy)methyl)-6-((2R,6S)-2,6-dimethylmorpholino)-7-fluoro-N-(thiophen-2-ylmethyl)benzo[d]isoxazole-3-carboxamide (Intermediate 227)

MS (ES) MH$^+$: 420 for $C_{20}H_{22}FN_3O_4S$

Intermediate 280

6-((2R,6R)-2,6-dimethylmorpholino)-7-fluoro-5-(hydroxymethyl)-N-methylbenzo[d]isoxazole-3-carboxamide Starting material: 5-((tert-butyldiphenylsilyloxy)methyl)-6-((2R,6R)-2,6-dimethylmorpholino)-7-fluoro-N-methyl-benzo[d]isoxazole-3-carboxamide (Intermediate 260)

MS (ES) MH$^+$: 338 for $C_{16}H_{20}FN_3O_4$ $^1$H NMR (300 MHz, CHLOROFORM-d) δ ppm 1.29-1.48 (m, 6H) 2.90-3.03 (m, 2H) 3.09 (d, J=5.27 Hz, 3H) 3.31 (br. s., 2H) 4.18 (m, 2H) 4.78-4.94 (m, 2H) 6.92 (br. s., 1H) 8.01 (s, 1H)

Intermediate 281

6-((2R,6R)-2,6-dimethylmorpholino)-7-fluoro-5-(hydroxymethyl)benzo[d]isoxazole-3-carboxamide Starting material: 5-((tert-butyldiphenylsilyloxy)methyl)-6-((2R,6R)-2,6-dimethylmorpholino)-7-fluorobenzo[d]isoxazole-3-carboxamide (Intermediate 261)

MS (ES) MH$^+$: 324 for $C_{15}H_{18}FN_3O_4$ $^1$H NMR (300 MHz, DMSO-d$_6$) δ ppm 1.23 (d, J=6.03 Hz, 6H) 2.82 (m, 2H) 3.19 (d, J=11.30 Hz, 2H) 3.95-4.13 (m, 2H) 4.64-4.80 (m, 2H) 5.43 (t, J=5.27 Hz, 1H) 7.97 (s, 1H) 8.10 (s, 1H) 8.45 (s, 1H)

Intermediate 282

(3-(6-chloropyrazin-2-yl)-6-((2R,6S)-2,6-dimethylmorpholino)-7-fluorobenzo[d]isoxazol-5-yl)methanol 5-((tert-Butyldiphenylsilyloxy)methyl)-3-(6-chloropyrazin-2-yl)-6-((2R,6S)-2,6-dimethylmorpholino)-7-fluorobenzo[d]isoxazole (Intermediate 329, 320 mg, 0.51 mmol) was dissolved in ethanol (10 ml) and was treated with 15 ml of 10% aq HCl, the mixture was heated at 70° C. for 1 hour. The reaction was cooled and diluted with EtOAc before being quenched with aqueous sodium bicarbonate solution. The mixture was extracted with EtOAc, which was washed with brine, dried (MgSO$_4$) and concentrated.

MS (ES) MH$^+$: 393 for $C_{18}H_{18}ClFN_4O_3$

Intermediate 283

(6-((2R,6S)-2,6-dimethylmorpholino)-7-fluoro-3-(5-(methylthio)pyrazin-2-yl)benzo[d]isoxazol-5-yl)methanol 1-{5-({[tert-Butyl(diphenyl)silyl]oxy}methyl)-4-[(2R,6S)-2,6-dimethylmorpholin-4-yl]-2,3-difluorophenyl}-1-(5-chloropyrazin-2-yl)-N-hydroxymethanimine (Intermediate 200, 400 mg, 0.61 mmol) in DMF (5 mL) was treated with sodium thiomethoxide (45.3 mg, 0.61 mmol) at room temperature, the mixture was stirred at room temperature for 10 min. K$_2$CO$_3$ (5 eq) was added and the mixture was heated to 100° C. for 1 hour. The reaction mixture was diluted with ethylacetate (20 ml). Organic layer washed with water and brine, then dried over sodium sulfate, filtered, and the filtrate was concentrated, purified by silica gel column chromatography (Hexanses/EtOAc, gradiant) to give the desired product (97 mg, 39.0%).

MS (ES) MH$^+$: 405 for $C_{19}H_{21}FN_4O_3S$

Intermediate 284 was prepared from the indicated starting materials using a method similar to the one described for the syntheses of Intermediate 283:

Intermediate 284

(6-((2R,6R)-2,6-dimethylmorpholino)-7-fluoro-3-(2-(methylthio)pyrimidin-4-yl)benzo[d]isoxazol-5-yl) methanol Starting material: (5-((tert-butyldiphenylsilyloxy)methyl)-4-((2R,6R)-2,6-dimethylmorpholino)-2,3-difluorophenyl)(2-(methylthio)pyrimidin-4-yl)methanone (Intermediate 106)

MS (ES) MH$^+$: 405 (M+H) for $C_{19}H_{21}FN_4O_3S$

Intermediate 285

6-((2R,6S)-2,6-dimethylmorpholino)-7-fluoro-5-(hydroxymethyl)benzo[d]isoxazol-3-yl)(morpholino) methanone 2-(5-((tert-Butyldiphenylsilyloxy)methyl)-4-((2R,6S)-2,6-dimethylmorpholino)-2,3-difluorophenyl)-2-(hydroxyimino)-1-morpholinoethanone, (Intermediate 168, 133 mg, 0.20 mmol) was dissolved in DMF and stirred at 60° C. with cesium carbonate (332 mg, 1.02 mmol) for 6 hours. The reaction stirred at room temperature over 2 days. The reaction was diluted with water and extracted three times with ethyl acetate. The organic layers were combined and washed 5× with brine, dried over MgSO$_4$ and concentrated to give an oil. The oil was purified by silica gel column chromatography using a gradient of hexanes to ethyl acetate to give the title compound (34 mg, 0.086 mmol).

MS (ES) MH$^+$: 394 for $C_{19}H_{24}FN_3O_5$ $^1$H NMR (300 MHz, CHLOROFORM-d) δ ppm 1.25 (d, 6H), 2.9-3.0 (m, 2H), 3.0-3.2 (m, 2H), 3.7-3.9 (m, 8H), 3.9-4.0 (m, 2H), 4.8 (s, 2H), 7.7 (s, 1H).

Intermediates 286 to 301 were prepared from the indicated starting materials using a method similar to the one described for the synthesis of Intermediate 285:

Intermediate 286

6-((2R,6S)-2,6-dimethylmorpholino)-7-fluoro-5-(hydroxymethyl)-N,N-dimethylbenzo[d]isoxazole-3-carboxamide 2-(5-((tert-butyldiphenylsilyloxy)methyl)-4-((2R,6S)-2,6-dimethylmorpholino)-2,3-difluorophenyl)-2-(hydroxyimino)-N,N-dimethylacetamide (Intermediate 169).

MS (ES) MH$^+$: 352 for $C_{17}H_{22}FN_3O_4$ $^1$H NMR (300 MHz, CHLOROFORM-d) δ ppm 1.25 (d, 6H), 3.0-3.05 (m, 2H), 3.1 (m, 2H), 3.2 (s, 3H), 3.35 (s, 3H), 3.9 (m, 2H), 4.8 (s, 2H), 7.7 (s, 1H Intermediate 287

(6-((2R,6S)-2,6-dimethylmorpholino)-7-fluoro-3-(pyridin-4-yl)benzo[d]isoxazol-5-yl)methanol Starting material: 1-{5-({[tert-butyl(diphenyl)silyl]oxy}methyl)-4-[(2R,6S)-2,6-dimethylmorpholin-4-yl]-2,3-difluorophenyl}-N-hydroxy-1-pyridin-4-ylmethanimine (Intermediate 161).

MS (ES) MH$^+$: 358 for $C_{19}H_{20}FN_3O_3$ $^1$H NMR (300 MHz, CDCl$_3$) δ: ppm 1.23 (d, 6H), 2.87-3.17 (m, 4H), 3.37 (s, 1H), 3.71-3.92 (m, 2H), 4.85 (s, 2H), 7.64 (s, 1H), 7.86 (d, 2H), 8.84 (d, 2H).

Intermediate 288

(3-((1H-1,2,4-triazol-1-yl)methyl)-6-((2R,6S)-2,6-dimethylmorpholino)-7-fluorobenzo[d]isoxazol-5-yl) methanol Starting material: 1-{5-({[tert-butyl(diphenyl)silyl]oxy}methyl)-4-[(2R,6S)-2,6-dimethylmorpholin-4-yl]-2,3-difluorophenyl}-N-hydroxy-2-(1H-1,2,4-triazol-1-yl)ethanimine (Intermediate 163).

MS (ES) MH$^+$: 362 for $C_{17}H_{20}FN_5O_3$ $^1$H NMR (300 MHz, CDCl$_3$) δ: 1.21 (d, 6H), 2.76-3.13 (m, 5H), 3.60-3.93 (m, 2H), 4.75 (s, 2H) 5.72 (s, 2H), 7.36 (s, 1H), 7.99 (s, 1H), 8.23 (s, 1H).

Intermediate 289

(6-((2R,6S)-2,6-dimethylmorpholino)-7-fluoro-3-(furan-2-yl)benzo[d]isoxazol-5-yl)methanol Starting material: 1-{5-({[tert-butyl(diphenyl)silyl]oxy}methyl)-4-[(2R,6S)-2,6-dimethylmorpholin-4-yl]-2,3-difluorophenyl}-1-furan-2-yl-N-hydroxymethanimine (Intermediate 162).

MS (ES) MH$^+$: 347 for $C_{18}H_{19}FN_2O_4$ $^1$H NMR (300 MHz, CDCl$_3$) δ:1.23 (d, 6H), 2.89-3.17 (m, 4H), 3.72-3.92 (m, 2H), 4.84 (s, 2H) 6.63 (d, 1H), 7.19 (d, 1H), 7.70 (s, 1H), 7.78 (s, 1H).

Intermediate 290

(6-((2R,6S)-2,6-dimethylmorpholino)-7-fluoro-3-(trifluoromethyl)benzo[d]isoxazol-5-yl)methanol Starting material: 1-{5-({[tert-butyl(diphenyl)silyl]oxy}methyl)-4-[(2R,6S)-2,6-dimethylmorpholin-4-yl]-2,3-difluorophenyl}-2,2,2-trifluoro-N-hydroxyethanimine (Intermediate 159).

MS (ES) MH$^+$: 349 for $C_{15}H_{16}F_4N_2O_3$ $^1$H NMR (300 MHz, CDCl$_3$) δ: 1.22 (d, 6H), 1.97 (broad peak, 1H), 2.85-3.15 (m, 4H), 3.66-3.93 (m, 2H), 4.82 (s, 2H) 7.55 (s, 1H).

Intermediate 291

(3-(difluoromethyl)-6-((2R,6S)-2,6-dimethylmorpholino)-7-fluorobenzo[d]isoxazol-5-yl)methanol Starting material: 1-{5-({[tert-butyl(diphenyl)silyl]oxy}methyl)-4-[(2R,6S)-2,6-dimethylmorpholin-4-yl]-2,3-difluorophenyl}-2,2-difluoro-N-hydroxyethanimine (Intermediate 160).

MS (ES) MH$^+$: 331 for $C_{15}H_{17}F_3N_2O_3$ $^1$H NMR (300 MHz, CDCl$_3$) δ: 1.23 (d, 6H), 2.88-3.16 (m, 4H), 3.72-3.95 (m, 2H), 4.83 (s, 2H), 7.00 (t, 1H), 7.61 (s, 1H).

Intermediate 292

(3-(difluoromethyl)-6-((2R,6R)-2,6-dimethylmorpholino)-7-fluorobenzo[d]isoxazol-5-yl)methanol Starting materials 1-{5-({[tert-butyl(diphenyl)silyl]oxy}methyl)-4-[(2R,6R)-2,6-dimethylmorpholin-4-yl]-2,3-difluorophenyl}-2,2-difluoro-N-hydroxyethanimine (Intermediate 164).

MS (ES) MH$^+$: 331 for $C_{15}H_{17}F_3N_2O_3$

¹H NMR (300 MHz, CDCl₃) δ: 1.34 (d, 6H) 2.79-3.41 (m, 4H) 4.02-4.28 (m, 2H) 4.68-5.07 (m, 2H) 7.00 (t, 1H) 7.66 (s, 1H).

Intermediate 293

7-chloro-6-((2R,6S)-2,6-dimethylmorpholino)-5-(hydroxymethyl)-N-methylisoxazolo[4,5-b]pyridine-3-carboxamide Starting material: 5-((tert-butyldiphenylsilyloxy)methyl)-7-chloro-6-((2R,6S)-2,6-dimethylmorpholino)-N-methylisoxazolo[4,5-b]pyridine-3-carboxamide (Intermediate 230).

MS (ES) MH⁺: 355 for C₁₅H₁₉ClN₄O₄

¹H NMR (300 MHz, DMSO-d₆) δ: 1.1 (d, 6H), 2.9 (d, 3H), 2.9-3.1 (m, 4H), 3.7-3.9 (m, 2H), 4.8 (d, 2H), 5.4 (br t, 1H). 8.9 (m, 1H).

Intermediate 294

7-chloro-6-((2R,6S)-2,6-dimethylmorpholino)-N-ethyl-5-(hydroxymethyl)isoxazolo[4,5-b]pyridine-3-carboxamide Starting material: 5-((tert-butyldiphenylsilyloxy)methyl)-7-chloro-6-((2R,6S)-2,6-dimethylmorpholino)-N-ethylisoxazolo[4,5-b]pyridine-3-carboxamide (Intermediate 231).

MS (ES) MH⁺: 369 for C₁₆H₂₁ClN₄O₄

¹H NMR (300 MHz, DMSO-d₆) δ: 1.1 (d, 6H), 1.2 (t, 3H), 2.9-3.1 (m, 4H), 3.3-3.5 (m, 2H), 3.7-3.9 (m, 2H), 4.8 (d, 2H), 5.3 (br t, 1H). 9.0 (m, 1H).

Intermediate 295

7-chloro-6-((2R,6S)-2,6-dimethylmorpholino)-5-(hydroxymethyl)-N-isopropylisoxazolo[4,5-b]pyridine-3-carboxamide Starting material: 5-((tert-butyldiphenylsilyloxy)methyl)-7-chloro-6-((2R,6S)-2,6-dimethylmorpholino)-N-isopropylisoxazolo[4,5-b]pyridine-3-carboxamide (Intermediate 232).

MS (ES) MH⁺: 383 for C₁₇H₂₃ClN₄O₄

¹H NMR (300 MHz CD₂Cl₂) δ: 1.2 (d, 6H), 1.3 (d, 6H), 2.8-2.9 (m, 2H), 3.1-3.3 (m, 2H), 3.5 (br s, 1H), 3.8-3.9 (m, 2H), 4.3 (m, 1H), 4.9 (br s, 2H). 7.5 (br s, 1H).

Intermediate 296

N-tert-butyl-7-chloro-6-((2R,6S)-2,6-dimethylmorpholino)-5-(hydroxymethyl)isoxazolo[4,5-b]pyridine-3-carboxamide Starting material: N-tert-butyl-5-((tert-butyldiphenylsilyloxy)methyl)-7-chloro-6-((2R,6S)-2,6-dimethylmorpholino)isoxazolo[4,5-]pyridine-3-carboxamide (Intermediate 233).

MS (ES) MH⁺: 397 for C₁₈H₂₅ClN₄O₄

¹H NMR (300 MHz, CD₂Cl₂) δ: 1.2 (d, 6H), 1.5 (s, 9H), 2.7-2.9 (m, 2H), 3.2-3.3 (m, 2H), 3.4 (m, 1H), 3.7-3.9 (m, 2H), 4.9 (d, 2H), 7.6 (br s, 1H).

Intermediate 297

7-chloro-6-((2R,6S)-2,6-dimethylmorpholino)-5-(hydroxymethyl)-N-neopentylisoxazolo[4,5-b]pyridine-3-carboxamide Starting material: 5-((tert-butyldiphenylsilyloxy)methyl)-7-chloro-6-((2R,6S)-2,6-dimethylmorpholino)-N-neopentylisoxazolo[4,5-b]pyridine-3-carboxamide (Intermediate 234).

MS (ES) MH⁺: 411 for C₁₉H₂₇ClN₄O₄

¹H NMR (300 MHz, CD₂Cl₂) δ: 1.0 (s, 9H), 1.2 (d, 6H), 2.8-2.9 (m, 2H), 3.2-3.3 (m, 2H), 3.3-3.4 (overlapping m, 3H), 3.8-3.9 (m, 2H), 4.9 (d, 2H), 7.9 (br s 1H).

Intermediate 298

(7-chloro-6-((2R,6S)-2,6-dimethylmorpholino)-5-(hydroxymethyl)isoxazolo[4,5-b]pyridin-3-yl)(3,3-difluoroazetidin-1-yl)methanone Starting material: (5-((tert-butyldiphenylsilyloxy)methyl)-7-chloro-6-((2R,6S)-2,6-dimethylmorpholino)isoxazolo[4,5-b]pyridin-3-yl)(3,3-difluoroazetidin-1-yl)methanone (Intermediate 235).

MS (ES) MH⁺: 417 for C₁₇H₁₉ClF₂N₄O₄

¹H NMR (300 MHz, CD₂Cl₂) δ: 1.2 (d, 6H), 2.8-2.9 (m, 2H), 3.1-3.3 (m, 2H), 3.8-3.9 (m, 2H), 3.9 (brs, 1H), 4.6 (t, 2H), 4.8-4.9 (m, 4H).

Intermediate 299

N-benzyl-7-chloro-6-((2R,6S)-2,6-dimethylmorpholino)-5-(hydroxymethyl)isoxazolo[4,5-b]pyridine-3-carboxamide Starting material: N-benzyl-5-((tert-butyldiphenylsilyloxy)methyl)-7-chloro-6-((2R,6S)-2,6-dimethylmorpholino)isoxazolo[4,5-b]pyridine-3-carboxamide (Intermediate 236).

MS (ES) MH⁺: 431 for C₂₁H₂₃ClN₄O₄

¹H NMR (300 MHz, CD₂Cl₂) δ: 1.2 (d, 6H), 2.8-2.9 (m, 2H), 3.2-3.3 (m, 2H), 3.8-3.9 (m, 2H), 4.7 (d, 2H), 4.9 (s, 2H), 7.3-7.4 (m, 5H), 8.0 (br s, 1H).

Intermediate 300

7-chloro-N-(4-cyanobenzyl)-6-((2R,6S)-2,6-dimethylmorpholino)-5-(hydroxymethyl)isoxazolo[4,5-b]pyridine-3-carboxamide Starting material: 5-((tert-butyldiphenylsilyloxy)methyl)-7-chloro-N-(4-cyanobenzyl)-6-((2R,6S)-2,6-dimethylmorpholino)isoxazolo[4,5-b]pyridine-3-carboxamide (Intermediate 237).

MS (ES) MH⁺: 456 for C₂₂H₂₂ClN₅O₄

¹H NMR (300 MHz, CD₂Cl₂) δ: 1.2 (d, 6H), 2. 8-2.9 (m, 2H), 3.1-3.3 (m, 2H), 3.4 (m, 1H). 3.8-3.9 (m, 2H), 4.8, (d, 2H), 4.9 (d, 2H), 7.5 (d, 2H), 7.7 (d, 2H), 8.1 (br s, 1H).

Intermediate 301

7-chloro-N-(3-cyanobenzyl)-6-((2R,6S)-2,6-dimethylmorpholino)-5-(hydroxymethyl)isoxazolo[4,5-b]pyridine-3-carboxamide Starting material: 5-((tert-butyldiphenylsilyloxy)methyl)-7-chloro-N-(3-cyanobenzyl)-6-((2R,6S)-2,6-dimethylmorpholino)isoxazolo[4,5-b]pyridine-3-carboxamide (Intermediate 238).

MS (ES) MH⁺: 456 for C₂₂H₂₂ClN₅O₄

¹H NMR (300 MHz, CD₂Cl₂) δ: 1.2 (d, 6H), 2.8-2.9 (m, 2H), 3.1-3.3 (m, 2H), 3.4 (m, 1H). 3.7-3.9 (m, 2H), 4.8, (d, 2H), 4.9 (m, 2H), 7.5 (t, 1H), 7.6-7.7 (m, 3H), 8.2 (m, 1H).

Intermediate 302

7-chloro-6-[(2R,6S)-2,6-dimethylmorpholin-4-yl]-3-methyl-1,2-benzoxazole-5-carboxylic To a solution of methyl 3-chloro-2-[(2R,6S)-2,6-dimethylmorpholin-4-yl]-4-fluoro-5-[N-hydroxyethanimidoyl]benzoate (Intermediate 171, 700 mg, 1.94 mmol) in DMF (4 mL) was added Cs$_2$CO$_3$ (1.9 g, 5.84 mmol) and the mixture was heated to 130° C. for 14 hours. The reaction mixture was cooled to room temperature and filtered through a celite bed. The solvent was removed under vacuum and the residue was purified by silica gel chromatography column using ethyl acetate-pet. ether gradient to obtain product. Yield 250 mg, (41%).

MS (ES) MH$^+$: 335 for C$_{15}$H$_{17}$ClN$_2$O$_4$

Intermediates 303 to 325 were prepared from the indicated starting materials using a method similar to the one described for the synthesis of Intermediate 302:

Intermediate 303

{7-chloro-6-[(2R,6S)-2,6-dimethylmorpholin-4-yl]-3-(pyridin-2-yl)-1,2-benzoxazol-5-yl}methanol Starting material: 1-{5-({[tert-butyl(diphenyl)silyl]oxy}methyl)-3-chloro-4-[(2R,6S)-2,6-dimethylmorpholin-4-yl]-2-fluorophenyl}-N-hydroxy-1-(pyridin-2-yl)methanimine (Intermediate 172).

MS (ES) MH$^+$: 374 for C$_{19}$H$_{20}$ClN$_3$O$_3$

Intermediate 304

{7-chloro-6-[(2R,6S)-2,6-dimethylmorpholin-4-yl]-3-(6-methylpyridin-3-yl)-1,2-benzoxazol-5-yl}methanol Starting material: 1-{5-({[tert-butyl(diphenyl)silyl]oxy}methyl)-3-chloro-4-[(2R,6S)-2,6-dimethylmorpholin-4-yl]-2-fluorophenyl}-N-hydroxy-1-(6-methylpyridin-3-yl)methanimine (Intermediate 173).

MS (ES) MH$^+$: 388.4 for C$_{20}$H$_{22}$ClN$_3$O$_3$.

Intermediate 305

{7-chloro-6-[(2R,6S)-2,6-dimethylmorpholin-4-yl]-3-(1,3-thiazol-5-yl)-7,7a-dihydro-1,2-benzoxazol-5-yl}methanol Starting material: 1-{5-({[tert-butyl(diphenyl)silyl]oxy}methyl)-3-chloro-4-[(2R,6S)-2,6-dimethylmorpholin-4-yl]-2-fluorophenyl}-N-hydroxy-1-(1,3-thiazol-5-yl)methanimine (Intermediate 174)

MS (ES) MH$^+$: 382.2 for C$_{17}$H$_{20}$ClN$_3$O$_3$S

Intermediate 306

{7-chloro-6-[(2R,6S)-2,6-dimethylmorpholin-4-yl]-3-(pyridin-4-yl)-1,2-benzoxazol-5-yl}methanol Starting material: 1-{5-({[tert-butyl(diphenyl)silyl]oxy}methyl)-3-chloro-4-[(2R,6S)-2,6-dimethylmorpholin-4-yl]-2-fluorophenyl}-N-hydroxy-1-(pyridin-4-yl)methanimine (Intermediate 175).

MS (ES) MH$^+$: 374 for C$_{19}$H$_{20}$ClN$_3$O$_3$

Intermediate 307

{7-chloro-6-[(2R,6S)-2,6-dimethylmorpholin-4-yl]-3-(pyridin-3-yl)-1,2-benzoxazol-5-yl}methanol Starting material: 1-{5-({[tert-butyl(diphenyl)silyl]oxy}methyl)-3-chloro-4-[(2R,6S)-2,6-dimethylmorpholin-4-yl]-2-fluorophenyl}-N-hydroxy-1-(pyridin-3-yl)methanimine (Intermediate 176).

MS (ES) MH$^+$: 374 for C$_{19}$H$_{20}$ClN$_3$O$_3$

Intermediate 308

{7-chloro-6-[(2R,6S)-2,6-dimethylmorpholin-4-yl]-3-(1,3-thiazol-2-yl)-1,2-benzoxazol-5-yl}methanol Starting material: 1-{5-({[tert-butyl(diphenyl)silyl]oxy}methyl)-3-chloro-4-[(2R,6S)-2,6-dimethylmorpholin-4-yl]-2-fluorophenyl}-N-hydroxy-1-(1,3-thiazol-2-yl)methanimine (Intermediate 177).

MS (ES) MH$^+$: 380 for C$_{17}$H$_{18}$ClN$_3$O$_3$S

Intermediate 309

{7-chloro-6-[(2R,6S)-2,6-dimethylmorpholin-4-yl]-3-(1-methyl-1H-imidazol-2-yl)-1,2-benzoxazol-5-yl}methanol Starting material: 1-{5-({[tert-butyl(diphenyl)silyl]oxy}methyl)-3-chloro-4-[(2R,6S)-2,6-dimethylmorpholin-4-yl]-2-fluorophenyl}-N-hydroxy-1-(1-methyl-1H-imidazol-2-yl)methanimine (Intermediate 178).

MS (ES) MH$^+$: 377 for C$_{18}$H$_{21}$ClN$_4$O$_3$

Intermediate 310

{7-chloro-6-[(2R,6S)-2,6-dimethylmorpholin-4-yl]-3-(methoxymethyl)-1,2-benzoxazol-5-yl}methanol Starting material: (1E)-1-{5-({[tert-butyl(diphenyl)silyl]oxy}methyl)-3-chloro-4-[(2R,6S)-2,6-dimethylmorpholin-4-yl]-2-fluorophenyl}-N-hydroxy-2-methoxyethanimine (Intermediate 179).

MS (ES) MH$^+$: 341 for C$_{16}$H$_{21}$ClN$_2$O$_4$

Intermediate 311

{6-[(2R,6S)-2,6-dimethylmorpholin-4-yl]-7-fluoro-3-(2-methyl-1,3-oxazol-4-yl)-1,2-benzoxazol-5-yl}methanol Starting material: 1-{5-({[tert-butyl(diphenyl)silyl]oxy}methyl)-4-[(2R,6S)-2,6-dimethylmorpholin-4-yl]-2,3-difluorophenyl}-N-hydroxy-1-(2-methyl-1,3-oxazol-4-yl)methanimine (Intermediate 185)

MS (ES) MH$^+$: 362 for C$_{18}$H$_{20}$FN$_2$O$_4$

Intermediate 312

{6-[(2R,6S)-2,6-dimethylmorpholin-4-yl]-7-fluoro-3-(5-methyl-1,2-oxazol-3-yl)-1,2-benzoxazol-5-yl}methanol Starting material: 1-{5-({[tert-butyl(diphenyl)silyl]oxy}methyl)-4-[(2R,6S)-2,6-dimethylmorpholin-4-yl]-2,3-difluorophenyl}-N-hydroxy-1-(5-methyl-1,2-oxazol-3-yl)methanimine (Intermediate 186)

MS (ES) MH$^+$: 362 for C$_{18}$H$_{20}$FN$_3$O$_4$;

Intermediate 313

{6-[(2R,6S)-2,6-dimethylmorpholin-4-yl]-3-(3,5-dimethyl-1,2-oxazol-4-yl)-7-fluoro-1,2-benzoxazol-5-yl}methanol Starting material: 1-{5-({[tert-butyl(diphenyl)silyl]oxy}methyl)-4-[(2R,6S)-2,6-dimethylmorpholin-4-yl]-2,3-difluorophenyl}-1-(3,5-dimethyl-1,2-oxazol-4-yl)-N-hydroxymethanimine (Intermediate 187)

MS (ES) MH$^+$: 376 for C$_{19}$H$_{22}$FN$_3$O$_4$;

Intermediate 314

{6-[(2R,6S)-2,6-dimethylmorpholin-4-yl]-7-fluoro-3-(1-methyl-1H-imidazol-2-yl)-1,2-benzoxazol-5-yl}methanol Starting material: 1-{5-({[tert-butyl(diphenyl)silyl]oxy}methyl)-4-[(2R,6S)-2,6-dimethylmorpholin-4-yl]-2,3-difluorophenyl}-N-hydroxy-1-(1-methyl-1H-imidazol-2-yl)methanimine (Intermediate 188)

MS (ES) MH$^+$: 361 for C$_{18}$H$_{21}$FN$_4$O$_3$

Intermediate 315

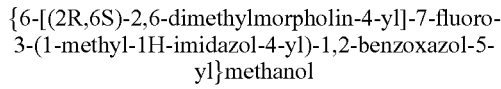
{6-[(2R,6S)-2,6-dimethylmorpholin-4-yl]-7-fluoro-3-(1-methyl-1H-imidazol-4-yl)-1,2-benzoxazol-5-yl}methanol Starting material: 1-{5-({[tert-butyl(diphenyl)silyl]oxy}methyl)-4-[(2R,6S)-2,6-dimethylmorpholin-4-yl]-2,3-difluorophenyl}-N-hydroxy-1-(1-methyl-1H-imidazol-4-yl)methanimine (Intermediate 189)

MS (ES) MH$^+$: 361.2 for $C_{18}H_{21}FN_4O_3$;

Intermediate 316

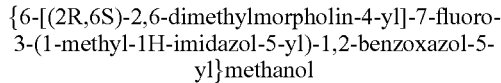
{6-[(2R,6S)-2,6-dimethylmorpholin-4-yl]-7-fluoro-3-(1-methyl-1H-imidazol-5-yl)-1,2-benzoxazol-5-yl}methanol Starting material: 1-{5-({[tert-butyl(diphenyl)silyl]oxy}methyl)-4-[(2R,6S)-2,6-dimethylmorpholin-4-yl]-2,3-difluorophenyl}-N-hydroxy-1-(1-methyl-1H-imidazol-5-yl)methanimine (Intermediate 190)

MS (ES) MH$^+$: 361 for $C_{18}H_{21}FN_4O_3$;

Intermediate 317

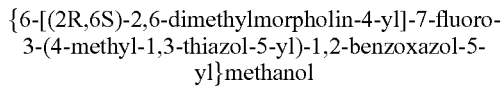
{6-[(2R,6S)-2,6-dimethylmorpholin-4-yl]-7-fluoro-3-(4-methyl-1,3-thiazol-5-yl)-1,2-benzoxazol-5-yl}methanol Starting material: 1-{5-({[tert-butyl(diphenyl)silyl]oxy}methyl)-4-[(2R,6S)-2,6-dimethylmorpholin-4-yl]-2,3-difluorophenyl}-N-hydroxy-1-(4-methyl-1,3-thiazol-5-yl)methanimine (Intermediate 191)

MS (ES) MH$^+$: 378 for $C_{18}H_{20}FN_3O_3S$

Intermediate 318

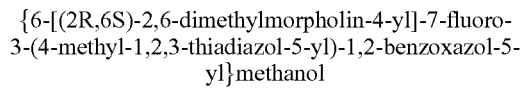
{6-[(2R,6S)-2,6-dimethylmorpholin-4-yl]-7-fluoro-3-(4-methyl-1,2,3-thiadiazol-5-yl)-1,2-benzoxazol-5-yl}methanol Starting material: 1-{5-({[tert-butyl(diphenyl)silyl]oxy}methyl)-4-[(2R,6S)-2,6-dimethylmorpholin-4-yl]-2,3-difluorophenyl}-N-hydroxy-1-(4-methyl-1,2,3-thiadiazol-5-yl)methanimine (Intermediate 192)

MS (ES) MH$^+$: 379 for $C_{17}FN_{19}FN_4O_3S$;

Intermediate 319

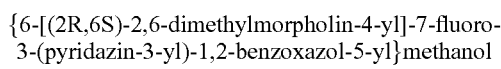
{6-[(2R,6S)-2,6-dimethylmorpholin-4-yl]-7-fluoro-3-(pyridazin-3-yl)-1,2-benzoxazol-5-yl}methanol Starting material: 1-{5-({[tert-butyl(diphenyl)silyl]oxy}methyl)-4-[(2R,6S)-2,6-dimethylmorpholin-4-yl]-2,3-difluorophenyl}-N-hydroxy-1-(pyridazin-3-yl)methanimine (Intermediate 193)

MS (ES) MH$^+$: 359 for $C_{18}H_{19}FN_4O_3$;

Intermediate 320

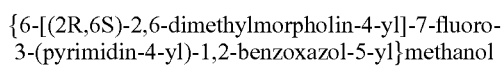
{6-[(2R,6S)-2,6-dimethylmorpholin-4-yl]-7-fluoro-3-(pyrimidin-4-yl)-1,2-benzoxazol-5-yl}methanol Starting material: 1-{5-({[tert-butyl(diphenyl)silyl]oxy}methyl)-4-[(2R,6S)-2,6-dimethylmorpholin-4-yl]-2,3-difluorophenyl}-N-hydroxy-1-(pyrimidin-4-yl)methanimine (Intermediate 194)

MS (ES) MH$^+$: 359 for $C_{18}H_{19}FN_4O_3$

Intermediate 321

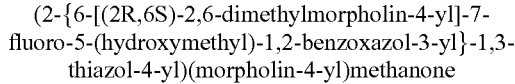
(2-{6-[(2R,6S)-2,6-dimethylmorpholin-4-yl]-7-fluoro-5-(hydroxymethyl)-1,2-benzoxazol-3-yl}-1,3-thiazol-4-yl)(morpholin-4-yl)methanone Starting material: {2-[{5-({[tert-butyl(diphenyl)silyl]oxy}methyl)-4-[(2R,6S)-2,6-dimethylmorpholin-4-yl]-2,3-difluorophenyl}(hydroxyimino)methyl]-1,3-thiazol-4-yl}(morpholin-4-yl)methanone (Intermediate 180).

MS (ES) MH$^+$: 477 for $C_{22}H_{25}FN_4O_4S$.

Intermediate 322

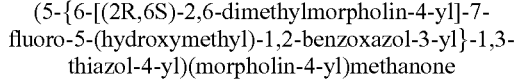
(5-{6-[(2R,6S)-2,6-dimethylmorpholin-4-yl]-7-fluoro-5-(hydroxymethyl)-1,2-benzoxazol-3-yl}-1,3-thiazol-4-yl)(morpholin-4-yl)methanone Starting material: {5-[{5-({[tert-butyl(diphenyl)silyl]oxy}methyl)-4-[(2R,6S)-2,6-dimethylmorpholin-4-yl]-2,3-difluorophenyl}(hydroxyimino)methyl]-1,3-thiazol-4-yl}(morpholin-4-yl)methanone (Intermediate 181)

MS (ES) MH$^+$: 477 for $C_{22}H_{25}FN_4O_4S$.

Intermediate 323

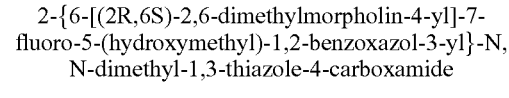
2-{6-[(2R,6S)-2,6-dimethylmorpholin-4-yl]-7-fluoro-5-(hydroxymethyl)-1,2-benzoxazol-3-yl}-N,N-dimethyl-1,3-thiazole-4-carboxamide Starting material: 2-[{5-({[tert-butyl(diphenyl)silyl]oxy}methyl)-4-[(2R,6S)-2,6-dimethylmorpholin-4-yl]-2,3-difluorophenyl}(hydroxyimino)methyl]-N,N-dimethyl-1,3-thiazole-4-carboxamide (Intermediate 182)

MS (ES) MH$^+$: 435.2 for $C_{20}H_{23}FN_4O_4S$

Intermediate 324

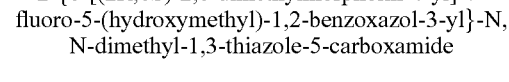
2-{6-[(2R,6S)-2,6-dimethylmorpholin-4-yl]-7-fluoro-5-(hydroxymethyl)-1,2-benzoxazol-3-yl}-N,N-dimethyl-1,3-thiazole-5-carboxamide Starting material: 2-[{5-({[tert-butyl(diphenyl)silyl]oxy}methyl)-4-[(2R,6S)-2,6-dimethylmorpholin-4-yl]-2,3-difluorophenyl}(hydroxyimino)methyl]-N,N-dimethyl-1,3-thiazole-5-carboxamide (Intermediate 183)

MS (ES) MH$^+$: 435 for $C_{20}H_{23}FN_4O_4S$

Intermediate 325

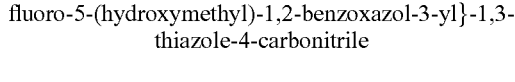
5-{6-[(2R,6S)-2,6-dimethylmorpholin-4-yl]-7-fluoro-5-(hydroxymethyl)-1,2-benzoxazol-3-yl}-1,3-thiazole-4-carbonitrile Starting material: 5-[{5-({[tert-butyl(diphenyl)silyl]oxy}methyl)-4-[(2R,6S)-2,6-dimethylmorpholin-4-yl]-2,3-difluorophenyl}(hydroxyimino)methyl]-1,3-thiazole-4-carbonitrile (Intermediate 184)

MS (ES) MH$^+$: 388 for $C_{18}H_{17}FN_4O_3S$.

Intermediate 326

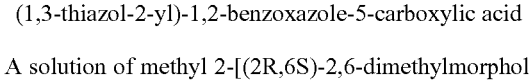
6-[(2R,6S)-2,6-dimethylmorpholin-4-yl]-7-methyl-3-(1,3-thiazol-2-yl)-1,2-benzoxazole-5-carboxylic acid A solution of methyl 2-[(2R,6S)-2,6-dimethylmorpholin-4-yl]-4-fluoro-5-[(hydroxyimino)(1,3-thiazol-2-yl)methyl]-3-methylbenzoic acid (Intermediate 195, 0.31 g, 0.8 mmol), $K_2CO_3$ (0.4 g, 2.3 mmol) and potassium iodide (0.03 g, 0.2 mmol) in DMF (10 mL) was heated at 130° C. for 12 hours. Solvents were removed under vacuum and the residue was treated with 1.5N hydrochloric acid and extracted with ethyl acetate, which was dried over sodium sulfate. Removal of solvent by vacuum afforded product. Yield: 0.18 g (62%).

MS (ES) MH$^+$: 373 for $C_{18}H_{19}N_3O_4S$

Intermediate 327 was prepared from the indicated starting material using a method similar to the one described for the synthesis of Intermediate 326:

Intermediate 327

6-[(2R,6S)-2,6-dimethylmorpholin-4-yl]-7-methyl-3-(pyrazin-2-yl)-1,2-benzoxazole-5-carboxylic acid Starting material: 2-[(2R,6S)-2,6-dimethylmorpholin-4-yl]-4-fluoro-5-[(hydroxyimino)(pyrazin-2-yl)methyl]-3-methylbenzoic acid (Intermediate 196).

MS (ES) MH$^+$: 368 for $C_{19}H_{20}N_4O_4$

Intermediate 328

(3-(3-chloropyrazin-2-yl)-6-((2R,6S)-2,6-dimethylmorpholino)-7-fluorobenzo[d]isoxazol-5-yl)methanol {5-[(3-chloropyrazin-2-yl)(hydroxyimino)methyl]-2-[(2R,6S)-2,6-dimethylmorpholin-4-yl]-3,4-difluorophenyl}methanol (Intermediate 198, 106 mg, 0.26 mmol) in MeCN (4 mL) was treated with $K_2CO_3$ (53.2 mg, 0.39 mmol) at 120° C. for 1 hr. The mixture was diluted with EtOAc and washed with water and brine. The EtOAc solution was dried over anhydrous sodium sulfate, filtered and concentrated to afford 90 mg of product.

MS (ES) MH$^+$: 393 for $C_{18}H_{18}ClFN_4O_3$

Intermediate 329 was prepared from the indicated starting material using a method similar to the one described for the synthesis of Intermediate 328:

Intermediate 329

5-((tert-butyldiphenylsilyloxy)methyl)-3-(6-chloropyrazin-2-yl)-6-((2R,6S)-2,6-dimethylmorpholino)-7-fluorobenzo[d]isoxazole Starting material: 1-{5-({[tert-butyl(diphenyl)silyl]oxy}methyl)-4-[(2R,6S)-2,6-dimethylmorpholin-4-yl]-2,3-difluorophenyl}-1-(6-chloropyrazin-2-yl)-N-hydroxymethanimine (Intermediate 199)

MS (ES) MH$^+$: 632 for $C_{34}H_{36}ClFN_4O_3Si$

Intermediate 330

6-[(2R,6S)-2,6-dimethylmorpholin-4-yl]-7-methyl-3-(1,3-thiazol-2-yl)-1,2-benzoxazol-5-carbaldehyde Oxalyl chloride (0.31 g, 2.4 mmol) was added to a stirred solution of 6-[(2R,6S)-2,6-dimethylmorpholin-4-yl]-7-methyl-3-(1,3-thiazol-2-yl)-1,2-benzoxazole-5-carboxylic acid (Intermediate 326, 0.18 g, 0.4 mmol) and two drops DMF in dichloromethane (5 mL) at 0° C. and the mixture was stirred at room temperature for 2 hours. Solvent was removed under reduced pressure and the residue was dissolved in THF (10 mL) and the solution was cooled to −78° C. and 1M solution of lithium tri(t-butoxy)aluminum hydride (0.28 g, 1.1 mmol) was added slowly and it was stirred for 30 mins at the same temperature. The reaction was quenched with 1.5N hydrochloric acid and extracted with ethyl acetate, the combined organic layers were dried over sodium sulfate and the solvent was removed. The brown viscous oil thus obtained was purified by silica gel column chromatography (20% ethyl acetate in hexane) affording the product as yellow solid. Yield: 0.06 g (35%).

MS (ES) MH$^+$: 357 for $C_{18}H_{19}N_3O_3S$

Intermediate 331 was prepared from the indicated starting material using a method similar to the one described for the synthesis of Intermediate 330:

Intermediate 331

6-[(2R,6S)-2,6-dimethylmorpholin-4-yl]-7-methyl-3-(pyrazin-2-yl)-1,2-benzoxazole-5-carbaldehyde Starting material: 6-[(2R,6S)-2,6-dimethylmorpholin-4-yl]-7-methyl-3-(pyrazin-2-yl)-1,2-benzoxazole-5-carboxylic acid (Intermediate 327).

MS (ES) MH$^+$: 352 for $C_{19}H_{20}N_4O_3$ $^1$H NMR (400 MHz, CDCl$_3$) δ: 1.2 (d, 6H), 2.7 (s, 3H), 3.0 (d, 2H), 3.2 (t, 2H), 3.9 (m, 2H), 8.7 (s, 1H), 8.8 (s, 2H), 9.4 (s, 1H), 10.5 (s, 1H).

Intermediate 332

1-(5-((tert-butyldiphenylsilyloxy)methyl)-2,3,4-trifluorophenyl)ethanone

A solution of s-butyllithium (1.4 M in cyclohexane) (6.42 ml, 8.99 mmol) was added slowly to a solution of tert-butyl-diphenyl(2,3,4-trifluorobenzyloxy)silane (Intermediate 48, 3 g, 7.49 mmol) in THF (30 ml) cooled in a dry ice-acetone bath to maintain a temperature below −60° C. After stirring in the dry-ice acetone bath for 20 minutes, N-methoxy-N-methylacetamide (1.035 ml, 9.74 mmol) was added dropwise maintaining a temperature below −60° C. The mixture was stirred cold for 40 minutes before being quenched with NH$_4$Cl (aqueous) and warmed to room temperature. The solution was partitioned between EtOAc and water. The EtOAc was separated and washed with brine. The combined aqueous layers were extracted with EtOAc, which was washed with brine. The combined EtOAc was dried (MgSO$_4$) and concentrated to give an oil that was chromatographed on silica gel (10% CH$_2$Cl$_2$ in hexanes followed by gradient elution to 70% CH$_2$Cl$_2$ in hexanes) to give 2 materials, the first eluting component (0.76 g) being consistant with starting material and the second eluting component (2.05 g) being consistant with product.

$^1$H NMR (300 MHz, CHLOROFORM-d) δ ppm 1.1 (s, 9H), 2.6 (d, 3H), 4.8 (s, 2H), 7.3-7.5 (m, 6H) 7.6-7.7 (m, 4H), 7.8-7.95 (m, 1H).

Intermediate 333 was prepared from the indicated starting material and tert-butyldiphenyl(2,3,4-trifluorobenzyloxy)silane (Intermediate 48) using a method similar to the one described for the synthesis of Intermediate 332:

Intermediate 333

(5-((tert-butyldiphenylsilyloxy)methyl)-2,3,4-trifluorophenyl)(1-methyl-1H-1,2,4-triazol-5-yl)methanone Starting material: N-methoxy-N,1-dimethyl-1H-1,2,4-triazole-5-carboxamide (Intermediate 49)

MS ES$^+$ MH$^+$ 510 for $C_{27}H_{26}F_3N_3O_2Si$ $^1$H NMR (300 MHz, CHLOROFORM-d) δ ppm 1.1 (s, 9H), 4.3 (s, 3H), 4.8 (s, 2H), 7.3-7.5 (m, 5H), 7.6-7.7 (m, 4H), 7.95 (s, 1H), 8.0 (m, 1H).

Intermediate 334

(6,7-difluoro-3-methyl-1,2-benzisoxazol-5-yl)methanol

To a stirred solution of propan-2-one oxime (1.73 g, 23.7 mmol) in THF (25 ml) was added potassium t-butoxide (1M solution in THF, 23.8 mL) at 0° C. under nitrogen atmosphere and the mixture was stirred with warming to room temperature for 1 hour. The mixture was cooled to −78° C. and a solution of 1-(5-((tert-butyldiphenylsilyloxy)methyl)-2,3,4-trifluorophenyl)ethanone (Intermediate 332, 3.0 g, 6.8 mmol) in THF (15 mL) was added to the mixture and stirred for 20 minutes at −78° C. then at −20° C. for 2 hours. The reaction was quenched with a saturated aqueous NH$_4$Cl solution and extracted with EtOAc. The organic layer was dried (Na$_2$SO$_4$), filtered, and concentrated to give material that was used for the next step without any further purification. A stirred solution of the material dissolved in ethanol (130 ml) was treated with 5 ml of 5% aqueous HCl at 45° C. for 8 hours. The reaction quenched with 10% aqueous sodium bicarbonate solution and extracted with EtOAc. The organic layer washed with water, dried, and concentrated. The residue was purified over a silica gel flash column (elution with 15-20% EtOAc in hexanes) to give title compound as yellow solid. Yield: 600 mg, (46%).

MS (ES) M$^+$: 200 for C$_9$H$_7$F$_2$NO$_2$ $^1$H NMR (400 MHz, DMSO-d$_6$) δ: 2.6 (s, 3H), 4.6 (d, 2H), 5.55 (s, 1H), 7.7 (d, 1H).

Intermediate 335 was prepared from the indicated starting material and propan-2-one oxime using a method similar to the one described for the synthesis of Intermediate 334:

Intermediate 335

(6-((2R,6R)-2,6-dimethylmorpholino)-7-fluoro-3-(5-morpholinopyrazin-2-yl)benzo[d]isoxazol-5-yl)methanol Starting material: (5-((tert-butyldiphenylsilyloxy)methyl)-4-((2R,6R)-2,6-dimethylmorpholino)-2,3-difluorophenyl)(5-morpholinopyrazin-2-yl)methanone (Intermediate 134)

MS (ES) MH$^+$: 444 (M+H) for C$_{22}$H$_{26}$FN$_5$O$_4$

Intermediate 336

1-(6-((tert-Butyldiphenylsilyloxy)methyl)-4-chloro-5-((2R,6S)-2,6-dimethylmorpholino)-3-(propan-2-ylideneaminooxy)pyridin-2-yl)ethanone Propan-2-one oxime (104 mg, 1.43 mmol) was dissolved in 2 ml THF, and potassium tert-butoxide, 1M in THF (1.427 mL, 1.43 mmol), was added to give a white mixture which was stirred at room temperature for 45 min. The mixture was cooled in an ice bath, and a solution of 1-(6-((tert-butyldiphenylsilyloxy)methyl)-4-chloro-5-((2R,6S)-2,6-dimethylmorpholino)-3-fluoropyridin-2-yl)ethanone (Intermediate 148, 660 mg, 1.19 mmol) in 3 ml THF was added to give a yellow solution. Stirred at 0° C. After about.30 minutes, saturated NH$_4$Cl was added to quench the reaction, which was followed by extraction with EtOAc. The phases were separated, and the combined organic phase dried over MgSO$_4$ before concentrating to a pale yellow oil, 635 mg (88%).

MS (ES) MH$^+$: 608 for C$_{33}$H$_{42}$ClN$_3$O$_4$Si

Intermediates 337 to 344 were prepared from the indicated starting material and propan-2-one oxime using a method similar to the one described for the synthesis of Intermediate 336:

Intermediate 337

(5-((tert-butyldiphenylsilyloxy)methyl)-4-((2R,6S)-2,6-dimethylmorpholino)-3-fluoro-2-(propan-2-ylideneaminooxy)phenyl)(thiazol-5-yl)methanone Starting materials (5-((tert-butyldiphenylsilyloxy)methyl)-4-((2R,6S)-2,6-dimethylmorpholino)-2,3-difluorophenyl)(thiazol-5-yl)methanone (Intermediate 123).

MS (ES) MH$^+$: 660 for C$_{36}$H$_{42}$FN$_3$O$_4$SSi $^1$H NMR (300 MHz, CDCl$_3$) δ: 0.84-1.10 (overlapping doublet and singlet, 15H), 1.58-1.92 (6H), 2.43-2.97 (m, 4H), 3.24-3.60 (m, 2H) 4.68 (s, 2H), 7.23-7.45 (m, 7H), 7.47-7.71 (m, 4H), 8.11 (s, 1H) 8.93 (s, 1H).

Intermediate 338

(5-((tert-butyldiphenylsilyloxy)methyl)-4-((2R,6S)-2,6-dimethylmorpholino)-3-fluoro-2-(propan-2-ylideneaminooxy)phenyl)(6-methylpyridin-3-yl)methanone Starting material: (5-((tert-butyldiphenylsilyloxy)methyl)-4-((2R,6S)-2,6-dimethylmorpholino)-2,3-difluorophenyl)(6-methylpyridin-3-yl)methanone (Intermediate 124).

MS (ES) MH$^+$: 660 for C$_{39}$H$_{46}$FN$_3$O$_4$Si $^1$H NMR (300 MHz, CDCl$_3$) δ: 1.01-1.11 (overlapping doublet and singlet, 15H), 1.62 (3H), 1.68 (3H), 2.64 (s, 3H), 2.66-2.90 (m, 4H), 3.39-3.55 (m, 2H), 4.74 (s, 2H), 7.22 (d, 1H), 7.31-7.46 (m, 7H), 7.59-7.68 (m, 4H), 7.96 (d, 1H), 8.86 (s, 1H).

Intermediate 339

(5-((tert-butyldiphenylsilyloxy)methyl)-4-((2R,6S)-2,6-dimethylmorpholino)-3-fluoro-2-(propan-2-ylideneaminooxy)phenyl)(2-fluorophenyl)methanone Starting materials (5-((tert-butyldiphenylsilyloxy)methyl)-4-((2R,6S)-2,6-dimethylmorpholino)-2,3-difluorophenyl)(2-fluorophenyl)methanone (Intermediate 125).

MS (ES) MH$^+$: 671 for C$_{39}$H$_{44}$F$_2$N$_2$O$_4$Si $^1$H NMR (300 MHz, CDCl$_3$) δ: 1.03 (s, 9H), 1.07 (d, 6H), 1.53 (s, 3H), 1.73 (s, 3H), 2.55-2.91 (m, 4H), 3.30-3.64 (m, 2H), 4.73 (s, 2H), 6.94-7.74 (m, 15H).

Intermediate 340

(5-((tert-butyldiphenylsilyloxy)methyl)-4-((2R,6S)-2,6-dimethylmorpholino)-3-fluoro-2-(propan-2-ylideneaminooxy)phenyl)(tetrahydro-2H-pyran-4-yl)methanone Starting materials (5-((tert-butyldiphenylsilyloxy)methyl)-4-((2R,6S)-2,6-dimethylmorpholino)-2,3-difluorophenyl)(tetrahydro-2H-pyran-4-yl)methanone (Intermediate 126).

MS (ES) MH$^+$: 661 for C$_{38}$H$_{49}$FN$_2$O$_5$Si

Intermediate 341

(5-((tert-butyldiphenylsilyloxy)methyl)-4-((2R,6R)-2,6-dimethylmorpholino)-3-fluoro-2-(propan-2-ylideneaminooxy)phenyl)(thiazol-2-yl)methanone Starting materials (5-((tert-butyldiphenylsilyloxy)methyl)-4-((2R,6R)-2,6-dimethylmorpholino)-2,3-difluorophenyl)(thiazol-2-yl)methanone (Intermediate 131).

MS (ES) MH$^+$: C$_{36}$H$_{42}$FN$_3$O$_4$SSi

Intermediate 342

(5-((tert-Butyldiphenylsilyloxy)methyl)-3-chloro-4-((2R,6S)-2,6-dimethylmorpholino)-2-(propan-2-ylideneaminooxy)phenyl)(pyrazin-2-yl)methanone Starting material: (5-((tert-butyldiphenylsilyloxy)methyl)-3-chloro-4-((2R,6S)-2,6-dimethylmorpholino)-2-fluorophenyl)(pyrazin-2-yl)methanone (Intermediate 72, 847 mg, 1.37 mmol).

MS (ES) MH$^+$: 671 for C$_{37}$H$_{43}$ClN$_4$O$_4$Si

Intermediate 343

(5-((tert-butyldiphenylsilyloxy)methyl)-4-((2R,6R)-2,6-dimethylmorpholino)-3-fluoro-2-(propan-2-ylideneaminooxy)phenyl)(pyrazin-2-yl)methanone Starting material: (5-((tert-butyldiphenylsilyloxy)methyl)-4-((2R,6R)-2,6-dimethylmorpholino)-2,3-difluorophenyl)(pyrazin-2-yl)methanone (Intermediate 133)

MS (ES) MH+: 655 for $C_{37}H_{43}FN_4O_4Si$

Intermediate 344

(5-((tert-butyldiphenylsilyloxy)methyl)-4-((2R,6R)-2,6-dimethylmorpholino)-3-fluoro-2-(propan-2-ylideneaminooxy)phenyl)(6-methoxypyrazin-2-yl)methanone Starting material: (5-((tert-butyldiphenylsilyloxy)methyl)-4-((2R,6R)-2,6-dimethylmorpholino)-2,3-difluorophenyl)(6-methoxypyrazin-2-yl)methanone (Intermediate 138)

MS (ES) MH+: 685 for $C_{38}H_{45}FN_4O_5Si$

Intermediates 345 to 351 were prepared from the indicated starting materials using a method similar to the one described for the synthesis of Intermediate 33:

Intermediate 345

(6-((2R,6S)-2,6-dimethylmorpholino)-7-fluoro-3-(thiazol-5-yl)benzo[d]isoxazol-5-yl)methanol Starting material: (5-((tert-butyldiphenylsilyloxy)methyl)-4-((2R,6S)-2,6-dimethylmorpholino)-3-fluoro-2-(propan-2-ylideneaminooxy)phenyl)(thiazol-5-yl)methanone (Intermediate 337).

MS (ES) MH+: 364 for $C_{17}H_{18}FN_3O_3S$

1H NMR (300 MHz, CDCl3) δ: 1.23 (d, 6H), 2.85-3.20 (m, 4H), 3.70-3.94 (m, 2H), 4.80 (s, 2H), 7.66 (s, 1H, 8.57 (s, 1H), 9.00 (s, 1H).

Intermediate 346

(6-((2R,6S)-2,6-dimethylmorpholino)-7-fluoro-3-(6-methylpyridin-3-yl)benzo[d]isoxazol-5-yl)methanol Starting material: (5-((tert-butyldiphenylsilyloxy)methyl)-4-((2R,6S)-2,6-dimethylmorpholino)-3-fluoro-2-(propan-2-ylideneaminooxy)phenyl)(6-methylpyridin-3-yl)methanone (Intermediate 338).

MS (ES) MH+: 372 for $C_{20}H_{22}FN_3O_3$

1H NMR (300 MHz, CDCl3) δ: 1.22 (s, 3H), 1.24 (s, 3H), 2.68 (s, 3H), 2.82-3.22 (m, 4H), 3.29-3.55 (broad peak, 1H), 3.67-4.00 (m, 2H), 4.82 (s, 2H), 7.37 (d, 1H), 7.60 (s, 1H), 8.15 (d, 1H), 9.06 (s, 1H).

Intermediate 347

(6-((2R,6S)-2,6-dimethylmorpholino)-7-fluoro-3-(2-fluorophenyl)benzo[d]isoxazol-5-yl)methanol Starting material: (5-((tert-butyldiphenylsilyloxy)methyl)-4-((2R,6S)-2,6-dimethylmorpholino)-3-fluoro-2-(propan-2-ylideneaminooxy)phenyl)(2-fluorophenyl)methanone (Intermediate 339).

MS (ES) MH+: 375 for $C_{20}H_{20}F_2N_2O_3$

1H NMR (300 MHz, CDCl3) δ: 1.23 (d, 6H), 2.90-3.18 (m, 4H), 3.69-3.94 (m, 2H), 4.81 (s, 2H), 7.25-7.88 (m, 5H).

Intermediate 348

(6-((2R,6S)-2,6-dimethylmorpholino)-7-fluoro-3-(tetrahydro-2H-pyran-4-yl)benzo[d]isoxazol-5-yl)methanol Starting material: (5-((tert-butyldiphenylsilyloxy)methyl)-4-((2R,6S)-2,6-dimethylmorpholino)-3-fluoro-2-(propan-2-ylideneaminooxy)phenyl)(tetrahydro-2H-pyran-4-yl)methanone (Intermediate 340).

MS (ES) MH+: 365 for $C_{19}H_{25}FN_2O_4$

1H NMR (300 MHz, CDCl3) δ: 1.22 (d, 6H), 1.87-2.24 (m, 4H), 2.84-2.99 (m, 2H), 3.07 (t, 2H), 3.24-3.39 (m, 1H), 3.59 (t, 2H), 3.71-3.94 (m, 2H), 4.00-4.21 (m, 2H), 4.80 (s, 2H), 7.40 (s, 1H).

Intermediate 349

(6-((2R,6R)-2,6-dimethylmorpholino)-7-fluoro-3-(thiazol-2-yl)benzo[d]isoxazol-5-yl)methanol Starting material: (5-((tert-butyldiphenylsilyloxy)methyl)-4-((2R,6R)-2,6-dimethylmorpholino)-3-fluoro-2-(propan-2-ylideneaminooxy)phenyl)(thiazol-2-yl)methanone (Intermediate 341).

MS (ES) MH+: 364 for $C_{17}H_{18}FN_3O_3S$

1H NMR (300 MHz, CDCl3) δ: 1.35 (d, 6H), 2.90-3.08 (m, 2H), 3.20-3.47 (m, 2H), 4.04-4.29 (m, 2H), 4.76-4.99 (m, 2H), 7.57 (d, 1H), 8.09 (d, 1H), 8.18 (s, 1H).

Intermediate 350

(6-((2R,6R)-2,6-dimethylmorpholino)-7-fluoro-3-(pyrazin-2-yl)benzo[d]isoxazol-5-yl)methanol Starting material: (5-((tert-butyldiphenylsilyloxy)methyl)-4-((2R,6R)-2,6-dimethylmorpholino)-3-fluoro-2-(propan-2-ylideneaminooxy)phenyl)(pyrazin-2-yl)methanone (Intermediate 343).

MS (ES) MH+: 359 for $C_{18}H_{19}FN_4O_3$

Intermediate 351

(6-((2R,6R)-2,6-dimethylmorpholino)-7-fluoro-3-(6-methoxypyrazin-2-yl)benzo[d]isoxazol-5-yl)methanol Starting material: (5-((tert-butyldiphenylsilyloxy)methyl)-4-((2R,6R)-2,6-dimethylmorpholino)-3-fluoro-2-(propan-2-ylideneaminooxy)phenyl)(6-methoxypyrazin-2-yl)methanone (Intermediate 344)

MS (ES) MH+: 389 for $C_{19}H_{21}FN_4O_4$

Intermediate 352

(7-Chloro-6-((2R,6S)-2,6-dimethylmorpholino)-3-methylisoxazolo[4,5-b]pyridin-5-yl)methanol 1-(6-((tert-Butyldiphenylsilyloxy)methyl)-4-chloro-5-((2R,6S)-2,6-dimethylmorpholino)-3-(propan-2-ylideneaminooxy)pyridin-2-yl)ethanone (Intermediate 336, 821 mg, 1.35 mmol) was dissolved in 13 ml of EtOH. Aqueous 1M HCl, (4.33 ml, 4.33 mmol) was added to give an immediate precipitate, which dissolved to give a hazy yellow solution. The mixture was heated at 75° C. After 1 hour, 15 minutes, the reaction was cooled and diluted with EtOAc. Added saturated NaHCO3 to quench was followed by extraction 2× with EtOAc. The combined organic phase was dried over MgSO4 and concentrated. The crude was purified on SiO2 using 15-40% EtOAc/hexanes. Recovered 389 mg (88%) of the title compound as white solid.

MS (ES) MH+: 312 for $C_{14}H_{18}ClN_3O_3$

¹H NMR (300 MHz, CD₂Cl₂) δ: 1.2 (d, 6H), 2.6 (s, 3H), 2.7-2.8 (m, 2H), 3.2-3.3 (m, 2H), 3.7-3.9 (m, 2H), 4.0 (br s, 1H), 4.9 (d, 2H).

Intermediate 353 was prepared from the indicated starting materials using a method similar to the one described for the synthesis of Intermediate 352:

Intermediate 353

(7-Chloro-6-((2R,6S)-2,6-dimethylmorpholino)-3-(pyrazin-2-yl)benzo[d]isoxazol-5-yl)methanol Starting material: (5-((tert-Butyldiphenylsilyloxy)methyl)-3-chloro-4-((2R,6S)-2,6-dimethylmorpholino)-2-(propan-2-ylideneaminooxy)phenyl)(pyrazin-2-yl)methanone (Intermediate 342).

MS (ES) MH⁺: 375 for $C_{18}H_{19}ClN_4O_3$

¹H NMR (DMSO-d₆) δ: 1.1 (d, 6H), 2.8-3.0 (m, 2H), 3.1-3.2 (m, 2H), 3.7-3.8 (m, 2H), 4.7-4.8 (m, 2H), 5.4 (m, 1H), 8.4 (br s, 1H), 8.9 (d, 1H), 9.0 (m, 1H), 9.4 (m, 1H).

Intermediate 354

7-chloro-3-cyclopropyl-6-[(2R,6S)-2,6-dimethylmorpholin-4-yl]-1,2-benzoxazole-5-carboxylic acid To a stirred solution of propan-2-one oxime (80 mg, 1.10 mmol) in THF (10 ml) was added potassium t-butoxide (1M solution in THF, 2.0 ml, 2.0 mmol) at −20° C. After stirring for 45 minutes a solution of methyl 3-chloro-5-(cyclopropylcarbonyl)-2-[(2R,6S)-2,6-dimethylmorpholin-4-yl]-4-fluorobenzoate (Intermediate 91) (370 mg, 1.0 mmol) in THF (5 mL) was added, and the mixture was stirred for 20 minutes at −20° C. before warming to room temperature for 1 hour. The reaction was quenched with saturated aqueous ammonium chloride solution and extracted with EtOAc. The organic layer was dried (Na₂SO₄), filtered, and concentrated to give the crude material, which was used for the next step without any further purification. A stirred solution of crude material (500 mg) from above reaction dissolved in ethanol (20 ml) was treated with 5 ml of 5% aqueous HCl at 50° C. for 12 hours. The reaction quenched with 10% aqueous sodium bicarbonate solution and extracted with EtOAc. The organic layer washed with water, dried, and concentrated. The residue purified over a silica gel flash column (elution with 50-70% EtOAc in hexanes) to give product. Yield: 100 mg (28%).

MS (ESP): 295.4 for $C_{15}H_{19}FN_2O_3$

Intermediates 355 to 371 were prepared from the indicated starting materials using a method similar to the one described for the synthesis of Intermediate 354:

Intermediate 355

{7-chloro-6-[(2R,6S)-2,6-dimethylmorpholin-4-yl]-3-(pyrimidin-2-yl)-1,2-benzoxazol-5-yl}methanol Starting material: {5-({[tert-butyl(diphenyl)silyl]oxy}methyl)-3-chloro-4-[(2R,6S)-2,6-dimethylmorpholin-4-yl]-2-fluorophenyl}(pyrimidin-2-yl)methanone (Intermediate 109)

MS (ES) MH⁺: 375.2 for $C_{18}H_{19}ClN_4O_3$.

Intermediate 356

{7-chloro-6-[(2R,6S)-2,6-dimethylmorpholin-4-yl]-3-(pyrimidin-4-yl)-1,2-benzoxazol-5-yl}methanol Starting material: {5-({[tert-butyl(diphenyl)silyl]oxy}methyl)-3-chloro-4-[(2R,6S)-2,6-dimethylmorpholin-4-yl]-2-fluorophenyl}(pyrimidin-4-yl)methanone (Intermediate 110)

MS (ES) MH⁺: 375.2 for $C_{18}H_{19}ClN_4O_3$.

Intermediate 357

{7-chloro-6-[(2R,6S)-2,6-dimethylmorpholin-4-yl]-3-(pyrimidin-5-yl)-1,2-benzoxazol-5-yl}methanol Starting material: {5-({[tert-butyl(diphenyl)silyl]oxy}methyl)-3-chloro-4-[(2R,6S)-2,6-dimethylmorpholin-4-yl]-2-fluorophenyl}(pyrimidin-5-yl)methanone (Intermediate 111).

MS (ES) MH⁺: 375.2 for $C_{18}H_{19}ClN_4O_3$

Intermediate 358

{7-chloro-6-[(2R,6S)-2,6-dimethylmorpholin-4-yl]-3-(pyridazin-4-yl)-1,2-benzoxazol-yl}methanol Starting material: {5-({[tert-butyl(diphenyl)silyl]oxy}methyl)-3-chloro-4-[(2R,6S)-2,6-dimethylmorpholin-4-yl]-2-fluorophenyl}(pyridazin-4-yl)methanone (Intermediate 112).

MS (ES) MH⁺: 375.2 for $C_{18}H_{19}ClN_4O_3$

Intermediate 359

(6,7-difluoro-3-(1-methyl-1H-1,2,4-triazol-5-yl)benzo[d]isoxazol-5-yl)methanol

Starting material: (5-((tert-butyldiphenylsilyloxy)methyl)-2,3,4-trifluorophenyl)(1-methyl-1H-1,2,4-triazol-5-yl)methanone (Intermediate 333).

MS (ES) MH⁺: 267 for $C_{11}H_8F_2N_4O_2$

¹H NMR (300 MHz, DMSO-d₆) δ ppm 4.3 (s, 3H), 4.7 (d, 2H), 5.7 (t, 1H), 8.3 (d, 1H), 8.4 (s, 1H).

Intermediate 360

(7-chloro-6-((2R,6S)-2,6-dimethylmorpholino)-3-(pyrazin-2-yl)isoxazolo[4,5-b]pyridin-5-yl)methanol Starting material: (6-((tert-butyldiphenylsilyloxy)methyl)-4-chloro-5-((2R,6S)-2,6-dimethylmorpholino)-3-fluoropyridin-2-yl)(pyrazin-2-yl)methanone (1.1 g, 1.78 mmol) (Intermediate 143).

MS (ES) MH⁺: 376 for $C_{17}H_{18}ClN_5O_3$

¹H NMR (300 MHz, DMSO-d₆) δ: 1.0-1.1 (m, 6H), 3.0 (d, 4H), 3.7-3.9 (m, 2H), 4.8 (td, 2H), 5.2 (br.s., 1H), 8.7-8.8 (m, 2H), 9.5 (d, 1H).

Intermediate 361

(7-chloro-6-((2R,6S)-2,6-dimethylmorpholino)-3-(thiazol-2-yl)isoxazolo[4,5-b]pyridin-5-yl)methanol Starting material: (6-((tert-butyldiphenylsilyloxy)methyl)-4-chloro-5-((2R,6S)-2,6-dimethylmorpholino)-3-fluoropyridin-2-yl)(thiazol-2-yl)methanone (Intermediate 144).

MS (ES) MH⁺: 381 for $C_{16}H_{17}ClN_4O_3S$

¹H NMR (300 MHz, CDCl₃) δ: 1.1-1.2 (m, 6H), 2.8 (br.s., 4H), 3.3 (br.s., 2H), 3.8 (br.s., 2H), 4.9 (s, 1H), 7.7 (d, 1H), 8.2 (d, 1H).

Intermediate 362

(7-chloro-6-((2R,6S)-2,6-dimethylmorpholino)-3-(4-methylthiazol-2-yl)isoxazolo[4,5-b]pyridin-5-yl)methanol Starting material: (6-((tert-butyldiphenylsilyloxy)methyl)-4-chloro-5-((2R,6S)-2,6-dimethylmorpholino)-3-fluoropyridin-2-yl)(4-methylthiazol-2-yl)methanone (Intermediate 145).

MS (ES) MH$^+$: 395 for $C_{17}H_{19}ClN_4O_3S$
$^1$H NMR (300 MHz, CDCl$_3$) δ: 1.1-1.2 (m, 6H), 2.7 (br.s., 4H), 2.8 (s, 3H), 3.3 (br.s., 2H), 3.8 (br.s., 2H), 4.9 (s, 1H), 7.5 (s, 1H).

Intermediate 363

(7-chloro-6-((2R,6S)-2,6-dimethylmorpholino)-3-(1-methyl-1H-imidazol-2-yl)isoxazolo[4,5-b]pyridin-5-yl)methanol Starting material: (6-((tert-butyldiphenylsilyloxy)methyl)-4-chloro-5-((2R,6S)-2,6-dimethylmorpholino)-3-fluoropyridin-2-yl)(1-methyl-1H-imidazol-2-yl)methanone (Intermediate 99).

MS (ES) MH$^+$: 378 for $C_{17}H_{20}ClN_5O_3$
$^1$H NMR (300 MHz, CDCl$_3$) δ: 1.1-1.2 (m, 6H), 2.8 (br.s., 4H), 3.2 (br.s., 2H), 3.8 (br.s., 2H), 4.0 (s, 3H), 4.9 (br.s., 1H), 7.1 (s, 1H), 7.3 (br.s., 1H).

Intermediate 364

(7-chloro-6-((2R,6S)-2,6-dimethylmorpholino)-3-(thiazol-5-yl)isoxazolo[4,5-b]pyridin-5-yl)methanol Starting material: (6-((tert-butyldiphenylsilyloxy)methyl)-4-chloro-5-((2R,6S)-2,6-dimethylmorpholino)-3-fluoropyridin-2-yl)(thiazol-5-yl)methanone (Intermediate 100).

MS (ES) MH$^+$: 381 for $C_{16}H_{17}ClN_4O_3S$
$^1$H NMR (300 MHz, CDCl$_3$) δ: 1.1-1.2 (m, 6H), 2.8 (br.s., 2H), 3.3 (br.s., 2H), 3.8 (br.s., 2H), 4.9 (s, 2H), 9.0 (2s, 2H).

Intermediate 365

(7-chloro-6-((2R,6S)-2,6-dimethylmorpholino)-3-(2-methylthiazol-5-yl)isoxazolo[4,5-b]pyridin-5-yl)methanol Starting material: (6-((tert-butyldiphenylsilyloxy)methyl)-4-chloro-5-((2R,6S)-2,6-dimethylmorpholino)-3-fluoropyridin-2-yl)(2-methylthiazol-5-yl)methanone (Intermediate 101).

MS (ES) MH$^+$: 395 for $C_{16}H_{17}ClN_4O_3S$
$^1$H NMR (300 MHz, CDCl$_3$) δ: 1.1-1.2 (m, 6H) 2.7-2.9 (m, 5H), 3.3 (br.s., 2H), 3.8 (br.s., 2H), 4.9 (s, 2H), 8.7 (s, 1H).

Intermediate 366

(7-chloro-6-((2R,6S)-2,6-dimethylmorpholino)-3-(1-methyl-1H-1,2,4-triazol-5-yl)isoxazolo[4,5-b]pyridin-5-yl)methanol Starting material: (6-((tert-butyldiphenylsilyloxy)methyl)-4-chloro-5-((2R,6S)-2,6-dimethylmorpholino)-3-fluoropyridin-2-yl)(1-methyl-1H-1,2,4-triazol-5-yl)methanone (Intermediate 146).

MS (ES) MH$^+$: 379 for $C_{16}H_{19}ClN_6O_3$

Intermediate 367

4-(7-chloro-6-((2R,6S)-2,6-dimethylmorpholino)-5-(hydroxymethyl)isoxazolo[4,5-b]pyridin-3-yl)-2-fluorobenzonitrile Starting material: 4-(6-((tert-butyldiphenylsilyloxy)methyl)-4-chloro-5-((2R,6S)-2,6-dimethylmorpholino)-3-fluoropicolinoyl)-2-fluorobenzonitrile (Intermediate 102).

MS (ES) MH$^+$: 417 for $C_{20}H_{18}ClN_4O_3$
$^1$H NMR (300 MHz, CDCl$_3$) δ: 1.1-1.3 (m, 6H), 2.8 (br.s., 2H), 3.3 (br.s., 2H), 3.8 (br.s., 2H), 4.9 (s, 2H), 7.8 (dd, 1H), 8.2-8.4 (m, 2H).

Intermediate 368

(7-chloro-6-((2R,6S)-2,6-dimethylmorpholino)-3-(5-methylthiazol-2-yl)isoxazolo[4,5-b]pyridin-5-yl)methanol Starting material: (6-((tert-butyldiphenylsilyloxy)methyl)-4-chloro-5-((2R,6S)-2,6-dimethylmorpholino)-3-fluoropyridin-2-yl)(5-methylthiazol-2-yl)methanone (Intermediate 103).

MS (ES) MH$^+$: 395 for $C_{17}H_{19}ClN_4O_3S$
$^1$H NMR (300 MHz, CDCl$_3$) δ: 1.1-1.2 (m, 6H), 2.5-2.7 (m, 3H), 2.8 (br.s., 2H), 3.3 (br.s., 2H), 3.8 (br.s., 2H), 4.9 (s, 2H), 7.8 (d, 1H).

Intermediate 369

5-(7-chloro-6-((2R,6S)-2,6-dimethylmorpholino)-5-(hydroxymethyl)isoxazolo[4,5-b]pyridin-3-yl)picolinonitrile Starting material: 5-(6-((tert-butyldiphenylsilyloxy)methyl)-4-chloro-5-((2R,6S)-2,6-dimethylmorpholino)-3-fluoropicolinoyl)picolinonitrile (Intermediate 147).

MS (ES) MH$^+$: 400 for $C_{19}H_{18}ClN_5O_3$
$^1$H NMR (300 MHz, CDCl$_3$) δ: 1.1-1.2 (m, 6H), 2.8 (br.s., 2H), 3.3 (br.s., 2H), 3.8 (br.s., 2H), 4.9 (s, 2H), 8.8 (dd, 1H), 9.7 (d, 1H).

Intermediate 370

(3-(2-bromothiazol-5-yl)-7-chloro-6-((2R,6S)-2,6-dimethylmorpholino)isoxazolo[4,5-b]pyridin-5-yl)methanol Starting material: (2-bromothiazol-5-yl)(6-((tert-butyldiphenylsilyloxy)methyl)-4-chloro-5-((2R,6S)-2,6-dimethylmorpholino)-3-fluoropyridin-2-yl)methanone (Intermediate 104).

MS (ES) MH$^+$: 460 for $C_{16}H_{16}ClBrN_4O_3S$
$^1$H NMR (300 MHz, CDCl$_3$) δ: 1.1-1.2 (m, 6H), 2.7-2.9 (m, 2H), 3.3 (br.s., 2H), 3.8 (br.s., 2H), 4.9 (s, 2H), 8.6 (s, 1H).

Intermediate 371

(7-chloro-3-(2,4-dichlorothiazol-5-yl)-6-((2R,6S)-2,6-dimethylmorpholino)isoxazolo[4,5-b]pyridin-5-yl)methanol Starting material: (6-((tert-butyldiphenylsilyloxy)methyl)-4-chloro-5-((2R,6S)-2,6-dimethylmorpholino)-3-fluoropyridin-2-yl)(2,4-dichlorothiazol-5-yl)methanone (Intermediate 105).

MS (ES) MH$^+$: 449 for $C_{16}H_{15}Cl_3N_4O_3S$
$^1$H NMR (300 MHz, CDCl$_3$) δ: 1.1-1.2 (m, 6H), 2.7-2.9 (m, 2H), 3.3 (br.s., 2H), 3.8 (br.s., 2H), 4.9 (s, 2H).

Intermediate 372

{7-chloro-6-[(2R,6S)-2,6-dimethylmorpholin-4-yl]-3-methyl-1,2-benzoxazol-5-yl}methanol To a stirred solution of NaBH$_4$ (78 mg, 2.43 mmol) in diglyme (1 mL) was added BF3 (1.6 mL, 2.59 mmol), and the thus generated diborane gas was purged into solution of 7-chloro-6-[(2R,6S)-2,6-dimethylmorpholin-4-yl]-3-methyl-1,2-benzoxazole-5-carboxylic acid (Intermediate 302, 250 mg, 0.8 mmol) in THF (1 mL). The mixture was stirred at room temperature for 30 minutes before being quenched with methanol (1 mL) and concentrated. The residue was purified by column chromatography to give product as solid. Yield: 130 mg (52%).

MS (ES) MH$^+$: 311 for $C_{15}H_{19}ClN_2O_3$.

Intermediate 373 was prepared from the indicated starting material using a method similar to the one described for the synthesis of Intermediate 372:

Intermediate 373

{7-chloro-3-cyclopropyl-6-[(2R,6S)-2,6-dimethyl-morpholin-4-yl]-1,2-benzoxazol-5-yl}methanol Starting material: 7-chloro-3-cyclopropyl-6-[(2R,6S)-2,6-dimethylmorpholin-4-yl]-1,2-benzoxazole-5-carboxylic acid (Intermediate 354).

MS (ES) MH$^+$: 337 for $C_{17}H_{21}ClN_2O_3$

Intermediate 374

6,7-difluoro-3-methylbenzo[d]isoxazole-5-carbaldehyde

To an ice-cooled solution of (6,7-difluoro-3-methyl-1,2-benzisoxazol-5-yl)methanol (Intermediate 334, 200 mg, 1.0 mmol) in $CH_2Cl_2$ (10 mL) was added NMO (235 mg, 2.0 mmol) followed TPAP (35 mg, 0.1 mmol) and mixture stirred for 2 hours at room temperature. The reaction mixture filtered thorough silica gel bed and washed with EtOAc. The organic phase was concentrated under reduced pressure to give product as a yellow solid. Yield: 150 mg (76%).

MS (ES) MH$^+$: 198 for $C_9H_5F_2NO_2$ $^1$H NMR (400 MHz, DMSO-d$_6$) δ: 2.5 (s, 3H), 8.3 (dd, 1H), 10.2 (s, 1H).

Intermediate 374 (Alternate Method)

6,7-difluoro-3-methylbenzo[d]isoxazole-5-carbaldehyde

A mixture of (6,7-difluoro-3-methyl-1,2-benzisoxazol-5-yl)methanol (Intermediate 334, 0.7 g, 3.51 mmol) and manganese dioxide (6.11 g, 70.30 mmol) in $CH_2Cl_2$ (70 ml) was stirred at room temperature for 3 days. TLC shows conversion to a higher Rf spot with starting material. Additional $MnO_2$ (5 g) was added and the mixture was heated to reflux for 24 hours. The mixture was filtered through celite and rinsed well with $CH_2Cl_2$. Solvent was removed from the filtrate to give 640 mg of product as a tan solid.

MS (ES) MH$^+$: 198 for $C_9H_5F_2NO_2$ $^1$H NMR (300 MHz, CHLOROFORM-d) δ ppm 2.6 (s, 3H), 8.0 (d, 1H), 10.4 (s, 1H).

Intermediate 375

7-chloro-6-[(2R,6S)-2,6-dimethylmorpholin-4-yl]-3-methyl-1,2-benzoxazole-5-carbaldehyde To the solution of {7-chloro-6-[(2R,6S)-2,6-dimethylmorpholin-4-yl]-3-methyl-1,2-benzoxazol-5-yl}methanol (Intermediate 372, 130 mg, 4.4 mmol) in anhydrous DCM (5 mL), was added NMO (103 mg, 8.8 mmol) and TPAP (31 mg, 0.88 mmol) at 0° C. and allowed to stir for 1 h at room temperature. The reaction mixture was filtered and the solvents were removed under vacuum and the residue was purified over silica gel chromatography column using ethylacetate-pet. ether gradient to give solid. Yield: 35 mg, (27%).

MS (ES) MH$^+$: 309 for $C_{15}H_{17}ClN_2O_3$

Intermediates 376 to 393 were prepared from the indicated starting materials using a method similar to the one described for the synthesis of Intermediate 375:

Intermediate 376

7-chloro-6-[(2R,6S)-2,6-dimethylmorpholin-4-yl]-3-(pyridin-2-yl)-1,2-benzoxazole-5-carbaldehyde Starting material: {7-chloro-6-[(2R,6S)-2,6-dimethylmorpholin-4-yl]-3-(pyridin-2-yl)-1,2-benzoxazol-5-yl}methanol (Intermediate 303)

MS (ES) MH$^+$: 372 for $C_{19}H_{18}ClN_3O_3$.

Intermediate 377

7-chloro-3-cyclopropyl-6-[(2R,6S)-2,6-dimethylmorpholin-4-yl]-1,2-benzoxazole-5-carbaldehyde Starting material: {7-chloro-3-cyclopropyl-6-[(2R,6S)-2,6-dimethylmorpholin-4-yl]-1,2-benzoxazol-5-yl}methanol (Intermediate 373)

MS (ES) MH$^+$: 335 for $C_{17}H_{19}ClN_2O_3$.

Intermediate 378

7-chloro-6-[(2R,6S)-2,6-dimethylmorpholin-4-yl]-3-(6-methylpyridin-3-yl)-1,2-benzoxazole-5-carbaldehyde Starting material: {7-chloro-6-[(2R,6S)-2,6-dimethylmorpholin-4-yl]-3-(6-methylpyridin-3-yl)-1,2-benzoxazol-5-yl}methanol (Intermediate 304)

MS (ES) MH$^+$: 386.4 for $C_{20}H_{20}ClN_3O_3$.

Intermediate 379

7-chloro-6-[(2R,6S)-2,6-dimethylmorpholin-4-yl]-3-(1,3-thiazol-5-yl)-7,7a-dihydro-1,2-benzoxazole-5-carbaldehyde Starting material: {7-chloro-6-[(2R,6S)-2,6-dimethylmorpholin-4-yl]-3-(1,3-thiazol-5-yl)-7,7a-dihydro-1,2-benzoxazol-5-yl}methanol (Intermediate 305).

MS (ES) MH$^+$: 380 for $C_{17}H_{19}ClN_3O_3S$;

Intermediate 380

7-chloro-6-[(2R,6S)-2,6-dimethylmorpholin-4-yl]-3-(pyrimidin-2-yl)-1,2-benzoxazole-5-carbaldehyde Starting material: {7-chloro-6-[(2R,6S)-2,6-dimethylmorpholin-4-yl]-3-(pyrimidin-2-yl)-1,2-benzoxazol-5-yl}methanol (Intermediate 355).

MS (ES) MH$^+$: 373 for $C_{18}H_{17}ClN_4O_3$

Intermediate 381

7-chloro-6-[(2R,6S)-2,6-dimethylmorpholin-4-yl]-3-(pyrimidin-4-yl)-1,2-benzoxazole-5-carbaldehyde Starting material: {7-chloro-6-[(2R,6S)-2,6-dimethylmorpholin-4-yl]-3-(pyrimidin-4-yl)-1,2-benzoxazol-5-yl}methanol (Intermediate 356).

MS (ES) MH$^+$: 375.2 for $C_{18}H_{19}ClN_4O_3$.

Intermediate 382

7-chloro-6-[(2R,6S)-2,6-dimethylmorpholin-4-yl]-3-(pyrimidin-5-yl)-1,2-benzoxazole-5-carbaldehyde Starting material: {7-chloro-6-[(2R,6S)-2,6-dimethylmorpholin-4-yl]-3-(pyrimidin-5-yl)-1,2-benzoxazol-5-yl}methanol (Intermediate 357).

MS (ES) MH$^+$: 373 for $C_{18}H_{17}ClN_4O_3$

Intermediate 383

7-chloro-6-[(2R,6S)-2,6-dimethylmorpholin-4-yl]-3-(pyridazin-4-yl)-1,2-benzoxazole-5-carbaldehyde Starting material: {7-chloro-6-[(2R,6S)-2,6-dimethylmorpholin-4-yl]-3-(pyridazin-4-yl)-1,2-benzoxazol-5-yl}methanol (Intermediate 358).
MS (ES) MH$^+$: 373.2 for $C_{18}H_{17}ClN_4O_3$ Intermediate 384

7-chloro-6-[(2R,6S)-2,6-dimethylmorpholin-4-yl]-3-(pyridin-4-yl)-1,2-benzoxazole-5-carbaldehyde Starting material: {7-chloro-6-[(2R,6S)-2,6-dimethylmorpholin-4-yl]-3-(pyridin-4-yl)-1,2-benzoxazol-5-yl}methanol (Intermediate 306)
MS (ES) MH$^+$: 372 for $C_{19}H_{18}ClN_3O_3$ Intermediate 385

7-chloro-6-[(2R,6S)-2,6-dimethylmorpholin-4-yl]-3-(pyridin-3-yl)-1,2-benzoxazole-5-carbaldehyde Starting material: {7-chloro-6-[(2R,6S)-2,6-dimethylmorpholin-4-yl]-3-(pyridin-3-yl)-1,2-benzoxazol-5-yl}methanol (Intermediate 307).
MS (ES) MH$^+$: 372 for $C_{19}H_{18}ClN_3O_3$;

Intermediate 386

7-chloro-6-[(2R,6S)-2,6-dimethylmorpholin-4-yl]-3-(1,3-thiazol-2-yl)-1,2-benzoxazole-5-carbaldehyde Starting material: {7-chloro-6-[(2R,6S)-2,6-dimethylmorpholin-4-yl]-3-(1,3-thiazol-2-yl)-1,2-benzoxazol-5-yl}methanol (Intermediate 308).
MS (ES) MH$^+$: 380 for $C_{17}H_{18}ClN_3O_3S$;

Intermediate 387

7-chloro-6-[(2R,6S)-2,6-dimethylmorpholin-4-yl]-3-(1-methyl-1H-imidazol-2-yl)-1,2-benzoxazole-5-carbaldehyde Starting material: {7-chloro-6-[(2R,6S)-2,6-dimethylmorpholin-4-yl]-3-(1-methyl-1H-imidazol-2-yl)-1,2-benzoxazol-5-yl}methanol (Intermediate 309).
MS (ES) MH$^+$: 375.4 for $C_{18}H_{19}ClN_4O$;

Intermediate 388

7-chloro-6-[(2R,6S)-2,6-dimethylmorpholin-4-yl]-3-(methoxymethyl)-1,2-benzoxazole-5-carbaldehyde Starting material: {7-chloro-6-[(2R,6S)-2,6-dimethylmorpholin-4-yl]-3-(methoxymethyl)-1,2-benzoxazol-5-yl}methanol (Intermediate 310)
MS (ES) MH$^+$: 339 for $C_{16}H_{19}ClN_2O_4$.

Intermediate 389

6-[(2R,6S)-2,6-dimethylmorpholin-4-yl]-7-fluoro-3-[4-(morpholin-4-ylcarbonyl)-1,3-thiazol-2-yl]-1,2-benzoxazole-5-carbaldehyde Starting material: (2-{6-[(2R,6S)-2,6-dimethylmorpholin-4-yl]-7-fluoro-5-(hydroxymethyl)-1,2-benzoxazol-3-yl}-1,3-thiazol-4-yl)(morpholin-4-yl)methanone (Intermediate 321).
MS (ES) MH$^+$: 475 for $C_{22}H_{23}FN_4O_4S$.

Intermediate 390

6-[(2R,6S)-2,6-dimethylmorpholin-4-yl]-7-fluoro-3-[4-(morpholin-4-ylcarbonyl)-1,3-thiazol-5-yl]-1,2-benzoxazole-5-carbaldehyde Starting material: (5-{6-[(2R,6S)-2,6-dimethylmorpholin-4-yl]-7-fluoro-5-(hydroxymethyl)-1,2-benzoxazol-3-yl}-1,3-thiazol-4-yl)(morpholin-4-yl)methanone (Intermediate 322)
MS (ES) MH$^+$: 475 for $C_{22}H_{23}FN_4O_4S$ Intermediate 391

2-{6-[(2R,6S)-2,6-dimethylmorpholin-4-yl]-7-fluoro-5-formyl-1,2-benzoxazol-3-yl}-N,N-dimethyl-1,3-thiazole-4-carboxamide Starting material: 2-{6-[(2R,6S)-2,6-dimethylmorpholin-4-yl]-7-fluoro-5-(hydroxymethyl)-1,2-benzoxazol-3-yl}-N,N-dimethyl-1,3-thiazole-4-carboxamide (Intermediate 323)
MS (ES) MH$^+$: 433 for $C_{20}H_{21}FN_4O_4S$ Intermediate 392

2-{6-[(2R,6S)-2,6-dimethylmorpholin-4-yl]-7-fluoro-5-formyl-1,2-benzoxazol-3-yl}-N,N-dimethyl-1,3-thiazole-5-carboxamide Starting material: 2-{6-[(2R,6S)-2,6-dimethylmorpholin-4-yl]-7-fluoro-5-(hydroxymethyl)-1,2-benzoxazol-3-yl}-N,N-dimethyl-1,3-thiazole-5-carboxamide (Intermediate 324)
MS (ES) MH$^+$: 433.2 for $C_{20}H_{21}FN_4O_4S$ Intermediate 393

5-{6-[(2R,6S)-2,6-dimethylmorpholin-4-yl]-7-fluoro-5-formyl-1,2-benzoxazol-3-yl}-1,3-thiazole-4-carbonitrile Starting material: 5-{6-[(2R,6S)-2,6-dimethylmorpholin-4-yl]-7-fluoro-5-(hydroxymethyl)-1,2-benzoxazol-3-yl}-1,3-thiazole-4-carbonitrile (Intermediate 325)
MS (ES) MH$^+$: 386.4 for $C_{18}H_{15}FN_4O_3S$.

Intermediate 394

6-[(2R,6S)-2,6-dimethylmorpholin-4-yl]-7-fluoro-3-(2-methyl-1,3-oxazol-4-yl)-1,2-benzoxazole-5-carbaldehyde MnO$_2$ (227 mg, 2.8 mmol) was added at 0° C. to a solution of {6-[(2R,6S)-2,6-dimethylmorpholin-4-yl]-7-fluoro-3-(2-methyl-1,3-oxazol-4-yl)-1,2-benzoxazol-5-yl}methanol Intermediate 311, 50 mg, 0.13 mmol) in anhydrous DCM (5 mL), and the mixture was allowed to stir for 1 h at room temperature. The reaction mixture was filtered and the solvents were removed under vacuum and the residue was purified by silica gel chromatography using ethyl acetate-pet. ether gradient to give product as a solid. Yield: 37 mg, (75%).
MS (ES) MH$^+$: 360 for $C_{18}H_{18}FN_3O_4$ Intermediates 395 to 403 were prepared from the indicated starting materials using a method similar to the one described for the synthesis of Intermediate 394:

Intermediate 395

6-[(2R,6S)-2,6-dimethylmorpholin-4-yl]-7-fluoro-3-(5-methyl-1,2-oxazol-3-yl)-1,2-benzoxazole-5-carbaldehyde Starting material: {6-[(2R,6S)-2,6-dimethylmorpholin-4-yl]-7-fluoro-3-(5-methyl-1,2-oxazol-3-yl)-1,2-benzoxazol-5-yl}methanol (Intermediate 312)
MS (ES) MH$^+$: 360 for $C_{18}H_{18}FN_3O_4$

Intermediate 396

6-[(2R,6S)-2,6-dimethylmorpholin-4-yl]-3-(3,5-dimethyl-1,2-oxazol-4-yl)-7-fluoro-1,2-benzoxazole-5-carbaldehyde Starting material: {6-[(2R,6S)-2,6-dimethylmorpholin-4-yl]-3-(3,5-dimethyl-1,2-oxazol-4-yl)-7-fluoro-1,2-benzoxazol-5-yl}methanol (Intermediate 313)
MS (ES) MH$^+$: 374 for $C_{19}H_{20}FN_3O_4$

Intermediate 397

6-[(2R,6S)-2,6-dimethylmorpholin-4-yl]-7-fluoro-3-(1-methyl-1H-imidazol-2-yl)-1,2-benzoxazole-5-carbaldehyde Starting material: {6-[(2R,6S)-2,6-dimethylmorpholin-4-yl]-7-fluoro-3-(1-methyl-1H-imidazol-2-yl)-1,2-benzoxazol-5-yl}methanol (Intermediate 314)
MS (ES) MH$^+$: 359 for $C_{18}H_{19}FN_4O_3$;

Intermediate 398

6-[(2R,6S)-2,6-dimethylmorpholin-4-yl]-7-fluoro-3-(1-methyl-1H-imidazol-4-yl)-1,2-benzoxazole-5-carbaldehyde Starting material: {6-[(2R,6S)-2,6-dimethylmorpholin-4-yl]-7-fluoro-3-(1-methyl-1H-imidazol-4-yl)-1,2-benzoxazol-5-yl}methanol (Intermediate 315)
MS (ES) MH$^+$: 359 for $C_{18}H_{19}FN_4O_3$;

Intermediate 399

6-[(2R,6S)-2,6-dimethylmorpholin-4-yl]-7-fluoro-3-(1-methyl-1H-imidazol-5-yl)-1,2-benzoxazole-5-carbaldehyde Starting material: {6-[(2R,6S)-2,6-dimethylmorpholin-4-yl]-7-fluoro-3-(1-methyl-1H-imidazol-5-yl)-1,2-benzoxazol-5-yl}methanol (Intermediate 316)
MS (ES) MH$^+$: 359 for $C_{18}H_{19}FN_4O_3$;

Intermediate 400

6-[(2R,6S)-2,6-dimethylmorpholin-4-yl]-7-fluoro-3-(4-methyl-1,3-thiazol-5-yl)-1,2-benzoxazole-5-carbaldehyde Starting material: {6-[(2R,6S)-2,6-dimethylmorpholin-4-yl]-7-fluoro-3-(4-methyl-1,3-thiazol-5-yl)-1,2-benzoxazol-5-yl}methanol (Intermediate 317)
MS (ES) MH$^+$: 377 for $C_{18}H_{20}FN_3O_3S$;

Intermediate 401

6-[(2R,6S)-2,6-dimethylmorpholin-4-yl]-7-fluoro-3-(4-methyl-1,2,3-thiadiazol-5-yl)-1,2-benzoxazole-5-carbaldehyde Starting material: {6-[(2R,6S)-2,6-dimethylmorpholin-4-yl]-7-fluoro-3-(4-methyl-1,2,3-thiadiazol-5-yl)-1,2-benzoxazol-5-yl}methanol (Intermediate 318)
MS (ES) MH$^+$: 377.2 for $C_{17}H_{17}FN_4O_3S$

Intermediate 402

6-[(2R,6S)-2,6-dimethylmorpholin-4-yl]-7-fluoro-3-(pyridazin-3-yl)-1,2-benzoxazole-5-carbaldehyde Starting material: {6-[(2R,6S)-2,6-dimethylmorpholin-4-yl]-7-fluoro-3-(pyridazin-3-yl)-1,2-benzoxazol-5-yl}methanol (Intermediate 319)
MS (ES) MH$^+$: 357 for $C_{18}H_{17}FN_4O_3$

Intermediate 403

6-[(2R,6S)-2,6-dimethylmorpholin-4-yl]-7-fluoro-3-(pyrimidin-4-yl)-1,2-benzoxazole-5-carbaldehyde Starting material: {6-[(2R,6S)-2,6-dimethylmorpholin-4-yl]-7-fluoro-3-(pyrimidin-4-yl)-1,2-benzoxazol-5-yl}methanol (Intermediate 320)
MS (ES) MH$^+$: 357 for $C_{18}H_{17}FN_4O_3$ Intermediates 404 and 405 were prepared from the indicated starting materials using a method similar to the one described for the synthesis of Intermediate 374 (Alternate Method):

Intermediate 404

6,7-difluoro-3-(1-methyl-1H-1,2,4-triazol-5-yl)benzo[d]isoxazole-5-carbaldehyde

Starting material: (6,7-difluoro-3-(1-methyl-1H-1,2,4-triazol-5-yl)benzo[d]isoxazol-5-yl)methanol (Intermediate 359).
MS (ES) MH$^+$: 266 for $C_{11}H_6F_2N_2O_4$
$^1$H NMR (300 MHz, CHLOROFORM-d) δ ppm 4.4 (s, 3H), 8.1 (s, 1H), 8.8 (d, 1H), 10.4 (s, 1).

Intermediate 405

6-((2R,6S)-2,6-dimethylmorpholino)-7-fluoro-3-(5-oxo-4,5-dihydro-1,3,4-oxadiazol-2-yl)benzo[d]isoxazole-5-carbaldehyde Starting material: 5-(6-((2R,6S)-2,6-dimethylmorpholino)-7-fluoro-5-(hydroxymethyl)benzo[d]isoxazol-3-yl)-1,3,4-oxadiazol-2(3H)-one (Intermediate 209)
MS (ES) MH$^+$: 363 for $C_{16}H_{15}FN_4O_5$

Intermediate 406

7-chloro-6-((2R,6S)-2,6-dimethylmorpholino)-3-(pyridin-2-yl)isoxazolo[4,5-b]pyridine-5-carbaldehyde To a stirring solution of (7-chloro-6-((2R,6S)-2,6-dimethylmorpholino)-3-(pyridin-2-yl)isoxazolo[4,5-b]pyridin-5-yl)methanol (Intermediate 201, 0.39 g, 1.04 mmol) in dichloromethane (20 mL) was added Manganese dioxide (0.543 g, 6.24 mmol). The mixture was allowed to stir 2 days at room temperature. The reaction was filtered over Celite®, and the filtrate concentrated under vacuum to give clear oil. The oil was purified on short bed of silica using 20-30% acetone in n-hexane to give 0.16 g (42%) of the title compound as a yellow solid.
$^1$H NMR (300 MHz, DMSO-d$_6$) δ: 1.1 (m, 6H), 3.0-3.1 (m, 2H), 3.1-3.2 (m, 2H), 3.9 (td, 2H), 7.5 (dd, 1H), 7.9 (t, 1H), 8.6 (d, 1H), 8.9 (d, 1H), 10.2 (s, 1H).

Intermediates 407 to 438 were prepared from the indicated starting materials using a method similar to the one described for the synthesis of Intermediate 406:

Intermediate 407

7-chloro-6-((2R,6S)-2,6-dimethylmorpholino)-3-(pyridin-4-yl)isoxazolo[4,5-b]pyridine-5-carbaldehyde Starting material: (7-chloro-6-((2R,6S)-2,6-dimethylmorpholino)-3-(pyridin-4-yl)isoxazolo[4,5-b]pyridin-5-yl)methanol (Intermediate 202).

¹H NMR (300 MHz, DMSO-d₆) δ: 1.1 (m, 6H), 3.0-3.1 (m, 2H), 3.1-3.2 (m, 2H), 3.9 (td, 2H), 8.3-8.4 (m, 2H), 8.8 (dd, 2H), 10.2 (s, 1H).

Intermediate 408

7-chloro-6-((2R,6S)-2,6-dimethylmorpholino)-3-(pyridin-3-yl)isoxazolo[4,5-b]pyridine-5-carbaldehyde Starting material: (7-chloro-6-((2R,6S)-2,6-dimethylmorpholino)-3-(pyridin-3-yl)isoxazolo[4,5-b]pyridin-5-yl)methanol (Intermediate 203).

¹H NMR (300 MHz, DMSO-d₆) δ: 1.1 (m, 6H), 3.0-3.1 (m, 2H), 3.1-3.2 (m, 2H), 3.9 (td, 2H), 7.5 (dd, 1H), 8.7-8.8 (m, 2H), 9.7 (d, 1H), 10.2 (s, 1H)

Intermediate 409

7-chloro-6-((2R,6S)-2,6-dimethylmorpholino)-3-(pyrazin-2-yl)isoxazolo[4,5-b]pyridine-5-carbaldehyde Starting material: (7-chloro-6-((2R,6S)-2,6-dimethylmorpholino)-3-(pyrazin-2-yl)isoxazolo[4,5-b]pyridin-5-yl)methanol (Intermediate 360).

¹H NMR (300 MHz, DMSO-d₆) δ: 1.1 (m, 6H), 3.0-3.1 (m, 2H), 3.1-3.2 (m, 2H), 3.9 (td, 2H), 8.7-8.9 (m, 2H), 9.8 (d, 1H), 10.2 (s, 1H).

Intermediate 410

7-chloro-6-((2R,6S)-2,6-dimethylmorpholino)-3-(thiazol-2-yl)isoxazolo[4,5-b]pyridine-5-carbaldehyde Starting material: (7-chloro-6-((2R,6S)-2,6-dimethylmorpholino)-3-(thiazol-2-yl)isoxazolo[4,5-b]pyridin-5-yl)methanol (Intermediate 361).

¹H NMR (300 MHz, DMSO-d₆) δ: 1.1 (m, 6H), 2.9-3.0 (m, 2H), 3.1-3.2 (m, 2H), 3.9 (td, 2H), 7.7 (d, 1H), 8.2 (d, 1H), 10.2 (s, 1H).

Intermediate 411

7-chloro-6-((2R,6S)-2,6-dimethylmorpholino)-3-(4-methylthiazol-2-yl)isoxazolo[4,5-b]pyridine-5-carbaldehyde Starting material: (7-chloro-6-((2R,6S)-2,6-dimethylmorpholino)-3-(4-methylthiazol-2-yl)isoxazolo[4,5-b]pyridin-5-yl)methanol (Intermediate 362.

¹H NMR (300 MHz, DMSO-d₆) δ: 1.1 (m, 6H), 2.5 (s, 3H), 2.8-3.0 (m, 2H), 3.1-3.2 (m, 2H), 3.8 (d, 2H), 7.8 (s, 1H), 10.2 (s, 1H).

Intermediate 412

7-chloro-6-((2R,6S)-2,6-dimethylmorpholino)-3-(1-methyl-1H-imidazol-2-yl)isoxazolo[4,5-b]pyridine-5-carbaldehyde Starting material: (7-chloro-6-((2R,6S)-2,6-dimethylmorpholino)-3-(1-methyl-1H-imidazol-2-yl)isoxazolo[4,5-b]pyridin-5-yl)methanol (Intermediate 363).

¹H NMR (300 MHz, DMSO-d₆) δ: 1.1 (m, 6H), 2.9-3.0 (m, 2H), 3.1-3.2 (m, 2H), 3.9 (m, 2H), 4.1 (s, 3H), 7.1 (s, 1H), 7.4 (1H), 10.2 (s, 1H).

Intermediate 413

7-chloro-6-((2R,6S)-2,6-dimethylmorpholino)-3-(thiazol-5-yl)isoxazolo[4,5-b]pyridine-5-carbaldehyde Starting material: (7-chloro-6-((2R,6S)-2,6-dimethylmorpholino)-3-(thiazol-5-yl)isoxazolo[4,5-b]pyridin-5-yl)methanol (Intermediate 364).

¹H NMR (300 MHz, DMSO-d₆) δ: 1.0 (m, 6H), 3.0-3.1 (m, 2H), 3.2 (m, 2H), 3.9-4.0 (m, 2H), 9.1 (s, 1H), 9.3 (s, 1H), 10.2 (s, 1H).

Intermediate 414

7-chloro-6-((2R,6S)-2,6-dimethylmorpholino)-3-(2-methylthiazol-5-yl)isoxazolo[4,5-b]pyridine-5-carbaldehyde Starting material: (7-chloro-6-((2R,6S)-2,6-dimethylmorpholino)-3-(2-methylthiazol-5-yl)isoxazolo[4,5-b]pyridin-5-yl)methanol (Intermediate 365).

¹H NMR (300 MHz, DMSO-d₆) δ: 1.0 (m, 6H), 2.8 (s, 3H), 3.0-3.1 (m, 2H), 3.2 (m, 2H), 3.9-4.0 (m, 2H), 8.9 (s, 1H), 10.2 (s, 1H).

Intermediate 415

7-chloro-6-((2R,6S)-2,6-dimethylmorpholino)-3-(1-methyl-1H-1,2,4-triazol-5-yl)isoxazolo[4,5-b]pyridine-5-carbaldehyde Starting material: (7-chloro-6-((2R,6S)-2,6-dimethylmorpholino)-3-(1-methyl-1H-1,2,4-triazol-5-yl)isoxazolo[4,5-b]pyridin-5-yl)methanol (Intermediate 366).

¹H NMR (300 MHz, DMSO-d₆) δ: 1.2 (m, 6H), 2.8-2.9 (m, 2H), 3.0-3.1 (m, 2H), 3.9 (td, 2H), 4.3 (s, 3H), 8.2 (s, 1H), 10.2 (s, 1H).

Intermediate 416

4-(7-chloro-6-((2R,6S)-2,6-dimethylmorpholino)-5-formylisoxazolo[4,5-b]pyridin-3-yl)-2-fluorobenzonitrile Starting material: 4-(7-chloro-6-((2R,6S)-2,6-dimethylmorpholino)-5-(hydroxymethyl)isoxazolo[4,5-b]pyridin-3-yl)-2-fluorobenzonitrile (Intermediate 367).

¹H NMR (300 MHz, DMSO-d₆) δ: 1.1-1.3 (m, 6H), 2.9-3.1 (m, 2H), 3.1-3.2 (m, 2H), 3.9 (td, 2H), 7.8 (dd, 1H), 8.4-8.5 (m, 2H), 10.2 (s, 1H).

Intermediate 417

5-(7-chloro-6-((2R,6S)-2,6-dimethylmorpholino)-5-formylisoxazolo[4,5-b]pyridin-3-yl)picolinonitrile Starting material: 5-(7-chloro-6-((2R,6S)-2,6-dimethylmorpholino)-5-(hydroxymethyl)isoxazolo[4,5-b]pyridin-3-yl)picolinonitrile (Intermediate 369).

¹H NMR (300 MHz, DMSO-d₆) δ: 1.2 (d, 6H), 3.1-3.2 (m, 4H), 3.9-4.1 (m, 2H), 7.9 (dd, 1H), 8.3-8.5 (m, 1H), 8.9-9.0 (m, 1H), 10.2 (s, 1H).

Intermediate 418

7-chloro-6-((2R,6S)-2,6-dimethylmorpholino)-3-(5-methylthiazol-2-yl)isoxazolo[4,5-b]pyridine-5-carbaldehyde Starting material: (7-chloro-6-((2R,6S)-2,6-dimethylmorpholino)-3-(5-methylthiazol-2-yl)isoxazolo[4,5-b]pyridin-5-yl)methanol (0.49 g, 1.24 mmol, Intermediate 368)

¹H NMR (300 MHz, DMSO-d₆) δ: 1.2 (d, 6H), 2.6 (s, 3H), 3.0-3.1 (m, 2H), 3.1-3.2 (m, 2H), 3.8-4.0 (m, 2H), 7.8 (d, 1H), 10.2 (s, 1H).

Intermediate 419

7-chloro-6-((2R,6S)-2,6-dimethylmorpholino)-3-(2-bromothiazol-5-yl)isoxazolo[4,5-b]pyridine-5-carbaldehyde Starting material: (3-(2-bromothiazol-5-yl)-7-chloro-6-((2R,6S)-2,6-dimethylmorpholino)isoxazolo[4,5-b]pyridin-5-yl)methanol (Intermediate 370).

¹H NMR (300 MHz, DMSO-d₆) δ: 1.0 (m, 6H), 3.0-3.1 (m, 2H), 3.2 (m, 2H), 3.9-4.0 (m, 2H), 8.9 (s, 1H), 10.2 (s, 1H).

Intermediate 420

7-chloro-6-((2R,6S)-2,6-dimethylmorpholino)-3-(2,4-dichlorothiazol-5-yl)isoxazolo[4,5-b]pyridine-5-carbaldehyde Starting material: (7-chloro-3-(2,4-dichlorothiazol-5-yl)-6-((2R,6S)-2,6-dimethylmorpholino)isoxazolo[4,5-b]pyridin-5-yl)methanol (Intermediate 371).

¹H NMR (300 MHz, DMSO-d₆) δ: 1.0 (m, 6H), 3.0-3.1 (m, 2H), 3.2 (m, 2H), 3.9-4.0 (m, 2H), 10.2 (s, 1H).

Intermediate 421

6-((2R,6S)-2,6-dimethylmorpholino)-7-fluoro-3-(6-methylpyridin-3-yl)benzo[d]isoxazole-5-carbaldehyde Starting material: (6-((2R,6S)-2,6-dimethylmorpholino)-7-fluoro-3-(6-methylpyridin-3-yl)benzo[d]isoxazol-5-yl)methanol (Intermediate 346).

MS (ES) MH⁺: 370 for $C_{20}H_{20}FN_3O_3$

¹H NMR (300 MHz, CDCl₃) δ: 1.23 (d, 6H), 2.70 (s, 3H), 2.98-3.28 (m, 4H), 3.74-4.00 (m, 2H), 7.40 (d, 1H), 8.03-8.33 (m, 2H), 9.09 (d, 1H), 10.38 (s, 1H).

Intermediate 422

6-((2R,6S)-2,6-dimethylmorpholino)-7-fluoro-3-(thiazol-5-yl)benzo[d]isoxazole-5-carbaldehyde Starting material: (6-((2R,6S)-2,6-dimethylmorpholino)-7-fluoro-3-(thiazol-5-yl)benzo[d]isoxazol-5-yl)methanol (Intermediate 345).

MS (ES) MH⁺: 362 for $C_{17}H_{16}FN_3O_3S$

¹H NMR (300 MHz, CDCl₃) δ: 1.23 (d, 6H), 2.44-3.23 (m, 4H), 3.75-4.03 (m, 2H), 8.21 (s, 1H), 8.62 (s, 1H), 9.04 (s, 1H), 10.38 (s, 1H).

Intermediate 423

6-((2R,6S)-2,6-dimethylmorpholino)-7-fluoro-3-(2-fluorophenyl)benzo[d]isoxazole-5-carbaldehyde Starting material: (6-((2R,6S)-2,6-dimethylmorpholino)-7-fluoro-3-(2-fluorophenyl)benzo[d]isoxazol-5-yl)methanol (Intermediate 347).

MS (ES) MH⁺: 373 for $C_{17}H_{16}FN_3O_3S$

¹H NMR (400 MHz, CDCl₃) δ: 1.23 (d, 6H), 2.94-3.30 (m, 4H), 3.79-3.97 (m, 2H), 7.27-7.86 (m, 4H), 8.09 (d, 1H), 10.37 (s, 1H).

Intermediate 424

6-((2R,6S)-2,6-dimethylmorpholino)-7-fluoro-3-(tetrahydro-2H-pyran-4-yl)benzo[d]isoxazole-5-carbaldehyde Starting material: (6-((2R,6S)-2,6-dimethylmorpholino)-7-fluoro-3-(tetrahydro-2H-pyran-4-yl)benzo[d]isoxazol-5-yl)methanol (Intermediate 348).

MS (ES) MH⁺: 363 for $C_{19}H_{23}FN_2O_4$

¹H NMR (400 MHz, CDCl₃) δ: 1.22 (d, 6H), 1.91-2.19 (m, 4H), 2.98-3.21 (m, 4H), 3.25-3.41 (m, 1H), 3.53-3.67 (m, 2H), 3.75-3.97 (m, 2H), 4.06-4.16 (m, 2H), 8.00 (s, 1H), 10.37 (s, 1H).

Intermediate 425

3-((1H-1,2,4-triazol-1-yl)methyl)-6-((2R,6S)-2,6-dimethylmorpholino)-7-fluorobenzo[d]isoxazole-5-carbaldehyde Starting material: (3-((1H-1,2,4-triazol-1-yl)methyl)-6-((2R,6S)-2,6-dimethylmorpholino)-7-fluorobenzo[d]isoxazol-5-yl)methanol (Intermediate 288).

MS (ES) MH⁺: 360 for $C_{17}H_{18}FN_5O_3$

¹H NMR (300 MHz, CDCl₃) δ: 1.08 (d, 6H), 2.81-3.24 (m, 4H), 3.67-3.94 (m, 2H), 6.00 (s, 2H), 7.93 (s, 1H, 8.04 (s, 1H), 8.83 (s, 1H), 10.22 (s, 1H).

Intermediate 426

6-((2R,6S)-2,6-dimethylmorpholino)-7-fluoro-3-(pyridin-4-yl)benzo[d]isoxazole-5-carbaldehyde Starting material: (6-((2R,6S)-2,6-dimethylmorpholino)-7-fluoro-3-(pyridin-4-yl)benzo[d]isoxazol-5-yl)methanol (Intermediate 287).

MS (ES) MH⁺: 356 for $C_{19}H_{18}FN_3O_3$

¹H NMR (300 MHz, CDCl₃) δ: 1.24 (d, 6H), 3.03-3.27 (m, 4H), 3.77-4.01 (m, 2H), 7.87 (d, 2H), 8.20 (s, 1H), 8.86 (d, 2H), 10.38 (s, 1H).

Intermediate 427

6-((2R,6S)-2,6-dimethylmorpholino)-7-fluoro-3-(furan-2-yl)benzo[d]isoxazole-5-carbaldehyde Starting material: (6-((2R,6S)-2,6-dimethylmorpholino)-7-fluoro-3-(furan-2-yl)benzo[d]isoxazol-5-yl)methanol (Intermediate 289).

MS (ES) MH⁺: 345 for $C_{18}H_{17}FN_2O_4$

¹H NMR (300 MHz, CDCl₃) δ: 1.23 (d, 6H), 2.99-3.26 (m, 4H), 3.77-3.98 (m, 2H), 6.65 (dd, 1H), 7.24 (s, 1H), 7.73 (d, 1H), 8.38 (d, 1H), 10.39 (s, 1H).

Intermediate 428

3-(difluoromethyl)-6-((2R,6S)-2,6-dimethylmorpholino)-7-fluorobenzo[d]isoxazole-5-carbaldehyde Starting material: (3-(difluoromethyl)-6-((2R,6S)-2,6-dimethylmorpholino)-7-fluorobenzo[d]isoxazol-5-yl)methanol (Intermediate 291).

MS (ES) MH⁺: 329 for $C_{15}H_{15}F_3N_2O_3$

¹H NMR (300 MHz, CDCl₃) δ: 1.22 (d, 6H), 3.04-3.23 (m, 4H), 3.80-3.99 (m, 2H), 7.00 (t, 1H), 8.15 (s, 1H), 10.34 (s, 1H).

Intermediate 429

6-((2R,6S)-2,6-dimethylmorpholino)-7-fluoro-3-(trifluoromethyl)benzo[d]isoxazole-5-carbaldehyde Starting material: (6-((2R,6S)-2,6-dimethylmorpholino)-7-fluoro-3-(trifluoromethyl)benzo[d]isoxazol-5-yl)methanol (Intermediate 290).
MS (ES) MH$^+$: 347 for $C_{15}H_{14}F_4N_2O_3$
$^1$H NMR (300 MHz, CDCl$_3$) δ: 1.23 (d, 6H), 2.96-3.29 (m, 4H), 3.74-4.03 (m, 2H), 8.06 (s, 1H), 10.32 (s, 1H).

Intermediate 430

6-((2R,6R)-2,6-dimethylmorpholino)-7-fluoro-3-(thiazol-2-yl)benzo[d]isoxazole-5-carbaldehyde Starting material: (6-((2R,6R)-2,6-dimethylmorpholino)-7-fluoro-3-(thiazol-2-yl)benzo[d]isoxazol-5-yl)methanol (Intermediate 349).
MS (ES) MH$^+$: 362 for $C_{17}H_{16}FN_3O_3S$
$^1$H NMR (300 MHz, CDCl$_3$) δ: 1.33 (d, 6H), 2.89-3.22 (m, 2H), 3.31-3.52 (m, 2H), 4.07-4.36 (m, 2H), 7.59 (d, 1H), 8.12 (d, 1H), 8.55-8.72 (s, 1H), 10.48 (s, 1H).

Intermediate 431

3-(difluoromethyl)-6-((2R,6R)-2,6-dimethylmorpholino)-7-fluorobenzo[d]isoxazole-5-carbaldehyde Starting material: (3-(difluoromethyl)-6-((2R,6R)-2,6-dimethylmorpholino)-7-fluorobenzo[d]isoxazol-5-yl)methanol (Intermediate 292).
MS (ES) MH$^+$: 329 for $C_{15}H_{15}F_3N_2O_3$
$^1$H NMR (300 MHz, CDCl$_3$) δ: 1.32 (d, 6H), 2.93-3.52 (m, 4H), 4.07-4.36 (m, 2H), 7.01 (t, 1H), 8.16 (s, 1H), 10.44 (s, 1H).

Intermediate 432

3-(3-chloropyrazin-2-yl)-6-((2R,6S)-2,6-dimethylmorpholino)-7-fluorobenzo[d]isoxazole-5-carbaldehyde Starting material: (3-(3-chloropyrazin-2-yl)-6-((2R,6S)-2,6-dimethylmorpholino)-7-fluorobenzo[d]isoxazol-5-yl)methanol (Intermediate 328).
MS (ES) MH$^+$: 391 for $C_{18}H_{16}ClFN_4O_3$ Intermediate 433

6-((2R,6R)-2,6-dimethylmorpholino)-7-fluoro-3-(5-morpholinopyrazin-2-yl)benzo[d]isoxazole-5-carbaldehyde Starting material: (6-((2R,6R)-2,6-dimethylmorpholino)-7-fluoro-3-(5-morpholinopyrazin-2-yl)benzo[d]isoxazol-5-yl)methanol (Intermediate 335).
MS (ES) MH$^+$: 442 (M+H) for $C_{22}H_{24}FN_5O_4$ Intermediate 434

3-(6-chloropyrazin-2-yl)-6-((2R,6S)-2,6-dimethylmorpholino)-7-fluorobenzo[d]isoxazole-5-carbaldehyde Starting material: (3-(6-chloropyrazin-2-yl)-6-((2R,6S)-2,6-dimethylmorpholino)-7-fluorobenzo[d]isoxazol-5-yl)methanol (Intermediate 282)
MS (ES) MH$^+$: 391 for $C_{18}H_{16}ClFN_4O_3$ Intermediate 435

6-((2R,6S)-2,6-dimethylmorpholino)-7-fluoro-3-(5-(methylthio)pyrazin-2-yl)benzo[d]isoxazole-5-carbaldehyde Starting material: (6-((2R,6S)-2,6-dimethylmorpholino)-7-fluoro-3-(5-(methylthio)pyrazin-2-yl)benzo[d]isoxazol-5-yl)methanol (Intermediate 283)
MS (ES) MH$^+$: 403 for $C_{19}H_{19}FN_4O_3S$ Intermediate 436

6-((2R,6R)-2,6-dimethylmorpholino)-7-fluoro-3-(6-methoxypyrazin-2-yl)benzo[d]isoxazole-5-carbaldehyde Starting material: (6-((2R,6R)-2,6-dimethylmorpholino)-7-fluoro-3-(6-methoxypyrazin-2-yl)benzo[d]isoxazol-5-yl)methanol (Intermediate 351)
MS (ES) MH$^+$: 387 for $C_{19}H_{19}FN_4O_4$ Intermediate 437

6-((2R,6R)-2,6-dimethylmorpholino)-7-fluoro-3-(2-(methylthio)pyrimidin-4-yl)benzo[d]isoxazole-5-carbaldehyde Starting material: (6-((2R,6R)-2,6-dimethylmorpholino)-7-fluoro-3-(2-(methylthio)pyrimidin-4-yl)benzo[d]isoxazol-5-yl)methanol (Intermediate 284)
MS (ES) MH$^+$: 403 (M+H) for $C_{19}H_{19}FN_4O_3S$ Intermediate 438

6-((2R,6R)-2,6-dimethylmorpholino)-7-fluoro-3-(pyrazin-2-yl)benzo[d]isoxazole-5-carbaldehyde Starting material: (6-((2R,6R)-2,6-dimethylmorpholino)-7-fluoro-3-(pyrazin-2-yl)benzo[d]isoxazol-5-yl)methanol (Intermediate 350).
MS (ES) MH$^+$: 357 for $C_{18}H_{17}FN_4O_3$ Intermediate 439 ethyl 6-((2R,6S)-2,6-dimethylmorpholino)-7-fluoro-5-formylbenzo[d]isoxazole-3-carboxylate Ethyl 6-((2R,6S)-2,6-dimethylmorpholino)-7-fluoro-5-(hydroxymethyl)benzo[d]isoxazole-3-carboxylate (Intermediate 262, 430 mg, 1.22 mmol) was dissolved in dichloromethane (100 ml). Manganese dioxide (2122 mg, 24.41 mmol) was added and the reaction was stirred vigorously overnight. The reaction was incomplete so an additional 2 g of MnO$_2$ was added and the reaction was stirred for 4 hours. The reaction was still incomplete so an additional 2 g of MnO2 was added and the reaction was stirred overnight. The reaction was filtered through celite and washed through with DCM and ethyl acetate. The filtrate was concentrated to give the title compound (350 mg, 0.999 mmol, 82%)
MS (ES) MH$^+$: 351 for $C_{17}H_{19}FN_2O_5$
$^1$H NMR (300 MHz, CHLOROFORM-d) δ ppm 1.3 (d, 6H), 1.5 (t, 3H), 3.0-3.3 (m, 4H), 3.9 (br. s., 2H), 4.6 (q, 2H), 8.4 (s, 1H), 10.4 (s, 1H).

Intermediates 440 to 470 were prepared from the indicated starting materials using a method similar to the one described for the synthesis of Intermediate 439:

Intermediate 440

6-((2R,6S)-2,6-dimethylmorpholino)-7-fluoro-3-(morpholine-4-carbonyl)benzo[d]isoxazole-5-carbaldehyde Starting material: (6-((2R,6S)-2,6-dimethylmorpholino)-7-fluoro-5-(hydroxymethyl)benzo[d]isoxazol-3-yl)(morpholino)methanone (Intermediate 285).
MS (ES) MH$^+$: 392 for $C_{19}H_{22}FN_3O_5$
$^1$H NMR (300 MHz, CHLOROFORM-d) δ ppm 1.2 (d, 6H), 3.0-3.2 (m, 4H), 3.6-3.7 (m, 2H), 3.7-3.9 (m, 8H), 8.2 (s, 1H), 10.25 (s, 1H).

Intermediate 441

6-((2R,6S)-2,6-dimethylmorpholino)-7-fluoro-5-formyl-N-methoxy-N-methylbenzo[d]isoxazole-3-carboxamide Starting material: 6-((2R,6S)-2,6-dimethylmorpholino)-7-fluoro-5-(hydroxymethyl)-N-methoxy-N-methylbenzo[d]isoxazole-3-carboxamide (Intermediate 263)
MS (ES) MH$^+$: 366 for $C_{17}H_{20}FN_3O_5$

Intermediate 442

6-((2R,6S)-2,6-dimethylmorpholino)-N-ethyl-7-fluoro-5-formylbenzo[d]isoxazole-3-carboxamide Starting material: 6-((2R,6S)-2,6-dimethylmorpholino)-N-ethyl-7-fluoro-5-(hydroxymethyl)benzo[d]isoxazole-3-carboxamide (Intermediate 264)
MS (ES) MH$^+$: 350 for $C_{17}H_{20}FN_3O_4$
$^1$H NMR (300 MHz, CHLOROFORM-d) δ ppm 1.23 (d, J=6.03 Hz, 6H) 1.31 (t, J=7.16 Hz, 3H) 3.02-3.22 (m, 4H) 3.48-3.65 (m, 2H) 3.82-3.98 (m, 2H) 6.81-6.96 (br. s., 1H) 8.51 (s, 1H) 10.33 (s, 1H)

Intermediate 443

6-((2R,6S)-2,6-dimethylmorpholino)-N-ethyl-7-fluoro-5-formyl-N-methylbenzo[d]isoxazole-3-carboxamide Starting material: 6-((2R,6S)-2,6-dimethylmorpholino)-N-ethyl-7-fluoro-5-(hydroxymethyl)-N-methylbenzo[d]isoxazole-3-carboxamide (Intermediate 265)
MS (ES) MH$^+$: 364 for $C_{18}H_{22}FN_3O_4$

Intermediate 444

6-((2R,6S)-2,6-dimethylmorpholino)-7-fluoro-5-formyl-N-methylbenzo[d]isoxazole-3-carboxamide Starting material: 6-((2R,6S)-2,6-dimethylmorpholino)-7-fluoro-5-(hydroxymethyl)-N-methylbenzo[d]isoxazole-3-carboxamide (Intermediate 266)
MS (ES) MH$^+$: 336 for $C_{16}H_{18}FN_3O_4$
$^1$H NMR (300 MHz, CHLOROFORM-d) δ ppm 1.25 (d, J=6.78 Hz, 6H) 3.04-3.23 (m, 7H) 3.91 (br. s., 1H) 6.83-6.99 (m, 1H) 8.53 (s, 1H) 10.34 (s, 1H)

Intermediate 445

6-((2R,6S)-2,6-dimethylmorpholino)-7-fluoro-3-(4-methyl-3-oxopiperazine-1-carbonyl)benzo[d]isoxazole-5-carbaldehyde Starting material: 4-(6-((2R,6S)-2,6-dimethylmorpholino)-7-fluoro-5-(hydroxymethyl)benzo[d]isoxazole-3-carbonyl)-1-methylpiperazin-2-one (Intermediate 267)
MS (ES) MH$^+$: 419 for $C_{20}H_{23}FN_4O_5$

Intermediate 446

3-(3,3-difluoroazetidine-1-carbonyl)-6-((2R,6S)-2,6-dimethylmorpholino)-7-fluorobenzo[d]isoxazole-5-carbaldehyde Starting material: (3,3-difluoroazetidin-1-yl)(6-((2R,6S)-2,6-dimethylmorpholino)-7-fluoro-5-(hydroxymethyl)benzo[d]isoxazol-3-yl)methanone (Intermediate 268)
MS (ES) MH$^+$: 398 for $C_{18}H_{18}F_3N_3O_4$
$^1$H NMR (300 MHz, CHLOROFORM-d) δ ppm 1.23 (d, J=6.78 Hz, 6H) 3.03-3.18 (m, 4H) 3.78-3.97 (m, 2H) 4.60 (t, J=12.06 Hz, 2H) 4.96 (t, J=11.68 Hz, 2H) 8.39-8.46 (m, 1H) 10.26-10.36 (m, 1H)

Intermediate 447

6-((2R,6S)-2,6-dimethylmorpholino)-7-fluoro-5-formylbenzo[d]isoxazole-3-carboxamide Starting material: 6-((2R,6S)-2,6-dimethylmorpholino)-7-fluoro-5-(hydroxymethyl)benzo[d]isoxazole-3-carboxamide (Intermediate 269)
MS (ES) MH$^+$: 322 for $C_{15}H_{16}FN_3O_4$

Intermediate 448

6-((2R,6S)-2,6-dimethylmorpholino)-7-fluoro-5-formyl-N-(2-methoxyethyl)benzo[d]isoxazole-3-carboxamide Starting material: 6-((2R,6S)-2,6-dimethylmorpholino)-7-fluoro-5-(hydroxymethyl)-N-(2-methoxyethyl)benzo[d]isoxazole-3-carboxamide (Intermediate 270)
MS (ES) MH$^+$: 380 for $C_{18}H_{22}FN_3O_5$
$^1$H NMR (300 MHz, CHLOROFORM-d) δ ppm 1.23 (d, J=6.03 Hz, 6H) 3.04-3.20 (m, 4H) 3.41 (s, 3H) 3.60 (t, J=4.90 Hz, 2H) 3.65-3.78 (m, 2H) 3.89 (br. s., 2H) 7.18-7.26 (m, 1H) 8.49 (s, 1H) 10.33 (s, 1H)

Intermediate 449

N-tert-butyl-6-((2R,6S)-2,6-dimethylmorpholino)-7-fluoro-5-formylbenzo[d]isoxazole-3-carboxamide Starting material: N-tert-butyl-6-((2R,6S)-2,6-dimethylmorpholino)-7-fluoro-5-(hydroxymethyl)benzo[d]isoxazole-3-carboxamide (Intermediate 271)
MS (ES) MH$^+$: 378 for $C_{19}H_{24}FN_3O_4$
$^1$H NMR (300 MHz, CHLOROFORM-d) δ ppm 1.23 (d, J=6.03 Hz, 6H) 1.52 (s, 9H) 3.02-3.21 (m, 4H) 3.89 (br. s., 2H) 6.73 (br. s., 1H) 8.51 (s, 1H) 10.32 (s, 1H)

Intermediate 450

6-[(2R,6S)-2,6-dimethylmorpholin-4-yl]-3-[(1,1-dioxidothiomorpholin-4-yl)carbonyl]-7-fluoro-1,2-benzisoxazole-5-carbaldehyde Starting material: {6-[(2R,6S)-2,6-dimethylmorpholin-4-yl]-3-[(1,1-dioxidothiomorpholin-4-yl)carbonyl]-7-fluoro-1,2-benzisoxazol-5-yl}methanol (Intermediate 272)
MS (ES) MH$^+$: 440 for $C_{19}H_{22}FN_3O_6S$
$^1$H NMR (300 MHz, CHLOROFORM-d) δ ppm 1.26 (d, J=6.03 Hz, 6H) 3.09-3.32 (m, 8H) 3.84-4.02 (m, 2H) 4.32-4.43 (m, 2H) 4.43-4.52 (m, 2H) 8.28 (s, 1H) 10.34 (s, 1H)

Intermediate 451

6-((2R,6S)-2,6-dimethylmorpholino)-7-fluoro-5-formyl-N-(tetrahydro-2H-pyran-4-yl)benzo[d]isoxazole-3-carboxamide

Starting material: 6-((2R,6S)-2,6-dimethylmorpholino)-7-fluoro-5-(hydroxymethyl)-N-(tetrahydro-2H-pyran-4-yl)benzo[d]isoxazole-3-carboxamide (Intermediate 273)

MS (ES) MH$^+$: 406 for $C_{20}H_{24}FN_3O_5$
$^1$H NMR (300 MHz, CHLOROFORM-d) δ ppm 1.25 (d, J=6.03 Hz, 6H) 1.59-1.77 (m, 2H) 1.94-2.14 (m, 2H) 3.01-3.24 (m, 4H) 3.48-3.65 (m, 2H) 3.81-3.98 (m, 2H) 3.98-4.13 (m, 2H) 4.17-4.35 (m, 1H) 6.79 (br. s., 1H) 8.51 (s, 1H) 10.35 (s, 1H)

Intermediate 452

6-((2R,6S)-2,6-dimethylmorpholino)-7-fluoro-5-formyl-N-isopropylbenzo[d]isoxazole-3-carboxamide

Starting material: 6-((2R,6S)-2,6-dimethylmorpholino)-7-fluoro-5-(hydroxymethyl)-N-isopropylbenzo[d]isoxazole-3-carboxamide (Intermediate 274)

MS (ES) MH$^+$: 364 for $C_{18}H_{22}FN_3O_4$
$^1$H NMR (300 MHz, CHLOROFORM-d) δ ppm 1.25 (d, J=6.78 Hz, 6H) 1.34 (d, J=6.78 Hz, 6H) 3.05-3.23 (m, 4H) 3.84-3.98 (m, 2H) 4.28-4.44 (m, 1H) 6.65-6.77 (m, 1H) 8.53 (s, 0H) 10.34 (s, 1H)

Intermediate 453

N-cyclopropyl-6-((2R,6S)-2,6-dimethylmorpholino)-7-fluoro-5-formylbenzo[d]isoxazole-3-carboxamide

Starting material: N-cyclopropyl-6-((2R,6S)-2,6-dimethylmorpholino)-7-fluoro-5-(hydroxymethyl)benzo[d]isoxazole-3-carboxamide (Intermediate 275)

MS (ES) MH$^+$: 361.9 for $C_{18}H_{20}FN_3O_4$
$^1$H NMR (300 MHz, CHLOROFORM-d) δ ppm 0.74 (br. s., 2H) 0.90-1.02 (m, 2H) 1.25 (d, J=6.03 Hz, 6H) 2.97 (br. s., 1H) 3.07-3.21 (m, 4H) 3.80-4.00 (m, 2H) 6.98 (br. s., 1H) 8.53 (s, 1H) 10.34 (s, 1H)

Intermediate 454

6-((2R,6S)-2,6-dimethylmorpholino)-7-fluoro-3-(4-methoxypiperidine-1-carbonyl)benzo[d]isoxazole-5-carbaldehyde

Starting material: (6-((2R,6S)-2,6-dimethylmorpholino)-7-fluoro-5-(hydroxymethyl)benzo[d]isoxazol-3-yl)(4-methoxypiperidin-1-yl)methanone (Intermediate 276).

MS (ES) MH$^+$: 420 for $C_{21}H_{26}FN_3O_5$
$^1$H NMR (300 MHz, CHLOROFORM-d) d ppm 1.25 (d, J=6.03 Hz, 6H) 1.65-2.06 (m, 4H) 3.02-3.26 (m, 4H) 3.53-3.63 (m, 1H) 3.63-3.75 (m, 1H) 3.75-4.07 (m, 5H) 8.22 (s, 1H) 10.35 (s, 1H)

Intermediate 455

N-(cyclopropylmethyl)-6-((2R,6S)-2,6-dimethylmorpholino)-7-fluoro-5-formylbenzo[d]isoxazole-3-carboxamide

Starting material: N-(cyclopropylmethyl)-6-((2R,6S)-2,6-dimethylmorpholino)-7-fluoro-5-(hydroxymethyl)benzo[d]isoxazole-3-carboxamide (Intermediate 277)

MS (ES) MH$^+$: 376 for $C_{19}H_{22}FN_3O_4$

Intermediate 456

6-[(2R,6S)-2,6-dimethylmorpholin-4-yl]-7-fluoro-3-(1,2-oxazinan-2-ylcarbonyl)-1,2-benzisoxazole-5-carbaldehyde

Starting material: 6-[(2R,6S)-2,6-dimethylmorpholin-4-yl]-7-fluoro-3-(1,2-oxazinan-2-ylcarbonyl)-1,2-benzisoxazol-5-yl}methanol (Intermediate 278)

MS (ES) MH$^+$: 392 for $C_{19}H_{22}FN_3O_5$
$^1$H NMR (300 MHz, CHLOROFORM-d) δ ppm 1.23 (d, J=6.03 Hz, 6H) 1.92 (br. s., 4H) 3.02-3.24 (m, 4H) 3.89 (br. s., 2H) 4.05 (br. s., 4H) 8.16 (s, 1H) 10.35 (s, 1H)

Intermediate 457

6-((2R,6S)-2,6-dimethylmorpholino)-7-fluoro-5-formyl-N-(thiophen-2-ylmethyl)benzo[d]isoxazole-3-carboxamide

Starting material: 6-((2R,6S)-2,6-dimethylmorpholino)-7-fluoro-5-(hydroxymethyl)-N-(thiophen-2-ylmethyl)benzo[d]isoxazole-3-carboxamide (Intermediate 279)

MS (ES) MH$^+$: 418 for $C_{20}H_{20}FN_3O_4S$

Intermediate 458

6-((2R,6S)-2,6-dimethylmorpholino)-7-fluoro-5-formyl-N-(pyridin-4-ylmethyl)benzo[d]isoxazole-3-carboxamide

Starting material: 6-((2R,6S)-2,6-dimethylmorpholino)-7-fluoro-5-(hydroxymethyl)-N-(pyridin-4-ylmethyl)benzo[d]isoxazole-3-carboxamide (Intermediate 249)

MS (ES) MH$^+$: 413 for $C_{21}H_{21}FN_4O_4$

Intermediate 459

N-(cyclohexylmethyl)-6-((2R,6S)-2,6-dimethylmorpholino)-7-fluoro-5-formylbenzo[d]isoxazole-3-carboxamide

Starting material: N-(cyclohexylmethyl)-6-((2R,6S)-2,6-dimethylmorpholino)-7-fluoro-5-(hydroxymethyl)benzo[d]isoxazole-3-carboxamide (Intermediate 250)

MS (ES) MH$^+$: 418 for $C_{22}H_{28}FN_3O_4$

Intermediate 460

3-(4,4-difluoropiperidine-1-carbonyl)-6-((2R,6S)-2,6-dimethylmorpholino)-7-fluorobenzo[d]isoxazole-5-carbaldehyde

Starting material: (4,4-difluoropiperidin-1-yl)(6-((2R,6S)-2,6-dimethylmorpholino)-7-fluoro-5-(hydroxymethyl)benzo[d]isoxazol-3-yl)methanone (Intermediate 251)

MS (ES) MH$^+$: 426 for $C_{20}H_{22}F_3N_3O_4$

Intermediate 461

3-(3,3-difluoropyrrolidine-1-carbonyl)-6-((2R,6S)-2,6-dimethylmorpholino)-7-fluorobenzo[d]isoxazole-5-carbaldehyde

Starting material: (3,3-difluoropyrrolidin-1-yl)(6-((2R,6S)-2,6-dimethylmorpholino)-7-fluoro-5-(hydroxymethyl)benzo[d]isoxazol-3-yl)methanone (Intermediate 252)

MS (ES) MH$^+$: 412 for $C_{19}H_{20}F_3N_3O_4$

Intermediate 462

6-((2R,6S)-2,6-dimethylmorpholino)-7-fluoro-5-formyl-N-(1-methylazetidin-3-yl)benzo[d]isoxazole-3-carboxamide Starting material: 6-((2R,6S)-2,6-dimethylmorpholino)-7-fluoro-5-(hydroxymethyl)-N-(1-methylazetidin-3-yl)benzo[d]isoxazole-3-carboxamide (Intermediate 253)
MS (ES) MH$^+$: 391 for $C_{19}H_{23}FN_4O_4$

Intermediate 463

N-(1-(6-((2R,6S)-2,6-dimethylmorpholino)-7-fluoro-5-formylbenzo[d]isoxazole-3-carbonyl)azetidin-3-yl)acetamide Starting material: N-(1-(6-((2R,6S)-2,6-dimethylmorpholino)-7-fluoro-5-(hydroxymethyl)benzo[d]isoxazole-3-carbonyl)azetidin-3-yl)acetamide (Intermediate 254)
MS (ES) MH$^+$: 419 for $C_{20}H_{23}FN_4O_5$

Intermediate 464

6-((2R,6S)-2,6-dimethylmorpholino)-7-fluoro-5-formyl-N-((1-methyl-1H-pyrazol-3-yl)methyl)benzo[d]isoxazole-3-carboxamide Starting material: 6-((2R,6S)-2,6-dimethylmorpholino)-7-fluoro-5-(hydroxymethyl)-N-((1-methyl-1H-pyrazol-3-yl)methyl)benzo[d]isoxazole-3-carboxamide (Intermediate 255)
MS (ES) MH$^+$: 416 for $C_{20}H_{22}FN_5O_4$

Intermediate 465

6-((2R,6S)-2,6-dimethylmorpholino)-7-fluoro-5-formyl-N-((1-methyl-1H-pyrazol-5-yl)methyl)benzo[d]isoxazole-3-carboxamide Starting material: 6-((2R,6S)-2,6-dimethylmorpholino)-7-fluoro-5-(hydroxymethyl)-N-((1-methyl-1H-pyrazol-5-yl)methyl)benzo[d]isoxazole-3-carboxamide (Intermediate 256)
MS (ES) MH$^+$: 416 for $C_{20}H_{22}FN_5O_4$

Intermediate 466

N-(1,3-dimethoxy-2-(methoxymethyl)propan-2-yl)-6-((2R,6S)-2,6-dimethylmorpholino)-7-fluoro-5-formylbenzo[d]isoxazole-3-carboxamide Starting material: N-(1,3-dimethoxy-2-(methoxymethyl)propan-2-yl)-6-((2R,6S)-2,6-dimethylmorpholino)-7-fluoro-5-(hydroxymethyl)benzo[d]isoxazole-3-carboxamide (Intermediate 257)
MS (ES) MH$^+$: 468 for $C_{22}H_{30}FN_3O_7$

Intermediate 467

N-(2,2-difluoroethyl)-6-((2R,6S)-2,6-dimethylmorpholino)-7-fluoro-5-formylbenzo[d]isoxazole-3-carboxamide Starting material: N-(2,2-difluoroethyl)-6-((2R,6S)-2,6-dimethylmorpholino)-7-fluoro-5-(hydroxymethyl)benzo[d]isoxazole-3-carboxamide (Intermediate 258)
MS (ES) MH$^+$: 386 for $C_{17}H_{18}F_3N_3O_4$

Intermediate 468

1-(6-((2R,6S)-2,6-dimethylmorpholino)-7-fluoro-5-formylbenzo[d]isoxazole-3-carbonyl)azetidine-3-carbonitrile Starting material: 1-(6-((2R,6S)-2,6-dimethylmorpholino)-7-fluoro-5-(hydroxymethyl)benzo[d]isoxazole-3-carbonyl)azetidine-3-carbonitrile (Intermediate 259)
MS (ES) MH$^+$: 387.2 for $C_{19}H_{19}FN_4O_4$

Intermediate 469

6-((2R,6R)-2,6-dimethylmorpholino)-7-fluoro-5-formylbenzo[d]isoxazole-3-carboxamide Starting Material: 6-((2R,6R)-2,6-dimethylmorpholino)-7-fluoro-5-(hydroxymethyl)benzo[d]isoxazole-3-carboxamide (Intermediate 281)
MS (ES) MH$^+$: 322 for $C_{15}H_{16}FN_3O_4$
$^1$H NMR (300 MHz, DMSO-d$_6$) δ ppm 1.22 (d, J=6.78 Hz, 6H) 3.02 (m, 2H) 3.39 (d, J=12.06 Hz, 2H) 4.15 (m, 2H) 8.22 (s, 1H) 8.24 (s, 1H) 8.56 (s, 1H) 10.35 (s, 1H)

Intermediate 470

6-((2R,6S)-2,6-dimethylmorpholino)-7-fluoro-5-formyl-N,N-dimethylbenzo[d]isoxazole-3-carboxamide Starting material: 6-((2R,6S)-2,6-dimethylmorpholino)-7-fluoro-5-(hydroxymethyl)-N,N-dimethylbenzo[d]isoxazole-3-carboxamide (Intermediate 286).
MS (ES) MH$^+$: 350 for $C_{17}H_{20}FN_3O_4$

Intermediate 471

7-Chloro-6-((2R,6S)-2,6-dimethylmorpholino)-3-methylisoxazolo[4,5-b]pyridine-5-carbaldehyde (7-Chloro-6-((2R,6S)-2,6-dimethylmorpholino)-3-methylisoxazolo[4,5-b]pyridin-5-yl)methanol (Intermediate 352, 459 mg, 1.47 mmol) was dissolved in about 10 ml CH$_2$Cl$_2$. Manganese dioxide (1920 mg, 22.08 mmol) was added, and the slurry was stirred at room temperature for three days. The mixture was filtered through celite and concentrated. The crude was purified by chromatography on SiO$_2$ using 10-30% EtOAc/hexanes. Recovered a yellow solid, 185 mg (41%).
MS (ES) MH$^+$: 310 for $C_{14}H_{16}ClN_3O_3$
$^1$H NMR (300 MHz, CD$_2$Cl$_2$) δ: 1.2 (d, 6H), 2.7 (s, 3H), 2.9-3.0 (m, 2H), 3.1-3.2 (m, 2H), 3.8-4.0 (m, 2H), 10.2 (s, 1H).

Intermediates 472 to 481 were prepared from the indicated starting materials using a method similar to the one described for the synthesis of Intermediate 471:

Intermediate 472

7-chloro-6-((2R,6S)-2,6-dimethylmorpholino)-3-(pyrazin-2-yl)benzo[d]isoxazole-5-carbaldehyde Starting material: (7-chloro-6-((2R,6S)-2,6-dimethylmorpholino)-3-(pyrazin-2-yl)benzo[d]isoxazol-5-yl)methanol (Intermediate 353).
MS (ES) MH$^+$: 373 for $C_{18}H_{17}ClN_4O_3$
$^1$H NMR (DMSO-d$_6$) δ: 1.1 (d, 6H), 3.1-3.2 (m, 4H), 3.8-3.9 (m, 2H), 8.7 (s, 1H), 8.9 (d, 1H), 9.0 (m, 1H), 9.4 (m, 1H), 10.3 (s, 1H).

Intermediate 473

7-chloro-6-((2R,6S)-2,6-dimethylmorpholino)-5-formyl-N-methylisoxazolo[4,5-b]pyridine-3-carboxamide Starting material: 7-chloro-6-((2R,6S)-2,6-dimethylmorpholino)-5-(hydroxymethyl)-N-methylisoxazolo[4,5-b]pyridine-3-carboxamide (Intermediate 293) in 20 ml $CH_2Cl_2$.

MS (ES) MH$^+$: 353 for $C_{15}H_{17}ClN_4O_4$
$^1$H NMR (300 MHz, $CD_2Cl_2$) δ: 1.2 (d, 6H), 3.0-3.2 (overlapping m, 7H), 3.9-4.0 (m, 2H), 7.9 (br s, 1H), 10.2 (s, 1H).

Intermediate 474

7-chloro-6-((2R,6S)-2,6-dimethylmorpholino)-N-ethyl-5-formylisoxazolo[4,5-b]pyridine-3-carboxamide Starting material: 7-chloro-6-((2R,6S)-2,6-dimethylmorpholino)-N-ethyl-5-(hydroxymethyl)isoxazolo[4,5-b]pyridine-3-carboxamide (Intermediate 294).

MS (ES) MH$^+$: 367 for $C_{16}H_{19}ClN_4O_4$
$^1$H NMR (300 MHz, $CD_2Cl_2$) δ: 1.2 (d, 6H), 1.3 (t, 3H), 3.0-3.2 (m, 4H), 3.5-3.7 (m, 2H), 3.9-4.0 (m, 2H), 7.9 (br s, 1H), 10.2 (s, 1H).

Intermediate 475

7-chloro-6-((2R,6S)-2,6-dimethylmorpholino)-5-formyl-N-isopropylisoxazolo[4,5-b]pyridine-3-carboxamide Starting material: 7-chloro-6-((2R,6S)-2,6-dimethylmorpholino)-5-(hydroxymethyl)-N-isopropylisoxazolo[4,5-b]pyridine-3-carboxamide (Intermediate 295)

MS (ES) MH$^+$: 381 for $C_{17}H_{21}ClN_4O_4$

Intermediate 476

N-tert-butyl-7-chloro-6-((2R,6S)-2,6-dimethylmorpholino)-5-formylisoxazolo[4,5-b]pyridine-3-carboxamide Starting material: N-tert-butyl-7-chloro-6-((2R,6S)-2,6-dimethylmorpholino)-5-(hydroxymethyl)isoxazolo[4,5-b]pyridine-3-carboxamide (Intermediate 296).

MS (ES) MH$^+$: 395 for $C_{18}H_{23}ClN_4O_4$
$^1$H NMR (300 MHz, $CD_2Cl_2$) δ: 1.2 (d, 6H), 1.5 (s, 9H), 3.0-3.2 (m, 4H), 3.9-4.0 (m, 2H), 7.9 (br s, 1H), 10.2 (s, 1H).

Intermediate 477

7-chloro-6-((2R,6S)-2,6-dimethylmorpholino)-5-formyl-N-neopentylisoxazolo[4,5-b]pyridine-3-carboxamide Starting material: 7-chloro-6-((2R,6S)-2,6-dimethylmorpholino)-5-(hydroxymethyl)-N-neopentylisoxazolo[4,5-b]pyridine-3-carboxamide (Intermediate 297).

MS (ES) MH$^+$: 409 for $C_{19}H_{25}ClN_4O_4$
$^1$H NMR (300 MHz, $CD_2Cl_2$) δ: 1.0 (s, 9H), 1.2 (d, 6H), 3.0-3.2 (m, 4H), 3.4 (d, 2H), 3.9-4.0 (m, 2H), 8.2 (br s, 1H), 10.2 (s, 1H).

Intermediate 478

7-chloro-3-(3,3-difluoroazetidine-1-carbonyl)-6-((2R,6S)-2,6-dimethylmorpholino)isoxazolo[4,5-b]pyridine-5-carbaldehyde Starting material: (7-chloro-6-((2R,6S)-2,6-dimethylmorpholino)-5-(hydroxymethyl)isoxazolo[4,5-b]pyridin-3-yl)(3,3-difluoroazetidin-1-yl)methanone (Intermediate 298).

MS (ES) MH$^+$: 415 for $C_{17}H_{17}ClF_2N_4O_4$
$^1$H NMR (300 MHz, $CD_2Cl_2$) δ: 1.2 (d, 6H), 3.0-3.1 (m, 4H), 3.9-4.0 (m, 2H), 4.6 (t, 2H), 4.9 (t, 2H), 10.2 (s, 1H).

Intermediate 479

N-benzyl-7-chloro-6-((2R,6S)-2,6-dimethylmorpholino)-5-formylisoxazolo[4,5-b]pyridine-3-carboxamide Starting material: N-benzyl-7-chloro-6-((2R,6S)-2,6-dimethylmorpholino)-5-(hydroxymethyl)isoxazolo[4,5-b]pyridine-3-carboxamide (Intermediate 299).

MS (ES) MH$^+$: 429 for $C_{21}H_{21}ClN_4O_4$
$^1$H NMR (300 MHz, $CD_2Cl_2$) δ: 1.2 (d, 6H), 2.9-3.2 (m, 4H), 3.8-4.00 (m, 2H), 4.7 (d, 2H), 7.2-7.5 (m, 5H), 8.2 (br s, 1H), 10.1 (s, 1H).

Intermediate 480

7-chloro-N-(4-cyanobenzyl)-6-((2R,6S)-2,6-dimethylmorpholino)-5-formylisoxazolo[4,5-b]pyridine-3-carboxamide Starting material: 7-chloro-N-(4-cyanobenzyl)-6-((2R,6S)-2,6-dimethylmorpholino)-5-(hydroxymethyl)isoxazolo[4,5-b]pyridine-3-carboxamide (Intermediate 300).

MS (ES) MH$^+$: 454 for $C_{22}H_{20}ClN_5O_4$
$^1$H NMR (300 MHz, $CD_2Cl_2$) δ: 1.2 (d, 6H), 3.0-3.2 (m, 4H), 3.7-4.0 (m, 2H), 4.8 (m, 2H), 7.5 (d, 2H), 7.7 (d, 2H), 8.4 (br s, 1H), 10.1 (s, 1H).

Intermediate 481

7-chloro-N-(3-cyanobenzyl)-6-((2R,6S)-2,6-dimethylmorpholino)-5-formylisoxazolo[4,5-b]pyridine-3-carboxamide Starting material: 7-chloro-N-(3-cyanobenzyl)-6-((2R,6S)-2,6-dimethylmorpholino)-5-(hydroxymethyl)isoxazolo[4,5-b]pyridine-3-carboxamide (Intermediate 301).

MS (ES) MH$^+$: 454 for $C_{22}H_{20}ClN_5O_4$

Intermediate 482

1-benzylamino-butan-2-ol

To a solution of benzylamine (29.65 g, 277.0 mmol) in ethanol (40 mL) was added 1,2-epoxybutane (4 g, 55.47 mmol) and the mixture was heated to 150° C. for 2 h in a autoclave. It was concentrated and distilled at 140-150° C./2 mm Hg to give product as color less liquid, which slowly crystallizes at room temperature after 2 days. Yield: 8.5 g (85%)

MS (ES) MH$^+$: 180 for $C_{11}H_{17}NO$
$^1$H NMR (300 MHz—$CDCl_3$) δ: 0.9 (t, 3H), 1.4 (m, 2H), 2.45 (t, 1H), 2.8 (dd, 1H), 3.55 (m, 1H), 3.8 (q, 2H), 7.2 (m, 5H).

Intermediates 483 to 485 were prepared from the indicated starting materials using a method similar to the one described for the synthesis of Intermediate 482:

Intermediate 483

3-(benzylamino)-1,1,1-trifluoropropan-2-ol

Starting material: benzylamine and 2-(trifluoromethyl)oxirane

MS (ES) MH$^+$: 220 for $C_{10}H_{12}F_3NO$
$^1$H NMR (300 MHz—$CDCl_3$) δ: 2.8 (m, 1H), 2.9 (m, 1H), 3.55 (m, 1H), 3.8 (s, 2H), 4.0 (m, 1H), 7.3-7.4 (m, 5H).

Intermediate 484

1-(benzylamino)-3-methoxypropan-2-ol

Starting materials: benzyl amine and 2-(methoxymethyl)oxirane
MS (ES) MH$^+$: 196 for $C_{11}H_{17}NO_2$
$^1$H NMR (300 MHz—CDCl$_3$) δ: 2.7 (m, 2H), 2.9 (s, 2H), 3.3-3.4 (m, 5H), 3.8 (d, 2H), 3.9 (m, 1H), 7.3 (m, 5H).

Intermediate 485

1-(benzyloxy)-3-[(2,4-dimethoxybenzyl)amino]propan-2-ol

Starting materials: 2,4-dimethoxy-benzylamine and 2-[(benzyloxy)methyl]oxirane
MS (ES) MH$^+$: 332 for $C_{19}H_{25}NO_4$
$^1$H NMR (300 MHz—CDCl$_3$) δ: 2.4 (m, 1H), 2.5-2.6 (m, 1H), 3.4 (m, 2H), 3.6 (m, 2H), 3.75 (s, 6H), 4.5 (s, 2H), 6.45 (m, 1H), 6.5 (d, 1H), 7.15 (d, 1H), 7.3-7.4 (m, 5H).

Intermediate 486

1-[Benzyl-(2-hydroxy-propyl)-amino]-butan-2-ol

To a solution of 1-benzylamino-butan-2-ol (Intermediate 482, 8.5 g, 47.48 mmol) in ethanol (150 mL) was added propylene oxide (8.8 g, 151 mmole) and the mixture was heated at 150° C. for 2 h in autoclave. After concentration of the mixture under reduced pressure, the residue was purified by column chromatography using methanol in dichloromethane to give product as an oil. Yield: 10.2 g (93%).
MS (ES) MH$^+$: 238 for $C_{14}H_{23}NO_2$
$^1$H NMR (300 MHz—CDCl$_3$) δ: 0.9 (t, 3H), 1.2 (m, 3H), 1.9 (m, 2H), 2.6 (m, 3H), 2.65 (m, 1H), 2.9 (bs, 2H), 3.8 (m, 2H), 3.9 (m, 2H), 7.2 (m, 5H).

Intermediate 487

N-benzyl-2-bromo-N-(3,3,3-trifluoro-2-hydroxypropyl)propanamide

To an ice cooled solution of 3-(benzylamino)-1,1,1-trifluoropropan-2-ol (Intermediate 483, 1.0 g, 4.5 mmol) in DCM (10 mL) was added TEA (0.8 mL, 5.7 mmol) followed by 2-bromopropanoyl chloride (0.86 g, 5.0) dropwise and the mixture was stirred at room temperature for 1 hour. The reaction mixture was diluted with DCM (10 mL), washed with 1.5 N HCl (2×10 mL), saturated aqueous NaHCO$_3$ (2×10 mL) before drying over anhydrous Na$_2$SO$_4$, filtering and concentrating. The residue was used for next step without further purification. Yield: 1.4 g.
MS (ES) MH$^+$: 354 for $C_{13}H_{15}BrF_3NO_2$ Intermediates 488 and 489 were prepared from the indicated starting material, 2-bromopropanoyl chloride, and TEA, using a method similar to the one described for the synthesis of Intermediate 487:

Intermediate 488

N-benzyl-2-bromo-N-(2-hydroxy-3-methoxypropyl)propanamide

Starting material: 1-(benzylamino)-3-methoxypropan-2-ol (Intermediate 484)
MS (ES) MH$^+$: 330 for $C_{14}H_{20}BrNO_3$

Intermediate 489

N-[3-(benzyloxy)-2-hydroxypropyl]-2-bromo-N-(2,4-dimethoxybenzyl)propanamide Starting material: 1-(benzyloxy)-3-[(2,4-dimethoxybenzyl)amino]propan-2-ol (Intermediate 485)
MS (ES) MH$^+$: 466 for $C_{22}H_{28}BrNO_3$

Intermediate 490

4-benzyl-6-methyl-2-(trifluoromethyl)morpholin-3-one

To an ice cooled solution of N-benzyl-2-bromo-N-(3,3,3-trifluoro-2-hydroxypropyl) propanamide (Intermediate 487, 1.4 g, 4.0 mmol) in THF (10 mL) was added NaH (0.188 mg, 7.8 mmol) and mixture was stirred at room temperature for 1 hour. The reaction mixture was quenched with MeOH (5 mL) and poured into 1.5 N HCl (10 mL). The aqueous layer was extracted with diethyl ether (2×25 mL). The organic layer was washed with saturated NaHCO$_3$ (2×10 mL), dried over anhydrous Na$_2$SO$_4$, filtered and concentrated to product as a solid. Yield: 1.0 g.
MS (ES) MH$^+$: 274 for $C_{13}H_{14}F_3NO_2$ Intermediates 490 and 491 were prepared from the indicated starting material and NaH using a method similar to the one described for the synthesis of Intermediate 490:

Intermediate 491

4-benzyl-2-(methoxymethyl)-6-methylmorpholin-3-one

Starting material: N-benzyl-2-bromo-N-(2-hydroxy-3-methoxypropyl)propanamide (Intermediate 488)
MS (ES) MH$^+$: 250 for $C_{14}H_{19}NO_3$

Intermediate 492

2-[(benzyloxy)methyl]-4-(2,4-dimethoxybenzyl)-6-methylmorpholin-3-one

Starting material: N-[3-(benzyloxy)-2-hydroxypropyl]-2-bromo-N-(2,4-dimethoxybenzyl)propanamide (Intermediate 489)
MS (ES) MH$^+$: 386 for $C_{22}H_{27}NO_5$

Intermediate 493

(2S,6S)-rel-4-benzyl-2-methyl-6-(trifluoromethyl)morpholine

To an ice cooled solution of LAH (0.291 mg, 7.6 mmol) in dry THF (10 mL) was added 4-benzyl-6-methyl-2-(trifluoromethyl)morpholin-3-one (Intermediate 490, 1.0 g, 3.6 mmol) in THF (10 mL) dropwise and the mixture was stirred at 60° C. for 1 hour. The reaction mixture was quenched with MeOH (5 mL) and poured into 1.5 N HCl (10 mL). The aqueous layer was extracted with diethyl ether (2×25 mL). The organic layer was washed with saturated NaHCO$_3$ (2×10 mL), dried over anhydrous Na$_2$SO$_4$, filtered and concentrated. The residue was purified by silica gel column chromatography to afford the product as solid. Yield: 350 mg. Also isolated was the trans-isomer (2S,6R)-rel-4-benzyl-2-methyl-6-(trifluoromethyl)morpholine.
MS (ES) MH$^+$: 260 for $C_{13}H_{16}F_3NO$
$^1$H NMR (300 MHz—CDCl$_3$) δ: 1.2 (d, 3H), 1.9 (t, 1H), 2.1 (t, 1H), 2.7 (d, 1H), 2.9 (d, 1H), 3.5-3.6 (m, 2H), 3.8 (m, 1H), 4.0 (m, 1H), 7.3-7.4 (m, 5H).

Intermediates 494 and 495 were prepared from the indicated starting material and LAH using a method similar to the one described for the synthesis of Intermediate 493:

Intermediate 494

(2S,6S)-rel-4-benzyl-2-(methoxymethyl)-6-methylmorpholine

Starting material: 4-benzyl-2-(methoxymethyl)-6-methylmorpholin-3-one (Intermediate 491)

MS (ES) MH$^+$: 236 for $C_{14}H_{21}NO_2$
$^1$H NMR (300 MHz—CDCl$_3$) δ: 1.2 (d, 3H), 1.7-1.9 (m, 2H), 2.7 (t, 2H), 3.3-3.5 (m, 5H), 3.6 (s, 2H), 3.7-3.9 (m, 2H), 7.2-7.4 (m, 5H).
Intermediate 495

(2S,6S)-rel-2-[(benzyloxy)methyl]-4-(2,4-dimethoxybenzyl)-6-methylmorpholine

Starting material: 2-[(benzyloxy)methyl]-4-(2,4-dimethoxybenzyl)-6-methylmorpholin-3-one (Intermediate 492)
MS (ES) MH$^+$: 372 for $C_{22}H_{29}NO_4$
$^1$H NMR (300 MHz—CDCl$_3$) δ: 1.2 (d, 3H), 1.8-1.9 (m, 2H), 2.7 (t, 1H), 2.8 (d, 1H), 3.4 (m, 1H), 3.5 (m, 3H), 3.7 (m, 1H), 3.8 (s, 6H), 3.9 (m, 1H), 4.5 (m, 2H), 6.5 (m, 2H), 7.2-7.4 (m, 6H).
Intermediate 496

4-Benzyl-2-ethyl-6-methyl-morpholine

A mixture of 1-[Benzyl-(2-hydroxy-propyl)-amino]-butan-2-ol (Intermediate 486, 10.5 g, 44.30 mmol) and sulfuric acid (70% w/w, 10 mL) was heated at 150° C. for 36 hour. The reaction mixture was cooled to 0° C., basified with 10% NaHCO3 to pH~10 and extracted with diethyl ether (3×50 mL). The organic layer was washed with brine (2×25 mL), water (2×25 mL), dried over sodium sulfate, filtered and concentrated. The residue was purified by column chromatography using n-heptane in diethyl ether to give product as a light yellow oil. Yield: 2.0 g (20%)
MS (ES) MH$^+$: 220 for $C_{14}H_{21}NO$
$^1$H NMR (300 MHz—CDCl$_3$) δ: 0.9 (t, 3H), 1.2 (m, 3H), 1.5 (m, 2H), 1.8 (q, 2H), 2.8 (q, 2H), 3.5 (m, 3H), 3.7 (m, 1H), 7.3 (t, 5H).
Intermediate 497

2-Ethyl-6-methyl-morpholine

To a solution of 4-benzyl-2-ethyl-6-methyl-morpholine (Intermediate 496, 2.0 g, 9.13 mmol) in methanol (30 mL) was added ammonium formate (2.35 g, 10.77 mmol) followed by 10% Pd/C (1.0 g) and mixture was heated at 65° C. for 1 hour. It was cooled and filtered through celite pad, washed with excess methanol and concentrated. The residue thus obtained was distilled. Yield: 1.0 g (85%)
MS (ES) MH$^+$: 130 for $C_7H_{15}NO$
$^1$H NMR (300 MHz—CDCl$_3$) δ: 0.9 (t, 3H), 1.2 (dd, 3H), 1.55 (m, 2H), 2.5 (m, 2H), 2.9 (t, 2H), 3.35 (m, 1H), 3.6 (m, 1H).
Intermediates 498 and 499 were prepared from the indicated starting material using a method similar to the one described for the synthesis of Intermediate 497:
Intermediate 498

(2S,6S)-rel-2-methyl-6-(trifluoromethyl)morpholine

Starting material: To a solution of (2S,6S)-rel-4-benzyl-2-methyl-6-(trifluoromethyl)morpholine (Intermediate 493).
MS (ES) MH$^+$: 170 for $C_6H_{10}F_3NO$
$^1$H NMR (300 MHz—CDCl$_3$) δ: 1.1 (d, 3H), 2.5 (m, 1H), 2.7 (m, 1H), 2.8 (m, 1H), 3.1 (m, 1H), 3.8 (m, 1H), 3.9 (m, 1H).
Intermediate 499

(2S,6S)-rel-2-(methoxymethyl)-6-methylmorpholine

Starting material: (2S,6S)-rel-4-benzyl-2-(methoxymethyl)-6-methylmorpholine (Intermediate 494).

MS (ES) MH$^+$: 146 for $C_7H_{15}NO_2$
$^1$H NMR (300 MHz—CDCl$_3$) δ: 1.1 (d, 3H), 2.4 (m, 1H), 2.6 (m, 1H), 2.9 (m, 1H), 3.3-3.5 (m, 5H), 3.6-3.7 (m, 2H).
Intermediate 500

(2S,6S)-rel-2-[(benzyloxy)methyl]-6-methylmorpholine

To a solution of (2S,6S)-rel-2-[(benzyloxy)methyl]-4-(2,4-dimethoxybenzyl)-6-methylmorpholine (Intermediate 495, 0.6 g, 1.6 mmol) in DCM (15 mL) was added 1-chloroethyl chloroformate (0.6 mL, 6.9 mmol) and mixture was heated at 50° C. for 10 hour. To the reaction mixture methanol was added and heating was continued for 1 hour. After cooling, the mixture was concentrated give product as solid.
Yield: 0.5 g
MS (ES) MH$^+$: 222 for $C_{13}H_{19}NO_2$
Intermediate 501

6-(2-ethyl-6-methylmorpholin-4-yl)-7-fluoro-3-methyl-1,2-benzisoxazole-5-carbaldehyde To an ice cooled and stirred solution of 6,7-difluoro-3-methylbenzo[d]isoxazole-5-carbaldehyde (Intermediate 374, 150 mg, 0.8 mmol) in anhydrous acetonitrile was added TEA (204 mg, 2.0 mmol) followed by 2-Ethyl-6-methyl-morpholine (Intermediate 497, 98 mg, 0.8 mmol) and the mixture heated at 80° C. for 12 hour. It was cooled to room temperature and concentrated. The residue thus obtained was purified over silica gel column using a gradient of ethyl acetate in pet. ether to give product as a solid. Yield: 75 mg (74%).
MS (ES) MH$^+$: 307 for $C_{16}H_{19}F_2N_2O_3$
$^1$H NMR (400 MHz, DMSO-d$_6$) δ: 0.9 (t, 3H), 1.1 (d, 3H), 1.5 (m, 2H), 2.6 (s, 3H), 3.0 (m, 2H), 3.2 (d, 2H), 3.6 (m, 1H), 3.8 (m, 1H), 8.1 (s, 1H), 10.3 (s, 1H)
Intermediates 502 and 503 were prepared from the indicated starting material, TEA, and 6,7-difluoro-3-methylbenzo[d]isoxazole-5-carbaldehyde (Intermediate 374), using a method similar to the one described for the synthesis of Intermediate 501:
Intermediate 502

7-fluoro-3-methyl-6-[(2S,6S)-rel-2-methyl-6-(trifluoromethyl) morpholin-4-yl]-1,2-benzoxazole-5-carbaldehyde Starting material: (2S,6S)-rel-2-methyl-6-(trifluoromethyl)morpholine (Intermediate 498)
MS (ES) MH$^+$: 347 for $C_{15}H_{14}F_4N_2O_3$
Intermediate 503

7-fluoro-6-[(2S,6S)-rel-2-(methoxymethyl)-6-methylmorpholin-4-yl]-3-methyl-1,2-benzoxazole-5-carbaldehyde Starting material: (2S,6S)-rel-2-(methoxymethyl)-6-methylmorpholine (Intermediate 499)
MS (ES) MH$^+$: 323.2 for $C_{16}H_{19}FN_2O_4$
$^1$H NMR (300 MHz, CDCl$_3$) δ: 1.3 (d, 3H), 2.6 (s, 3H), 3.2 (m, 2H), 3.3 (m, 2H), 3.4 (s, 3H), 4.0 (m, 2H), 8.0 (d, 1H), 10.4 (s, 1H).
Intermediate 504

{3-(benzylamino)-6-[(2R,6S)-2,6-dimethylmorpholin-4-yl]-7-fluoro-1,2-benzoxazol-5-yl}methanol To an ice cooled solution of benzaldehyde (0.08 mL, 2.54 mmol) in TFA (5 mL) was added triethylsilane (0.4 mL, 2.5 mmol) followed by {3-amino-6-[(2R,6S)-2,6-dimethylmorpholin-4-yl]-7-fluoro-1,2-benzisoxazol-5-yl}methanol (Intermediate 7, 250 mg, 0.84 mmol), and slowly allowed to reach room temperature and stirred for 12 hour. The reaction mixture was concentrated and the residue thus obtained was purified column chromatography using EtOAc in petether to give the title compound as solid. Yield: 70 mg (21%).

MS (ES) MH$^+$: 386 for $C_{21}H_{24}FN_3O_3$

Intermediates 505 to 514 were prepared from the indicated starting material, triethylsilane and {3-amino-6-[(2R,6S)-2,6-dimethylmorpholin-4-yl]-7-fluoro-1,2-benzisoxazol-5-yl}methanol (Intermediate 7), using a method similar to the one described for the synthesis of Intermediate 504:

Intermediate 505

{6-[(2R,6S)-2,6-dimethylmorpholin-4-yl]-7-fluoro-3-[(1,3-thiazol-2-ylmethyl)amino]-1,2-benzoxazol-5-yl}methanol Starting material: 2-thiazole carboxaldehyde.
MS (ES) MH$^+$: 393 for $C_{18}H_{21}FN_4O_3S$.

Intermediate 506

{6-[(2R,6S)-2,6-dimethylmorpholin-4-yl]-7-fluoro-3-[(1H-imidazol-4-ylmethyl)amino]-1,2-benzoxazol-5-yl}methanol Starting material: 4-imidazole carboxaldehyde
MS (ES) MH$^+$: 376.2 for $C_{18}H_{22}FN_5O_3$.
$^1$H NMR (400 MHz, DMSO-$d_6$) δ: 1.1 (d, 6H), 2.8 (m, 2H), 2.9 (d, 2H), 3.7 (m, 2H), 4.45 (d, 2H), 4.6 (s, 1H), 7.5 (s, 1H), 7.7 (m, 2H), 8.75 (s, 1H).

Intermediate 507

(6-[(2R,6S)-2,6-dimethylmorpholin-4-yl]-7-fluoro-3-{[(1-methyl-1H-pyrazol-4-yl)methyl]amino}-1,2-benzoxazol-5-yl)methanol Starting material: 1-methyl-1H-pyrazole-4-carboxaldehyde
MS (ES) MH$^+$: 390 for $C_{19}H_{24}FN_5O_3$.

Intermediate 508

(6-[(2R,6S)-2,6-dimethylmorpholin-4-yl]-7-fluoro-3-{[(5-methyl-1,2-oxazol-3-yl)methyl]amino}-1,2-benzoxazol-5-yl)methanol Starting material: 5-methylisoxazole-3-carboxaldehyde
MS (ES) MH$^+$: 391 for $C_{19}H_{23}FN_4O_4$.

Intermediate 509

{6-[(2R,6S)-2,6-dimethylmorpholin-4-yl]-7-fluoro-3-[(pyridin-2-ylmethyl)amino]-1,2-benzoxazol-5-yl}methanol Starting material: pyridine-2-carboxaldehyde
MS (ES) MH$^+$: 387 for $C_{20}H_{23}FN_4O_3$.

Intermediate 510

{6-[(2R,6S)-2,6-dimethylmorpholin-4-yl]-7-fluoro-3-[(pyridin-3-ylmethyl)amino]-1,2-benzoxazol-5-yl}methanol Starting material: pyridine-3-carboxaldehyde
MS (ES) MH$^+$: 387 for $C_{20}H_{23}FN_4O_3$.

Intermediate 511

{6-[(2R,6S)-2,6-dimethylmorpholin-4-yl]-7-fluoro-3-[(pyridin-4-ylmethyl)amino]-1,2-benzoxazol-5-yl}methanol Starting material: pyridine-4-carboxaldehyde
MS (ES) MH$^+$: 387 for $C_{20}H_{23}FN_4O_3$.

Intermediate 512

{3-[(cyclopropylmethyl)amino]-6-[(2R,6S)-2,6-dimethylmorpholin-4-yl]-7-fluoro-1,2-benzoxazol-5-yl}methanol Starting material: cyclopropyl carboxaldehyde
MS (ES) MH$^+$: 350 for $C_{18}H_{24}FN_3O_3$.

Intermediate 513

{3-[(cyclohexylmethyl)amino]-6-[(2R,6S)-2,6-dimethylmorpholin-4-yl]-7-fluoro-1,2-benzoxazol-5-yl}methanol Starting material: cyclohexane carboxaldehyde
MS (ES) MH$^+$: 391 for $C_{21}H_{30}FN_3O_3$.

Intermediate 514

{6-[(2R,6S)-2,6-dimethylmorpholin-4-yl]-7-fluoro-3-[(tetrahydro-2H-pyran-4-ylmethyl)amino]-1,2-benzoxazol-5-yl}methanol Starting material: Tetrahydropyran-4-carbaldehyde
MS (ES) MH$^+$: 394 for $C_{20}H_{28}FN_3O_4$.

Intermediate 515

3-(benzylamino)-6-[(2R,6S)-2,6-dimethylmorpholin-4-yl]-7-fluoro-1,2-benzoxazole-5-carbaldehyde To an ice-cooled solution of {3-(benzylamino)-6-[(2R,6S)-2,6-dimethylmorpholin-4-yl]-7-fluoro-1,2-benzoxazol-5-yl}methanol (Intermediate 504, 160 mg, 0.41 mmol) in acetonitrile (2 mL) was added NMO (73 mg, 1.5 mmol) followed TPAP (15 mg, 0.1 mmol) and mixture stirred for 2 hours at room temperature. The reaction mixture filtered thorough silica gel bed and washed with EtOAc. The organic phase concentrated under reduced pressure to give title compound as a yellow solid. Yield: 75 mg, (47%).

MS (ES) MH$^+$: 384 for $C_{21}H_{22}FN_3O_3$

Intermediates 516 to 525 were prepared from the indicated starting material, NMO, and TPAP using a method similar to the one described for the synthesis of Intermediate 515:

Intermediate 516

6-[(2R,6S)-2,6-dimethylmorpholin-4-yl]-7-fluoro-3-[(1,3-thiazol-2-ylmethyl)amino]-1,2-benzoxazole-5-carbaldehyde Starting material: {6-[(2R,6S)-2,6-dimethylmorpholin-4-yl]-7-fluoro-3-[(1,3-thiazol-2-ylmethyl)amino]-1,2-benzoxazol-5-yl}methanol (Intermediate 505)
MS (ES) MH$^+$: 391 for $C_{18}H_{19}FN_4O_3S$.

Intermediate 517

6-[(2R,6S)-2,6-dimethylmorpholin-4-yl]-7-fluoro-3-[(1H-imidazol-4-ylmethyl)amino]-1,2-benzoxazole-5-carbaldehyde Starting material: {6-[(2R,6S)-2,6-dimethylmorpholin-4-yl]-7-fluoro-3-[(1H-imidazol-4-ylmethyl)amino]-1,2-benzoxazol-5-yl}methanol (Intermediate 506)
MS (ES) MH$^+$: 374.2 for $C_{18}H_{20}FN_5O_3$.

Intermediate 518

(6-[(2R,6S)-2,6-dimethylmorpholin-4-yl]-7-fluoro-3-{[(1-methyl-1H-pyrazol-4-yl)methyl]amino}-1,2-benzoxazole-5-carbaldehyde Starting material: (6-[(2R,6S)-2,6-dimethylmorpholin-4-yl]-7-fluoro-3-{[(1-methyl-1H-pyrazol-4-yl)methyl]amino}-1,2-benzoxazol-5-yl)methanol (Intermediate 507)
MS (ES) MH$^+$: 388 for $C_{19}H_{22}FN_5O_3$.

Intermediate 519

(6-[(2R,6S)-2,6-dimethylmorpholin-4-yl]-7-fluoro-3-{[(5-methyl-1,2-oxazol-3-yl)methyl]amino}-1,2-benzoxazole-5-carbaldehyde Starting material: (6-[(2R,6S)-2,6-dimethylmorpholin-4-yl]-7-fluoro-3-{[(5-methyl-1,2-oxazol-3-yl)methyl]amino}-1,2-benzoxazol-5-yl)methanol (Intermediate 508)
MS (ES) MH$^+$: 389 for $C_{19}H_{21}FN_4O_4$.

Intermediate 520

6-[(2R,6S)-2,6-dimethylmorpholin-4-yl]-7-fluoro-3-[(pyridin-2-ylmethyl)amino]-1,2-benzoxazole-5-carbaldehyde Starting material: {6-[(2R,6S)-2,6-dimethylmorpholin-4-yl]-7-fluoro-3-[(pyridin-2-ylmethyl)amino]-1,2-benzoxazol-5-yl}methanol (Intermediate 509)
MS (ES) MH$^+$: 385 for $C_{20}H_{21}FN_4O_3$.

Intermediate 521

{6-[(2R,6S)-2,6-dimethylmorpholin-4-yl]-7-fluoro-3-[(pyridin-3-ylmethyl)amino]-1,2-benzoxazole-5-carbaldehyde Starting material: {6-[(2R,6S)-2,6-dimethylmorpholin-4-yl]-7-fluoro-3-[(pyridin-3-ylmethyl)amino]-1,2-benzoxazol-5-yl}methanol (Intermediate 510)
MS (ES) MH$^+$: 385 for $C_{20}H_{21}FN_4O_3$.

Intermediate 522

{6-[(2R,6S)-2,6-dimethylmorpholin-4-yl]-7-fluoro-3-[(pyridin-4-ylmethyl)amino]-1,2-benzoxazole-5-carbaldehyde Starting material: {6-[(2R,6S)-2,6-dimethylmorpholin-4-yl]-7-fluoro-3-[(pyridin-4-ylmethyl)amino]-1,2-benzoxazol-5-yl}methanol (Intermediate 511)
MS (ES) MH$^+$: 385 for $C_{20}H_{21}FN_4O_3$.

Intermediate 523

{3-[(cyclopropylmethyl)amino]-6-[(2R,6S)-2,6-dimethylmorpholin-4-yl]-7-fluoro-1,2-benzoxazole-5-carbaldehyde Starting material: {3-[(cyclopropylmethyl)amino]-6-[(2R,6S)-2,6-dimethylmorpholin-4-yl]-7-fluoro-1,2-benzoxazol-5-yl}methanol (Intermediate 512)
MS (ES) MH$^+$: 348 for $C_{18}H_{22}FN_3O_3$.

Intermediate 524

{3-[(cyclohexylmethyl)amino]-6-[(2R,6S)-2,6-dimethylmorpholin-4-yl]-7-fluoro-1,2-benzoxazole-5-carbaldehyde Starting material: {3-[(cyclohexylmethyl)amino]-6-[(2R,6S)-2,6-dimethylmorpholin-4-yl]-7-fluoro-1,2-benzoxazol-5-yl}methanol (Intermediate 513)
MS (ES) MH$^+$: 390 for $C_{21}H_{28}FN_3O_3$ Intermediate 525

6-[(2R,6S)-2,6-dimethylmorpholin-4-yl]-7-fluoro-3-[(tetrahydro-2H-pyran-4-ylmethyl)amino]-1,2-benzoxazole-5-carbaldehyde Starting material: {6-[(2R,6S)-2,6-dimethylmorpholin-4-yl]-7-fluoro-3-[(tetrahydro-2H-pyran-4-ylmethyl)amino]-1,2-benzoxazol-5-yl}methanol (Intermediate 514)
MS (ES) MH$^+$: 392 for $C_{20}H_{26}FN_3O_4$ Intermediate 526

Methyl 3,4-difluoro-2-hydroxybenzoate

A solution of 3,4-difluoro-2-hydroxybenzoic acid (6.45 g, 37.05 mmol) and sulfuric acid (6 ml, 113 mmol) in MeOH (25 ml) was heated at reflux overnight. The mixture was diluted with water and extracted with ether. The ether was washed with aqueous NaHCO$_3$, water and brine. The combined aqueous layers were twice more extracted with ether, which was washed with NaHCO$_3$, water, and brine. The combined ether extracts were dried (MgSO$_4$) and concentrated to give 6.4 g of product as a white solid.
MS (ES) MH$^-$: 187 for $C_8H_6F_2O_3$
$^1$H NMR (300 MHz, DMSO-d$_6$) δ: 3.9 (s, 3H), 6.9-7.1 (m, 1H), 7.65 (m, 1H), 10.8 (s, 1H).

Intermediate 527

3,4-difluoro-N,2-dihydroxybenzamide

A solution of hydroxylamine (50% in water) (50 ml, 816 mmol) was added to a solution of methyl 3,4-difluoro-2-hydroxybenzoate (7.75 g, 41.2 mmol) (Intermediate 526) in dioxane (200 ml) and the mixture was stirred at room temperature for 3 days. The mixture was partitioned between water and EtOAc. The aqueous layer was acidified with concentrated HCl and extracted with EtOAc twice more. The EtOAc layers were washed with brine, combined and concentrated to give 7.9 g of a solid.
LC-MS ES MH$^+$ 190 for $C_7H_5F_2NO_3$.
$^1$H NMR (300 MHz, DMSO-d$_6$) δ ppm 7.0 (ddd, 1H), 7.4-7.7 (m, 1H), 9.5 (s, 1H), 11.7 (s, 1H), 13.1 (s, 1H).

Intermediate 528

6,7-difluoro-1,2-benzisoxazol-3(2H)-one

A mixture of 3,4-difluoro-N,2-dihydroxybenzamide (Intermediate 527, 7.91 g, 41.8 mmol) and carbonyl diimidazole (13.6 g, 83.7 mmol) in THF (200 ml) was heated at reflux for 90 min. The mixture was partitioned between EtOAC and water and acidified with conc. HCl. The solution was extracted 3 times with EtOAc, each extract being washed with water and brine. Drying (MgSO$_4$) of the combined extracts and removal of solvent gave 6.88 g of product as an off-white solid.
MS (ES) M–H$^-$: 170 for $C_7H_3F_2NO_2$;
$^1$H NMR (300 MHz, DMSO-d$_6$) δ ppm 7.3-7.5 (m, 1H), 7.6 (m, 1H), 12.9 (s, 1H).

Intermediate 529

3-chloro-6,7-difluorobenzordlisoxazole

TEA (5.6 ml, 40.2 mmol) was added to an ice bath cooled mixture of 6,7-difluoro-1,2-benzisoxazol-3(2H)-one (Intermediate 528, 6.88 g, 40.2 mmol) and POCl$_3$ (13.1 ml, 141 mmol) (exotherm results) in a microwave reactor vessel and the mixture was heated at 140° C. for 6 hours in a microwave reactor. The mixture was taken up in ether and washed with Na$_2$CO$_3$ (2×) and brine. The combined aqueous layers were twice more extracted with ether, which was washed with Na$_2$CO$_3$ and brine. The combined ether layers were dried (MgSO$_4$) and concentrated to give an oil that slowly solidified. The material was chromatographed on silica gel (hexanes followed by gradient elution to 50% CH$_2$Cl$_2$ in hexanes) to afford 5.64 g of product as an off-white solid.

$^1$H NMR (CDCl$_3$) δ 7.2-7.35 (m, 1H), 7.4-7.5 (m, 1H).

Intermediate 530 tert-butyl 6,7-difluoro-1,2-benzisoxazol-3-yl carbonate

To a solution of 6,7-difluoro-1,2-benzisoxazol-3(2H)-one (Intermediate 528, 5.0 g, 29.2 mmol) in dry THF (50 mL), was added dimethylaminopyridine (3.5 g, 29.2 mmol) followed by Boc anhydride (12.7 g, 58.4 mmol) and the mixture heated to 65° C. for 12 hours. The reaction mixture was concentrated and the residue thus obtained was purified over silica gel column using a gradient of ethyl acetate in petroleum ether to give product as yellow solid. Yield: 4.0 g (50%).

$^1$H NMR (400 MHz, DMSO-d$_6$) δ: 1.6 (s, 9H), 7.4 (m, 1H), 7.5 (m, 1H).

Intermediate 531 tert-butyl 6,7-difluoro-5-formyl-1,2-benzisoxazol-3-yl carbonate

To a solution of diisopropylamine (3.2 g, 32.4 mmol) in THF (20 mL) was added n-butyl lithium (20.2 mL, 1.6N), dropwise at −10° C. and the solution stirred for 30 min. The reaction mixture was cooled to −78° C. and into this was added, tert-butyl 6,7-difluoro-1,2-benzisoxazol-3-yl carbonate (Intermediate 530, 4.0 g, 14.7 mmol) in THF (20 mL). It was stirred at −78° C. for 2 h and then treated with dimethylformamide (3.2 g, 44.2 mmol) and continued the stirring at −78° C. for 1 hour. The reaction was quenched by the addition of saturated solution of ammonium chloride and then extracted with ethyl acetate (2×20 mL). The combined organic layers were washed with water followed by brine and then dried over anhydrous sodium sulfate. The solution was filtered and the filtrate evaporated under vacuum, and the residue was purified over silica gel using a gradient of ethyl acetate in pet. ether to give product as a yellow solid Yield: 3.0 g (68%).

MS (ES) MH$^+$: 300 for C$_{13}$H$_{11}$F$_2$NO$_5$;

$^1$H NMR (400 MHz, DMSO-d$_6$) δ: 1.6 (s, 9H), 8.0 (d, 1H), 10.1 (s, 1H).

Intermediate 532

3-chloro-6,7-difluorobenzo[d]isoxazole-5-carbaldehyde

A solution of n-butyllithium (2.5 M in hexanes) (16.7 ml, 42 mmol) was added slowly to a solution of 2,2,6,6-tetramethylpiperidine (7.6 ml, 45 mmol) in THF (50 ml) cooled in a dry ice-acetone bath. The solution was warmed to 0° C. and re-cooled in a dry-ice acetone bath before transferring via syringe to a solution of 3-chloro-6,7-difluorobenzo[d]isoxazole (Intermediate 529, 5.64 g, 30 mmol) in THF (50 ml). After 1 hour stirring, DMF (1.0 ml, 13.2 mmol) was added all at once and the mixture was stirred with cooling in a dry-ice acetone bath for 45 min. The mixture transferred via cannula to a solution of acetic acid (6.8 ml, 119 mmol) in 100 ml Et$_2$O and the mixture was warmed to room temperature. The mixture was diluted with EtOAc and washed with brine. The combined aqueous layers were extracted again with EtOAc, which was washed with brine. Drying (MgSO$_4$) of the combined extracts and removal of solvent gave a brown oil that was chromatographed on silica gel (10% CH$_2$Cl$_2$ in hexanes followed by gradient elution to 100% CH$_2$Cl$_2$) to give 3.32 g of product as a white solid.

$^1$H NMR (300 MHz, CHLOROFORM-d) δ ppm 8.1 (dd, 1H) 10.4 (s, 1H).

Intermediate 533 tert-butyl 6-[(2R,6S)-2,6-dimethylmorpholin-4-yl]-7-fluoro-5-formyl-2,3-dihydro-1,2-benzisoxazol-3-yl carbonate To an ice cooled and stirred solution of tert-butyl 6,7-difluoro-5-formyl-1,2-benzisoxazol-3-yl carbonate (Intermediate 531, 3.0 g, 10.0 mmol) in anhydrous acetonitrile was added DIPEA (2.56 g, 20.0 mmol) followed by cis 2,6-dimethylmorpholine (1.27 g, 11.0 mmol) and the mixture heated at 80° C. for 12 hours. It was cooled to room temperature and concentrated. The residue was dissolved in ethyl acetate, washed with water followed by brine and then dried over anhydrous sodium sulfate. It was filtered and the filtrate evaporated under reduced pressure. The residue was purified on a silica gel column using a gradient of ethyl acetate in pet.ether to give product as a solid. Yield: 2.9 g (74%).

MS (ES) MH$^+$: 395 for C$_{13}$H$_{11}$F$_2$NO$_5$;

$^1$H NMR (400 MHz, DMSO-d$_6$) δ: 1.0 (d, 6H), 1.6 (s, 9H), 2.9 (t, 2H), 3.1 (d, 2H), 3.8 (m, 2H), 7.7 (s, 1H), 10.2 (s, 1H).

Intermediate 534

3-chloro-6-[(2R,6S)-2,6-dimethylmorpholin-4-yl]-7-fluoro-1,2-benzoxazole-5-carbaldehyde To an ice cooled and stirred solution of 3-chloro-6,7-difluorobenzo[d]isoxazole-5-carbaldehyde (Intermediate 532, 1.0 g, 8.75 mmol) in anhydrous acetonitrile was added DIPEA (1.8 mL, 10.5 mmol) followed by cis 2,6-dimethylmorpholine (1.3 mL, 10.5 mmol) and the mixture heated at 85° C. for 4 hours. It was cooled to room temperature and concentrated. The residue was dissolved in ethyl acetate, washed with water followed by brine and then dried over anhydrous sodium sulfate. It was filtered and the filtrate evaporated under reduced pressure. The residue was purified over silica gel column using a gradient of ethylacetate in pet.ether to give title compound as solid. Yield: 2.3 g (85%).

MS (ES) MH$^+$: 313 for C$_{14}$H$_{14}$ClFN$_2$O$_3$;

$^1$H NMR (400 MHz, DMSO-d$_6$) δ: 1.0 (d, 6H), 2.9 (t, 2H), 3.1 (d, 2H), 3.8 (m, 2H), 7.7 (s, 1H), 10.2 (s, 1H).

Intermediate 535

3-chloro-6-((2R,6R)-2,6-dimethylmorpholino)-7-fluorobenzo[d]isoxazole-5-carbaldehyde A solution of 3-chloro-6,7-difluorobenzo[d]isoxazole-5-carbaldehyde (Intermediate 532, 3.32 g, 10.6 mmol), (2R,6R)-2,6-dimethylmorpholine (Purchased from BASF®, 2.64 g, 22.9 mmol) and DIEA (4 ml, 22.9 mmol) in acetonitrile (20 ml) was heated at reflux for 3 hours. The mixture was cooled to room temperature before being partitioned between EtOAc and 1N HCl. The EtOAc was separated and washed with brine. The combined aqueous layers were extracted with EtOAc, which was washed with brine. The combined EtOAc was dried (MgSO$_4$) and concentrated to give an oil that was chromatographed on silica gel (50% hexanes in CH$_2$Cl$_2$ followed by gradient elution to 100% $CH_2Cl_2$ followed by gradient elution to 5% EtOAc in $CH_2Cl_2$) to give 2 materials in order of elution: the first material (265 mg) is consistent with starting material and the second (3.33 g) with desired product.

LC-MS ES $MH^+$: 313

$^1H$ NMR (300 MHz, CHLOROFORM-d) δ ppm 1.3 (d, 6H) 3.1 (m, 2H) 3.4 (m, 2H) 4.2 (m., 2H) 8.0 (s, 1H) 10.45 (s, 1H).

Intermediates 536 to 538 were prepared from the indicated starting material using a method similar to the one described for the synthesis of Intermediate 535:

Intermediate 536

6-((2R,6R)-2,6-dimethylmorpholino)-7-fluoro-3-methylbenzo[d]isoxazole-5-carbaldehyde Starting materials: 6,7-difluoro-3-methylbenzo[d]isoxazole-5-carbaldehyde (Intermediate 374) and (2R,6R)-2,6-dimethylmorpholine.

MS (ES) $MH^+$: 293 for $C_{15}H_{17}FN_2O_3$ $^1H$ NMR (300 MHz, CHLOROFORM-d) δ ppm 1.3 (d, 6H), 2.6 (s, 3H), 2.9-3.1 (m, 2H) 3.4 (m, 2H) 4.2 (m, 2H) 8.0 (s, 1H) 10.5 (s, 1H).

Intermediate 537

6-((2R,6R)-2,6-dimethylmorpholino)-7-fluoro-3-(1-methyl-1H-1,2,4-triazol-5-yl)benzo[d]isoxazole-5-carbaldehyde Starting materials: 6,7-difluoro-3-(1-methyl-1H-1,2,4-triazol-5-yl)benzo[d]isoxazole-5-carbaldehyde (Intermediate 404) and (2R,6R)-2,6-dimethylmorpholine.

MS (ES) $MH^+$: 360 for $C_{17}H_{18}FN_5O_3$ $^1H$ NMR (300 MHz, CHLOROFORM-d) δ ppm 1.3 (d, 6H), 3.1 (dd, 2H), 3.5 (d, 2H) 4.3 (td, 2H), 4.4 (s, 3H), 8.1 (s, 1H), 8.7 (s, 1H), 10.5 (s, 1H).

Intermediate 538

6-((3S,5R)-3,5-dimethylpiperidin-1-yl)-7-fluoro-3-methylbenzo[d]isoxazole-5-carbaldehyde Starting materials: 6,7-difluoro-3-methylbenzo[d]isoxazole-5-carbaldehyde (Intermediate 374) and (3S,5R)-3,5-dimethylpiperidine (HCl Salt).

MS (ES) $MH^+$: 291 for $C_{16}H_{19}FN_2O_2$ $^1H$ NMR (300 MHz, CHLOROFORM-d) δ ppm 0.7-0.9 (q, 1H), 0.94 (d, 6H), 1.9 (m, 4H), 2.6 (s, 3H), 2.8-3.0 (m, 2H), 3.2-3.3 (m, 2H), 7.9 (s, 1H), 10.3 (s, 1H).

Intermediate 539

6-[(2R,6S)-2,6-dimethylmorpholin-4-yl]-7-fluoro-3-(1H-1,2,4-triazol-1-yl)-1,2-benzoxazole-5-carbaldehyde To a solution of 3-chloro-6-[(2R,6S)-2,6-dimethylmorpholin-4-yl]-7-fluoro-1,2-benzoxazole-5-carbaldehyde (Intermediate 534, 0.2 g, 0.68 mmol) in acetonitrile was added DBU (0.19 mL, 1.28 mmol) followed by 1,2,4-triazole (0.053 g, 0.76 mmol), and the mixture was stirred at 100° C. for 12 hours. The reaction mixture was concentrated, the residue was purified by silica gel column chromatography using EtOAc in pet. ether to give title product.

Yield: 35 mg (16%);

MS (ES) $MH^+$: 346 for $C_{16}H_{16}FN_5O_3$;

$^1H$ NMR (400 MHz, DMSO-$d_6$) δ: 1.0 (d, 6H), 3.0 (t, 2H), 3.3 (m, 2H), 3.8 (m, 2H), 8.4 (s, 1H), 8.6 (s, 1H), 9.6 (s, 1H), 10.2 (s, 1H).

Intermediates 540 to 552 were prepared from the indicated starting material, DBU and 3-chloro-6-[(2R,6S)-2,6-dimethylmorpholin-4-yl]-7-fluoro-1,2-benzoxazole-5-carbaldehyde (Intermediate 534) using a method similar to the one described for the synthesis of Intermediate 539:

Intermediate 540

6-[(2R,6S)-2,6-dimethylmorpholin-4-yl]-7-fluoro-3-(3-methyl-1H-1,2,4-triazol-1-yl)-1,2-benzoxazole-5-carbaldehyde Starting material: 3-methyl-1,2,4-triazole MS (ES) $MH^+$: 360 for $C_{17}H_{18}FN_5O_3$ Intermediate 541

1-{6-[(2R,6S)-2,6-dimethylmorpholin-4-yl]-7-fluoro-5-formyl-1,2-benzoxazol-3-yl}-1H-1,2,4-triazole-3-carbonitrile Starting material: 3-cyano-1,2,4-triazole MS (ES) $MH^+$: 371 for $C_{17}H_{15}FN_6O_3$ $^1H$ NMR (400 MHz, DMSO-$d_6$) δ: 1.0 (d, 6H), 3.0 (m, 2H), 3.3 (m, 2H), 3.8 (m, 2H), 8.3 (s, 1H), 10.0 (s, 1H), 10.2 (s, 1H).

Intermediate 542 and Intermediate 543

6-[(2R,6S)-2,6-dimethylmorpholin-4-yl]-7-fluoro-3-(1H-1,2,3-triazol-1-yl)-1,2-benzoxazole-5-carbaldehyde (Intermediate 542) and 6-[(2R,6S)-2,6-dimethylmorpholin-4-yl]-7-fluoro-3-(1H-1,2,3-triazol-2-yl)-1,2-benzoxazole-5-carbaldehyde (Intermediate 543)

Starting material: 1,2,3-triazole

MS (ES) $MH^+$: 346 for $C_{16}H_{16}FN_5O_3$ $^1H$ NMR (400 MHz, DMSO-$d_6$) δ: 1.1 (d, 6H), 3.0 (m, 2H), 3.3 (m, 2H), 3.8 (m, 2H), 8.2 and 9.1 (2s, total of 1H), 8.4 (2s, total of 1H), 8.5 (s, 1H), 10.3 (s, 1H).

Intermediate 544

6-[(2R,6S)-2,6-dimethylmorpholin-4-yl]-7-fluoro-3-(1H-imidazol-1-yl)-1,2-benzoxazole-5-carbaldehyde Starting material: imidazole MS (ES) $MH^+$: 345.2 for $C_{17}H_{17}FN_4O_3$.

Intermediate 545

6-[(2R,6S)-2,6-dimethylmorpholin-4-yl]-7-fluoro-3-[4-(trifluoromethyl)-1H-imidazol-1-yl]-1,2-benzoxazole-5-carbaldehyde Starting material: 4-(trifluromethyl)-imidazole MS (ES) $MH^+$: 359 for $C_{18}H_{19}FN_4O_3$ Intermediate 546

6-[(2R,6S)-2,6-dimethylmorpholin-4-yl]-7-fluoro-3-(4-methyl-1H-pyrazol-1-yl)-1,2-benzoxazole-5-carbaldehyde Starting material: 4-methyl-pyrazole MS (ES) $MH^+$: 413.2 for $C_{18}H_{16}F_4N_4O_3$ Intermediate 547

3-(4-chloro-1H-pyrazol-1-yl)-6-[(2R,6S)-2,6-dimethylmorpholin-4-yl]-7-fluoro-1,2-benzoxazole-5-carbaldehyde Starting material: 4-chloro-pyrazole MS (ES) $MH^+$: 379 for $C_{17}H_{16}ClFN_4O_3$

Intermediate 548

3-amino-1-{6-[(2R,6S)-2,6-dimethylmorpholin-4-yl]-7-fluoro-5-formyl-1,2-benzoxazol-3-yl}-1H-pyrazole-4-carbonitrile Starting material: 3-amino-1H-pyrazole-4-carbonitrile
MS (ES) MH$^+$: 385 for $C_{18}H_{17}FN_6O_3$

Intermediate 549

6-[(2R,6S)-2,6-dimethylmorpholin-4-yl]-7-fluoro-3-[4-(pyrimidin-4-yl)-1H-pyrazol-1-yl]-1,2-benzoxazole-5-carbaldehyde Starting material: 4-(1H-pyrazol-4-yl)pyrimidine
MS (ES) MH$^+$: 423 for $C_{21}H_{19}FN_6O_3$;

Intermediate 550

6-[(2R,6S)-2,6-dimethylmorpholin-4-yl]-7-fluoro-3-[4-(pyrazin-2-yl)-1H-pyrazol-1-yl]-1,2-benzoxazole-5-carbaldehyde Starting material: 2-(1H-pyrazol-4-yl)pyrazine.
MS (ES) MH$^+$: 423 for $C_{21}H_{19}FN_6O_3$;

Intermediate 551

6-[(2R,6S)-2,6-dimethylmorpholin-4-yl]-7-fluoro-3-(4-iodo-1H-pyrazol-1-yl)-1,2-benzoxazole-5-carbaldehyde Starting material: 4-iodo-pyrazine.
MS (ES) MH$^+$: 470 for $C_{17}H_{16}FIN_4O_3$

Intermediate 552 ethyl 1-{6-[(2R,6S)-2,6-dimethylmorpholin-4-yl]-7-fluoro-5-formyl-1,2-benzoxazol-3-yl}-1H-pyrazole-4-carboxylate Starting material: ethyl-pyrazole-4-carboxylate.
MS (ES) MH$^+$: 416 for $C_{20}H_{21}FN_4O_5$

Intermediate 553

6-[(2R,6S)-2,6-dimethylmorpholin-4-yl]-7-fluoro-3-(methylsulfanyl)-1,2-benzoxazole-5-carbaldehyde To an ice cold solution of 3-chloro-6-[(2R,6S)-2,6-dimethylmorpholin-4-yl]-7-fluoro-1,2-benzoxazole-5-carbaldehyde (Intermediate 534, 0.3 g, 0.916 mmol) in dioxane was added sodium thiomethoxide (21% aq solution, 0.134 mL, 1.923 mmol) and stirred at room temperature for 12 hours. Reaction mixture was diluted with water and extracted with EtOAc (50 mL). Organic phase washed with brine (2×10 mL), dried over anhydrous sodium sulfate and, filtered, concentrated to give tilt product as white solid. Yield: 280 mg (90%).

MS (ES) MH$^+$: 325 for $C_{15}H_{17}FN_2O_3S$
$^1$H NMR (400 MHz, DMSO-d$_6$) δ: 1.1 (d, 6H), 2.7 (s, 3H), 3.0 (m, 2H), 3.2 (m, 2H), 3.8 (m, 2H), 7.9 (s, 1H), 10.2 (s, 1H).

Intermediate 554

6-[(2R,6S)-2,6-dimethylmorpholin-4-yl]-3-(3,5-dimethyl-1H-pyrazol-1-yl)-7-fluoro-1,2-benzoxazole-5-carbaldehyde To a stirred and degassed solution of 3-chloro-6-[(2R,6S)-2,6-dimethylmorpholin-4-yl]-7-fluoro-1,2-benzoxazole-5-carbaldehyde (Intermediate 534, 0.15 g, 0.48 mmol) in toluene was added K$_3$PO$_4$ (0.51 g, 2.40 mmol), 3,5-dimethyl-1H-pyrazole (92 mg, 0.96 mmol), 2-dicyclohexylphosphino-2',6'-dimethoxybiphenyl (S-phos) (4 mg, 0.009 mmol) and tris(dibenzylideneacetone)dipalladium(0) (8 mg, 0.009 mmol), sequentially and the reaction mixture was heated to 150° C. for 2 h in microwave reactor. The reaction mixture was diluted with EtOAc (15 mL). The organic layer was washed successively with water (2×10 mL), brine (2×10 mL), dried over anhydrous Na$_2$SO$_4$ and, after filtration, concentrated. The residue was purified over silica gel column using a gradient of ethylacetate in pet.ether to give product title compound as solid. Yield: 100 mg (56%).

MS (ES) MH$^+$: 373.5 for $C_{19}H_{21}FN_4O_3$;
$^1$H NMR (400 MHz, DMSO-d$_6$) δ: 1.1 (d, 6H), 2.3 (s, 3H), 2.6 (s, 3H), 3.0 (t, 2H), 3.3 (m, 2H), 3.8 (m, 2H), 6.3 (s, 1H), 8.5 (s, 1H), 10.25 (s, 1H).

Intermediate 555

6-[(2R,6S)-2,6-dimethylmorpholin-4-yl]-7-fluoro-3-(1H-pyrazol-4-yl)-1,2-benzoxazole-5-carbaldehyde 1H-pyrazole-4-boronic acid pinacolate ester, 3-chloro-6-[(2R,6S)-2,6-dimethylmorpholin-4-yl]-7-fluoro-1,2-benzoxazole-5-carbaldehyde (Intermediate 534), 2-dicyclohexylphosphino-2',6'-dimethoxybiphenyl (S-phos), and tris(dibenzylideneacetone)dipalladium(0) were reacted using a method similar to the one described for the synthesis of Intermediate 554.

MS (ES) MH$^+$: 345 for $C_{17}H_{17}FN_4O_3$
$^1$H NMR (400 MHz, DMSO-d$_6$) δ: 1.25 (d, 6H), 3.2 (m, 4H), 3.9 (m, 2H), 6.6 (m, 1H), 7.9 (s, 1H), 8.3 (s, 1H), 8.7 (s, 1H), 10.35 (s, 1H).

Intermediate 556

6-[(2R,6S)-2,6-dimethylmorpholin-4-yl]-7-fluoro-3-hydroxy-1,2-benzisoxazole-5-carbaldehyde To a stirred solution of tert-butyl 6-[(2R,6S)-2,6-dimethylmorpholin-4-yl]-7-fluoro-5-formyl-2,3-dihydro-1,2-benzisoxazol-3-yl carbonate (Intermediate 533, 0.5 g, 1.2 mmol) in methanol (5 ml) was added 5 ml of 5% aqueous HCl before heating at 75° C. for 2 hours. The reaction mixture was quenched with 10% aqueous sodium bicarbonate solution and extracted with EtOAc. The organic layer were washed with water, dried (sodium sulfate), and concentrated. The residue purified over a silica gel flash column (elution with 50-70% EtOAc in hexanes) to give product.

Yield: 0.4 g, (100%).
MS (ES) MH$^+$: 295 for $C_{14}H_{15}FN_2O_4$.
$^1$H NMR (400 MHz, DMSO-d$_6$) δ: 1.0 (d, 6H), 2.9 (t, 2H), 3.2 (d, 2H), 3.8 (m, 2H), 7.9 (s, 1H), 10.2 (s, 1H).

Intermediate 557

6-[(2R,6S)-2,6-dimethylmorpholin-4-yl]-7-fluoro-3-methoxy-1,2-benzisoxazole-5-carbaldehyde To a solution of 6-[(2R,6S)-2,6-dimethylmorpholin-4-yl]-7-fluoro-3-hydroxy-1,2-benzisoxazole-5-carbaldehyde (Intermediate 556, 0.15 g, 0.5 mmol) in acetonitrile was added K$_2$CO$_3$ (0.08 g, 0.6 mmol) followed by MeI (0.07 mL, 0.5 mmol). The reaction mixture was stirred at 60° C. for 2 hours. The reaction mixture was concentrated, washed with water and extracted with EtOAc (2×10 mL). The organic layer was dried over Na$_2$SO$_4$, filtered and concentrated to provide the title product, along with a by-product, 6-[(2R,6S)-2,6-dimethylmorpholin-4-yl]-7-fluoro-2-methyl-3-oxo-2,3-dihydro-1,2-benzoxazole-5-carbaldehyde. The mixture was used in the next step with out further purification.

Yield: 120 mg (76%)
MS (ES) MH$^+$: 309.2 for $C_{15}H_{17}FN_2O_4$.
S)-)

Intermediate 558

3-(benzyloxy)-6-[(2R,6S)-2,6-dimethylmorpholin-4-yl]-7-fluoro-1,2-benzisoxazole-5-carbaldehyde Benzyl bromide and 6-[(2R,6S)-2,6-dimethylmorpholin-4-yl]-7-fluoro-3-hydroxy-1,2-benzisoxazole-5-carbaldehyde (Intermediate 556) were reacted using a method similar to the one described for the synthesis of Intermediate 557, providing the title product, along with a by-product, 2-benzyl-6-[(2R,6S)-2,6-dimethylmorpholin-4-yl]-7-fluoro-3-oxo-2,3-dihydro-1,2-benzoxazole-5-carbaldehyde. The mixture was used in the next step with out further purification.

MS (ES) MH$^+$: 385 for $C_{21}H_{21}FN_2O_4$.

Intermediate 559

3-(4-acetylpiperazin-1-yl)-6-[(2R,6S)-2,6-dimethyl-morpholin-4-yl]-7-fluoro-2,3-dihydro-1,2-benzisoxazole-5-carbaldehyde To a solution of 6-[(2R,6S)-2,6-dimethylmorpholin-4-yl]-7-fluoro-3-hydroxy-1,2-benzisoxazole-5-carbaldehyde (Intermediate 556, 0.15 g, 0.5 mmol) in acetonitrile was added BOP (0.275 g, 0.66 mmol) followed by DBU (0.23 g, 1.53 mmol), and the mixture was stirred for 10 minutes at room temperature. To this mixture was added the N-acetyl-piperizine (0.09 g, 0.71 mmol), and the mixture was stirred for 12 h at room temperature. The reaction mixture was concentrated, diluted with water and extracted with EtOAc (2×10 mL). The organic layer was dried over $Na_2SO_4$, filtered and concentrated. The residue thus was purified by silica gel column chromatography using EtOAc in pet. ether to give product.

Yield: 25 mg (12%);
MS (ES) MH$^+$: 405 for $C_{20}H_{25}FN_4O_4$.

Intermediates 560 to 573 were prepared from the indicated starting material and 6-[(2R,6S)-2,6-dimethylmorpholin-4-yl]-7-fluoro-3-hydroxy-1,2-benzisoxazole-5-carbaldehyde (Intermediate 556) using a method similar to the one described for the synthesis of Intermediate 559:

Intermediate 560 tert-butyl 4-{6-[(2R,6S)-2,6-dimethylmorpholin-4-yl]-7-fluoro-5-formyl-1,2-benzisoxazol-3-yl}piperazine-1-carboxylate Starting material: tert-Butyl 1-piperazinecarboxylate.
MS (ES) MH$^+$: 463 for $C_{23}H_{31}FN_4O_5$ Intermediate 561

6-[(2R,6S)-2,6-dimethylmorpholin-4-yl]-7-fluoro-3-(piperidin-1-yl)-1,2-benzisoxazole-5-carbaldehyde Starting material: piperidine.
MS (ES) MH$^+$: 362 for $C_{19}H_{24}FN_3O_3$.

Intermediate 562

6-[(2R,6S)-2,6-dimethylmorpholin-4-yl]-7-fluoro-3-(morpholin-4-yl)-1,2-benzisoxazole-5-carbaldehyde Starting material: morpholine.
MS (ES) MH$^+$: 364 for $C_{18}H_{22}FN_3O_4$.

Intermediate 563

3-(diethylamino)-6-[(2R,6S)-2,6-dimethylmorpholin-4-yl]-7-fluoro-1,2-benzisoxazole-5-carbaldehyde Starting material: N,N-diethylamine.
MS (ES) MH$^+$: 350 for $C_{18}H_{24}FN_3O_3$.

Intermediate 564

3-(dimethylamino)-6-[(2R,6S)-2,6-dimethylmorpholin-4-yl]-7-fluoro-1,2-benzisoxazole-5-carbaldehyde Starting material: N,N-dimethyl amine.
MS (ES) MH$^+$: 322.2 for $C_{16}H_{20}FN_3O_3$.

Intermediate 565

6-[(2R,6S)-2,6-dimethylmorpholin-4-yl]-7-fluoro-3-(pyrrolidin-1-yl)-1,2-benzisoxazole-5-carbaldehyde Starting material: pyrrolidine.
MS (ES) MH$^+$: 348 for $C_{18}H_{22}FN_3O_3$;
$^1$H NMR (400 MHz, DMSO-$d_6$) δ: 1.0 (d, 6H), 2.0 (t, 4H), 2.9 (m, 2H), 3.2 (d, 2H), 3.6 (t, 4H), 3.8 (m, 2H), 8.0 (s, 1H), 10.2 (s, 1H).

Intermediate 566

3-(azepan-1-yl)-6-[(2R,6S)-2,6-dimethylmorpholin-4-yl]-7-fluoro-1,2-benzisoxazole-5-carbaldehyde Starting material: azepane.
MS (ES) MH$^+$: 350.2 for $C_{20}H_{26}FN_3O_3$.

Intermediate 567

6-[(2R,6S)-2,6-dimethylmorpholin-4-yl]-7-fluoro-3-[5-methyl-3-(trifluoromethyl)-1H-pyrazol-1-yl]-1,2-benzisoxazole-5-carbaldehyde Starting material: 3-methyl-5-(trifluoromethyl) pyrazole.
MS (ES) MH$^+$: 427 for $C_{19}H_{18}F_4N_4O_3$.

Intermediate 568

N-[1-[6-[(2S,6R)-2,6-dimethylmorpholin-4-yl]-7-fluoro-5-formyl-1,2-benzoxazol-3-yl]pyrazol-3-yl] acetamide Starting material: N-1H-pyrazol-3-ylacetamide
MS (ES) MH$^+$: MS (ES) MH$^+$: 402 for $C_{19}H_{20}FN_5O_4$ Intermediate 569

6-[(2R,6S)-2,6-dimethylmorpholin-4-yl]-7-fluoro-3-[3-(trifluoromethyl)-1H-pyrazol-1-yl]-1,2-benzisoxazole-5-carbaldehyde Starting material: (3-(trifluoromethyl) pyrazole.
MS (ES) MH$^+$: 413 for $C_{18}H_{16}F_4N_4O_3$.

Intermediate 570

3-[3-(difluoromethyl)-1H-pyrazol-1-yl]-6-[(2R,6S)-2,6-dimethylmorpholin-4-yl]-7-fluoro-1,2-benzisoxazole-5-carbaldehyde Starting material: 3-(difluoromethyl)-5-methyl pyrazole.
MS (ES) MH$^+$: 409 for $C_{19}H_{19}F_3N_4O_3$.

Intermediate 571

6-[(2R,6S)-2,6-dimethylmorpholin-4-yl]-7-fluoro-3-(propylamino)-1,2-benzoxazole-5-carbaldehyde Starting material: N-propylamine
MS (ES) MH$^+$: 336 for $C_{17}H_{22}FN_3O_3$.

Intermediate 572

3-[benzyl(methyl)amino]-6-[(2R,6S)-2,6-dimethyl-morpholin-4-yl]-7-fluoro-1,2-benzoxazole-5-carbaldehyde Starting material: N-Methyl-1-benzylamine
MS (ES) MH$^+$: 463 for $C_{22}H_{24}FN_3O_3$.

Intermediate 573

6-[(2R,6S)-2,6-dimethylmorpholin-4-yl]-7-fluoro-3-[methyl(propyl)amino]-1,2-benzoxazole-5-carbaldehyde Starting material: N-Methyl-propane-1-amine
MS (ES) MH$^+$: 362 for $C_{18}H_{24}FN_3O_3$.

Intermediate 574

6-((2R,6R)-2,6-dimethylmorpholino)-7-fluoro-3-(1H-1,2,4-triazol-1-yl)benzo[d]isoxazole-5-carbaldehyde Sodium hydride (60% dispersion) (0.288 g, 7.19 mmol) was added to a solution of 1H-1,2,4-triazole (0.530 g, 7.67 mmol) and 3-chloro-6-((2R,6R)-2,6-dimethylmorpholino)-7-fluorobenzo[d]isoxazole-5-carbaldehyde (Intermediate 535, 1.5 g, 4.80 mmol) in DMF (10 ml), and the mixture was stirred at room temperature overnight. The mixture was quenched with aqueous NH$_4$Cl and diluted with water before being extracted with CH$_2$Cl$_2$ 5 times. The combined extracts were dried (MgSO$_4$) and concentrated to give a solid that was taken up in CH$_2$Cl$_2$. Insoluble solids were filtered off and rinsed with additional CH$_2$Cl$_2$. The solids were dried in vacuo and were consistent with desired product. The filtrate was concentrated and chromatographed on silica gel (100% CH$_2$Cl$_2$ followed by gradient elution to 50% EtOAc in CH$_2$Cl$_2$) to give additional desired product. Total of 866 mg.

MS (ES) MH$^+$: 345 for $C_{16}H_{16}FN_5O_3$
$^1$H NMR (300 MHz, CHLOROFORM-d) δ ppm 1.3 (d, 6H), 3.0-3.2 (m, 2H), 3.4-3.6 (m, 2H), 4.25 (m, 2H), 8.3 (s, 1H), 8.6 (d, 1H), 9.0 (s, 1H), 10.4 (s, 1H).

Intermediate 575

(2R,4S,4aS)-rel-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidine]-8-carbothioamide To a stirred solution of (2R,4S,4aS)-rel-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidine]-8-carbonitrile (Example 183, 210 mg, 0.51 mmol) in DMF was added ammonium sulfide (0.35 mL, 1.02 mmol) and the mixture was stirred at room temperature for 1 hour. The reaction mixture was concentrated to give product as a pale yellow solid.

Yield: 215 mg (97%).
MS (ES) MH$^+$: 448 for $C_{19}H_{18}FN_5O_5S$;
$^1$H NMR (400 MHz, DMSO-d$_6$) δ: 0.9 (d, 3H), 1.1 (d, 3H), 2.9 (d, 1H), 3.1 (m, 1H), 3.7 (m, 1H), 3.8 (m, 2H), 4.0 (d, 1H), 4.1 (d, 1H), 7.6 (s, 1H), 10.0 (s, 1H), 10.35 (s, 1H), 11.5 (s, 1H), 11.8 (s, 1H).

When tested in an in-vitro assay based on the DNA gyrase supercoiling activity fluorescence polarisation assay described above, Intermediate 575 had *E. coli* DNA gyrase supercoiling IC$_{50}$ assay inhibitory activity measured at 1.0 μM.

Intermediate 576

6-[(2R,6S)-2,6-dimethylmorpholin-4-yl]-7-fluoro-3-methyl-1,2-benzothiazole-5-carbaldehyde To an ice-cooled solution of {6-[(2R,6S)-2,6-dimethylmorpholin-4-yl]-7-fluoro-3-methyl-1,2-benzothiazol-5-yl}methanol (Intermediate 157, 0.18 g, 0.6 mmol) in DCM/CH$_3$CN mixture (3 mL, 1:1 v/v) was added NMO (0.12 g, 0.7 mmol) followed TPAP (0.04, 0.2 mmol) and mixture stirred for 2 h at room temperature. The reaction mixture filtered through silica gel bed and washed with EtOAc. The organic phase concentrated under reduced pressure to give title compound as a yellow crystalline solid. Yield: 0.12 g (67%).

MS (ES) MH$^+$: 309 for $C_{15}H_{17}FN_2O_2S$
$^1$H NMR (400 MHz, Methanol-d$_4$): δ 1.2 (d, 6H), 2.7 (s, 3H), 3.1 (m, 2H), 3.2 (m, 2H), 3.9 (m, 2H), 8.3 (s, 2H), 10.5 (s, 1H).

Intermediate 577 was prepared from the indicated starting material using a method similar to the one described for the synthesis of Intermediate 576:

Intermediate 577

6-[(2R,6S)-2,6-dimethylmorpholin-4-yl]-7-fluoro-3-(pyridin-2-yl)-1,2-benzothiazole-5-carbaldehyde Starting material: {6-[(2R,6S)-2,6-dimethylmorpholin-4-yl]-7-fluoro-3-(pyridin-2-yl)-1,2-benzothiazol-5-yl}methanol (Intermediate 158)

MS (ES) MH$^+$: 372 for $C_{19}H_{18}FN_3O_2S$
$^1$H NMR (400 MHz, CDCl$_3$) δ: 1.24 (d, 6H), 3.1 (d, 4H), 3.9 (m, 2H), 7.4 (m, 1H), 7.9 (t, 1H), 8.3 (d, 1H), 8.8 (d, 1H), 9.4 (s, 1H), 10.5 (s, 1H).

Intermediate 578 was prepared from the indicated starting materials using a method similar to the one described for the synthesis of Intermediate 62:

Intermediate 578

{5-({[tert-Butyl(diphenyl)silyl]oxy}methyl)-4-[(2R,6S)-2,6-dimethylmorpholin-4-yl]-2,3-difluorophenyl}(pyrazin-2-yl)methanol Starting material: (2R,6S)-4-[6-({[tert-butyl(diphenyl)silyl]oxy}methyl)-2,3-difluoro phenyl]-2,6-dimethylmorpholine (Intermediate 3) and pyrazine-2-carboxaldehyde.

MS (ES) MH$^+$: 604.8 for $C_{34}H_{39}F_2N_3O_3Si$

Intermediate 579 was prepared from the indicated starting materials using a method similar to the one described for the synthesis of Intermediate 20:

Intermediate 579

{5-({[tert-butyl(diphenyl)silyl]oxy}methyl)-4-[(2R,6S)-2,6-dimethylmorpholin-4-yl]-2,3-difluorophenyl}(pyrazin-2-yl)methanone Starting material: {5-({[tert-Butyl(diphenyl)silyl]oxy}methyl)-4-[(2R,6S)-2,6-dimethylmorpholin-4-yl]-2,3-difluorophenyl}(pyrazin-2-yl)methanol (Intermediate 578).

MS (ES) MH$^+$: 602.8 for $C_{34}H_{37}F_2N_3O_3Si$

Intermediate 580 was prepared from the indicated starting materials using a method similar to the one described for the synthesis of Intermediate 23:

Intermediate 580

{4-[(2R,6S)-2,6-dimethylmorpholin-4-yl]-2,3-difluoro-5-(hydroxymethyl)phenyl}(pyrazin-2-yl)methanone Starting material: {5-({[tert-butyl(diphenyl)silyl]oxy}methyl)-4-[(2R,6S)-2,6-dimethylmorpholin-4-yl]-2,3-difluorophenyl}(pyrazin-2-yl)methanone (Intermediate 579)
MS (ES) MH$^+$: 364.4 for $C_{18}H_{19}F_2N_3O_3$ Intermediate 581 was prepared from the indicated starting materials using a method similar to the one described for the synthesis of Intermediate 26:

Intermediate 581

2-[(2R,6S)-2,6-dimethylmorpholin-4-yl]-3,4-difluoro-5-(pyrazin-2-ylcarbonyl)benzaldehyde Starting material: {4-[(2R,6S)-2,6-dimethylmorpholin-4-yl]-2,3-difluoro-5-(hydroxymethyl)phenyl}(pyrazin-2-yl)methanone (Intermediate 580)
MS (ES) MH$^+$: 362.4 for $C_{18}H_{17}F_2N_3O_3$ Intermediate 582 was prepared from the indicated starting materials using a method similar to the one described for the synthesis of Intermediate 12:

Intermediate 582

(2R,4S,4aS)-rel-9,10-difluoro-2,4-dimethyl-8-(pyrazin-2-ylcarbonyl)-1,2,4,4a-tetrahydro-2'H,6H-spiro[1,4-oxazino[4,3-a]quinoline-5,5'-pyrimidine]-2',4',6'(1'H,3'H)-trione Starting material: 2-[(2R,6S)-2,6-dimethylmorpholin-4-yl]-3,4-difluoro-5-(pyrazin-2-ylcarbonyl)benzaldehyde (Intermediate 581).
MS (ES) MH$^+$: 472.4 for $C_{22}H_{19}F_2N_5O_5$ Intermediate 583 was prepared from the indicated starting materials using a method similar to the one described for the synthesis of Intermediate 29:

Intermediate 583

(2R,4S,4aS)-rel-9,10-difluoro-8-[(hydroxyimino)(pyrazin-2-yl)methyl]-2,4-dimethyl-1,2,4,4a-tetrahydro-2'H,6H-spiro[1,4-oxazino[4,3-a]quinoline-5,5'-pyrimidine]-2',4',6'(1'H,3'H)-trione Starting material: (2R,4S,4aS)-rel-9,10-difluoro-2,4-dimethyl-8-(pyrazin-2-ylcarbonyl)-1,2,4,4a-tetrahydro-2'H,6H-spiro[1,4-oxazino[4,3-a]quinoline-5,5'-pyrimidine]-2',4',6'(1'H,3'H)-trione (Intermediate 582).
MS (ES) MH$^+$: 487.4 for $C_{22}H_{20}F_2N_6O_5$ Intermediate 584 was prepared from the indicated starting materials using a method similar to the one described for the synthesis of Intermediate 62:

Intermediate 584

{5-({[tert-butyl(diphenyl)silyl]oxy}methyl)-4-[(2R,6S)-2,6-dimethylmorpholin-4-yl]-2,3-difluorophenyl}(pyrimidin-2-yl)methanone Starting materials: (2R,6S)-4-[6-({[tert-butyl(diphenyl)silyl]oxy}methyl)-2,3-difluorophenyl]-2,6-dimethylmorpholine (Intermediate 3) and N-methoxy-N-methylpyrimidine-2-carboxamide (prepared according to the procedure shown in PCT Pub. No. WO03/059911).
MS (ES) MH$^+$: 603 for $C_{34}H_{37}F_2N_3O_3Si$ Intermediate 585 was prepared from the indicated starting materials using a method similar to the one described for the synthesis of Intermediate 336:

Intermediate 585

{5-({[tert-butyl(diphenyl)silyl]oxy}methyl)-4-[(2R,6S)-2,6-dimethylmorpholin-4-yl]-3-fluoro-2-[(propan-2-ylideneamino)oxy]phenyl}(pyrimidin-2-yl)methanone Starting material: {5-({[tert-butyl(diphenyl)silyl]oxy}methyl)-4-[(2R,6S)-2,6-dimethylmorpholin-4-yl]-2,3-difluorophenyl}(pyrimidin-2-yl)methanone (Intermediate 584)
MS (ES) MH$^+$: 655.8 for $C_{37}H_{43}FN_4O_4Si$ Intermediate 586 was prepared from the indicated starting materials using a method similar to the one described for the synthesis of Intermediate 33:

Intermediate 586

{6-[(2R,6S)-2,6-dimethylmorpholin-4-yl]-7-fluoro-3-(pyrimidin-2-yl)-1,2-benzoxazol-5-yl}methanol Starting material: {5-({[tert-butyl(diphenyl)silyl]oxy}methyl)-4-[(2R,6S)-2,6-dimethylmorpholin-4-yl]-3-fluoro-2-[(propan-2-ylideneamino)oxy]phenyl}(pyrimidin-2-yl)methanone (Intermediate 585).
MS (ES) MH$^+$: 359.4 for $C_{18}H_{19}FN_4O_3$ Intermediate 587 was prepared from the indicated starting materials using a method similar to the one described for the synthesis of Intermediate 27:

Intermediate 587

6-[(2R,6S)-2,6-dimethylmorpholin-4-yl]-7-fluoro-3-(pyrimidin-2-yl)-1,2-benzoxazole-5-carbaldehyde Starting material: {6-[(2R,6S)-2,6-dimethylmorpholin-4-yl]-7-fluoro-3-(pyrimidin-2-yl)-1,2-benzoxazol-5-yl}methanol (Intermediate 586)
MS (ES) MH$^+$: 357.4 for $C_{18}H_{17}FN_4O_3$ Example 1

(2R,4S,4aS)-rel-8-amino-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione

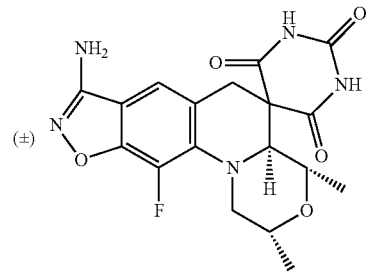

To a solution of 3-amino-6-[(2R,6S)-2,6-dimethylmorpholin-4-yl]-7-fluoro-1,2-benzisoxazole-5-carbaldehyde (Intermediate 8, 100 mg, 0.34 mmol) in IPA was added barbituric acid (48 mg, 0.34 mmol) and the mixture heated at 85° C. for 12 hours. Solvents were evaporated and the residue was purified over neutral alumina using a gradient of methanol in $CH_2Cl_2$ to give the title compound as a racemic mixture in the form of a pale yellow solid. Yield: 18 mg, (13%).

MS (ES) (M–H)⁻: 402.6 for $C_{18}H_{18}FN_5O_5$

¹H NMR (400 MHz, DMSO-$d_6$) δ: 0.9 (d, 3H), 1.1 (d, 3H), 2.9 (d, 1H), 3.0 (t, 1H), 3.4 (d, 1H), 3.6 (t, 1H), 3.75 (d, 1H), 3.9 (d, 1H), 4.0 (d, 1H), 6.2 (bs, 2H), 7.1 (s, 1H), 11.4 (s, 1H), 11.8 (s, 1H).

Example 2

(2R,4S,4aS)-rel-11-fluoro-2,4,8-trimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione

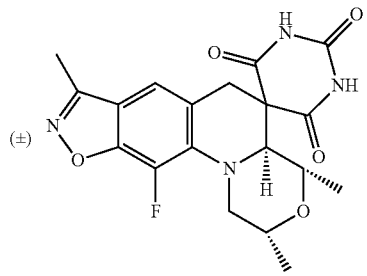

To a solution of (2R,4S,4aS)-rel-9,10-difluoro-8-[(1E)-N-hydroxyethanimidoyl]-2,4-dimethyl-1,2,4,4a-tetrahydro-2'H,6H-spiro[1,4-oxazino[4,3-a]quinoline-5,5'-pyrimidine]-2',4',6'(1'H,3'H)-trione (Intermediate 16, 250 mg, 0.63 mmol) in DMSO, was added K—O-t-Bu (47 mg, 0.636 mmol) and the mixture was heated to 120° C. for 12 hours. After cooling to room temperature and removal of solvent, the residue was purified using normal phase HPLC (95:5: Hexane:IPA) to give the title compound as a racemic mixture in the form of a pale yellow solid. Yield: 50 mg (20%).

MS (ES) MH⁺: 403.2 for $C_{19}H_{19}FN4O_5$

¹H NMR (400 MHz, DMSO-$d_6$) δ: 0.9 (d, 3H), 1.1 (d, 3H), 2.4 (d, 3H), 2.5 (d, 1H), 2.9 (t, 1H), 3.5 (d, 1H), 3.6 (m, 1H), 3.8 (d, 1H), 3.9 (d, 1H), 4.0 (d, 1H), 7.2 (s, 1H), 11.4 (s, 1H), 11.8 (s, 1H).

Example 2 was also prepared using the following synthesis:

Example 2

Alternate Preparation (2R,4S,4aS)-rel-11-fluoro-2,4,8-trimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

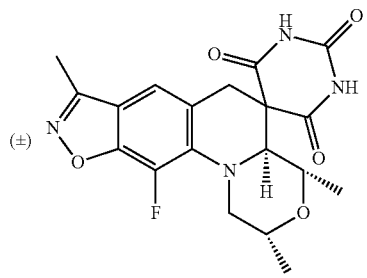

To a stirred solution of 6-((2R,6S)-2,6-dimethylmorpholino)-7-fluoro-3-methylbenzo[d]isoxazole-5-carbaldehyde (Intermediate 34, 543 mg, 1.86 mmol) in isopropanol (50 ml) was added pyrimidine-2,4,6(1H,3H,5H)-trione (238 mg, 1.86 mmol), and the reaction mixture was stirred for 16 hours at 80° C. Solvent was removed and the residue was triturated with isopropanol. The solid was filtered, washed with isopropanol, and dried in vacuo. The filtrate was concentrated and purified on silica gel (30-50% EtOAc in hexanes). The product thus obtained was combined with the filtered solid in methanol and concentrated to give the title compound (528 mg, 71%) as a racemic mixture.

MS (ES): 403 (M+H) for $C_{19}H_{19}FN_4O_5$

¹H NMR (400 MHz, DMSO-$d_6$) d ppm 0.9 (d, 3H) 1.1 (d, 3H) 2.4 (s, 3H), 2.9-4.2 (m, 7H) 7.2 (s, 1H) 11.4 (s, 1H) 11.8 (s, 1H).

The (2S,4R,4aR) and (2R,4S,4aS) enantiomers of Example 2 were separated by Supercritical Fluid Chromatography using a Chiralpak AD, 21×250 mm, 5 g column (elution with 20% MeOH, 80% $CO_2$ at 60 ml/min, 40° C., and 100 bar with detection at 220 nm), providing Example 2(a) and Example 2(b):

Example 2(a)

First Eluting Compound (2S,4R,4aR)-11-fluoro-2,4,8-trimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

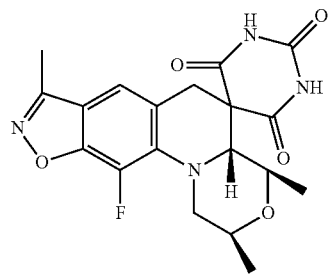

MS (ES): 403 (M+H) for $C_{19}H_{19}FN_4O_5$

¹H NMR (400 MHz, DMSO-$d_6$) δ ppm 0.9 (d, 3H) 1.1 (d, 3H) 2.4 (s, 3H) 2.9-4.2 (m, 7H) 7.2 (s, 1H) 11.6 (s, broad, 2H). yield: (202 mg, 40%).

>98% ee by chiral HPLC; [α]=+296 (c=0.1 in MeOH).

Example 2(b)

Second Eluting Compound (2R,4S,4aS)-11-fluoro-2,4,8-trimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

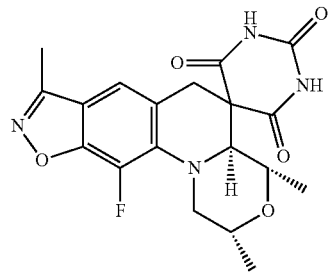

MS (ES): 403 (M+H) for $C_{19}H_{19}FN_4O_5$

¹H NMR (400 MHz, DMSO-$d_6$) δ ppm 0.9 (d, 3H) 1.1 (d, 3H) 2.4 (s, 3H) 2.9-4.2 (m, 7H) 7.2 (s, 1H) 11.6 (s, broad, 2H). yield: (199 mg, 39%).

>98% ee by chiral HPLC; [α]=−291 (c=0.1 in MeOH).

Example 3

(2R,4S,4aS)-rel-11-fluoro-2,4-dimethyl-8-phenyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione

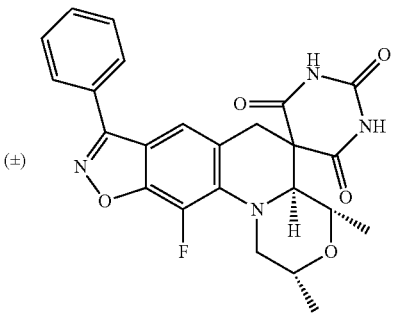

Cs$_2$CO$_3$ (130 mg, 0.0004 mmol) was added to a solution of (2R,4S,4aS)-rel-9,10-difluoro-8-[(E)-(hydroxyimino)(phenyl)methyl]-2,4-dimethyl-1,2,4,4a-tetrahydro-2'H,6H-spiro[1,4-oxazino[4,3-a]quinoline-5,5'-pyrimidine]-2',4',6'(1'H,3'H)-trione (Intermediate 29, 100 mg, 0.0002 mmol) in DMF (1.5 mL), and the mixture was heated to 100° C. for 14 h. The reaction mixture was cooled to room temperature and filtered through a Celite bed. The solvent was removed, and the residue was subjected to reverse phase prep-HPLC purification (10 mM ammonium acetate in water, CH$_3$CN) providing the title compound as a racemic mixture. Yield: 9.97 g (9%).

MS (ES) MH$^+$: 465.2 for C$_{24}$H$_{21}$FN$_4$O$_5$ $^1$H NMR (400 MHz, DMSO-d$_6$) δ: 0.9 (d, 3H), 1.1 (d, 3H), 3.0 (d, 1H), 3.1 (t, 1H), 3.6 (d, 1H), 3.7 (m, 1H), 3.75 (m, 1H), 3.9 (d, 1H), 4.1 (d, 1H), 7.6 (m, 4H), 7.9 (s, 2H), 11.5 (bs, 2H).

Examples 4 and 5 were prepared from the indicated starting materials using a method similar to the one described for the syntheses of Example 3. Each was obtained as a racemic mixture.

Example 4

(2R,4S,4aS)-rel-8-cyclopropyl-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione

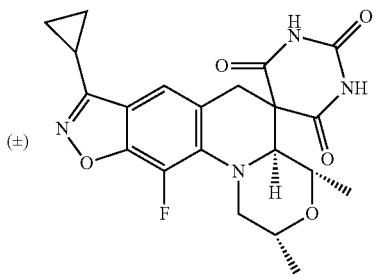

Starting material: (2R,4S,4aS)-rel-8-[(E)-Cyclopropyl(hydroxyimino)methyl]-9,10-difluoro-2,4-dimethyl-1,2,4,4a-tetrahydro-2'H,6H-spiro[1,4-oxazino[4,3-a]quinoline-5,5'-pyrimidine]-2',4',6'(1'H,3'H)-trione (Intermediate 31).

MS (ES) MH$^+$: 429.1 for C$_{21}$H$_{21}$FN$_4$O$_5$ $^1$H NMR (400 MHz, DMSO-d$_6$) δ: 0.9 (d, 3H), 1.0 (m, 4H), 1.1 (d, 3H), 2.2 (m, 1H), 2.9 (d, 1H), 3.1 (t, 1H), 3.6 (d, 1H), 3.7 (m, 1H), 3.75 (m, 1H), 3.9 (d, 1H), 4.1 (d, 1H), 7.2 (s, 1H), 11.0 (bs, 2H).

Example 5

(2R,4S,4aS)-rel-11-fluoro-2,4-dimethyl-8-pyridin-2-yl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione

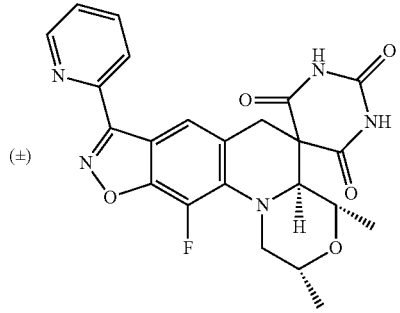

Starting material: (2R,4S,4aS)-rel-9,10-Difluoro-8-[(Z)-(hydroxyimino)(pyridin-2-yl)methyl]-2,4-dimethyl-1,2,4,4a-tetrahydro-2'H,6H-spiro[1,4-oxazino[4,3-a]quinoline-5,5'-pyrimidine]-2',4',6'(1'H,3'H)-trione (Intermediate 30).

MS (ES) MH$^+$: 466.2 for C$_{23}$H$_{20}$FN$_5$O$_5$ $^1$H NMR (400 MHz, DMSO-d$_6$) δ: 0.9 (d, 3H), 1.1 (d, 3H), 2.9 (d, 1H), 3.1 (t, 1H), 3.6 (m, 1H), 3.7 (m, 1H), 3.75 (m, 1H), 4.0 (d, 1H), 4.1 (d, 1H), 7.6 (m, 1H), 7.8 (s, 1H), 8.0 (t, 1H), 8.1 (d, 1H), 8.8 (d, 1H), 11.4 (bs, 2H).

Example 6

N-[(2R,4S,4aS)-rel-11-fluoro-2,4-dimethyl-2',4',6'-trioxo-1,1',2,3',4,4',4a,6'-octahydro-2'H,6H-spiro[isoxazolo[4,5-g][1,4]oxazino[4,3-a]quinoline-5,5'-pyrimidin]-8-yl]acetamide

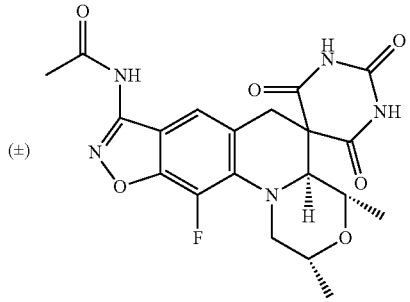

Pyridine (0.01 mL, 0.2 mmol) and acetic anhydride (0.10 mL, 0.14 mmol) were added sequentially to a solution of (2R,4S,4aS)-rel-8-amino-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione (Example 1, 54 mg, 0.13 mmol) in ethylene dichloride, and the mixture was stirred at 130° C. for 12 hours. After cooling to room temperature, solvent was removed, and the residue was purified over a silica gel flash column using a gradient of methanol in chloroform to give the title compound as a racemic mixture in the form of a yellow solid. Yield: 7.5 mg, (13%).

MS (ES) MH+: 446.3 for $C_{20}H_{20}FN_5O_6$

1H NMR (400 MHz, DMSO-d6) δ: 0.9 (d, 3H), 1.1 (d, 3H), 2.1 (s, 3H), 2.9 (d, 1H), 3.0 (t, 1H), 3.4 (d, 1H), 3.6 (t, 1H), 3.75 (d, 1H), 3.9 (d, 1H), 4.0 (d, 1H), 7.4 (s, 1H), 11.0 (s, 1H), 11.4 (s, 1H), 11.8 (s, 1H).

Example 7

(2R,4S,4aS)-rel-11-chloro-2,4,8-trimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

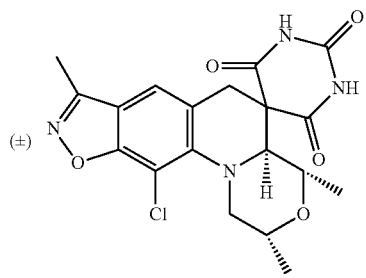

To a solution of 7-chloro-6-[(2R,6S)-2,6-dimethylmorpholin-4-yl]-3-methyl-1,2-benzoxazole-5-carbaldehyde (Intermediate 375, 35 mg, 0.119 mmol) in IPA was added barbituric acid (16 mg, 0.113 mmol) and the mixture heated at 85° C. for 16 hours. Solvents were evaporated and the residue thus obtained was purified over silica column using a gradient of methanol in chloroform to give product as a solid. Yield: 10 mg (25%).

MS (ES) MH+: 419 for $C_{19}H_{19}ClN_4O_5$;

1H NMR (400 MHz, DMSO-D6) δ: 0.9 (d, 3H), 1.1 (d, 3H), 2.4 (s 3H), 3.0 (m, 2H), 3.5 (d, 1H), 3.6 (m, 1H), 3.9 (m, 2H), 4.5 (d, 1H), 7.3 (s, 1H), 11.45 (s, 1H), 11.85 (s, 1H).

Example 8

(2R,4S,4 aS)-rel-8-(4-acetylpiperazin-1-yl)-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione

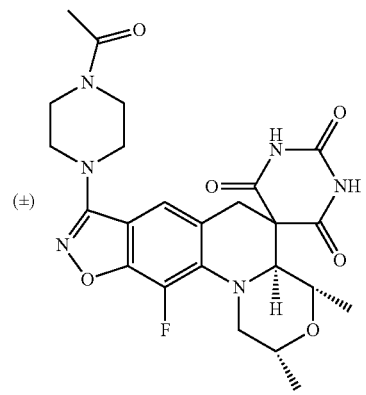

To a stirred solution of 3-(4-acetylpiperazin-1-yl)-6-[(2R, 6S)-2,6-dimethylmorpholin-4-yl]-7-fluoro-2,3-dihydro-1,2-benzisoxazole-5-carbaldehyde (Intermediate 559, 25 mg, 0.062 mmol) in dry IPA (1 mL) was added barbituric acid (8 mg, 0.062 mmol) and the solution heated around 80° C. for 12 h. Solvents were evaporated and the residue was purified over a silica gel-column to give product as white solid. Yield: 17 mg (55%).

MS (ES) MH+: 515 for $C_{24}H_{27}FN_6O_6$

1H NMR (400 MHz, DMSO-d6) δ: 0.9 (d, 3H), 1.2 (d, 3H), 2.0 (s, 3H), 2.95 (d, 1H), 3.05 (t, 1H), 3.4-3.5 (m, 5H), 3.6 (d, 4H), 3.7 (m, 1H), 3.8 (m, 1H), 3.9 (d, 1H), 4.0 (d, 1H), 7.4 (s, 1H), 11.5 (s, 1H), 11.85 (s, 1H).

Examples 9 to 53 were prepared from the indicated starting material and pyrimidine-2,4,6(1H,3H,5H)-trione using a method similar to the one described for the synthesis of Example 8:

Example 9

(2R,4S,4 aS)-rel-8-(benzylamino)-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

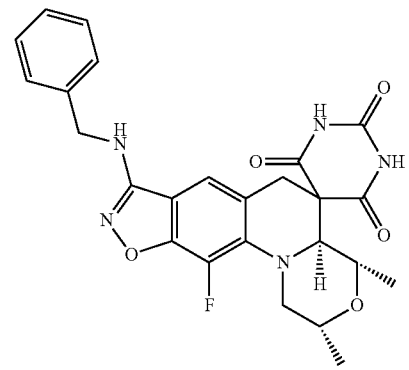

Starting material: 3-(benzylamino)-6-[(2R,6S)-2,6-dimethylmorpholin-4-yl]-7-fluoro-1,2-benzoxazole-5-carbaldehyde (Intermediate 515)

MS (ES) MH+: 495 for $C_{25}H_{24}FN_5O_5$

1H NMR (400 MHz, DMSO-d6) δ: 0.9 (d, 3H), 1.1 (d, 3H), 2.9 (d, 1H), 3.0 (m, 1H), 3.4 (d, 1H), 3.6 (t, 1H), 3.8 (d, 1H), 3.9 (d, 1H), 4.0 (d, 1H), 4.4 (d, 2H), 7.1 (s, 1H), 7.35 (q, 5H), 11.45 (s, 1H), 11.8 (s, 1H).

Example 10

(2R,4S,4aS)-rel-11-fluoro-2,4-dimethyl-8-[(1,3-thiazol-2-ylmethyl)amino]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

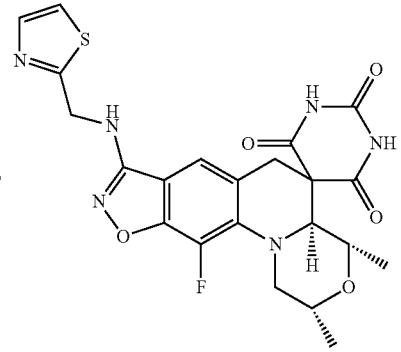

Starting material: 6-[(2R,6S)-2,6-dimethylmorpholin-4-yl]-7-fluoro-3-[(1,3-thiazol-2-ylmethyl)amino]-1,2-benzoxazole-5-carbaldehyde (Intermediate 516)
MS (ES) MH$^+$: 501 for $C_{22}H_{21}FN_6O_5S$.
$^1$H NMR (400 MHz, DMSO) δ: 0.9 (d, 3H), 1.1 (d, 3H), 2.9 (d, 1H), 3.0 (t, 1H), 3.5 (d, 1H), 3.6 (m, 1H), 3.75 (m, 1H), 3.9 (d, 1H), 4.0 (d, 1H), 4.7 (d, 1H), 7.1 (s, 1H), 7.6 (d, 1H), 7.7 (d, 1H), 7.8 (t, 1H).

Example 11

(2R,4S,4aS)-rel-11-fluoro-8-[(1H-imidazol-4-ylmethyl)amino]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

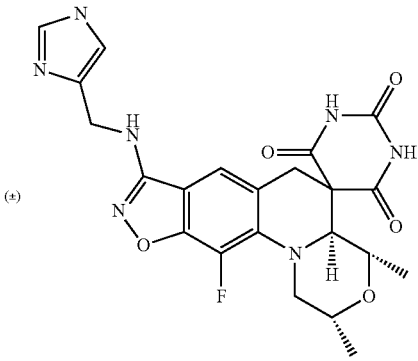

Starting material: 6-[(2R,6S)-2,6-dimethylmorpholin-4-yl]-7-fluoro-3-[(1H-imidazol-4-ylmethyl)amino]-1,2-benzoxazole-5-carbaldehyde (Intermediate 517)
MS (ES) MH$^+$: 484 for $C_{22}H_{22}FN_7O_5$.
$^1$H NMR (400 MHz, DMSO) δ: 0.9 (d, 3H), 1.1 (d, 3H), 2.9 (t, 1H), 3.0 (t, 1H), 3.4 (m, 1H), 3.6 (t, 1H), 3.8 (m, 1H), 3.9 (d, 1H), 4.0 (d, 1H), 4.2 (bs, 2H), 7.0 (m, 1H), 7.2 (s, 1H), 7.6 (ds, 1H), 11.5 (bs, 1H), 11.9 (bs, 1H).

Example 12

(2R,4S,4aS)-rel-11-fluoro-2,4-dimethyl-8-{[(1-methyl-1H-pyrazol-4-yl)methyl]amino}-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

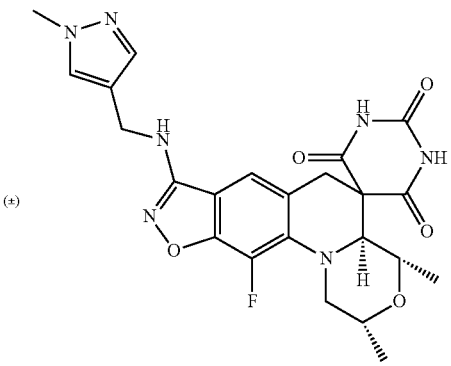

Starting material: (6-[(2R,6S)-2,6-dimethylmorpholin-4-yl]-7-fluoro-3-{[(1-methyl-1H-pyrazol-4-yl)methyl]amino}-1,2-benzoxazole-5-carbaldehyde (Intermediate 518)
MS (ES) MH$^+$: 498 for $C_{23}H_{24}FN_7O_5$.
$^1$H NMR (400 MHz, DMSO) δ: 0.9 (d, 3H), 1.1 (d, 3H), 2.9 (d, 1H), 3.05 (s, 1H), 3.4 (m, 1H), 3.6 (m, 1H), 3.7 (s, 3H), 3.9 (d, 1H), 4.0 (d, 1H), 4.2 (d, 1H), 7.0 (t, 1H), 7.1 (s, 1H), 7.4 (s, 1H), 7.6 (s, 1H), 11.4 (s, 1H), 11.8 (s, 1H).

Example 13

(2R,4S,4aS)-rel-11-fluoro-2,4-dimethyl-8-{[(5-methyl-1,2-oxazol-3-yl)methyl]amino}-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

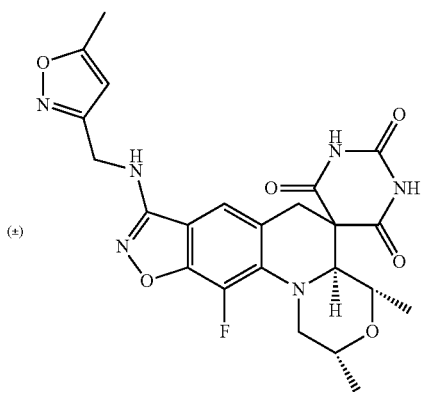

Starting material: (6-[(2R,6S)-2,6-dimethylmorpholin-4-yl]-7-fluoro-3-{[(5-methyl-1,2-oxazol-3-yl)methyl]amino}-1,2-benzoxazole-5-carbaldehyde (Intermediate 519)
MS (ES) MH$^+$: 499 for $C_{23}H_{23}FN_6O_6$.
$^1$H NMR (400 MHz, DMSO) δ: 0.9 (d, 3H), 1.1 (d, 3H), 2.3 (s, 3H), 2.9 (d, 1H), 3.05 (t, 1H), 3.5 (d, 1H), 3.6 (m, 1H), 3.75 (t, 1H), 3.9 (d, 1H), 4.0 (d, 1H), 4.4 (d, 2H), 6.2 (s, 1H), 7.1 (s, 1H), 7.4 (t, 1H), 11.4 (s, 1H), 11.8 (s, 1H).

Example 14

(2R,4S,4aS)-rel-11-fluoro-2,4-dimethyl-8-[(pyridin-2-ylmethyl)amino]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

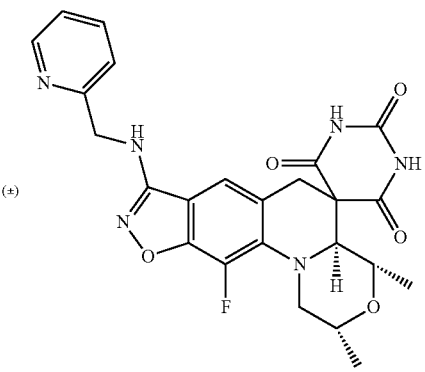

Starting material: {6-[(2R,6S)-2,6-dimethylmorpholin-4-yl]-7-fluoro-3-[(pyridin-2-ylmethyl)amino]-1,2-benzoxazole-5-carbaldehyde (Intermediate 520)
MS (ES) MH$^+$: 495 for $C_{24}H_{23}FN_6O_5$.
$^1$H NMR (400 MHz, DMSO) δ: 0.9 (d, 3H), 1.1 (d, 3H), 2.9 (d, 1H), 3.05 (t, 1H), 3.5 (d, 1H), 3.6 (t, 1H), 3.8 (m, 1H), 3.9

(d, 1H), 4.0 (d, 1H), 4.5 (d, 2H), 7.2 (s, 1H), 7.3 (t, 1H), 7.4 (d, 1H), 7.5 (t, 1H), 7.75 (t, 1H), 8.5 (d, 1H), 11.5 (s, 1H), 11.8 (s, 1H).

Example 15

(2R,4S,4aS)-rel-11-fluoro-2,4-dimethyl-8-[(pyridin-3-ylmethyl)amino]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

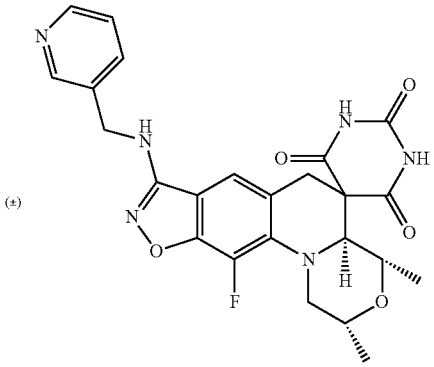

(±)

Starting material: {6-[(2R,6S)-2,6-dimethylmorpholin-4-yl]-7-fluoro-3-[(pyridin-3-ylmethyl)amino]-1,2-benzoxazole-5-carbaldehyde (Intermediate 521)

MS (ES) MH+: 495 for $C_{24}H_{23}FN_6O_5$.

$^1$H NMR (400 MHz, DMSO) δ: 0.9 (d, 3H), 1.1 (d, 3H), 2.9 (d, 1H), 3.05 (t, 1H), 3.5 (d, 1H), 3.6 (t, 1H), 3.7 (m, 1H), 3.9 (d, 1H), 4.0 (d, 1H), 4.4 (d, 2H), 7.1 (s, 1H), 7.35 (m, 1H), 7.4 (t, 1H), 7.8 (d, 1H), 8.45 (d, 1H), 8.6 (s, 1H), 11.4 (s, 1H), 11.8 (s, 1H).

Example 16

(2R,4S,4aS)-rel-11-fluoro-2,4-dimethyl-8-[(pyridin-4-ylmethyl)amino]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

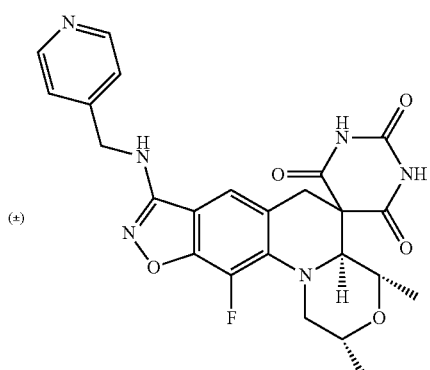

(±)

Starting material: {6-[(2R,6S)-2,6-dimethylmorpholin-4-yl]-7-fluoro-3-[(pyridin-4-ylmethyl)amino]-1,2-benzoxazole-5-carbaldehyde (Intermediate 522)

MS (ES) MH+: 495 for $C_{24}H_{23}FN_6O_5$.

$^1$H NMR (400 MHz, DMSO) δ: 0.9 (d, 3H), 1.1 (d, 3H), 2.9 (d, 1H), 3.0 (t, 2H), 3.7 (m, 2H), 3.95 (d, 1H), 4.0 (d, 1H), 4.4 (d, 2H), 7.1 (s, 1H), 7.3 (d, 1H), 7.5 (t, 1H), 8.5 (d, 1H).

Example 17

(2R,4S,4aS)-rel-8-[(cyclopropylmethyl)amino]-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

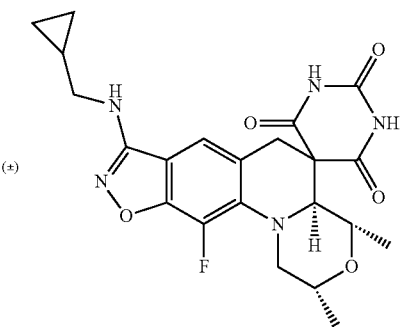

(±)

Starting material: {3-[(cyclopropylmethyl)amino]-6-[(2R,6S)-2,6-dimethylmorpholin-4-yl]-7-fluoro-1,2-benzoxazole-5-carbaldehyde (Intermediate 523)

MS (ES) MH+: 458 for $C_{22}H_{24}FN_5O_5$ $^1$H NMR (400 MHz, DMSO) δ: 0.2 (m, 2H), 0.5 (m, 2H), 0.9 (d, 3H), 1.1 (d, 3H), 2.9 (d, 1H), 3.0 (m, 3H), 3.4 (d, 1H), 3.6 (m, 1H), 3.8 (m, 1H), 3.9 (d, 1H), 4.0 (d, 1H), 6.9 (t, 1H), 7.15 (s, 1H).

Example 18

(2R,4S,4aS)-rel-8-[(cyclohexylmethyl)amino]-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

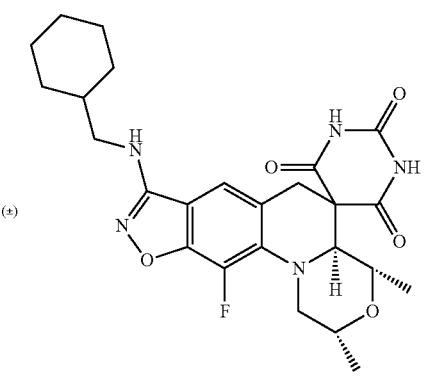

(±)

Starting material: {3-[(cyclohexylmethyl)amino]-6-[(2R,6S)-2,6-dimethylmorpholin-4-yl]-7-fluoro-1,2-benzoxazole-5-carbaldehyde (Intermediate 524)

MS (ES) MH+: 500 for $C_{25}H_{30}FN_5O_5$.

$^1$H NMR (400 MHz, DMSO) δ: 0.9 (d, 3H), 0.95 (m, 2H), 1.1 (d, 3H), 1.2 (m, 3H), 1.6-1.8 (m, 6H), 2.9-3.0 (m, 4H), 3.5

(d, 1H), 3.65 (t, 1H), 3.8 (m, 1H), 3.9 (d, 1H), 4.0 (d, 2H), 6.8 (s, 1H), 7.1 (s, 1H), 11.4 (s, 1H), 11.8 (s, 1H).

Example 19

(2R,4S,4aS)-rel-11-fluoro-2,4-dimethyl-8-[(tetrahydro-2H-pyran-4-ylmethyl)amino]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

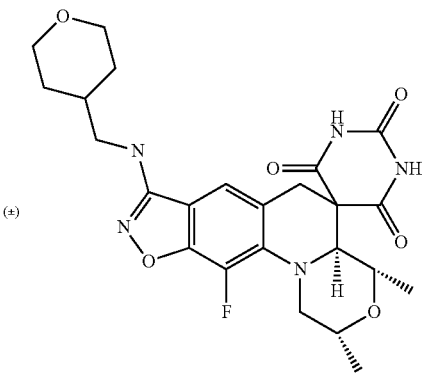

Starting material: 6-[(2R,6S)-2,6-dimethylmorpholin-4-yl]-7-fluoro-3-[(tetrahydro-2H-pyran-4-ylmethyl)amino]-1,2-benzoxazole-5-carbaldehyde (Intermediate 525)

MS (ES) MH$^+$: 502.3 for $C_{24}H_{28}FN_5O_6$ $^1$H NMR (400 MHz, DMSO) δ: 0.9 (d, 3H), 1.1 (d, 3H), 1.2 (m, 3H), 1.6 (d, 2H), 1.9 (m, 1H), 2.9-3.0 (m, 4H), 3.5 (d, 1H), 3.65 (t, 1H), 3.8 (m, 1H), 3.9 (d, 1H), 4.0 (d, 2H), 6.8 (s, 1H), 7.1 (s, 1H), 11.4 (s, 1H), 11.8 (s, 1H).

Example 20 tert-butyl 4-[(2R,4S,4aS)-rel-11-fluoro-2,4-dimethyl-2',4',6'-trioxo-1,1',2,3',4,4',4a,6'-octahydro-2'H,6H-spiro[isoxazolo[4,5-g][1,4]oxazino[4,3-c]quinoline-5,5'-pyrimidin]-8-yl]piperazine-1-carboxylate

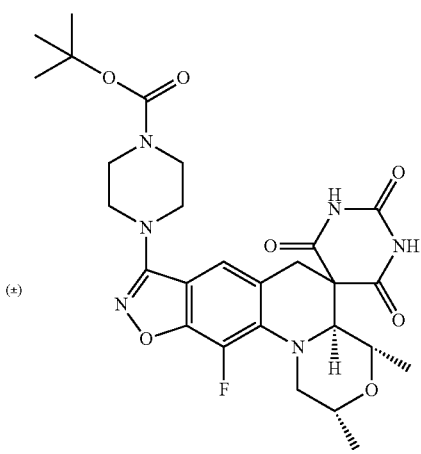

Starting material: tert-butyl 4-{6-[(2R,6S)-2,6-dimethylmorpholin-4-yl]-7-fluoro-5-formyl-1,2-benzisoxazol-3-yl}piperazine-1-carboxylate (Intermediate 560)

MS (ES) MH$^+$: 573 for $C_{27}H_{33}FN_6O_7$ $^1$H NMR (400 MHz, DMSO-d$_6$) δ: 0.9 (d, 3H), 1.1 (d, 3H), 1.4 (s, 9H), 2.95 (d, 1H), 3.05 (t, 1H), 3.40 (m, 4H), 3.45 (m, 5H), 3.65 (m, 1H), 3.8 (m, 1H), 3.9 (d, 1H), 4.05 (d, 1H), 7.4 (s, 1H), 11.5 (s, 1H), 11.85 (s, 1H).

Example 21

(2R,4S,4aS)-rel-11-fluoro-2,4-dimethyl-8-(piperazin-1-yl)-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione

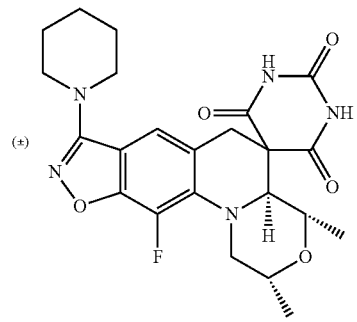

Starting material: 6-[(2R,6S)-2,6-dimethylmorpholin-4-yl]-7-fluoro-3-(piperidin-1-yl)-1,2-benzisoxazole-5-carbaldehyde (Intermediate 561)

MS (ES) MH$^+$: 472 for $C_{23}H_{26}FN_5O_5$ $^1$H NMR (400 MHz, DMSO-d$_6$) δ: 0.9 (d, 3H), 1.1 (d, 3H), 1.6 (bs, 6H), 2.9 (d, 1H), 3.0 (t, 1H), 3.35 (bs, 4H), 3.5 (d, 1H), 3.7 (m, 1H), 3.8 (m, 1H), 3.9 (d, 1H), 4.05 (d, 1H), 7.1 (d, 1H).

Example 22

(2R,4S,4aS)-rel-11-fluoro-2,4-dimethyl-8-(morpholin-4-yl)-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione

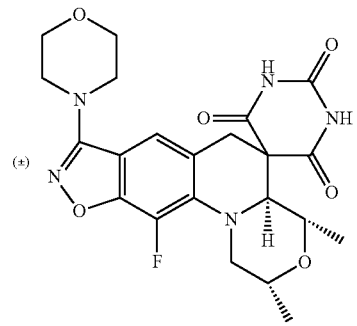

Starting material: 6-[(2R,6S)-2,6-dimethylmorpholin-4-yl]-7-fluoro-3-(morpholin-4-yl)-1,2-benzisoxazole-5-carbaldehyde (Intermediate 562)

MS (ES) MH$^+$: 474 for $C_{22}H_{24}FN_5O_6$

¹H NMR (400 MHz, DMSO-d₆) δ: 0.9 (d, 3H), 1.1 (d, 3H), 2.9 (d, 1H), 3.1 (t, 1H), 3.4 (bs, 5H), 3.45 (d, 1H), 3.7 (m, 1H), 3.75 (bs, 4H), 3.9 (d, 1H), 4.1 (d, 1H), 7.4 (s, 1H), 11.5 (s, 1H), 11.9 (s, 1H).

Example 23

(2R,4S,4aS)-rel-8-(diethylamino)-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione

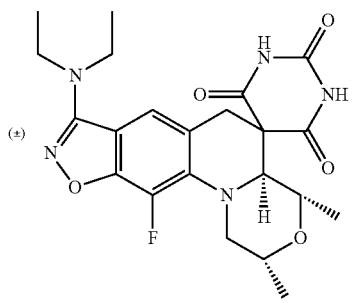

Starting material: 3-(diethylamino)-6-[(2R,6S)-2,6-dimethylmorpholin-4-yl]-7-fluoro-1,2-benzisoxazole-5-carbaldehyde (Intermediate 563)

MS (ES) MH⁺: 460 for $C_{22}H_{26}FN_5O_5$

¹H NMR (400 MHz, DMSO-d₆) δ: 0.9 (d, 3H), 1.1 (m, 9H), 2.9 (d, 1H), 3.1 (t, 1H), 3.3-3.45 (m, 4H), 3.5 (d, 1H), 3.6 (d, 1H), 3.7 (m, 1H), 3.9 (d, 1H), 4.1 (d, 1H), 7.2 (s, 1H), 11.5 (s, 1H), 11.8 (s, 1H).

Example 24

(2R,4S,4aS)-rel-8-(dimethylamino)-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione

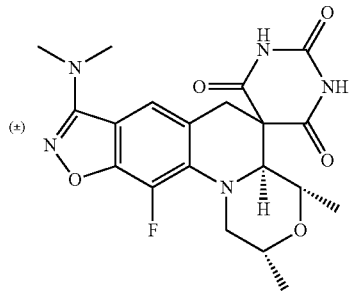

Starting material: 3-(dimethylamino)-6-[(2R,6S)-2,6-dimethylmorpholin-4-yl]-7-fluoro-1,2-benzisoxazole-5-carbaldehyde (Intermediate 564)

MS (ES) MH⁺: 432 for $C_{20}H_{22}FN_5O_5$

¹H NMR (400 MHz, DMSO-d₆) δ: 0.9 (d, 3H), 1.1 (d, 3H), 2.95 (d, 1H), 3.0 (s, 6H), 3.05 (s, 1H), 3.5 (d, 1H), 3.6 (d, 1H), 3.7 (m, 1H), 3.9 (d, 1H), 4.1 (d, 1H), 7.4 (s, 1H), 11.5 (s, 1H), 11.85 (s, 1H).

Example 25

(2R,4S,4aS)-rel-11-fluoro-2,4-dimethyl-8-(pyrrolidin-1-yl)-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione

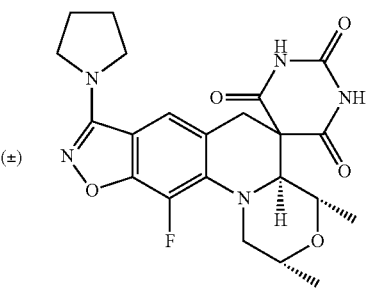

Starting material: 6-[(2R,6S)-2,6-dimethylmorpholin-4-yl]-7-fluoro-3-(pyrrolidin-1-yl)-1,2-benzisoxazole-5-carbaldehyde (Intermediate 565)

MS (ES) MH⁺: 458 for $C_{22}H_{24}FN_5O_5$

¹H NMR (400 MHz, DMSO-d₆) δ: 0.9 (d, 3H), 1.1 (d, 3H), 1.9 (t, 4H), 2.9 (d, 1H), 3.0 (t, 1H), 3.65 (m, 5H), 3.7 (d, 1H), 3.8 (m, 1H), 3.9 (d, 1H), 4.1 (d, 1H), 7.3 (s, 1H), 11.5 (s, 1H), 11.8 (s, 1H).

Example 26

(2R,4S,4aS)-rel-8-(azepan-1-yl)-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione

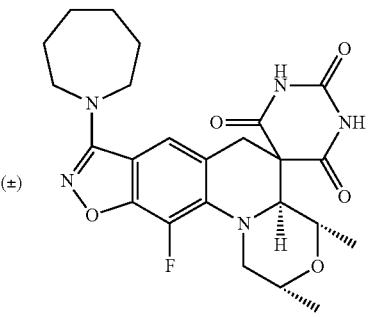

Starting material: 3-(azepan-1-yl)-6-[(2R,6S)-2,6-dimethylmorpholin-4-yl]-7-fluoro-1,2-benzisoxazole-5-carbaldehyde (Intermediate 566)

MS (ES) MH⁺: 486 for $C_{24}H_{28}FN_5O_5$

¹H NMR (400 MHz, DMSO-d₆) δ: 0.9 (d, 3H), 1.1 (d, 3H), 1.5 (bs, 4H), 1.7 (bs, 4H), 2.95 (d, 1H), 3.0 (s, 1H), 3.5 (m, 5H), 3.7 (d, 1H), 3.8 (m, 1H), 3.9 (d, 1H), 4.1 (d, 1H), 7.3 (s, 1H), 11.5 (s, 1H), 11.8 (s, 1H).

Example 27

(2R,4S,4aS)-rel-11-fluoro-2,4-dimethyl-8-[5-methyl-3-(trifluoromethyl)-1H-pyrazol-1-yl]-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione

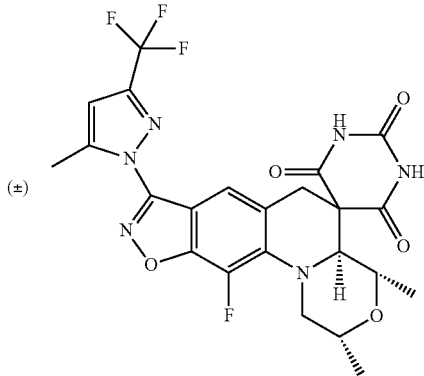

Starting material: 6-[(2R,6S)-2,6-dimethylmorpholin-4-yl]-7-fluoro-3-[5-methyl-3-(trifluoromethyl)-1H-pyrazol-1-yl]-1,2-benzisoxazole-5-carbaldehyde (Intermediate 567)

MS (ES) MH$^+$: 537 for $C_{23}H_{20}F_4N_6O_5$ $^1$H NMR (400 MHz, DMSO-d$_6$) δ: 0.9 (d, 3H), 1.1 (d, 3H), 2.6 (s, 3H), 2.9 (d, 1H), 3.1 (t, 1H), 3.6-3.8 (m, 3H), 4.0 (d, 1H), 4.1 (d, 1H), 7.0 (s, 1H), 7.5 (s, 1H), 11.5 (br, 2H).

Example 28

N-{1-[(2R,4S,4aS)-rel-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-1H-pyrazol-3-yl}acetamide

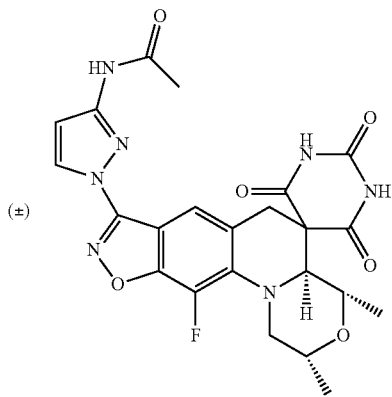

Starting material: N-[1-[6-[(2S,6R)-2,6-dimethylmorpholin-4-yl]-7-fluoro-5-formyl-1,2-benzoxazol-3-yl]pyrazol-3-yl]acetamide (Intermediate 568)

MS (ES) MH$^+$: 512 for $C_{23}H_{22}FN_7O_6$ $^1$H NMR (400 MHz, DMSO-d$_6$) δ: 0.9 (d, 3H), 1.1 (d, 3H), 2.1 (s, 3H), 3.0 (d, 1H), 3.1 (t, 1H), 3.5 (d, 1H), 3.7 (m, 1H), 3.8 (m, 1H), 4.0 (d, 1H), 4.1 (d, 1H), 7.0 (d, 1H), 7.6 (s, 1H), 8.4 (d, 1H), 10.85 (s, 1H), 11.5 (bs, 1H), 11.9 (bs, 1H).

Example 29

(2R,4S,4aS)-rel-11-fluoro-2,4-dimethyl-8-[3-(trifluoromethyl)-1H-pyrazol-1-yl]-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione

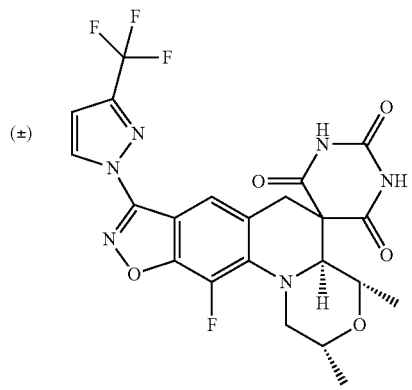

Starting material: 6-[(2R,6S)-2,6-dimethylmorpholin-4-yl]-7-fluoro-3-[3-(trifluoromethyl)-1H-pyrazol-1-yl]-1,2-benzisoxazole-5-carbaldehyde (Intermediate 569)

MS (ES) MH$^+$: 523 for $C_{22}H_{18}F_4N_6O_5$ $^1$H NMR (400 MHz, DMSO-d$_6$) δ: 0.9 (d, 3H), 1.1 (d, 3H), 2.9 (d, 2H), 3.1 (t, 1H), 3.6 (m, 1H), 3.8 (m, 1H), 4.0 (d, 1H), 4.1 (d, 1H), 7.2 (d, 1H), 7.55 (s, 1H), 8.8 (d, 1H), 11.5 (s, 1H), 11.9 (s, 1H).

Example 30

(2R,4S,4aS)-rel-8-[3-(difluoromethyl)-5-methyl-1H-pyrazol-1-yl]-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione

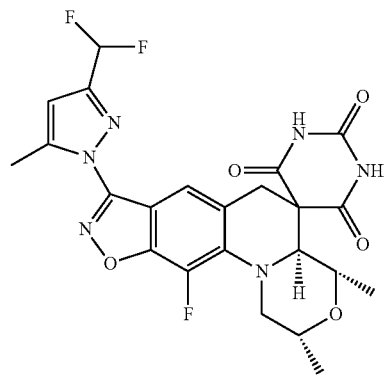

Starting material: 3-[3-(difluoromethyl)-1H-pyrazol-1-yl]-6-[(2R,6S)-2,6-dimethylmorpholin-4-yl]-7-fluoro-1,2-benzisoxazole-5-carbaldehyde (Intermediate 570)

MS (ES) MH$^+$: MS (ES) MH$^+$: 519 for $C_{23}H_{21}F_3N_6O_5$

¹H NMR (400 MHz, DMSO-d₆) δ: 0.9 (d, 3H), 1.1 (d, 3H), 2.6 (s, 3H), 2.9 (d, 2H), 3.1 (t, 1H), 3.6 (m, 1H), 3.8 (m, 1H), 4.0 (d, 1H), 4.1 (d, 1H), 6.8 (s, 1H), 7.1 (t, 1H), 7.6 (s, 1H), 11.5 (s, 1H), 11.9 (s, 1H).

Example 31

(2R,4S,4aS)-rel-11-fluoro-2,4-dimethyl-8-(propylamino)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

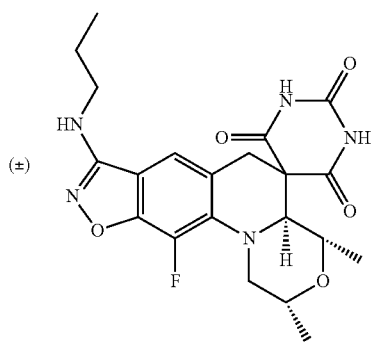

Starting material: 6-[(2R,6S)-2,6-dimethylmorpholin-4-yl]-7-fluoro-3-(propylamino)-1,2-benzoxazole-5-carbaldehyde (Intermediate 571)

MS (ES) MH⁺: 446 for $C_{21}H_{24}FN_5O_5$

¹H NMR (400 MHz, DMSO-d₆) δ: 0.9 (d, 6H), 1.1 (d, 3H), 1.6 (t, 2H), 2.9 (d, 1H), 3.0 (m, 1H), 3.3 (m, 2H), 3.55 (d, 1H), 3.65 (m, 1H), 3.7 (m, 1H), 3.9 (d, 1H), 4.0 (d, 1H), 6.8 (m, 1H), 7.1 (s, 1H), 11.45 (bs, 1H), 11.8 (bs, 1H).

Example 32

(2R,4S,4aS)-rel-8-[benzyl(methyl)amino]-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

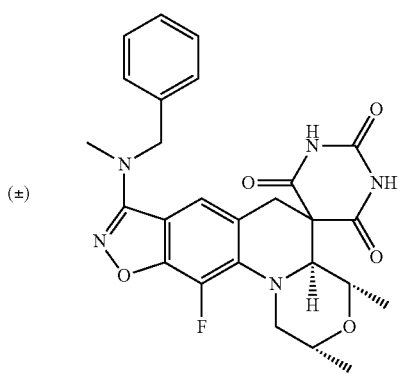

Starting material: 3-[benzyl(methyl)amino]-6-[(2R,6S)-2,6-dimethylmorpholin-4-yl]-7-fluoro-1,2-benzoxazole-5-carbaldehyde (Intermediate 572)

MS (ES) MH⁺: 508.3 for $C_{26}H_{26}FN_5O_5$

¹H NMR (400 MHz, DMSO-d₆) δ: 0.9 (d, 3H), 1.1 (d, 3H), 2.9 (d, 1H), 3.0 (s, 3H), 3.1 (m, 1H), 3.5 (d, 1H), 3.7 (m, 1H), 3.8 (m, 1H), 3.9 (d, 1H), 4.1 (d, 1H), 4.6 (d, 1H), 4.7 (d, 1H), 7.2-7.35 (m, 5H), 11.5 (s, 1H), 11.8 (s, 1H).

Example 33

3-amino-1-[(2R,4S,4aS)-rel-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-1H-pyrazole-4-carbonitrile

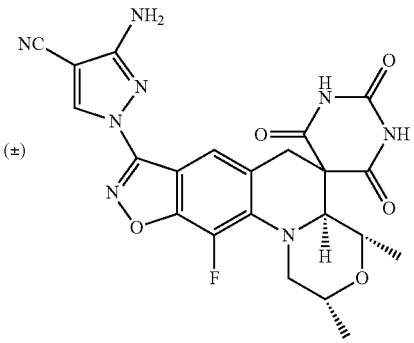

Starting material: 3-amino-1-{6-[(2R,6S)-2,6-dimethylmorpholin-4-yl]-7-fluoro-5-formyl-1,2-benzoxazol-3-yl}-1H-pyrazole-4-carbonitrile (Intermediate 548).

MS (ES) MH⁺: 495 for $C_{22}H_{19}FN_8O_5$

¹H NMR (400 MHz, DMSO-d₆) δ: 0.9 (d, 3H), 1.1 (d, 3H), 2.9 (d, 1H), 3.1 (m, 1H), 3.6 (d, 1H), 3.7 (m, 1H), 3.8 (m, 1H), 4.0 (d, 1H), 4.1 (d, 1H), 6.25 (s, 2H), 7.55 (s, 1H), 9.0 (s, 1H), 11.5 (bs, 1H), 11.9 (bs, 1H).

Example 34

(2R,4S,4aS)-rel-11-fluoro-2,4-dimethyl-8-[4-(pyrimidin-4-yl)-1H-pyrazol-1-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

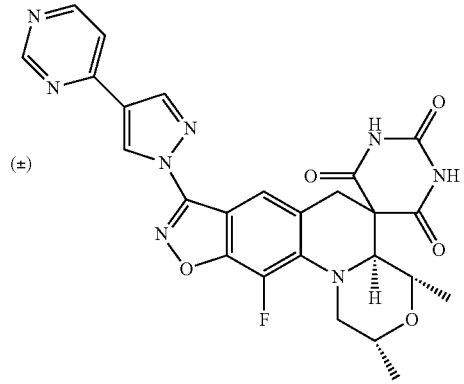

Starting material: 6-[(2R,6S)-2,6-dimethylmorpholin-4-yl]-7-fluoro-3-[4-(pyrimidin-4-yl)-1H-pyrazol-1-yl]-1,2-benzoxazole-5-carbaldehyde (Intermediate 549)

MS (ES) MH⁺: 533.5 for $C_{25}H_{21}FN_8O_5$

¹H NMR (400 MHz, DMSO-d₆) δ: 0.9 (d, 3H), 1.1 (d, 3H), 2.9 (d, 1H), 3.15 (t, 1H), 3.7 (m, 1H), 3.8 (m, 2H), 4.0 (d, 1H), 4.1 (d, 1H), 7.7 (s, 1H), 8.0 (s, 1H), 8.7 (s, 1H), 8.9 (d, 1H), 9.2 (s, 1H), 9.3 (s, 1H), 11.5 (s, 1H), 11.9 (s, 1H).

Example 35

(2R,4S,4aS)-rel-11-fluoro-2,4-dimethyl-8-[4-(pyrazin-2-yl)-1H-pyrazol-1-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

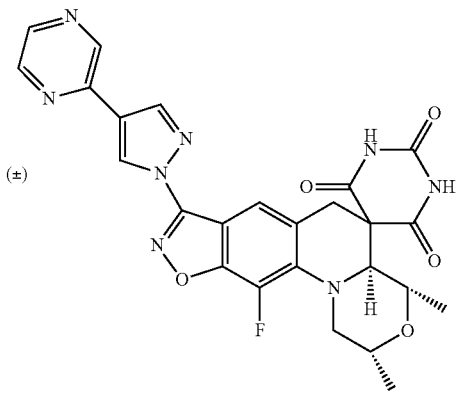

Starting material: 6-[(2R,6S)-2,6-dimethylmorpholin-4-yl]-7-fluoro-3-[4-(pyrazin-2-yl)-1H-pyrazol-1-yl]-1,2-benzoxazole-5-carbaldehyde (Intermediate 550)

MS (ES) MH$^+$: 533.5 for $C_{25}H_{21}FN_8O_5$ $^1$H NMR (400 MHz, DMSO-d$_6$) δ: 0.9 (d, 3H), 1.1 (d, 3H), 2.9 (d, 1H), 3.15 (t, 1H), 3.7 (m, 1H), 3.8 (m, 2H), 4.0 (d, 1H), 4.1 (d, 1H), 7.7 (s, 1H), 8.0 (s, 1H), 8.7 (s, 1H), 8.9 (d, 1H), 9.2 (s, 1H), 9.3 (s, 1H), 11.5 (s, 1H), 11.9 (s, 1H).

Example 36

(2R,4S,4aS)-rel-11-fluoro-8-(4-iodo-1H-pyrazol-1-yl)-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

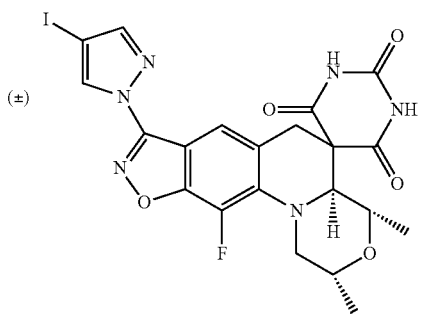

Starting material: 6-[(2R,6S)-2,6-dimethylmorpholin-4-yl]-7-fluoro-3-(4-iodo-1H-pyrazol-1-yl)-1,2-benzoxazole-5-carbaldehyde (Intermediate 551)

MS (ES) MH$^+$: 529.5 for $C_{21}H_{18}FIN_6O_5$;

$^1$H NMR (400 MHz, DMSO-d$_6$) δ: 0.9 (d, 3H), 1.15 (d, 3H), 2.9 (d, 1H), 3.1 (t, 1H), 3.7 (m, 1H), 3.8 (m, 2H), 4.0 (d, 1H), 4.1 (d, 1H), 7.6 (s, 1H), 8.1 (s, 1H), 8.7 (s, 1H), 11.5 (s, 1H), 11.9 (s, 1H).

Example 37 ethyl 1-[(2R,4S,4aS)-rel-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-1H-pyrazole-4-carboxylate

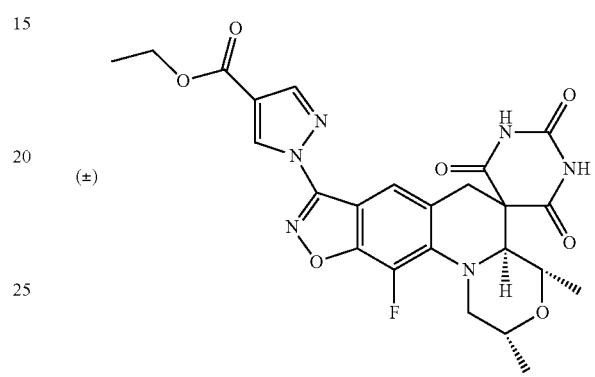

Starting material: ethyl 1-{6-[(2R,6S)-2,6-dimethylmorpholin-4-yl]-7-fluoro-5-formyl-1,2-benzoxazol-3-yl}-1H-pyrazole-4-carboxylate (Intermediate 552)

MS (ES) MH$^+$: 527.4 for $C_{24}H_{23}FN_6O_7$;

$^1$H NMR (400 MHz, DMSO-d$_6$) δ: 0.7 (d, 3H), 0.9 (d, 3H), 2.6 (d, 1H), 2.8 (m, 1H), 3.0 (d, 1H), 3.6 (m, 1H), 3.8 (d, 1H), 3.9 (d, 1H), 7.8 (s, 1H), 8.0 (s, 1H), 9.1 (s, 1H), 8.7 (s, 1H), 11.6 (s, 1H), 11.9 (s, 2H).

Example 38

(2R,4S,4aS)-rel-11-chloro-2,4-dimethyl-8-(pyridin-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

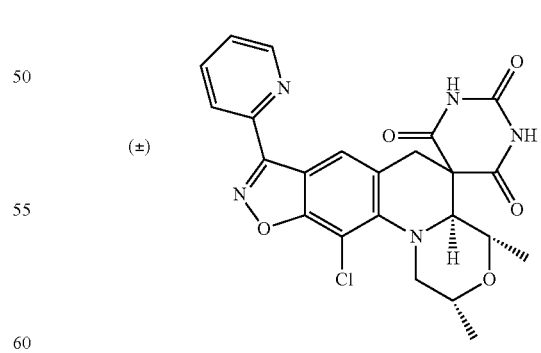

Starting material: 7-chloro-6-[(2R,6S)-2,6-dimethylmorpholin-4-yl]-3-(pyridin-2-yl)-1,2-benzoxazole-5-carbaldehyde (Intermediate 376)

MS (ES) MH$^+$: 482 for $C_{23}H_{20}ClN_5O_5$ $^1$H NMR (400 MHz, DMSO-D6) δ: 0.9 (d, 3H), 1.5 (d, 3H), 2.9 (d, 1H), 3.08 (t, 1H), 3.7 (m, 1H), 3.8 (d, 1H), 4.0 (m, 2H), 4.5 (d, 1H), 7.6 (q, 1H), 7.95 (s, 1H), 8.0 (m, 1H), 8.1 (d, 1H), 8.8 (s, 1H), 11.5 (s, 1H), 11.8 (s, 1H).

Example 39

(2R,4S,4aS)-rel-11-chloro-8-cyclopropyl-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

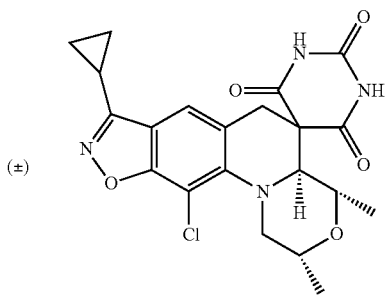

Starting material: 7-chloro-3-cyclopropyl-6-[(2R,6S)-2,6-dimethylmorpholin-4-yl]-1,2-benzoxazole-5-carbaldehyde (Intermediate 377)

MS (ES) MH$^+$: 445.0 for $C_{21}H_{21}ClN_4O_5$;

$^1$H NMR (400 MHz, DMSO-D6) δ: 0.9 (d, 3H), 1.0 (m, 1H), 1.1 (m, 3H), 1.15 (d, 3H), 2.2 (m, 1H), 3.0 (m, 2H), 3.5 (d, 1H), 3.6 (m, 1H), 4.0 (m, 2H), 4.4 (d, 1H), 7.3 (s, 1H), 11.45 (s, 1H), 11.8 (s, 1H).

Example 40

(2R,4S,4aS)-rel-11-chloro-2,4-dimethyl-8-(6-methylpyridin-3-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione isolated as the TFA salt from reverse phase HPLC purification

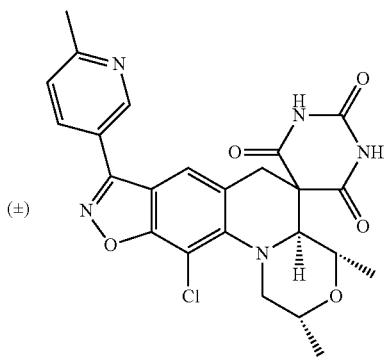

Starting material: 7-chloro-6-[(2R,6S)-2,6-dimethylmorpholin-4-yl]-3-(6-methylpyridin-3-yl)-1,2-benzoxazole-5-carbaldehyde (Intermediate 378)

MS (ES) MH$^+$: 496 for $C_{24}H_{22}ClN_5O_5$ $^1$H NMR (400 MHz, DMSO-D6) δ: 0.9 (d, 3H), 1.1 (d, 3H), 2.6 (s, 3H), 3.1 (m, 2H), 3.6 (d, 1H), 3.7 (m, 1H), 3.95 (m, 1H), 4.0 (m, 1H), 4.5 (d, 1H), 7.5 (d, 1H), 7.7 (s, 1H), 8.2 (dd, 1H), 9.0 (d, 1H), 11.5 (s, 1H), 11.9 (s, 1H)

Example 41

(2R,4S,4aS)-rel-11-chloro-2,4-dimethyl-8-(1,3-thiazol-5-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

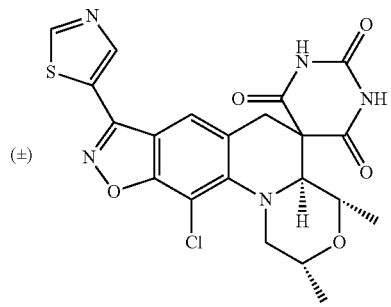

Starting material: 7-chloro-6-[(2R,6S)-2,6-dimethylmorpholin-4-yl]-3-(1,3-thiazol-5-yl)-7,7a-dihydro-1,2-benzoxazole-5-carbaldehyde (Intermediate 379)

MS (ES) MH$^+$: 488.0 for $C_{21}H_{18}ClN_5O_5S$;

$^1$H NMR (400 MHz, DMSO-D6) δ: 0.9 (d, 3H), 1.1 (d, 3H), 3.0 (m, 2H), 3.6 (d, 1H), 3.7 (m, 1H), 4.0 (m, 1H), 4.5 (d, 1H), 4.5 (d, 1H), 7.9 (s, 1H), 8.7 (s, 1H), 9.4 (s, 1H), 11.5 (s, 1H), 11.9 (s, 1H).

Example 42

(2R,4S,4aS)-rel-11-chloro-2,4-dimethyl-8-(pyrimidin-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

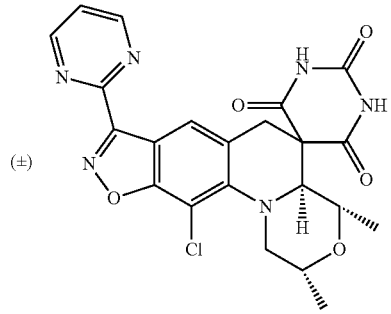

Starting material: 7-chloro-6-[(2R,6S)-2,6-dimethylmorpholin-4-yl]-3-(pyrimidin-2-yl)-1,2-benzoxazole-5-carbaldehyde (Intermediate 380)

MS (ES) MH$^+$: 483 for $C_{22}H_{19}ClN_6O_5$ $^1$H NMR (400 MHz, DMSO-D6) δ: 0.9 (d, 3H), 1.1 (d, 3H), 3.0 (m, 2H), 3.7 (m, 1H), 3.75 (d, 1H), 4.0 (m, 2H), 4.5 (d, 1H), 7.7 (t, 1H), 7.9 (s, 1H), 9.0 (m, 2H), 11.5 (s, 1H), 11.8 (s, 1H).

Example 43

(2R,4S,4aS)-rel-11-chloro-2,4-dimethyl-8-(pyrimidin-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

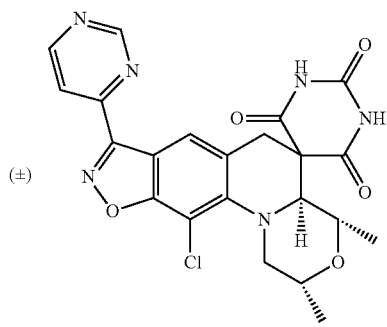

(±)

Starting material: 7-chloro-6-[(2R,6S)-2,6-dimethylmorpholin-4-yl]-3-(pyrimidin-4-yl)-1,2-benzoxazole-5-carbaldehyde (Intermediate 381)

MS (ES) MH$^+$: 483 for $C_{22}H_{19}ClN_6O_5$ $^1$H NMR (400 MHz, DMSO-D6) δ 0.9 (d, 3H), 1.2 (d, 3H), 3.0 (d, 1H), 3.1 (m, 1H), 3.7 (m, 1H), 3.8 (d, 1H), 4.0 (m, 2H), 4.5 (d, 1H), 7.95 (s, 1H), 8.2 (dd, 1H), 9.0 (d, 1H), 9.4 (d, 1H), 11.5 (s, 1H), 11.85 (s, 1H).

Example 44

(2R,4S,4aS)-rel-11-chloro-2,4-dimethyl-8-(pyrimidin-5-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

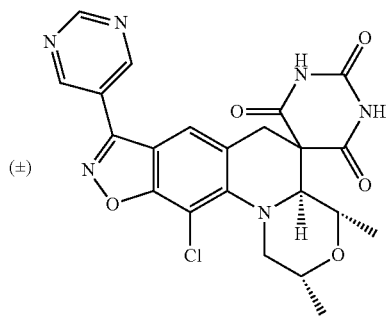

(±)

Starting material: 7-chloro-6-[(2R,6S)-2,6-dimethylmorpholin-4-yl]-3-(pyrimidin-5-yl)-1,2-benzoxazole-5-carbaldehyde (Intermediate 382)

MS (ES) MH$^+$: 483 for $C_{22}H_{19}ClN_6O_5$ $^1$H NMR (400 MHz, DMSO-D6) δ 0.9 (d, 3H), 1.1 (d, 3H), 3.05 (m, 2H), 3.7 (d, 1H), 3.72 (t, 1H), 3.9 (t, 1H), 4.0 (d, 1H), 4.5 d, 1H), 7.79 (s, 1H), 9.3 (s, 1H), 9.4 (s, 1H), 11.3 (s, 1H).

Example 45

(2R,4S,4aS)-rel-11-chloro-2,4-dimethyl-8-(pyridazin-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

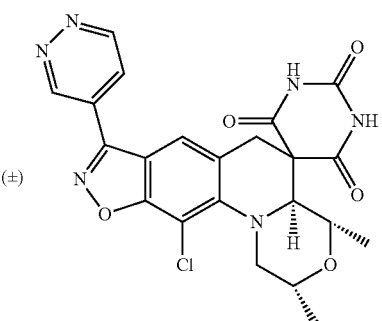

(±)

Starting material: 7-chloro-6-[(2R,6S)-2,6-dimethylmorpholin-4-yl]-3-(pyridazin-4-yl)-1,2-benzoxazole-5-carbaldehyde (Intermediate 383)

MS (ES) MH$^+$: 483 for $C_{22}H_{19}ClN_6O_5$ $^1$H NMR (400 MHz, DMSO-D6) δ 0.9 (d, 3H), 1.2 (d, 3H), 3.1 (m, 1H), 3.6 (d, 1H), 3.7 (m, 1H), 4.0 (m, 1H), 4.05 (d, 1H), 4.5 (d, 1H), 7.85 (s, 1H), 8.2 (dd, 1H), 9.5 (d, 1H), 9.75 (s, 1H), 11.5 (s, 1H), 11.9 (s, 1H).

Example 46

(2R,4S,4aS)-rel-11-chloro-2,4-dimethyl-8-(pyridin-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

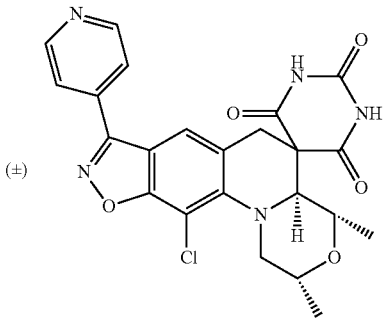

(±)

Starting material: 7-chloro-6-[(2R,6S)-2,6-dimethylmorpholin-4-yl]-3-(pyridin-4-yl)-1,2-benzoxazole-5-carbaldehyde (Intermediate 384)

MS (ES) MH$^+$: 482 for $C_{23}H_{20}ClN_5O_5$;

$^1$H NMR (400 MHz, DMSO-D6) δ: 0.9 (d, 3H), 1.1 (d, 3H), 3.1 (m, 2H), 3.6 (m, 1H), 3.9 (m, 1H), 4.0 (d, 1H), 4.5 (d, 1H) 7.75 (s, 1H), 7.9 (d, 2H), 8.8 (bs, 2H), 11.5 (s, 1H), 11.9 (s, 1H)

Example 47

(2R,4S,4aS)-rel-11-chloro-2,4-dimethyl-8-(pyridin-3-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione (isolated as the TFA salt from reverse phase HPLC purification)

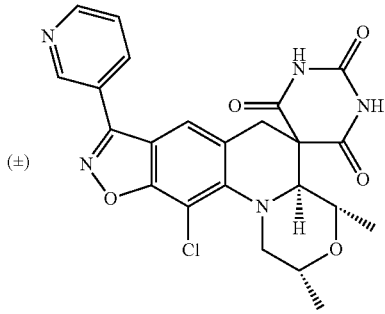

Starting material: 7-chloro-6-[(2R,6S)-2,6-dimethylmorpholin-4-yl]-3-(pyridin-3-yl)-1,2-benzoxazole-5-carbaldehyde (Intermediate 385)

MS (ES) MH$^+$: 482 for $C_{23}H_{20}ClN_5O_5$ $^1$H NMR (400 MHz, DMSO-D6) δ: 0.9 (d, 3H), 1.1 (d, 3H), 3.0 (m, 2H), 3.6 (m, 1H), 3.7 (m, 1H), 4.0 (m, 2H), 4.5 (d, 1H), 7.6 (t, 1H), 7.7 (s, 1H), 8.3 (d, 1H), 8.8 (s, 1H), 9.1 (s, 1H), 11.5 (s, 1H), 11.9 (s, 1H).

Example 48

(2R,4S,4aS)-rel-11-chloro-2,4-dimethyl-8-(1,3-thiazol-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

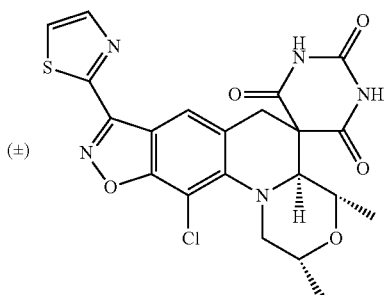

Starting material: 7-chloro-6-[(2R,6S)-2,6-dimethylmorpholin-4-yl]-3-(1,3-thiazol-2-yl)-1,2-benzoxazole-5-carbaldehyde (Intermediate 386)

MS (ES) MH$^+$: 488 for $C_{21}H_{18}ClN_5O_5S$;

$^1$H NMR (400 MHz, DMSO-D6) δ: 0.9 (d, 3H), 1.1 (d, 3H), 3.0 (d, 1H), 3.1 (m, 1H), 3.7 (m, 1H), 3.8 (d, 1H), 4.0 (m, 1H), 4.5 (d, 1H), 7.8 (s, 1H), 8.1 (d, 1H), 8.2 (d, 1H), 11.5 (s, 1H), 11.8 (s, 1H).

Example 49

(2R,4S,4aS)-rel-11-chloro-8-(methoxymethyl)-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

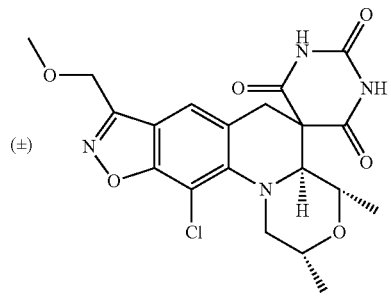

Starting material: 7-chloro-6-[(2R,6S)-2,6-dimethylmorpholin-4-yl]-3-(methoxymethyl)-1,2-benzoxazole-5-carbaldehyde (Intermediate 388)

MS (ES) MH$^+$: 449 for $C_{20}H_{21}ClN_4O_6$ $^1$H NMR (400 MHz, DMSO-D6) δ: 0.9 (d, 3H), 1.1 (d, 3H), 2.95-3.1 (m, 2H), 3.3 (s, 3H), 3.6-3.7 (m, 2H), 3.9-4.0 (m, 2H), 4.5 (d, 1H), 4.7 (s, 2H), 7.3 (s, 1H), 11.4 (s, 1H), 11.8 (s, 1H).

Example 50

(2R,4S,4aS)-rel-11-fluoro-2,4-dimethyl-8-[methyl(propyl)amino]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)trione

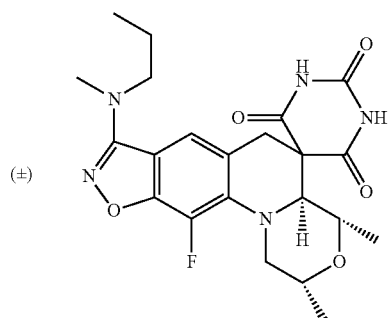

Starting material: 6-[(2R,6S)-2,6-dimethylmorpholin-4-yl]-7-fluoro-3-[methyl(propyl)amino]-1,2-benzoxazole-5-carbaldehyde (Intermediate 573)

MS (ES) MH$^+$: 460 for $C_{22}H_{26}FN_5O_5$ $^1$H NMR (400 MHz, DMSO-d$_6$) δ: 0.9 (d, 6H), 1.1 (d, 3H), 1.6 (t, 2H), 2.9 (d, 1H), 3.0 (m, 5H), 3.3 (s, 1H), 3.55 (d, 1H), 3.65 (m, 1H), 3.7 (m, 1H), 3.9 (d, 1H), 4.0 (d, 1H), 7.3 (s, 1H), 11.5 (bs, 1H), 11.8 (bs, 1H).

Example 51

(2R,4S,4aS)-rel-11-fluoro-8-methoxy-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

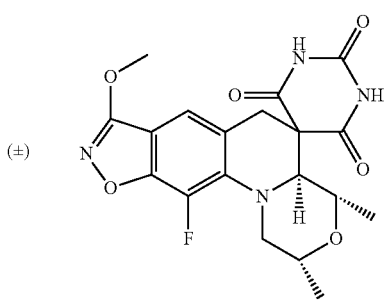

(±)

Starting material: 6-[(2R,6S)-2,6-Dimethylmorpholin-4-yl]-7-fluoro-3-methoxy-1,2-benzisoxazole-5-carbaldehyde (Intermediate 557)

MS (ES) MH$^+$: 419 for $C_{19}H_{19}FN_4O_6$ $^1$H NMR (400 MHz, DMSO-d$_6$) δ: 0.9 (d, 3H), 1.2 (d, 3H), 2.9 (d, 1H), 3.1 (t, 1H), 3.6 (d, 1H), 3.7 (m, 1H), 3.8 (m, 1H), 3.9 (d, 1H), 4.0 (s, 3H), 4.1 (d, 1H), 7.1 (s, 1H), 11.5 (s, 1H), 11.9 (s, 1H).

Example 52

(2R,4S,4aS)-rel-8-(benzyloxy)-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

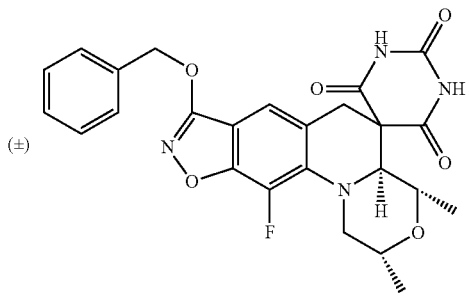

(±)

Starting material: 3-(benzyloxy)-6-[(2R,6S)-2,6-dimethylmorpholin-4-yl]-7-fluoro-1,2-benzisoxazole-5-carbaldehyde (Intermediate 558)

MS (ES) MH$^+$: 495 for $C_{25}H_{23}FN_4O_6$ $^1$H NMR (400 MHz, DMSO-d$_6$) δ: 0.9 (d, 3H), 1.2 (d, 3H), 2.9 (d, 1H), 3.1 (t, 1H), 3.6 (d, 1H), 3.7 (m, 1H), 3.8 (m, 1H), 3.9 (d, 1H), 4.0 (s, 1H), 5.4 (s, 2H), 7.1 (s, 1H), 7.4 (m, 3H), 7.5 (d, 2H), 11.5 (s, 1H), 11.85 (s, 1H).

Example 53

(2R,4S,4aS)-rel-11-fluoro-2,4-dimethyl-8-(1H-1,2,4-triazol-1-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

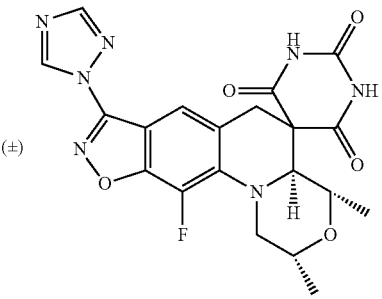

(±)

Starting material: 6-[(2R,6S)-2,6-dimethylmorpholin-4-yl]-7-fluoro-3-(1H-1,2,4-triazol-1-yl)-1,2-benzoxazole-5-carbaldehyde (Intermediate 539)

MS (ES) MH$^+$: 456 for $C_{20}H_{18}FN_7O_5$ $^1$H NMR (400 MHz, DMSO-d$_6$) δ: 0.9 (d, 3H), 1.1 (d, 3H), 2.9 (d, 1H), 3.1 (t, 1H), 3.7 (m, 1H), 3.8 (m, 2H), 4.0 (d, 1H), 4.1 (d, 1H), 7.6 (s, 1H), 8.5 (s, 1H), 9.4 (s, 1H), 11.5 (bs, 1H), 11.9 (bs, 1H).

The (2R,4S,4aS) enantiomer of Example 53 was also prepared using the chiral synthesis shown below for Example 53(a):

Example 53(a)

Chiral Synthesis (2R,4S,4aS)-11-fluoro-2,4-dimethyl-8-(1H-1,2,4-triazol-1-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

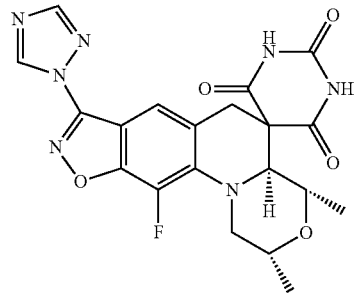

A mixture of 6-((2R,6R)-2,6-dimethylmorpholino)-7-fluoro-3-(1H-1,2,4-triazol-1-yl)benzo[d]isoxazole-5-carbaldehyde (Intermediate 574, 500 mg, 1.45 mmol) and pyrimidine-2,4,6(1H,3H,5H)-trione (185 mg, 1.45 mmol) in DMSO (6 ml) was heated at 150° C. for 2 hours in a microwave reactor. The reaction mixture was purified by Super Critical Fluid chromatography on a Chiralpac IC column with a 35% MeOH, 65% $CO_2$ mobile phase to give 290 mg of product as a solid as the first eluting compound.

MS (ES) MH$^+$: 456 for $C_{20}H_{18}FN_7O_5$

¹H NMR (300 MHz, DMSO-d₆) δ: 0.9 (d, 3H), 1.2 (d, 3H), 2.9 (d, 1H) 3.1 (t, 1H), 3.6-3.9 (m, 3H), 4. (d, 1H), 4.1 (d, 1H), 7.6 (s, 1H), 8.5 (s, 1H), 9.4 (s, 1H), 11.5 (br. s., 1H), 11.9 (br. s., 1H).

Example 53(b)

(2R,4R,4aR)-11-fluoro-2,4-dimethyl-8-(1H-1,2,4-triazol-1-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

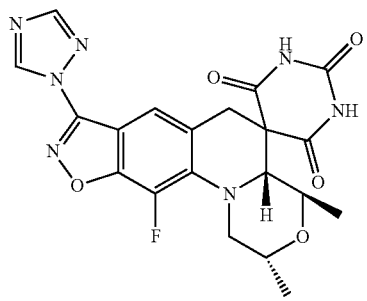

The (2R,4R,4aR) diastereomer was produced as a by-product of the reaction described for the synthesis of Example 53(a). The chromatography described for Example 53(a) afforded 25 mg of the (2R,4R,4aR) diastereomer as the second eluting compound.

MS (ES) MH⁺: 456 for $C_{20}H_{18}FN_7O_5$
¹H NMR (300 MHz, DMSO-d₆) δ: 0.9 (d, 3H), 1.3 (dd, 3H), 3.0-3.2 (m, 1H), 3.5-3.7 (m, 1H), 3.7-3.8 (m, 1H), 3.85 (s, 1H), 3.9-4.4 (m, 2H), 4.0-4.2 (m, 1H), 7.6 (s, 1H), 8.5 (s, 1H), 9.4 (s, 1H), 11.5 (br. s., 1H), 11.8 (br. s., 1H.)

Examples 54 to 83 were prepared from the indicated starting material and pyrimidine-2,4,6(1H,3H,5H)-trione using a method similar to the one described for the synthesis of Example 8:

Example 54

(2R,4S,4aS)-rel-11-fluoro-2,4-dimethyl-8-(3-methyl-1H-1,2,4-triazol-1-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

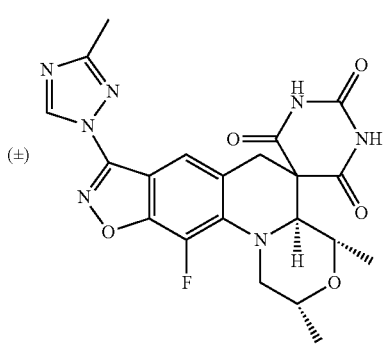

Starting material: 6-[(2R,6S)-2,6-dimethylmorpholin-4-yl]-7-fluoro-3-(3-methyl-1H-1,2,4-triazol-1-yl)-1,2-benzoxazole-5-carbaldehyde (Intermediate 540)

MS (ES) MH⁺: 470 for $C_{21}H_{20}FN_7O_5$
¹H NMR (400 MHz, DMSO-d₆) δ: 0.9 (d, 3H), 1.1 (d, 3H), 2.4 (s, 3H), 2.9 (d, 1H), 3.1 (t, 1H), 3.7 (m, 1H), 3.8 (m, 2H), 4.0 (d, 1H), 4.1 (d, 1H), 7.6 (s, 1H), 9.3 (s, 1H), 11.5-11.9 (bs, 2H).

Example 55

1-[(2R,4S,4aS)-rel-11-fluoro-2,4-dimethyl-2',4',6'-trioxo-1,1',2,3',4,4',4a,6-octahydro-2'H,6H-spiro[1,4-oxazino[4,3-a][1,2]oxazolo[4,5-g]quinoline-5,5'-pyrimidin]-8-yl]-1H-1,2,4-triazole-3-carbonitrile

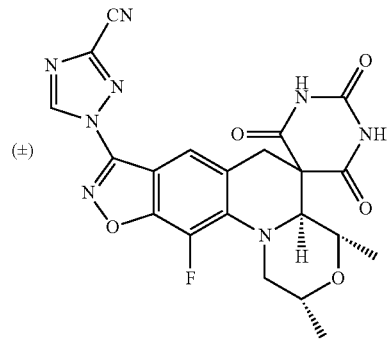

Starting material: 1-{6-[(2R,6S)-2,6-dimethylmorpholin-4-yl]-7-fluoro-5-formyl-1,2-benzoxazol-3-yl}-1H-1,2,4-triazole-3-carbonitrile (Intermediate 541)

MS (ES) MH–: 479 for $C_{21}H_{17}FN_8O_5$
¹H NMR (400 MHz, DMSO-d₆) δ: 0.9 (d, 3H), 1.15 (d, 3H), 2.9 (d, 1H), 3.2 (t, 1H), 3.7 (m, 1H), 3.9 (m, 2H), 4.0 (d, 1H), 4.1 (d, 1H), 7.6 (s, 1H), 9.8 (s, 1H), 11.5 (s, 1H), 11.9 (s, 1H).

Example 56

(2R,4S,4aS)-rel-11-fluoro-2,4-dimethyl-8-(2H-1,2,3-triazol-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

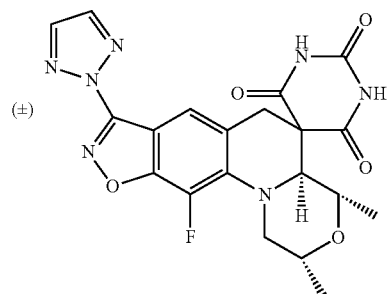

Starting material: 6-[(2R,6S)-2,6-dimethylmorpholin-4-yl]-7-fluoro-3-(1H-1,2,3-triazol-2-yl)-1,2-benzoxazole-5-carbaldehyde (Intermediate 543), as part of a mixture that includes 6-[(2R,6S)-2,6-dimethylmorpholin-4-yl]-7-fluoro-3-(1H-1,2,3-triazol-1-yl)-1,2-benzoxazole-5-carbaldehyde (Intermediate 542)

MS (ES) MH⁺: 456 for $C_{20}H_{18}FN_7O_5$

¹H NMR (400 MHz, DMSO-d₆) δ: 0.9 (d, 3H), 1.15 (d, 3H), 2.9 (d, 1H), 3.1 (m, 1H), 3.7 (m, 1H), 3.8 (m, 2H), 4.0 (d, 1H), 4.1 (d, 1H), 7.7 (s, 1H), 8.4 (s, 2H), 11.6 (bs, 2H).

Example 57

(2R,4S,4aS)-rel-11-fluoro-2,4-dimethyl-8-(1H-1,2,3-triazol-1-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

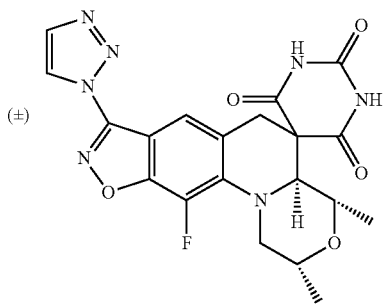

Starting material: 6-[(2R,6S)-2,6-dimethylmorpholin-4-yl]-7-fluoro-3-(1H-1,2,3-triazol-1-yl)-1,2-benzoxazole-5-carbaldehyde (Intermediate 542), as part of a mixture that includes 6-[(2R,6S)-2,6-dimethylmorpholin-4-yl]-7-fluoro-3-(1H-1,2,3-triazol-2-yl)-1,2-benzoxazole-5-carbaldehyde (Intermediate 543)

MS (ES) MH⁺: 456.5 for $C_{20}H_{18}FN_7O_5$

¹H NMR (400 MHz, DMSO-d₆) δ: 0.9 (d, 3H), 1.15 (d, 3H), 2.9 (d, 1H), 3.1 (m, 1H), 3.7 (m, 1H), 3.8 (m, 2H), 4.0 (d, 1H), 4.15 (d, 1H), 7.7 (s, 1H), 8.15 (d, 1H), 9.0 (s, 1H), 11.6 (bs, 1H).

Example 58

(2R,4S,4aS)-rel-11-fluoro-8-(1H-imidazol-1-yl)-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

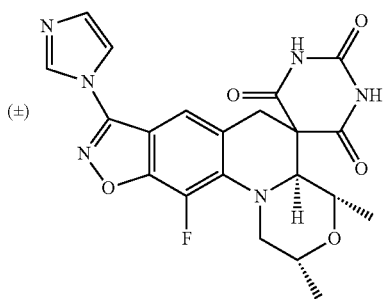

Starting material: 6-[(2R,6S)-2,6-dimethylmorpholin-4-yl]-7-fluoro-3-(1H-imidazol-1-yl)-1,2-benzoxazole-5-carbaldehyde (Intermediate 544)

MS (ES) MH⁺: 455 for $C_{21}H_{19}FN_6O_5$

¹H NMR (400 MHz, DMSO-d₆) δ: 0.9 (d, 3H), 1.15 (d, 3H), 3.0 (d, 1H), 3.2 (t, 1H), 3.55 (d, 1H), 3.7 (m, 1H), 3.8 (m, 1H), 4.0 (d, 1H), 4.1 (d, 1H), 7.3 (s, 1H), 7.65 (s, 1H), 7.9 (s, 1H), 8.5 (s, 1H), 11.6 (s, 1H), 11.9 (s, 1H).

Example 59

(2R,4S,4aS)-rel-11-fluoro-2,4-dimethyl-8-[4-(trifluoromethyl)-1H-imidazol-1-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

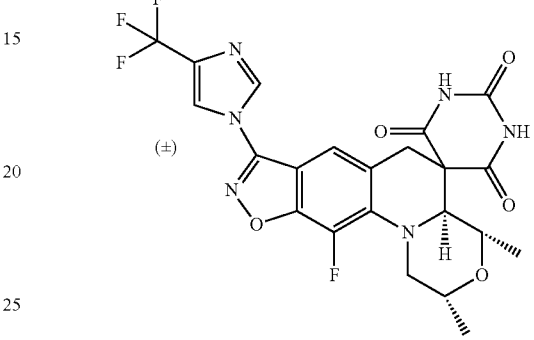

Starting material: 6-[(2R,6S)-2,6-dimethylmorpholin-4-yl]-7-fluoro-3-[4-(trifluoromethyl)-1H-imidazol-1-yl]-1,2-benzoxazole-5-carbaldehyde (Intermediate 545)

MS (ES) MH⁺: 523 for $C_{22}H_{18}F_4N_6O_5$

¹H NMR (400 MHz, DMSO-d₆) δ: 0.9 (d, 3H), 1.1 (d, 3H), 3.0 (d, 1H), 3.1 (t, 1H), 3.5 (m, 1H), 3.7 (m, 1H), 3.8 (m, 1H), 4.0 (d, 1H), 4.1 (d, 1H), 7.6 (d, 1H), 8.6 (d, 1H), 8.65 (s, 1H).

Example 60

(2R,4S,4aS)-rel-11-fluoro-2,4-dimethyl-8-(4-methyl-1H-pyrazol-1-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

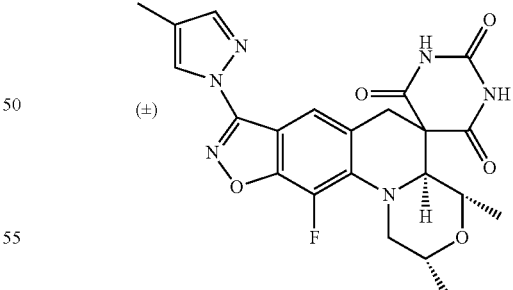

Starting material: 6-[(2R,6S)-2,6-dimethylmorpholin-4-yl]-7-fluoro-3-(4-methyl-1H-pyrazol-1-yl)-1,2-benzoxazole-5-carbaldehyde (Intermediate 546)

MS (ES) MH⁺: 469 for $C_{22}H_{21}FN_6O_5$

¹H NMR (400 MHz, DMSO-d₆) δ: 0.9 (d, 3H), 1.1 (d, 3H), 2.1 (s, 3H), 2.9 (d, 1H), 3.1 (t, 1H), 3.7 (m, 2H), 3.8 (m, 1H), 3.95 (d, 1H), 4.1 (d, 1H), 7.7 (s, 1H), 7.8 (s, 1H), 8.3 (s, 1H), 11.5 (s, 1H), 11.8 (s, 1H).

Example 61

(2R,4S,4aS)-rel-8-(4-chloro-1H-pyrazol-1-yl)-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

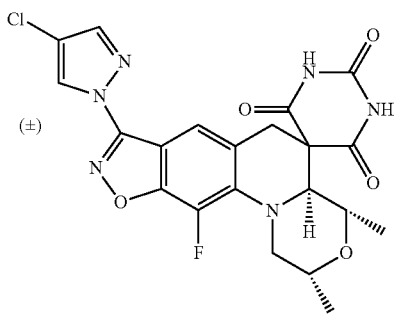

Starting material: 3-(4-chloro-1H-pyrazol-1-yl)-6-[(2R,6S)-2,6-dimethylmorpholin-4-yl]-7-fluoro-1,2-benzoxazole-5-carbaldehyde (Intermediate 547)

MS (ES) MH$^+$: 489 for $C_{21}H_{18}ClFN_6O_5$ $^1$H NMR (400 MHz, DMSO-d$_6$) δ: 0.9 (d, 3H), 1.1 (d, 3H), 2.9 (d, 1H), 3.1 (t, 1H), 3.7 (m, 1H), 3.8 (d, 2H), 4.0 (d, 1H), 4.1 (d, 1H), 7.6 (s, 1H), 8.1 (s, 1H), 8.8 (s, 1H), 11.5 (s, 1H), 11.85 (s, 1H).

Example 62

(2R,4S,4aS)-rel-11-fluoro-2,4-dimethyl-8-(methylsulfanyl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

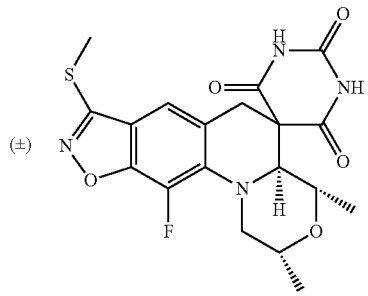

Starting material: 6-[(2R,6S)-2,6-dimethylmorpholin-4-yl]-7-fluoro-3-(methylsulfanyl)-1,2-benzoxazole-5-carbaldehyde (Intermediate 553)

MS (ES) MH$^+$: 435 for $C_{19}H_{19}FN_4O_5S$ $^1$H NMR (400 MHz, DMSO-d$_6$) δ: 0.9 (d, 3H), 1.1 (d, 3H), 2.7 (s, 3H), 2.9 (d, 1H), 3.1 (t, 1H), 3.6 (m, 1H), 3.7 (m, 1H), 3.8 (m, 1H), 4.0 (d, 1H), 4.1 (d, 1H), 7.1 (s, 1H), 11.5 (s, 1H), 11.9 (s, 1H).

Example 63

(2R,4S,4aS)-rel-8-(3,5-dimethyl-1H-pyrazol-1-yl)-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

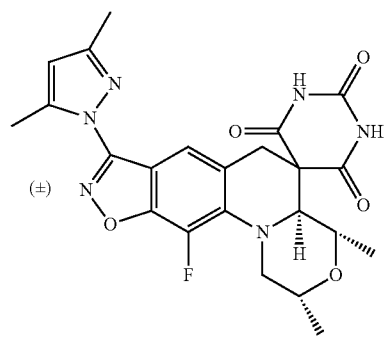

Starting material: 6-[(2R,6S)-2,6-dimethylmorpholin-4-yl]-3-(3,5-dimethyl-1H-pyrazol-1-yl)-7-fluoro-1,2-benzoxazole-5-carbaldehyde (Intermediate 554)

MS (ES) MH$^+$: 483.5 for $C_{23}H_{23}FN_6O_5$ $^1$H NMR (400 MHz, DMSO-d$_6$) δ: 0.9 (d, 3H), 1.1 (d, 3H), 2.25 (s, 3H), 2.5 (s, 3H), 2.9 (d, 1H), 3.1 (t, 1H), 3.7 (m, 1H), 3.8 (m, 2H), 3.95 (d, 1H), 4.1 (d, 1H), 6.25 (s, 1H), 7.6 (s, 1H), 11.5 (bs, 1H), 11.9 (bs, 2H).

Example 64

(2R,4S,4aS)-rel-11-fluoro-2,4-dimethyl-8-(1H-pyrazol-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

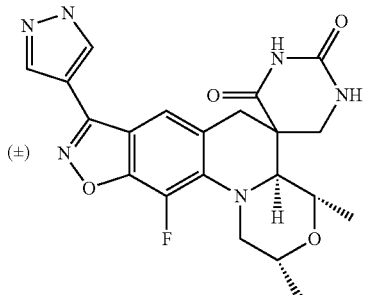

Starting material: 6-[(2R,6S)-2,6-dimethylmorpholin-4-yl]-7-fluoro-3-(1H-pyrazol-4-yl)-1,2-benzoxazole-5-carbaldehyde (Intermediate 555)

MS (ES) MH$^+$: 455 for $C_{21}H_{19}FN_6O_5$ $^1$H NMR (400 MHz, DMSO-d$_6$) δ: 0.9 (d, 3H), 1.5 (d, 3H), 2.9 (d, 1H), 3.1 (t, 1H), 3.7 (m, 1H), 3.8 (m, 2H), 4.0 (d, 1H), 4.1 (d, 1H), 6.7 (s, 1H), 7.7 (s, 1H), 8.0 (s, 1H), 8.5 (s, 1H), 11.5 (s, 1H), 11.8 (s, 2H).

Example 65

(2R,4S,4aS)-rel-11-fluoro-2,4-dimethyl-8-(2-methyl-1,3-oxazol-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

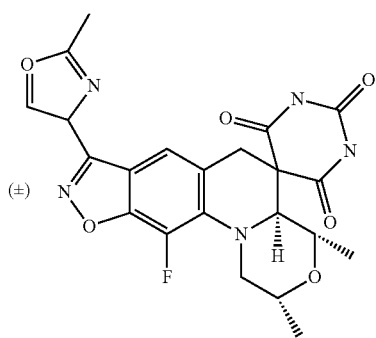

Starting material: 6-[(2R,6S)-2,6-dimethylmorpholin-4-yl]-7-fluoro-3-(2-methyl-1,3-oxazol-4-yl)-1,2-benzoxazole-5-carbaldehyde (Intermediate 394)

MS (ES) MH$^+$: 470 for $C_{22}H_{20}FN_5O_6$ $^1$H NMR (400 MHz, DMSO-D6) δ: 0.9 (d, 3H), 1.5 (d, 3H), 2.5 (s, 3H), 3.0 (d, 1H), 3.3 (t, 1H), 3.7 (m, 2H), 3.8 (m, 1H), 4.0 (d, 1H), 4.1 (d, 1H), 7.6 (s, 1H), 8.8 (s, 1H), 11.5 (s, 1H), 11.8 (s, 1H).

Example 66

(2R,4S,4aS)-rel-11-fluoro-2,4-dimethyl-8-(5-methyl-1,2-oxazol-3-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

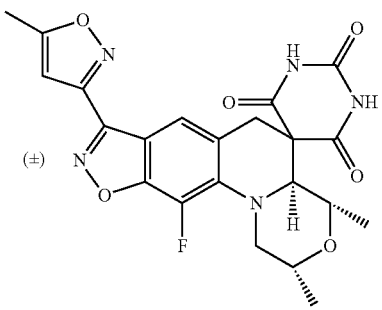

Starting material: 6-[(2R,6S)-2,6-dimethylmorpholin-4-yl]-7-fluoro-3-(5-methyl-1,2-oxazol-3-yl)-1,2-benzoxazole-5-carbaldehyde (Intermediate 395)

MS (ES) MH$^+$: 470 for $C_{22}H_{20}FN_5O_6$;

$^1$H NMR (400 MHz, DMSO-D6) δ: 0.9 (d, 3H), 1.5 (d, 3H), 2.5 (s, 3H), 3.0 (d, 1H), 3.3 (t, 1H), 3.7 (m, 1H), 3.8 (m, 2H), 4.0 (d, 1H), 4.1 (d, 1H), 6.85 (s, 1H), 7.55 (s, 1H), 11.5 (s, 1H), 11.85 (s, 1H).

Example 67

(2R,4S,4aS)-rel-8-(3,5-dimethyl-1,2-oxazol-4-yl)-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

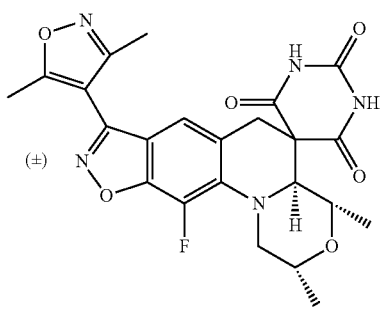

Starting material: 6-[(2R,6S)-2,6-dimethylmorpholin-4-yl]-3-(3,5-dimethyl-1,2-oxazol-4-yl)-7-fluoro-1,2-benzoxazole-5-carbaldehyde (Intermediate 396).

MS (ES) MH$^+$: 484 for $C_{23}H_{22}FN_5O_6$ $^1$H NMR (400 MHz, DMSO-D6) δ: 0.9 (d, 3H), 1.5 (d, 3H), 2.3 (s, 3H), 2.5 (s, 3H), 3.0 (d, 1H), 3.1 (t, 1H), 3.6 (d, 1H), 3.7 (m, 1H), 3.8 (m, 1H), 4.0 (d, 1H), 4.1 (d, 1H), 7.3 (s, 1H), 11.5 (s, 1H), 11.9 (s, 1H).

Example 68

(2R,4S,4aR)-rel-11-fluoro-2,4-dimethyl-8-(1-methyl-1H-imidazol-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

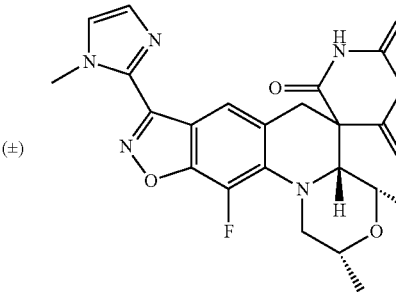

Starting material: 6-[(2R,6S)-2,6-dimethylmorpholin-4-yl]-7-fluoro-3-(1-methyl-1H-imidazol-2-yl)-1,2-benzoxazole-5-carbaldehyde (Intermediate 397)

MS (ES) MH$^+$: 469 for $C_{22}H_{21}FN_6O_6$ $^1$H NMR (400 MHz, DMSO-D6) δ: δ: 1.1 (d, 3H), 1.2 (d, 3H), 3.2 (m, 1H), 3.4 (m, 1H), 3.5 (m, 2H), 3.6 (m, 1H), 3.9 (m, 1H), 4.1 (s, 3H), 4.15 (m, 1H), 7.2 (s, 1H), 7.6 (s, 1H), 7.9 (d, 1H), 11.5 (s, 1H), 11.7 (s, 1H).

Example 69

(2R,4S,4aS)-rel-11-fluoro-2,4-dimethyl-8-(1-methyl-1H-imidazol-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

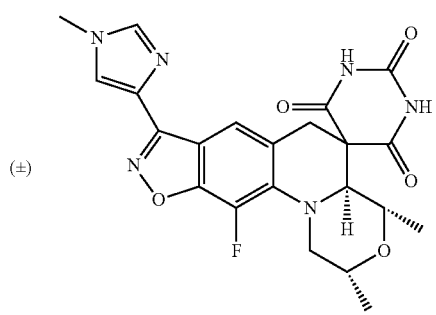

(±)

Starting material: 6-[(2R,6S)-2,6-dimethylmorpholin-4-yl]-7-fluoro-3-(1-methyl-1H-imidazol-4-yl)-1,2-benzoxazole-5-carbaldehyde (Intermediate 398)

MS (ES) MH$^+$: 469 for $C_{22}H_{21}FN_6O_6$;

$^1$H NMR (400 MHz, DMSO-D6) δ: 0.9 (d, 3H), 1.1 (d, 3H), 3.0 (d, 1H), 3.1 (m, 1H), 3.1 (m, 1H), 3.6 (d, 1H), 3.7 (m, 2H), 3.7 (s, 3H), 3.72 (m, 1H), 4.0 (d, 1H), 4.1 (d, 1H), 7.4 (s, 1H), 7.8 (d, 1H), 11.4 (bs, 1H), 11.8 (bs, 1H).

Example 70

(2R,4S,4aS)-rel-11-fluoro-2,4-dimethyl-8-(1-methyl-1H-imidazol-5-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

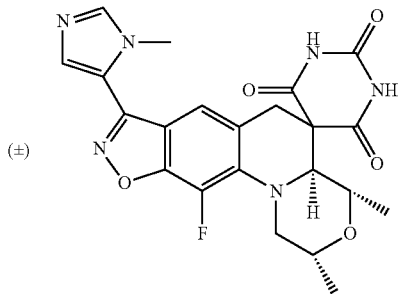

(±)

Starting material: 6-[(2R,6S)-2,6-dimethylmorpholin-4-yl]-7-fluoro-3-(1-methyl-1H-imidazol-5-yl)-1,2-benzoxazole-5-carbaldehyde (Intermediate 399).

MS (ES) MH$^+$: 469.5 for $C_{22}H_{21}FN_6O_6$ $^1$H NMR (400 MHz, DMSO-D6) δ: 0.9 (d, 3H), 1.15 (d, 3H), 3.1 (d, 1H), 3.15 (t, 1H), 3.6 (d, 1H), 3.7 (m, 1H), 3.8 (m, 1H), 4.0 (d, 1H), 4.0 (s, 3H), 4.1 (d, 1H), 7.3 (s, 1H), 8.0 (s, 1H), 8.5 (s, 1H), 11.5 (s, 1H), 11.9 (s, 1H).

Example 71

(2R,4S,4aS)-rel-11-fluoro-2,4-dimethyl-8-(4-methyl-1,3-thiazol-5-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

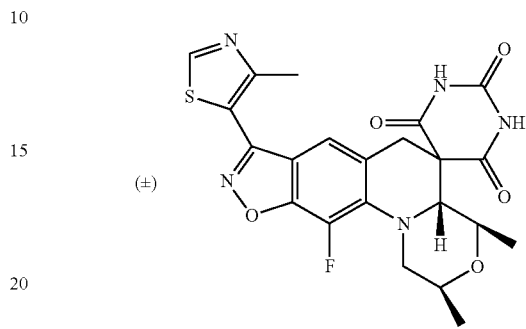

(±)

Starting material: 6-[(2R,6S)-2,6-dimethylmorpholin-4-yl]-7-fluoro-3-(4-methyl-1,3-thiazol-5-yl)-1,2-benzoxazole-5-carbaldehyde (Intermediate 400)

MS (ES) MH$^+$: 486 for $C_{22}H_{20}FN_6O_5S$;

$^1$H NMR (400 MHz, DMSO-D6) δ: 0.9 (d, 3H), 1.5 (d, 3H), 2.6 (s, 3H), 3.0 (d, 1H), 3.1 (t, 1H), 3.7 (m, 2H), 3.8 (m, 1H), 4.0 (d, 1H), 4.1 (d, 1H), 7.3 (s, 1H), 9.35 (s, 1H), 11.5 (s, 1H), 11.9 (s, 1H).

Example 72

(2R,4S,4aS)-rel-11-fluoro-2,4-dimethyl-8-(4-methyl-1,2,3-thiadiazol-5-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

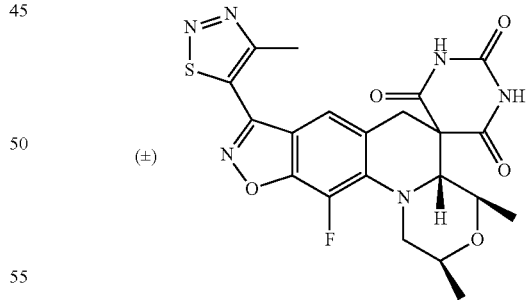

(±)

Starting material: 6-[(2R,6S)-2,6-dimethylmorpholin-4-yl]-7-fluoro-3-(4-methyl-1,2,3-thiadiazol-5-yl)-1,2-benzoxazole-5-carbaldehyde (Intermediate 401)

MS (ES) MH$^+$: 487 for $C_{21}H_{19}FN_6O_5S$ $^1$H NMR (400 MHz, DMSO-D6) δ: 0.9 (d, 3H), 1.15 (d, 3H), 2.9 (s, 3H), 3.0 (d, 1H), 3.1 (t, 1H), 3.6 (d, 1H), 3.7 (m, 1H), 3.8 (m, 1H), 4.0 (d, 1H), 4.1 (d, 1H), 7.4 (s, 1H), 11.5 (s, 1H), 11.9 (s, 1H).

Example 73

(2R,4S,4aS)-rel-11-fluoro-2,4-dimethyl-8-(pyridazin-3-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

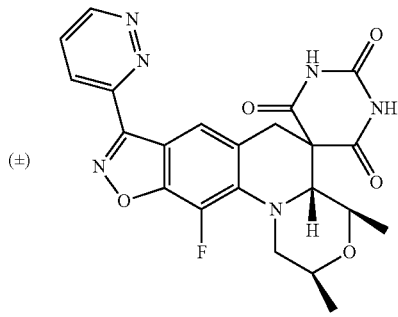

Starting material: 6-[(2R,6S)-2,6-dimethylmorpholin-4-yl]-7-fluoro-3-(pyridazin-3-yl)-1,2-benzoxazole-5-carbaldehyde (Intermediate 402)

MS (ES) MH$^+$: 467 for $C_{22}H_{19}FN_6O_5$ $^1$H NMR (400 MHz, DMSO-D6): δ 0.9 (d, 3H), 1.15 (d, 3H), 3.0 (d, 1H), 3.1 (t, 1H), 3.6 (d, 1H), 3.7 (m, 1H), 3.8 (m, 1H), 4.0 (d, 1H), 4.1 (d, 1H), 7.9 (m, 2H), 8.4 (m, 1H), 9.4 (m, 1H), 11.5 (s, 1H), 11.8 (s, 1H).

Example 74

(2R,4S,4aS)-rel-11-fluoro-2,4-dimethyl-8-(pyrimidin-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

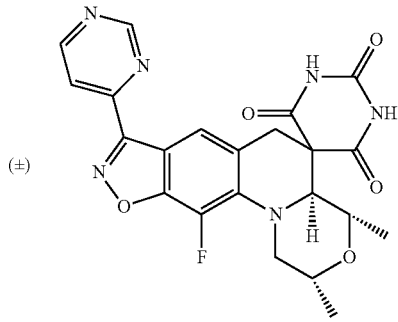

Starting material: 6-[(2R,6S)-2,6-dimethylmorpholin-4-yl]-7-fluoro-3-(pyrimidin-4-yl)-1,2-benzoxazole-5-carbaldehyde (Intermediate 403)

MS (ES) MH$^+$: 467 for $C_{22}H_{19}FN_6O_5$ $^1$H NMR (400 MHz, DMSO-D6) δ: 0.9 (d, 3H), 1.15 (d, 3H), 3.0 (d, 1H), 3.1 (t, 1H), 3.6 (d, 1H), 3.7 (m, 1H), 3.8 (m, 1H), 4.0 (d, 1H), 4.1 (d, 1H), 7.9 (m, 2H), 8.4 (m, 1H), 9.4 (m, 1H), 11.5 (s, 1H), 11.8 (s, 1H).

The (2S,4R,4aR) and (2R,4S,4aS) enantiomers of Example 74 separated by Supercritical Fluid Chromatography using a Chiralpak AD, 21×250 mm, 5μ column (elution with 25% MeOH, 75% CO$_2$ at 60 ml/min, 40° C., and 100 bar with detection at 220 nm).

Example 74(a)

First Eluting Compound (2S,4R,4aR)-11-fluoro-2,4-dimethyl-8-(pyrimidin-4-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

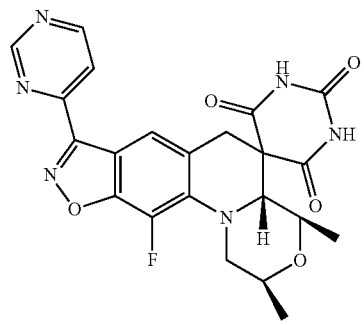

MS (ES) MH$^+$: 467 for $C_{22}H_{19}FN_6O_5$ $^1$H NMR (300 MHz, DMSO-d$_6$) δ: 0.9 (d, 3H) 1.2 (d, 3H) 2.2-3.0 (m, 2H) 3.6-4.3 (m, 5H) 7.8 (s, 1H) 8.1-8.2 (m, 1H) 9.0 (d, 1H) 9.4 (s, 1H) 11.6 (s, 2H)

>98% ee by chiral HPLC; [α]=+199 (c=0.1 in DMSO).

Example 74(b)

Second Eluting Compound (2R,4S,4aS)-11-fluoro-2,4-dimethyl-8-(pyrimidin-4-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

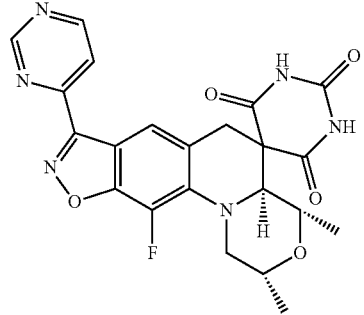

MS (ES) MH$^+$: 467 for $C_{22}H_{19}FN_6O_5$ $^1$H NMR (300 MHz, DMSO-d$_6$) δ: 0.9 (d, 3H) 1.2 (d, 3H) 2.8-3.2 (m, 2H) 3.6-4.2 (m, 5H) 7.8 (s, 1H) 8.0-8.4 (m, 1H) 9.0 (d, 1H) 9.4 (s, 1H) 11.5 (s, 2H)

>98% ee by chiral HPLC; [α]=−196 (c=0.1 in DMSO).

Example 75

(2R,4S,4aS)-rel-11-fluoro-2,4,8-trimethyl-1,2,4,4a-tetrahydro-2'H,6H-spiro[1,4-oxazino[4,3-a][1,2]thiazolo[4,5-g]quinoline-5,5'-pyrimidine]-2',4',6'(1'H,3'H)-trione

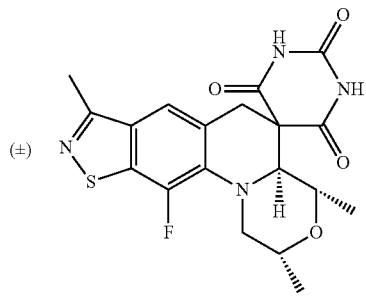

Starting material: 6-[(2R,6S)-2,6-dimethylmorpholin-4-yl]-7-fluoro-3-methyl-1,2-benzothiazole-5-carbaldehyde (Intermediate 576).

MS (ES) MH$^+$: 419 for $C_{19}H_{19}FN_4O_4S$ $^1$H NMR (400 MHz, DMSO-d$_6$) δ: 0.9 (d, 3H), 1.1 (d, 3H), 2.5 (s, 3H), 3.0 (m, 2H), 3.6 (d, 1H), 3.7 (m, 1H), 3.8 (m, 1H), 4.0 (d, 1H), 4.1 (d, 1H), 7.5 (s, 1H), 11.5 (s, 1H), 11.9 (s, 1H).

Example 76

(2R,4S,4aS)-rel-11-fluoro-2,4-dimethyl-8-(pyridin-2-yl)-1,2,4,4a-tetrahydro-2'H,6H-spiro[1,4-oxazino[4,3-a][1,2]thiazolo[4,5-g]quinoline-5,5'-pyrimidine]-2',4',6'(1'H,3'H)-trione

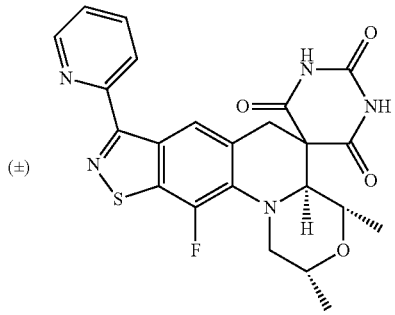

Starting material: 6-[(2R,6S)-2,6-dimethylmorpholin-4-yl]-7-fluoro-3-(pyridin-2-yl)-1,2-benzothiazole-5-carbaldehyde (Intermediate 577)

MS (ES) MH$^+$: 481 for $C_{23}H_{20}FN_5O_4S$ $^1$H NMR (400 MHz, DMSO-d$_6$) δ: 0.9 (d, 3H), 1.2 (d, 3H), 3.0 (d, 1H), 3.1 (t, 1H), 3.7 (m, 1H), 3.8 (m, 2H), 4.0 (d, 1H), 4.15 (d, 1H), 7.5 (m, 1H), 8.0 (t, 1H), 8.2 (d, 1H), 8.5 (s, 1H), 8.8 (d, 1H), 11.5 (s, 1H), 11.8 (s, 1H).

Example 77

(2S,4R,4aR)-rel-11-fluoro-2,4,8-trimethyl-1,2,3,4,4a,6-hexahydro-1'H-spiro[isoxazolo[4,5-g]pyrido[1,2-a]quinoline-5,5'-pyrimidine]-2',4',6'(3'H)-trione

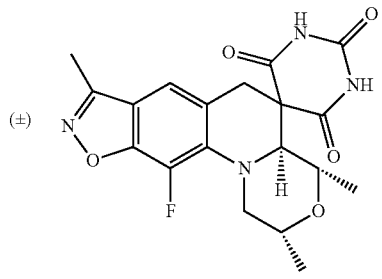

Starting material: 6-((3S,5R)-3,5-dimethylpiperidin-1-yl)-7-fluoro-3-methylbenzo[d]isoxazole-5-carbaldehyde (Intermediate 538)

MS (ES) MH$^+$: 401 for $C_{20}H_{21}FN_4O_4$ $^1$H NMR (300 MHz, DMSO-d$_6$) δ ppm 0.6 (d, 3H), 0.8-1.1 (m, 1H), 0.9 (d, 3H), 1.8 (m, 3H), 2.4 (s, 3H), 2.6-3.1 (m, 2H) 3.5 (d, 1H), 3.8 (d, 1H) 3.9-4.0 (m, 1H) 7.1 (s, 1H), 11.4 (br. s., 2H).

Example 78

(2R,4S,4aS)-rel-8-(3-chloropyrazin-2-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

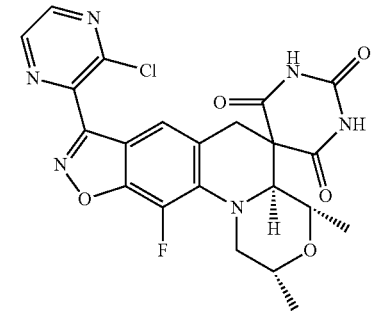

Starting material: 3-(3-chloropyrazin-2-yl)-6-((2R,6S)-2,6-dimethylmorpholino)-7-fluorobenzo[d]isoxazole-5-carbaldehyde (Intermediate 432)

MS (ES) MH$^+$: 501 for $C_{22}H_{18}ClFN_6O_5$ $^1$H NMR (300 MHz, DMSO-d$_6$) δ ppm 0.9 (d, 3H) 1.2 (d, 3H), 3.0 (d, 1H), 3.1 (m, 1H), 3.6-3.7 (m, 2H), 3.7 (m, 1H), 3.9 (d, 1H), 4.2 (d, 1H), 7.9 (d, 1H), 8.9 (d, 1H), 9.0 (d, 1H), 11.5 (s, 1H), 11.9 (s, 1H)

Example 79

(2R,4S,4aS)-rel-8-(6-chloropyrazin-2-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

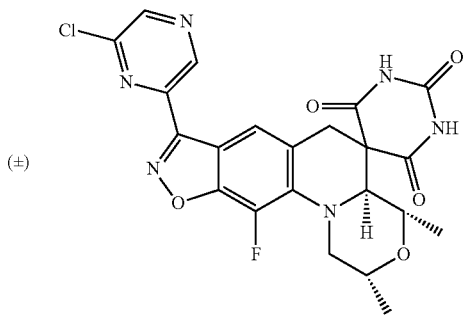

Starting material: 3-(6-chloropyrazin-2-yl)-6-((2R,6S)-2,6-dimethylmorpholino)-7-fluorobenzo[d]isoxazole-5-carbaldehyde (Intermediate 434)

MS (ES) MH$^+$: 501 for $C_{22}H_{18}ClFN_6O_5$ $^1$H NMR (300 MHz, DMSO-d$_6$) δ ppm 0.9 (d, 3H), 1.2 (d, 3H), 3.0 (d, 1H), 3.1-3.2 (m, 1H), 3.7 (dd, 1H), 3.8 (m, 2H), 4.0 (d, 1H), 4.1-4.2 (m, 1H), 7.7 (s, 1H), 9.0 (s, 1H), 9.3 (s, 1H), 11.5 (s, 1H), 11.9 (s, 1H)

Example 80

(2R,4S,4aS)-rel-11-fluoro-2,4-dimethyl-8-(5-(methylthio)pyrazin-2-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

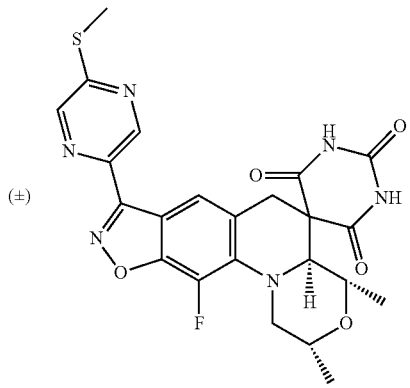

Starting material: 6-((2R,6S)-2,6-dimethylmorpholino)-7-fluoro-3-(5-(methylthio)pyrazin-2-yl)benzo[d]isoxazole-5-carbaldehyde (Intermediate 435)

MS (ES) MH$^+$: 513 for $C_{23}H_{21}FN_6O_5S$ $^1$H NMR (300 MHz, DMSO-d$_6$) δ ppm 0.9 (d, 3H), 1.2 (d, 3H), 2.7 (s, 3H), 3.0 (d, 1H), 3.1-3.2 (m, 1H), 3.7 (m, 3H), 3.9-4.1 (m, 1H), 4.1 (d, 1H), 7.7 (s, 1H), 8.8 (d, 1H), 9.2 (d, 1H), 11.5 s., 1H), 11.8 (br. s., 1H)

Example 81

(2R,4S,4aS)-rel-8-((1H-1,2,4-triazol-1-yl)methyl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

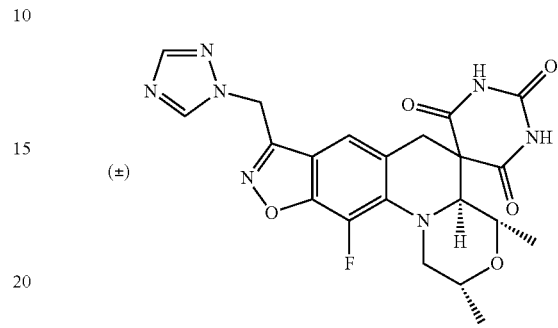

Starting material: 3-((1H-1,2,4-triazol-1-yl)methyl)-6-((2R,6S)-2,6-dimethylmorpholino)-7-fluorobenzo[d]isoxazole-5-carbaldehyde (Intermediate 425).

MS (ES) MH$^+$: 470 for $C_{21}H_{20}FN_7O_5$ $^1$H NMR (300 MHz, CDCl$_3$) δ: 0.87 (d, 3H), 1.12 (d, 3H), 2.85-3.19 (m, 2H), 3.46-4.15 (m, 5H), 5.68-5.93 (m, 2H), 7.01 (s, 1H), 8.00 (s, 1H), 8.76 (s, 1H), 11.45 (s, 1H), 11.81 (s, 1H).

Example 82

(2R,4S,4aS)-rel-11-fluoro-2,4-dimethyl-8-(pyridin-4-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

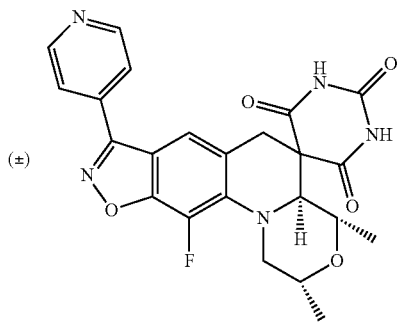

Starting material: 6-((2R,6S)-2,6-dimethylmorpholino)-7-fluoro-3-(pyridin-4-yl)benzo[d]isoxazole-5-carbaldehyde (Intermediate 426).

MS (ES) MH$^+$: 466 for $C_{23}H_{20}FN_5O_5$ $^1$H NMR (300 MHz, DMSO-d$_6$) δ: 0.89 (d, 3H), 1.15 (d, 3H), 2.90-4.23 (m, 7H), 7.63 (s, 1H, 7.90 (d, 2H), 8.81 (d, 2H), 11.50 (s, 1H), 11.87 (s, 1H).

Example 83

(2R,4S,4aS)-rel-11-fluoro-8-(5-hydroxy-1,3,4-oxadiazol-2-yl)-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione

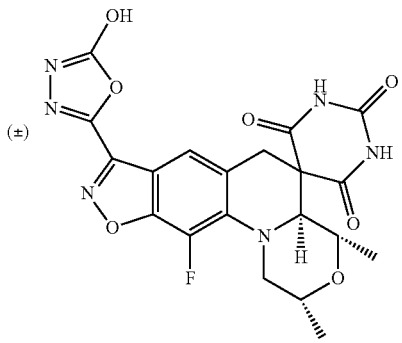

Starting material: 6-((2R,6S)-2,6-dimethylmorpholino)-7-fluoro-3-(5-oxo-4,5-dihydro-1,3,4-oxadiazol-2-yl)benzo[d]isoxazole-5-carbaldehyde (Intermediate 405)

MS (ES) MH$^+$: 473 for $C_{20}H_{17}FN_6O_7$ $^1$H NMR (300 MHz, DMSO-d$_6$) δ: 0.9 (d, 3H) 1.1 (d, 3H) 2.8-3.2 (m, 2H) 3.6-4.2 (m, 5H) 7.5 (s, 1H) 11.5 (br s, 1H) 11.8 (br s, 1H) 13.1 (br s, 1H)

Example 84

(2R,4S,4aS)-rel-11-fluoro-2,4-dimethyl-8-[4-(morpholin-4-ylcarbonyl)-1,3-thiazol-2-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

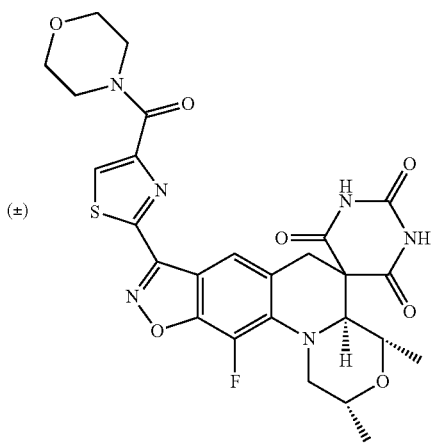

To a solution of 6-[(2R,6S)-2,6-dimethylmorpholin-4-yl]-7-fluoro-3-[4-(morpholin-4-ylcarbonyl)-1,3-thiazol-2-yl]-1,2-benzoxazole-5-carbaldehyde (Intermediate 389, 90 mg, 0.19 mmol) in IPA was added barbituric acid (24 mg, 0.103 mmol) and the mixture heated at 85° C. for 16 hours. Solvents were evaporated and the residue was purified by reverse phase HPLC to give product as solid (as a TFA salt). Yield: 16 mg (14%).

MS (ES) MH$^+$: 585 for $C_{26}H_{25}FN_6O_7S$ $^1$H NMR (400 MHz, DMSO-D6) δ: 0.9 (d, 3H), 1.5 (d, 3H), 3.0 (d, 1H), 3.1 (t, 1H), 3.6-3.8 (m, 11H), 4.0 (d, 1H), 4.1 (d, 1H), 7.6 (s, 1H), 8.4 (s, 1H).

Examples 85 to 93 were prepared from the indicated starting materials using a method similar to the one described for the synthesis of Example 84:

Example 85

(2R,4S,4aS)-rel-11-fluoro-2,4-dimethyl-8-[4-(morpholin-4-ylcarbonyl)-1,3-thiazol-5-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

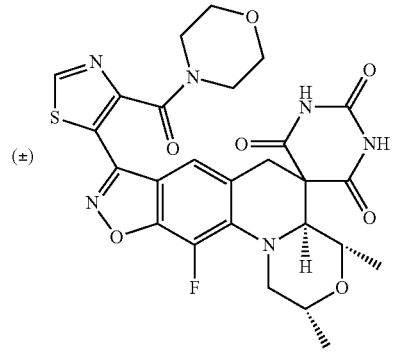

Starting material: 6-[(2R,6S)-2,6-dimethylmorpholin-4-yl]-7-fluoro-3-[4-(morpholin-4-ylcarbonyl)-1,3-thiazol-5-yl]-1,2-benzoxazole-5-carbaldehyde (Intermediate 390)

MS (ES) MH$^+$: 585.5 for $C_{26}H_{25}FN_6O_7S$ $^1$H NMR (400 MHz, DMSO-D6) δ: 0.9 (d, 3H), 1.15 (d, 3H), 2.9 (d, 1H), 3.1 (t, 1H), 3.3 (m, 2H), 3.4 (m, 2H), 3.5 (m, 4H), 3.7 (m, 2H), 3.8 (m, 1H), 4.0 (d, 1H), 4.1 (d, 1H), 7.1 (s, 1H), 9.45 (s, 1H), 11.5 (s, 1H), 11.9 (s, 1H).

Example 86

2-[(2R,4S,4aS)-rel-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-N,N-dimethyl-1,3-thiazole-4-carboxamide

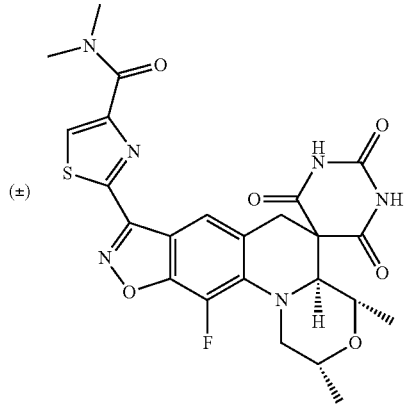

Starting material: 2-{6-[(2R,6S)-2,6-dimethylmorpholin-4-yl]-7-fluoro-5-formyl-1,2-benzoxazol-3-yl}-N,N-dimethyl-1,3-thiazole-4-carboxamide (Intermediate 391)

MS (ES) MH$^+$: 543 for $C_{24}H_{23}FN_6O_6S$.

$^1$H NMR (400 MHz, DMSO-D6) δ: 0.9 (d, 3H), 1.15 (d, 3H), 2.9 (s, 3H), 3.0 (s, 3H), 3.05 (d, 1H), 3.2 (t, 1H), 3.7 (m, 2H), 3.8 (m, 1H), 4.0 (d, 1H), 4.1 (d, 1H), 7.1 (s, 1H), 9.4 (s, 1H), 11.5 (bs, 1H), 11.8 (bs, 1H).

Example 87

2-[(2R,4S,4aS)-rel-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-N,N-dimethyl-1,3-thiazole-5-carboxamide

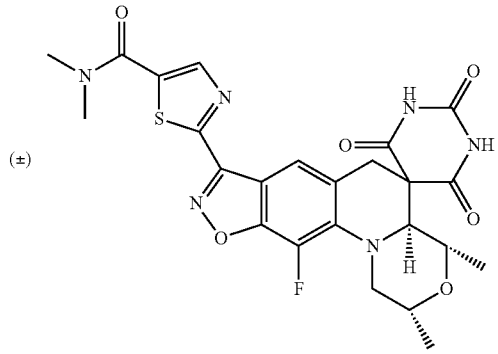

Starting material: 2-{6-[(2R,6S)-2,6-dimethylmorpholin-4-yl]-7-fluoro-5-formyl-1,2-benzoxazol-3-yl}-N,N-dimethyl-1,3-thiazole-5-carboxamide (Intermediate 392)

MS (ES) MH$^+$: 543 for $C_{24}H_{23}FN_6O_6S$.

$^1$H NMR (400 MHz, DMSO-D6) δ: 0.9 (d, 3H), 1.15 (d, 3H), 2.9 (d, 1H), 3.0 (s, 3H), 3.1 (m, 1H), 3.2 (s, 3H), 3.7 (m, 1H), 3.8 (m, 2H), 4.0 (d, 1H), 4.1 (d, 1H), 7.1 (s, 1H), 9.4 (s, 1H), 11.5 (bs, 1H), 11.8 (bs, 1H).

Example 88

5-[(2R,4S,4aS)-rel-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-1,3-thiazole-4-carbonitrile

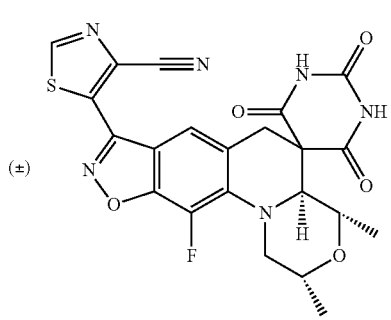

Starting material: 5-{6-[(2R,6S)-2,6-dimethylmorpholin-4-yl]-7-fluoro-5-formyl-1,2-benzoxazol-3-yl}-1,3-thiazole-4-carbonitrile (Intermediate 393)

MS (ES) MH$^+$: 497 for $C_{22}H_{17}FN_6O_5S$.

$^1$H NMR (400 MHz, DMSO-D6) δ: 0.9 (d, 3H), 1.15 (d, 3H), 3.0 (d, 1H), 3.1 (m, 1H), 3.6-3.8 (m, 3H), 4.0 (d, 1H), 4.1 (d, 1H), 7.4 (s, 1H), 9.6 (s, 1H), 11.5 (bs, 1H), 11.9 (bs, 1H).

Example 89

(2R,4S,4aS)-rel-11-chloro-2,4-dimethyl-8-(1-methyl-1H-imidazol-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione isolated as the TFA salt from reverse phase HPLC purification

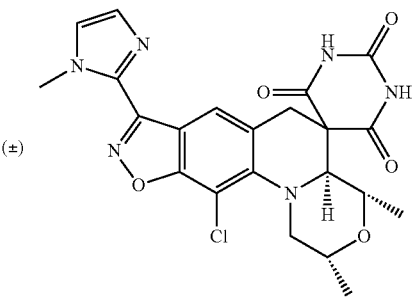

Starting material: 7-chloro-6-[(2R,6S)-2,6-dimethylmorpholin-4-yl]-3-(1-methyl-1H-imidazol-2-yl)-1,2-benzoxazole-5-carbaldehyde (Intermediate 387).

MS (ES) MH$^+$: 485 for $C_{22}H_{21}ClN_6O_5$;

$^1$H NMR (400 MHz, DMSO-D6) δ: 0.9 (d, 3H), 1.1 (d, 3H), 3.0 (d, 1H), 3.1 (m, 1H), 3.8 (m, 2H), 4.0 (m, 5H), 4.5 (d, 1H), 7.2 (s, 1H), 7.5 (s, 1H), 7.9 (s, 1H), 11.4 (s, 1H), 11.8 (s, 1H).

Example 90

(2R,4S,4aS)-rel-2,4,11-trimethyl-8-(1,3-thiazol-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

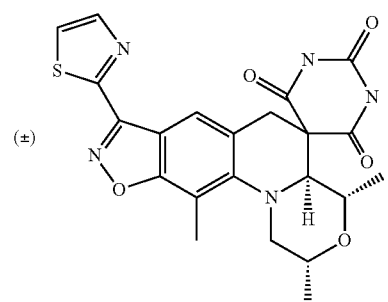

Starting material: 6-[(2R,6S)-2,6-dimethylmorpholin-4-yl]-7-methyl-3-(1,3-thiazol-2-yl)-1,2-benzoxazole-5-carbaldehyde (Intermediate 330).

MS (ES) MH$^+$: 468 for $C_{22}H_{21}N_5O_5S$ $^1$H NMR (400 MHz, DMSO-d6) δ: 0.9 (d, 3H), 1.2 (d, 3H), 2.5 (s, 3H), 3.1 (m, 2H), 3.6 (m, 2H), 3.9 (m, 2H), 4.1 (d, 1H), 7.7 (s, 1H), 8.0 (d, 1H), 8.1 (d, 1H) 11.4 (s, 1H), 11.8 (s, 1H).

Example 91

(2R,4S,4aS)-rel-11-fluoro-2,4-dimethyl-8-(6-methylpyridin-3-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

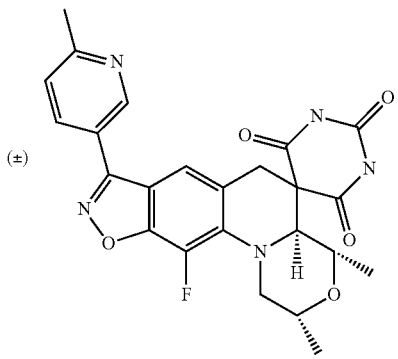

Starting material: 6-((2R,6S)-2,6-dimethylmorpholino)-7-fluoro-3-(6-methylpyridin-3-yl)benzo[d]isoxazole-5-carbaldehyde (Intermediate 421).
MS (ES) MH$^+$: 480 for $C_{24}H_{22}FN_5O_5$
$^1$H NMR (300 MHz, DMSO-d$_6$) δ: 0.89 (d, 3H), 1.15 (d, 3H), 2.57 (s, 3H), 2.88-3.24 (m, 2H), 3.51-4.22 (m, 5H), 7.49 (d, 1H), 7.59 (s, 1H), 8.19 (d, 1H), 8.97 (s, 1H), 11.48 (s, 1H), 11.86 (s, 1H).

Example 92

(2R,4S,4aS)-rel-11-fluoro-2,4-dimethyl-8-(trifluoromethyl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

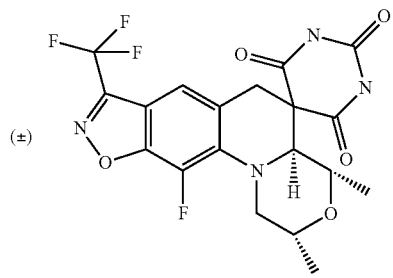

Starting material: 6-((2R,6S)-2,6-dimethylmorpholino)-7-fluoro-3-(trifluoromethyl)benzo[d]isoxazole-5-carbaldehyde (Intermediate 429).
MS (ES) MH$^+$: 457 for $C_{19}H_{16}F_4N_4O_5$
$^1$H NMR (300 MHz, DMSO-d$_6$) δ: 0.89 (d, 3H), 1.14 (d, 3H), 2.86-3.24 (m, 2H), 3.54-4.28 (m, 5H), 7.35 (s, 1H), 11.56 (s, 1H), 11.91 (s, 1H).

The (2S,4R,4aR) and (2R,4S,4aS) enantiomers of Example 92 were separated by Supercritical Fluid Chromatography using a Chiralpak AD, 21×250 mm, 5μ column (elution with 25% MeOH, 75% CO$_2$ at 60 ml/min, 40° C., and 100 bar with detection at 220 nm), providing Example 92(a) and Example 92(b):

Example 92(a)

First Eluting Compound (2S,4R,4aR)-11-fluoro-2,4-dimethyl-8-(trifluoromethyl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

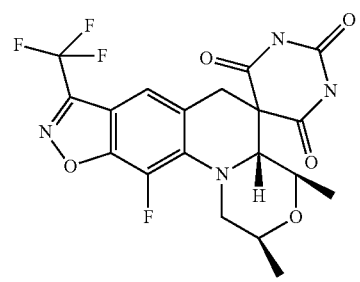

MS (ES) MH$^+$: 457 for $C_{19}H_{16}F_4N_4O_5$
$^1$H NMR (300 MHz, DMSO-d$_6$) δ: 0.89 (d, 3H), 1.14 (d, 3H), 2.83-3.21 (m, 2H), 3.57-4.23 (m, 5H), 7.34 (s, 1H), 11.72 (s, 2H).
>98% ee by chiral HPLC; [α]=+285 (c=0.1 in MeOH).

Example 92(b)

Second Eluting Compound (2R,4S,4aS)-11-fluoro-2,4-dimethyl-8-(trifluoromethyl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

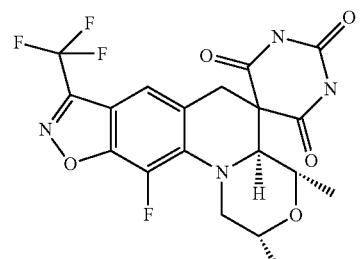

MS (ES) MH$^+$: 457 for $C_{19}H_{16}F_4N_4O_5$
$^1$H NMR (300 MHz, DMSO-d$_6$) δ: 0.89 (d, 3H), 1.14 (d, 3H), 2.89-3.25 (m, 2H), 3.56-4.30 (m, 5H), 7.34 (s, 1H), 11.72 (s, 2H).
>98% ee by chiral HPLC; [α]=−305 (c=0.1 in MeOH).

Example 93

(2R,4S,4aS)-rel-8-(difluoromethyl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'-(3'H)-trione

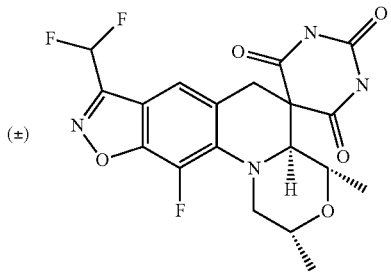

Starting material: 3-(difluoromethyl)-6-((2R,6S)-2,6-dimethylmorpholino)-7-fluorobenzo[d]isoxazole-5-carbaldehyde (Intermediate 428).

MS (ES) MH+: 439 for $C_{19}H_{17}F_3N_4O_5$ $^1$H NMR (300 MHz, DMSO-d$_6$) δ: 0.88 (d, 3H), 1.14 (d, 3H), 2.82-3.24 (m, 2H), 3.55-4.20 (m, 5H), 7.30 (s, 1H), 7.52 (t, 1H), 11.52 (s, 1H), 11.87 (s, 1H).

The (2S,4R,4aR) and (2R,4S,4aS) enantiomers of Example 93 were separated by Supercritical Fluid Chromatography using a Chiralpak AD, 21×250 mm, 5µ column (elution with 25% MeOH, 75% CO$_2$ at 60 ml/min, 40° C., and 100 bar with detection at 220 nm), providing Example 93(a) and Example 93(b):

Example 93(a)

First Eluting Compound (2S,4R,4aR)-8-(difluoromethyl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

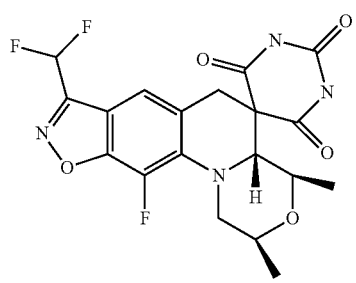

MS (ES) MH+: 439 for $C_{19}H_{17}F_3N_4O_5$ $^1$H NMR (300 MHz, DMSO-d$_6$) δ: 0.88 (d, J=6.41 Hz, 3H), 1.14 (d, J=6.03 Hz, 3H), 2.84-3.21 (m, 2H), 3.56-4.19 (m, 5H), 7.30 (s, 1H), 7.52 (t, J=52.65 Hz, 1H), 11.67 (br s, 2H).

>98% ee by chiral HPLC; [α]=+276 (c=0.1 in MeOH).

Example 93(b)

Second Eluting Compound (2R,4S,4aS)-8-(difluoromethyl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

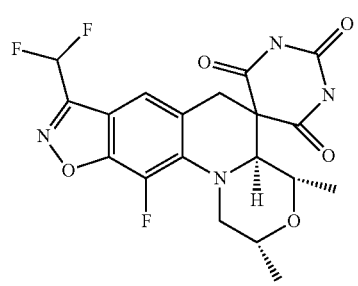

MS (ES) MH+: 439 for $C_{19}H_{17}F_3N_4O_5$ $^1$H NMR (300 MHz, DMSO-d$_6$) δ: 0.90 (d, 3H), 1.15 (d, 3H), 2.81-3.24 (m, 2H), 3.57-4.21 (m, 5H), 7.31 (s, 1H), 7.53 (t, 1H), 11.70 (br s, 2H).

>98% ee by chiral HPLC; [α]=−289 (c=0.1 in MeOH).

Using an alternate route, Example 93(b) was also obtained via a chiral synthesis similar to the one described for the synthesis of Example 96, using the indicated starting material:

Example 93(b)

Chiral Synthesis (2R,4S,4aS)-8-(difluoromethyl)-11-fluoro-2,4-dimethyl-2,4,4a,6-tetrahydro-1H,1'H-spiro[isoxazolo][4,5-g][1,4]oxazino[4,3-a]quinoline-5,5'-pyrimidine]-2',4',6'(3'H)-trione

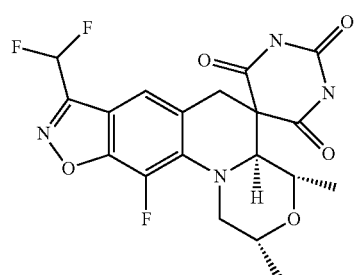

Starting material: 3-(difluoromethyl)-6-((2R,6R)-2,6-dimethylmorpholino)-7-fluorobenzo[d]isoxazole-5-carbaldehyde (Intermediate 431).

MS (ES) MH+: 439 for $C_{19}H_{17}F_3N_4O_5$ $^1$H NMR (300 MHz, DMSO-d$_6$) δ: 0.90 (d, 3H), 1.15 (d, 3H), 2.81-3.24 (m, 2H), 3.57-4.21 (m, 5H), 7.31 (s, 1H), 7.53 (t, 1H), 11.70 (br s, 2H).

Example 94

(2R,4S,4aS)-rel-N-(2,2-difluoroethyl)-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide

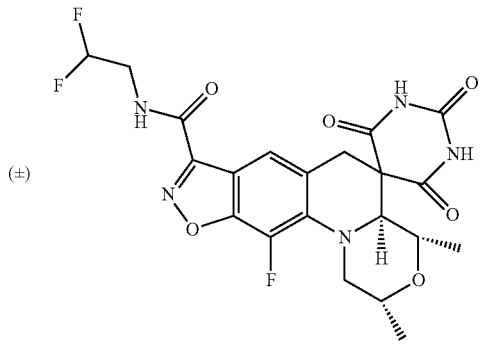

Starting material: Barbituric acid and N-(2,2-difluoroethyl)-6-((2R,6S)-2,6-dimethylmorpholino)-7-fluoro-5-formylbenzo[d]isoxazole-3-carboxamide were reacted (Intermediate 467) using a method similar to the one described for the synthesis of Example 134. The product was purified by reverse phase HPLC using a gradient of CH$_3$CN in water with 0.1% TFA.

MS (ES) MH$^+$: 496 for C$_{21}$H$_{20}$F$_3$N$_5$O$_6$ $^1$H NMR (300 MHz, DMSO-d$_6$) δ ppm 0.9 (d, 3H), 1.2 (d, 3H), 2.9 (d, 1H), 3.1 (t, 1H), 3.6-3.9 (m, 5H), 4.0 (d, 1H), 4.1 (d, 1H), 5.9-6.4 (m, 1H), 7.4 (s, 1H), 9.3 (t, 1H), 11.6 (br. s., 2H).

The (2S,4R,4aR) and (2R,4S,4aS) enantiomers of Example 94 were separated by Supercritical Fluid Chromatography using a Chiralpak AD, 21×250 mm, 5µ column (elution with 25% MeOH, 75% CO$_2$ at 60 ml/min, 40° C., and 100 bar with detection at 220 nm), providing Example 94(a) and Example 94(b):

Example 94(a)

First Eluting Compound (2S,4R,4aR)—N-(2,2-difluoroethyl)-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide

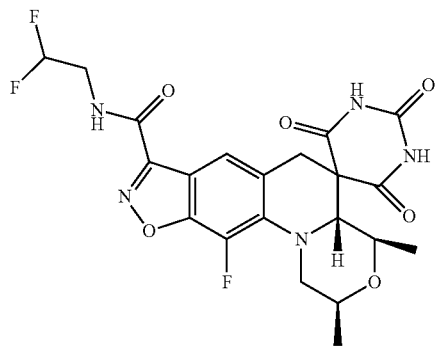

MS (ES) MH$^+$: 496 for C$_{21}$H$_{20}$F$_3$N$_5$O$_6$ $^1$H NMR (300 MHz, DMSO-d$_6$) δ ppm 0.9 (d, 3H), 1.2 (d, 3H), 2.9 (d, 1H), 3.1-3.2 (m, 1H), 3.6-3.9 (m, 5H), 4.0 (d, 1H), 4.1 (d, 1H), 5.9-6.4 (m, 1H), 7.5 (s, 1H), 9.3 (t, 1H), 11.5 (s, 1H), 11.8 (s, 1H).

>98% ee by chiral HPLC; [α]=+297 (c=0.1 in DMSO)

Example 94(b)

Second Eluting Compound (2R,4S,4aS)—N-(2,2-difluoroethyl)-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide

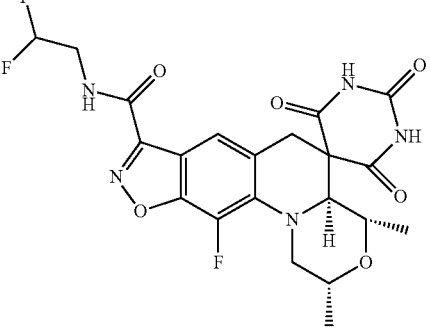

MS (ES) MH$^+$: 496 for C$_{21}$H$_{20}$F$_3$N$_5$O$_6$ $^1$H NMR (300 MHz, DMSO-d6) δ ppm 0.9 (d, 3H), 1.2 (d, 3H), 2.9 (d, 1H), 3.1-3.2 (m, 1H), 3.6-3.9 (m, 5H), 4.0 (d, 1H), 4.1 (d, 1H), 5.9-6.4 (m, 1H), 7.5 (s, 1H), 9.3 (t, 1H), 11.5 (s, 1H), 11.8 (s, 1H).

>98% ee by chiral HPLC; [α]=−225 (c=0.1 in DMSO)

Using an alternate route, Example 94(b) was also obtained via a chiral synthesis similar to the one described for the synthesis of Example 95(a) below, using the indicated starting material:

Example 94(b)

Chiral Synthesis (2R,4S,4aS)—N-(2,2-difluoroethyl)-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide

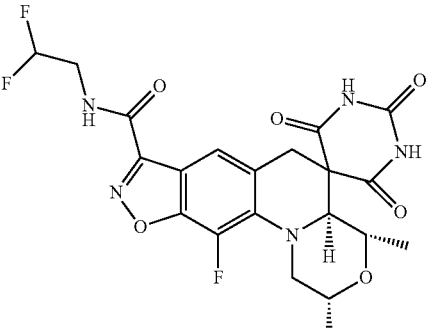

Starting Material: N-(2,2-difluoroethyl)-6-((2R,6R)-2,6-dimethylmorpholino)-7-fluoro-5-formylbenzo[d]isoxazole-3-carboxamide (Intermediate 248)

MS (ES) MH$^+$: 246 for C$_{21}$H$_{20}$F$_3$N$_5$O$_6$

>98% ee by chiral HPLC; [α]=−256 (c=0.1 in MeOH)

¹H NMR (300 MHz, DMSO-d6) δ ppm 0.9 (d, 3H), 1.2 (d, 3H), 2.9 (d, 1H), 3.1 (t, 1H), 3.6-3.9 (m, 4H), 4.0 (d, 1H), 4.1 (d, 1H), 5.9-6.4 (m, 1H), 7.4 (s, 1H), 9.3 (t, J=6.0 Hz, 1H), 11.5 (br. s., 1H), 11.8 (br. s., 1H)

Example 95 was prepared from the indicated starting material and barbituric acid using a method similar to the one described for the synthesis of Example 134. The compounds were purified by silica gel column chromatography using a gradient of DCM to ethyl acetate.

Example 95

(2R,4S,4aS)-rel-8-(3,3-difluoroazetidine-1-carbonyl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

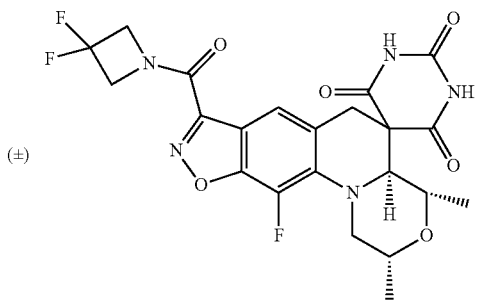

Starting Material: 3-(3,3-difluoroazetidine-1-carbonyl)-6-((2R,6S)-2,6-dimethylmorpholino)-7-fluorobenzo[d]isoxazole-5-carbaldehyde (Intermediate 446)

MS (ES) MH⁺: 508 for $C_{22}H_{20}F_3N_5O_6$

¹H NMR (300 MHz, DMSO-d₆) δ ppm 0.8 (d, 3H), 1.1 (d, 3H), 2.8 (d, 1H), 3.1 (t, 1H), 3.5-3.8 (m, 3H), 3.9 (d, 1H), 4.1 (d, 1H), 4.5 (t, 2H), 4.9 (t, 2H), 7.4 (s, 1H), 11.4 (br. s., 1H), 11.8 (br. s., 1H).

In an alternate route, the (2R,4S,4aS) enantiomer of Example 95 was synthesized via a chiral synthesis, providing Example 95(a):

Example 95(a)

(2R,4S,4aS)-8-(3,3-difluoroazetidine-1-carbonyl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

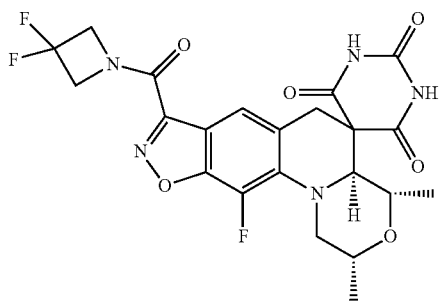

3-(3,3-difluoroazetidine-1-carbonyl)-6-((2R,6R)-2,6-dimethylmorpholino)-7-fluorobenzo[d]isoxazole-5-carbaldehyde (Intermediate 245, 2.08 g, 5.23 mmol) was dissolved in ~100 ml of ethanol and heated with barbituric acid (0.704 g, 5.50 mmol) at 105° C. (external temperature) for 6 days. The reaction was absorbed onto celite then purified on by silica gel chromatography using a gradient of DCM to ethyl acetate. Fractions were combined and concentrated. This material was then purified by Supercritical Fluid Chromatography (separation of diastereomers), using a Chiralpak AD, 21×250 mm, 5µ column (elution with 40% isopropanol, 60% $CO_2$ at 60 ml/min, 40° C., and 100 bar with detection at 220 nm), to give the title compound (2.16 g, 4.26 mmol, 81%) as the first eluting compound.

MS (ES) MH⁺: 508 for $C_{22}H_{20}F_3N_5O_6$

¹H NMR (300 MHz, DMSO-d₆) δ ppm 0.9 (d, 3H), 1.1 (d, 3H), 2.9 (d, 1H), 3.2 (t, 1H), 3.6-3.9 (m, 3H), 4.0 (d, 1H), 4.1 (d, 1H), 4.6 (t, 2H), 4.9 (t, 2H), 7.5 (s, 1H), 11.5 (br. s., 1H), 11.9 (br. s., 1H).

>98% ee by chiral HPLC; [α]=−296 (c=0.1 in MeOH)

Example 95(b)

(2R,4R,4aR)-8-(3,3-difluoroazetidine-1-carbonyl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

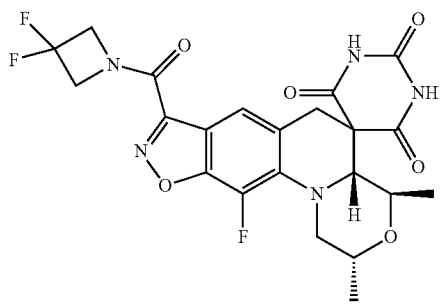

The (2R,4R,4aR) diastereomer was produced as a by-product of the reaction described for the synthesis of Example 95(a). The chromatography described for Example 95(a) afforded (2R,4R,4aR) diastereomer as the second eluting compound.

MS (ES) MH⁺: 508 for $C_{22}H_{20}F_3N_5O_6$

¹H NMR (300 MHz, DMSO-d₆) δ ppm 0.9 (d, 3H), 1.3 (d, 3H), 3.1 (d, 1H), 3.6 (d, 1H), 3.7 (d, 1H), 3.8 (d, 1H), 3.9-4.0 (m, 2H), 4.0-4.2 (m, 1H), 4.6 (t, 2H), 4.9 (t, 2H), 7.5 (s, ml H), 11.5 (br. s., 1H), 11.8 (br. s., 1H)

[α]=+169 (c=0.1 in Methanol)

Example 96

(2R,4S,4aS)-11-fluoro-2,4-dimethyl-8-(thiazol-2-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

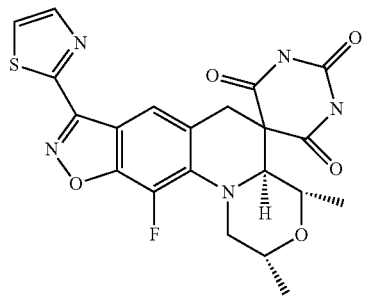

A mixture of 6-((2R,6R)-2,6-dimethylmorpholino)-7-fluoro-3-(thiazol-2-yl)benzo[d]isoxazole-5-carbaldehyde (Intermediate 430, 1.414 g, 3.91 mmol) and pyrimidine-2,4, 6(1H,3H,5H)-trione (0.501 g, 3.91 mmol) in ethanol (200 ml) was heated at 90° C. for 5 days. Solvent removed. LCMS of crude reaction indicates 9:1 mixture of two diastereomeric products. The major product was purified by reverse phase preparative HPLC to give the title compound (1.320 g, 71.6%).

MS (ES) MH$^+$: 472 for $C_{21}H_{18}FN_5O_5S$ $^1$H NMR (300 MHz, DMSO-d$_6$) δ: 0.89 (d, 3H), 1.15 (d, 3H), 2.85-3.23 (m, 2H), 3.60-4.22 (m, 5H), 7.72 (s, 1H), 8.08 (d, 1H), 8.17 (d, 1H), 11.48 (s, 1H), 11.84 (s, 1H).

Example 97

(2R,4S,4aS)-rel-11-fluoro-8-(furan-2-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

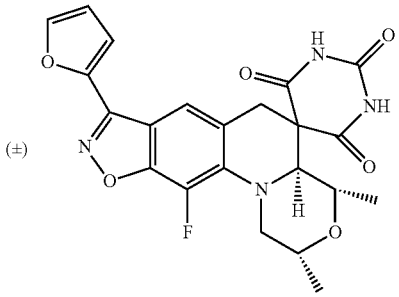

A mixture of 6-((2R,6S)-2,6-dimethylmorpholino)-7-fluoro-3-(furan-2-yl)benzo[d]isoxazole-5-carbaldehyde (Intermediate 427, 95 mg, 0.28 mmol) and pyrimidine-2,4,6(1H,3H,5H)-trione (38.9 mg, 0.30 mmol) in isopropanol (10 ml) was heated at 90° C. for 2 days. Solvent removed. Residue was triturated with methanol and the solid was filtered, washed with small amount of methanol, and dried to give title compound (107 mg, 85%).

MS (ES) MH$^+$: 455 for $C_{22}H_{19}FN_4O_6$ $^1$H NMR (300 MHz, DMSO-d$_6$) δ: 0.89 (d, 3H), 1.14 (d, 3H), 2.89-4.23 (m, 7H), 6.79 (dd, 1H), 7.33 (d, 1H), 7.59 (s, 1H), 8.01 (d, 1H), 11.50 (s, 1H), 11.87 (s, 1H).

Examples 98 to 101 were prepared from the indicated starting materials using a method similar to the one described for the synthesis of Example 97:

Example 98

(2R,4S,4aS)-rel-11-fluoro-2,4-dimethyl-8-(thiazol-5-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

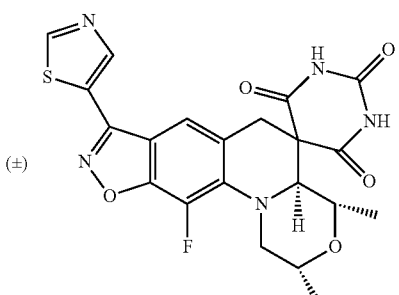

Starting material: 6-((2R,6S)-2,6-dimethylmorpholino)-7-fluoro-3-(thiazol-5-yl)benzo[d]isoxazole-5-carbaldehyde (Intermediate 422)

MS (ES) MH$^+$: 472 for $C_{21}H_{18}FN_5O_5S$ $^1$H NMR (300 MHz, DMSO-d$_6$) δ: 0.89 (d, 3H), 1.15 (d, 3H,) 2.92-3.24 (m, 2H), 3.43-4.23 (m, 5H), 7.74 (s, 1H), 8.72 (s, 1H), 9.37 (s, 1H), 11.52 (s, 1H), 11.89 (s, 1H).

Example 99

(2R,4S,4aS)-rel-11-fluoro-8-(2-fluorophenyl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

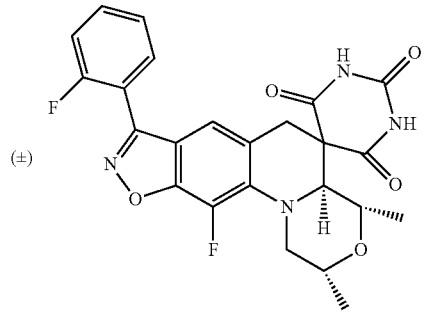

Starting material: 6-((2R,6S)-2,6-dimethylmorpholino)-7-fluoro-3-(2-fluorophenyl)benzo[d]isoxazole-5-carbaldehyde (Intermediate 423):

MS (ES) MH$^+$: 483 for $C_{24}H_{20}F_2N_4O_5$ $^1$H NMR (300 MHz, DMSO-d$_6$) δ: 0.88 (d, 3H), 1.15 (d, 3H), 2.86-3.21 (m, 2H), 3.50-4.21 (m, 5H), 7.22 (s, 1H), 7.30-7.88 (m, 4H), 11.46 (s, 1H), 11.82 (s, 1H).

Example 100

(2R,4S,4aS)-rel-11-fluoro-2,4-dimethyl-8-(tetrahydro-2H-pyran-4-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

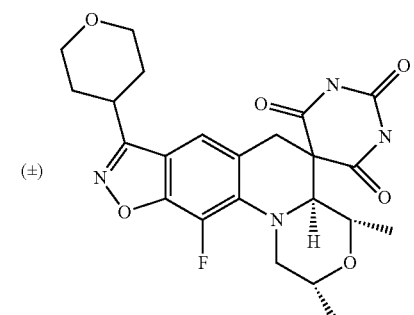

Starting material: 6-((2R,6S)-2,6-dimethylmorpholino)-7-fluoro-3-(tetrahydro-2H-pyran-4-yl)benzo[d]isoxazole-5-carbaldehyde (Intermediate 424).

MS (ES) MH$^+$: 473 for $C_{23}H_{25}FN_4O_6$

¹H NMR (300 MHz, DMSO-d₆) δ: 0.88 (d, 3H), 1.13 (d, 3H), 1.71-1.97 (m, 4H), 2.87-4.15 (m, 12H), 7.34 (s, 1H), 11.48 (s, 1H), 11.83 (s, 1H).

Example 101

(2R,4S,4aS)-rel-2,4,11-trimethyl-8-(pyrazin-2-yl)-1, 2,4,4a-tetrahydro-2'H,6H-spiro[1,4-oxazino[4,3-a][1, 2]oxazolo[4,5-g]quinoline-5,5'-pyrimidine]-2',4',6' (1'H,3'H)-trione

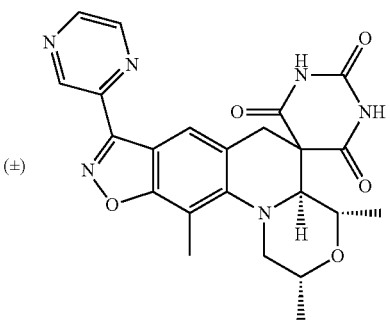

Starting material: 6-[(2R,6S)-2,6-dimethylmorpholin-4-yl]-7-methyl-3-(pyrazin-2-yl)-1,2-benzoxazole-5-carbaldehyde (Intermediate 331).

MS (ES) MH⁺: 463 for $C_{23}H_{22}N_6O_5$

¹N NMR (400 MHz, DMSO-d6) δ: 0.9 (d, 3H), 1.2 (d, 3H), 2.5 (s, 3H), 3.1 (m, 2H), 3.6 (m, 2H), 3.9 (m, 2H), 4.1 (d, 1H), 7.7 (s, 1H), 8.3 (s, 1H), 8.8 (d, 1H), 8.9 (d, 1H), 9.3 (s, 1H), 11.5 (brs, 2H).

Example 102 tert-butyl (2R,4S,4aS)-rel-11-fluoro-2,4-dimethyl-2', 4',6'-trioxo-1,1',2,3',4,4',4a,6'-octahydro-2'H,6H-spiro[isoxazolo[4,5-g][1,4]oxazino[4,3-a]quinoline-5,5'-pyrimidin]-8-yl carbonate

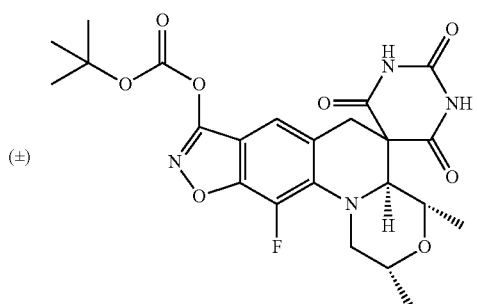

To a stirred solution of tert-butyl 6,7-difluoro-5-formyl-1, 2-benzisoxazol-3-yl carbonate Intermediate 531 (175 mg, 0.44 mmol) in dry IPA (10 mL) was added barbituric acid (8 mg, 0.062 mmol), and the solution heated around 80° C. for 12 h. Solvents were evaporated and the residue was purified over a silica gel column to give product as a white solid. Yield: 40 mg (18%).

¹H NMR (400 MHz, DMSO-d₆) δ: 0.9 (d, 3H), 1.1 (d, 3H), 1.6 (s, 9H), 2.9 (d, 1H), 3.1 (t, 1H), 3.6 (d, 1H), 3.7 (m, 1H), 3.8 (m, 1H), 3.9 (d, 1H), 4.0 (d, 1H), 7.0 (s, 1H), 11.5 (s, 1H), 11.8 (s, 1H).

Examples 103 and 104

(2R,4S,4aS)-rel-8-acetyl-9,10-difluoro-2,4-dimethyl-1,2,4,4a-tetrahydro-2'H,6H-spiro[1,4-oxazino[4,3-a] quinoline-5,5'-pyrimidine]-2',4',6'(1'H,3'H)-trione (Example 103) and (2R,4S,4aS)-rel-2-ethyl-11-fluoro-4,8-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione (Example 104)

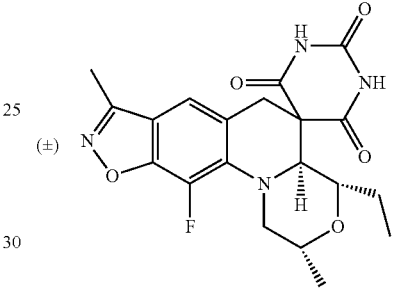

+

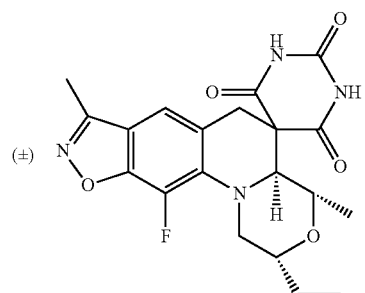

To a solution of 6-(2-ethyl-6-methylmorpholin-4-yl)-7-fluoro-3-methyl-1,2-benzisoxazole-5-carbaldehyde (Intermediate 501, 3.0 g, 9.17 mmol) in IPA was added barbituric acid (1.4 g, 11.00 mmol) and the mixture heated at 85° C. for 12 hours. Solvents were evaporated and the residue thus obtained was purified over neutral alumina using a gradient of methanol in $CH_2Cl_2$ to give the product as an off white solid as a mixture of isomers. Yield: 3.0 g (75%).

MS (ES) MH⁺: 417 for $C_{20}H_{21}FN_4O_5$

¹H NMR (400 MHz-DMSO-D6) δ: 0.8 (t, 2H), 0.80 (d, 2H), 0.9 (t, 2H), 1.1 (t, 2H), 1.4 (m 1H), 2.35 (s, 3H), 2.9 (m, 1H), 3.0 (m, 1H), 3.5 (m, 2H), 3.6-3.7 (m, 1H), 3.9 (m, 1H), 4.0 (m, 1H), 7.1 (d, 1H), 11.5 (br, 2H).

Examples 105 and 106 were prepared from the indicated starting materials using a method similar to the one described for the synthesis of Example 103 and 104. The resulting 2 regioisomers were separated by chromatography.

Example 105

First Eluting Compound (2R,4R,4aS)-rel-11-fluoro-4-(methoxymethyl)-2,8-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

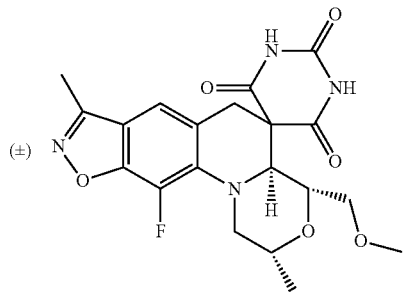

Starting material: 7-fluoro-6-[(2S,6S)-2-(methoxymethyl)-6-methylmorpholin-4-yl]-3-methyl-1,2-benzoxazole-5-carbaldehyde (Intermediate 503)

MS (ES) MH$^+$: 433 for $C_{20}H_{21}FN_4O_6$ $^1$H NMR (400 MHz, DMSO-$d_6$) δ: 1.1 (d, 3H), 2.5 (s, 3H), 2.9 (d, 1H), 3.05 (s, 3H), 3.1 (m, 2H), 3.3 (m, 1H), 3.4 (m, 1H), 3.8 (m, 2H), 4.0 (m, 2H), 7.2 (s, 6H), 11.0 (s, 1H), 11.5 (s, 1H).

Example 106

Second Eluting Compound (2S,4S,4aS)-rel-11-fluoro-2-(methoxymethyl)-4,8-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

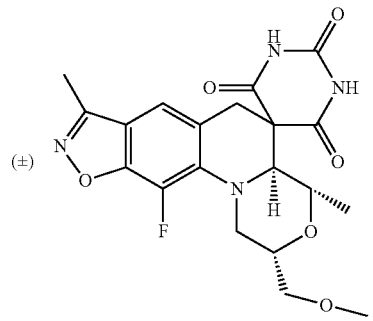

Starting material: 7-fluoro-6-[(2S,6S)-2-(methoxymethyl)-6-methylmorpholin-4-yl]-3-methyl-1,2-benzoxazole-5-carbaldehyde (Intermediate 503)

MS (ES) MH$^+$: 433 for $C_{20}H_{21}FN_4O_6$ $^1$H NMR (400 MHz, DMSO-$d_6$) δ: 0.9 (d, 3H), 2.5 (s, 3H), 3.0 (d, 1H), 3.25 (m, 1H), 3.3 (s, 3H), 3.3-3.4 (m, 2H), 3.5 (m, 1H), 3.7 (m, 1H), 3.8 (m, 1H), 3.9 (d, 1H), 4.1 (d, 1H), 7.2 (s, 6H), 11.4-11.8 (br, 2H).

Example 107

(2R,4S,4aS)-rel-11-chloro-2,4-dimethyl-8-(pyridyin-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione (trifluoroacetic acid salt)

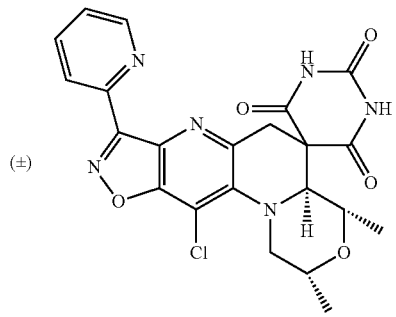

A mixture of 7-chloro-6-((2R,6S)-2,6-dimethylmorpholino)-3-(pyridin-2-yl)isoxazolo[4,5-b]pyridine-5-carbaldehyde (Intermediate 406, 0.165 g, 0.44 mmol) and barbituric acid (0.057 g, 0.44 mmol) in 10 ml IPA was heated to 80° C. for 2 days. The mixture was concentrated, and the residue was purified by chromatography on silica gel using 10% methanol (0.1% ammonium hydroxide) in dichloromethane to give 170 mg of product as a white solid. Further purification was achieved by reverse phase HPLC on a Waters XBridge C-18 column eluting with 20-90% water/acetonitrile with trifluoroacetic acid to give 25 mg of the title compound as the mono trifluoracetic acid salt.

MS (ES) MH$^+$: 483 for $C_{22}H_{19}ClN_6O_5$ (trifluoroacetic acid salt)

$^1$H NMR (300 MHz, DMSO-$d_6$) δ: 0.9 (d, 3H) 1.2 (br.s., 1H) 1.2 (d, 3H) 3.1 (dd, 1H) 3.3 (d, 1H) 3.5-3.7 (m, 1H) 3.9-4.0 (m, 1H) 4.4 (d, 1H) 5.7 (br.s., 1H) 7.6 (dd, 1H) 8.0 (t, 1H) 8.3 (d, 1H) 8.8 (d, 1H) 11.6 (s, 1H) 11.9 (s, 1H).

Examples 108 to 111 were prepared from the indicated starting materials using a method similar to the one described for the synthesis of Example 107:

Example 108

(2R,4S,4aS)-rel-11-chloro-2,4-dimethyl-8-(pyridyin-4-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione (trifluoroacetic acid salt)

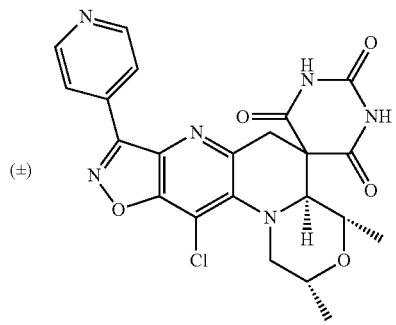

Starting material: 7-chloro-6-((2R,6S)-2,6-dimethylmorpholino)-3-(pyridin-4-yl)isoxazolo[4,5-b]pyridine-5-carbaldehyde (Intermediate 407).

MS (ES) MH+: 483 for C22H19ClN6O5

1H NMR (300 MHz, DMSO-d6) δ: 0.9 (d, 3H), 1.1 (d, 3H), 3.1 (m, 1H), 3.3 (d, 1H), 3.6 (dd, 3.7 (d, 1H), 4.0 (d, 2H), 4.4 (d, 1H), 8.3 (d, 2H), 8.8 (d, 2H), 11.6 (s, 1H), 12.0 (s, 1H).

Example 109

(2R,4S,4aS)-rel-11-chloro-2,4-dimethyl-8-(pyridyin-3-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione (trifluoroacetic acid salt)

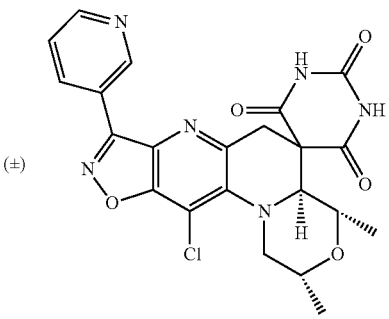

Starting material: 7-chloro-6-((2R,6S)-2,6-dimethylmorpholino)-3-(pyridin-3-yl)isoxazolo[4,5-b]pyridine-5-carbaldehyde (Intermediate 408).

MS (ES) MH+: 483 for C22H19ClN6O5

1H NMR (300 MHz, DMSO-d6) δ: 0.9 (d, 3H), 1.1 (d, 4H), 3.1 (dd, 1H), 3.3 (d, 1H), 3.6 (dd, 1H), 3.7 (d, 1H), 3.9-4.0 (m, 2H), 4.4 (d, 1H), 7.6 (dd, 2H), 8.6 (dt, 1H), 8.8 (dd, 1H), 9.4 (d, 1H), 11.6 (s, 1H), 11.9 (s, 1H).

Example 110

(2R,4S,4aS)-rel-11-chloro-2,4-dimethyl-8-(pyrazin-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione (trifluoroacetic acid salt)

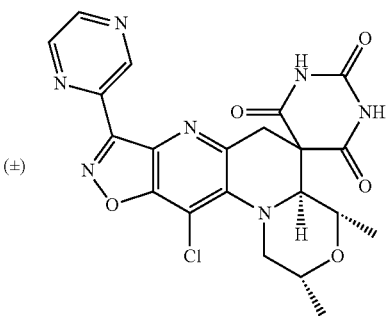

Starting material: 7-chloro-6-((2R,6S)-2,6-dimethylmorpholino)-3-(pyrazin-2-yl)isoxazolo[4,5-b]pyridine-5-carbaldehyde (Intermediate 409).

MS (ES) MH+: 484 for C21H18ClN7O5

1H NMR (300 MHz, DMSO-d6) δ: 0.9 (d, 3H), 1.1-1.2 (m, 3H), 3.1 (d, 1H), 3.3 (d, 1H), 3.6 (d, 1H), 3.7 (d, 1H), 3.9-4.0 (m, 2H), 4.4 (d, 1H), 8.8-8.9 (m, 2H), 9.5 (d, 1H), 11.6 (s, 1H), 11.9 (s, 1H).

Example 111

(2R,4S,4aS)-rel-11-chloro-2,4-dimethyl-8-(thiazol-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione

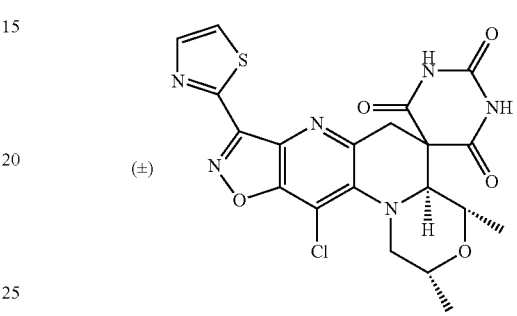

Starting material: 7-chloro-6-((2R,6S)-2,6-dimethylmorpholino)-3-(thiazol-2-yl)isoxazolo[4,5-b]pyridine-5-carbaldehyde (Intermediate 410).

MS (ES) MH+: 489 for C20H17ClN6O5S

1H NMR (300 MHz, DMSO-d6) δ: 0.9 (d, 3H), 1.1-0.2 (m, 4H), 3.1 (dd, 1H), 3.3 (d, 1H), 3.6 (dd, 1H), 3.7 (d, 1H), 3.9 (m, 1H), 4.0 (d, 1H), 4.4 (br.s, 1H), 8.1-8.2 (m, 1H), 11.6 (s, 1H), 11.9 (s, 1H).

The (2S,4R,4aR) and (2R,4S,4aS) enantiomers of Example 111 were separated by Supercritical Fluid Chromatography using a Chiralpak AD, 21×250 mm, 5μ column (elution with 25% MeOH, 75% CO2 at 60 ml/min, 40° C., and 100 bar with detection at 220 nm), providing Example 111(a) and Example 111(b):

Example 111(a)

First Eluting Compound (2S,4R,4aR)-11-chloro-2,4-dimethyl-8-(thiazol-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3H)-trione

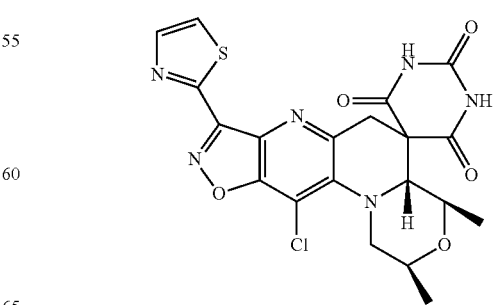

MS (ES) MH+: 489 for C20H17ClN6O5S

¹H NMR (300 MHz, DMSO-d₆) δ: 0.9 (d, 3H) 1.0 (m, 1H) 1.1 (d, 3H) 3.1 (dd, 1H) 3.5-3.6 (m, 1H) 3.7 (d, 1H) 3.9 (m, 1H) 4.0 (d, 1H) 4.4 (d, 1H) 8.1 (m, 2H) 11.6 (s, 1H) 11.9 (s, 1H).

[α]=+130 (c=0.1 in ethanol)

Example 111(b)

Second Eluting Compound (2R,4S,4aS)-11-chloro-2,4-dimethyl-8-(thiazol-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione

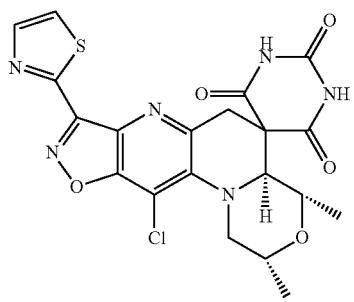

MS (ES) MH⁺: 489 for C₂₀H₁₇ClN₆O₅S

¹H NMR (300 MHz, DMSO-d₆) δ: 0.9 (d, 3H), 1.1 (d, 3H), 3.1 (dd, 1H), 3.5-3.6 (m, 2H), 3.6-3.7 (m, 1H), 3.9 (m, 1H), 4.0 (d, 1H), 4.4 (d, 1H), 8.1-8.2 (m, 2H), 11.6 (s, 1H), 11.9 (s, 1H).

[α]=−132 (c=0.1 in ethanol)

Example 112

(2R,4S,4aS)-rel-11-fluoro-2,4-dimethyl-8-(1-methyl-1H-imidazol-2-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

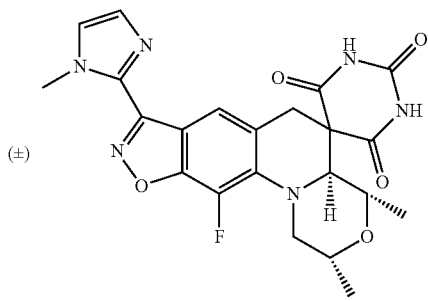

A solution of (2R,4S,4aR)-rel-11-fluoro-2,4-dimethyl-8-(1-methyl-1H-imidazol-2-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione (Example 68, 50 mg, 0.11 mmol) in ethanol (40 ml) was heated to reflux for 4 days. The solvent was removed and the residue was triturated with methanol. The resulting solid was filtered, washed with methanol, and dried to give 44 mg of product.

MS (ES) MH⁺: 469 for C₂₂H₂₁FN₆O₅

¹H NMR (300 MHz, DMSO-d₆) δ: 0.9 (d, 3H) 1.1 (d, 3H) 7.2 (s, 1H) 7.6 (s, 1H) 7.8 (s, 1H) 11.4 (s, 1H) 11.8 (s, 1H).

Examples 113 to 116 were prepared from the indicated starting materials using a method similar to the one described for the synthesis of Example 107:

Example 113

(2R,4S,4aS)-rel-11-Chloro-2,4-dimethyl-8-(4-methylthiazol-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione

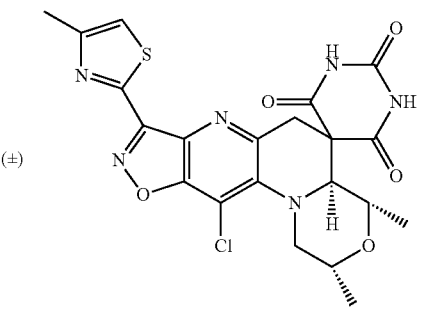

Starting material: 7-chloro-6-((2R,6S)-2,6-dimethylmorpholino)-3-(4-methylthiazol-2-yl)isoxazolo[4,5-b]pyridine-5-carbaldehyde (Intermediate 411).

MS (ES) MH⁺: 503 for C₂₁H₁₉ClN₆O₅S.01[Trifluoroacetic acid]

¹H NMR (300 MHz, MeOD) δ: 1.0 (d, 3H) 1.2 (br.s, 1H) 1.2 (d, 3H) 2.4-2.6 (m, 3H) 3.16 (dd, 1H) 3.3-3.4 (m, 1H) 3.5-3.6 (m, 1H) 3.7 (d, 1H) 4.0-4.1 (m, 2H) 4.6 (dd, 1H) 4.8 (s, 2H) 7.4 (s, 1H).

Example 114

(2R,4S,4aS)-rel-11-Chloro-2,4-dimethyl-8-(1-methyl-1H-imidazol-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione (trifluoroacetic acid salt)

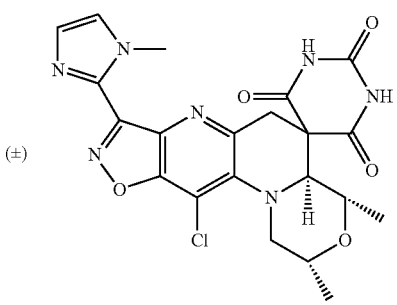

Starting material: 7-chloro-6-((2R,6S)-2,6-dimethylmorpholino)-3-(1-methyl-1H-imidazol-2-yl)isoxazolo[4,5-b]pyridine-5-carbaldehyde (Intermediate 412).

MS (ES) MH⁺: 486 for C₂₁H₂₀ClN₇O₅

$^1$H NMR (300 MHz, DMSO-d$_6$) δ: 0.8 (d, 3H), 1.0 (m, 3H), 1.8 (s, 1H), 3.0-3.1 (m, 1H), 3.1 (d, 2H), 3.5-3.7 (m, 2H), 3.8 (m, 1H), 3.8-4.1 (m, 3H), 4.0 (d, 1H), 4.4 (d, 1H), 7.1 (s, 1H), 7.4-7.5 (m, 1H).

Example 115

(2R,4S,4aS)-rel-11-chloro-2,4-dimethyl-8-(thiazol-5-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3H)-trione (trifluoroacetic acid salt)

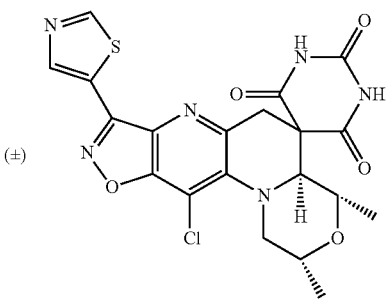

Starting material: 7-chloro-6-((2R,6S)-2,6-dimethylmorpholino)-3-(thiazol-5-yl)isoxazolo[4,5-b]pyridine-5-carbaldehyde (Intermediate 413).

MS (ES) MH$^+$: 489 for C$_{20}$H$_{17}$ClN$_6$O$_5$S $^1$H NMR (300 MHz, DMSO-d$_6$) δ: 0.9 (d, 3H), 1.0-1.2 (m, 3H), 3.1 (dd, 1H), 3.3 (d, 1H) 3.5-3.6 (m, 1H), 3.8 (m, 1H), 3.9-4.0 (m, 2H), 4.4 (d, 1H), 8.9-9.0 (m, 1H), 9.3-9.5 (m, 1H), 11.5-11.6 (m, 1H), 11.9 (s, 1H).

Example 116

(2R,4S,4aS)-rel-11-chloro-2,4-dimethyl-8-(2,4-dichlorothiazol-5-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione (trifluoroacetic acid salt)

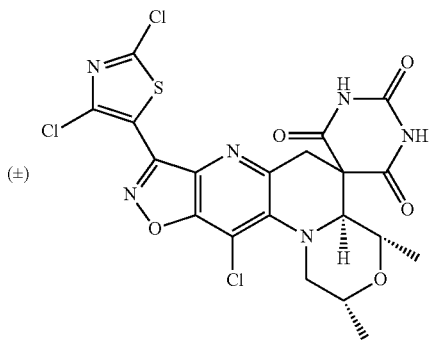

Starting material: 7-chloro-6-((2R,6S)-2,6-dimethylmorpholino)-3-(2,4-dichlorothiazol-5-yl)isoxazolo[4,5-b]pyridine-5-carbaldehyde (Intermediate 420).

MS (ES) MH$^+$: 557 for C$_{20}$H$_{15}$Cl$_3$N$_6$O$_5$S $^1$H NMR (300 MHz, DMSO-d$_6$) δ: 0.9 (d, 3H), 1.1 (d, 3H), 3.1 (m, 1H), 3.1 (dd, 1H), 3.5-3.7 (m, 2H), 3.9-4.0 (m, 2H), 4.4 (d, 1H), 11.6 (s, 1H), 11.9 (s, 1H).

Example 117

(2R,4S,4aS)-rel-11-Chloro-2,4-dimethyl-8-(2-methylthiazol-5-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3H)-trione

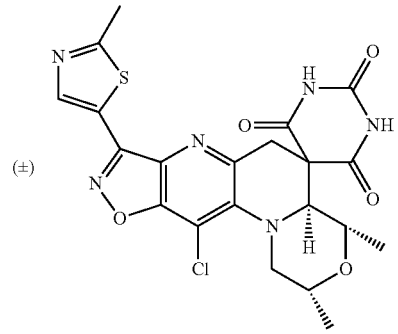

To isopropanol (20 ml) was added to 7-chloro-6-((2R,6S)-2,6-dimethylmorpholino)-3-(2-methylthiazol-5-yl)isoxazolo[4,5-b]pyridine-5-carbaldehyde (Intermediate 414, 0.26 g, 0.66 mmol) and barbituric acid (0.085 g, 0.66 mmol), and the mixture was heated to 80° C. for about 2 days. The mixture was concentrated, and crystallization of the crude mixture from methanol gave 45 mg of the title compound.

MS (ES) MH$^+$: 503 for C$_{21}$H$_{19}$ClN$_6$O$_5$S $^1$N NMR (300 MHz, DMSO-d$_6$) δ: 0.9 (d, 3H), 1.1 (d, 3H), 2.6-2.8 (m, 3H), 3.0-3.2 (m, 1H), 3.3 (m, 1H), 3.5-3.6 (m, 1H), 3.7 (d, 1H), 4.0 (d, 2H), 4.4 (d, 1H), 8.6 (s, 1H), 11.6 (br.s, 1H), 11.9 (br.s, 1H).

Examples 118 and 119 were prepared from the indicated starting materials using a method similar to the one described for the synthesis of Example 117:

Example 118

(2R,4S,4aS)-rel-11-chloro-2,4-dimethyl-8-(1-methyl-1H-1,2,4-triazol-5-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione

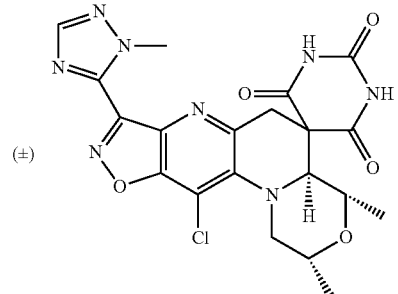

Starting material: 7-chloro-6-((2R,6S)-2,6-dimethylmorpholino)-3-(1-methyl-1H-1,2,4-triazol-5-yl)isoxazolo[4,5-b]pyridine-5-carbaldehyde (Intermediate 415).

MS (ES) MH⁺: 487 for $C_{20}H_{19}ClN_8O_5$

¹H NMR (300 MHz, DMSO-d₆) δ: 1.1 (d, 3H), 1.2 (d, 3H), 3.2 (t, 1H), 3.4-3.6 (m, 3H), 3.6-3.7 (m, 1H), 3.9 (m, 1H), 4.1 (d, 1H), 4.2 (s, 3H), 8.3 (s, 1H), 11.5 (s, 1H), 11.67 (s, 1H).

Example 119

(2R,4S,4aS)-rel-11-chloro-2,4-dimethyl-8-(2-bromothiazol-5-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione

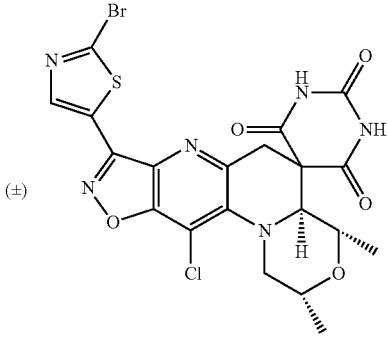

Starting material: 7-chloro-6-((2R,6S)-2,6-dimethylmorpholino)-3-(2-bromothiazol-5-yl)isoxazolo[4,5-b]pyridine-5-carbaldehyde (Intermediate 419).

MS (ES) MH⁺: 568 for $C_{20}H_{16}BrClN_6O_5S$

¹H NMR (300 MHz, chloroform-d) δ: 0.9 (d, 3H), 1.1 (d, 3H), 1.2 (d, 1H), 3.1 (m, 1H), 3.1 (d, 1H), 3.3 (s, 1H), 3.6 (dd, 1H), 3.7 (d, 1H), 3.9-4.0 (m, 2H), 4.4 (d, 1H), 8.6 (d, 1H).

Example 120

(2R,4S,4aS)-rel-11-chloro-2,4-dimethyl-8-(pyrazin-2-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

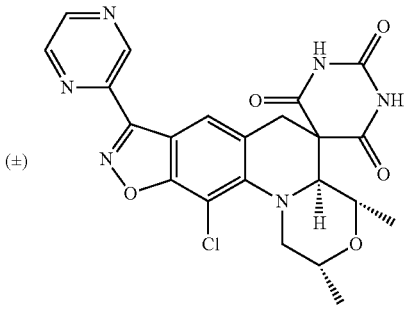

Isopropanol (10 ml) was added to 7-chloro-6-((2R,6S)-2,6-dimethylmorpholino)-3-(pyrazin-2-yl)benzo[d]isoxazole-5-carbaldehyde (Intermediate 472, 198 mg, 0.53 mmol) to give a yellow slurry. The pyrimidine-2,4,6(1H,3H,5H)-trione (barbituric acid) (68.0 mg, 0.53 mmol) was added and the yellow mixture was heated to 80° C. The resulting solution was stirred overnight. The resulting off-white suspension cooled to room temperature, then filtered. The filtercake was washed with MeOH/hexanes to give a white solid, 171 mg (67%).

MS (ES) MH⁺: 483 for $C_{22}H_{19}ClN_6O_5$

¹H NMR (300 MHz, DMSO-d₆) δ: 0.9 (d, 3H), 1.2 (d, 3H), 3.0-3.1 (m, 2H), 3.6-3.8 (m, 2H), 3.9-4.1 (m, 2H), 4.5 (d, 1H). 7.9 (s, 1H), 8.8-8.9 (m, 2H), 9.3 (s, 1H), 11.4 (br s, 1H), 11.8 (br s, 1H).

Example 121

4-((2R,4S,4aS)-rel-11-chloro-2,4-dimethyl-2',4',6'-trioxo-2,2',3',4,4a4',6,6'-octahydro-1H,1'H-spiro[isoxazolo[4,5-g][1,4]oxazino[4,3-a][1,5]naphthyridine-5,5'-pyrimidine]-8-yl)-2-fluorobenzonitrile

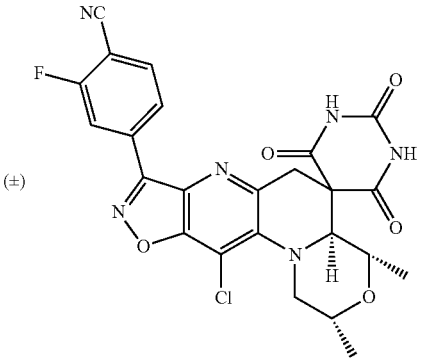

To isopropanol (20 ml) was added to 4-(7-chloro-6-((2R,6S)-2,6-dimethylmorpholino)-5-formylisoxazolo[4,5-b]pyridin-3-yl)-2-fluorobenzonitrile (Intermediate 416, 0.126 g, 0.30 mmol) and barbituric acid (0.039 g, 0.30 mmol). The mixture was heated to 80° C. for about 2 days. The mixture was concentrated, and the residue was purified by chromatography on silica using 20% acetone in n-hexane. The solids obtained were triturated with methanol gave 41 mg of product.

MS (ES) MH⁺: 525 for $C_{24}H_{18}ClFN_6O_5$

¹H NMR (300 MHz, DMSO-d₆) δ0.9 (d, 3H), 1.1 (d, 3H), 3.1 (dd, 1H), 3.3 (m, 1H), 3.6 (dd, 1H), 3.8 (d, 1H), 4.0 (d, 2H), 4.4 (m, 1H), 8.1 (t, 1H), 8.3-8.4 (m, 2H), 11.6 (s, 1H), 11.9 (s, 1H).

Examples 122 and 123 were prepared from the indicated starting materials using a method similar to the one described for the synthesis of Example 121:

Example 122

(2R,4S,4aS)-rel-11-Chloro-2,4-dimethyl-8-(5-methylthiazol-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione

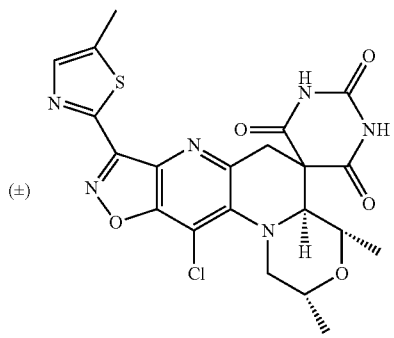

Starting material: 7-chloro-6-((2R,6S)-2,6-dimethylmorpholino)-3-(5-methylthiazol-2-yl)isoxazolo[4,5-b]pyridine-5-carbaldehyde (Intermediate 418).

MS (ES) MH⁺: 503 for $C_{21}H_{19}ClN_6O_5S$
¹H NMR (300 MHz, DMSO-d₆) δ: 1.1 (d, 3H), 1.2 (d, 3H), 2.6 (s, 3H), 3.1-3.3 (m, 2H), 3.1-3.7 (m, 1H), 3.8-4.0 (m, 1H), 4.1 (dd, 1H), 7.9 (s, 1H), 11.5 (s, 1H), 11.6 (s, 1H).

Example 123

5-((2R,4S,4aS)-rel-11-chloro-2,4-dimethyl-2',4',6'-trioxo-2,2',3',4,4a4',6,6'-octahydro-1H,1'H-spiro[isoxazolo[4,5-g][1,4]oxazino[4,3-a][1,5]naphthyridine-5,5'-pyrimidine]-8-yl)picolinamide

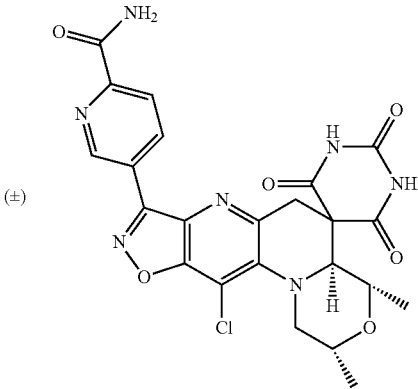

Starting material: 5-(7-chloro-6-((2R,6S)-2,6-dimethylmorpholino)-5-formylisoxazolo[4,5-b]pyridin-3-yl)picolinonitrile (Intermediate 417).

MS (ES) MH⁺: 526 for $C_{23}H_{20}ClN_7O_6$
¹H NMR (300 MHz, DMSO-d₆) δ: 0.9 (d, 3H), 1.1 (d, 3H), 3.1 (dd, 1H), 3.3-3.4 (m, 1H), 3.6 (dd, 1H), 3.7 (d, 1H), 4.0 (d, 1H), 4.4 (d, 1H), 7.8 (s, 1H), 8.1-8.3 (m, 2H), 8.8 (dd, 1H), 9.4 (d, 1H), 11.6 (s, 1H), 11.9 (s, 1H).

Example 124

(2R,4S,4aS)-rel-11-Chloro-2,4,8-trimethyl-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione

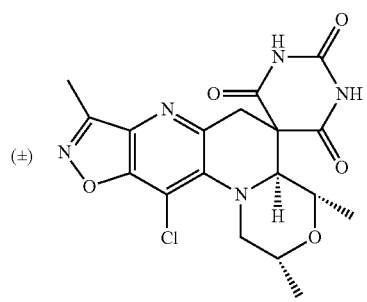

Isopropanol (12 ml) was added to 7-chloro-6-((2R,6S)-2,6-dimethylmorpholino)-3-methylisoxazolo[4,5-b]pyridine-5-carbaldehyde (Intermediate 471, 165 mg, 0.53 mmol) to give a yellow slurry; pyrimidine-2,4,6(1H,3H,5H)-trione (barbituric acid) (68.2 mg, 0.53 mmol) was added, and the mixture was heated to 80° C. After about 5 days, the mixture was concentrated. The crude was purified by chromatography using 10-50% EtOAc/CH₂Cl₂ to give 95 mg yellow solid which was subsequently recrystallized from EtOAc/hexanes. A total of 57 mg (19%) of the title product was obtained as a yellow solid.

MS (ES) MH⁺: 420 for $C_{18}H_{18}ClN_5O_5$
¹H NMR (300 MHz, DMSO-d₆) δ: 0.9 (d, 3H), 1.2 (d, 3H), 2.5 (s, 3H), 3.1 (m, 1H), 3.3 (m, under water peak, 1H), 3.5-3.7 (m 2H), 3.9-4.1 (m, 2H), 4.4 (dd, 1H), 11.6 (br s, 1H), 11.7 (br s, 1H).

Example 125

(2R,4S,4aS)-rel-11-Chloro-N,2,4-trimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide

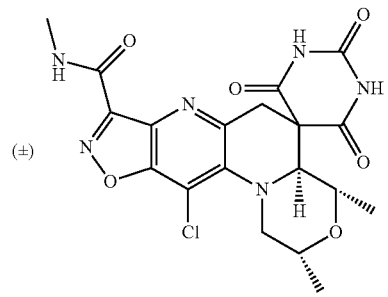

7-Chloro-6-((2R,6S)-2,6-dimethylmorpholino)-5-formyl-N-methylisoxazolo[4,5-b]pyridine-3-carboxamide (Intermediate 473, 68 mg, 0.19 mmol) was dissolved in isopropanol to give a yellow solution, and pyrimidine-2,4,6(1H,3H,5H)-trione (24.69 mg, 0.19 mmol) was added to give a bright yellow slurry, which was heated to 80° C. for three days. The resulting dark orange suspension was concentrated, then purified by chromatography on SiO₂ using 20-60% EtOAc/CH₂Cl₂. A total of 32 mg (36%) of an off-white solid was obtained.

MS (ES) MH⁺: 463 for $C_{19}H_{19}ClN_6O_6$
¹H NMR (300 MHz, DMSO-d₆) δ: 0.9 (d, 3H), 1.2 (d, 3H), 2.8 (d, 3H), 3.1 (m, 1H), 3.3 (m under water peak, 1H), 3.5-3.7 (m, 2H), 3.9-4.1 (m, 2H), 4.4 (d, 1H). 8.8 (m, 1H), 11.6 (br s, 1H), 11.9 (br s, 1H).

Examples 126 to 133 were prepared from the indicated starting material and barbituric acid using a method similar to the one described for the syntheses of Example 125:

Example 126

(2R,4S,4aS)-rel-11-chloro-N-ethyl-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide

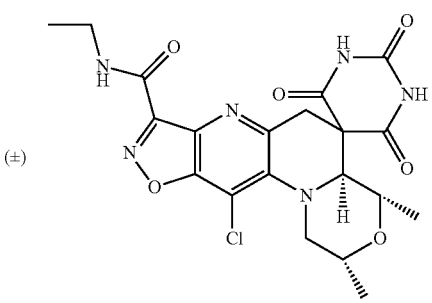

Starting material: 7-chloro-6-((2R,6S)-2,6-dimethylmorpholino)-N-ethyl-5-formylisoxazolo[4,5-b]pyridine-3-carboxamide (Intermediate 474).

MS (ES) MH+: 477 for $C_{20}H_{21}ClN_6O_6$
1H NMR (300 MHz, DMSO-d6) δ: 0.9 (d, 3H), 1.1-1.2 (overlapping m, 6H), 3.1 (m, 1H), 3.3 (m, under water peak, 3H), 3.5-3.7 (m, 2H), 3.9-4.1 (m, 2H), 4.4 (d, 1H). 8.8 (br t, 1H), 11.6 (br s, 1H), 11.9 (br s, 1H).

Example 127

(2R,4S,4aS)-rel-Chloro-N-isopropyl-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide

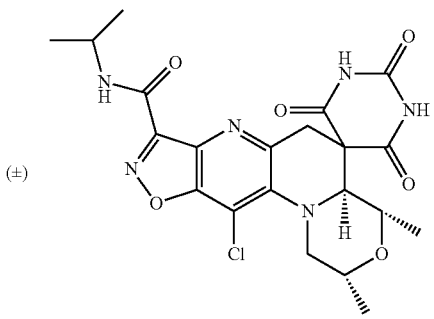

Starting material: 7-chloro-6-((2R,6S)-2,6-dimethylmorpholino)-5-formyl-N-isopropylisoxazolo[4,5-b]pyridine-3-carboxamide (Intermediate 475).
MS (ES) MH+: 491 for $C_{21}H_{23}ClN_6O_6$
1H NMR (300 MHz, DMSO-d6) δ: 0.9 (d, 3H), 1.1-1.2 (overlapping m, 9H), 3.1 (m, 1H), 3.3 (m, under water peak, 1H), 3.6 (m, 1H), 3.7 (d, 1H), 3.9 (m, 1H), 4.0 (d, 1H), 4.1 (m, 1H), 4.4 (d, 1H). 8.8 (d, 1H), 11.6 (br s, 1H), 11.9 (br s, 1H).

Example 128

(2R,4S,4aS)-rel-N-tert-butyl-11-chloro-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide

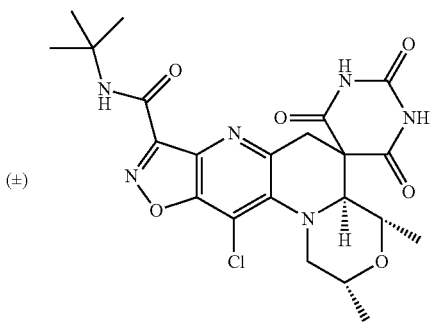

Starting material: N-tert-butyl-7-chloro-6-((2R,6S)-2,6-dimethylmorpholino)-5-formylisoxazolo[4,5-b]pyridine-3-carboxamide (Intermediate 476).
MS (ES) MH+: 505 for $C_{22}H_{25}ClN_6O_6$
1H NMR (300 MHz, DMSO-d6) δ: 0.9 (d, 3H), 1.2 (d, 3H), 1.4 (s, 9H), 3.1 (m, 1H), 3.3 (m under water peak, 1H), 3.6 (m, 1H), 3.7 (d, 1H), 3.9 (m, 1H), 4.0 (d, 1H), 4.4 (d, 1H), 8.4 (s, 1H), 11.6 (br s, 1H), 11.9 (br s, 1H).

Example 129

(2R,4S,4aS)-rel-11-Chloro-2,4-dimethyl-N-neopentyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide

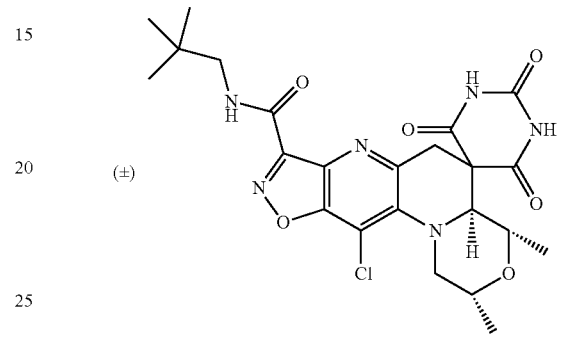

Starting material: 7-chloro-6-((2R,6S)-2,6-dimethylmorpholino)-5-formyl-N-neopentylisoxazolo[4,5-b]pyridine-3-carboxamide (Intermediate 477).
MS (ES) MH+: 519 for $C_{23}H_{27}ClN_6O_6$
1H NMR (300 MHz, DMSO-d6) δ: 0.9-1.0 (overlapping m, 12H), 1.2 (d, 3H), 3.1-3.2 (overlapping m, 3H), 3.3 (m under water peak, 1H), 3.4-3.7 (m, 2H), 3.9-4.1 (m, 2H), 4.4 (m, 1H). 8.8 (t, 1H), 11.6 (br s, 1H), 11.9 (br s, 1H).

Example 130

(2R,4S,4aS)-rel-11-Chloro-8-(3,3-difluoroazetidine-1-carbonyl)-2,4-dimethyl-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione

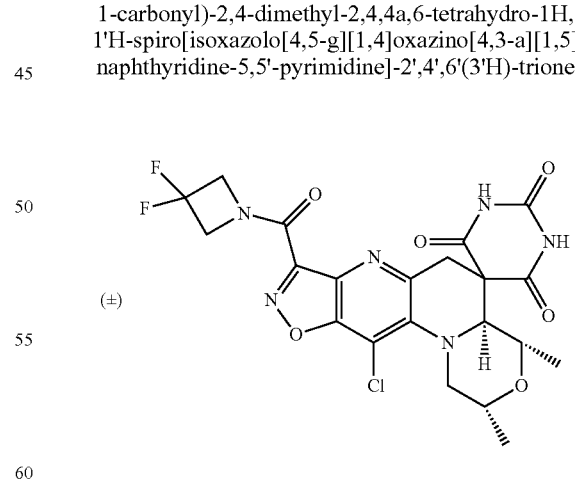

Starting material: 7-chloro-3-(3,3-difluoroazetidine-1-carbonyl)-6-((2R,6S)-2,6-dimethylmorpholino)isoxazolo[4,5-b]pyridine-5-carbaldehyde (Intermediate 478).
MS (ES) MH+: 525 for $C_{21}H_{19}ClF_2N_6O_6$
1H NMR (300 MHz, DMSO-d6) δ: 0.9 (d, 3H), 1.2 (d, 3H), 3.1 (m, 1H), 3.3 (m under water peak, 1H), 3.6 (m, 1H), 3.7 (d, 1H), 3.9 (m, 1H), 4.0 (d, 1H), 4.4 (d, 1H). 4.6 (t, 2H), 4.8 (t, 2H), 11.6 (br s, 1H), 11.9 (br s, 1H).

Example 131

(2R,4S,4aS)-rel-N-benzyl-11-chloro-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide

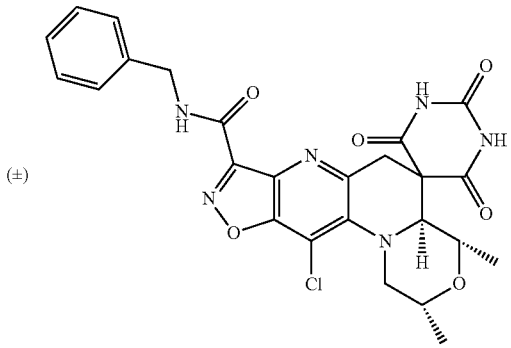

(±)

Starting material: N-benzyl-7-chloro-6-((2R,6S)-2,6-dimethylmorpholino)-5-formylisoxazolo[4,5-b]pyridine-3-carboxamide (Intermediate 479).

MS (ES) MH$^+$: 539 for $C_{25}H_{23}ClN_6O_6$ $^1$H NMR (300 MHz, DMSO-d$_6$) δ: 0.9 (d, 3H), 1.2 (d, 3H), 3.1 (m, 1H), 3.3 (m under water peak, 1H), 3.5-3.7 (m, 2H), 3.9-4.1 (m, 2H), 4.4-4.6 (m, 3H), 7.2-7.4 (m, 5H), 9.4 (t, 1H), 11.6 (br s, 1H), 11.9 (br s, 1H).

Example 132

(2R,4S,4aS)-rel-11-chloro-N-(4-cyanobenzyl)-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide

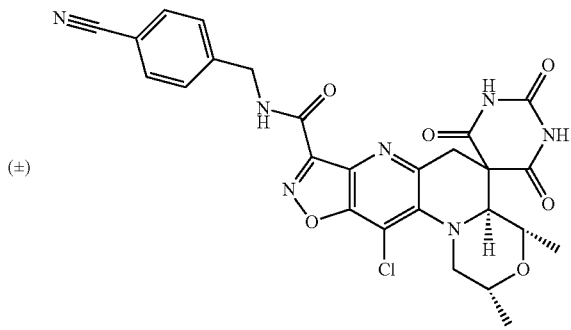

(±)

Starting material: 7-chloro-N-(4-cyanobenzyl)-6-((2R,6S)-2,6-dimethylmorpholino)-5-formylisoxazolo[4,5-b]pyridine-3-carboxamide (Intermediate 480).

MS (ES) MH$^+$: 564 for $C_{26}H_{22}ClN_7O_6$ $^1$H NMR (300 MHz, DMSO-d$_6$) δ: 0.9 (d, 3H), 1.2 (d, 3H), 3.1 (m, 1H), 3.3 (m under water peak, 1H), 3.6-3.7 (m, 2H), 3.9 (m, 1H), 4.0 (d, 1H), 4.4 (d, 1H), 4.6 (d, 2H), 7.6 (d, 2H), 7.8 (d, 2H), 9.5 (t, 1H), 11.6 (br s, 1H), 11.9 (br s, 1H).

Example 133

(2R,4S,4aS)-rel-11-chloro-N-(3-cyanobenzyl)-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide

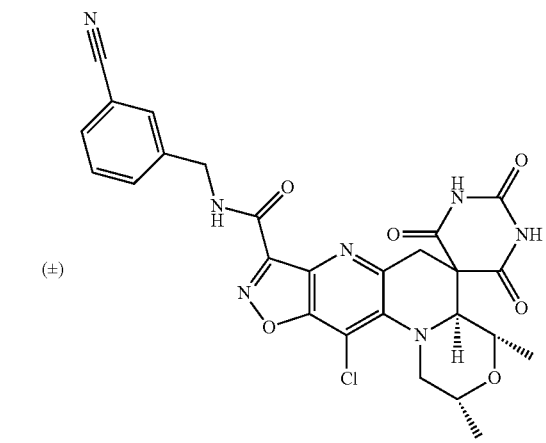

(±)

Starting material: 7-chloro-N-(3-cyanobenzyl)-6-((2R,6S)-2,6-dimethylmorpholino)-5-formylisoxazolo[4,5-b]pyridine-3-carboxamide (Intermediate 481).

MS (ES) MH$^+$: 564 for $C_{26}H_{22}ClN_7O_6$ $^1$H NMR (300 MHz, DMSO-d$_6$) δ: 0.9 (d, 3H), 1.2 (d, 3H), 3.1 (m, 1H), 3.3 (m under peak, 1H), 3.5-3.7 (m, 2H), 3.9 (m, 1H), 4.0 (d, 1H), 4.4 (d, 1H), 4.6 (s, 2H), 7.6 (t, 1H), 7.7-7.8 (m, 2H), 7.8 (s, 1H), 8.5 (t, 1H), 11.6 (br s, 1H), 11.9 (br s, 1H).

Example 134

(2R,4S,4aS)-rel-ethyl 11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxylate

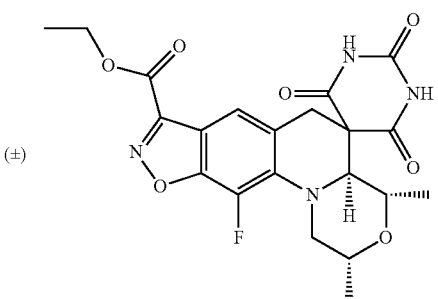

(±)

Ethyl 6-((2R,6S)-2,6-dimethylmorpholino)-7-fluoro-5-formylbenzo[d]isoxazole-3-carboxylate (Intermediate 439, 350 mg, 1.00 mmol) and barbituric acid (141 mg, 1.10 mmol) were heated to reflux in ethanol (45 ml) for 64 hours. The reaction was concentrated. The residue was dissolved in DCM, absorbed onto silica and purified by silica gel column chromatography using a gradient of DCM to ethyl acetate, to give the title compound (412 mg, 76%) as a racemic mixture.

MS (ES) MH$^+$: 461 for $C_{21}H_{21}FN_4O_7$ $^1$H NMR (300 MHz, DMSO-d$_6$) δ ppm 0.89 (d, 3H) 1.04-1.25 (m, 6H) 2.93 (d, 1H) 3.13 (t, 1H) 3.60-3.71 (m, 1H) 3.72-3.87 (m, 2H) 3.97 (d, 1H) 4.12 (d, 1H) 4.44 (q, 2H) 7.43 (s, 1H) 11.49 (br. s., 1H) 11.86 (br. s., 1H)

Examples 135 to 140 were prepared from the indicated starting material and barbituric acid using a method similar to the one described for the synthesis of Example 134. The compounds were purified either by silica gel column chromatography using a gradient of DCM to ethyl acetate or by reverse phase HPLC using a gradient of CH$_3$CN in water with 0.1% TFA.

Example 135

(2R,4S,4aS)-rel-11-fluoro-2,4-dimethyl-8-(morpholine-4-carbonyl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

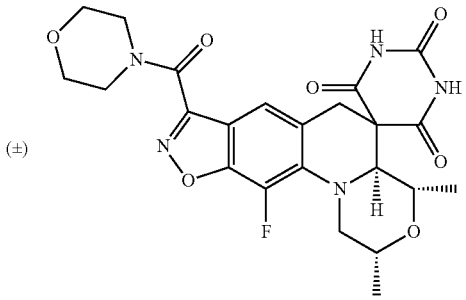

Starting material: 6-((2R,6S)-2,6-dimethylmorpholino)-7-fluoro-3-(morpholine-4-carbonyl)benzo[d]isoxazole-5-carbaldehyde (Intermediate 440).

MS (ES) MH$^+$: 502 for $C_{23}H_{24}FN_5O_7$ $^1$H NMR (300 MHz, DMSO-d$_6$) δ ppm 0.9 (d, 3H), 1.15 (d, 3H), 2.9 (d, 1H), 3.1 (t, 1H), 3.6-3.8 (m, 10H), 3.7-3.9 (m, 1H), 4.0 (d, 1H), 4.12 (d, 1H), 7.3 (s, 1H), 11.5 (br. s., 1H), 11.9 (br. s., 1H).

Example 136

(2R,4S,4aS)-rel-11-fluoro-N,N,2,4-tetramethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide

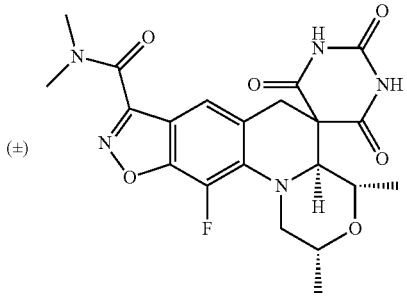

Starting material: 6-((2R,6S)-2,6-dimethylmorpholino)-7-fluoro-5-formyl-N,N-dimethylbenzo[d]isoxazole-3-carboxamide (Intermediate 470).

MS (ES) MH$^+$: 460 for $C_{21}H_{22}FN_5O_6$ $^1$H NMR (300 MHz, DMSO-d$_6$) δ ppm 0.9 (d, 3H), 1.1 (d, 3H), 2.9 (d, 1H), 3.1 (d, 7H), 3.6-3.7 (m, 2H), 3.7-3.9 (m, 1H), 4.0 (d, 1H), 4.1 (d, 1H), 7.2 (s, 1H), 11.5 (br. s., 1H), 11.9 (br. s., 1H).

Example 137

(2R,4S,4aS)-rel-11-fluoro-N-methoxy-N,2,4-trimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide

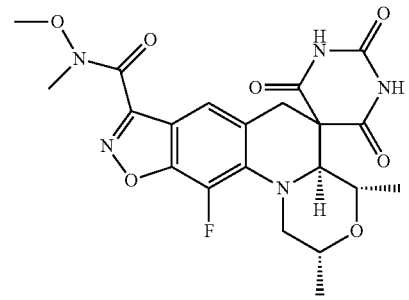

Starting material: 6-((2R,6S)-2,6-dimethylmorpholino)-7-fluoro-5-formyl-N-methoxy-N-methylbenzo[d]isoxazole-3-carboxamide (Intermediate 441)

MS (ES) MH$^+$: 476 for $C_{21}H_{22}FN_5O_7$ $^1$H NMR (300 MHz, DMSO-d$_6$) δ ppm 0.9 (d, 3H), 1.2 (d, 3H), 2.9 (d, 1H), 3.1 (t, 1H), 3.4 (br. s., 3H), 3.6-3.9 (m, 6H), 4.0 (d, 1H), 4.1 (d, 1H), 7.3 (s, 1H), 11.5 (s, 1H), 11.9 (s, 1H).

Example 138

(2R,4S,4aS)-rel-N-ethyl-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide

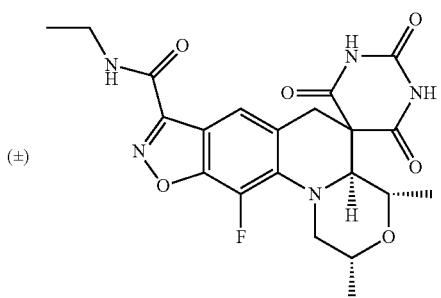

Starting material: 6-((2R,6S)-2,6-dimethylmorpholino)-N-ethyl-7-fluoro-5-formylbenzo[d]isoxazole-3-carboxamide, (Intermediate 442)

MS (ES) MH$^+$: 460 for $C_{21}H_{22}FN_5O_6$ $^1$H NMR (300 MHz, DMSO-d$_6$) δ ppm 0.9 (d, 3H), 1.1-1.2 (m, 6H), 2.9 (d, 1H), 3.1 (t, 1H), 3.3-3.3 (m, 2H), 3.6-3.9 (m, 3H), 4.0 (d, 1H), 4.1 (d, 1H), 7.4 (s, 1H), 9.0 (t, 1H), 11.5 (s, 1H), 11.9 (s, 1H).

Example 139

(2R,4S,4aS)-rel-N-ethyl-11-fluoro-N,2,4-trimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide

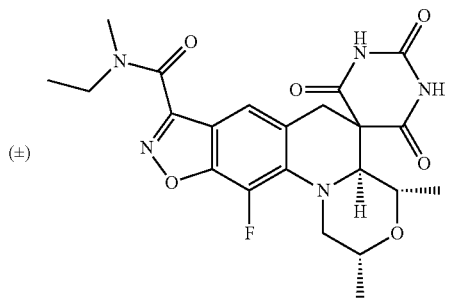

(±)

Starting Material: 6-((2R,6S)-2,6-dimethylmorpholino)-N-ethyl-7-fluoro-5-formyl-N-methylbenzo[d]isoxazole-3-carboxamide (Intermediate 443)

MS (ES) MH+: 474 for $C_{22}H_{24}FN_5O_6$ $^1$H NMR (300 MHz, DMSO-d$_6$) δ ppm 0.9 (d, 3H), 1.1-1.2 (m, 6H), 2.9 (d, 1H), 3.1 (d, 3H), 3.15 (d, 1H), 3.4-3.5 (m, 1H), 3.5 (d, 1H), 3.6-3.7 (m, 2H), 3.7-3.9 (m, 1H), 3.9 (d, 1H), 4.1 (d, 1H), 7.2 (d, 1H), 11.5 (br. s., 1H), 11.9 (br. s., 1H).

Example 140

(2R,4S,4aS)-rel-11-fluoro-N,2,4-trimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide

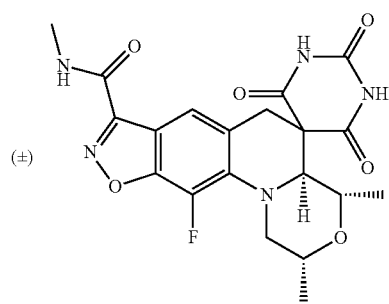

(±)

Starting Material: 6-((2R,6S)-2,6-dimethylmorpholino)-7-fluoro-5-formyl-N-methylbenzo[d]isoxazole-3-carboxamide (Intermediate 444)

MS (ES) MH+: 446 for $C_{20}H_{20}FN_5O_6$ $^1$H NMR (300 MHz, DMSO-d$_6$) δ ppm 0.9 (d, 3H), 1.1 (d, 3H), 2.8 (d, 3H), 2.9 (d, 1H), 3.1 (t, 1H), 3.6-3.9 (m, 3H), 3.95 (d, 1H), 4.1 (d, 1H), 7.4 (s, 1H), 8.8-9.0 (m, 1H), 11.5 (br. s., 1H), 11.8 (br. s., 1H).

In an alternate route, the (2R,4S,4aS) enantiomer of Example 140 was synthesized via a chiral synthesis similar to the one described for the synthesis of Example 95(a), using barbituric acid and the indicated starting material, providing Example 140(a):

Example 140(a)

Chiral Synthesis (2R,4S,4aS)-11-fluoro-N,2,4-trimethyl-2',4',6'-trioxo-2,2',3',4,4a,6,6'-octahydro-1H,1'H-spiro[isoxazolo[4,5-g][1,4]oxazino[4,3-a]quinoline-5,5'-pyrimidine]-8-carboxamide

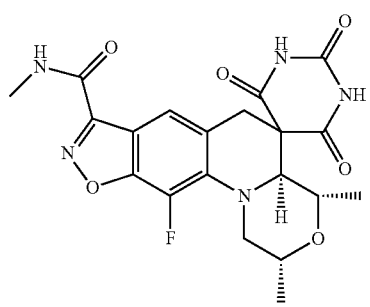

Starting material: 6-((2R,6R)-2,6-dimethylmorpholino)-7-fluoro-5-formyl-N-methylbenzo[d]isoxazole-3-carboxamide (Intermediate 247; purification by reverse phase HPLC using a gradient of CH$_3$CN in water with 0.1% TFA.

MS (ES) MH+: 446 for $C_{20}H_{20}FN_5O_6$ $^1$H NMR (300 MHz, DMSO-d$_6$) δ ppm 0.9 (d, 3H), 1.2 (d, 3H), 2.8 (d, 3H), 2.9 (d, 1H), 3.1 (t, 1H), 3.6-3.9 (m, 4H), 4.0 (d, 1H), 4.1 (d, 1H), 7.5 (s, 1H), 8.9 (d, 1H), 11.5 (s, 1H), 11.9 (s, 1H).

>98% ee by chiral HPLC; [α]=−263 (c=0.1 in MeOH)

Examples 141 and 142 were prepared from the indicated starting material and barbituric acid using a method similar to the one described for the synthesis of Example 134. The compounds were purified either by silica gel column chromatography using a gradient of DCM to ethyl acetate or by reverse phase HPLC using a gradient of CH$_3$CN in water with 0.1% TFA.

Example 141

(2R,4S,4aS)-rel-11-fluoro-2,4-dimethyl-8-(4-methyl-3-oxopiperazine-1-carbonyl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

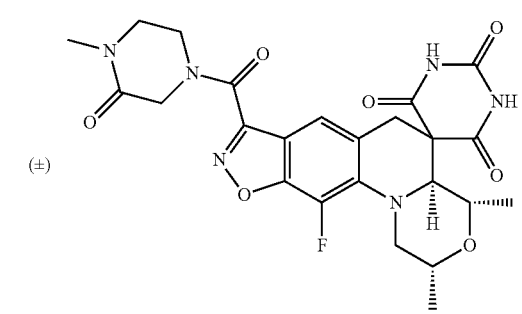

(±)

Starting Material: 6-((2R,6S)-2,6-dimethylmorpholino)-7-fluoro-3-(4-methyl-3-oxopiperazine-1-carbonyl)benzo[d]isoxazole-5-carbaldehyde (Intermediate 445)

MS (ES) MH+: 529 for $C_{24}H_{25}FN_6O_7$

¹H NMR (300 MHz, DMSO-d₆) δ ppm 0.8 (d, 3H), 1.1 (d, 3H), 2.8 (d, 4H), 3.1 (t, 1H), 3.3-3.4 (m, 2H), 3.7 (d, 2H), 3.9 (d, 3H), 4.0 (d, 1H), 4.1-4.4 (m, 2H), 7.2-7.3 (m, 1H), 11.5 (br. s., 1H, 11.8 (s, 1H).

Example 142

(2R,4S,4aS)-rel-11-fluoro-2,4-dimethyl-2',4',6'-trioxo-2,2',3',4,4a,4',6,6'-octahydro-¹H,1'H-spiro[isoxazolo[4,5-g][1,4]oxazino[4,3-a]quinoline-5,5'-pyrimidine]-8-carboxamide

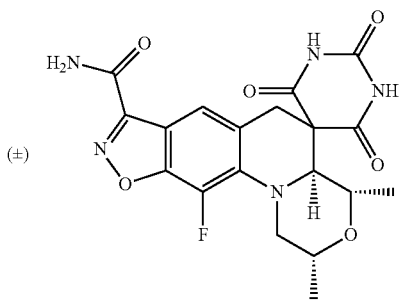

Starting material: 6-((2R,6S)-2,6-dimethylmorpholino)-7-fluoro-5-formylbenzo[d]isoxazole-3-carboxamide (Intermediate 447)

MS (ES) MH⁺: 432 for $C_{19}H_{18}FN_5O_6$

¹H NMR (300 MHz, DMSO-d₆) δ ppm 0.9 (d, 3H), 1.1-1.3 (m, 3H), 2.9 (d, 1H), 3.2 m, 1H), 3.6-3.9 (m, 3H), 3.9-4.2 (m, 2H), 7.5 (s, 1H), 8.0 (s, 1H), 8.3 (s, 1H), 11.5 (br. s., 1H), 11.8 (br. s., 1H).

Using an alternate route, the (2R,4S,4aS) enantiomer of Example 142 was also obtained via a chiral synthesis similar to the one described for the synthesis of Example 95(a), using barbituric acid and the indicated starting material:

Example 142(a)

(2R,4S,4aS)-11-fluoro-2,4-diethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide

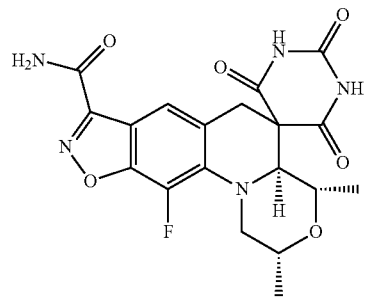

Starting material: 6-((2R,6R)-2,6-dimethylmorpholino)-7-fluoro-5-formylbenzo[d]isoxazole-3-carboxamide (Intermediate 469); purification by reverse phase HPLC using a gradient of CH₃CN in water with 0.1% TFA.

MS (ES) MH⁺: 432 for $C_{19}H_{18}FN_5O_6$

¹H NMR (300 MHz, DMSO-d₆) δ ppm 0.8 (d, 3H), 1.1 (d, 3H), 2.8 (d, 1H), 2.98-3.1 (m, 1H), 3.5-3.8 (m, 3H), 3.9 (d, 1H), 4.0 (d, 1H), 7.4 (s, 1H), 7.9 (s, 1H), 8.3 (s, 1H).

[α]=−204 (c=0.1 in MeOH)

Examples 143 to 147 were prepared from the indicated starting material and barbituric acid using a method similar to the one described for the synthesis of Example 134. The compounds were purified either by silica gel column chromatography using a gradient of DCM to ethyl acetate or by reverse phase HPLC using a gradient of CH₃CN in water with 0.1% TFA.

Example 143

(2R,4S,4aS)-rel-11-fluoro-N-(2-methoxyethyl)-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide

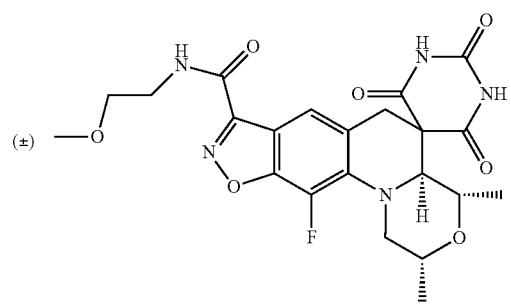

Starting material: 6-((2R,6S)-2,6-dimethylmorpholino)-7-fluoro-5-formyl-N-(2-methoxyethyl)benzo[d]isoxazole-3-carboxamide (Intermediate 448)

MS (ES) MH⁺: 490 for $C_{22}H_{24}FN_5O_7$

¹H NMR (300 MHz, DMSO-d₆) δ ppm 0.9 (d, 3H), 1.1 (d, 3H), 2.9 (d, 1H), 3.1 (t, 1H), 3.3 (s, 3H), 3.5 (br. s., 4H), 3.6-3.9 (m, 3H), 4.0 (d, 1H), 4.1 (d, 1H), 7.4 (s, 1H), 8.9 (br. s., 1H), 11.5 (br. s., 1H), 11.8 (br. s., 1H).

Example 144

(2R,4S,4aS)-rel-N-tert-butyl-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide

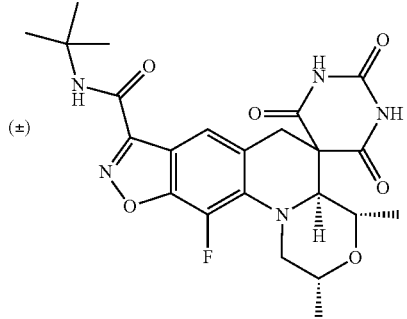

Starting material: N-tert-butyl-6-((2R,6S)-2,6-dimethylmorpholino)-7-fluoro-5-formylbenzo[d]isoxazole-3-carboxamide (Intermediate 449)

MS (ES) MH$^+$: 488 for $C_{23}H_{26}FN_5O_6$ $^1$H NMR (300 MHz, DMSO-d$_6$) δ ppm 0.9 (d, 3H), 1.1 (d, 3H), 1.4 (s, 9H), 2.9 (d, J=1H), 3.1 (t, 1H), 3.6-3.9 (m, 3H), 4.0 (d, 1H), 4.1 (d, 1H), 7.4 (s, 1H), 8.3 (s, 1H), 11.3-12.0 (m, 2H).

Example 145

(2R,4S,4aS)-rel-8-[(1,1-dioxidothiomorpholin-4-yl)carbonyl]-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione

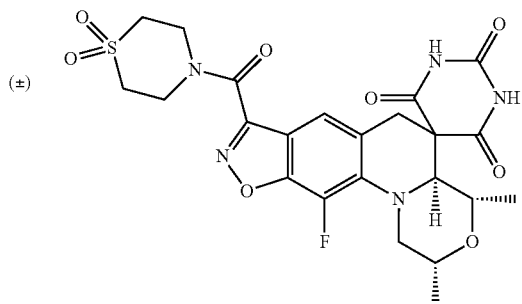

Starting material: 6-[(2R,6S)-2,6-dimethylmorpholin-4-yl]-3-[(1,1-dioxidothiomorpholin-4-yl)carbonyl]-7-fluoro-1,2-benzisoxazole-5-carbaldehyde (Intermediate 450)

MS (ES) MH$^+$: 550 for $C_{23}H_{24}FN_5O_8S$ $^1$H NMR (300 MHz, DMSO-d$_6$) δ ppm 0.8 (d, 3H), 1.1 (d, 3H), 2.81-2.9 (m, 2H), 2.9-3.1 (m, 2H), 3.3-3.4 (m, 2H), 3.5-3.7 (m, 2H), 3.7-3.8 (m, 1H), 3.0 (d, 1H), 4.0-4.2 (m, 5H), 7.3 (s, 1H), 11.2-12.0 (m, 1H).

Example 146

(2R,4S,4aS)-rel-11-fluoro-2,4-dimethyl-2',4',6'-trioxo-N-(tetrahydro-2H-pyran-4-yl)-2,2',3',4,4a,4',6,6'-octahydro-1H,1'H-spiro[isoxazolo[4,5-g][1,4]oxazino[4,3-a]quinoline-5,5'-pyrimidine]-8-carboxamide

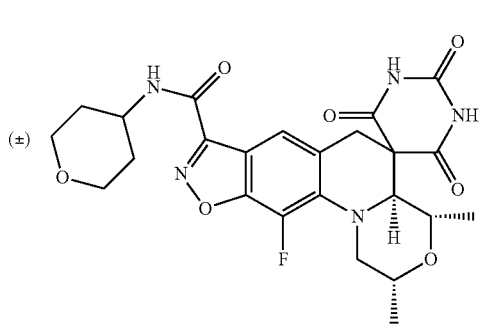

Starting material: 6-((2R,6S)-2,6-dimethylmorpholino)-7-fluoro-5-formyl-N-(tetrahydro-2H-pyran-4-yl)benzo[d]isoxazole-3-carboxamide (Intermediate 451)

MS (ES) MH$^+$: 516 for $C_{24}H_{26}FN_5O_7$ $^1$H NMR (300 MHz, DMSO-d$_6$) δ ppm 0.9 (d, 3H), 1.1 (d, 3H), 1.5-1.8 (m, 4H), 2.9 (d, 1H), 3.1 (t, 1H), 3.4-3.4 (m, 2H), 3.6-4.2 (m, 8H), 7.4 (s, 1H), 8.9 (d, 1H), 11.6 (br. s., 2H).

Example 147

(2R,4S,4aS)-rel-11-fluoro-N-isopropyl-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide

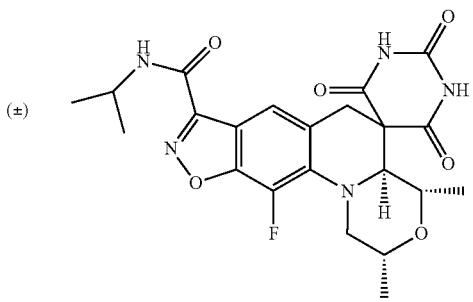

Starting material: 6-((2R,6S)-2,6-dimethylmorpholino)-7-fluoro-5-formyl-N-isopropylbenzo[d]isoxazole-3-carboxamide (Intermediate 452)

MS (ES) MH$^+$: 474 for $C_{22}H_{24}FN_5O_6$ $^1$H NMR (300 MHz, DMSO-d$_6$) δ ppm 0.9 (d, 3H), 1.1-1.3 (m, 9H), 2.9 (d, 1H), 3.1 (t, 1H), 3.6-3.9 (m, 3H), 4.0 (d, 1H), 4.0-4.2 (m, 2H), 7.4 (s, 1H), 8.8 (d, 1H).

Using an alternate route, the (2R,4S,4aS) enantiomer of Example 147 was also obtained via a chiral synthesis similar to the one described for the synthesis of Example 95(a), using barbituric acid and the indicated starting material:

Example 147(a)

(2R,4S,4aS)-11-fluoro-N-isopropyl-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide

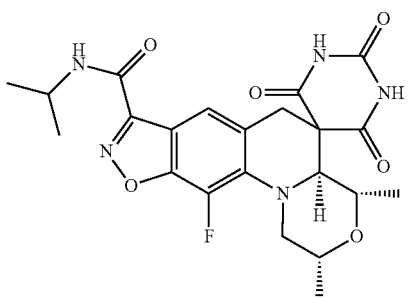

Starting materials: 6-((2R,6R)-2,6-dimethylmorpholino)-7-fluoro-5-formyl-N-isopropylbenzo[d]isoxazole-3-carboxamide (Intermediate 246); purification by Super Critical Fluid chromatography on a Chiralpac IC column with a 35% MeOH, 65% CO$_2$ mobile phase to give product as a solid as the first eluting compound.

MS (ES) MH$^+$: 474 for $C_{22}H_{24}FN_5O_6$ $^1$H NMR (300 MHz, DMSO-d6) δ ppm 0.9 (d, 3H), 1.1-1.3 (m, 9H), 2.9 (d, 1H), 3.1 (t, 1H), 3.6-3.8 (m, 2H), 3.8-3.9 (m, 1H), 4.0 (d, 1H), 4.0-4.2 (m, 2H), 7.4 (s, 1H), 8.8 (d, 1H), 11.5 (s, 1H), 11.8 (s, 1H).
>98% ee by chiral HPLC; [α]=−259 (c=0.1 in MeOH)

Example 147(b)

(2R,4R,4aR)-11-fluoro-N-isopropyl-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide

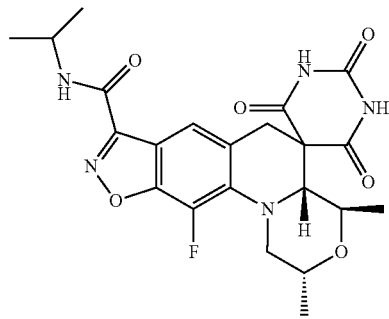

The (2R,4R,4aR) diastereomer was produced as a by-product of the reaction described for the synthesis of Example 147(a). The chromatography described for Example 147(a) afforded (2R,4R,4aR) diastereomer as the second eluting compound.
MS (ES) MH$^+$: 474 for $C_{22}H_{24}FN_5O_6$
$^1$H NMR (300 MHz, DMSO-d6) δ ppm 0.9 (d, 3H), 1.1 (d, 6H), 1.2 (d, 3H), 3.0 (d, 1H), 3.5-3.7 (m, 2H), 3.7 (d, 1H), 3.8-4.0 (m, 2H), 4.0-4.2 (m, 2H), 7.4 (s, 1H), 8.7 (d, 1H), 11.4 (br. s., 1H), 11.7 (br. s., 1H)

Example 148 was prepared from the indicated starting materials using a method similar to the one described for the synthesis of Example 97:

Example 148

(2R,4S,4aS)-rel-11-fluoro-2,4-dimethyl-8-(pyrimidin-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3H)-trione

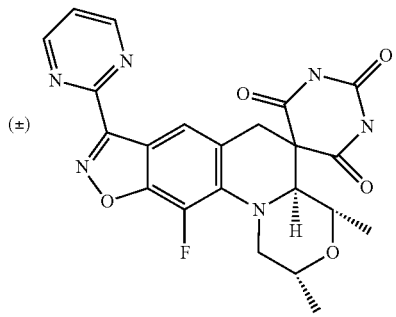

Starting material: 6-[(2R,6S)-2,6-dimethylmorpholin-4-yl]-7-fluoro-3-(pyrimidin-2-yl)-1,2-benzoxazole-5-carbaldehyde (Intermediate 587)
MS (ES) MH$^+$: 467 for $C_{22}H_{19}FN_6O_5$
$^1$H NMR (400 MHz, DMSO-d$_6$): 0.9 (d, 3H), 1.2 (d, 3H), 3.0 (d, 1H), 3.1 (t, 1H), 3.7 (m, 3H), 4.0 (d, 1H), 4.1 (d, 1H), 7.7 (m, 1H), 7.9 (s, 1H), 8.1 (d, 1H), 9.0 (s, 2H), 11.5 (s, 1H), 11.8 (s, 1H).

The (2S,4R,4aR) and (2R,4S,4aS) enantiomers of Example 148 were separated by Supercritical Fluid Chromatography using a Chiralpak AD, 21×250 mm, 5μ column (elution with 25% MeOH, 75% CO$_2$ at 60 ml/min, 40° C., and 100 bar with detection at 220 nm), providing Example 148(a) and Example 148(b):

Example 148(a)

First Eluting Compound (2S,4R,4aR)-11-fluoro-2,4-dimethyl-8-(pyrimidin-2-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

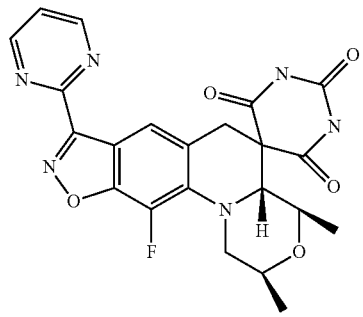

MS (ES) MH$^+$: 467 for $C_{22}H_{19}FN_6O_5$
$^1$H NMR (300 MHz, DMSO-d$_6$) δ: 0.9 (d, 3H) 1.2 (d, 3H) 2.9-3.2 (m, 3H), 3.6-4.2 (m, 5H) 7.7 (t, 1H) 7.8 (s, 1H) 9.0 (d, 2H) 11.4 (s, 1H) 11.8 (s, 1H)
>98% ee by chiral HPLC; [α]=+178 (c=0.1 in DMF).

Example 148(b)

Second Eluting Compound (2R,4S,4aS)-11-fluoro-2,4-dimethyl-8-(pyrimidin-2-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

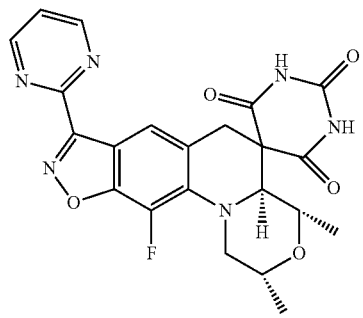

MS (ES) MH$^+$: 467 for $C_{22}H_{19}FN_6O_5$
$^1$H NMR (300 MHz, DMSO-d$_6$) δ: 0.9 (d, 3H) 1.2 (d, 3H) 2.9-3.2 (m, 2H), 3.6-4.2 (m, 5H) 7.7 (t, 1H) 7.8 (s, 1H) 9.0 (d, 2H) 11.5 (s, 1H) 11.8 (s, 1H)
>98% ee by chiral HPLC; [α]=−131 (c=0.1 in DMF).

Example 149 was prepared from the indicated starting materials using a method similar to the one described for the synthesis of Example 97:

Example 149

(2S,4S,4aS)-rel-11-fluoro-4,8-dimethyl-2-(trifluoromethyl)-1,2,4,4a-tetrahydro-2'H,6H-spiro[isoxazolo[4,5-g][1,4]oxazino[4,3-a]quinoline-5,5'-pyrimidine]-2',4',6'(1'H,3H)-trione

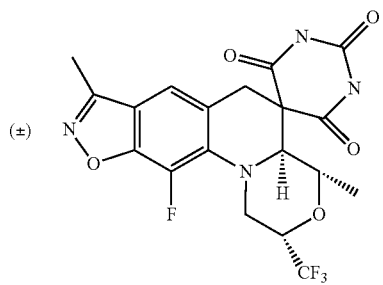

Starting material: 7-fluoro-3-methyl-6-[(2S,6S)-rel-2-methyl-6-(trifluoromethyl)morpholin-4-yl]-1,2-benzoxazole-5-carbaldehyde MS (ES) MH$^+$: 457 for $C_{19}H_{16}F_4N_4O_5$ $^1$H NMR (300 MHz, DMSO-d$_6$) δ: 0.95 (d, 3H), 2.4 (s, 3H), 3.0 (d, 1H), 3.5 (t, 1H), 3.6 (d, 1H), 3.9 (m, 1H), 4.1 (d, 1H), 4.3 (d, 1H), 4.5 (m, 1H), 7.2 (s, 1H), 11.5 (s, 1H), 11.9 (s, 1H).

Examples 150 to 164 were prepared from the indicated starting material and barbituric acid using a method similar to the one described for the synthesis of Example 134. The compounds were purified either by silica gel column chromatography using a gradient of DCM to ethyl acetate or by reverse phase HPLC using a gradient of CH$_3$CN in water with 0.1% TFA.

Example 150

(2R,4S,4aS)-rel-N-cyclopropyl-11-fluoro-2,4-dimethyl-2',4',6'-trioxo-2,2',4,4a,4',6,6'-octahydro-1H,1'H-spiro[isoxazolo[4,5-g][1,4]oxazino[4,3-a]quinoline-5,5'-pyrimidine]-8-carboxamide

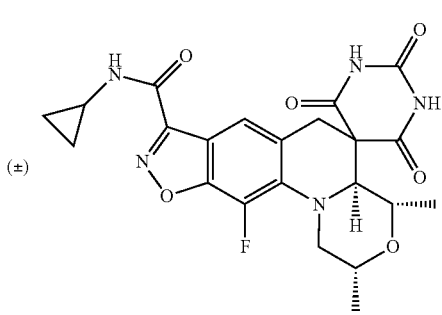

Starting material: N-cyclopropyl-6-((2R,6S)-2,6-dimethylmorpholino)-7-fluoro-5-formylbenzo[d]isoxazole-3-carboxamide (Intermediate 453)

MS (ES) MH$^+$: 472 for $C_{22}H_{22}FN_5O_6$ $^1$H NMR (300 MHz, DMSO-d$_6$) δ ppm 0.5-0.7 (m, 4H), 0.8 (d, 3H), 1.1 (d, 3H), 2.9 (d, 2H), 3.1 (t, 1H), 3.5-3.8 (m, 3H), 3.9 (d, 1H), 4.0 (d, 1H), 7.4 (s, 1H), 9.0 (d, 1H).

Example 151

(2R,4S,4aS)-rel-11-fluoro-8-(4-methoxypiperidine-1-carbonyl)-2,4-dimethyl-2,4,4a6-tetrahydro-1H,1'H-spiro[isoxazolo[4,5-g][1,4]oxazino[4,3-a]quinoline-5,5'-pyrimidine]-2',4',6'(3'H)-trione

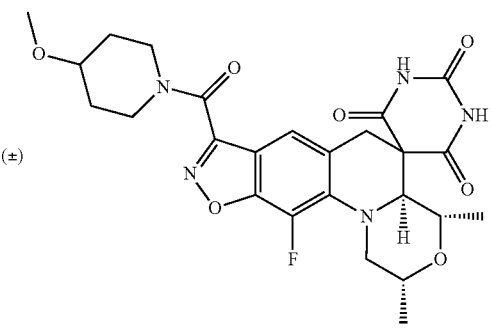

Starting material: 6-((2R,6S)-2,6-dimethylmorpholino)-7-fluoro-3-(4-methoxypiperidine-1-carbonyl)benzo[d]isoxazole-5-carbaldehyde (Intermediate 454)

MS (ES) MH$^+$: 530 for $C_{25}H_{28}FN_5O_7$ $^1$H NMR (300 MHz, DMSO-d$_6$) δ ppm 0.8 (d, 3H), 1.1 (d, 3H), 1.3-1.6 (m, 2H), 1.7-1.9 (m, 2H), 2.9 (d, 1H), 3.0-3.1 (m, 1H), 3.2 (s, 3H), 3.34-3.5 (m, 2H), 3.5-3.8 (m, 4H), 3.8-4.0 (m, 2H), 4.0 (d, 1H), 7.2 (s, 1H).

Example 152

(2R,4S,4aS)-rel-N-(cyclopropylmethyl)-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide

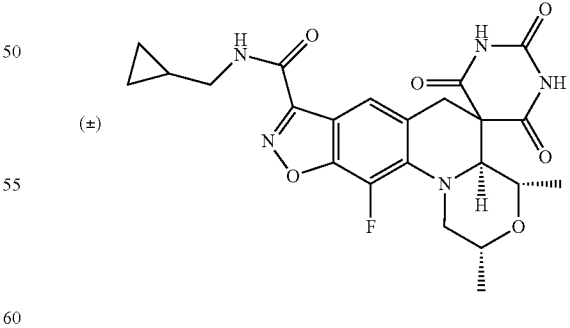

Starting material: N-(cyclopropylmethyl)-6-((2R,6S)-2,6-dimethylmorpholino)-7-fluoro-5-formylbenzo[d]isoxazole-3-carboxamide (Intermediate 455)

MS (ES) MH$^+$: 486 for $C_{23}H_{24}FN_5O_6$ $^1$H NMR (300 MHz, DMSO-d$_6$) δ ppm 0.01 (d, 2H), 0.2 (d, 2H), 0.6 (d, 3H), 0.7-0.9 (m, 1H), 0.9 (d, 3H), 2.7 (d, 1H), 2.8-3.0 (m, 3H), 3.3-3.5 (m, 2H), 3.5-3.6 (m, 1H), 3.7 (d, 1H), 3.9 (d, 1H,) 7.2 (s, 1H), 8.8 (t, 1H), 11.3 (br. s., 2H).

Example 153

(2R,4S,4aS)-rel-11-fluoro-2,4-dimethyl-8-(1,2-oxazinan-2-ylcarbonyl)-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione

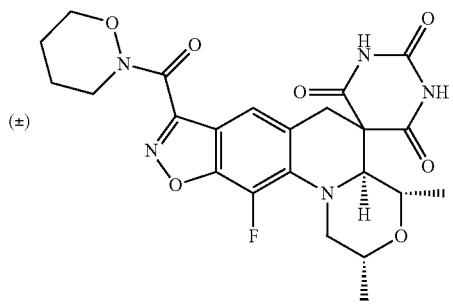

Starting material: 6-[(2R,6S)-2,6-dimethylmorpholin-4-yl]-7-fluoro-3-(1,2-oxazinan-2-ylcarbonyl)-1,2-benzisoxazole-5-carbaldehyde (Intermediate 456)

MS (ES) MH+: 502. for $C_{23}H_{24}FN_5O_7$ $^1$H NMR (300 MHz, DMSO-$d_6$) δ ppm 0.8 (d, 3H), 1.1 (d, 3H), 1.7 (br. s., 3H), 2.9 (d, 1H), 3.0-3.2 (m, 1H), 3.5-3.7 (m, 3H), 3.7-3.9 (m, 5H), 4.1 (d, 1H), 7.1-7.3 (m, 1H), 11.5 (s, 1H), 11.8 (s, 1H).

Example 154

(2R,4S,4aS)-rel-11-fluoro-2,4-dimethyl-2',4',6'-trioxo-N-(thiophen-2-ylmethyl)-2,2',3',4,4a,4',6,6'-octahydro-1H,1'H-spiro[isoxazolo[4,5-g][1,4]oxazino[4,3-a]quinoline-5,5'-pyrimide]-8-carboxamide

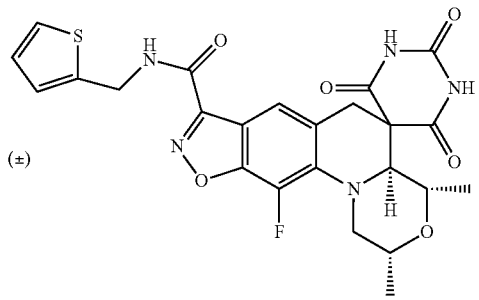

Starting material: 6-((2R,6S)-2,6-dimethylmorpholino)-7-fluoro-5-formyl-N-(thiophen-2-ylmethyl)benzo[d]isoxazole-3-carboxamide (Intermediate 457)

MS (ES) MH+: 528 for $C_{24}H_{22}FN_5O_6S$ $^1$H NMR (300 MHz, DMSO-$d_6$) δ ppm 0.9 (d, 3H), 1.2 (d, 3H), 2.9 (d, 1H), 3.0-3.2 (m, 1H), 3.6-3.7 (m, 2H), 3.8 (m, 1H), 4.0 (d, 1H), 4.1 (d, 1H), 4.6 (d, 2H), 6.9-7.0 (m, 1H), 7.0 (br. s., 1H), 7.4 (d, 1H), 7.4 (s, 1H), 9.6 (t, 1H).

Example 155

(2R,4S,4aS)-rel-11-fluoro-2,4-dimethyl-2',4',6'-trioxo-N-(pyridin-4-ylmethyl)-2,2',3',4,4a,4',6,6'-octahydro-1H,1'H-spiro[isoxazolo[4,5-g][1,4]oxazino[4,3-a]quinoline-5,5'-pyrimidine]-8-carboxamide

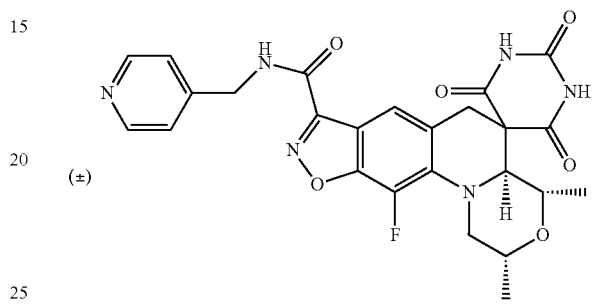

Starting material: 6-((2R,6S)-2,6-dimethylmorpholino)-7-fluoro-5-formyl-N-(pyridin-4-ylmethyl)benzo[d]isoxazole-3-carboxamide (Intermediate 458)

MS (ES) MH+: 523 for $C_{25}H_{23}FN_6O_6$ $^1$H NMR (300 MHz, DMSO-$d_6$) δ ppm 0.9 (d, 3H), 1.2 (d, 3H), 2.9 (d, 1H), 3.1 (t, 1H), 3.6-3.7 (m, 2H), 3.8-3.9 (m, 1H), 4.0 (d, 1H), 4.1 (d, 1H), 4.5 (d, 2H), 7.3 (d, 2H), 7.4 (s, 1H), 8.5 (d, 2H), 9.6 (t, 1H).

Example 156

(2R,4S,4aS)-rel-N-(cyclohexylmethyl)-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide

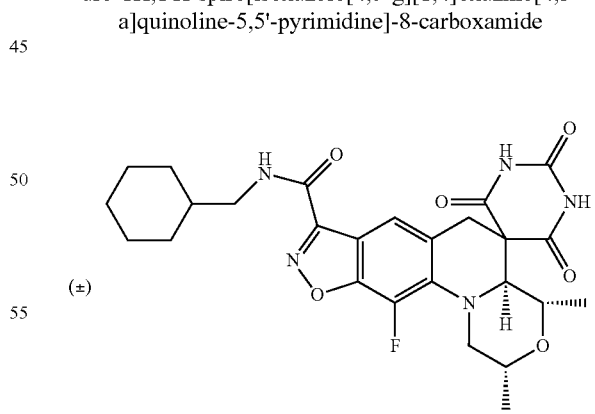

Starting material: N-(cyclohexylmethyl)-6-((2R,6S)-2,6-dimethylmorpholino)-7-fluoro-5-formylbenzo[d]isoxazole-3-carboxamide (Intermediate 459)

MS (ES) MH+: 528.3 for $C_{26}H_{30}FN_5O_6$ $^1$H NMR (300 MHz, DMSO-$d_6$) δ ppm 0.8-1.0 (m, 5H), 1.1-1.3 (m, 6H), 1.5-1.8 (m, 6H), 2.9 (d, 1H), 3.0-3.2 (m, 3H), 3.7 (d, 2H), 3.7-3.9 (m, 1H), 4.0 (d, 1H), 4.1 (d, 1H), 7.4 (s, 1H), 8.9 (t, 1H), 11.6 (br. s., 1H).

Example 157

(2R,4S,4aS)-rel-8-(4,4-difluoropiperidine-1-carbonyl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

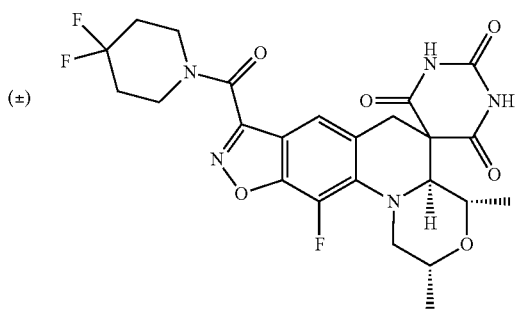

Starting material: 3-(4,4-difluoropiperidine-1-carbonyl)-6-((2R,6S)-2,6-dimethylmorpholino)-7-fluorobenzo[d]isoxazole-5-carbaldehyde (Intermediate 460)

MS (ES) MH+: 536 for $C_{24}H_{24}F_3N_5O_6$

1H NMR (300 MHz, DMSO-d6) δ ppm 0.9 (d, 3H), 1.2 (d, 3H), 2.0-2.2 (m, 4H), 3.0 (d, 1H), 3.1-3.2 (m, 1H), 3.6-3.9 (m, 7H), 4.0 (d, 1H), 4.1 (d, 1H), 7.3 (s, 1H), 11.5 (s, 1H), 11.9 (s, 1H).

Example 158

(2R,4S,4aS)-rel-8-(3,3-difluoropyrrolidine-1-carbonyl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidin]-2',4',6'(3'H)-trione

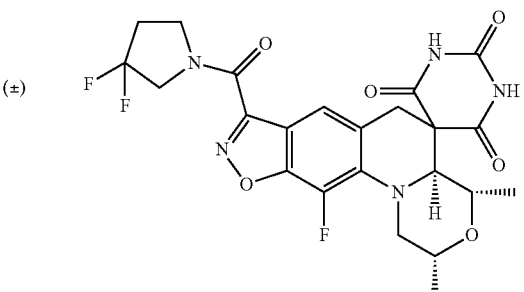

Starting material: 3-(3,3-difluoropyrrolidine-1-carbonyl)-6-((2R,6S)-2,6-dimethylmorpholino)-7-fluorobenzo[d]isoxazole-5-carbaldehyde (Intermediate 461)

MS (ES) MH+: 522 for $C_{23}H_{22}F_3N_5O_6$

1H NMR (300 MHz, DMSO-d6) δ ppm 0.9 (d, 3H), 1.2 (d, 3H), 2.9 (d, 1H), 3.1 (t, 1H), 3.6-3.9 (m, 4H), 3.9-4.2 (m, 4H), 4.3 (t, 1H), 7.4 (d, 1H), 11.5 (s, 1H), 11.9 (s, 1H).

Example 159

(2R,4S,4aS)-rel-11-fluoro-2,4-dimethyl-N-(1-methylazetidin-3-yl)-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide

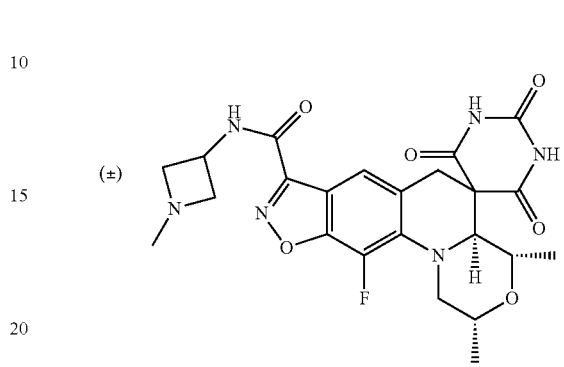

Starting material: 6-((2R,6S)-2,6-dimethylmorpholino)-7-fluoro-5-formyl-N-(1-methylazetidin-3-yl)benzo[d]isoxazole-3-carboxamide Intermediate 462)

MS (ES) MH+: 501 for $C_{23}H_{25}FN_6O_6$

1H NMR (300 MHz, DMSO-d6) δ ppm 0.8 (d, 3H), 1.1 (d, 3H), 2.2 (s, 3H), 2.9 (d, 1H), 3.0 (t, 2H), 3.1 (d, 1H), 3.5 (t, 2H), 3.6-3.7 (m, 2H), 3.7-3.8 (m, 1H), 3.9 (d, 1H), 4.0 (d, 1H), 4.3-4.4 (m, 1H), 7.3 (s, 1H), 9.3 (d, 1H).

Example 160

N-(1-((2R,4S,4aS)-rel-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-ylcarbonyl)azetidin-3-yl)acetamide

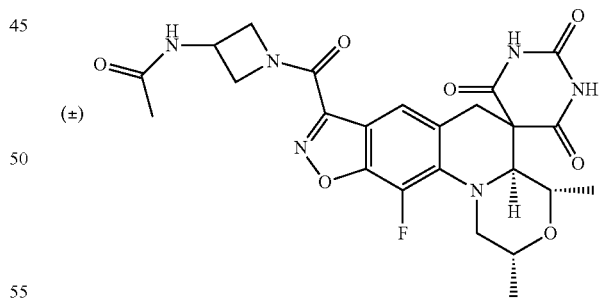

Starting material: N-(1-(6-((2R,6S)-2,6-dimethylmorpholino)-7-fluoro-5-formylbenzo[d]isoxazole-3-carbonyl)azetidin-3-yl)acetamide (Intermediate 463)

MS (ES) MH+: 529 for $C_{24}H_{25}FN_6O_7$

1H NMR (300 MHz, DMSO-d6) δ ppm 0.8 (d, 3H), 1.1 (d, 3H), 1.8 (s, 3H), 2.8 (d, 1H), 3.0-3.1 (m, 1H), 3.5-3.8 (m, 3H), 3.8-3.9 (m, 2H), 4.1 (d, 1H), 4.1-4.4 (m, 2H), 4.4-4.5 (m, 1H), 4.6-4.7 (m, 1H), 7.4 (s, 1H), 8.5 (d, 1H), 11.4 (s, 1H), 11.8 (s, 1H).

Example 161

(2R,4S,4aS)-rel-11-fluoro-2,4-dimethyl-N-((1-methyl-1H-pyrazol-3-yl)methyl)-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide

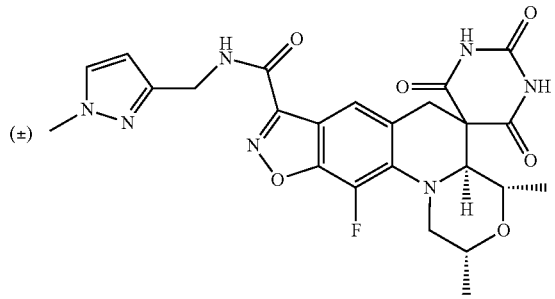

Starting material: 6-((2R,6S)-2,6-dimethylmorpholino)-7-fluoro-5-formyl-N-((1-methyl-1H-pyrazol-3-yl)methyl)benzo[d]isoxazole-3-carboxamide (Intermediate 464)

MS (ES) MH$^+$: 526 for $C_{24}H_{24}FN_7O_6$ $^1$H NMR (300 MHz, DMSO-d$_6$) δ ppm 0.9 (d, 3H), 1.1 (d, 3H), 2.9 (d, 1H), 3.0-3.2 (m, 1H), 3.6-3.9 (m, 6H), 4.0 (d, 1H), 4.1 (d, 1H), 4.4 (d, 2H), 6.2 (d, 1H), 7.5 (s, 1H), 7.6 (d, 1H), 9.3 (t, 1H), 11.5 (s, 1H), 11.8 (s, 1H).

Example 162

(2R,4S,4aS)-rel-11-fluoro-2,4-dimethyl-N-((1-methyl-1H-pyrazol-5-yl)methyl)-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide

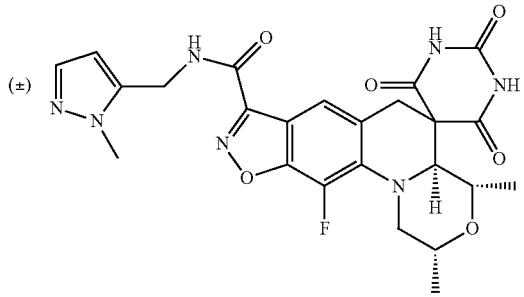

Starting material: 6-((2R,6S)-2,6-dimethylmorpholino)-7-fluoro-5-formyl-N-((1-methyl-1H-pyrazol-5-yl)methyl)benzo[d]isoxazole-3-carboxamide (Intermediate 465)

MS (ES) MH$^+$: 526 for $C_{24}H_{24}FN_7O_6$ $^1$H NMR (300 MHz, DMSO-d$_6$) δ ppm 0.9 (d, Hz, 3H), 1.1 (d, Hz, 3H), 2.9 (d, 1H), 3.1 (t, 1H), 3.6-3.8 (m, 3H), 3.8 (s, 3H), 4.0 (d, 1H), 4.1 (d, 1H), 4.4-4.6 (m, 2H), 6.2 (s, 1H), 7.3 (s, 1H), 7.4 (s, 1H), 9.5 (t, 1H), 11.5 (s, 1H), 11.8 (s, 1H).

Example 163

(2R,4S,4aS)-rel-N-(1,3-dimethoxy-2-(methoxymethyl)propan-2-yl)-11-fluoro-2,4-dimethyl-2',4',6'-trioxo-2,2',3',4,4a,4',6,6'-octahydro-1H,1'H-spiro[isoxazolo[4,5g][1,4]oxazino[4,3-a]quinoline-5,5'-pyrimidine]-8-carboxamide

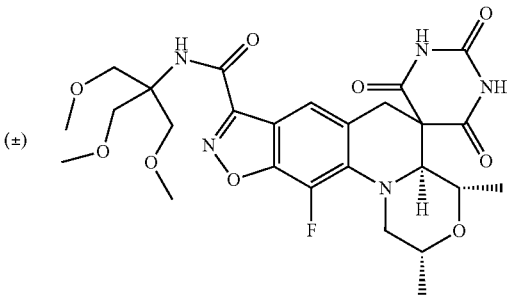

Starting material: N-(1,3-dimethoxy-2-(methoxymethyl)propan-2-yl)-6-((2R,6S)-2,6-dimethylmorpholino)-7-fluoro-5-formylbenzo[d]isoxazole-3-carboxamide (Intermediate 466)

MS (ES) MH$^+$: 578 for $C_{26}H_{32}FN_5O_9$ $^1$H NMR (300 MHz, DMSO-d$_6$) δ ppm 0.9 (d, 3H), 1.2 (d, 3H), 2.9 (d, 1H), 3.1-3.2 (m, 1H), 3.3 (s, 9H), 3.6-3.7 (m, 8H), 3.8-3.9 (m, 1H), 4.0 (d, 1H), 4.1 (d, 1H), 7.4 (s, 1H), 7.7 (s, 1H), 11.6 (br. s., 2H).

Example 164

1-((2R,4S,4aS)-rel-11-fluoro-2,4-dimethyl-2',4',6'-trioxo-2,2',3',4,4a,4',6,6'-octahydro-1H-1'H-spiro[isoxazolo[4,5-g][1,4]oxazino[4,3-a]quinoline-5,5'-pyrimidine]-8-ylcarbonyl)azetidine-3-carbonitrile

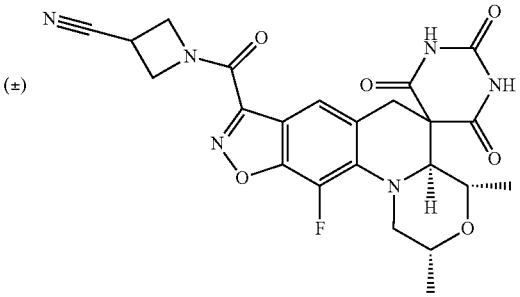

Starting material: 1-(6-((2R,6S)-2,6-dimethylmorpholino)-7-fluoro-5-formylbenzo[d]isoxazole-3-carbonyl)azetidine-3-carbonitrile (Intermediate 468)

MS (ES) MH$^+$: 497 for $C_{23}H_{21}FN_6O_6$ $^1$H NMR (300 MHz, DMSO-d$_6$) δ ppm 0.9 (d, 3H), 1.2 (d, 3H), 2.9 (d, 1H), 3.0-3.2 (m, 1H), 3.6-3.8 (m, 3H), 3.9-4.0 (m, 2H), 4.1 (d, 1H), 4.3 (t, 1H), 4.3-4.5 (m, 1H), 4.6-4.9 (m, 2H), 7.5 (s, 1H).

Example 165

(2R,4S,4aS)-rel-11-fluoro-2,4-dimethyl-8-(pyrazin-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

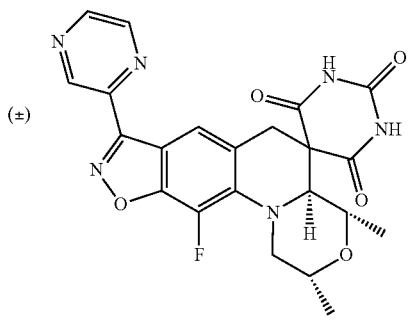

Barbituric acid and (2R,4S,4aS)-rel-9,10-difluoro-8-[(hydroxyimino)(pyrazin-2-yl)methyl]-2,4-dimethyl-1,2,4,4a-tetrahydro-2'H,6H-spiro[1,4-oxazino[4,3-a]quinoline-5,5'-pyrimidine]-2',4',6'(1'H,3'H)-trione (Intermediate 583) were reacted using a method similar to the one described for the synthesis of Example 8.

MS (ES) MH$^+$: 467 for $C_{22}H_{19}FN_6O_5$ $^1$H NMR (400 MHz, DMSO-d$_6$) δ: 0.9 (brs, 3H), 1.2 (brs, 3H), 2.9 (m, 1H), 3.1 (m, 1H), 3.8 (m, 2H), 4.0 (m, 1H), 4.2 (m, 1H), 7.6 (m, 1H), 7.8 (s, 1H), 8.9 (m, 2H), 9.3 (s, 1H), 11.5 (s, 1H), 11.8 (s, 1H).

In an alternative route, the (2R,4S,4aS) enantiomer of Example 165 was synthesized using a chiral synthesis, as described below for Example 165(b):

Example 165(a)

(2R,4S,4aR)-11-fluoro-2,4-dimethyl-8-(pyrazin-2-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

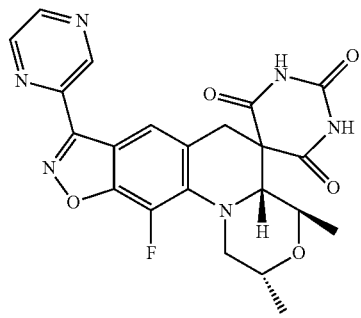

The (2R,4R,4aR) diastereomer was produced as a by-product of the reaction described for the synthesis of Example 165(b) below. The chromatography described for Example 165(b) afforded (2R,4R,4aR) diastereomer as the first eluting compound.

MS (ES) MH$^+$: 467 for $C_{22}H_{19}FN_6O_5$ $^1$H NMR (400 MHz, DMSO-d$_6$) δ ppm: 0.9 (d, 3H), 1.3 (d, 3H), 3.1 (d, 1H), 3.55 (d, 1H), 3.65 (d, 1H), 3.75 (d, 1H), 3.8-4.0 (m, 2H), 4.0-4.1 (m, 1H), 7.7 (s, 1H), 8.8 (m, 2H), 9.3 (d, 1H), 11.4 (s, 1H), 11.7 (d, 1H)

Example 165(b)

(2R,4S,4aS)-11-fluoro-2,4-dimethyl-8-(pyrazin-2-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

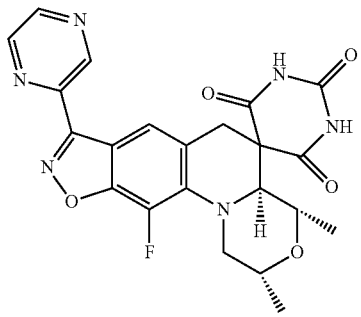

Barbituric acid and 6-((2R,6R)-2,6-dimethylmorpholino)-7-fluoro-3-(pyrazin-2-yl)benzo[d]isoxazole-5-carbaldehyde (Intermediate 438) were reacted using a method similar to the one described for the synthesis of Example 53(a). The product was purified by reverse phase HPLC using a gradient of CH$_3$CN in water with 0.1% TFA, and obtained as the second eluting compound.

MS (ES) MH$^+$: 467 for $C_{22}H_{19}FN_6O_5$ $^1$H NMR (400 MHz, DMSO-d$_6$) δ ppm: 0.9 (d, 3H), 1.2 (d, 3H), 3.0 (d, 1H), 3.1 (m, 1H), 3.5-3.9 (m, 3H), 4.0 (d, 1H), 4.2 (d, 1H), 7.8 (s, 1H), 8.7-9.0 (m, 2H), 9.4 (d, 1H), 11.5 (s, 1H), 11.8 (d, 1H)

Examples 166(a) to 167 were prepared from the indicated starting material and barbituric acid using a method similar to the one described for the chiral synthesis of Example 53(a):

Example 166(a)

(2R,4R,4aR)-11-fluoro-2,4-dimethyl-8-(5-morpholinopyrazin-2-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

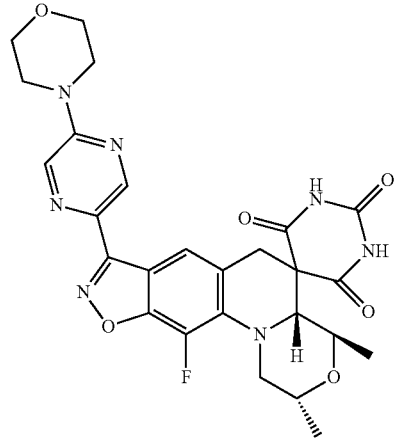

The (2R,4R,4aR) diastereomer was produced as a by-product of the reaction described for the synthesis of Example 166(b) below. The chromatography described for Example 166(b) afforded the (2R,4R,4aR) diastereomer as the first eluting compound.

MS (ES) MH$^+$: 552 for $C_{26}H_{26}FN_7O_6$ $^1$H NMR (300 MHz, DMSO-d$_6$) δ ppm 1.0 (d, 3H), 1.3 (d, 3H), 3.2 (d, 1H), 3.6 (m, 1H), 3.6-3.8 (m, 11H), 3.9-4.0 (m, 1H), 4.1 (m, 1H), 7.3 (d, 1H), 7.7 (s, 1H), 8.6 (d, 1H), 11.5 (s, 1H), 11.8 (s, 1H)

Example 166(b)

(2R,4S,4aS)-11-fluoro-2,4-dimethyl-8-(5-morpholinopyrazin-2-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

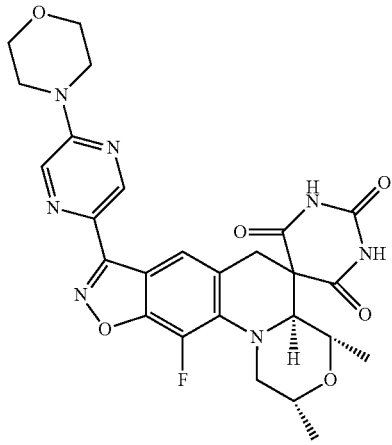

Starting material: 6-((2R,6R)-2,6-dimethylmorpholino)-7-fluoro-3-(5-morpholinopyrazin-2-yl)benzo[d]isoxazole-5-carbaldehyde (Intermediate 433). Purification by reverse phase HPLC using a gradient of CH$_3$CN in water with 0.1% TFA provided the (2R,4S,4aS diastereomer as the second eluting compound.
MS (ES) MH$^+$: 552 for C$_{26}$H$_{26}$FN$_7$O$_6$
$^1$H NMR (300 MHz, DMSO-d$_6$) δ ppm 0.9 (d, 3H), 1.2 (d, 3H), 3.0 (d, 1H), 3.1 (m, 1H), 3.6-3.8 (m, 11H), 4.0 (d, 1H), 4.1 (s, 1H), 7.7 (s, 1H), 8.5 (d, 1H), 8.8 (d, 1H), 11.5 (s, 1H), 11.8 (s, 1H)

Example 167

(2R,4S,4aS)-11-fluoro-8-(6-methoxypyrazin-2-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

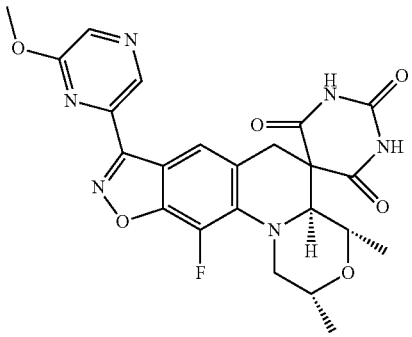

Starting material: 6-((2R,6R)-2,6-dimethylmorpholino)-7-fluoro-3-(6-methoxypyrazin-2-yl)benzo[d]isoxazole-5-carbaldehyde (Intermediate 436); purification by reverse phase HPLC using a gradient of CH$_3$CN in water with 0.1% TFA.

MS (ES) MH$^+$: 497 for C$_{23}$H$_{21}$FN$_6$O$_6$
$^1$H NMR (300 MHz, DMSO-d$_6$) δ ppm: 0.9 (d, 3H), 1.2 (d, 3H), 3.0 (d, 1H), 3.1-3.2 (m, 1H), 3.6-3.7 (m, 1H), 3.8 (d, 2H), 4.0 (d, 1H), 4.1 (s, 3H), 4.2 (d, 1H), 7.7 (s, 1H), 8.5 (s, 1H), 8.9 (s, 1H), 11.5 (s, 1H), 11.9 (s, 1H).

Example 168

(2R,4S,4aS)-11-fluoro-2,4-dimethyl-8-(2-(methylthio)pyrimidin-4-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

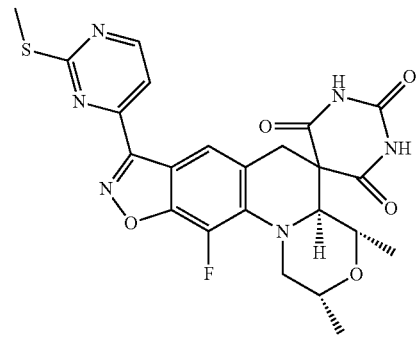

In a microwave reactor, 6-((2R,6R)-2,6-dimethylmorpholino)-7-fluoro-3-(2-(methylthio)pyrimidin-4-yl)benzo[d]isoxazole-5-carbaldehyde (Intermediate 437, 719 mg, 1.79 mmol) and 1,3,5-triazinane-2,4,6-trione (242 mg, 1.88 mmol) in EtOH (10 ml) were heated at 140° C. for 1 hour. The solution was concentrated to dryness to afford 916 mg of desired product, used in subsequent reactions without further purification.
MS (ES) MH$^+$: 513 for C$_{23}$H$_{21}$FN$_6$O$_5$S
$^1$H NMR (300 MHz, DMSO-d$_6$) δ ppm 0.9 (d, 3H), 1.2 (d, 3H), 2.6 (s, 3H), 3.0 (d, 1H), 3.1-3.2 (m, 1H), 3.7 (dd, 1H), 3.7-3.9 (m, 2H), 4.0 (d, 1H), 4.2 (d, 1H), 7.7 (s, 1H), 7.8 (d, 1H), 8.8 (d, 1H), 11.5 (br. s., 1H), 11.9 (br. s., 1H)

Example 169

(2R,4S,4aS)-11-fluoro-2,4-dimethyl-8-(2-(methylsulfonyl)pyrimidin-4-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

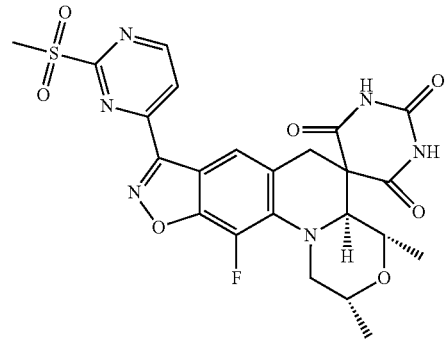

Oxone (5902 mg, 9.60 mmol) was added to a solution of (2R,4S,4aS)-11-fluoro-2,4-dimethyl-8-(2-(methylthio)pyrimidin-4-yl)-2,4,4a,6-tetrahydro-1H,1'H-spiro[isoxazolo[4, 5-g][1,4]oxazino[4,3-a]quinoline-5,5'-pyrimidine]-2',4',6'(3'H)-trione (Example 168, 984 mg, 1.92 mmol) in MeOH:THF:H$_2$O (30 ml)(1:1:1), and the mixture was stirred at room temperature for 48 hours. The reaction mixture was diluted with DCM (50 ml), stirred for 10 minutes, filtered, and the filter cake was washed with EtOH. The filtrate was washed with water and brine, concentrated under reduced pressure to give the desired product used in subsequent reactions without further purification.

MS (ES) MH$^+$: 545 for C$_{23}$H$_{21}$FN$_6$O$_7$S $^1$H NMR (300 MHz, DMSO-d$_6$) δ ppm 0.9 (d, 3H), 1.2 (d, 3H), 3.0 (s, 1H), 3.2 (d, 1H) 3.7 (m, 1H), 3.8 (d, 2H), 4.0 (d, 1H), 4.1 (d, 1H), 7.0 (m, 1H), 7.8 (s, 1H), 8.1 (m, 1H), 11.5 (s, 1H), 11.8 (d, 1H), 12.0-12.4 (br, s, 1H)

Example 170

(2R,4S,4aS)-11-fluoro-8-(2-(2-methoxyethylamino)pyrimidin-4-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

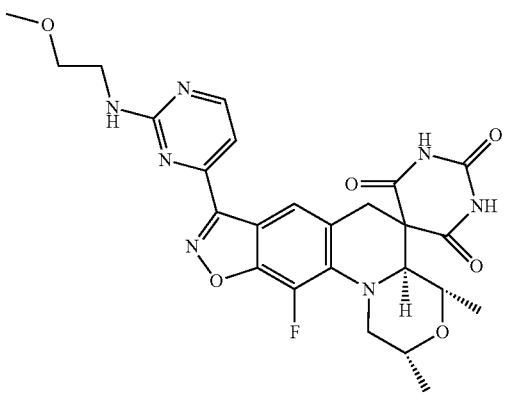

2-Methoxyethanamine (8.70 μL, 0.10 mmol) was added o a solution of (2R,4S,4aS)-11-fluoro-2,4-dimethyl-8-(2-(methylsulfonyl)pyrimidin-4-yl)-2,4,4a,6-tetrahydro-1H,1'H-spiro[isoxazolo[4,5-g][1,4]oxazino[4,3-a]quinoline-5,5'-pyrimidine]-2',4',6'(3H)-trione (Example 169, 50 mg, 0.09 mmol) in THF (5 mL), and the mixture was stirred at room temperature for 3 hours, DMSO (1 ml) was added followed by the addition of 2 more equivalence of methoxylethanamine, the mixture was stirred at room temperature for over night. The crude was concentrated and purified by reverse phase silica gel column chromatography (20-70% MeCN in water gradient, 0.1% TFA) to give 37 mg of product.

MS (ES) MH$^+$: 540 for C$_{25}$H$_{26}$FN$_7$O$_6$ $^1$H NMR (300 MHz, DMSO-d$_6$) δ ppm 0.9 (d, 3H), 1.7 (d, 3H), 3.1 (m, 2H), 3.2-3.3 (m, 3H), 3.4-3.5 (m, 4H), 3.7 (m, 2H), 3.8-3.9 (m, 1H), 4.0 (d, 1H), 4.1 (d, 1H), 7.2 (d, 1H), 7.5 (br. s., 1H), 7.9 (br. s, 1H), 8.5 (d, 1H), 11.5 (s, 1H), 11.9 (s, 1H)

Examples 171 to 177 were prepared from the indicated starting materials and using a method similar to the one described for the syntheses of Example 170:

Example 171

(2R,4S,4aS)-11-fluoro-8-(2-(2-hydroxyethylamino)pyrimidin-4-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

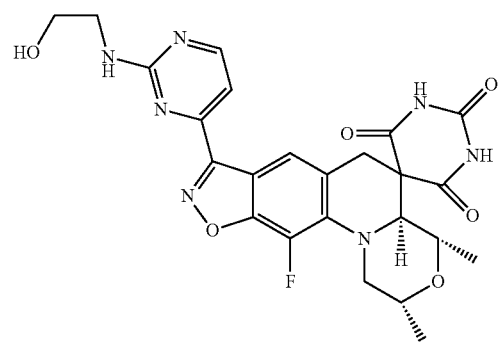

Starting material: (2R,4S,4aS)-11-fluoro-2,4-dimethyl-8-(2-(methylsulfonyl)pyrimidin-4-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione (Example 169) and 2-aminoethanol.

MS (ES) MH$^+$: 526 for C$_{24}$H$_{24}$FN$_7$O$_6$ $^1$H NMR (300 MHz, DMSO-d$_6$) δ ppm 0.9 (d, 3H), 1.2 (d, 3H), 3.1 (m, 1H), 3.5-3.7 (m, 6H), 3.7-3.8 (m, 2H), 3.8-3.9 (m, 1H), 4.0 (d, 1H), 4.1 (d, 1H), 7.2 (d, 1H), 7.4 (br. s., 1H), 7.7-8.1 (m, 1H), 8.5 (d, 1H), 11.5 (br. s., 1H) 11.9 (s, 1H).

Example 172

(2R,4S,4aS)-11-fluoro-8-(2-methoxypyrimidin-4-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

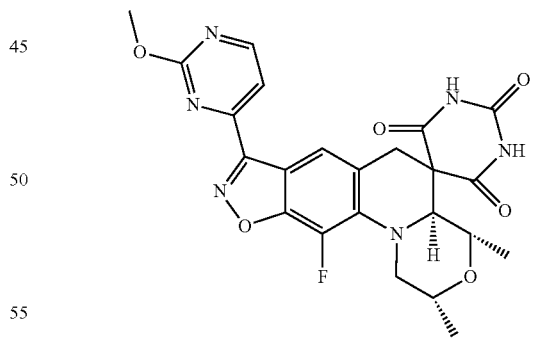

Starting material: (2R,4S,4aS)-11-fluoro-2,4-dimethyl-8-(2-(methylsulfonyl)pyrimidin-4-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione (Example 169) and 2M ammonia in methanol.

MS (ES) MH$^+$: 497 for C$_{23}$H$_{21}$FN$_6$O$_6$ $^1$H NMR (300 MHz, DMSO-d$_6$): δ ppm 0.8 (d, 3H), 1.1 (d, 3H), 2.9 (d, 1H), 3.0-3.2 (m, 1H), 3.6 (dd, 2H), 3.7-3.8 (m, 1H), 3.9 (d, 1H), 4.0 (s, 3H), 4.1 (d, 1H), 7.6-7.8 (m, 2H), 8.8 (d, 1H), 11.4 (s, 1H), 11.8 (s, 1H).

Example 173

4-((2R,4S,4aS)-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-yl)pyrimidine-2-carbonitrile

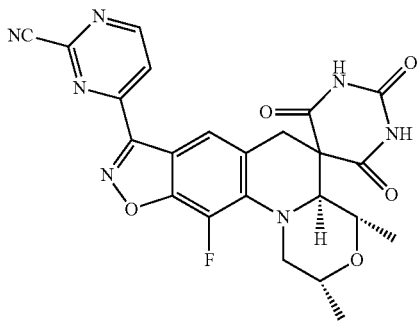

Starting material: (2R,4S,4aS)-11-fluoro-2,4-dimethyl-8-(2-(methylsulfonyl)pyrimidin-4-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione (Example 169) and potassium cyanide.

MS (ES) MH$^+$: 492 (M+H) for $C_{23}H_{18}FN_7O_5$ $^1$H NMR (300 MHz, DMSO-d$_6$) δ ppm 0.9 (d, 3H), 1.2 (d, 3H), 3.0 (d, 1H), 3.1-3.2 (m, 1H), 3.7 (dd, 1H), 3.8 (m, 1H), 3.9 (d, 1H), 4.0 (d, 1H), 4.2 (d, 1H), 7.7 (s, 1H), 8.5 (d, 1H), 9.2 (d, 1H), 11.5 (s, 1H), 11.8 (s, 1H).

Example 174

(2R,4S,4aS)-8-(2-aminopyrimidin-4-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

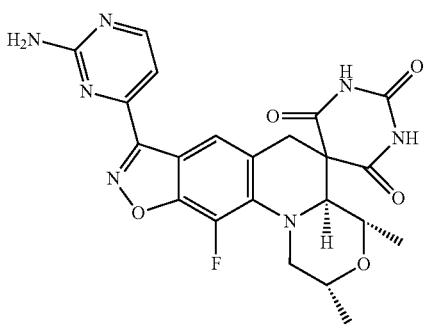

Starting materials: (2R,4S,4aS)-11-fluoro-2,4-dimethyl-8-(2-(methylsulfonyl)pyrimidin-4-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione (Example 169) and ammonia in dioxane (0.5M)

MS (ES) MH$^+$: 482 (M+H) for $C_{22}H_{20}FN_7O_5$ $^1$H NMR (300 MHz, DMSO-d$_6$) δ ppm 0.9 (d, 3H), 1.2 (d, 3H), 3.0-3.2 (m, 2H), 3.4-3.5 (m, 1H), 3.7 (dd, 1H), 3.8-3.9 (m, 1H), 4.0 (d, 1H), 4.1 (d, 1H), 7.0 (s, 2H), 7.2 (d, 1H), 7.9 (s, 1H), 8.4 (d, 1H), 11.5 (s, 1H), 11.9 (s, 1H).

Example 175

(2R,4S,4aS)-11-fluoro-8-(2-hydroxypyrimidin-4-yl)-2,4-dimethyl-1,2,4,4a-tetrahydro-2H,6H-spiro[isoxazolo[4,5-g][1,4]oxazino[4,3-a]quinoline-5,5'-pyrimidine]-2',4',6'(1'H,3H)-trione

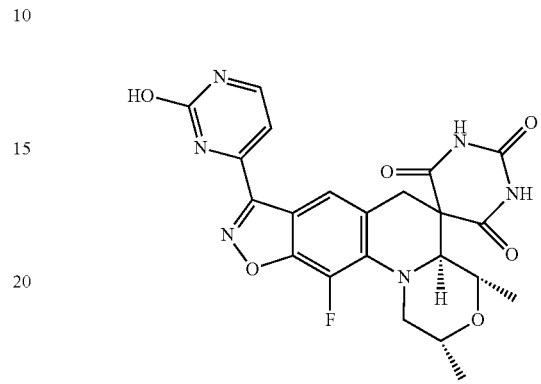

Starting materials: (2R,4S,4aS)-11-fluoro-2,4-dimethyl-8-(2-(methylsulfonyl)pyrimidin-4-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione (Example 169) and potassium trimethylsilanolate.

MS (ES) MH$^+$: 483 (M+H) for $C_{22}H_{19}FN_6O_6$ $^1$H NMR (300 MHz, DMSO-d$_6$) δ ppm 0.9 (d, 3H), 1.2 (d, 3H), 3.0 (s, 1H), 3.2 (d, 1H), 3.7 (m, 1H), 3.8 (d, 2H), 4.0 (d, 1H), 4.1 (d, 1H), 7.0 (br. s., 1H), 7.8 (s, 1H), 8.1 (br. s., 1H), 11.5 (s, 1H), 11.8 (d, 1H), 12.0-12.4 (m, 1H)

Example 176

(2R,4S,4aS)-11-fluoro-2,4-dimethyl-8-(2-morpholinopyrimidin-4-yl)-2,4,4a,6-tetrahydro-1H,1'H-spiro[isoxazolo[4,5-g][1,4]oxazino[4,3-a]quinoline-5,5'-pyrimidine]-2',4',6'-(3'H)-trione

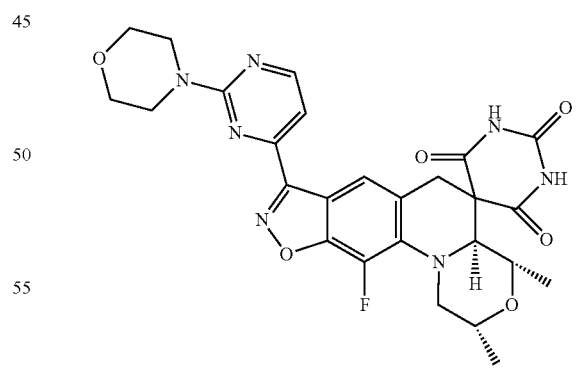

Starting materials: (2R,4S,4aS)-11-fluoro-2,4-dimethyl-8-(2-(methylsulfonyl)pyrimidin-4-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione (Example 169) and morpholine.

MS (ES) MH$^+$: 552 for $C_{26}H_{26}FN_7O_6$ $^1$H NMR (300 MHz, DMSO-d$_6$) δ ppm: 0.9 (d, 3H), 1.2 (d, 3H), 3.0 (d, 1H), 3.1-3.2 (m, 1H), 3.6-3.7 (m, 2H), 3.7 (m, 4H), 3.8-3.9 (m, 5H), 4.0 (d, 1H), 4.1 (d, 1H), 7.3 (d, 1H), 7.6 (s, 1H), 8.6 (d, 1H), 11.5 (s, 1H), 11.9 (s, 1H)

Example 177

(2R,4S,4aS)-rel-8-(6-(dimethylamino)pyrazin-2-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

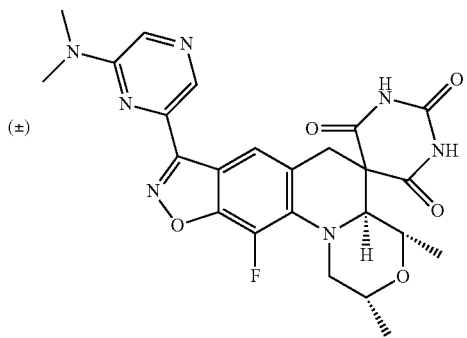

Starting materials: (2R,4S,4aS)-rel-8-(6-chloropyrazin-2-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione (Example 79) and 2N dimethylamine in THF.

MS (ES) MH$^+$: 510 for $C_{24}H_{24}FN_7O_5$ $^1$H NMR (300 MHz, DMSO-$d_6$) δ ppm 0.9 (d, 3H), 1.2 (d, 3H), 3.0 (d, 1H), 3.1 (m, 1H), 3.2 (s, 6H), 3.7-3.8 (m, 3H), 4.0 (d, 1H), 4.1 (d, 1H), 7.7 (s, 1H), 8.3 (s, 1H), 8.4 (s, 1H), 11.5 (br. s., 1H), 11.8 (br. s., 1H)

Example 178

(2R,4S,4aS)-11-fluoro-2,4-dimethyl-8-(1-methyl-1H-1,2,4-triazol-5-yl)-2,4,4a,6-tetrahydro-1H,1'H-spiro[isoxazolo[4,5-g][1,4]oxazino[4,3-a]quinoline-5,5'-pyrimidine]-2',4',6'(3H)-trione

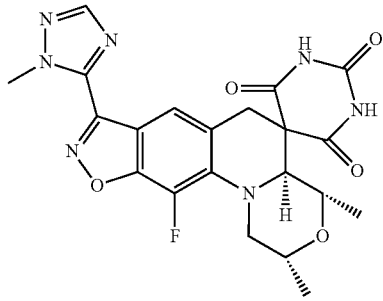

A mixture of 6-((2R,6R)-2,6-dimethylmorpholino)-7-fluoro-3-(1-methyl-1H-1,2,4-triazol-5-yl)benzo[d]isoxazole-5-carbaldehyde (Intermediate 537, 124 mg, 0.35 mmol) and pyrimidine-2,4,6(1H,3H,5H)-trione (44.2 mg, 0.35 mmol) in methanol (3 ml) was heated at 150° C. for 1 hour in a microwave reactor. Solvent was removed and the residue was purified by reverse phase HPLC (CH$_3$CN/water gradient with 0.1% TFA). The solid was taken up in 9:1 CH$_2$Cl$_2$— MeOH and washed with NaHCO$_3$ and brine. The aqueous layers were repeatedly extracted with additional 9:1 CH$_2$Cl$_2$-MeOH with each extract being washed with brine. The combined organic layers were dried (MgSO$_4$) and concentrated and the residue was dissolved in THF. After removal of solvent, the solid residue was dried in vacuo at 50° C. overnight to afford desired product.

$^1$H NMR (300 MHz, DMSO-$d_6$) δ ppm 0.9 (d, 3H), 1.2 (d, 3H), 2.9 (d, 1H), 3.0-3.2 (m, 1H), 3.6-3.8 (m, 1H), 3.8 (d, 2H) 4.0 (d, 1H) 4.1 (d, 1H), 4.2 (s, 3H), 7.7 (s, 1H), 8.3 (s, 1H), 11.5 (s, 1H), 11.85 (s, 1H).

Example 179

(2R,4S,4aS)-rel-11-fluoro-2,4-dimethyl-8-(piperazin-1-yl)-1,2,4,4a-tetrahydro-2',6H-spiro[isoxazolo[4,5-g][1,4]oxazino[4,3-a]quinoline-5,5'-pyrimidine]-2',4',6'(1'H,3'H)-trione

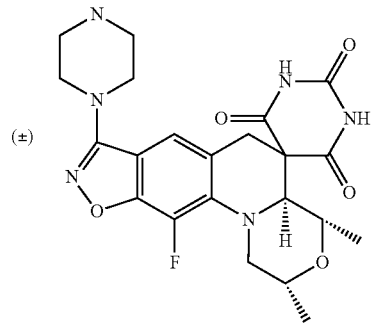

A mixture of tert-butyl 4-[(2R,4S,4aS)-rel-11-fluoro-2,4-dimethyl-2',4',6'-trioxo-1,1',2,3',4,4',4a,6'-octahydro-2'H,6H-spiro[isoxazolo[4,5-g][1,4]oxazino[4,3-a]quinoline-5,5'-pyrimidin]-8-yl]piperazine-1-carboxylate (Example 20, 50 mg, 0.08 mmol) and 4N HCl in MeOH (8 mL) was stirred at room temperature for 1 hours. It was concentrated under reduced pressure and the residue was triturated with pet ether to give the title compound as brown solid. Isolated as HCl salt. Yield: 28 mg (67%)

MS (ES) MH$^+$: 473 for $C_{22}H_{25}FN_6O_5$ $^1$H NMR (400 MHz, DMSO-$d_6$) δ: 0.9 (d, 3H), 1.1 (d, 3H), 2.95 (d, 1H), 3.05 (t, 1H), 3.40 (m, 4H), 3.45 (m, 1H), 3.6 (m, 5H), 3.8 (m, 1H), 3.9 (d, 1H), 4.05 (d, 1H), 7.3 (s, 1H), 9.15 (bs, 2H), 11.5 (s, 1H), 11.9 (s, 1H).

Example 180

(2R,4S,4aS)-8-chloro-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

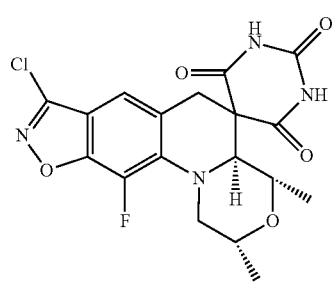

A mixture of 3-chloro-6-((2R,6R)-2,6-dimethylmorpholino)-7-fluorobenzo[d]isoxazole-5-carbaldehyde (Intermediate 535, 764 mg, 2.44 mmol) and pyrimidine-2,4,6(1H, 3H,5H)-trione (313 mg, 2.44 mmol) in iPrOH (3 ml) was heated at reflux for 3 days. Solvent was removed and the residue was recrystallized from methanol. The solids obtained were recrystallized from 1:1 EtOH-Water to afford 273 mg of product consistent with desired product.

MS (ES) MH+: 473 for $C_{22}H_{25}FN_6O_5$

1H NMR (300 MHz, DMSO-$d_6$) δ ppm 0.9 (d, 3H) 1.15 (d, 3H) 2.95 (d, 1H), 3.55-3.7 (m, 2H) 3.7-3.9 (m, 1H) 4.0 (d, 1H) 4.1 (m, 2H) 7.2 (s, 1H) 11.5 (s, 1H) 11.9 (s, 1H).

Example 181

(2R,4S,4aS)-rel-11-fluoro-2,4-dimethyl-8-(methylsulfinyl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

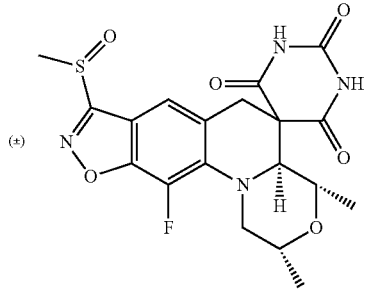

To a stirred solution of (2R,4S,4aS)-rel-11-fluoro-2,4-dimethyl-8-(methylsulfanyl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione Example 62, 50 mg, 0.11 mmol) in dry DCM (1 mL) was added m-chloroperbenzoic acid (39 mg, 0.23 mmol) and stirred at room temperature for 1 hours. Solvents were evaporated and the residue thus obtained purified over a silica gel column to give product as solid. Yield: 18 mg (35%).

MS (ES) MH+: 451 for $C_{19}H_{19}FN_4O_6S$

1H NMR (400 MHz, DMSO-$d_6$) δ: 0.9 (d, 3H), 1.15 (d, 3H), 2.9 (d, 1H), 3.1 (t, 1H), 3.2 (m, 3H), 3.7-3.8 (m, 3H), 4.0 (d, 1H), 4.1 (d, 1H), 7.1 (t, 1H), 11.5 (s, 1H), 11.9 (s, 1H).

Example 182

(2R,4S,4aS)-rel-11-fluoro-2,4-dimethyl-8-(methylsulfonyl)-1,2,4,4a-tetrahydro-2'H,6H-spiro[1,4-oxazino[4,3-a][1,2]oxazolo[4,5-g]quinoline-5,5'-pyrimidine]-2',4',6'(3'H)-trione

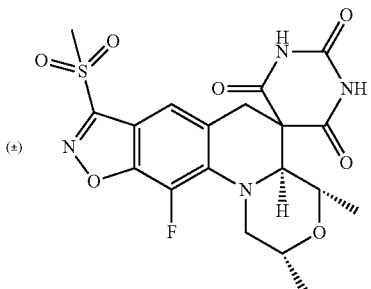

To a stirred solution of (2R,4S,4aS)-rel-11-fluoro-2,4-dimethyl-8-(methylsulfanyl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione (Example 62, 50 mg, 0.11 mmol) in dry DCM (1 mL) was added m-chloroperbenzoic acid (39 mg, 0.23 mmol) and heated to 80° C. for 1 hour. Solvents were evaporated and the residue thus obtained purified over a silica gel-column to give title compound as solid. Yield: 20 mg (43%).

MS (ES) MH+: 467 for $C_{19}H_{19}FN_4O_7S$;

1H NMR (400 MHz, DMSO-$d_6$) δ: 0.9 (d, 3H), 1.1 (d, 3H), 2.9 (d, 1H), 3.2 (t, 1H), 3.6 (s, 3H), 3.65 (m, 1H), 3.7 (m, 1H), 3.8 (m, 1H), 4.0 (d, 1H), 4.1 (d, 1H), 7.4 (s, 1H), 11.6 (s, 1H), 11.9 (s, 1H).

Example 183

(2R,4S,4aS)-rel-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidine]-8-carbonitrile

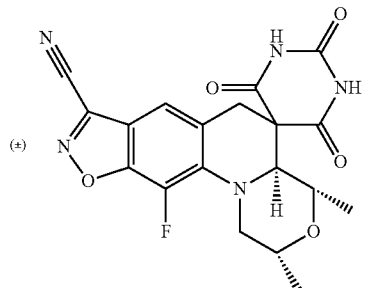

To a stirred solution of (2R,4S,4aS)-rel-11-fluoro-2,4-dimethyl-8-(methylsulfonyl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione (Example 182, 1.0 g, 2.15 mmol) in DMF was added KCN (700 mg, 10.75 mmol) followed by 18-crown-6 (catalytic) and the mixture was heated at 85° C. for 12 hours. The reaction mixture was cooled to room temperature and precipitated with diethyl ether (repeated twice to remove complete DMF). The precipitate was dissolved in EtOAc (50 mL) and washed with water (2×10 mL), dried over anhydrous sodium sulfate and, filtered, concentrated. The residue was purified by 'combiflash instrument' to give product as a pale yellow solid.

Yield: 211 mg (23%).

MS (ES) MH+: 414.5 for $C_{19}H_{16}FN_4O_5$;

1H NMR (400 MHz, DMSO-$d_6$) δ: 0.9 (d, 3H), 1.1 (d, 3H), 2.9 (d, 1H), 3.15 (m, 1H), 3.7 (m, 2H), 3.8 (m, 1H), 4.0 (d, 1H), 4.1 (d, 1H), 7.4 (s, 1H), 11.6 (bs, 1H), 11.9 (bs, 1H).

Example 184

Ethyl 2-[(2R,4S,4aS)-rel-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-1,3-thiazole-4-carboxylate

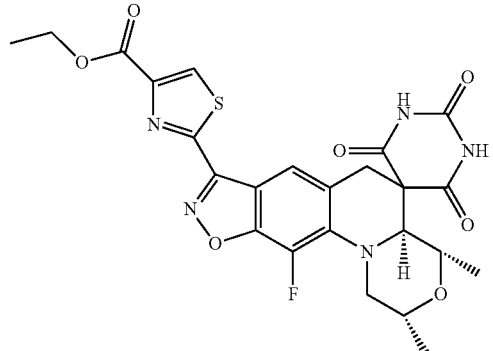

To a stirred solution of (2R,4S,4aS)-rel-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidine]-8-carbothioamide (Intermediate 575, 54 mg, 0.128 mmol) in mixture of EtOH:DMF (1 mL: 0.5 mL) were added ethyl bromopyruvate (47 mg, 0.24 mmol) and molecular sieves, and the mixture was stirred at 100° C. for 12 hours. The reaction mixture was concentrated, the residue was purified by silica gel column chromatography to give product as solid. Yield: 13 mg (20%).

MS (ES) MH+: 544 for $C_{24}H_{22}FN_5O_7S$ $^1$H NMR (400 MHz, DMSO-$d_6$) δ: 0.9 (d, 3H), 1.1 (d, 3H), 1.3 (t, 3H), 2.9 (d, 1H), 3.1 (m, 1H), 3.6 (m, 1H), 3.8 (m, 2H), 4.0 (d, 1H), 4.1 (d, 1H), 4.4 (q, 2H), 7.6 (s, 1H), 8.7 (s, 1H), 11.5 (s, 1H), 11.8 (s, 1H).

Example 185

(2R,4S,4aS)-rel-11-fluoro-8-(hydroxymethyl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

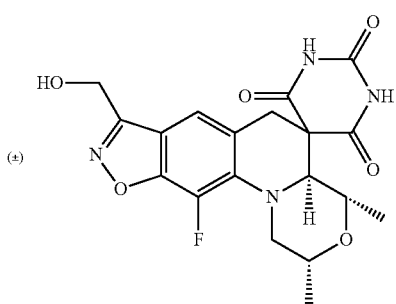

Lithium borohydride (0.434 ml, 0.87 mmol) was added to an ice cooled solution of methanol (0.035 ml, 0.87 mmol) in THF (10 ml). The solution was warmed to room temperature and stirred for 1 hour. 1.5 ml of the LiBH₄/MeOH solution was added to a solution of (2R,4S,4aS)-rel-ethyl 11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxylate (Example 134, 30 mg, 0.07 mmol) in 5 ml of THF. The reaction was stirred at room temperature of 1 hour. The reaction was diluted with water and extracted with ethyl acetate 2×. The organic layers were washed twice with brine, dried over MgSO₄ and concentrated. The residue was purified by HPLC (Acetonitrile (5 to 50%)/Water with a TFA modifier over 10 minutes). Freeze dried for 48 hours to give the title compound (22 mg, 0.053 mmol, 81%).

MS (ES) MH+: 419 for $C_{19}H_{19}FN_4O_6$ $^1$H NMR (300 MHz, DMSO-$d_6$) δ ppm 0.9 (d, 3H), 1.1 (d, 3H), 2.9 (d, 1H), 3.1 (t, 1H), 3.6-3.7 (m, 3H), 3.8-3.8 (m, 1H), 3.9 (d, 1H), 4.1 (d, 1H), 4.7 (s, 2H), 7.3 (s, 1H), 11.5 (s, 1H), 11.8 (s, 1H).

Example 186

1-[(2R,4S,4aS)-rel-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-1H-pyrazole-4-carboxylic acid

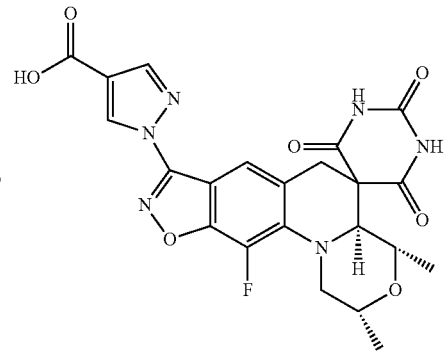

To a stirred solution of ethyl 1-[(2R,4S,4aS)-rel-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-1H-pyrazole-4-carboxylate (Example 37, 100 mg, 0.19 mmol) in acetonitrile (0.5 mL) was added 5% NaOH solution (14 mg, 0.11 mmol) and the mixture was stirred at room temperature for 2 hours. The reaction mixture was acidified to pH ~7 using 1.5 N HCl and extracted with EtOAc (5×10 mL). The organic layer was dried over anhydrous Na₂SO₄ and concentrated to give product as yellow solid. Yield: 45 mg MS (ES) MH+: 499.5 for $C_{22}H_{19}FN_6O_7$;

$^1$H NMR (400 MHz, DMSO-$d_6$) δ: 0.9 (d, 3H), 1.15 (d, 3H), 2.9 (d, 1H), 3.2 (t, 1H), 3.7 (m, 1H), 3.8 (m, 2H), 4.0 (d, 1H), 4.1 (d, 1H), 7.65 (s, 1H), 8.3 (s, 1H), 8.9 (s, 1H), 11.5 (s, 1H), 11.9 (s, 2H).

Example 187

1-[(2R,4S,4 aS)-rel-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-N,N-dimethyl-1H-pyrazole-4-carboxamide

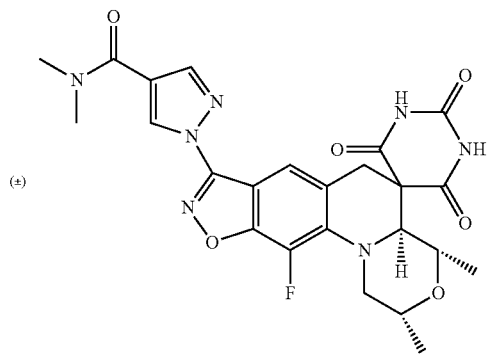

To a an ice cooled solution of 1-[(2R,4S,4aS)-rel-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-1H-pyrazole-4-carboxylic acid (Example 186, 100 mg, 0.19 mmol) in THF (0.5 mL) was added dimethyl amine, (30 mg, 0.11 mmol), DIPEA (139 mg, 1.08 mmol) followed by T₃P (172 mg, 0.54 mmol) and the mixture was stirred at room temperature for 1 hour. The reaction mixture was diluted with EtOAc (15 mL). The organic layer was washed with water (2×10 mL), dried over anhydrous Na₂SO₄ and concentrated. The residue was purified by silica gel column chromatography using a gradient of EtOAc in pet ether to give product as yellow solid.

Yield: 25 mg

MS (ES) MH⁺: 526.5 for $C_{24}H_{24}FN_7O_6$;

¹H NMR (400 MHz, DMSO-d₆) δ: 0.9 (d, 3H), 1.15 (d, 3H), 2.90 (d, 1H), 3.0 (s, 3H), 3.1 (m, 1H), 3.2 (s, 3H), 3.7 (m, 1H), 3.8 (m, 2H), 4.0 (d, 1H), 4.1 (d, 1H), 7.65 (s, 1H), 8.2 (s, 1H), 8.8 (s, 1H), 11.9 (br, 2H).

Examples 188 and 189 were prepared from the indicated starting material and pyrimidine-2,4,6(1H,3H,5H)-trione using a method similar to the one described for the synthesis of Example 187:

Example 188

1-[(2R,4S,4aS)-rel-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-N-methyl-1H-pyrazole-4-carboxamide

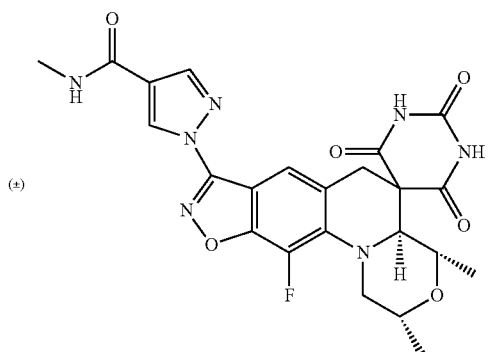

Starting material: 1-[(2R,4S,4aS)-rel-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-1H-pyrazole-4-carboxylic acid (Example 186) and methyl amine (0.16 mL, 2.0M in THF, 0.320 mmol).

MS (ES) MH⁺: 512 for $C_{23}H_{22}FN_7O_6$

¹H NMR (400 MHz, DMSO-d₆) δ: 0.9 (d, 3H), 1.15 (d, 3H), 2.8 (d, 3H), 2.9 (d, 1H), 3.1 (d, 1H), 3.7 (m, 1H), 3.8 (m, 2H), 4.0 (d, 1H), 4.1 (d, 1H), 7.7 (s, 1H), 8.3 (s, 1H), 8.4 (d, 1H), 8.9 (s, 1H), 11.5 (s, 1H), 11.9 (s, 1H).

Example 189

1-[(2R,4S,4aS)-rel-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-1H-pyrazole-4-carboxamide

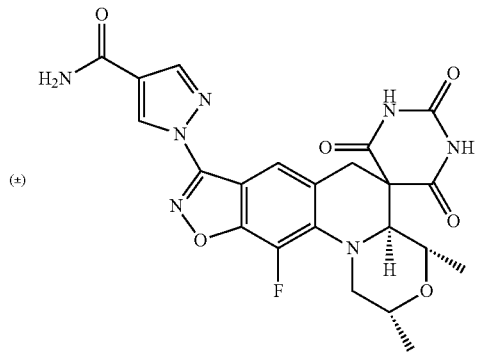

Starting materials: 1-[(2R,4S,4aS)-rel-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-1H-pyrazole-4-carboxylic acid (Example 186) and saturated NH₃ in THF (2 mL). Purification by reverse phase HPLC.

MS (ES) MH⁺: 498.5 for $C_{22}H_{20}FN_7O_6$

¹H NMR (400 MHz, DMSO-d₆) δ: 0.9 (d, 3H), 1.15 (d, 3H), 2.9 (d, 1H), 3.1 (d, 1H), 3.7 (m, 1H), 3.8 (m, 2H), 4.0 (d, 1H), 4.1 (d, 1H), 7.4 (s, 1H), 7.7 (s, 1H), 7.9 (d, 1H), 8.3 (s, 1H), 9.0 (s, 1H), 11.5 (brs, 2H).

Example 190

(2R,4S,4aS)-rel-11-fluoro-8-[4-(hydroxymethyl)-1H-pyrazol-1-yl]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

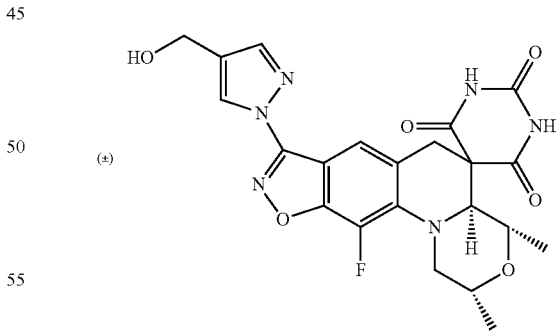

Lithium borohydride (0.434 mL, 0.87 mmol) was added to an ice cooled solution of methanol (0.035 mL, 0.87 mmol) in tetrahydrofuran (10 mL). The solution was warmed to room temp and stirred for 1 hour. 1.5 ml of this solution was added to a solution of ethyl 1-[(2R,4S,4aS)-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-1H-pyrazole-4-carboxylate (Example 37, 60 mg, 0.11 mmol). The reaction was stirred at room temp for 12 hours. The reaction mixture was diluted with water and extracted twice with ethyl acetate. The organic layers were washed twice with brine, dried over MgSO4 and concentrated. The residue was purified by reverse phase HPLC to give product as a solid. Yield: 20 mg.

MS (ES) MH$^+$: 485.5 for $C_{22}H_{21}FN_6O_6$ $^1$H NMR (400 MHz, DMSO-d$_6$) δ: 0.9 (d, 3H), 1.15 (d, 3H), 2.9 (d, 1H), 3.1 (t, 1H), 3.7 (m, 1H), 3.8 (m, 2H), 4.0 (d, 1H), 4.1 (d, 1H), 4.8 (d, 2H), 5.1 (s, 1H), 7.7 (s, 1H), 7.9 (s, 1H), 8.3 (s, 1H), 11.7 (br, 2H).

What is claimed is:

1. A compound of Formula (I),

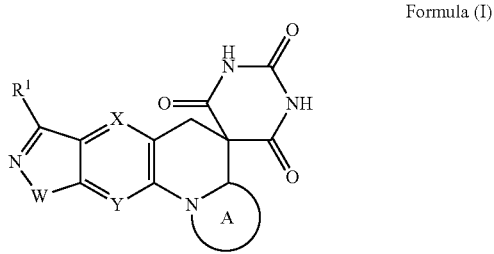

Formula (I)

or a pharmaceutically acceptable salt thereof, wherein:
Ring A is a fused morpholine optionally substituted on carbon with one or two $R^4$;
W is —O— or —S—
X is N or C—H;
Y is N or C—$R^3$;
$R^1$ is selected from halo, —CN, carbocyclyl, heterocyclyl, —OR$^{1a}$, —N(R$^{1a}$)$_2$, and —C(O)N(R$^{1a}$)$_2$, wherein said $C_{1-6}$alkyl, carbocyclyl, and heterocyclyl are optionally substituted on carbon with one or more $R^{10}$, and wherein any —NH— moiety of said heterocyclyl is optionally substituted with $R^{10}$*;
$R^{1a}$ in each occurrence is independently selected from H, carbocyclyl, and heterocyclyl, wherein said $C_{1-6}$alkyl, carbocyclyl, and heterocyclyl in each occurrence are optionally and independently substituted on carbon with one or more $R^{10}$, and wherein any —NH— moiety of said heterocyclyl is optionally substituted with $R^{10}$*;
$R^{1b}$ is $C_{1-6}$alkyl;
$R^3$ is chlorine, fluorine or methyl;
$R^4$ is methyl;
$R^{10}$ in each occurrence is independently selected from —CN, carbocyclyl, heterocyclyl, —OR$^{10a}$, —SR$^{10a}$, —N(R$^{10a}$)$_2$, —N(R$^{10a}$)C(O)R$^{10b}$, —C(O)R$^{10b}$, —C(O)$_2$R$^{10a}$, —C(O)N(R$^{10a}$)$_2$, and wherein said $C_{1-6}$alkyl, carbocyclyl and heterocyclyl in each occurrence are optionally and independently substituted on carbon with one or more $R^a$, and wherein any —NH— moiety of said heterocyclyl is optionally substituted with $R^{a}$*;
$R^{10}$* in each occurrence is independently selected from $C_{1-6}$alkyl, —C(O)R$^{10b}$ and —C(O)$_2$R$^{10a}$, wherein said $C_{1-6}$alkyl each occurrence is optionally and independently substituted on carbon with one or more $R^a$;
$R^{10a}$ in each occurrence is independently selected from H, $C_{1-6}$alkyl and heterocyclyl, wherein said $C_{1-6}$alkyl and heterocyclyl in each occurrence are optionally and independently substituted on carbon with one or more $R^a$, and wherein any —NH— moiety of said heterocyclyl is optionally substituted with $R^{a}$*;

$R^a$ in each occurrence is independently selected from halo, —CN, $C_{1-6}$alkyl and —OR$^m$;
$R^{a}$* in each occurrence is $C_{1-6}$alkyl; and
$R^m$ in each occurrence is independently selected from H, $C_{1-6}$alkyl, carbocyclyl, and heterocyclyl.

2. The compound of Formula (I), or a pharmaceutically acceptable salt thereof, as claimed in claim 1, wherein W is —O—.

3. The compound of Formula (I), or a pharmaceutically acceptable salt thereof, as claimed in claim 2, wherein X is C—H.

4. The compound of (I), or a pharmaceutically acceptable salt thereof, as claimed in claim 3, wherein $R^3$ is chlorine.

5. The compound of (I), or a pharmaceutically acceptable salt thereof, as claimed in claim 3, wherein $R^3$ is fluorine.

6. A compound, or a pharmaceutically acceptable salt thereof, selected from the group consisting of:
(2R,4S,4aS)-8-Amino-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;
(2R,4S,4aS)-11-Fluoro-2,4,8-trimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;
(2R,4S,4aS)-11-Fluoro-2,4-dimethyl-8-phenyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;
(2R,4S,4aS)-8-Cyclopropyl-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;
(2R,4S,4aS)-11-Fluoro-2,4-dimethyl-8-pyridin-2-yl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;
(2R,4S,4aS)-11-chloro-2,4,8-trimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;
(2R,4S,4aS)-8-(4-acetylpiperazin-1-yl)-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;
(2R,4S,4aS)-8-(benzylamino)-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;
(2R,4S,4aS)-11-fluoro-2,4-dimethyl-8-[(1,3-thiazol-2-ylmethyl)amino]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;
(2R,4S,4aS)-11-fluoro-8-[(1H-imidazol-4-ylmethyl)amino]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;
(2R,4S,4aS)-11-fluoro-2,4-dimethyl-8-{[(1-methyl-1H-pyrazol-4-yl)methyl]amino}-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;
(2R,4S,4aS)-11-fluoro-2,4-dimethyl-8-{[(5-methyl-1,2-oxazol-3-yl)methyl]amino}-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;
(2R,4S,4aS)-11-fluoro-2,4-dimethyl-8-[(pyridin-2-ylmethyl)amino]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-[(pyridin-3-ylmethyl)amino]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-[(pyridin-4-ylmethyl)amino]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-8-[(cyclopropylmethyl)amino]-1-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-8-[(cyclohexylmethyl)amino]-1-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-[(tetrahydro-2H-pyran-4-ylmethyl)amino]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

tert-butyl 4-[(2R,4S,4aS)-11-fluoro-2,4-dimethyl-2',4',6'-trioxo-1,1',2,3',4,4',4a,6'-octahydro-2'H,6H-spiro[isoxazolo[4,5-g][1,4]oxazino[4,3-a]quinoline-5,5'-pyrimidin]-8-yl]piperazine-1-carboxylate;

(2R,4S,4aS)-11-fluoro-2,4-dimethyl-8-(piperazin-1-yl)-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2R,4S,4aS)-11-fluoro-2,4-dimethyl-8-(morpholin-4-yl)-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2R,4S,4aS)-8-(diethylamino)-1-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2R,4S,4aS)-8-(dimethylamino)-1-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2R,4S,4aS)-11-fluoro-2,4-dimethyl-8-(pyrrolidin-1-yl)-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2R,4S,4aS)-8-(azepan-1-yl)-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2R,4S,4aS)-11-fluoro-2,4-dimethyl-8-[5-methyl-3-(trifluoromethyl)-1H-pyrazol-1-yl]-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

N-{1-[(2R,4S,4aS)-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-1H-pyrazol-3-yl}acetamide;

(2R,4S,4aS)-11-fluoro-2,4-dimethyl-8-[3-(trifluoromethyl)-1H-pyrazol-1-yl]-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2R,4S,4aS)-8-[3-(difluoromethyl)-5-methyl-1H-pyrazol-1-yl]-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2R,4S,4aS)-11-fluoro-2,4-dimethyl-8-(propylamino)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-8-[benzyl(methyl)amino]-1-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

3-amino-1-[(2R,4S,4aS)-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-1H-pyrazole-4-carbonitrile;

(2R,4S,4aS)-11-fluoro-2,4-dimethyl-8-[4-(pyrimidin-4-yl)-1H-pyrazol-1-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-[4-(pyrazin-2-yl)-1H-pyrazol-1-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-8-(4-iodo-1H-pyrazol-1-yl)-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

ethyl 1-[(2R,4S,4aS)-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-1H-pyrazole-4-carboxylate;

(2R,4S,4aS)-11-chloro-2,4-dimethyl-8-(pyridin-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-chloro-8-cyclopropyl-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-chloro-2,4-dimethyl-8-(6-methylpyridin-3-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-chloro-2,4-dimethyl-8-(1,3-thiazol-5-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-chloro-2,4-dimethyl-8-(pyrimidin-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-chloro-2,4-dimethyl-8-(pyrimidin-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-chloro-2,4-dimethyl-8-(pyrimidin-5-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-chloro-2,4-dimethyl-8-(pyridazin-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-chloro-2,4-dimethyl-8-(pyridin-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-chloro-2,4-dimethyl-8-(pyridin-3-yl)-1, 2,4,4a-tetrahydro-2'H,6H-spiro[1,4-oxazino[4,3-a][1, 2]oxazolo[4,5-g]quinoline-5,5'-pyrimidine]-2',4',6' (1'H,3'H)-trione (2R,4S,4aS)-11-chloro-2,4-dimethyl-8-(1,3-thiazol-2-yl)-1,2,4,4a-tetrahydro-2'H,6H-spiro[1,4-oxazino[4,3-a][1,2]oxazolo[4,5-g]quinoline-5,5'-pyrimidine]-2',4',6' (1'H,3'H)-trione;

(2R,4S,4aS)-11-chloro-8-(methoxymethyl)-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-[methyl(propyl) amino]-1,2,4,4a-tetrahydro-2'H,6H-spiro[1,4-oxazino [4,3-a][1,2]oxazolo[4,5-g]quinoline-5,5'-pyrimidine]-2',4',6'(1'H,3'H)trione;

(2R,4S,4aS)-11-fluoro-8-methoxy-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H, 3'H)-trione;

(2R,4S,4aS)-8-(benzyloxy)-1-fluoro-2,4-dimethyl-1,2,4, 4a-tetrahydro-2'H,6H-spiro[1,4-oxazino[4,3-a][1,2]oxazolo[4,5-g]quinoline-5,5'-pyrimidine]-2',4',6'(1'H, 3'H)-trione;

(2R,4S,4aS)-11-fluoro-2,4-dimethyl-8-(1H-1,2,4-triazol-1-yl)-1,2,4,4a-tetrahydro-2'H,6H-spiro[1,4-oxazino[4, 3-a][1,2]oxazolo[4,5-g]quinoline-5,5'-pyrimidine]-2', 4',6'(1'H,3'H)-trione;

(2R,4S,4aS)-11-fluoro-2,4-dimethyl-8-(3-methyl-1H-1,2, 4-triazol-1-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

1-[(2R,4S,4aS)-11-fluoro-2,4-dimethyl-2',4',6'-trioxo-1, 1',2,3',4,4',4a,6'-octahydro-2'H,6H-spiro[1,4-oxazino [4,3-a][1,2]oxazolo[4,5-g]quinoline-5,5'-pyrimidin-8-yl]-1H-1,2,4-triazole-3-carbonitrile;

(2R,4S,4aS)-11-fluoro-2,4-dimethyl-8-(2H-1,2,3-triazol-2-yl)-1,2,4,4a-tetrahydro-2'H,6H-spiro[1,4-oxazino[4, 3-a][1,2]oxazolo[4,5-g]quinoline-5,5'-pyrimidine]-2', 4',6'(1'H,3'H)-trione;

(2R,4S,4aS)-11-fluoro-2,4-dimethyl-8-(1H-1,2,3-triazol-1-yl)-1,2,4,4a-tetrahydro-2'H,6H-spiro[1,4-oxazino[4, 3-a][1,2]oxazolo[4,5-g]quinoline-5,5'-pyrimidine]-2', 4',6'(1'H,3'H)-trione;

(2R,4S,4aS)-11-fluoro-8-(1H-imidazol-1-yl)-2,4-dimethyl-1,2,4,4a-tetrahydro-2'H,6H-spiro[1,4-oxazino[4, 3-a][1,2]oxazolo[4,5-g]quinoline-5,5'-pyrimidine]-2', 4',6'(1'H,3'H)-trione;

(2R,4S,4aS)-11-fluoro-2,4-dimethyl-8-[4-(trifluoromethyl)-1H-imidazol-1-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-(4-methyl-1H-pyrazol-1-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-8-(4-chloro-1H-pyrazol-1-yl)-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-(methylsulfanyl)-1,2,4,4a-tetrahydro-2'H,6H-spiro[1,4-oxazino[4,3-a] [1,2]oxazolo[4,5-g]quinoline-5,5'-pyrimidine]-2',4',6' (1'H,3'H)-trione;

(2R,4S,4aS)-8-(3,5-dimethyl-1H-pyrazol-1-yl)-11-fluoro-2,4-dimethyl-1,2,4,4a-tetrahydro-2'H,6H-spiro [1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-(1H-pyrazol-4-yl)-1,2,4,4a-tetrahydro-2'H,6H-spiro[1,4-oxazino[4,3-a][1,2]oxazolo[4,5-g]quinoline-5,5'-pyrimidine]-2',4', 6'(1'H,3'H)-trione;

(2R,4S,4aS)-11-fluoro-2,4-dimethyl-8-(2-methyl-1,3-oxazol-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-(5-methyl-1,2-oxazol-3-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-8-(3,5-dimethyl-1,2-oxazol-4-yl)-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aR)-11-fluoro-2,4-dimethyl-8-(1-methyl-1H-imidazol-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-(1-methyl-1H-imidazol-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-(1-methyl-1H-imidazol-5-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-(4-methyl-1,3-thiazol-5-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-(4-methyl-1,2,3-thiadiazol-5-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-(pyridazin-3-yl)-1,2,4,4a-tetrahydro-2'H,6H-spiro[1,4-oxazino[4,3-a] [1,2]oxazolo[4,5-g]quinoline-5,5'-pyrimidine]-2',4',6' (1'H,3'H)-trione;

(2R,4S,4aS)-11-fluoro-2,4-dimethyl-8-(pyrimidin-4-yl)-1,2,4,4a-tetrahydro-2'H,6H-spiro[1,4-oxazino[4,3-a] [1,2]oxazolo[4,5-g]quinoline-5,5'-pyrimidine]-2',4',6' (1'H,3'H)-trione;

(2R,4S,4aS)-11-fluoro-2,4,8-trimethyl-1,2,4,4a-tetrahydro-2'H,6H-spiro[1,4-oxazino[4,3-a][1,2]thiazolo[4,5-g]quinoline-5,5'-pyrimidine]-2',4',6'(1'H,3'H)-trione;

(2R,4S,4aS)-11-fluoro-2,4-dimethyl-8-(pyridin-2-yl)-1,2, 4,4a-tetrahydro-2'H,6H-spiro[1,4-oxazino[4,3-a][1,2] thiazolo[4,5-g]quinoline-5,5'-pyrimidine]-2',4',6'(1'H, 3'H)-trione;

(2S,4R,4aR)-11-fluoro-2,4,8-trimethyl-1,2,3,4,4a,6-hexahydro-1'H-spiro[isoxazolo[4,5-g]pyrido[1,2-a] quinoline-5,5'-pyrimidine]-2',4',6'(3'H)-trione;

(2R,4S,4aS)-8-(3-chloropyrazin-2-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4', 6'(3'H)-trione;

(2R,4S,4aS)-8-(6-chloropyrazin-2-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4', 6'(3'H)-trione;

(2R,4S,4aS)-11-fluoro-2,4-dimethyl-8-(5-(methylthio) pyrazin-2-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-8-((1H-1,2,4-triazol-1-yl)methyl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-2,4-dimethyl-8-(pyridin-4-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-8-(5-hydroxy-1,3,4-oxadiazol-2-yl)-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2R,4S,4aS)-11-fluoro-2,4-dimethyl-8-[4-(morpholin-4-ylcarbonyl)-1,3-thiazol-2-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-[4-(morpholin-4-ylcarbonyl)-1,3-thiazol-5-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

2-[(2R,4S,4aS)-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-N,N-dimethyl-1,3-thiazole-4-carboxamide;

2-[(2R,4S,4aS)-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-N,N-dimethyl-1,3-thiazole-5-carboxamide;

5-[(2R,4S,4aS)-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-1,3-thiazole-4-carbonitrile;

(2R,4S,4aS)-11-chloro-2,4-dimethyl-8-(1-methyl-1H-imidazol-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-2,4,11-trimethyl-8-(1,3-thiazol-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-rel-11-fluoro-2,4-dimethyl-8-(6-methylpyridin-3-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-2,4-dimethyl-8-(trifluoromethyl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-8-(difluoromethyl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)—N-(2,2-difluoroethyl)-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)-8-(3,3-difluoroazetidine-1-carbonyl)-1-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-2,4-dimethyl-8-(thiazol-2-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-8-(furan-2-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-2,4-dimethyl-8-(thiazol-5-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-8-(2-fluorophenyl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-2,4-dimethyl-8-(tetrahydro-2H-pyran-4-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-2,4,11-trimethyl-8-(pyrazin-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-chloro-2,4-dimethyl-8-(pyridyin-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2R,4S,4aS)-11-chloro-2,4-dimethyl-8-(pyridyin-4-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2R,4S,4aS)-11-chloro-2,4-dimethyl-8-(pyridyin-3-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2R,4S,4aS)-11-chloro-2,4-dimethyl-8-(pyrazin-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2R,4S,4aS)-11-chloro-2,4-dimethyl-8-(thiazol-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2R,4S,4aS)-11-fluoro-2,4-dimethyl-8-(1-methyl-1H-imidazol-2-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-1-Chloro-2,4-dimethyl-8-(4-methylthiazol-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2R,4S,4aS)-1-Chloro-2,4-dimethyl-8-(1-methyl-1H-imidazol-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2R,4S,4aS)-11-chloro-2,4-dimethyl-8-(thiazol-5-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2R,4S,4aS)-11-chloro-2,4-dimethyl-8-(2,4-dichlorothiazol-5-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2R,4S,4aS)-11-Chloro-2,4-dimethyl-8-(2-methylthiazol-5-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2R,4S,4aS)-11-chloro-2,4-dimethyl-8-(1-methyl-1H-1,2,4-triazol-5-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2R,4S,4aS)-11-chloro-2,4-dimethyl-8-(2-bromothiazol-5-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2R,4S,4aS)-11-chloro-2,4-dimethyl-8-(pyrazin-2-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

4-((2R,4S,4aS)-11-chloro-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-yl)-2-fluorobenzonitrile;

(2R,4S,4aS)-11-Chloro-2,4-dimethyl-8-(5-methylthiazol-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

5-((2R,4S,4aS)-11-chloro-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-yl)picolinamide;

(2R,4S,4aS)-11-Chloro-2,4,8-trimethyl-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2R,4S,4aS)-11-Chloro-N,2,4-trimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2R,4S,4aS)-11-chloro-N-ethyl-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2R,4S,4aS)-Chloro-N-isopropyl-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2R,4S,4aS)—N-tert-butyl-11-chloro-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2R,4S,4aS)-11-Chloro-2,4-dimethyl-N-neopentyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2R,4S,4aS)-11-Chloro-8-(3,3-difluoroazetidine-1-carbonyl)-2,4-dimethyl-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2R,4S,4aS)—N-benzyl-11-chloro-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2R,4S,4aS)-11-chloro-N-(4-cyanobenzyl)-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2R,4S,4aS)-11-chloro-N-(3-cyanobenzyl)-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2R,4S,4aS)-11-fluoro-N,N,2,4-tetramethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)—N-ethyl-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)—N-ethyl-11-fluoro-N,2,4-trimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)-11-fluoro-N,2,4-trimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)-11-fluoro-2,4-dimethyl-2',4',6'-trioxo-2,2',3',4,4a,4',6,6'-octahydro-¹H,1'H-spiro[isoxazolo[4,5-g][1,4]oxazino[4,3-a]quinoline-5,5'-pyrimidine]-8-carboxamide;

(2R,4S,4aS)-11-fluoro-2,4-diethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)-11-fluoro-N-(2-methoxyethyl)-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)—N-tert-butyl-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)-11-fluoro-2,4-dimethyl-2',4',6'-trioxo-N-(tetrahydro-2H-pyran-4-yl)-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)-11-fluoro-N-isopropyl-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)-11-fluoro-2,4-dimethyl-8-(pyrimidin-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)—N-cyclopropyl-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)—N-(cyclopropylmethyl)-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)-11-fluoro-2,4-dimethyl-2',4',6'-trioxo-N-(thiophen-2-ylmethyl)-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)-11-fluoro-2,4-dimethyl-2',4',6'-trioxo-N-(pyridin-4-ylmethyl)-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)—N-(cyclohexylmethyl)-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)-11-fluoro-2,4-dimethyl-N-(1-methylazetidin-3-yl)-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)-11-fluoro-2,4-dimethyl-N-((1-methyl-1H-pyrazol-3-yl)methyl)-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)-11-fluoro-2,4-dimethyl-N-((1-methyl-1H-pyrazol-5-yl)methyl)-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2R,4S,4aS)—N-(1,3-dimethoxy-2-(methoxymethyl)propan-2-yl)-11-fluoro-2,4-dimethyl-2',4',6'-trioxo-2,2',3',4,4a,4',6,6'-octahydro-1H,1'H-spiro[isoxazolo[4,5g][1,4]oxazino[4,3-a]quinoline-5,5'-pyrimidine]-8-carboxamide;

(2R,4S,4aS)-11-fluoro-2,4-dimethyl-8-(pyrazin-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2R,4S,4aS)-11-fluoro-2,4-dimethyl-8-(5-morpholinopyrazin-2-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-8-(6-methoxypyrazin-2-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-2,4-dimethyl-8-(2-(methylthio)pyrimidin-4-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-2,4-dimethyl-8-(2-(methylsulfonyl)pyrimidin-4-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-8-(2-(2-methoxyethylamino)pyrimidin-4-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-8-(2-(2-hydroxyethylamino)pyrimidin-4-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-8-(2-methoxypyrimidin-4-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

4-((2R,4S,4aS)-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-yl)pyrimidine-2-carbonitrile;

(2R,4S,4aS)-8-(2-aminopyrimidin-4-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-fluoro-8-(2-hydroxypyrimidin-4-yl)-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2R,4S,4aS)-11-Fluoro-2,4-dimethyl-8-(2-morpholinopyrimidin-4-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-8-(6-(Dimethylamino)pyrazin-2-yl)-1-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-Fluoro-2,4-dimethyl-8-(1-methyl-1H-1,2,4-triazol-5-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-Fluoro-2,4-dimethyl-8-(piperazin-1-yl)-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2R,4S,4aS)-8-Chloro-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-11-Fluoro-2,4-dimethyl-2',4',6'-trioxo-1,1',2,3',4,4',4a,6-octahydro-2'H,6H-spiro[1,4-oxazino[4,3-a][1,2]oxazolo[4,5-g]quinoline-5,5'-pyrimidine]-8-carbonitrile;

ethyl 2-[(2R,4S,4aS)-11-fluoro-2,4-dimethyl-2',4',6'-trioxo-1,1',2,3',4,4',4a,6-octahydro-2'H,6H-spiro[1,4-oxazino[4,3-a][1,2]oxazolo[4,5-g]quinoline-5,5'-pyrimidin]-8-yl]-1,3-thiazole-4-carboxylate;

(2R,4S,4aS)-11-fluoro-8-(hydroxymethyl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

1-[(2R,4S,4aS)-11-fluoro-2,4-dimethyl-2',4',6'-trioxo-1,1',2,3',4,4',4a,6-octahydro-2'H,6H-spiro[1,4-oxazino[4,3-a][1,2]oxazolo[4,5-g]quinoline-5,5'-pyrimidin]-8-yl]-1H-pyrazole-4-carboxylic acid;

1-[(2R,4S,4aS)-11-fluoro-2,4-dimethyl-2',4',6'-trioxo-1,1',2,3',4,4',4a,6-octahydro-2'H,6H-spiro[1,4-oxazino[4,3-a][1,2]oxazolo[4,5-g]quinoline-5,5'-pyrimidin]-8-yl]-N,N-dimethyl-1H-pyrazole-4-carboxamide;

1-[(2R,4S,4aS)-11-fluoro-2,4-dimethyl-2',4',6'-trioxo-1,1',2,3',4,4',4a,6-octahydro-2'H,6H-spiro[1,4-oxazino[4,3-a][1,2]oxazolo[4,5-g]quinoline-5,5'-pyrimidin]-8-yl]-N-methyl-1H-pyrazole-4-carboxamide;

1-[(2R,4S,4aS)-11-fluoro-2,4-dimethyl-2',4',6'-trioxo-1,1',2,3',4,4',4a,6-octahydro-2'H,6H-spiro[1,4-oxazino[4,3-a][1,2]oxazolo[4,5-g]quinoline-5,5'-pyrimidin]-8-yl]-1H-pyrazole-4-carboxamide;

(2R,4S,4aS)-11-fluoro-8-[4-(hydroxymethyl)-1H-pyrazol-1-yl]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-8-Amino-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-11-Fluoro-2,4,8-trimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-11-Fluoro-2,4-dimethyl-8-phenyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-8-Cyclopropyl-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-11-Fluoro-2,4-dimethyl-8-pyridin-2-yl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-11-chloro-2,4,8-trimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-8-(4-acetylpiperazin-1-yl)-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-8-(benzylamino)-1-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-[(1,3-thiazol-2-ylmethyl)amino]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-8-[(1H-imidazol-4-ylmethyl)amino]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-{[(1-methyl-1H-pyrazol-4-yl)methyl]amino}-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-{[(5-methyl-1,2-oxazol-3-yl)methyl]amino}-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-[(pyridin-2-ylmethyl)amino]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-[(pyridin-3-ylmethyl)amino]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-[(pyridin-4-ylmethyl)amino]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-8-[(cyclopropylmethyl)amino]-1-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-8-[(cyclohexylmethyl)amino]-1-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-[(tetrahydro-2H-pyran-4-ylmethyl)amino]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

tert-butyl 4-[(2S,4R,4aR)-11-fluoro-2,4-dimethyl-2',4',6'-trioxo-1,1',2,3',4,4',4a,6'-octahydro-2'H,6H-spiro[isoxazolo[4,5-g][1,4]oxazino[4,3-a]quinoline-5,5'-pyrimidin]-8-yl]piperazine-1-carboxylate;

(2S,4R,4aR)-11-fluoro-2,4-dimethyl-8-(piperazin-1-yl)-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-11-fluoro-2,4-dimethyl-8-(morpholin-4-yl)-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-8-(diethylamino)-1-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-8-(dimethylamino)-1-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-11-fluoro-2,4-dimethyl-8-(pyrrolidin-1-yl)-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-8-(azepan-1-yl)-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-11-fluoro-2,4-dimethyl-8-[5-methyl-3-(trifluoromethyl)-1H-pyrazol-1-yl]-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

N-{1-[(2S,4R,4aR)-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-1H-pyrazol-3-yl}acetamide;

(2S,4R,4aR)-11-fluoro-2,4-dimethyl-8-[3-(trifluoromethyl)-1H-pyrazol-1-yl]-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-8-[3-(difluoromethyl)-5-methyl-1H-pyrazol-1-yl]-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-11-fluoro-2,4-dimethyl-8-(propylamino)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-8-[benzyl(methyl)amino]-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

3-amino-1-[(2S,4R,4aR)-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-1H-pyrazole-4-carbonitrile;

(2S,4R,4aR)-11-fluoro-2,4-dimethyl-8-[4-(pyrimidin-4-yl)-1H-pyrazol-1-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-[4-(pyrazin-2-yl)-1H-pyrazol-1-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-8-(4-iodo-1H-pyrazol-1-yl)-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

ethyl 1-[(2S,4R,4aR)-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-1H-pyrazole-4-carboxylate;

(2S,4R,4aR)-11-chloro-2,4-dimethyl-8-(pyridin-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-chloro-8-cyclopropyl-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-chloro-2,4-dimethyl-8-(6-methylpyridin-3-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-chloro-2,4-dimethyl-8-(1,3-thiazol-5-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-chloro-2,4-dimethyl-8-(pyrimidin-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-chloro-2,4-dimethyl-8-(pyrimidin-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-chloro-2,4-dimethyl-8-(pyrimidin-5-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-chloro-2,4-dimethyl-8-(pyridazin-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-chloro-2,4-dimethyl-8-(pyridin-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-chloro-2,4-dimethyl-8-(pyridin-3-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-chloro-2,4-dimethyl-8-(1,3-thiazol-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-chloro-8-(methoxymethyl)-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-[methyl(propyl)amino]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)trione;

(2S,4R,4aR)-11-fluoro-8-methoxy-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)l-8-(benzyloxy)-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-(1H-1,2,4-triazol-1-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-(3-methyl-1H-1,2,4-triazol-1-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-1H-1,2,4-triazole-3-carbonitrile;

(2S,4R,4aR)-11-fluoro-2,4-dimethyl-8-(2H-1,2,3-triazol-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-(1H-1,2,3-triazol-1-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-8-(1H-imidazol-1-yl)-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-[4-(trifluoromethyl)-1H-imidazol-1-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-(4-methyl-1H-pyrazol-1-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-8-(4-chloro-1H-pyrazol-1-yl)-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-(methylsulfanyl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-8-(3,5-dimethyl-1H-pyrazol-1-yl)-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-(1H-pyrazol-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-(2-methyl-1,3-oxazol-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-(5-methyl-1,2-oxazol-3-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-8-(3,5-dimethyl-1,2-oxazol-4-yl)-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-(1-methyl-1H-imidazol-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-(1-methyl-1H-imidazol-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-(1-methyl-1H-imidazol-5-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-(4-methyl-1,3-thiazol-5-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-(4-methyl-1,2,3-thiadiazol-5-yl)-1,2,4,4a-tetrahydro-2'H,6H-spiro[1,4- oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-(pyridazin-3-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-(pyrimidin-4-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4,8-trimethyl-1,2,4,4a-tetrahydro-2'H,6H-spiro[1,4-oxazino[4,3-a][1,2]thiazolo[4,5-g]quinoline-5,5'-pyrimidine]-2',4',6'(1'H,3'H)-trione;

(2S,4R,4aR)-11-fluoro-2,4-dimethyl-8-(pyridin-2-yl)-1,2,4,4a-tetrahydro-2'H,6H-spiro[1,4-oxazino[4,3-a][1,2]thiazolo[4,5-g]quinoline-5,5'-pyrimidine]-2',4',6'(1'H,3'H)-trione;

(2S,4R,4aR)-11-fluoro-2,4,8-trimethyl-1,2,3,4,4a,6-hexahydro-1'H-spiro[isoxazolo[4,5-g]pyrido[1,2-a]quinoline-5,5'-pyrimidine]-2',4',6'(3'H)-trione;

(2S,4R,4aR)-8-(3-chloropyrazin-2-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-8-(6-chloropyrazin-2-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-11-fluoro-2,4-dimethyl-8-(5-(methylthio)pyrazin-2-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-8-((1H-1,2,4-triazol-1-yl)methyl)-1-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-11-fluoro-2,4-dimethyl-8-(pyridin-4-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione (2S,4R,4aR)-11-fluoro-8-(5-hydroxy-1,3,4-oxadiazol-2-yl)-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-11-fluoro-2,4-dimethyl-8-[4-(morpholin-4-ylcarbonyl)-1,3-thiazol-2-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-[4-(morpholin-4-ylcarbonyl)-1,3-thiazol-5-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-2',4',6'-trioxo-1,1',2,3',4,4',4a,6-octahydro-2'H,6H-spiro[1,4-oxazino[4,3-a][1,2]oxazolo[4,5-g]quinoline-5,5'-pyrimidin]-8-yl]-N,N-dimethyl-1,3-thiazole-4-carboxamide;

(2S,4R,4aR)-11-fluoro-2,4-dimethyl-2',4',6'-trioxo-1,1',2,3',4,4',4a,6-octahydro-2'H,6H-spiro[1,4-oxazino[4,3-a][1,2]oxazolo[4,5-g]quinoline-5,5'-pyrimidin]-8-yl]-N,N-dimethyl-1,3-thiazole-5-carboxamide;

(2S,4R,4aR)-11-fluoro-2,4-dimethyl-2',4',6'-trioxo-1,1',2,3',4,4',4a,6-octahydro-2'H,6H-spiro[1,4-oxazino[4,3-a][1,2]oxazolo[4,5-g]quinoline-5,5'-pyrimidin]-8-yl]-1,3-thiazole-4-carbonitrile;

(2S,4R,4aR)-11-chloro-2,4-dimethyl-8-(1-methyl-1H-imidazol-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-2,4,11-trimethyl-8-(1,3-thiazol-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-2,4-dimethyl-8-(6-methylpyridin-3-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2R,4S,4aS)-rel-11-fluoro-2,4-dimethyl-8-(trifluoromethyl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-8-(difluoromethyl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)—N-(2,2-difluoroethyl)-1-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)-8-(3,3-difluoroazetidine-1-carbonyl)-1-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-11-fluoro-8-(furan-2-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-11-fluoro-2,4-dimethyl-8-(thiazol-5-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-11-fluoro-8-(2-fluorophenyl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-11-fluoro-2,4-dimethyl-8-(tetrahydro-2H-pyran-4-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-2,4,11-trimethyl-8-(pyrazin-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-chloro-2,4-dimethyl-8-(pyridyin-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2S,4R,4aR)-11-chloro-2,4-dimethyl-8-(pyridyin-4-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2S,4R,4aR)-11-chloro-2,4-dimethyl-8-(pyridyin-3-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2S,4R,4aR)-11-chloro-2,4-dimethyl-8-(pyrazin-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2S,4R,4aR)-11-chloro-2,4-dimethyl-8-(thiazol-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2S,4R,4aR)-11-fluoro-2,4-dimethyl-8-(1-methyl-1H-imidazol-2-yl)-2,4,4a,6-tetrahydro-1H,1H-spiro[isoxazolo[4,5-g][1,4]oxazino[4,3-a]quinoline-5,5'-pyrimidine]-2',4',6'(3'H)-trione;

(2S,4R,4aR)-11-Chloro-2,4-dimethyl-8-(1-methyl-1H-imidazol-2-yl)-2,4,4a,6-tetrahydro-1H,1H-spiro[isoxazolo[4,5-g][1,4]oxazino[4,3-a][1,5]naphthyridine-5,5'-pyrimidine]-2',4',6'(3'H)-trione;

(2S,4R,4aR)-11-Chloro-2,4-dimethyl-8-(1-methyl-1H-imidazol-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2S,4R,4aR)-11-chloro-2,4-dimethyl-8-(thiazol-5-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2S,4R,4aR)-11-chloro-2,4-dimethyl-8-(2,4-dichlorothiazol-5-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2S,4R,4aR)-11-Chloro-2,4-dimethyl-8-(2-methylthiazol-5-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2S,4R,4aR)-11-chloro-2,4-dimethyl-8-(1-methyl-1H-1,2,4-triazol-5-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2S,4R,4aR)-11-chloro-2,4-dimethyl-8-(2-bromothiazol-5-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2S,4R,4aR)-11-chloro-2,4-dimethyl-8-(pyrazin-2-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

4-((2S,4R,4aR)-11-chloro-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-yl)-2-fluorobenzonitrile;

(2S,4R,4aR)-11-Chloro-2,4-dimethyl-8-(5-methylthiazol-2-yl)-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

5-((2S,4R,4aR)-11-chloro-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-yl)picolinamide;

(2S,4R,4aR)-11-Chloro-2,4,8-trimethyl-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2S,4R,4aR)-11-Chloro-N,2,4-trimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2S,4R,4aR)-11-chloro-N-ethyl-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2S,4R,4aR)-Chloro-N-isopropyl-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2S,4R,4aR)—N-tert-butyl-11-chloro-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2S,4R,4aR)-11-Chloro-2,4-dimethyl-N-neopentyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2S,4R,4aR)-11-Chloro-8-(3,3-difluoroazetidine-1-carbonyl)-2,4-dimethyl-2,4,4a,6-tetrahydro-1H,1'H-spiro[isoxazolo[4,5-g][1,4]oxazino[4,3-a][1,5]naphthyridine-5,5'-pyrimidine]-2',4',6'(3'H)-trione;

(2S,4R,4aR)—N-benzyl-11-chloro-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2S,4R,4aR)-11-chloro-N-(4-cyanobenzyl)-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2S,4R,4aR)-11-chloro-N-(3-cyanobenzyl)-2,4-dimethyl-2',4',6'-trioxo-2,2',3',4,4a,4',6,6'-octahydro-1H,1'H-spiro[isoxazolo[4,5-g][1,4]oxazino[4,3-a][1,5]naphthyridine-5,5'-pyrimidine]-8-carboxamide;

(2S,4R,4aR)-11-chloro-N,N,2,4-tetramethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)—N-ethyl-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)—N-ethyl-11-fluoro-N,2,4-trimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)-11-fluoro-N,2,4-trimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)-11-fluoro-N-(2-methoxyethyl)-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)—N-tert-butyl-1-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)-11-fluoro-2,4-dimethyl-2',4',6'-trioxo-N-(tetrahydro-2H-pyran-4-yl)-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)-11-fluoro-N-isopropyl-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)-11-fluoro-2,4-dimethyl-8-(pyrimidin-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-11-fluoro-4,8-dimethyl-2-(trifluoromethyl)-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)—N-cyclopropyl-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)—N-(cyclopropylmethyl)-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)-11-fluoro-2,4-dimethyl-2',4',6'-trioxo-N-(thiophen-2-ylmethyl)-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)-11-fluoro-2,4-dimethyl-2',4',6'-trioxo-N-(pyridin-4-ylmethyl)-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)—N-(cyclohexylmethyl)-11-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)-11-fluoro-2,4-dimethyl-N-(1-methylazetidin-3-yl)-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)-11-fluoro-2,4-dimethyl-N-((1-methyl-1H-pyrazol-3-yl)methyl)-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)-11-fluoro-2,4-dimethyl-N-((1-methyl-1H-pyrazol-5-yl)methyl)-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide;

(2S,4R,4aR)—N-(1,3-dimethoxy-2-(methoxymethyl)propan-2-yl)-1-fluoro-2,4-dimethyl-2',4',6'-trioxo-2,2',3',4,4a,4',6,6'-octahydro-1H,1'H-spiro[isoxazolo[4,5g][1,4]oxazino[4,3-a]quinoline-5,5'-pyrimidine]-8-carboxamide;

(2S,4R,4aR)-11-fluoro-2,4-dimethyl-8-(pyrazin-2-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione;

(2S,4R,4aR)-8-(6-(Dimethylamino)pyrazin-2-yl)-1-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-11-Fluoro-2,4-dimethyl-8-(piperazin-1-yl)-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione;

(2S,4R,4aR)-11-Fluoro-2,4-dimethyl-2',4',6'-trioxo-1,1',2,3',4,4',4a,6-octahydro-2'H,6H-spiro[1,4-oxazino[4,3-a][1,2]oxazolo[4,5-g]quinoline-5,5'-pyrimidine]-8-carbonitrile;

ethyl 2-[(2S,4R,4aR)11-fluoro-2,4-dimethyl-2',4',6'-trioxo-1,1',2,3',4,4',4a,6-octahydro-2'H,6H-spiro[1,4-oxazino[4,3-a][1,2]oxazolo[4,5-g]quinoline-5,5'-pyrimidin]-8-yl]-1,3-thiazole-4-carboxylate;

(2S,4R,4aR)-11-fluoro-8-(hydroxymethyl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione;

(2S,4R,4aR)-11-fluoro-2,4-dimethyl-2',4',6'-trioxo-1,1',2,3',4,4',4a,6-octahydro-2'H,6H-spiro[1,4-oxazino[4,3-a][1,2]oxazolo[4,5-g]quinoline-5,5'-pyrimidin-8-yl]-1H-pyrazole-4-carboxylic acid;

(2S,4R,4aR)-11-fluoro-2,4-dimethyl-2',4',6'-trioxo-1,1',2,3',4,4',4a,6-octahydro-2'H,6H-spiro[1,4-oxazino[4,3-a][1,2]oxazolo[4,5-g]quinoline-5,5'-pyrimidin-8-yl]-N,N-dimethyl-1H-pyrazole-4-carboxamide;

(2S,4R,4aR)-11-fluoro-2,4-dimethyl-2',4',6'-trioxo-1,1',2,3',4,4',4a,6-octahydro-2'H,6H-spiro[1,4-oxazino[4,3-a][1,2]oxazolo[4,5-g]quinoline-5,5'-pyrimidin-8-yl]-N-methyl-1H-pyrazole-4-carboxamide;

(2S,4R,4aR)-11-fluoro-2,4-dimethyl-2',4',6'-trioxo-1,1',2,3',4,4',4a,6-octahydro-2'H,6H-spiro[1,4-oxazino[4,3-a][1,2]oxazolo[4,5-g]quinoline-5,5'-pyrimidin]-8-yl]-1H-pyrazole-4-carboxamide; and (2S,4R,4aR)-11-fluoro-8-[4-(hydroxymethyl)-1H-pyrazol-1-yl]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione, or a pharmaceutically acceptable salt thereof.

7. A pharmaceutical composition comprising a compound of Formula (I), or a pharmaceutically acceptable salt thereof, as claimed in claim 1, and a pharmaceutically acceptable carrier, diluent or excipient.

8. A pharmaceutical composition comprising a compound as claimed in claim 6, or a pharmaceutically acceptable salt thereof, and a pharmaceutically acceptable carrier, diluent or excipient.

* * * * *

UNITED STATES PATENT AND TRADEMARK OFFICE
CERTIFICATE OF CORRECTION

PATENT NO. : 8,658,641 B2
APPLICATION NO. : 13/124889
DATED : February 25, 2014
INVENTOR(S) : Kevin Barvian et al.

It is certified that error appears in the above-identified patent and that said Letters Patent is hereby corrected as shown below:

In the Claims:

Claim 1, column 289, line 34, insert --C1-6 alkyl,-- before the word carbocyclyl;

Claim 1, column 289, line 41, insert --C1-6 alkyl,-- before the word carbocyclyl;

Claim 1, column 289, line 50, insert --C1-6 alkyl,-- before the word carbocyclyl.

Signed and Sealed this
Thirtieth Day of December, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,658,641 B2 | Page 1 of 2 |
| APPLICATION NO. | : 13/124889 | |
| DATED | : February 25, 2014 | |
| INVENTOR(S) | : Kevin Barvian et al. | |

It is certified that error appears in the above-identified patent and that said Letters Patent is hereby corrected as shown below:

In the Claims:

Claim 6, Column 291, lines 34-37, replace
"(2R,4S,4aS)-8-(diethylamino)-1-fluoro-2,4-dimethyl-1,2,4,4a-tetrahydro-2'H,6H-spiro[isoxazolo
[4,5-g][1,4]oxazino[4,3-a]quinoline-5,5'-pyrimidine]-2',4',6'(1'H,3'H)-trione" with
--(2R,4S,4aS)-8-(diethylamino)-11-fluoro-2,4-dimethyl-1,2,4,4a-tetrahydro-2'H,6H-
spiro[isoxazolo[4,5-g][1,4]oxazino[4,3-a]quinoline-5,5'-pyrimidine]-2',4',6'(1'H,3'H)-trione--.
Claim 6, Column 291, lines 38-41, replace
"(2R,4S,4aS)-8-(dimethylamino)-1-fluoro-2,4-dimethyl-1,2,4,4a-tetrahydro-2'H,6H-spiro[isoxazolo
[4,5-g][1,4]oxazino[4,3-a]quinoline-5,5'-pyrimidine]-2',4',6'(1'H,3'H)-trione" with
--(2R,4S,4aS)-8-(dimethylamino)-11-fluoro-2,4-dimethyl-1,2,4,4a-tetrahydro-2'H,6H-spiro
[isoxazolo[4,5-g][1,4]oxazino[4,3-a]quinoline-5,5'-pyrimidine]-2',4',6'(1'H,3'H)-trione--.
Claim 6, Column 295, lines 64-67, replace
"(2R,4S,4aS)-8-(3,3-difluoroazetidine-1-carbonyl)-1-fluoro-2,4-dimethyl-2,4,4a,6-tetrahydro-1H,
1'H-spiro[isoxazolo[4,5-g][1,4]oxazino[4,3-a]quinoline-5,5'-pyrimidine]-2',4',6'(3'H)-trione" with
--(2R,4S,4aS)-8-(3,3-difluoroazetidine-1-carbonyl)-11-fluoro-2,4-dimethyl-2,4,4a,6-tetrahydro-
1H,1'H-spiro[isoxazolo[4,5-g][1,4]oxazino[4,3-a]quinoline-5,5'pyrimidine]-2',4',6'(3'H)-trione--.
Claim 6, Column 296, lines 51-54, replace
"(2R,4S,4aS)-1-Chloro-2,4-dimethyl-8-(4-methylthiazol-2-yl)-2,4,4a,6-tetrahydro-1H,1'H-
spiro[isoxazolo[4,5-g][1,4]oxazino[4,3-a][1,5]naphthyridine-5,5'-pyrimidine]-2',4',6'(3'H)-trione" with
--(2R,4R,4aS)-11-Chloro-2,4-dimethyl-8-(4-methylthiazol-2-yl)-2,4,4a,6-tetrahydro-1H,1'H-spiro
[isoxazolo[4,5-g][1,4]oxazino[4,3-a][1,5]naphthyridine-5,5'-pyrimidine]-2',4',6'(3'H)-trione--.
Claim 6, Column 296, lines 55-58, replace
"(2R,4S,4aS)-1-Chloro-2,4-dimethyl-8-(1-methyl-1H-imidazol-2-yl)-2,4,4a,6-tetrahydro-1H,1'H-spiro
[isoxazolo[4,5-g][1,4]oxazino[4,3-a][1,5]naphthyridine-5,5'-pyrimidine]-2',4',6'(3'H)-trione" with
--(2R,4R,4aS)-11-Chloro-2,4-dimethyl-8-(1-methyl-1H-imidazol-2-yl)-2,4,4a,6-tetrahydro-1H,1'H-
spiro [isoxazolo[4,5-g][1,4]oxazino[4,3-a][1,5]naphthyridine-5,5'-pyrimidine]-2',4',6'(3'H)-trione--.

Signed and Sealed this
Fourteenth Day of July, 2015

Michelle K. Lee
*Director of the United States Patent and Trademark Office*

CERTIFICATE OF CORRECTION (continued)
U.S. Pat. No. 8,658,641 B2

In the Claims:

Claim 6, Column 301, lines 39-42, replace
"(2S,4R,4aR)-8-[(cyclopropylmethyl)amino]-1-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione" with
--(2S,4R,4aR)-8-[(cyclopropylmethol)amino]-11-fluoro-2,4-dimethyl-1,2,4,4a-tetrahydro-2'H,6H-spiro[1,4-oxazino[4,3-a][1,2]oxazolo(4,5-g]quinoline-5,5'-pyrimidine]-2',4',6'(1'H,3'H)-trione--.
Claim 6, Column 301, lines 43-46, replace
"(2S,4R,4aR)-8-[(cyclohexylmethyl)amino]-1-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione" with
--(2S,4R,4aR)-8-[(cyclohexylmethyl)amino]-1-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione--.
Claim 6, Column 301, lines 64-67, replace
"(2S,4R,4aR)-8-(diethylamino)-1-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione" with
--(2S,4R,4aR)-8-(diethylamino)-11-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione--.
Claim 6, Column 302, lines 1-4, replace
"(2S,4R,4aR)-8-(dimethylamino)-1-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione" with
--(2S,4R,4aR)-8-(dimethylamino)-1-fluoro-2,4-dimethyl-1,2,4,4a-tetrahydro-2'H,6H-spiro[isoxazolo[4,5-g][1,4]oxazino[4,3-a]quinoline-5,5'-pyrimidine]-2',4',6'(1'H,3'H)-trione--.
Claim 6, Column 306, lines 20-23, replace
"(2S,4R,4aR)-N-(2,2-difluoroethyl)-1-fluoro-2,4-dimethyl-2',4',6'-trioxo-2,2',3',4,4a,4',6,6'-octahydro-1H,1'H-spiro[isoxazolo[4,5-g][1,4]oxazino[4,3-a]quinoline-5,5'-pyrimidine]-8-carboxamide" with
--(2S,4R,4aR)-N-(2,2-difluoroethyl)-11-fluoro-2,4-dimethyl-2',4',6-trioxo-2,2',3',4,4a,4',6,6'-octahydro-1H,1'H-spiro[isoxazolo[4,5-g][1,4]oxazino[4,3-a]quinoline-5,5'-pyrimidine)-8-carboxamide--.
Claim 6, Column 306, lines 24-27, replace
"(2S,4R,4aR)-8-(3,3-difluoroazetidine-1-carbonyl)-1-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione" with
--(2S,4R,4aR)-8-(3,3-difluoroazetidine-1-carbonyl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione--.
Claim 6, Column 307, lines 5-8, replace
"(2S,4R,4aR)-11-Chloro-2,4-dimethyl-8-(1-methyl-1H-imidazol-2-yl)-2,4,4a,6-tetrahydro-1H,1H-spiro[isoxazolo[4,5-g][1,4]oxazino[4,3-a][1,5]naphthyridine-5,5'-pyrimidine]-2',4',6'(3'H)-trione" with
--(2S,4R,4aR)-11-Chloro-2,4-dimethyl-8-(4-methyl-1H-imidazol-2-yl)-2,4,4a,6-tetrahydro-1H,1H-spiro[isoxazolo[4,5-g][1,4]oxazino[4,3-a][1,5]naphthyridine-5,5'-pyrimidine]-2',4',6'(3'H)-trione--.